(12) United States Patent
Xia et al.

(10) Patent No.: US 9,670,185 B2
(45) Date of Patent: Jun. 6, 2017

(54) ORGANIC ELECTROLUMINESCENT MATERIALS AND DEVICES

(71) Applicant: Universal Display Corporation, Ewing, NJ (US)

(72) Inventors: Chuanjun Xia, YLawrenceville, NJ (US); Chun Lin, Yardley, PA (US); Raymond Kwong, Fo Tan (HK); Scott Joseph, Ewing, NJ (US); James Esler, Yardley, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

(21) Appl. No.: 14/921,446

(22) Filed: Oct. 23, 2015

(65) Prior Publication Data

US 2016/0060251 A1    Mar. 3, 2016

Related U.S. Application Data

(62) Division of application No. 13/708,189, filed on Dec. 7, 2012, now Pat. No. 9,209,411.

(51) Int. Cl.
| | |
|---|---|
| *H01L 51/50* | (2006.01) |
| *C07D 403/14* | (2006.01) |
| *C09K 11/06* | (2006.01) |
| *C07D 405/14* | (2006.01) |
| *C07D 403/10* | (2006.01) |

(Continued)

(52) U.S. Cl.
CPC ......... *C07D 403/14* (2013.01); *C07D 403/10* (2013.01); *C07D 405/14* (2013.01); *C07D 409/14* (2013.01); *C07D 491/048* (2013.01); *C09K 11/06* (2013.01); *H01L 51/0067* (2013.01); *H01L 51/0072* (2013.01); *C09K 2211/1007* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0054* (2013.01); *H01L 51/0073* (2013.01)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Gregory Clark
(74) *Attorney, Agent, or Firm* — Duane Morris LLP

(57) ABSTRACT

Novel carbazole-containing compounds are provided. The novel compounds also contain electron donor groups, aryl linkers, and at least one nitrogen heterocycle. These novel organic compounds are useful in OLED devices and can exhibit delayed fluorescence.

20 Claims, 3 Drawing Sheets

(51) Int. Cl.
*C07D 409/14* (2006.01)
*C07D 491/048* (2006.01)
*H01L 51/00* (2006.01)

(56) References Cited

U.S. PATENT DOCUMENTS

| | | | |
|---|---|---|---|
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0151042 | A1 | 8/2003 | Hueschen |
| 2003/0152802 | A1 | 8/2003 | Tsuboyama et al. |
| 2003/0170491 | A1 | 9/2003 | Liao et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0170863 | A1 | 9/2004 | Kim et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0138402 | A1 | 6/2006 | Cao et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Pakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2011/0215710 | A1 | 9/2011 | Xia et al. |
| 2011/0279020 | A1 | 11/2011 | Inoue et al. |
| 2012/0086329 | A1 | 4/2012 | Dyatkin |
| 2012/0211736 | A1 | 8/2012 | Kim et al. |

FOREIGN PATENT DOCUMENTS

| | | | |
|---|---|---|---|
| EP | 2034538 | 3/2009 | |
| JP | 200511610 | 1/2005 | |
| JP | 2007123392 | 5/2007 | |
| JP | 2007254297 | 10/2007 | |
| JP | 2008074939 | 4/2008 | |
| JP | 2012-019172 | * 1/2012 | ............ H01L 51/50 |
| WO | 0139234 | 5/2001 | |
| WO | 0202714 | 1/2002 | |
| WO | 0215645 | 2/2002 | |
| WO | 03040257 | 5/2003 | |
| WO | 03060956 | 7/2003 | |
| WO | 2004093207 | 10/2004 | |
| WO | 2004107822 | 12/2004 | |
| WO | 2005014551 | 2/2005 | |
| WO | 2005019373 | 3/2005 | |
| WO | 2005030900 | 4/2005 | |
| WO | 2005089025 | 9/2005 | |
| WO | 2005123873 | 12/2005 | |
| WO | 2006009024 | 1/2006 | |
| WO | 2006056418 | 6/2006 | |
| WO | 2006072002 | 7/2006 | |
| WO | 2006082742 | 8/2006 | |
| WO | 2006098120 | 9/2006 | |
| WO | 2006100298 | 9/2006 | |
| WO | 2006103874 | 10/2006 | |
| WO | 2006114966 | 11/2006 | |
| WO | 2006132173 | 12/2006 | |
| WO | 2007002683 | 1/2007 | |
| WO | 2007004380 | 1/2007 | |
| WO | 2007063754 | 6/2007 | |
| WO | 2007063796 | 6/2007 | |
| WO | 2008056746 | 5/2008 | |
| WO | 2008101842 | 8/2008 | |
| WO | 2008132085 | 11/2008 | |
| WO | 2009000673 | 12/2008 | |
| WO | 2009003898 | 1/2009 | |
| WO | 2009008311 | 1/2009 | |
| WO | 2009018009 | 2/2009 | |
| WO | 2009050290 | 4/2009 | |
| WO | 2009021126 | 5/2009 | |
| WO | 2009062578 | 5/2009 | |
| WO | 2009063833 | 5/2009 | |
| WO | 2009066778 | 5/2009 | |
| WO | 2009066779 | 5/2009 | |
| WO | 2009086028 | 7/2009 | |
| WO | 2009100991 | 8/2009 | |
| WO | 2011055934 | 5/2011 | |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

(56) References Cited

OTHER PUBLICATIONS

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

Formula I

ORGANIC ELECTROLUMINESCENT MATERIALS AND DEVICES

CROSS-REFERENCE TO RELATED APPLICATIONS

This application is a divisional application of U.S. patent application Ser. No. 13/708,189, filed Dec. 7, 2012, the entire content of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to carbazole-containing compounds bearing an electron donor group that are suitable for use in OLED devices. These compounds also exhibit delayed fluorescence characteristics.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

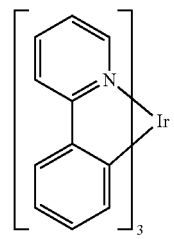

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound having the formula:

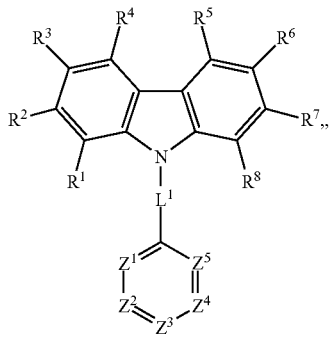

Formula I is provided.

$Z^1$, $Z^2$, $Z^3$, $Z^4$ and $Z^5$ are each independently selected from group consisting of $CR^9$ and N, and any adjacent $R^9$ are optionally joined to form a fused ring. At least one of $Z^1$, $Z^2$, $Z^3$, $Z^4$ and $Z^5$ is N.

$L^1$ is selected from the group consisting of:

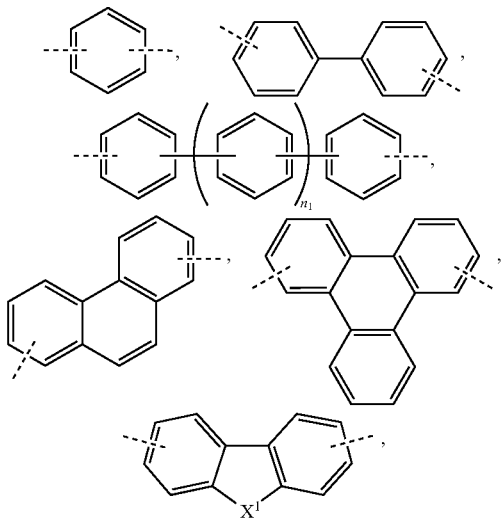

and combinations thereof;

where $X^1$ is O, S, or CRR' and R, R' are optionally joined to form a ring. $n_1$ is an integer from 1 to 20, and $L^1$ can be further substituted by a substituent selected from the group consisting of alkyl, aryl, and heteroaryl. At least one of $R^1$, $R^2$, $R^3$, $R^4$, $R^5$, $R^6$, $R^7$, and $R^8$ comprises at least one electron donor group selected from the group consisting of:

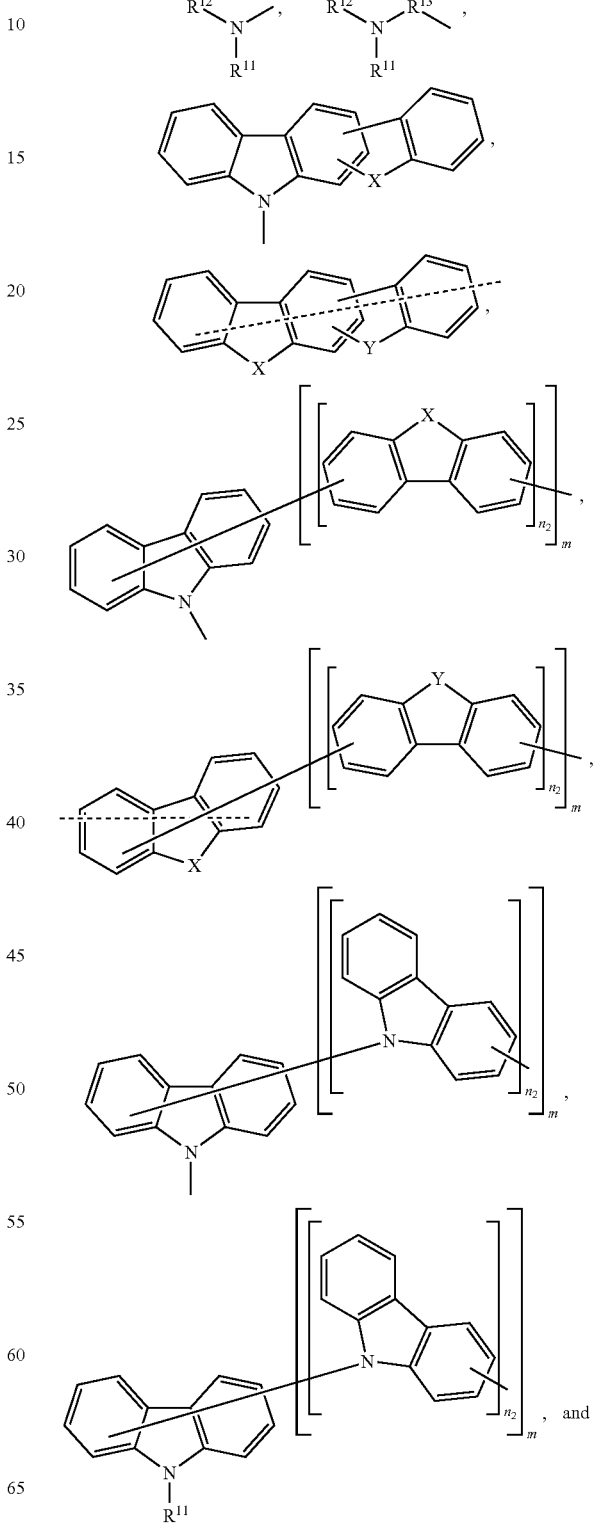

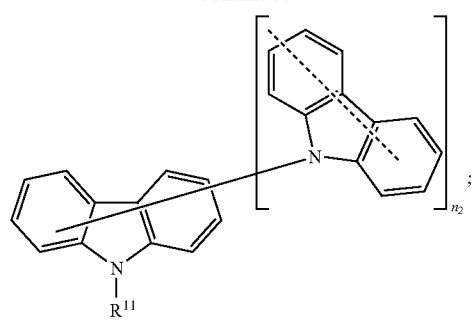

X and Y is selected from the group consisting of O, S, NR$^{14}$; and R$^{11}$, R$^{12}$, R$^{13}$ and R$^{14}$ are selected from the group consisting of aryl and heteroaryl. Any two adjacent R$^1$, R$^2$, R$^3$, R$^4$, R$^5$, R$^6$, R$^7$, and R$^8$ are not joined to form a ring, m is an integer from 1 to 20, and n$_2$ is an integer from 1 to 20. R$^1$, R$^2$, R$^3$, R$^4$, R$^5$, R$^6$, R$^7$, and R$^8$ do not contain an electron acceptor group, and R$^9$ does not contain an electron donor group.

R$^1$, R$^2$, R$^3$, R$^4$, R$^5$, R$^6$, R$^7$, and R$^8$ are independently selected from the group consisting of hydrogen, deuterium, alkyl, cycloalkyl, arylalkyl, alkoxy, aryloxy, amino, silyl, alkenyl, cycloalkenyl, heteroalkenyl, alkynyl, aryl, heteroaryl, and combinations thereof and R$^9$, R, and R' are independently selected from the group consisting of hydrogen, deuterium, alkyl, cycloalkyl, heteroalkyl, arylalkyl, silyl, alkenyl, cycloalkenyl, heteroalkenyl, alkynyl, aryl, heteroaryl, and combinations thereof.

In one aspect, at least one of R$^1$, R$^2$, R$^3$, R$^4$, R$^5$, R$^6$, R$^7$, and R$^8$ comprises the electron donor group selected from the group consisting of:

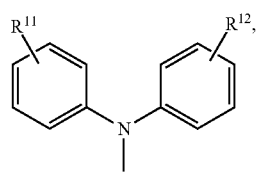

D$^1$

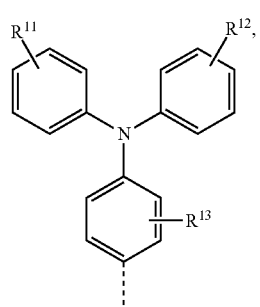

D$^2$

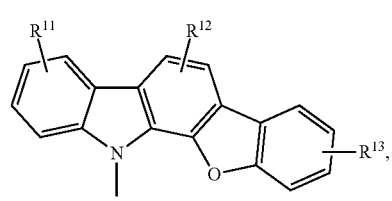

D$^3$

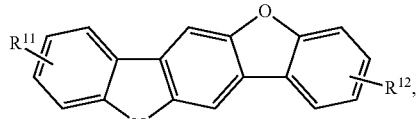

D$^4$

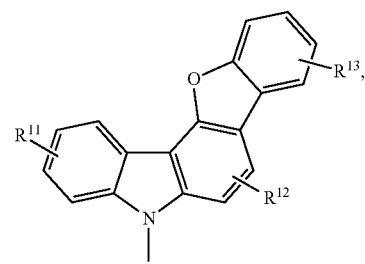

D$^5$

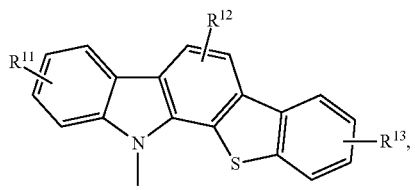

D$^6$

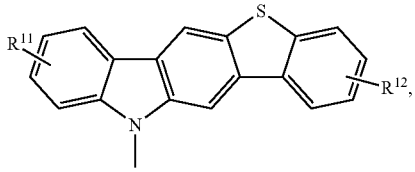

D$^7$

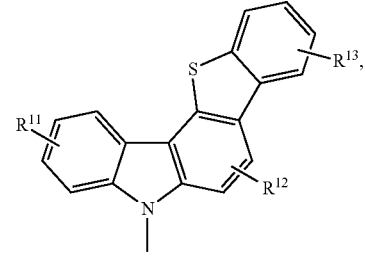

D$^8$

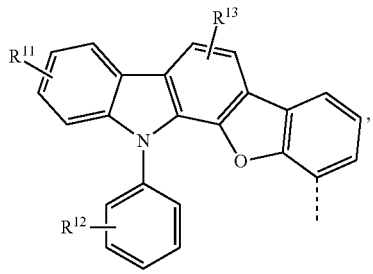

D$^9$

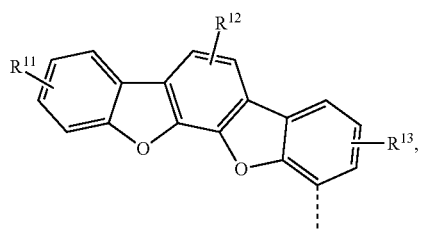

D$^{10}$

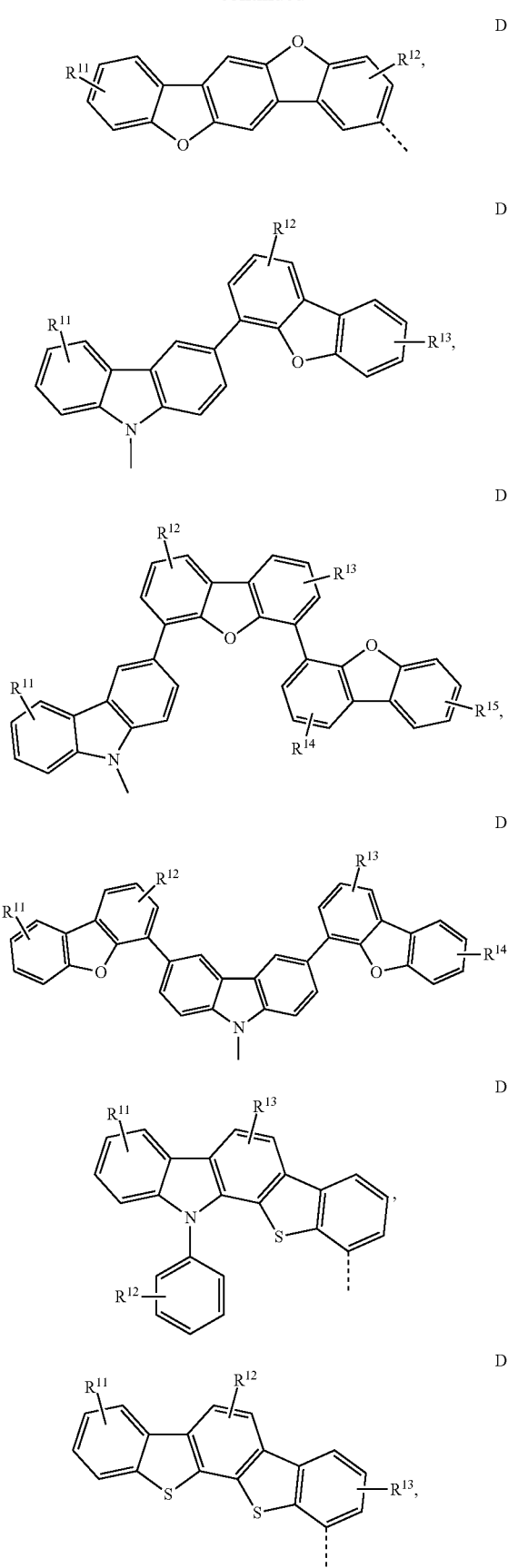
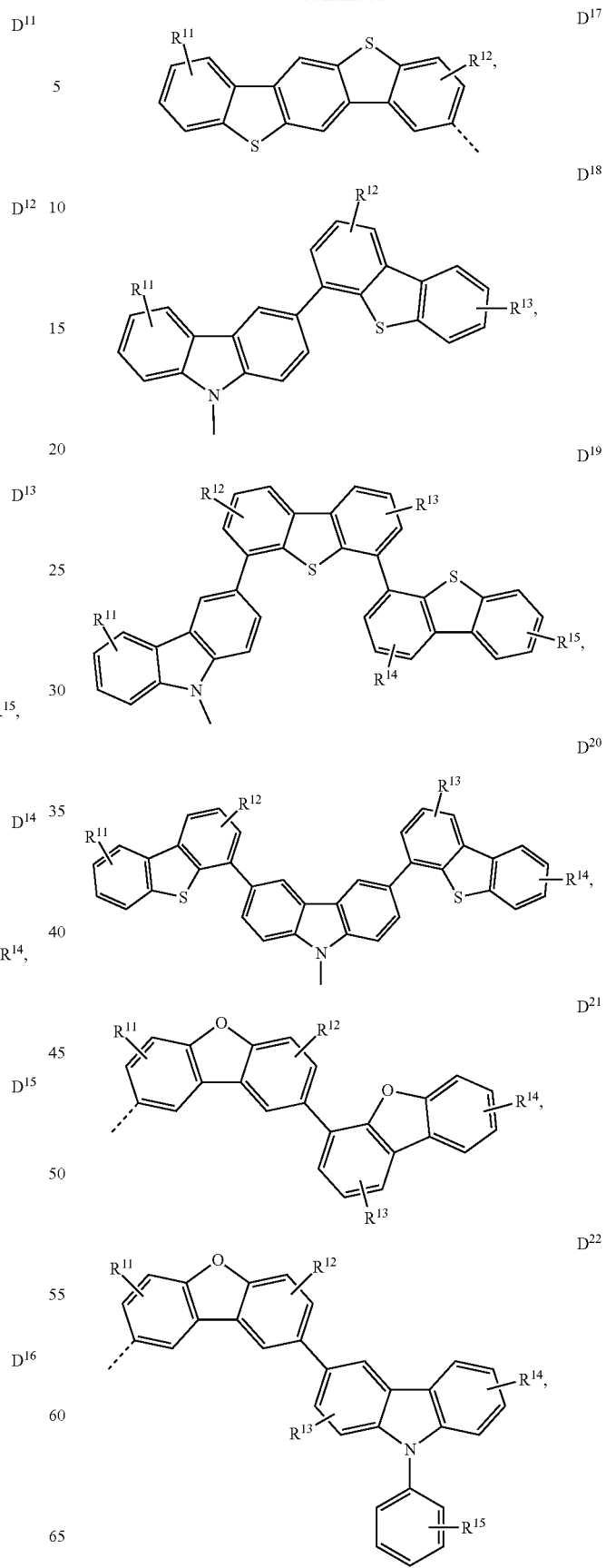

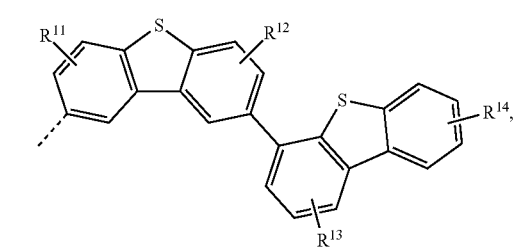
D23
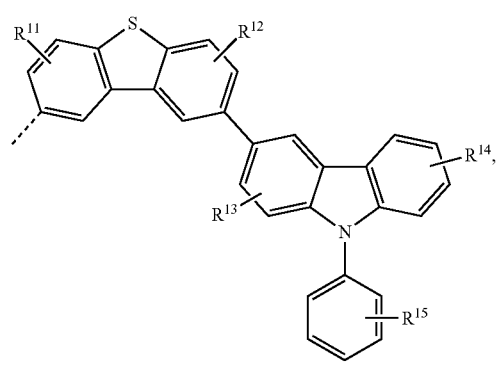
D24
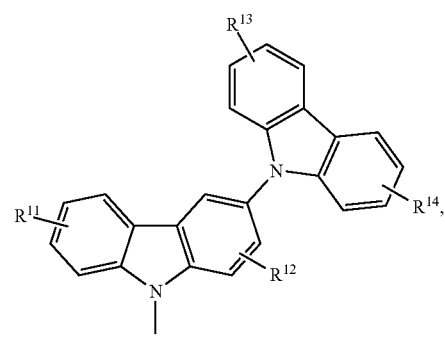
D25
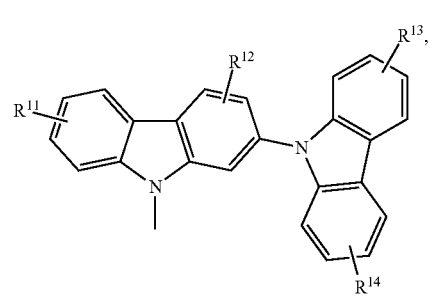
D26
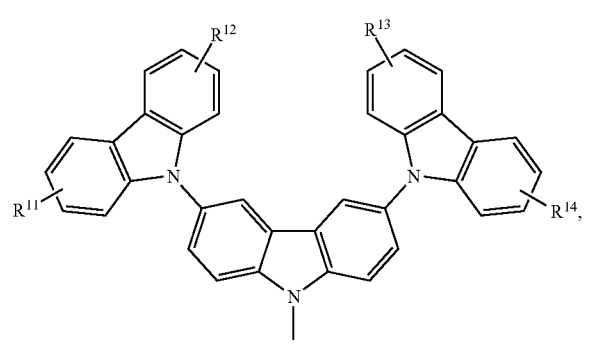
D27
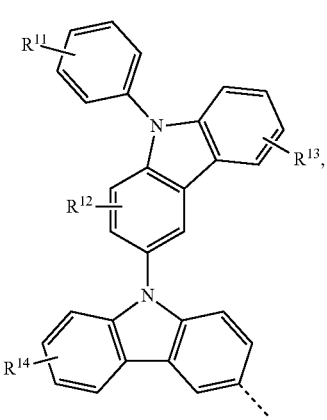
D28
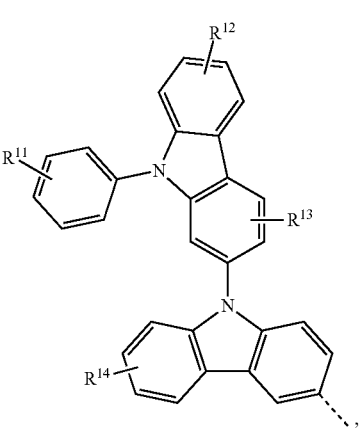
D29
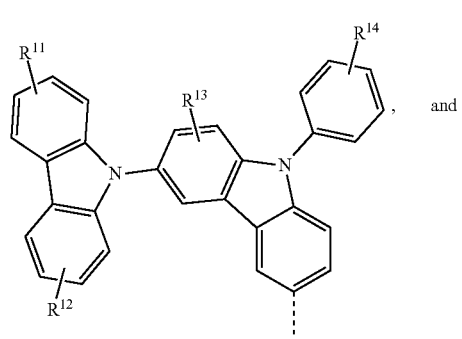
D30, and
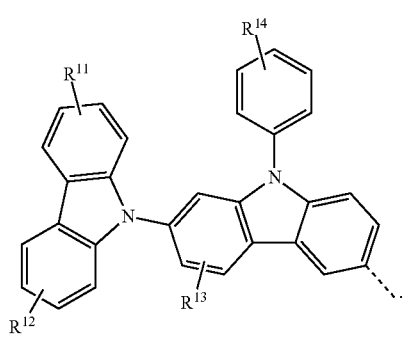
D31

In one aspect, the compound has the formula:
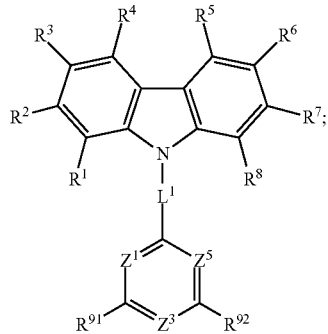
and where R⁹¹ and R⁹² are independently selected from aryl or heteroaryl, and can be further substituted.
In one aspect, the compound is selected from the group consisting of:
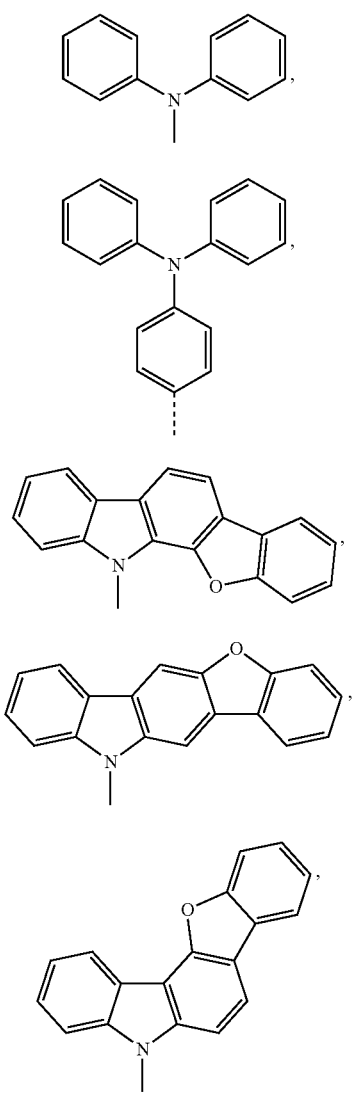
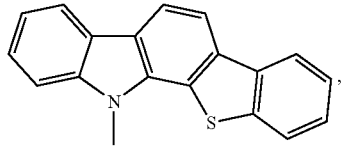
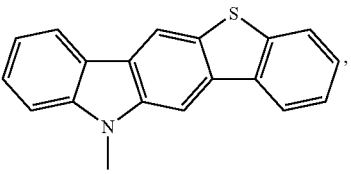
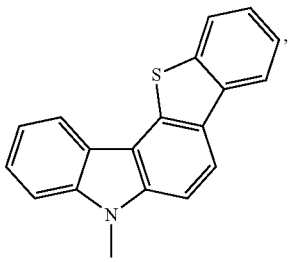
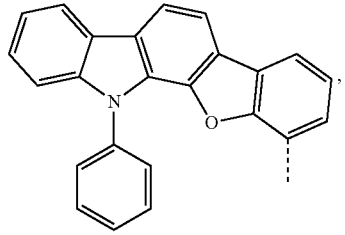
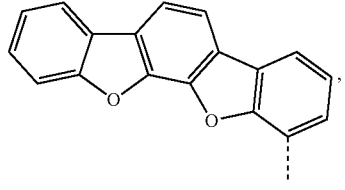
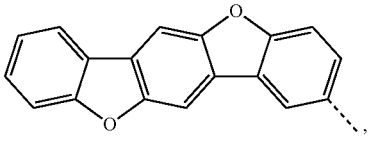
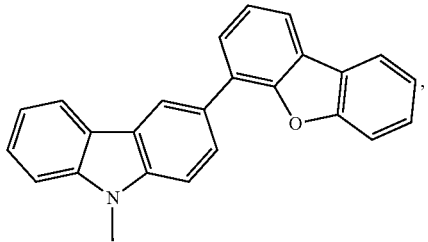

-continued
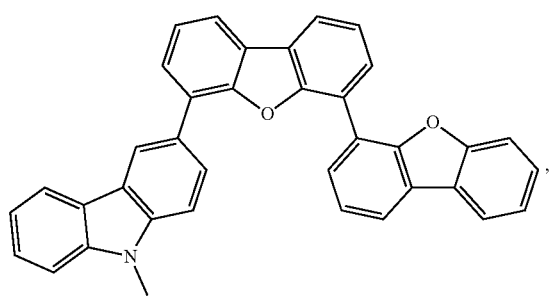
D¹¹³
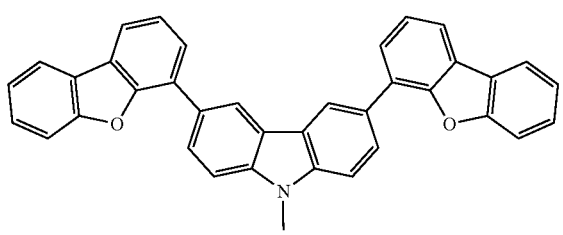
D¹¹⁴
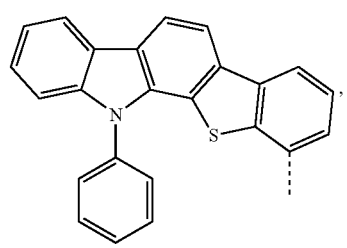
D¹¹⁵
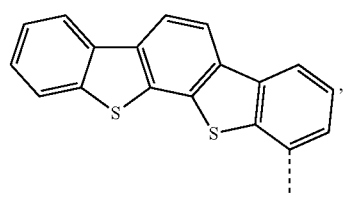
D¹¹⁶
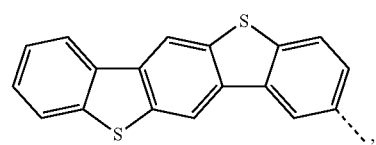
D¹¹⁷
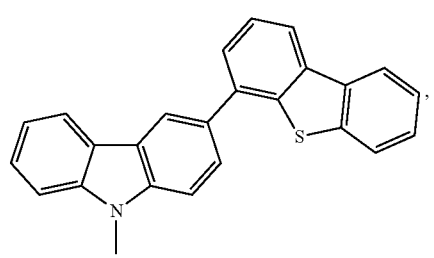
D¹¹⁸
-continued
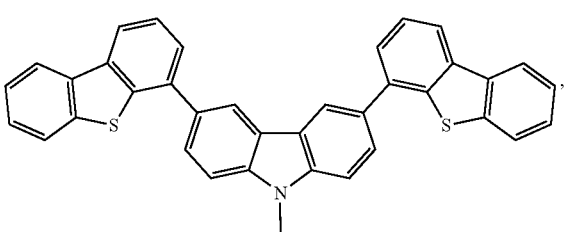
D¹¹⁹
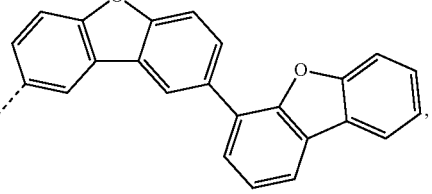
D¹²⁰
D¹²¹
D¹²²
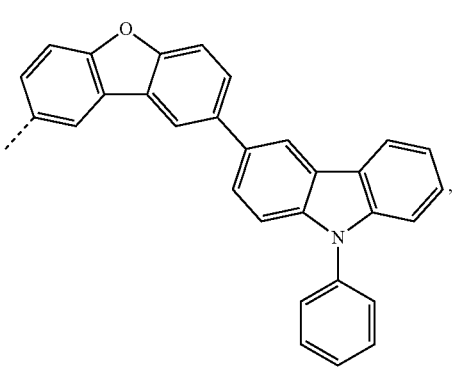
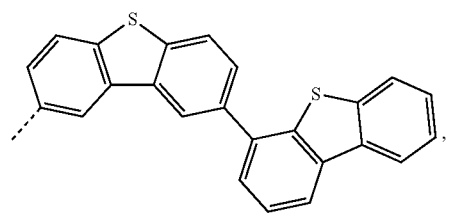
D¹²³

-continued

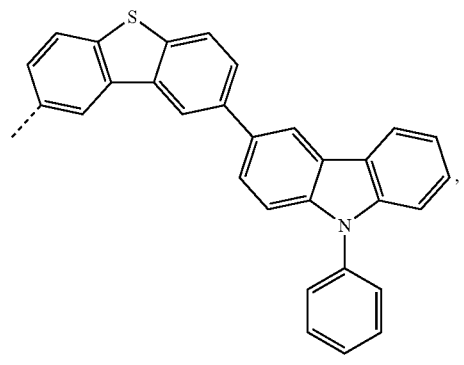
D[124]

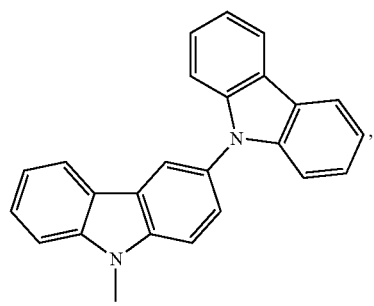
D[125]

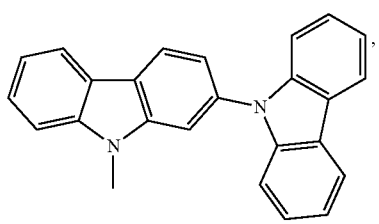
D[126]

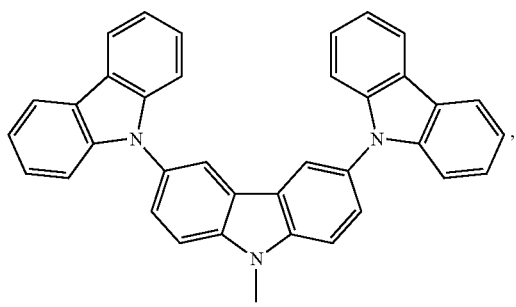
D[127]

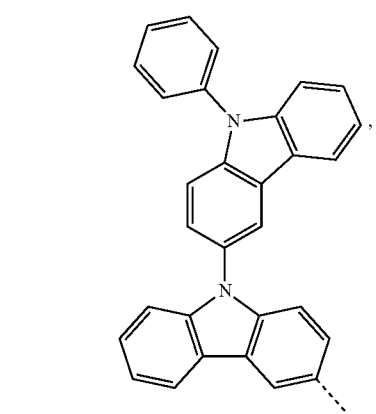
D[128]

-continued

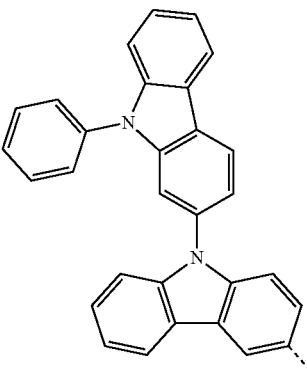
D[129], and

D[130]

In one aspect, the compound is selected from the group consisting of: Compounds 1, 5, 13, 9, 33, 37, 41, 45, 57, 61, 69, 65, 77, 73, 97, 101, 105, 121, 125, 109, 133, 129, 141, 137, 161, 165, 169, 173, 185, 189, 197, 193, 205, 201, 225, 229, 233, 237, 249, 253, 261, 257, 269, 265, 289, 293, 297, 301, 313, 317, 325, 321, 333, 329, 353, 357, 361, 365, 377, 381, 389, 385, 393, 417, 421, 425, 429, 441, 445, 453, 449, 461, 457, 481, 485, 489, 493, 505, 509, 517, 513, 525, 521, 545, 549, 553, 557, 569, 573, 581, 577, 589, 585, 609, 613, 617, 621, 633, 637, 645, 641, 653, 649, 673, 677, 681, 685, 697, 701, 709, 705, 717, 713, 737, 741, 745, 749, 761, 765, 773, 769, 781, 777, 801, 805, 809, 813, 825, 829, 837, 833, 845, 841, 865, 869, 873, 877, 889, 873, 877, 889, 893, 1029, 1025, 1037, 1033, 1057, 1061, 1065, 1069, 1081, 1085, 1093, 1089, 1111, 1097, 1121, 1125, 1129, 1133, 1145, 1149, 1157, 1153, 1165, 1161, 1185, 1189, 1193, 1197, 1209, 1213, 1221, 1217, 1229, 1225, 1249, 1253, 1257, 1261, 1173, 1177, 1477, 1473, 1485, 1481, 1505, 1509, 1513, 1517, 1529, 1533, 1605, 1601, 1613, 1609, 1633, 1637, 1641, 1645, 1657, 1661, 1669, 1665, 1677, 1673, 1697, 1701, 1705, 1709, 1721, 1725, 1797, 1793, 1805, 1801, 1833, 1837, 1853, 1849, 1861, 1857, 1869, 1865, 1889, 1893, 1897, 1901, 1913, 1917, 1989, 1985, 1997, 1993, 2017, 2021, 2025, 2029, 2041, and 2045.

In one aspect, a first device comprising a first organic light emitting device, further comprising an anode, a cathode; and an emissive layer, disposed between the anode and the cathode, wherein the emissive layer comprises a first emitting compound having the formula:

Formula I

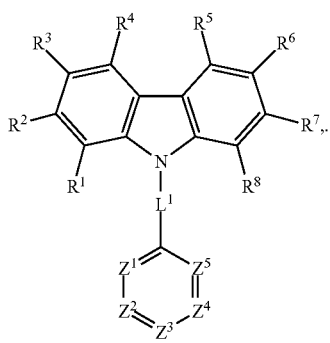

$Z^1$, $Z^2$, $Z^3$, $Z^4$ and $Z^5$ are each independently selected from group consisting of $CR^9$ and N, and any adjacent $R^9$ are optionally joined to form a fused ring. At least one of $Z^1$, $Z^2$, $Z^3$, $Z^4$ and $Z^5$ is N.

$L^1$ is selected from the group consisting of:

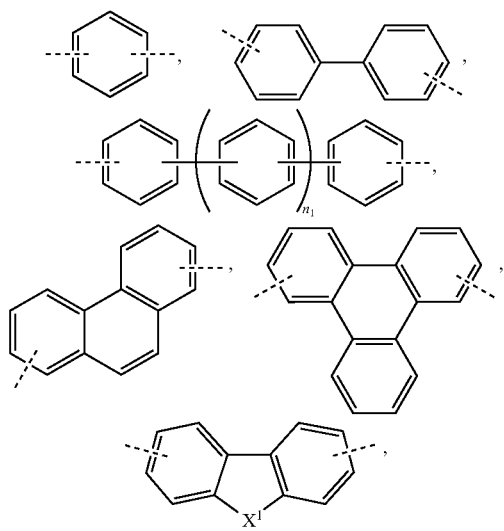

and combinations thereof;
where $X^1$ is O, S, or CRR' and R, R' are optionally joined to form a ring. $n_1$ is an integer from 1 to 20, and $L^1$ can be further substituted by a substituent selected from the group consisting of alkyl, aryl, and heteroaryl. At least one of $R^1$, $R^2$, $R^3$, $R^4$, $R^5$, $R^6$, $R^7$, and $R^8$ comprises an electron donor group.

Any two adjacent $R^1$, $R^2$, $R^3$, $R^4$, $R^5$, $R^6$, $R^7$, and $R^8$ are not joined to form a ring. $R^1$, $R^2$, $R^3$, $R^4$, $R^5$, $R^6$, $R^7$, and $R^8$ do not contain an electron acceptor group, and $R^9$ does not contain an electron donor group.

$R^1$, $R^2$, $R^3$, $R^4$, $R^5$, $R^6$, $R^7$, and $R^8$ are independently selected from the group consisting of hydrogen, deuterium, alkyl, cycloalkyl, arylalkyl, alkoxy, aryloxy, amino, silyl, alkenyl, cycloalkenyl, heteroalkenyl, alkynyl, aryl, heteroaryl, and combinations thereof; and $R^9$, R, and R' are independently selected from the group consisting of hydrogen, deuterium, alkyl, cycloalkyl, heteroalkyl, arylalkyl, silyl, alkenyl, cycloalkenyl, heteroalkenyl, alkynyl, aryl, heteroaryl, and combinations thereof.

In one aspect, the electron donor group comprises at least one chemical group selected from the group consisting of amino, indole, carbazole, benzothiohpene, benzofuran, benzoselenophene, dibenzothiophene, dibenzofuran, dibenzoselenophene, and combinations thereof.

In one aspect, the electron donor group comprises at least one chemical group selected from the group consisting of:

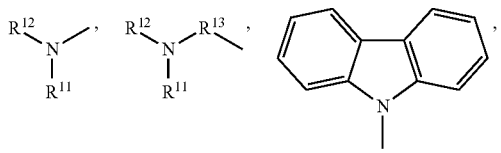

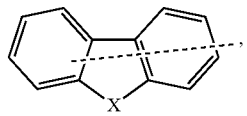

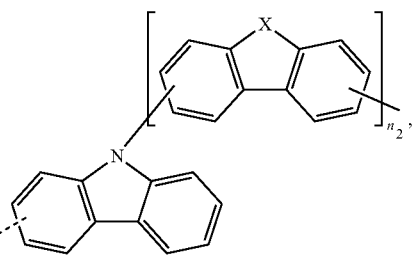

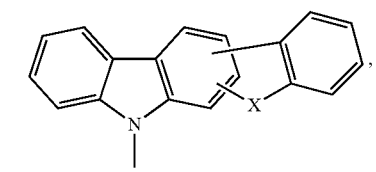

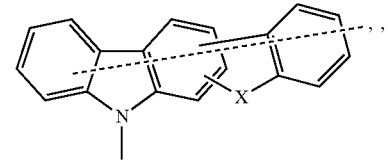

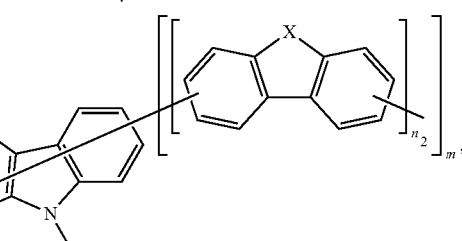

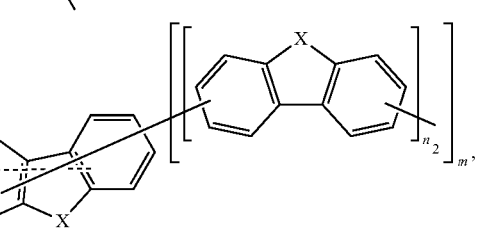

-continued
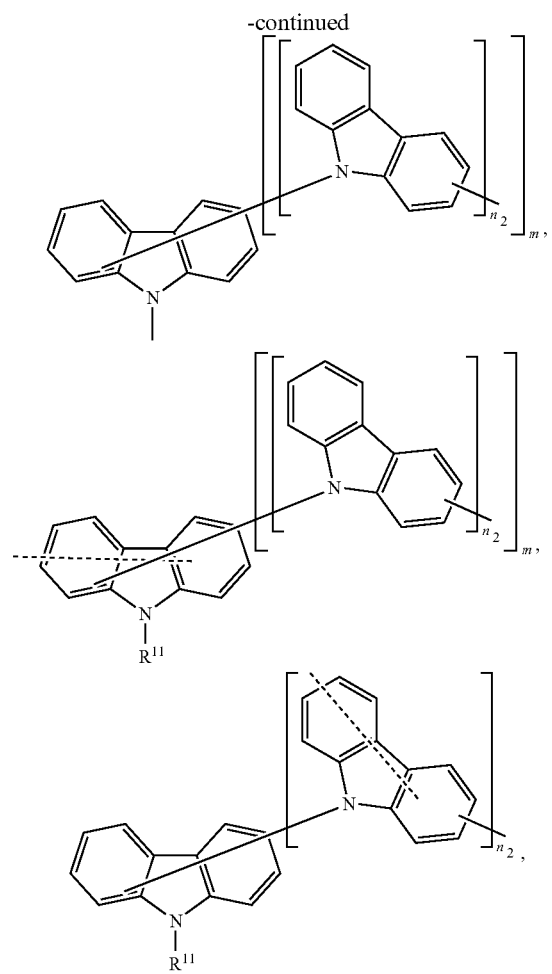
where X and Y are selected from the group consisting of O, S, NR$^{14}$, m is an integer from 1 to 20, $n_2$ is an integer from 1 to 20, and where R$^{11}$, R$^{12}$, R$^{13}$ and R$^{14}$ are selected from the group consisting of aryl and heteroaryl.
In one aspect, the donor group is selected from the group consisting of:
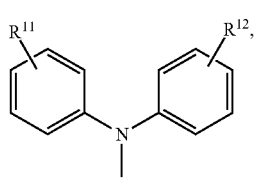
D$^1$
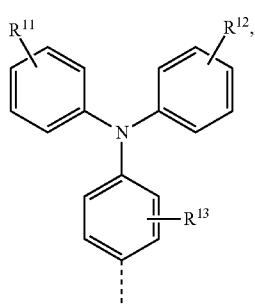
D$^2$
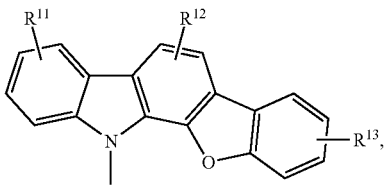
D$^3$
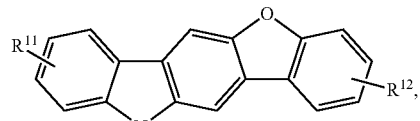
D$^4$
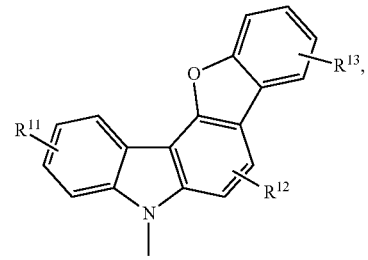
D$^5$
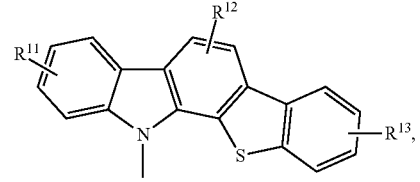
D$^6$
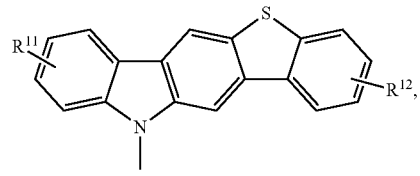
D$^7$
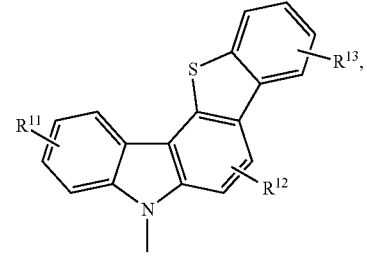
D$^8$
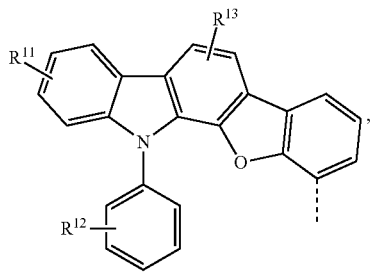
D$^9$

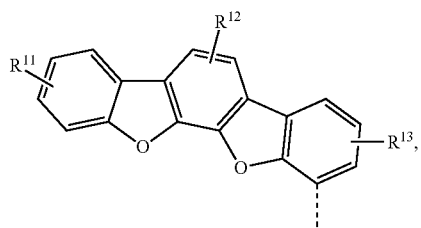
D¹⁰
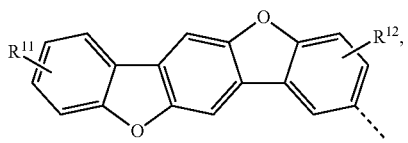
D¹¹
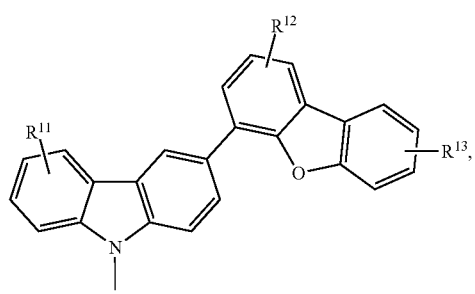
D¹²
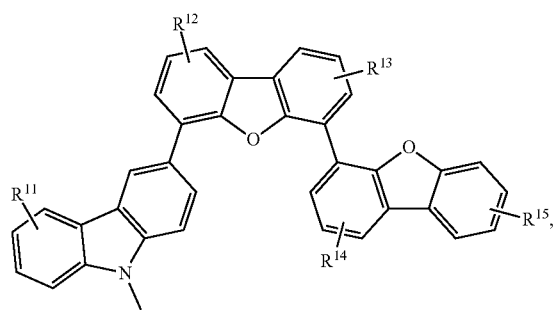
D¹³
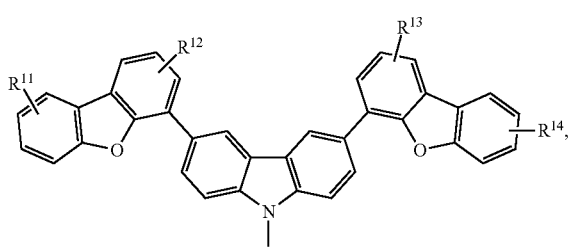
D¹⁴
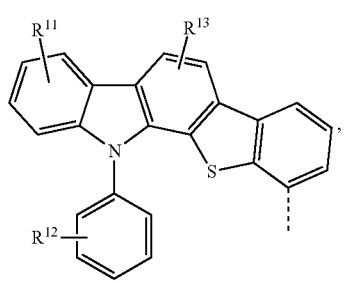
D¹⁵
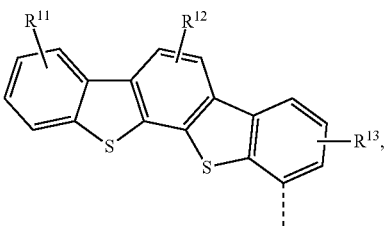
D¹⁶
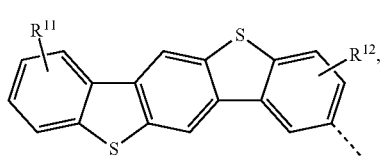
D¹⁷
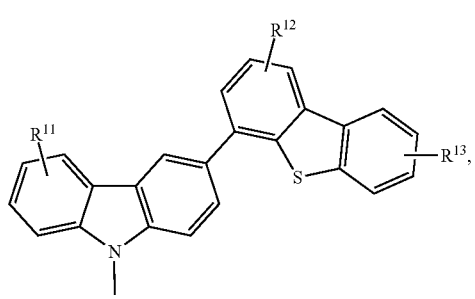
D¹⁸
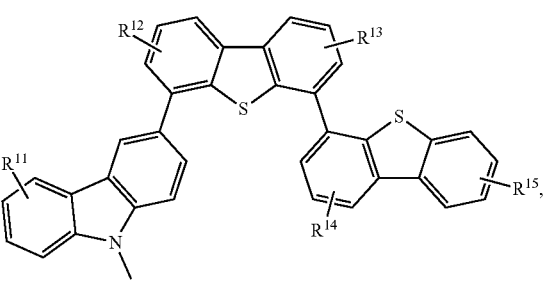
D¹⁹
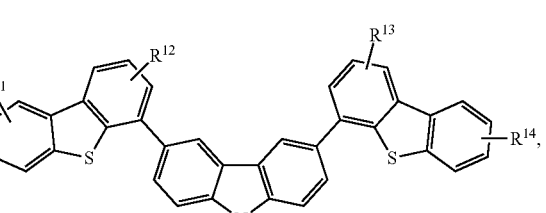
D²⁰
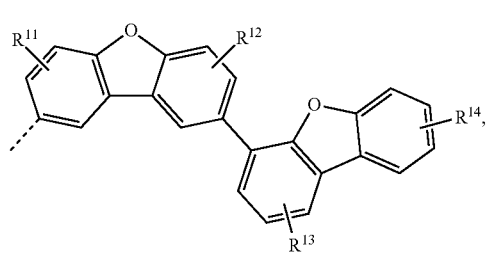
D²¹

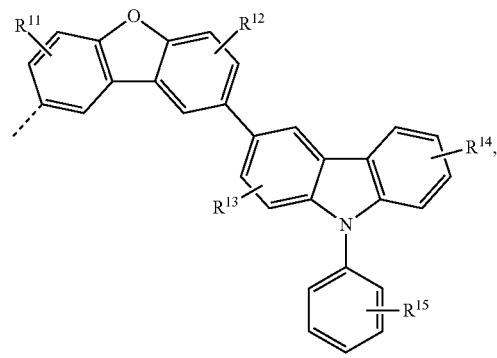
D22
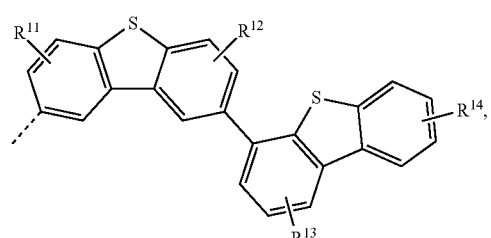
D23
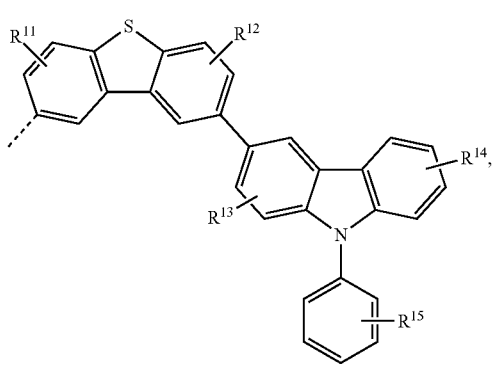
D24
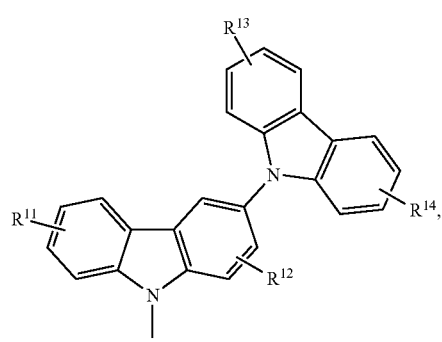
D25
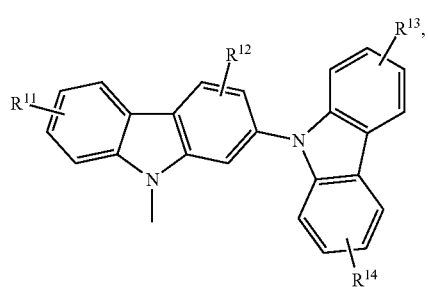
D26
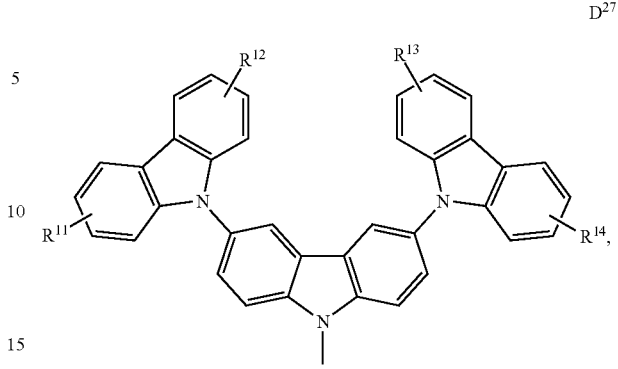
D27
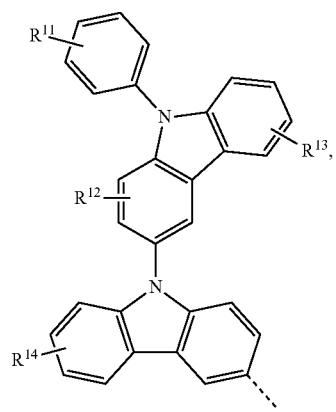
D28
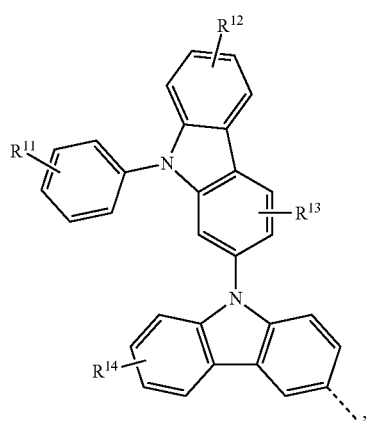
D29
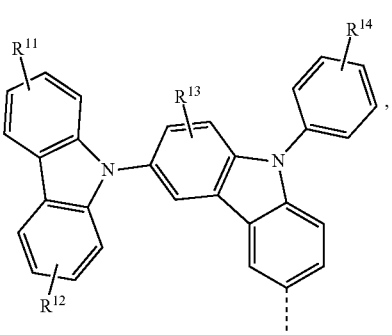
D30

-continued
D31 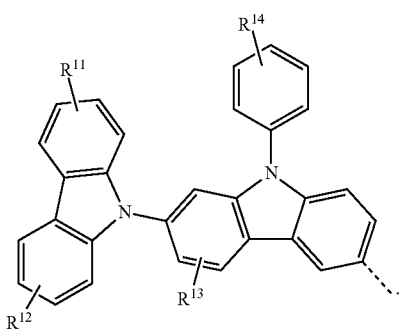
D32 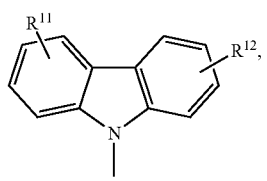
D33 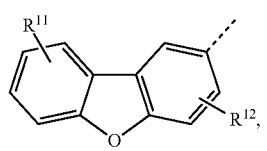
D34 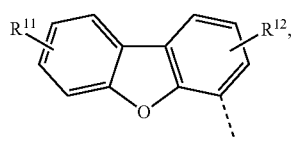
D35 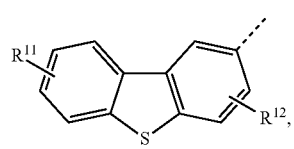
D36 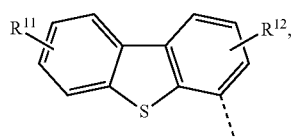
D37 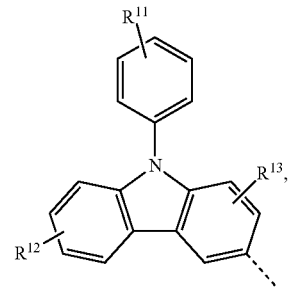
D38 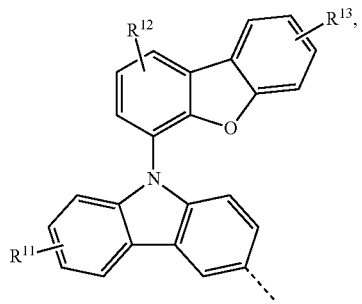
D39 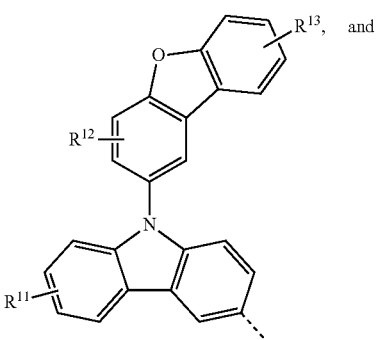
D40 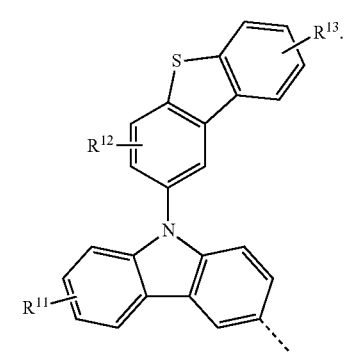
In one aspect, the first emitting compound having the formula:
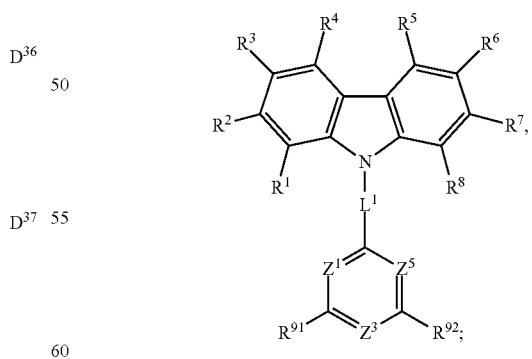
and
wherein $R^{91}$ and $R^{92}$ are independently selected from aryl or heteroaryl, and can be further substituted.
In one aspect, the electron donor group has a formula selected from the group consisting of:

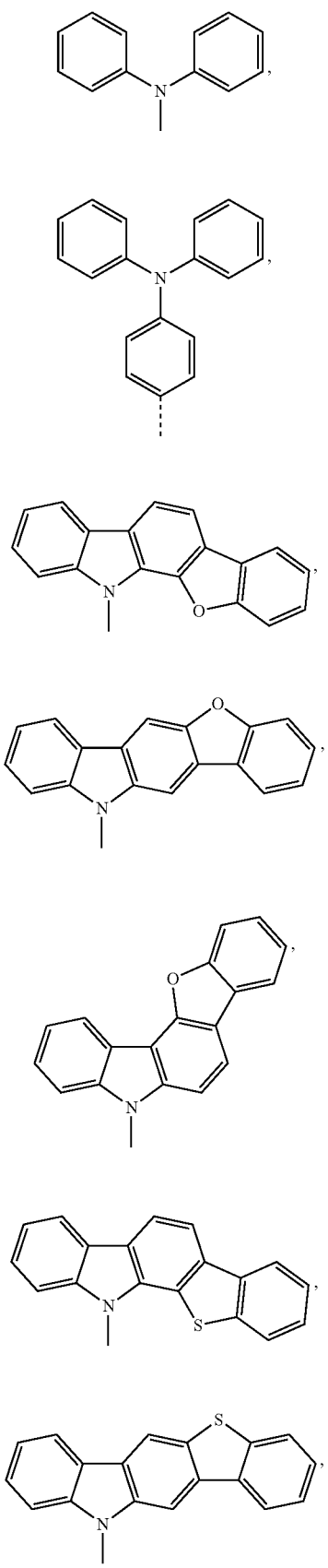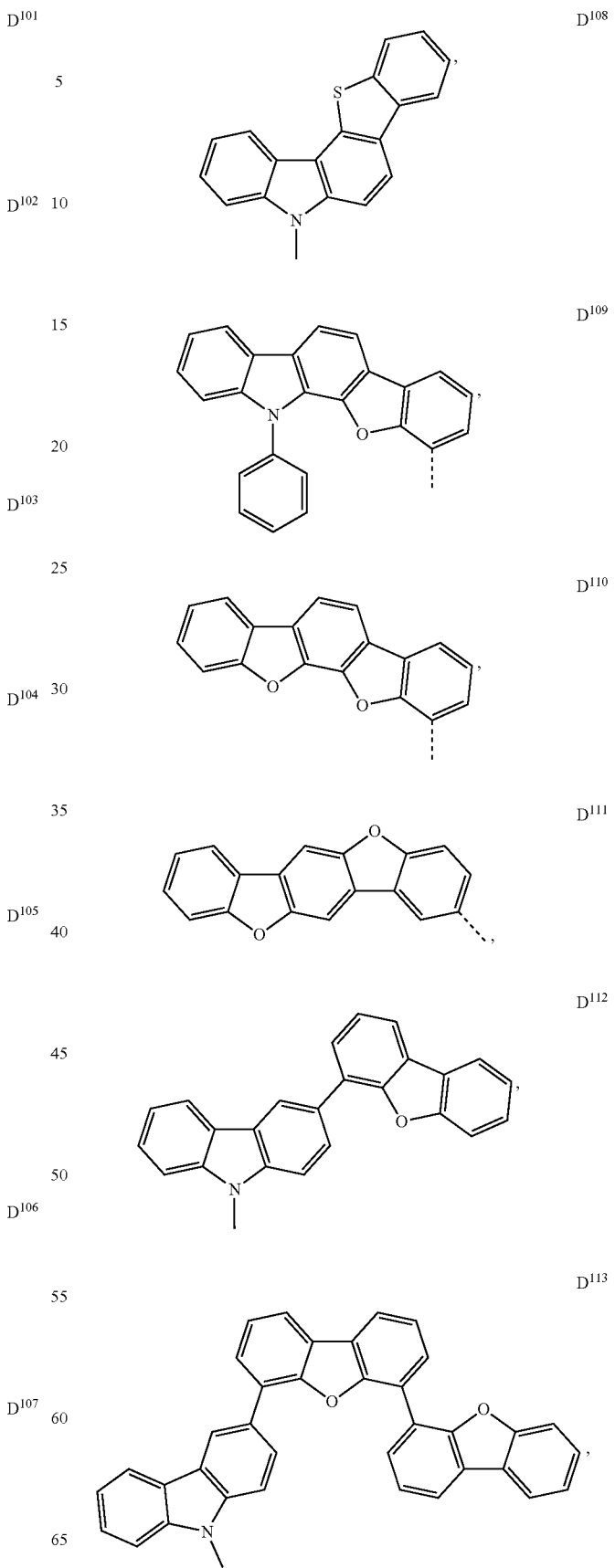

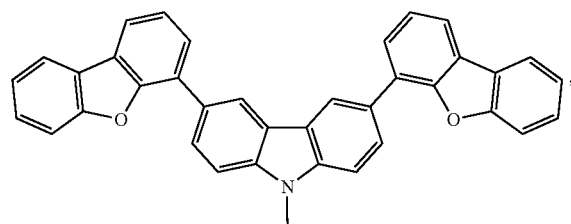
D114
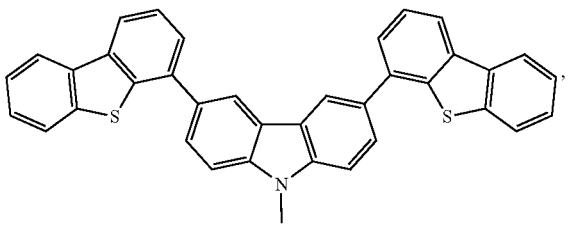
D120
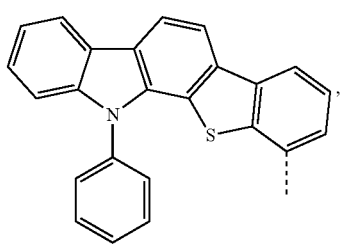
D115
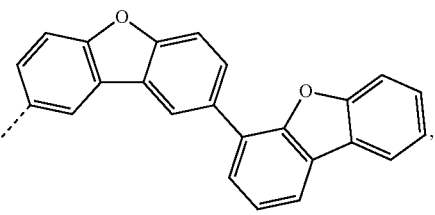
D121
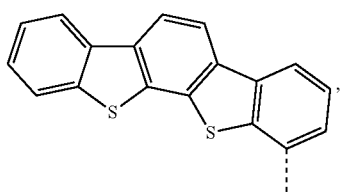
D116
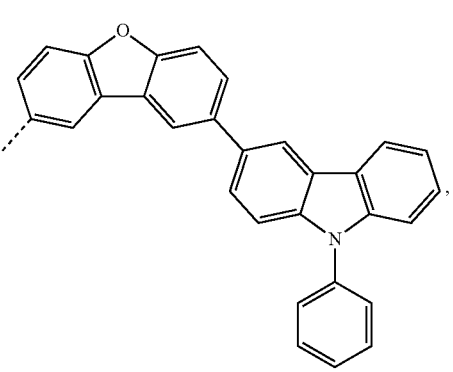
D122
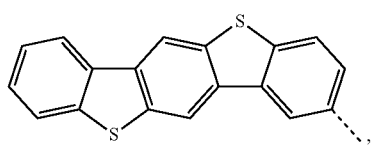
D117
D123
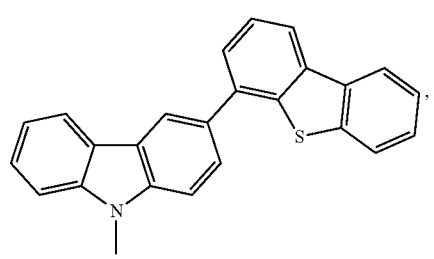
D118
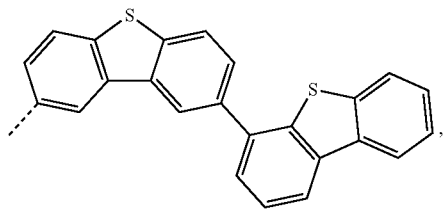
D124
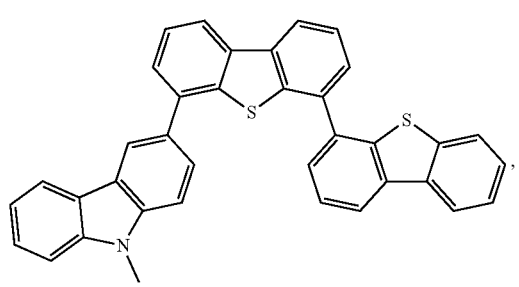
D119

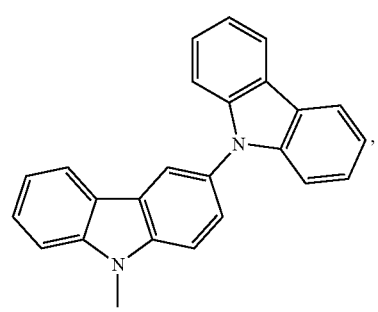
D¹²⁵
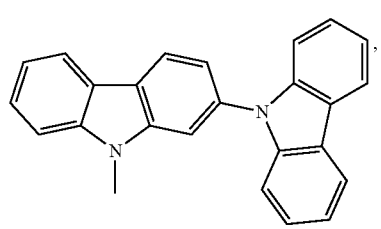
D¹²⁶
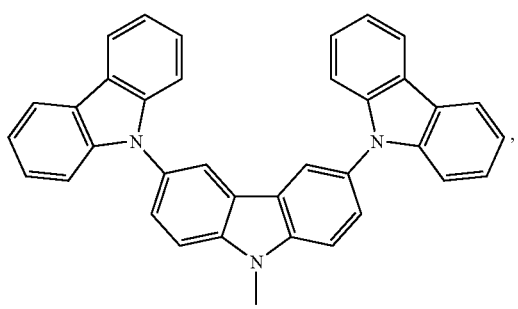
D¹²⁷
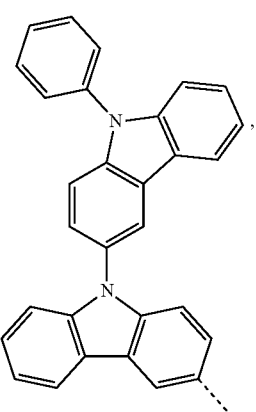
D¹²⁸
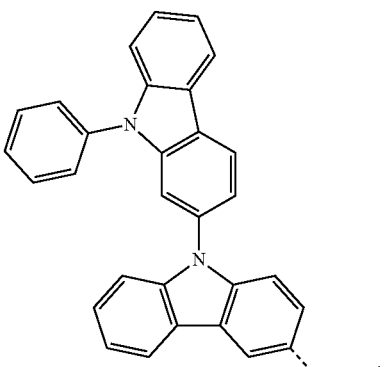
D¹²⁹
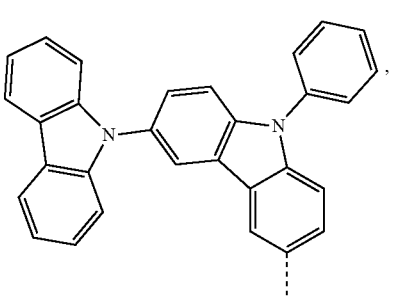
, and
D¹³⁰
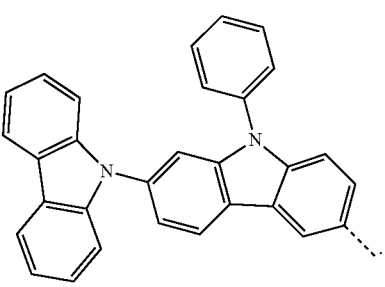
D¹³¹
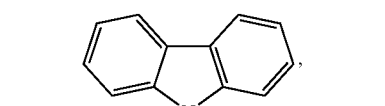
D¹³²
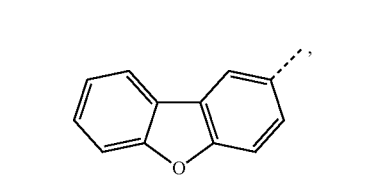
D¹³³
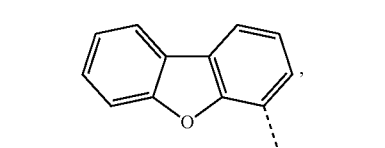
D¹³⁴
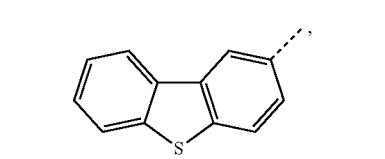
D¹³⁵

-continued

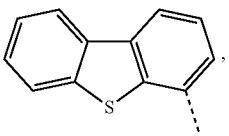
D¹³⁶

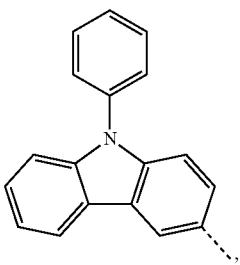
D¹³⁷

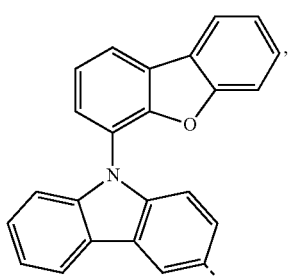
D¹³⁸

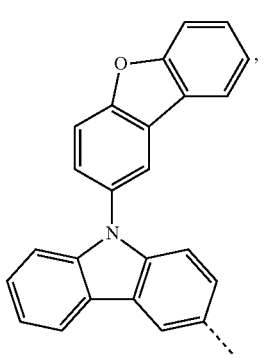
D¹³⁹ and

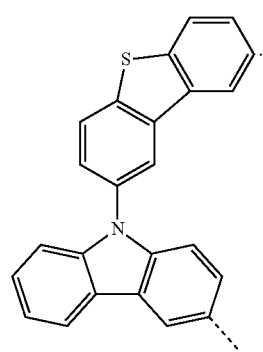
D¹⁴⁰

In one aspect, the first emitting compound has a formula selected from the group consisting of: Compounds 1, 5, 13, 9, 33, 37, 41, 45, 57, 61, 69, 65, 77, 73, 97, 101, 105, 121, 125, 109, 133, 129, 141, 137, 161, 165, 169, 173, 185, 189, 197, 193, 205, 201, 225, 229, 233, 237, 249, 253, 261, 257, 269, 265, 289, 293, 297, 301, 313, 317, 325, 321, 333, 329, 353, 357, 361, 365, 377, 381, 389, 385, 393, 417, 421, 425, 429, 441, 445, 453, 449, 461, 457, 481, 485, 489, 493, 505, 509, 517, 513, 525, 521, 545, 549, 553, 557, 569, 573, 581, 577, 589, 585, 609, 613, 617, 621, 633, 637, 645, 641, 653, 649, 673, 677, 681, 685, 697, 701, 709, 705, 717, 713, 737, 741, 745, 749, 761, 765, 773, 769, 781, 777, 801, 805, 809, 813, 825, 829, 837, 833, 845, 841, 865, 869, 873, 877, 889, 873, 877, 889, 893, 1029, 1025, 1037, 1033, 1057, 1061, 1065, 1069, 1081, 1085, 1093, 1089, 1111, 1097, 1121, 1125, 1129, 1133, 1145, 1149, 1157, 1153, 1165, 1161, 1185, 1189, 1193, 1197, 1209, 1213, 1221, 1217, 1229, 1225, 1249, 1253, 1257, 1261, 1173, 1177, 1477, 1473, 1485, 1481, 1505, 1509, 1513, 1517, 1529, 1533, 1605, 1601, 1613, 1609, 1633, 1637, 1641, 1645, 1657, 1661, 1669, 1665, 1677, 1673, 1697, 1701, 1705, 1709, 1721, 1725, 1797, 1793, 1805, 1801, 1833, 1837, 1853, 1849, 1861, 1857, 1869, 1865, 1889, 1893, 1897, 1901, 1913, 1917, 1989, 1985, 1997, 1993, 2017, 2021, 2025, 2029, 2041, 2045, 2117, 2113, 2125, 2121, 2145, 2149, 2153, 2157, 2169, 2173, 2181, 2177, 2189, 2185, 2209, 2213, 2217, 2221, 2233, 2237, 2245, 2241, 2253, 2249, 2273, 2277, 2281, 2285, 2297, 2301, 2373, 2369, 2381, 2277, 2401, 2405, 2409, 2413, 2425, 2429, 2503, 2497, 2511, 2507, 2529, 2533, 2537, 2541, 2553, 2557, 2629, 2625, 2637, 2633, 2657, 2661, 2665, 2669, 2681, 2685, 2757, 2753, 2765, 2761, 2785, 2789, 2793, 2797, 2809, 2813, 2885, 2881, 2893, 2889, 2913, 2917, 2921, 2925, 2937, 2941, 2949, 2945, 2957, 2953, 2977, 2981, 2985, 2989, 3001, 3005, 3013, 3009, 3021, 3017, 3041, 3045, 3049, 3053, 3065, and 3069.

In one aspect, the first device emits a luminescent radiation at room temperature when a voltage is applied across the organic light emitting device, wherein the luminescent radiation comprises a delayed fluorescence process.

In one aspect, the emissive layer further comprises a first phosphorescent emitting material.

In one aspect, the emissive layer further comprises a second phosphorescent emitting material.

In one aspect, the emissive layer further comprises a host material.

In one aspect, the first device emits a white light at room temperature when a voltage is applied across the organic light emitting device.

In one aspect, the first emitting compound emits a blue light with a peak wavelength of about 400 nm to about 500 nm.

In one aspect, the emitting compound emits a yellow light with a peak wavelength of about 530 nm to about 580 nm.

In one aspect, the first device comprises a second organic light emitting device, wherein the second organic light emitting device is stacked on the first organic light emitting device.

In one aspect, the first device is a consumer product.

In one aspect, the first device is an organic light-emitting device.

In one aspect, the first device is a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
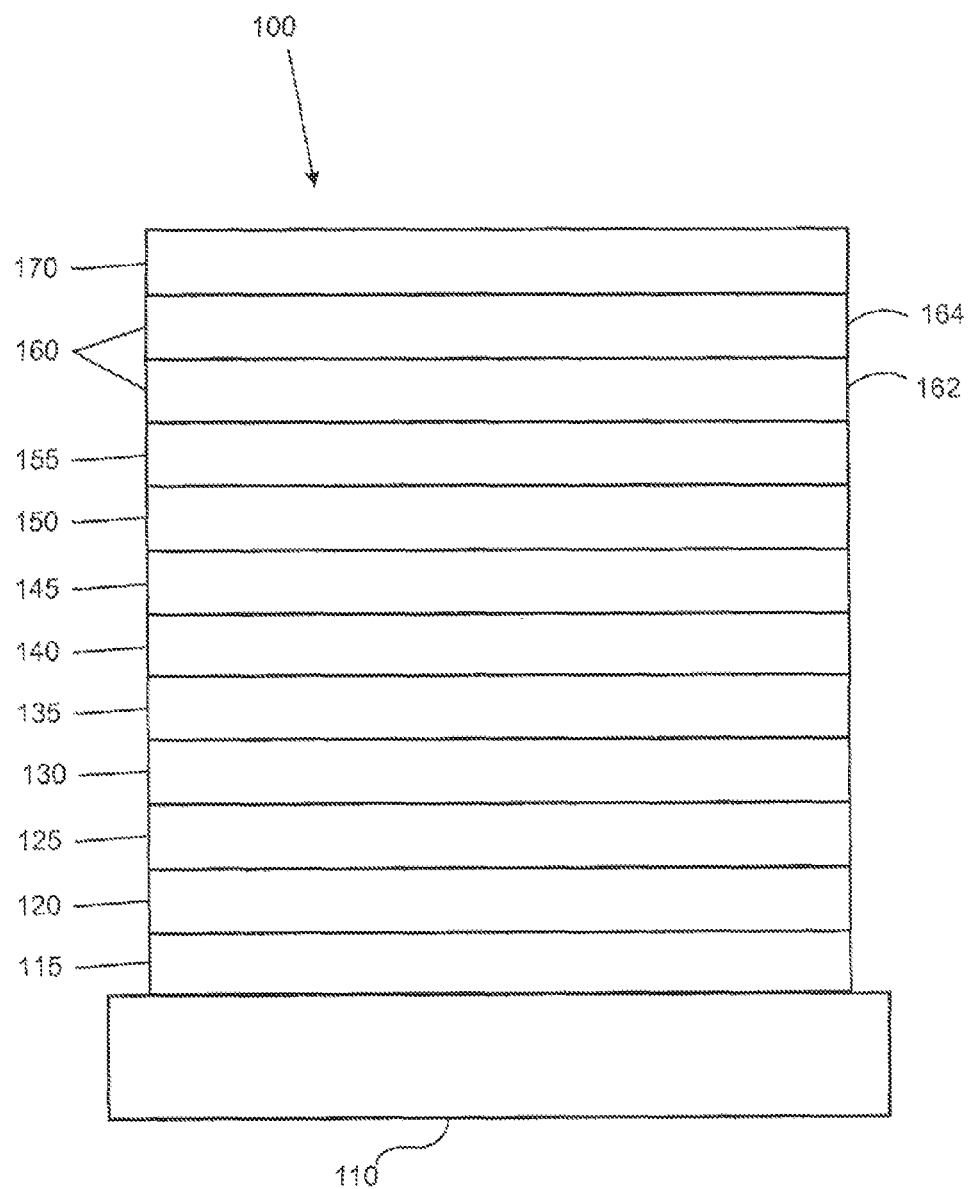
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
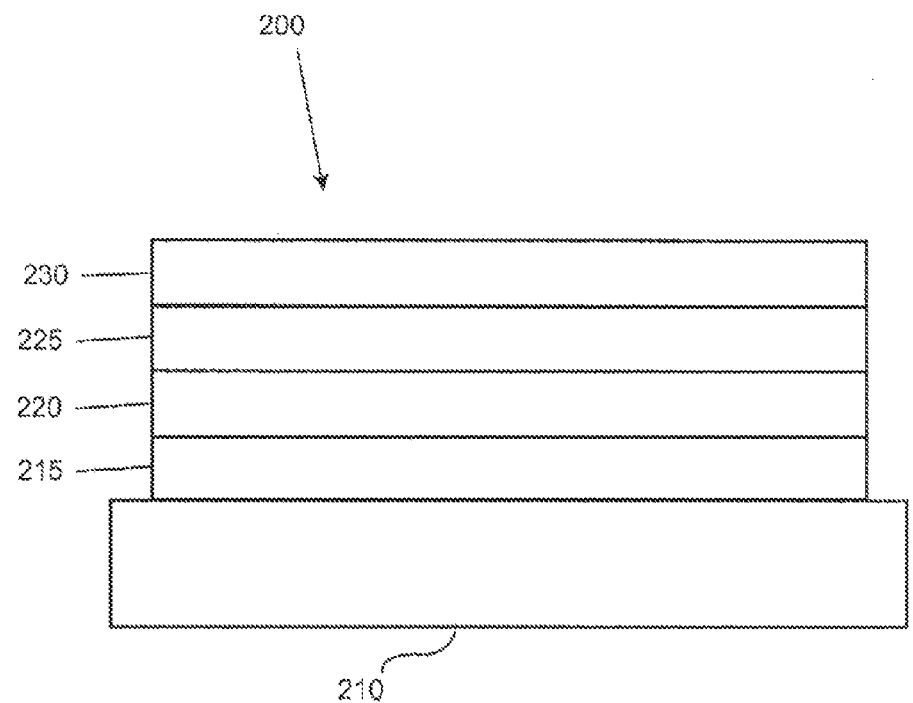
FIG. 2 shows an inverted organic light emitting device that does not have a separate electron transport layer.
Figure 3:
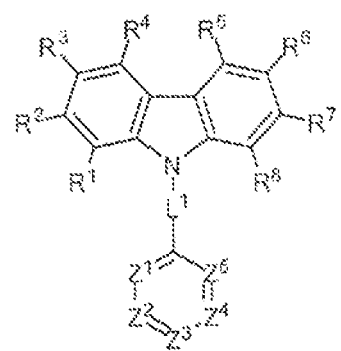
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the thermal population between the triplet states and the singlet excited states. Compounds that are capable of generating E-type delayed fluorescence are required to have very small singlet-triplet gaps. Thermal energy can activate the transition from the triplet state back to the singlet state. This type of delayed fluorescence is also known as thermally activated delayed fluorescence (TADF). A distinctive feature of TADF is that the delayed component increases as temperature rises due to the increased thermal energy. If the reverse intersystem crossing rate is fast enough to minimize the non-radiative decay from the triplet state, the fraction of back populated singlet excited states can potentially reach 75%. The total singlet fraction can be 100%, far exceeding the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

A compound having the formula:

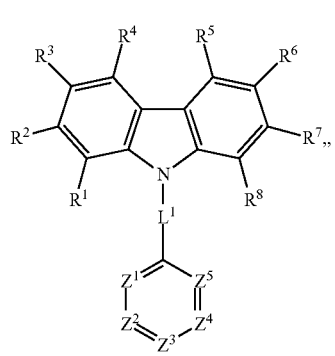

Formula I is provided.

$Z^1$, $Z^2$, $Z^3$, $Z^4$ and $Z^5$ are each independently selected from group consisting of $CR^9$ and N, and any adjacent $R^9$ are optionally joined to form a fused ring. At least one of $Z^1$, $Z^2$, $Z^3$, $Z^4$ and $Z^5$ is N.

$L^1$ is selected from the group consisting of:

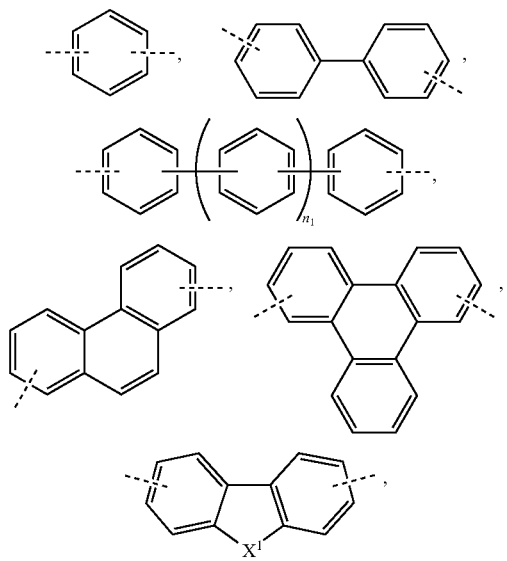

and combinations thereof;
where $X^1$ is O, S, or CRR' and R, R' are optionally joined to form a ring. $n_1$ is an integer from 1 to 20, and $L^1$ can be further substituted by a substituent selected from the group consisting of alkyl, aryl, and heteroaryl. At least one of R', $R^2$, $R^3$, $R^4$, $R^5$, $R^6$, $R^7$, and $R^8$ comprises at least one electron donor group selected from the group consisting of:

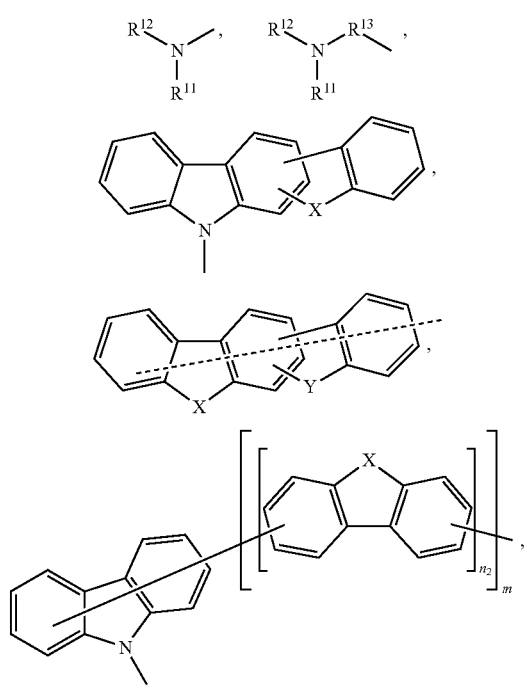

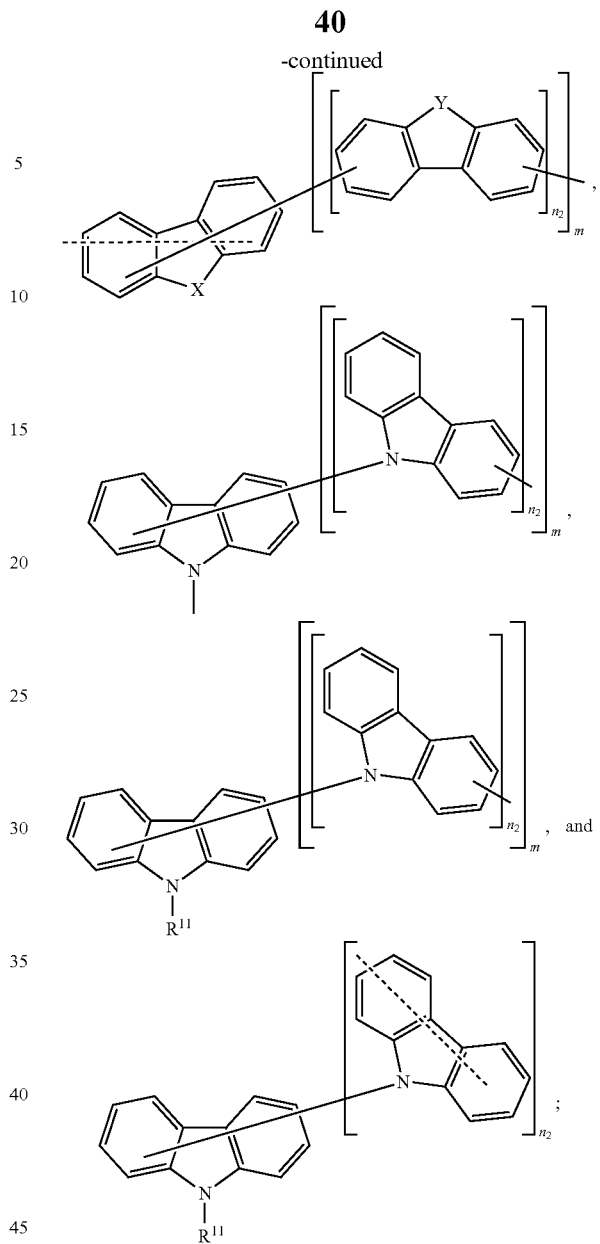

X and Y is selected from the group consisting of O, S, $NR^{14}$; and $R^{11}$, $R^{12}$, $R^{13}$ and $R^{14}$ are selected from the group consisting of aryl and heteroaryl. Any two adjacent $R^1$, $R^2$, $R^3$, $R^4$, $R^5$, $R^6$, $R^7$, and $R^8$ are not joined to form a ring, m is an integer from 1 to 20, and $n_2$ is an integer from 1 to 20. $R^1$, $R^2$, $R^3$, $R^4$, $R^5$, $R^6$, $R^7$, and $R^8$ do not contain an electron acceptor group, and $R^9$ does not contain an electron donor group.

$R^1$, $R^2$, $R^3$, $R^4$, $R^5$, $R^6$, $R^7$, and $R^8$ are independently selected from the group consisting of hydrogen, deuterium, alkyl, cycloalkyl, arylalkyl, alkoxy, aryloxy, amino, silyl, alkenyl, cycloalkenyl, heteroalkenyl, alkynyl, aryl, heteroaryl, and combinations thereof and $R^9$, R, and R' are independently selected from the group consisting of hydrogen, deuterium, alkyl, cycloalkyl, heteroalkyl, arylalkyl, silyl, alkenyl, cycloalkenyl, heteroalkenyl, alkynyl, aryl, heteroaryl, and combinations thereof.

In one embodiment, at least one of $R^1$, $R^2$, $R^3$, $R^4$, $R^5$, $R^6$, $R^7$, and $R^8$ comprises the electron donor group selected from the group consisting of:

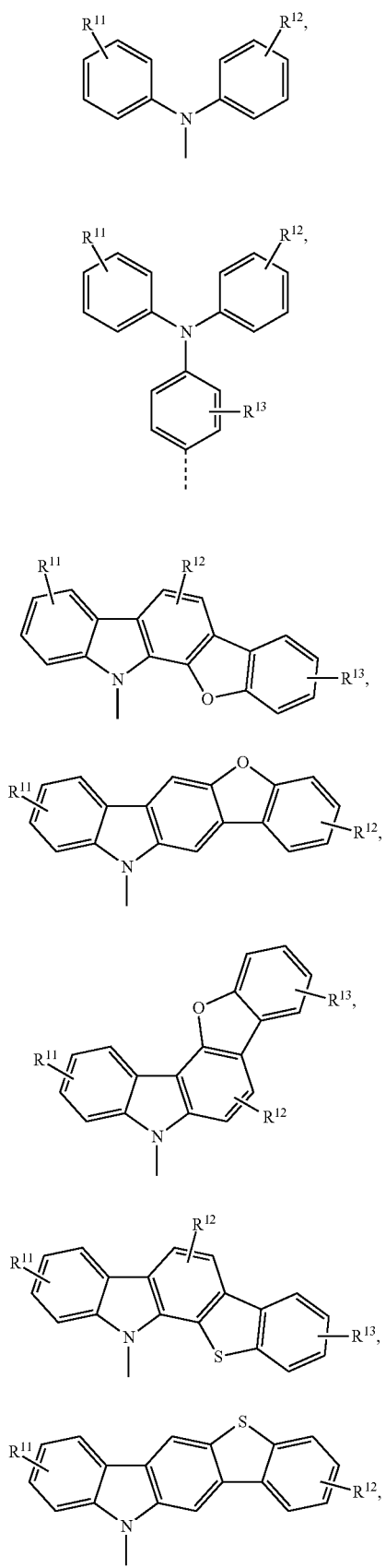
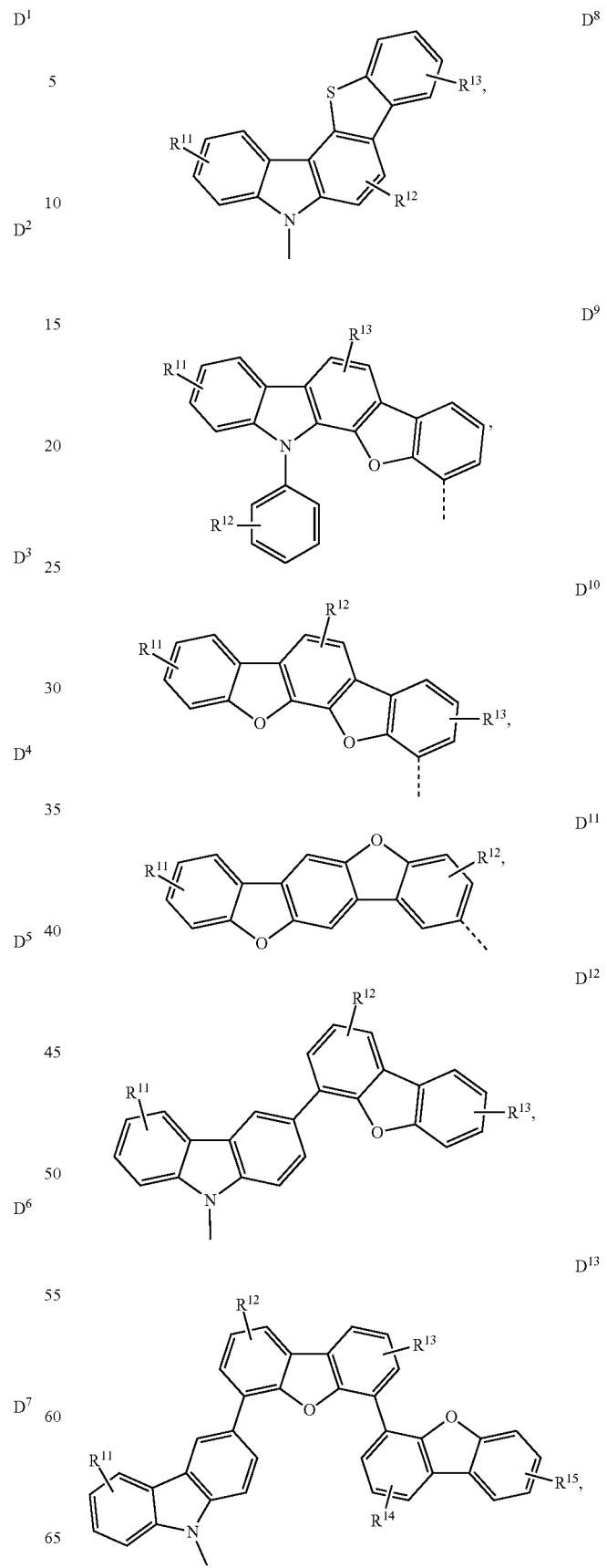

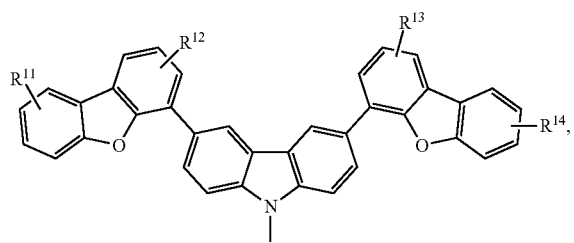
D14
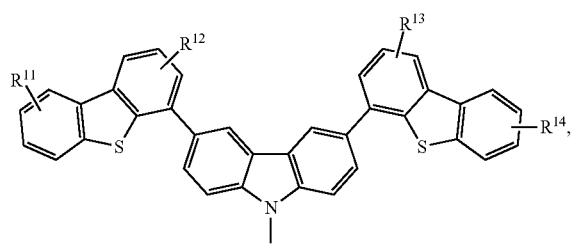
D20
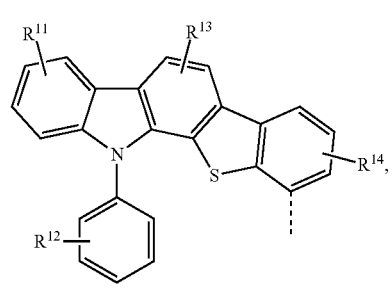
D15
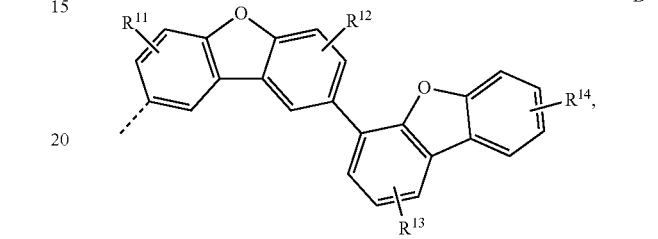
D21
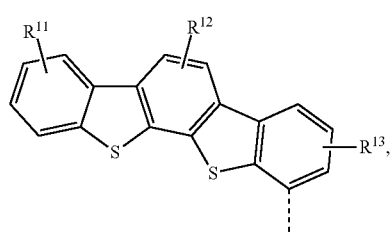
D16
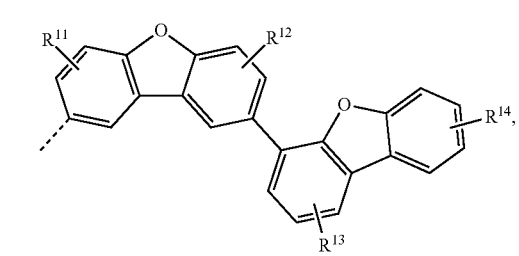
D22
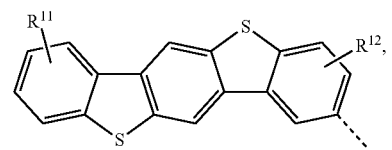
D17
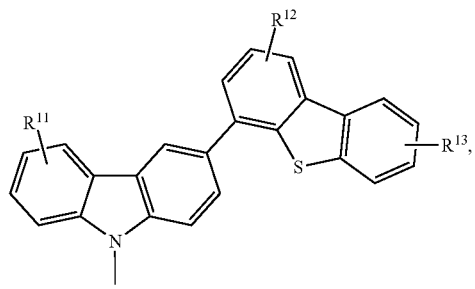
D18
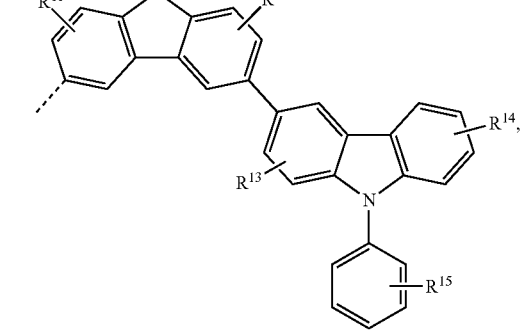
D23
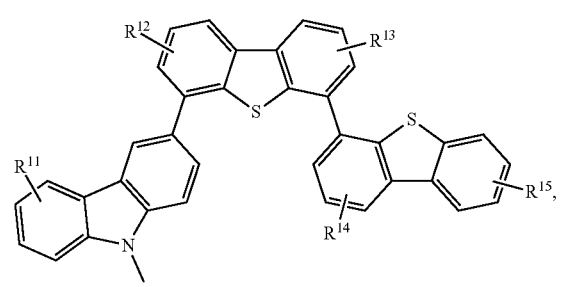
D19
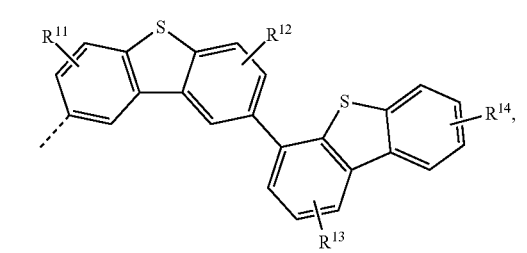
D24
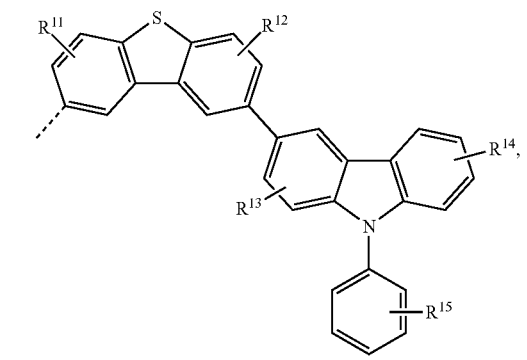

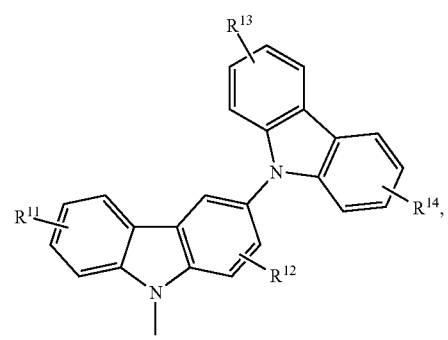D25
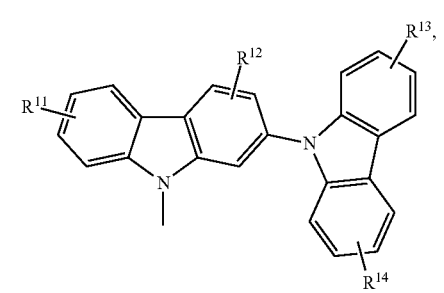D26
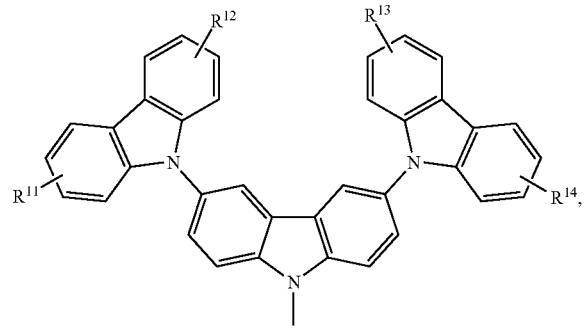D27
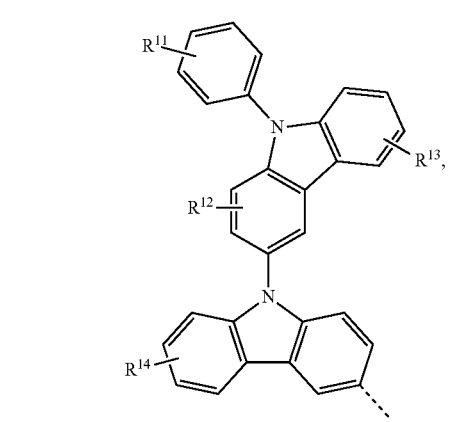D28
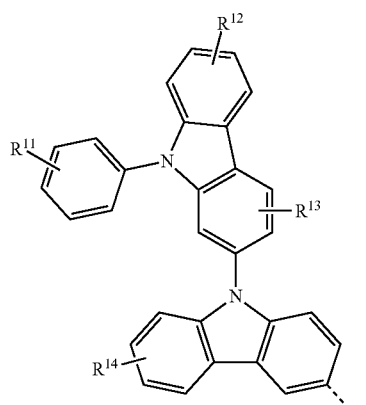D29
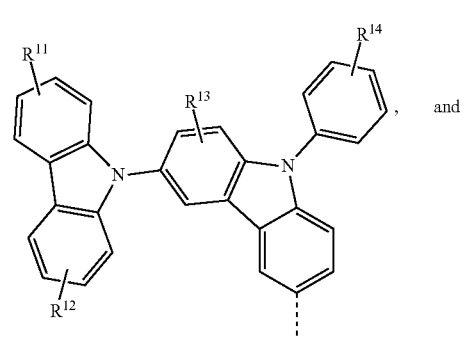D30
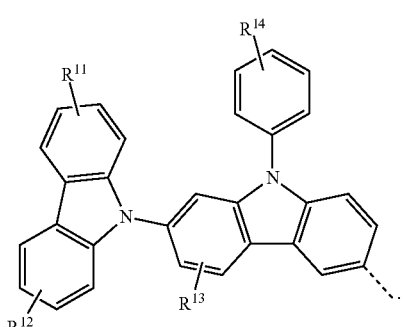D31
As used herein, the phrase "electron acceptor" means a fragment that can accept electron density from an aromatic system, and the phrase "electron donor" means a fragment that donates electron density into an aromatic system.
In one embodiment, the compound has the formula:
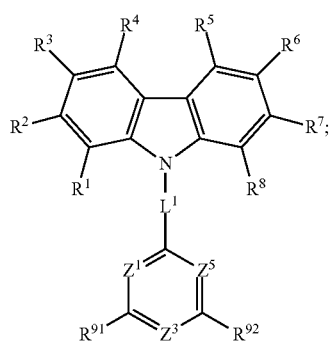

and where $R^{91}$ and $R^{92}$ are independently selected from aryl or heteroaryl, and can be further substituted.
In one embodiment, the compound is selected from the group consisting of:
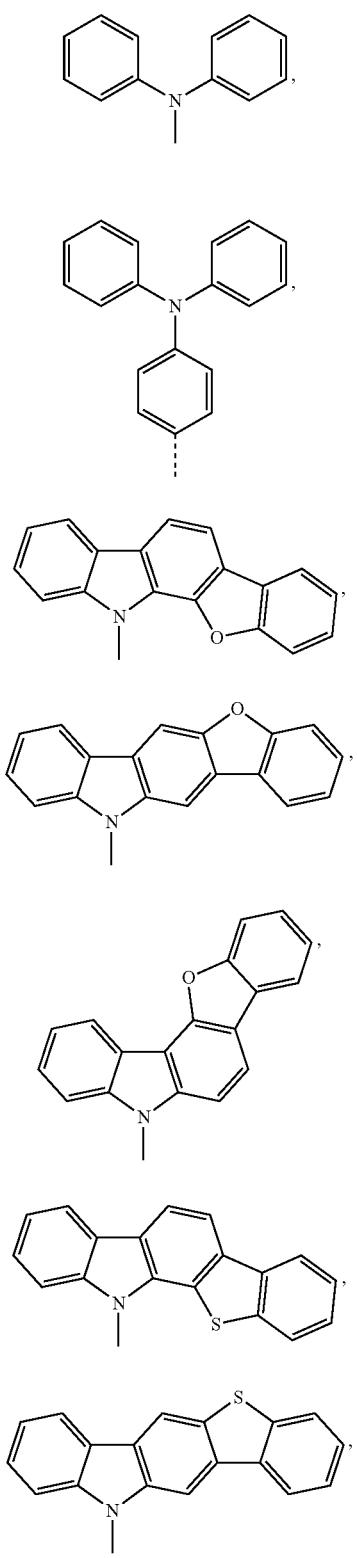
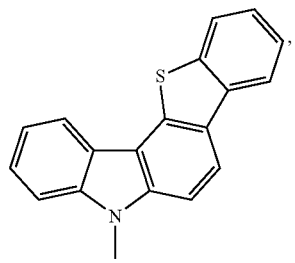
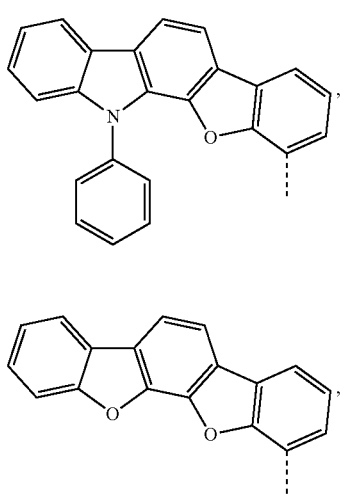
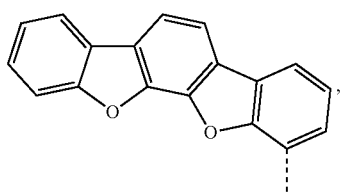
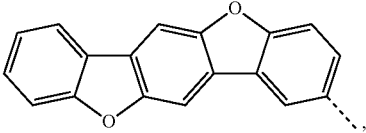
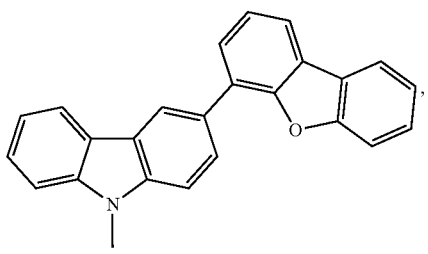
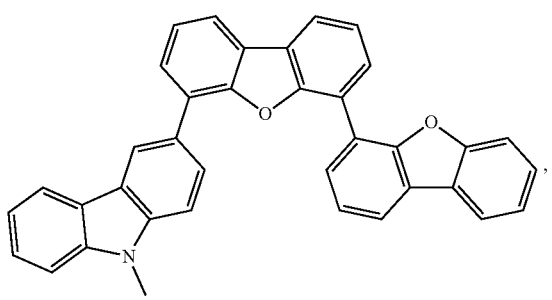

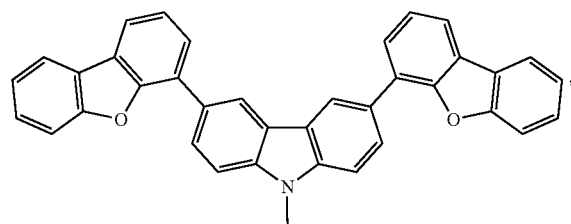
D114
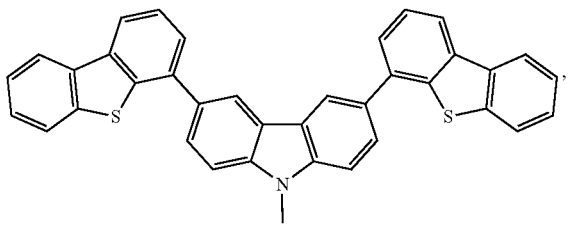
D120
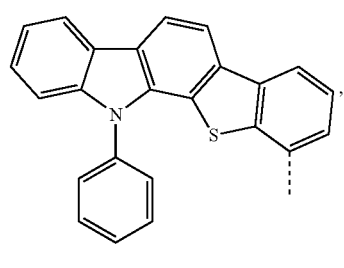
D115
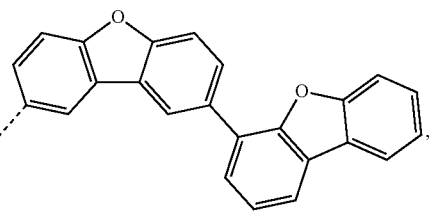
D121
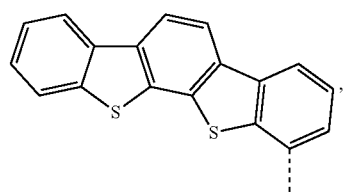
D116
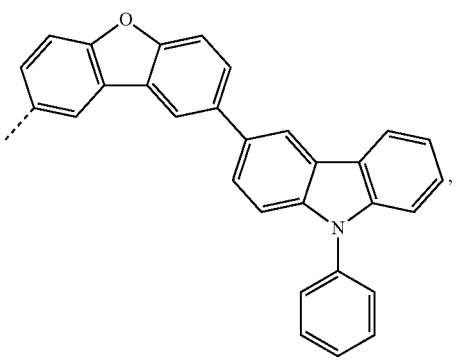
D122
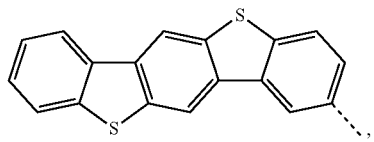
D117
D123
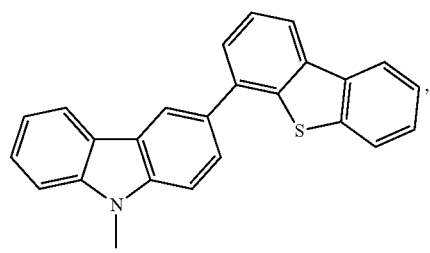
D118
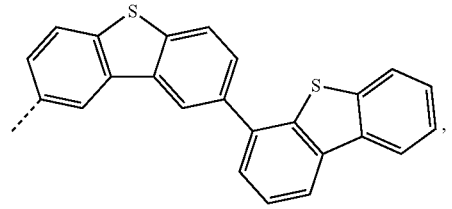
D124
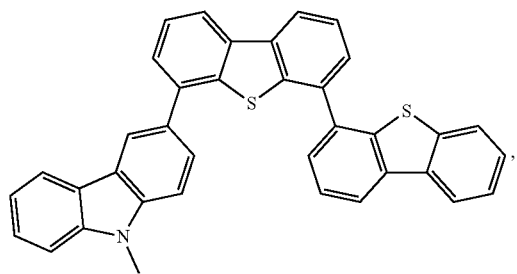
D119
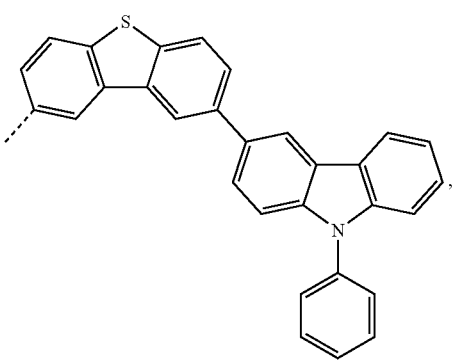

D125
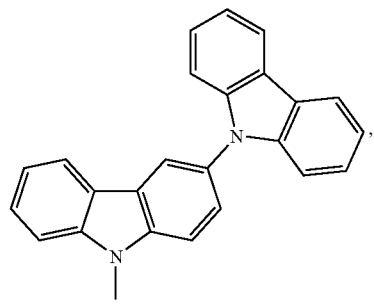
D126
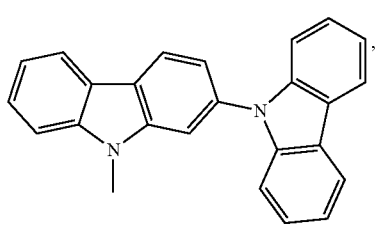
D127
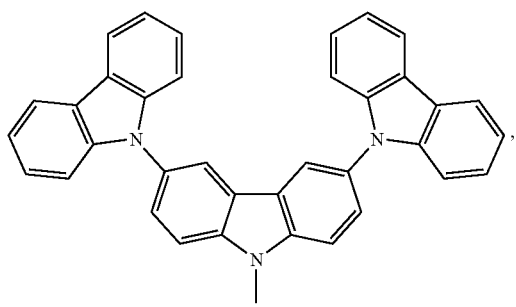
D128
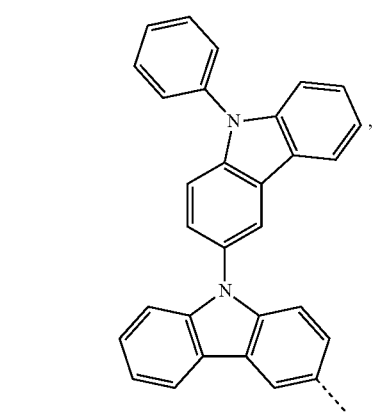
D129
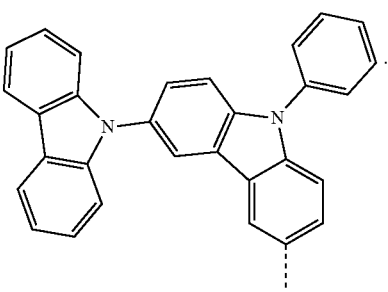
, and
D130
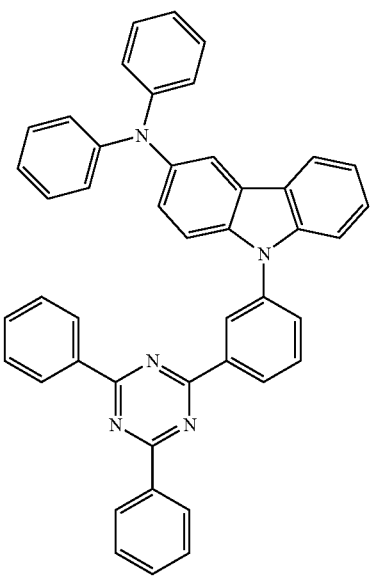
In one embodiment, the compound is selected from the group consisting of:
Compound 1

Compound 5
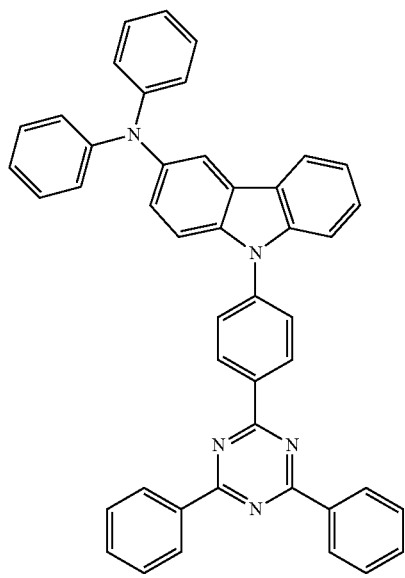
Compound 9
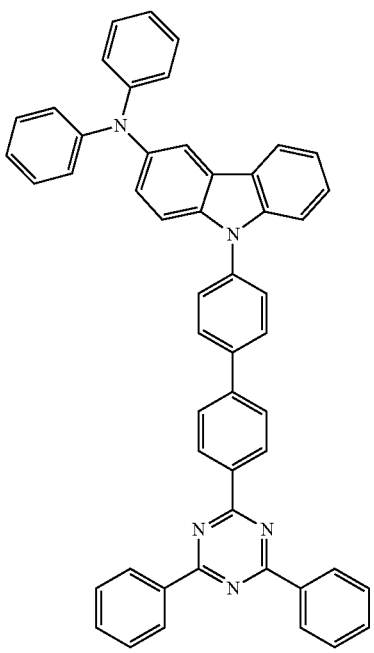
Compound 13
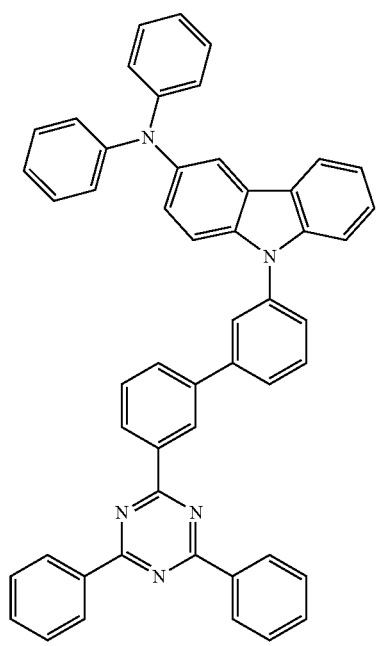
Compound 33
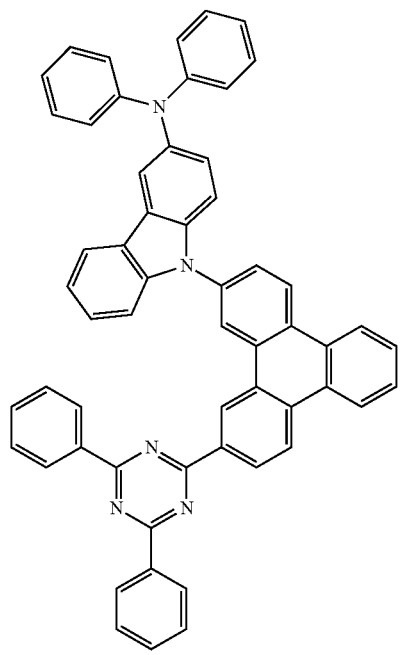

Compound 37
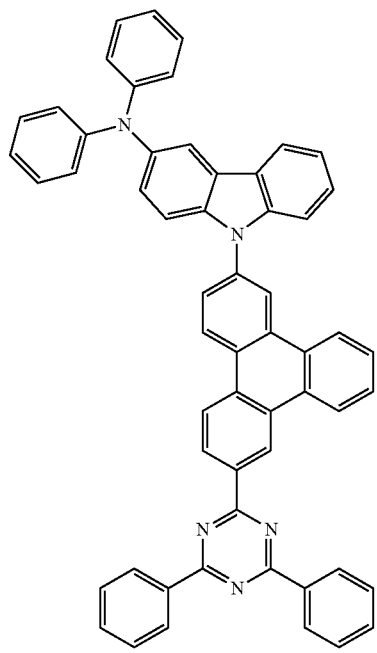
Compound 45
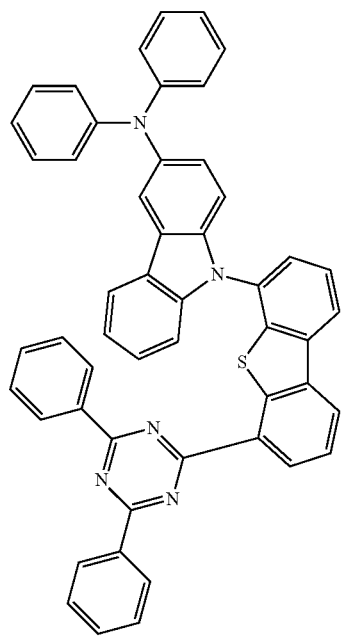
Compound 41
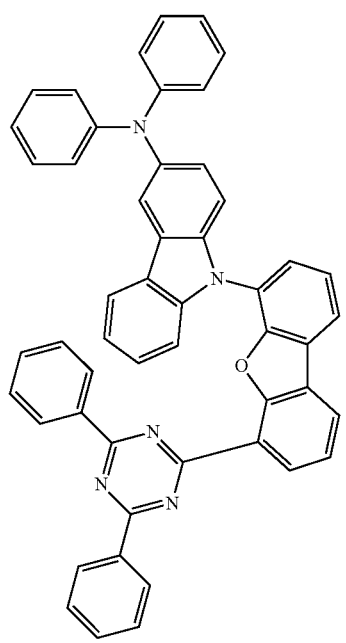
Compound 57
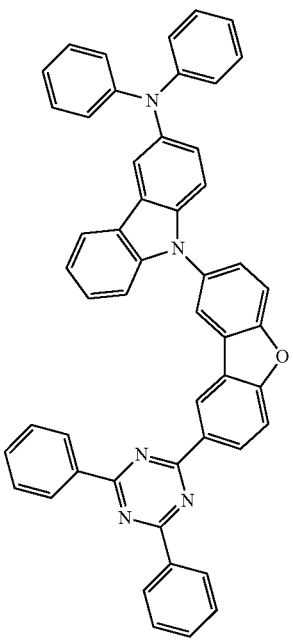

Compound 61
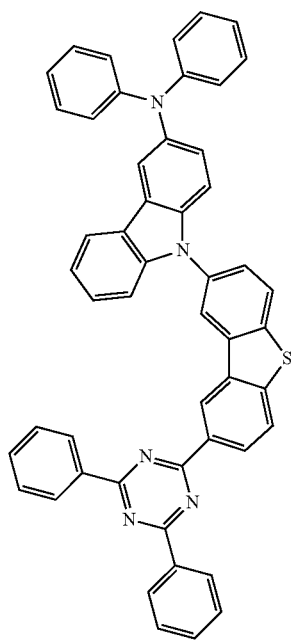
Compound 65
Compound 69
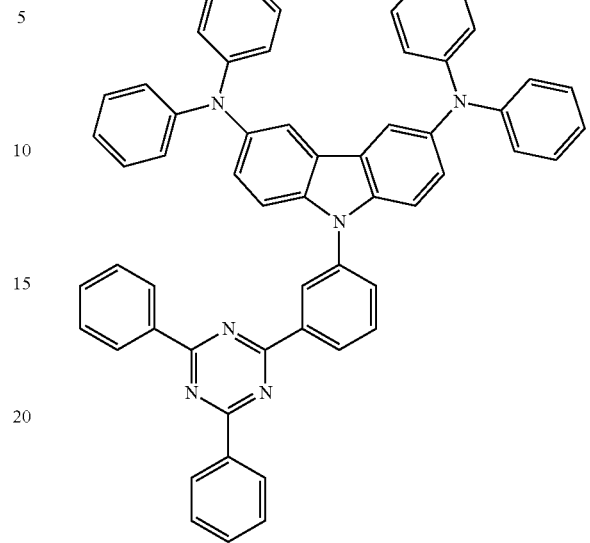
Compound 77
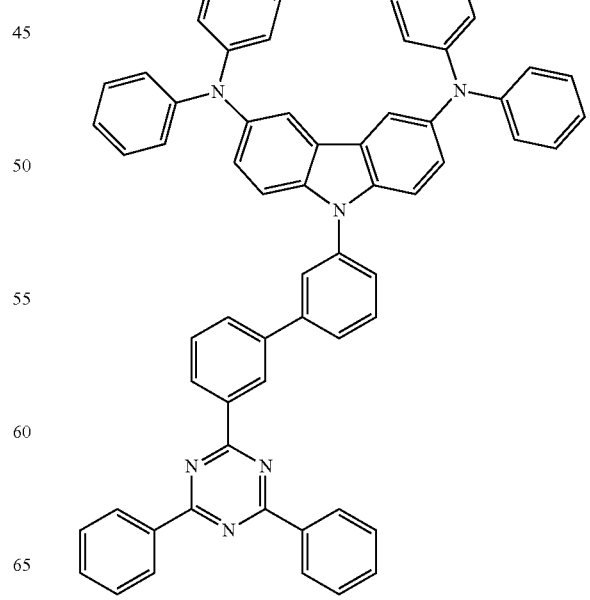

Compound 73
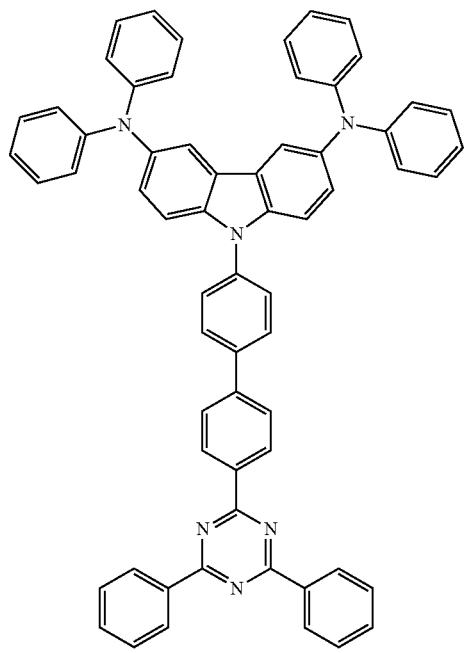
Compound 101
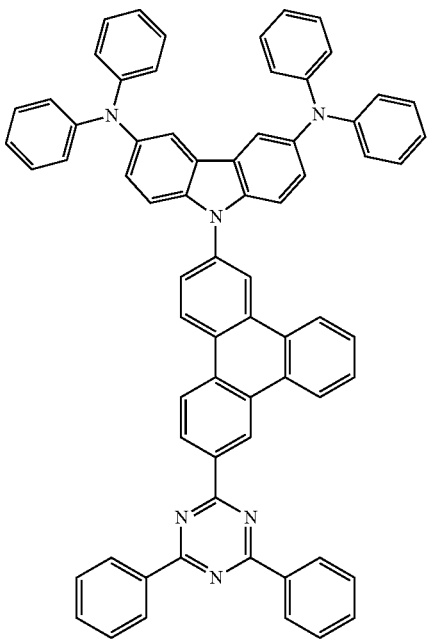
Compound 97
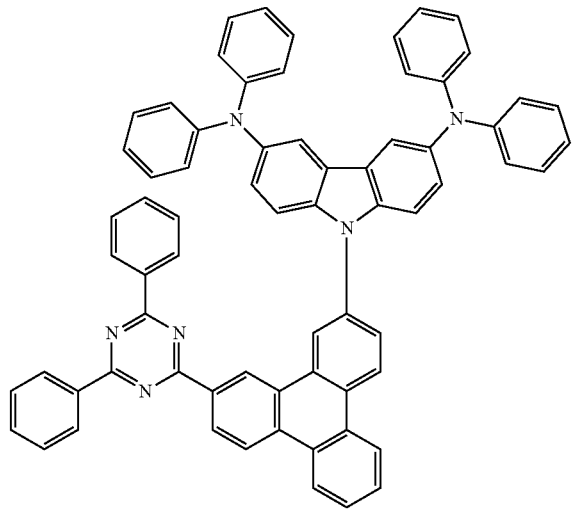
Compound 105
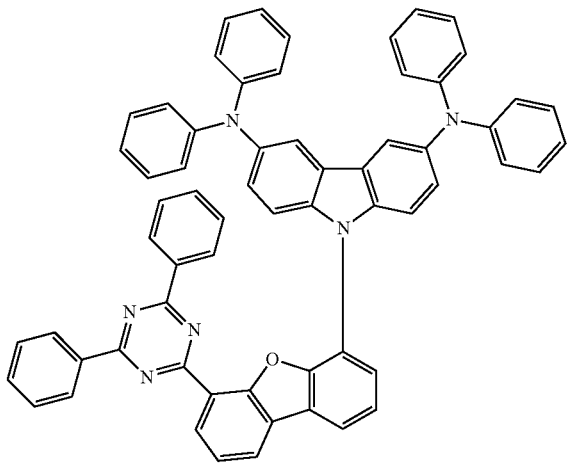

-continued
Compound 121
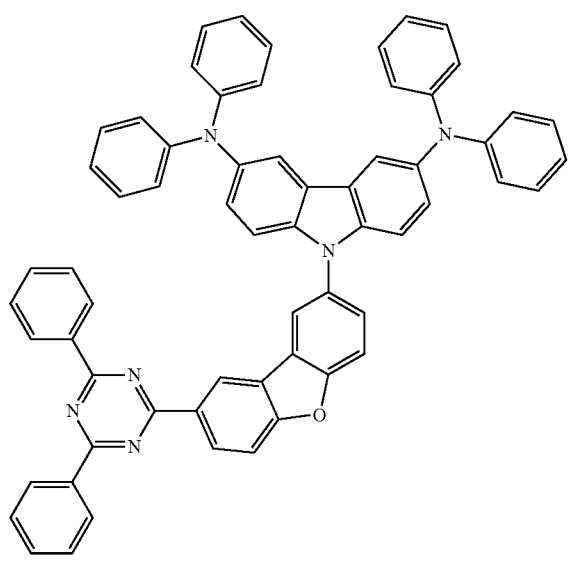
Compound 125
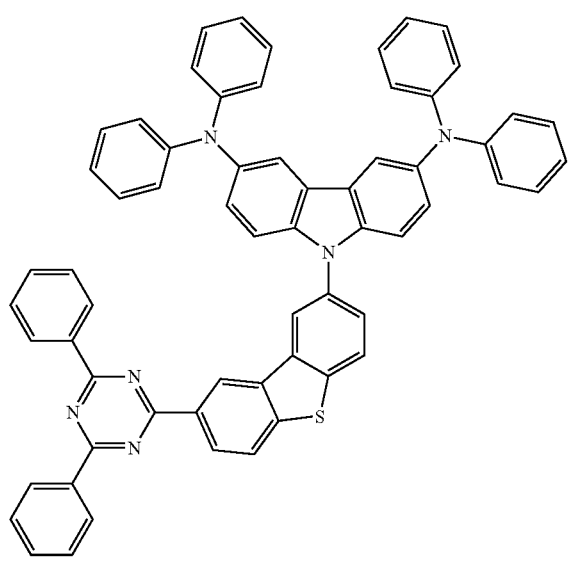
Compound 109
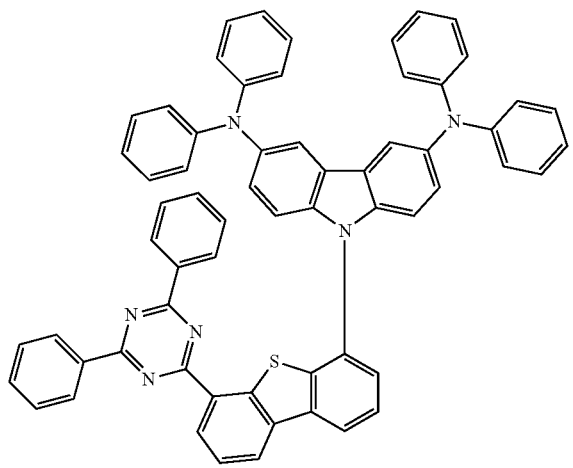
-continued
Compound 133
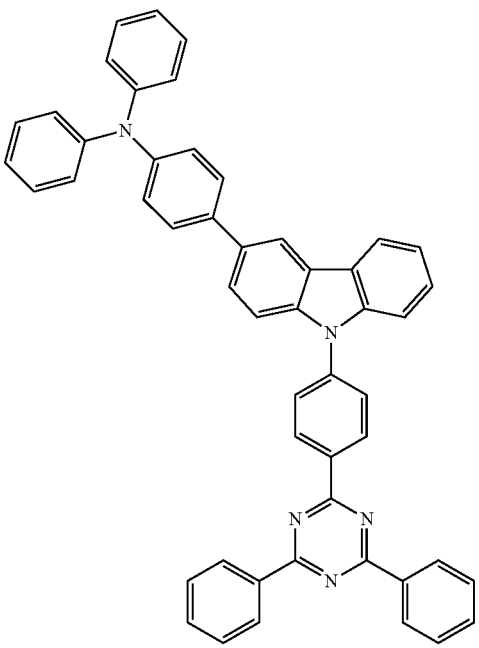
Compound 129
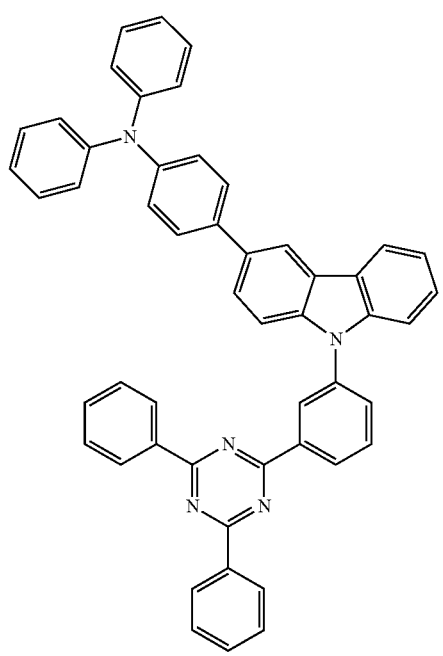

Compound 141
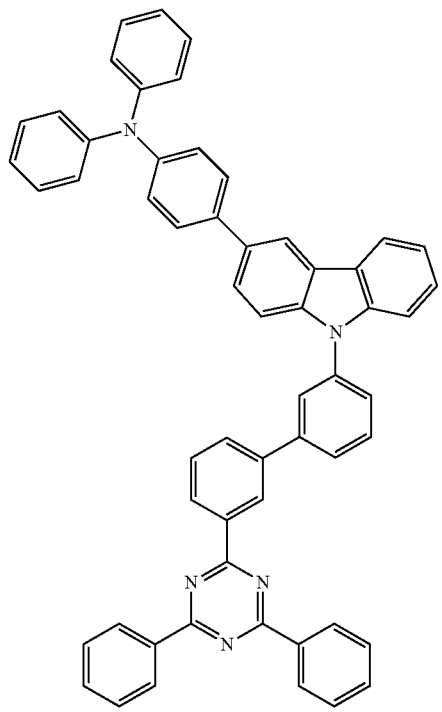
Compound 161
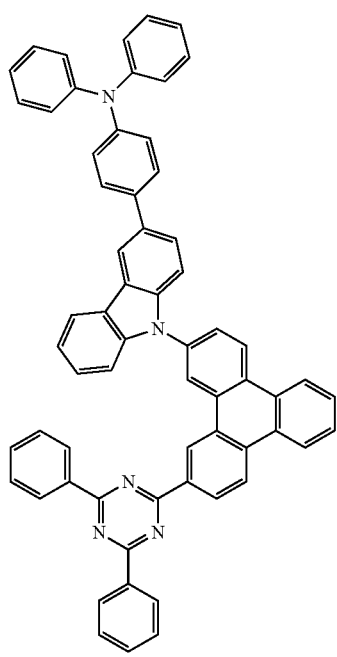
Compound 137
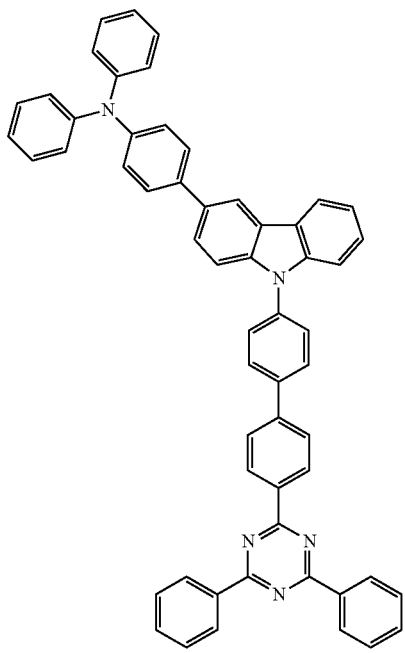
Compound 165
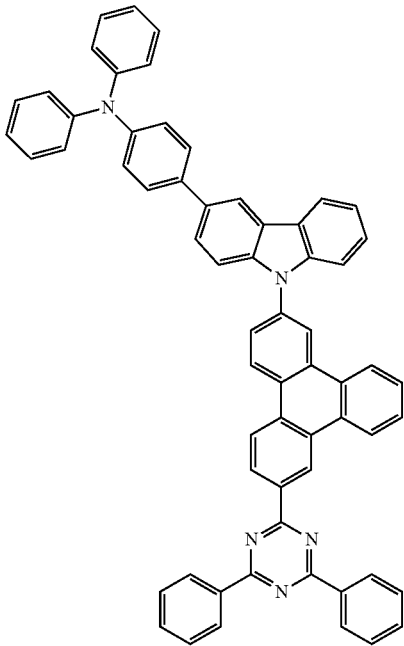

Compound 169
Compound 185
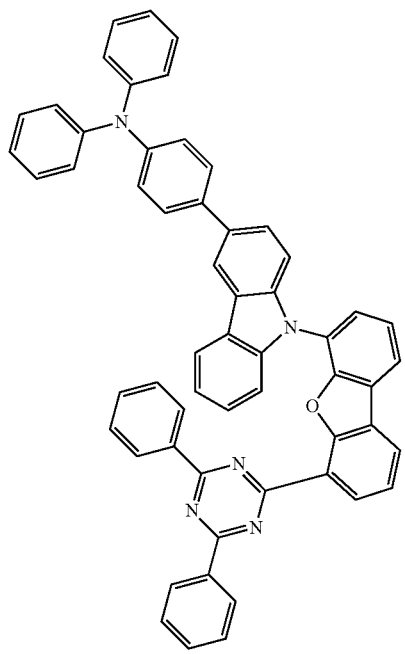
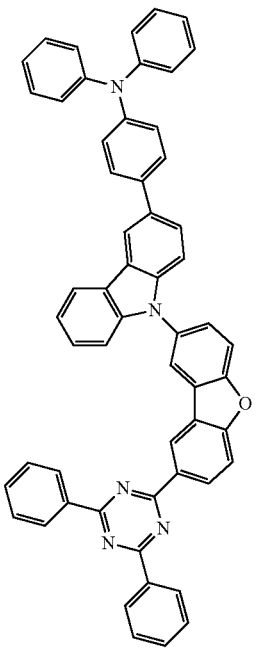
Compound 173
Compound 189
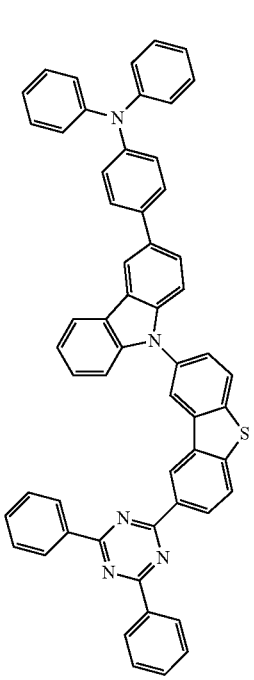

Compound 197
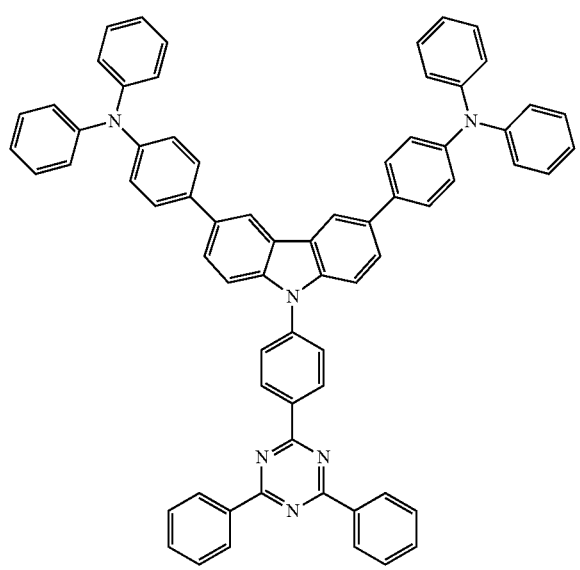
Compound 205
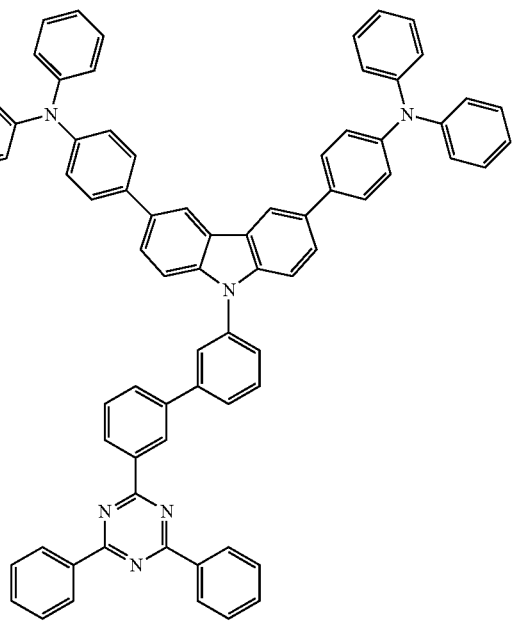
Compound 193
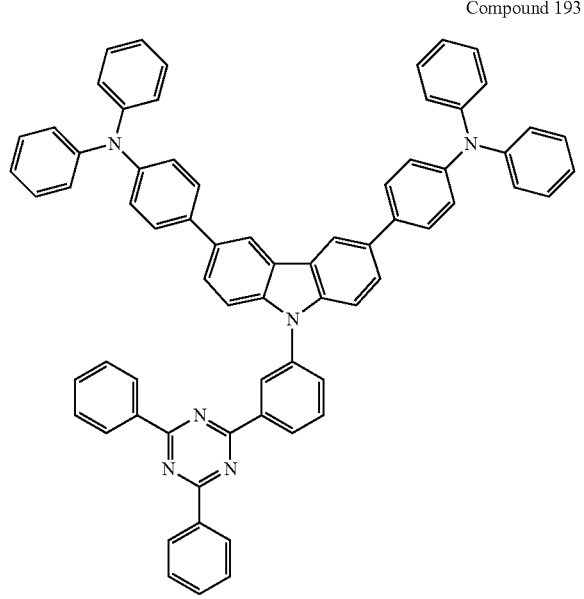
Compound 201
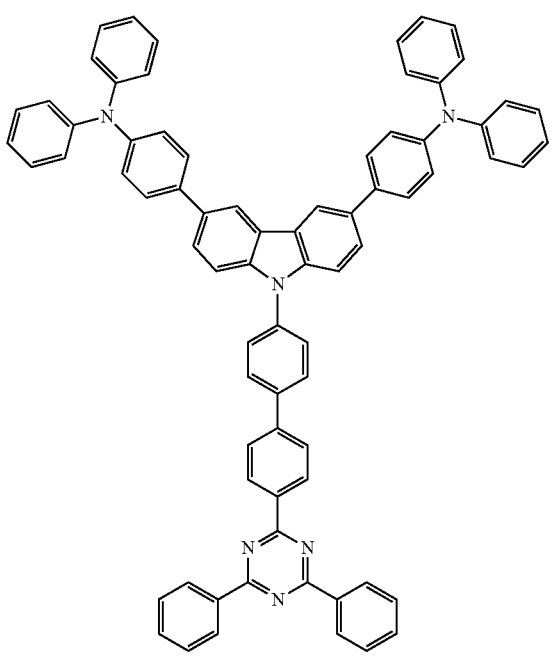

Compound 225
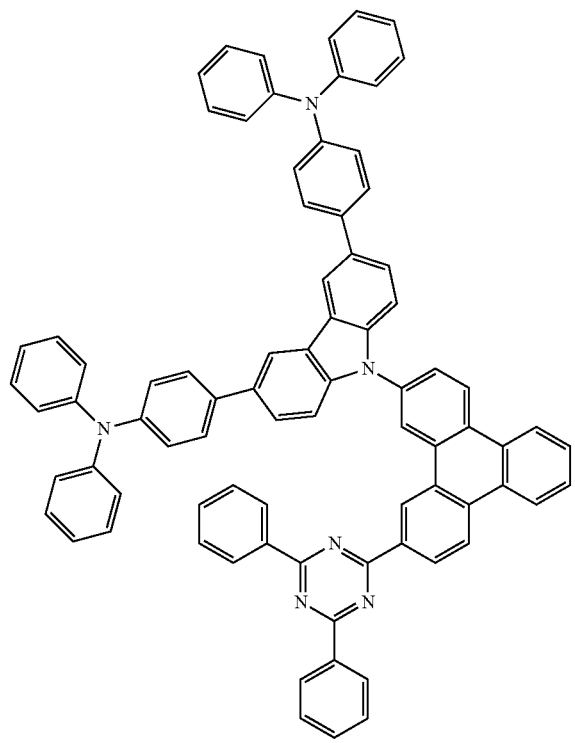
Compound 223
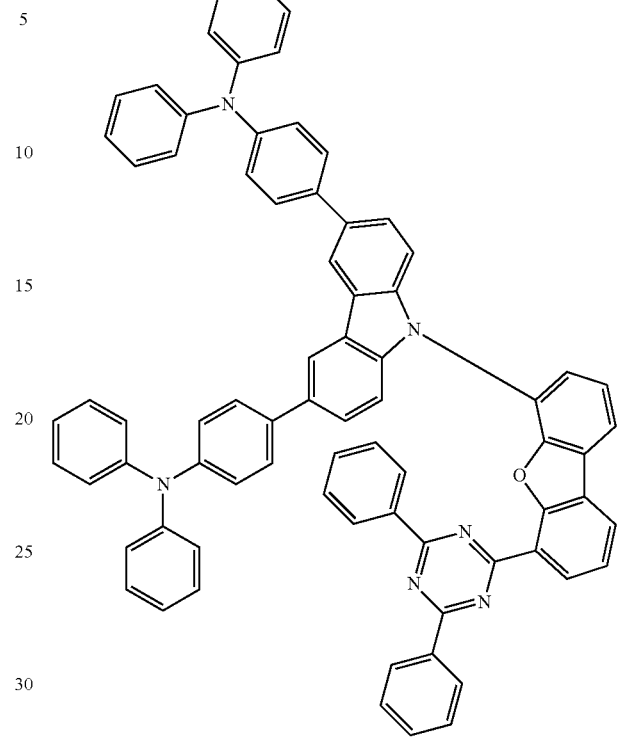
Compound 229
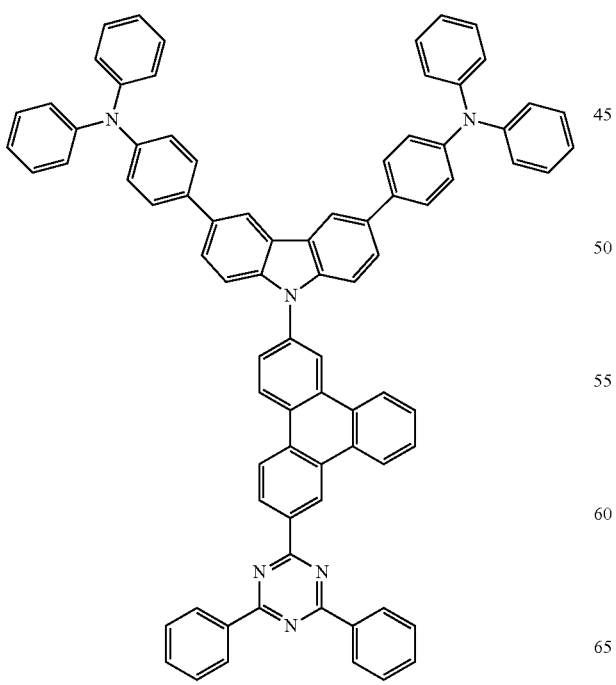
Compound 237
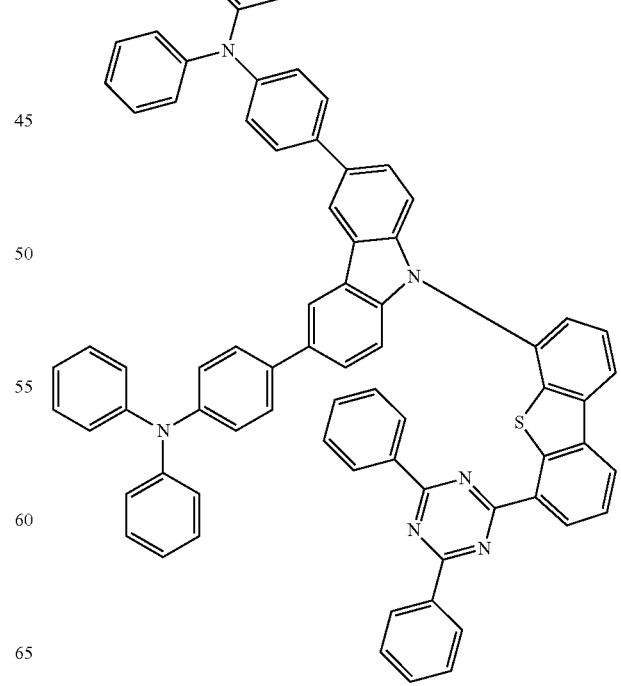

Compound 249
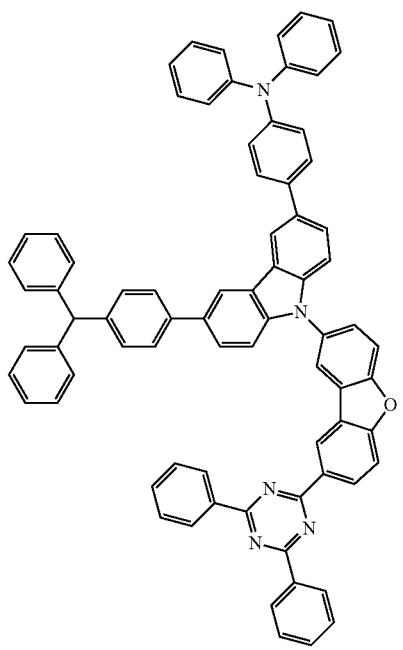
Compound 261
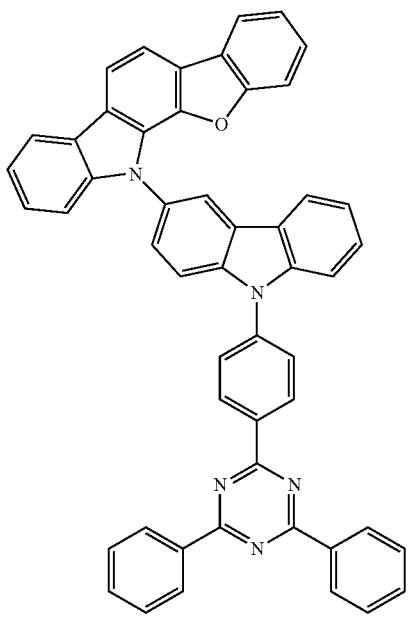
Compound 253
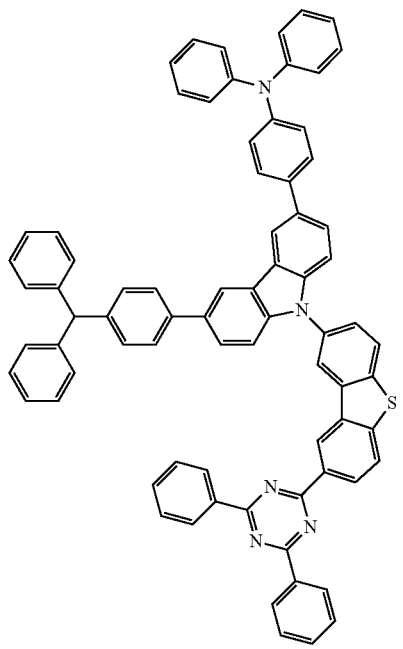
Compound 257

Compound 269
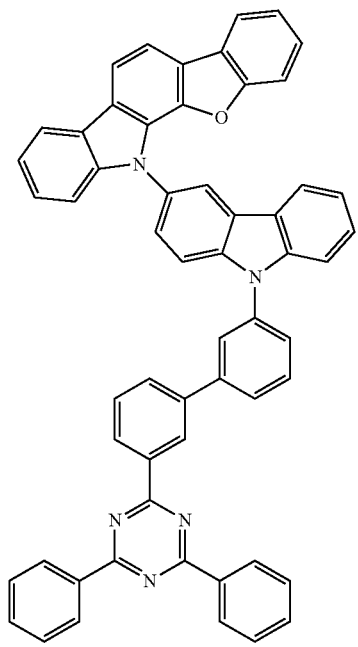
Compound 289
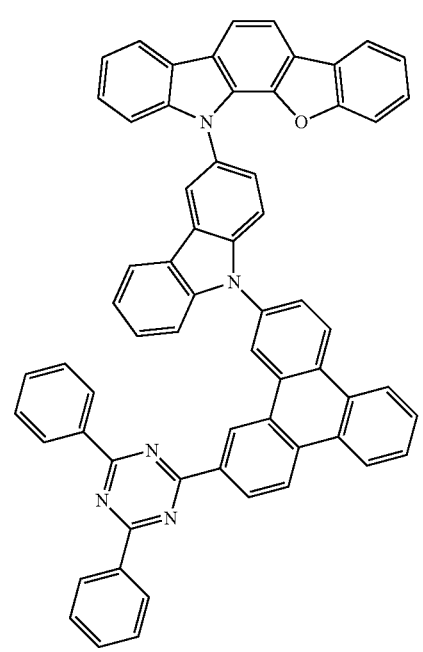
Compound 265
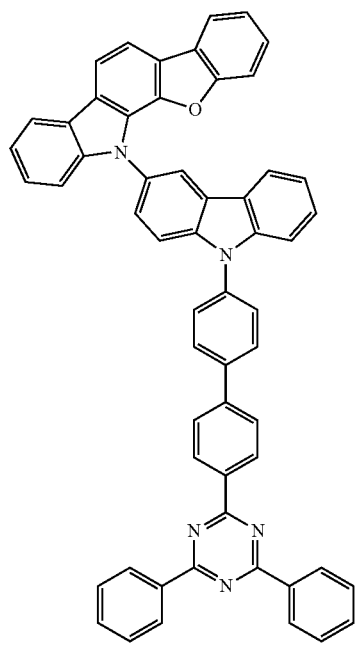
Compound 293
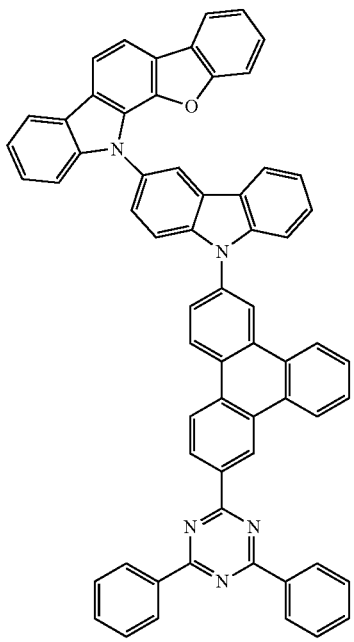

Compound 297
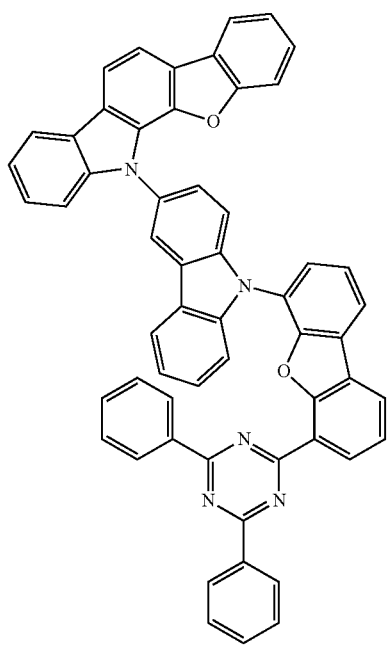
Compound 301
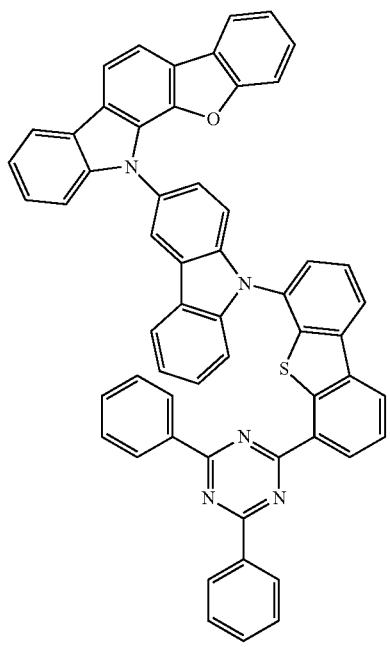
Compound 313
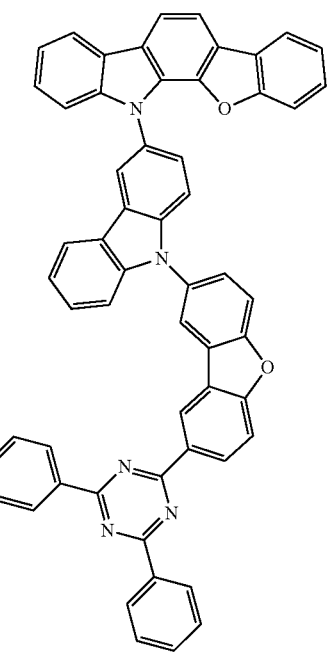
Compound 317
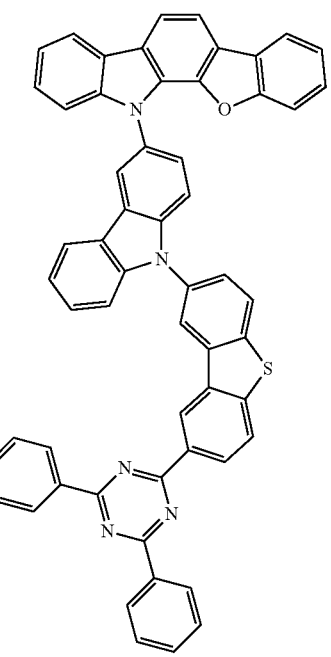

Compound 325
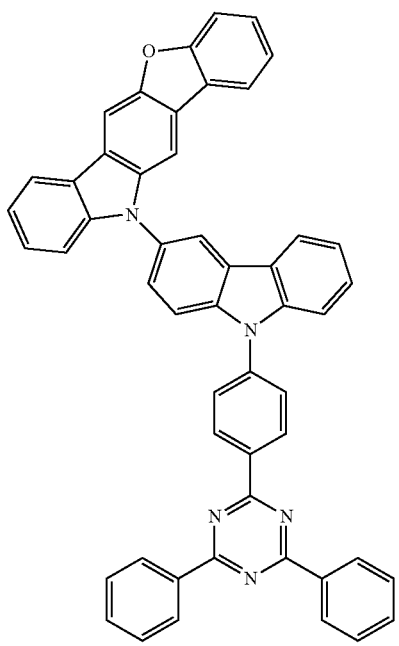
Compound 333
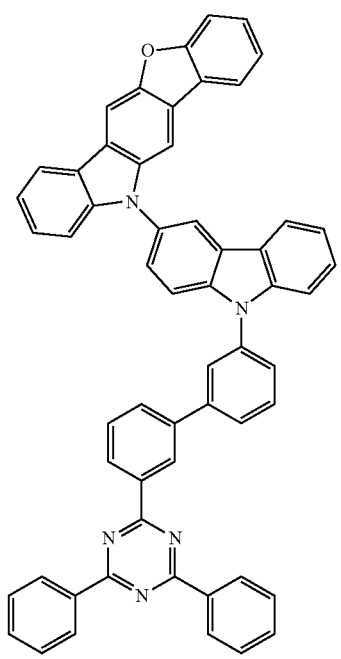
Compound 321
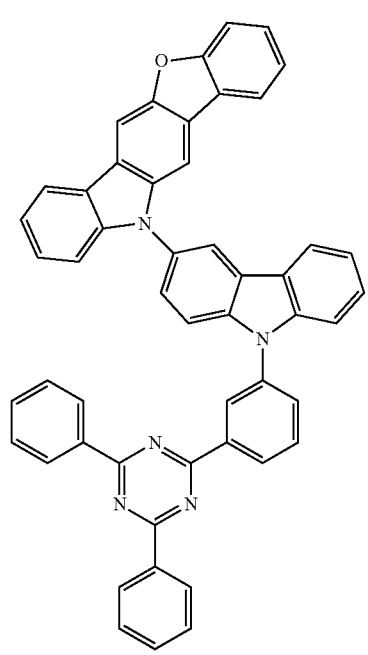
Compound 329
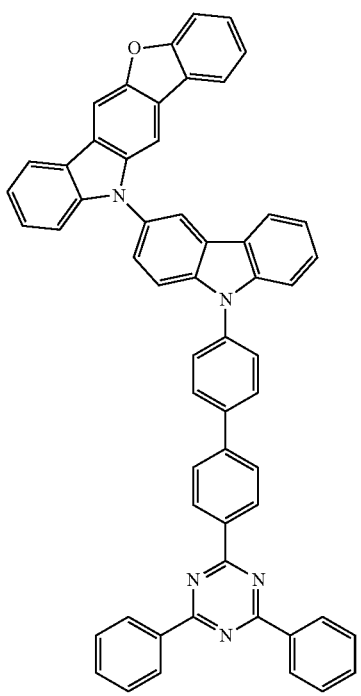

Compound 353
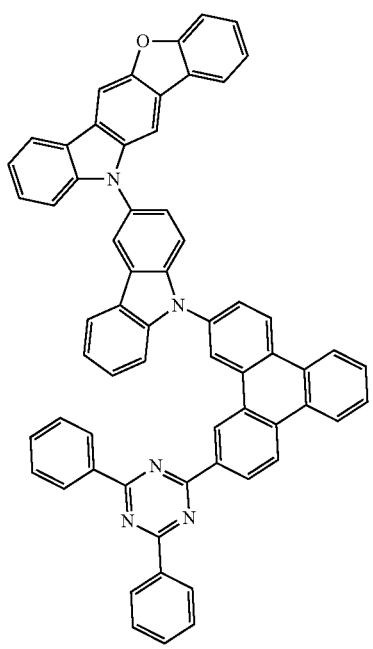
Compound 361
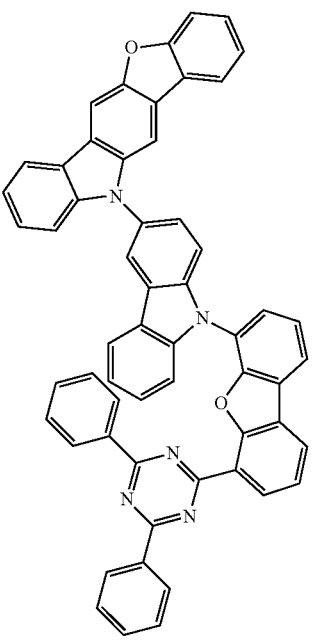
Compound 357
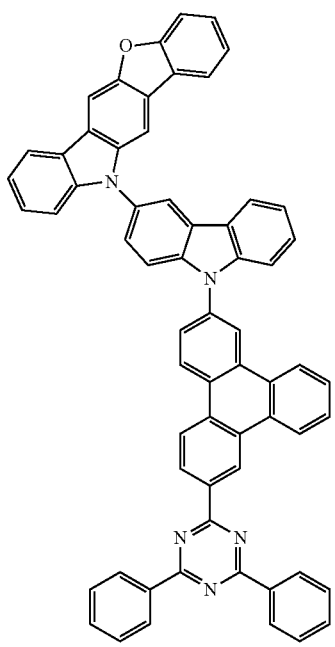
Compound 365
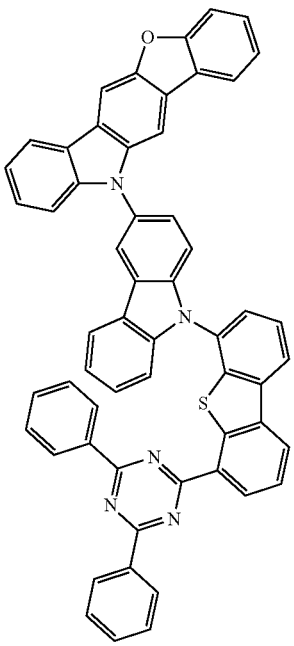

Compound 377
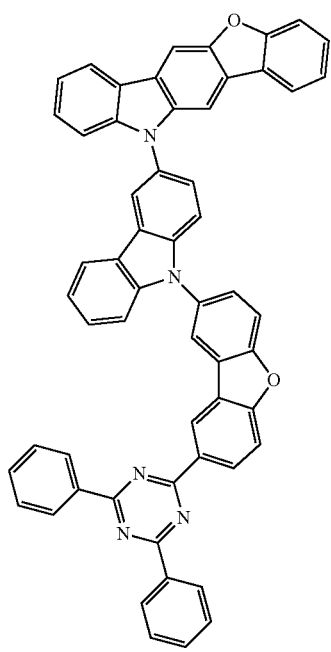
Compound 389
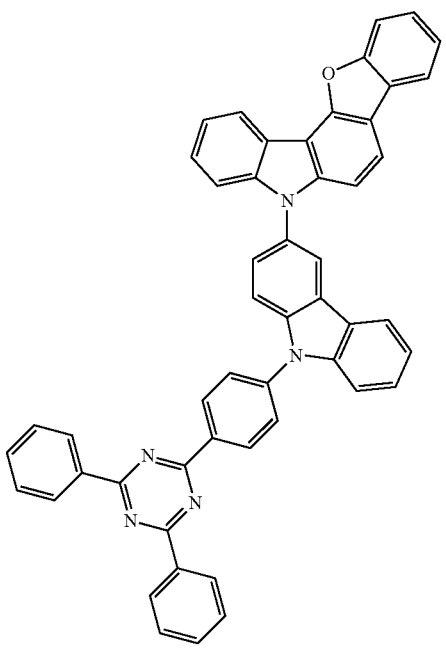
Compound 381
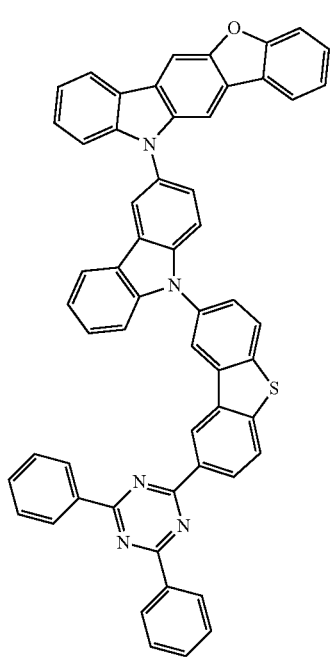
Compound 385
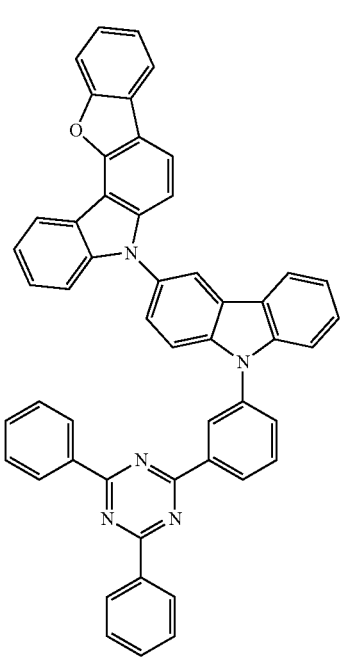

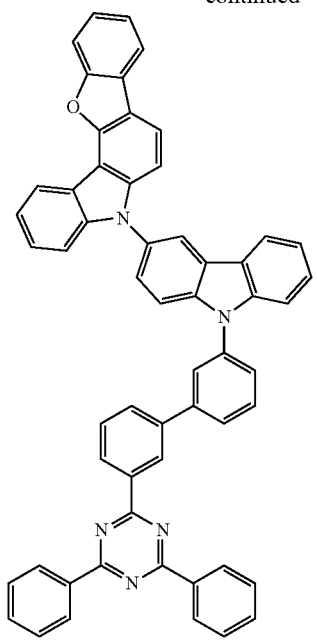
Compound 393
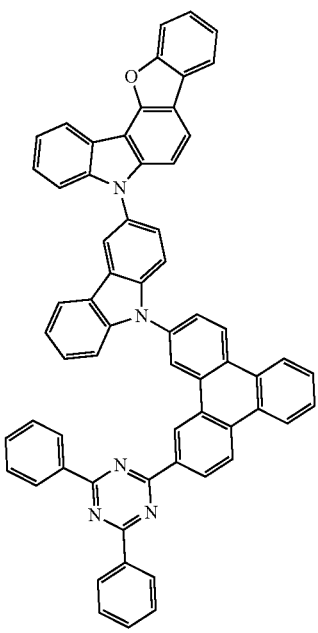
Compound 417
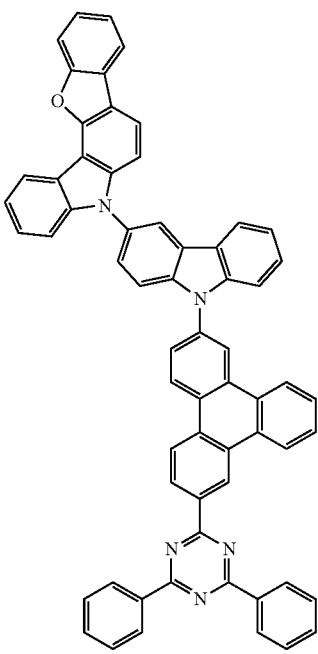
Compound 421

Compound 425
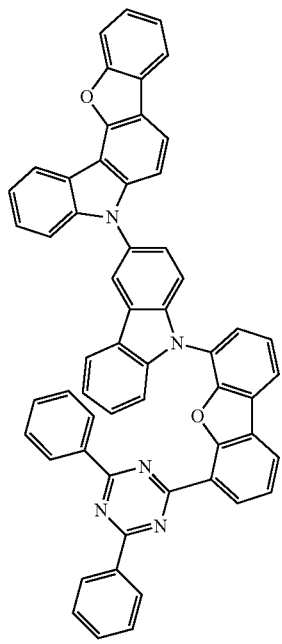
Compound 441
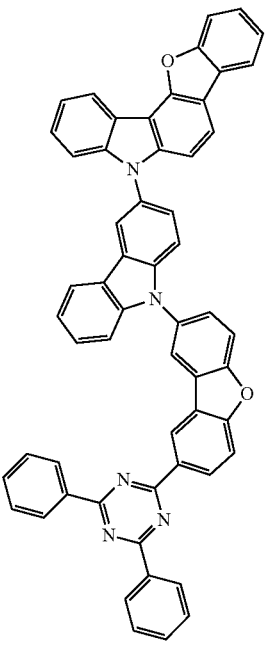
Compound 429
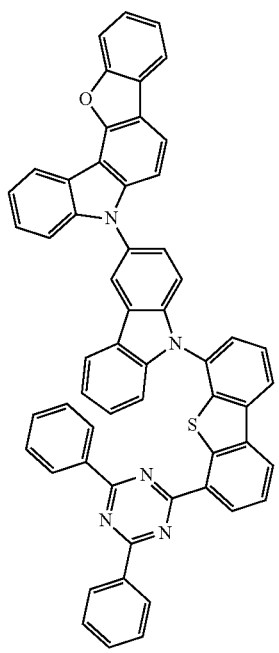
Compound 445
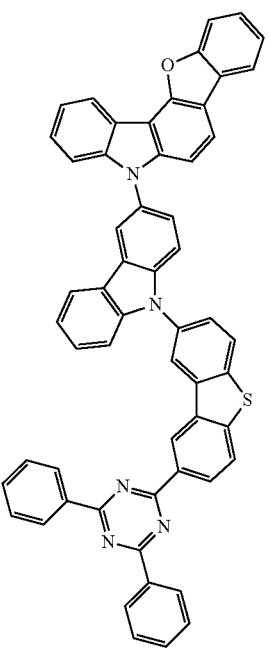

Compound 453
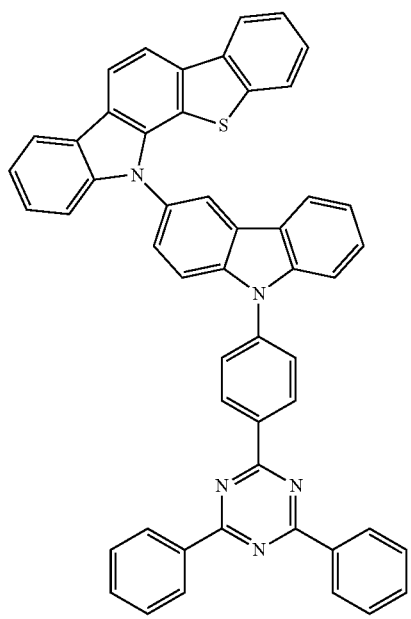
Compound 461
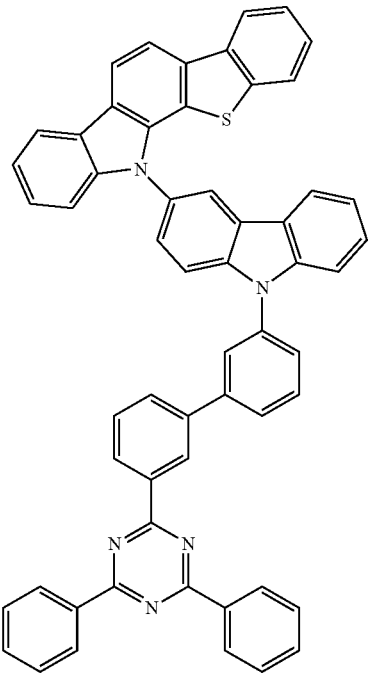
Compound 449
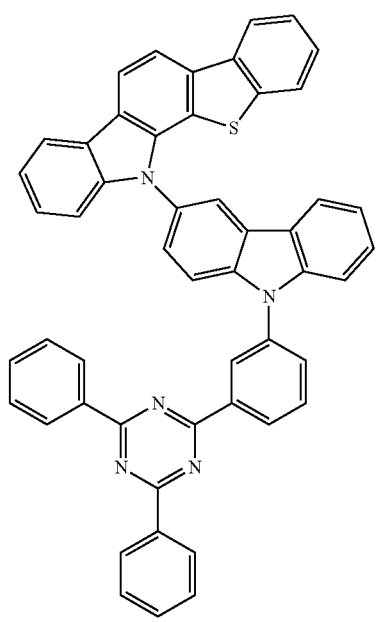
Compound 457
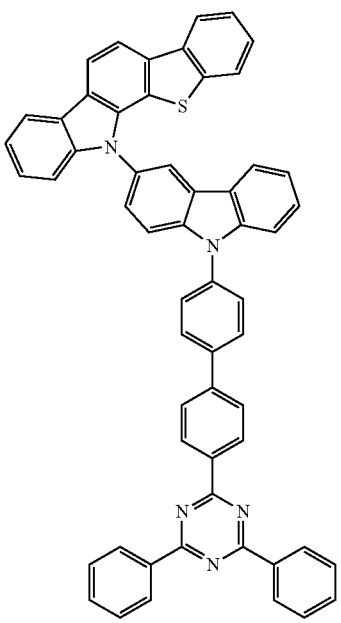

Compound 481
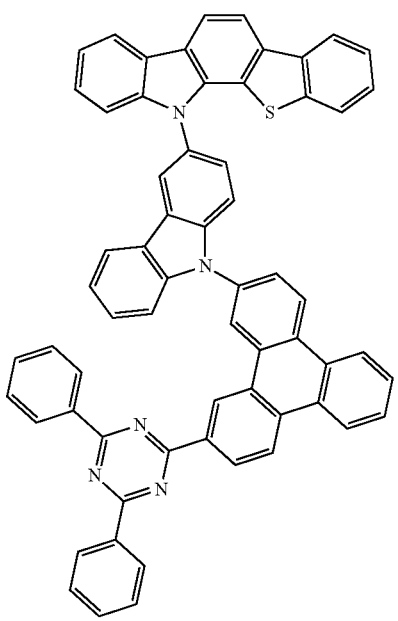
Compound 485
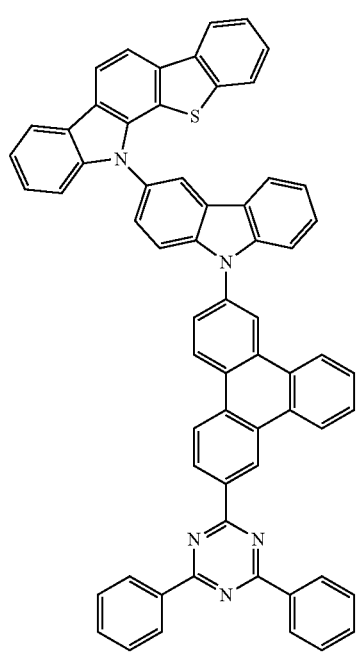
Compound 489
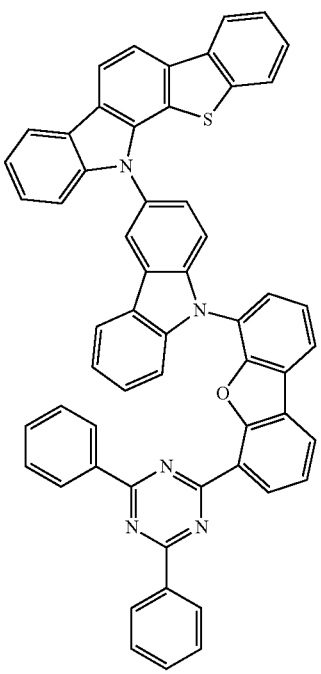
Compound 493
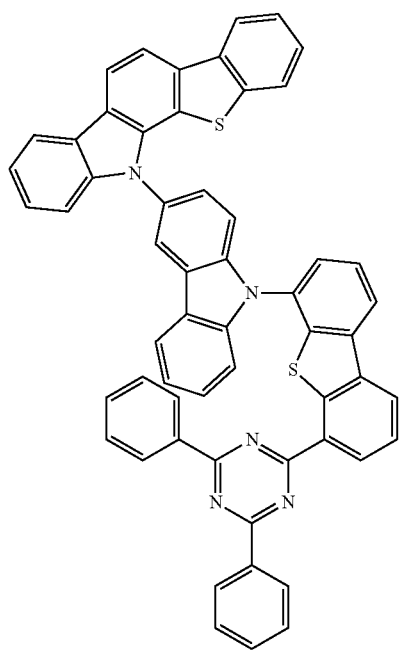

Compound 505
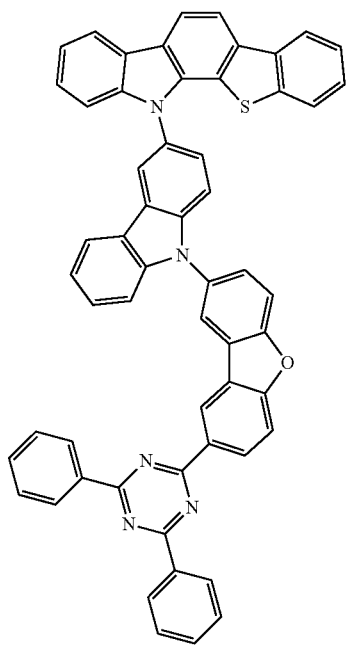
Compound 517
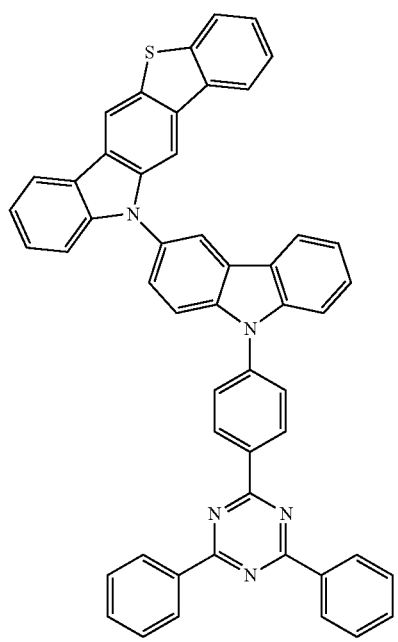
Compound 509
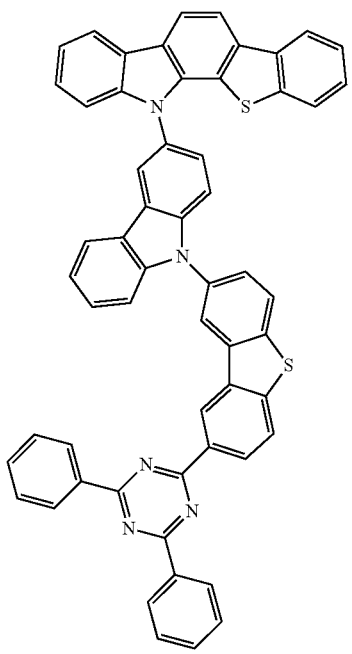
Compound 513
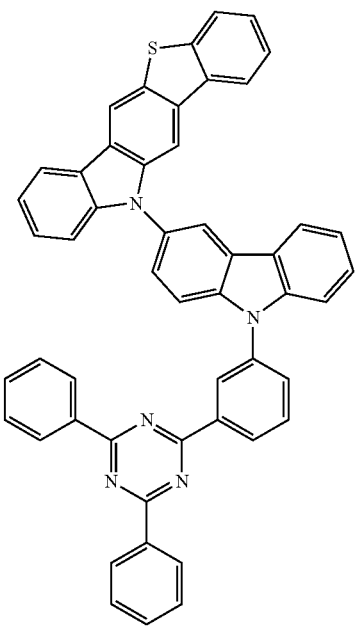

Compound 525
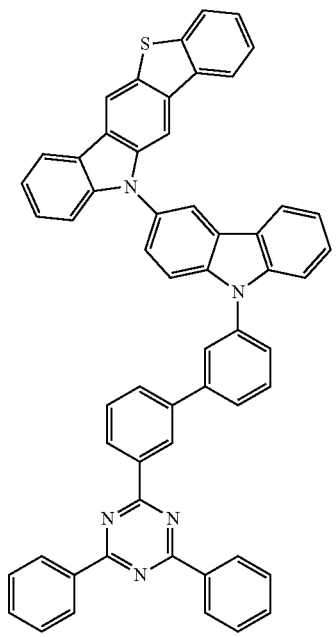
Compound 545
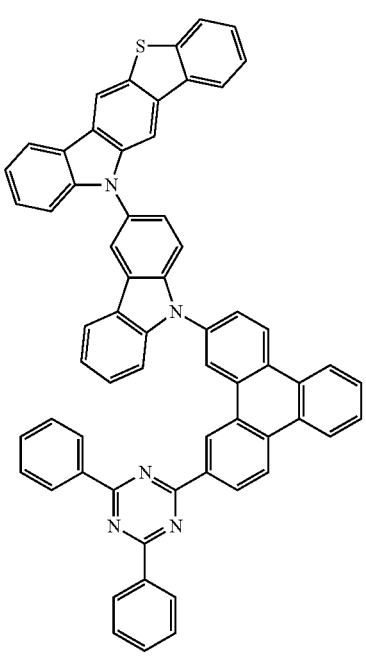
Compound 521
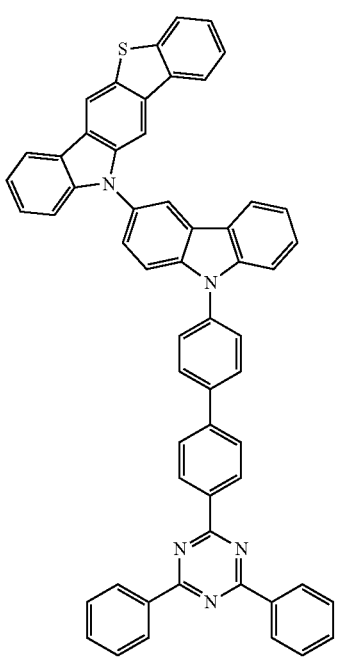
Compound 549
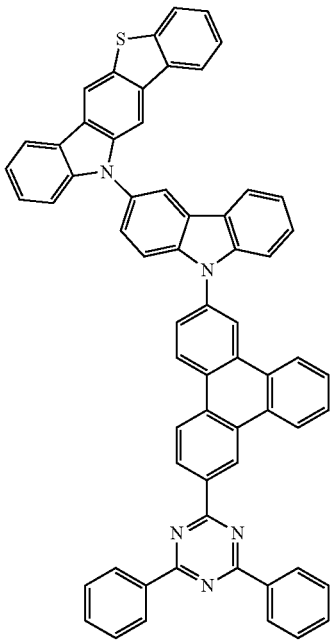

Compound 553
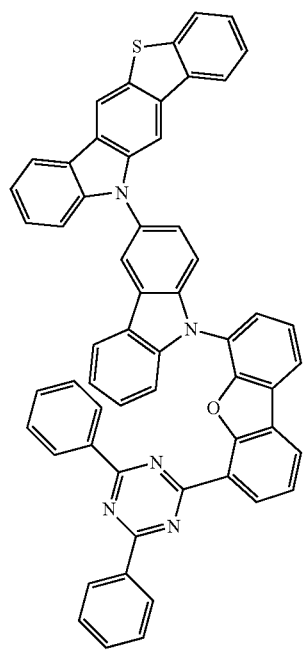
Compound 569
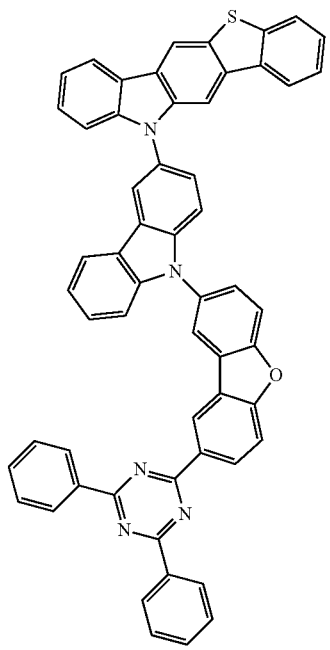
Compound 557
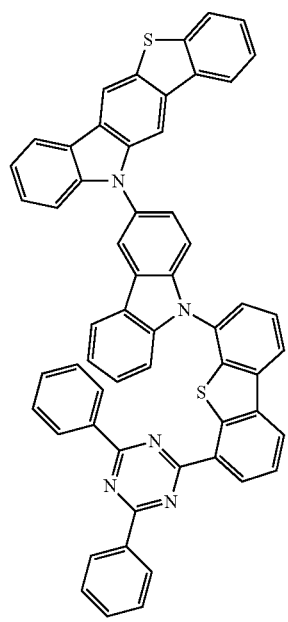
Compound 573
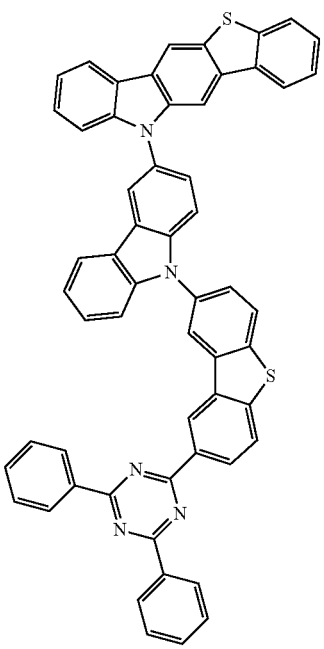

Compound 581
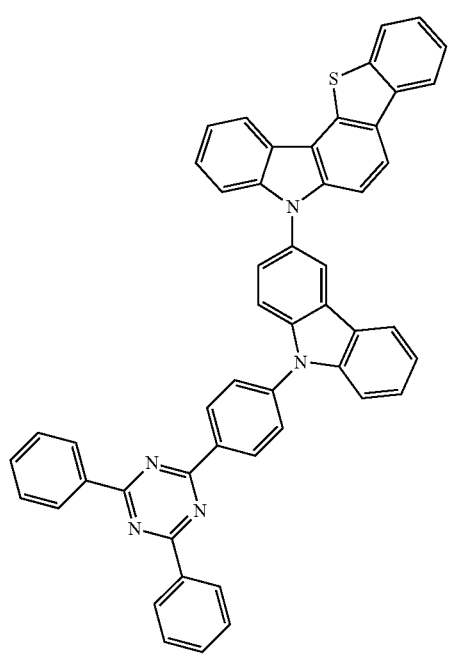
Compound 577
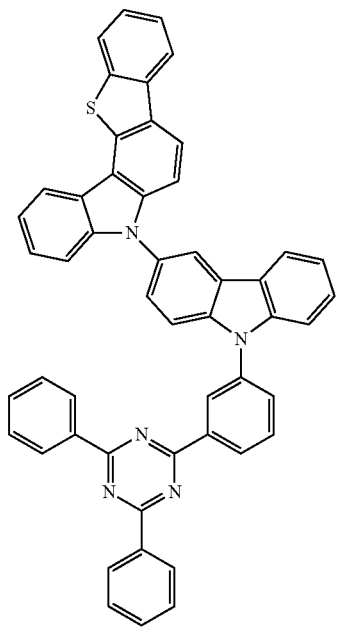
Compound 589
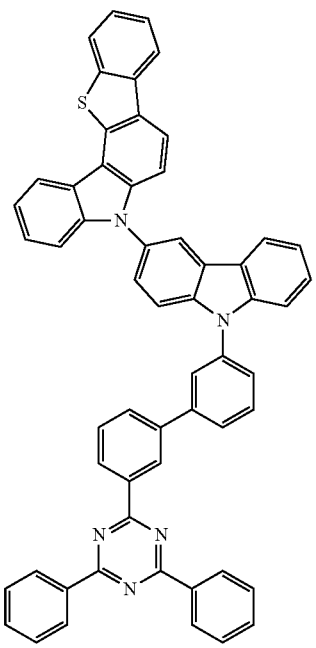
Compound 585

Compound 609
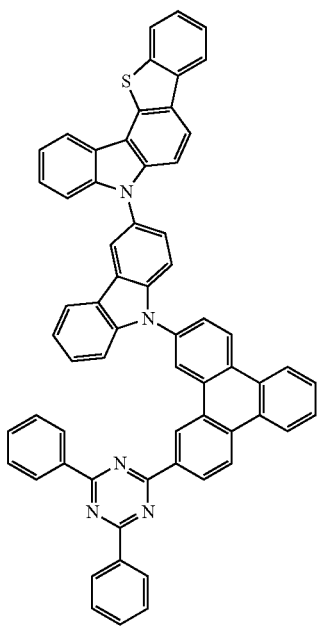
Compound 613
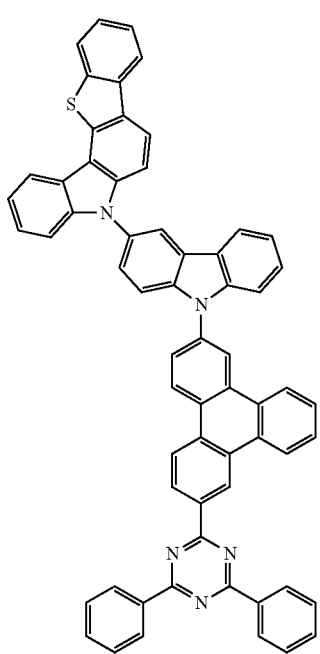
Compound 617
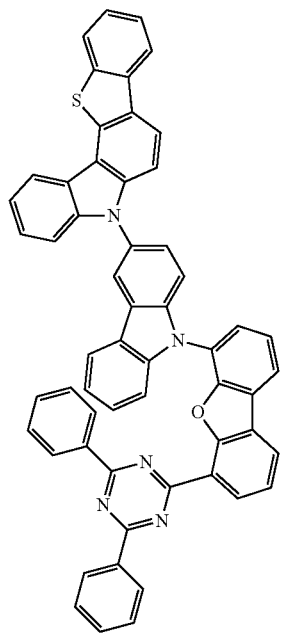
Compound 621
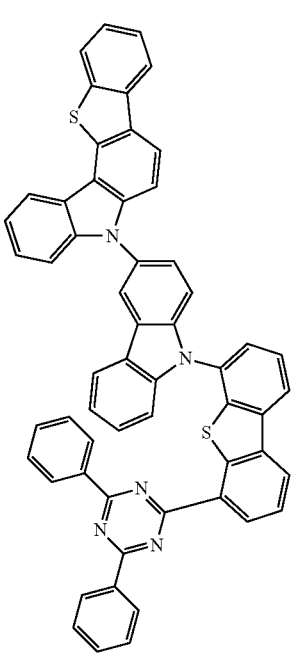

Compound 633
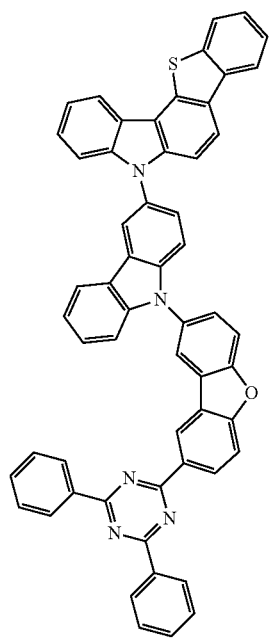
Compound 645
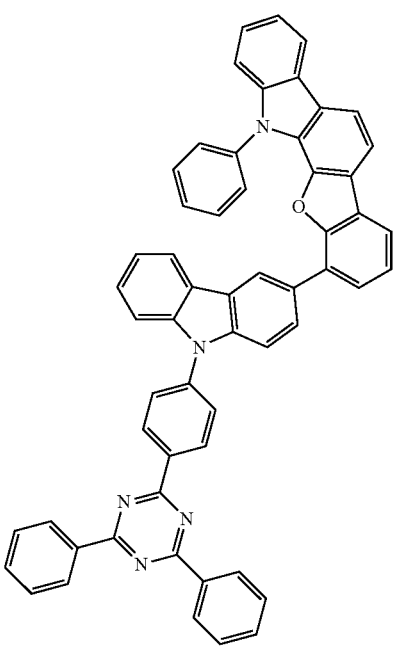
Compound 637
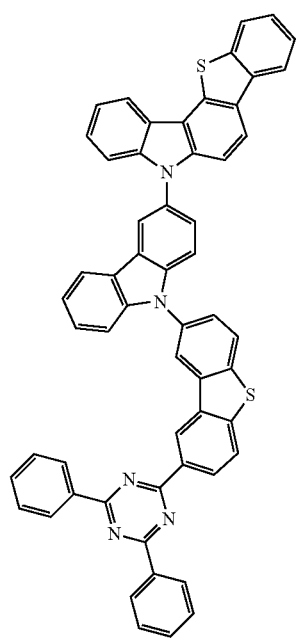
Compound 641
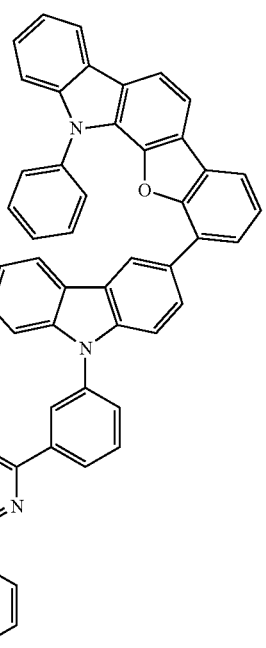

Compound 653
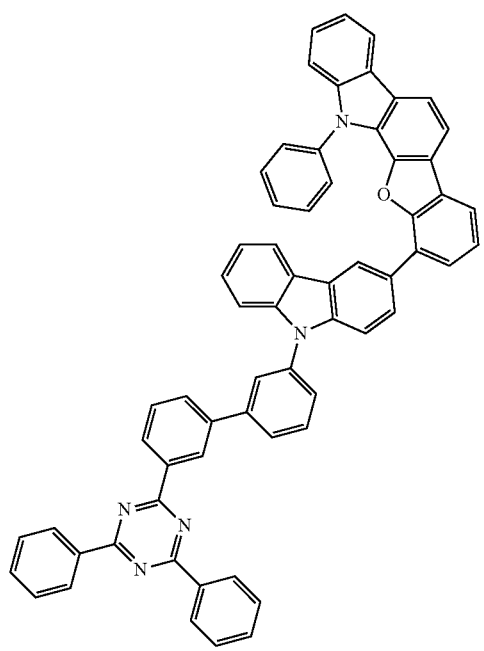
Compound 673
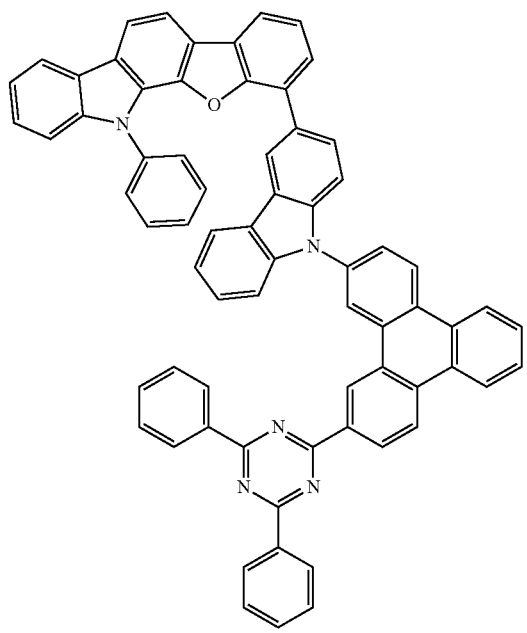
Compound 649
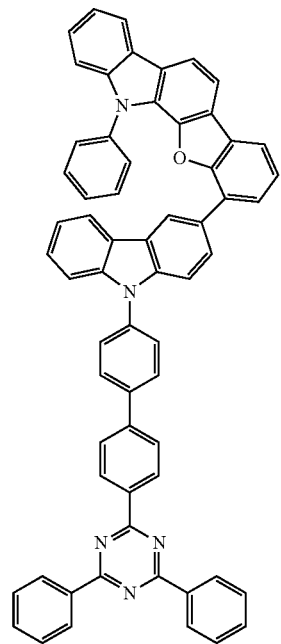
Compound 677
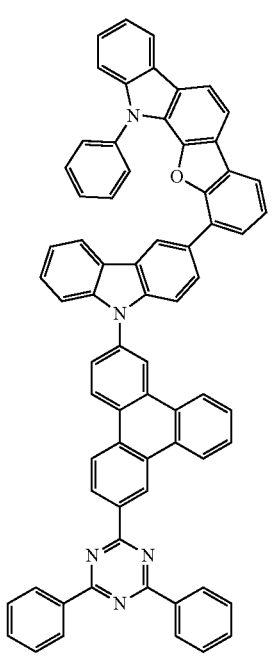

Compound 681
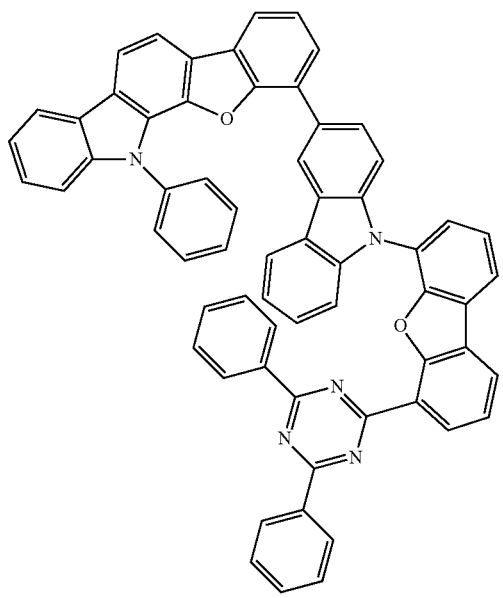
Compound 685
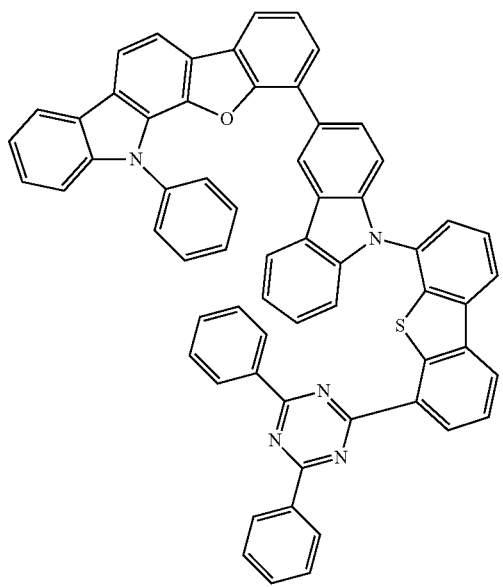
Compound 697
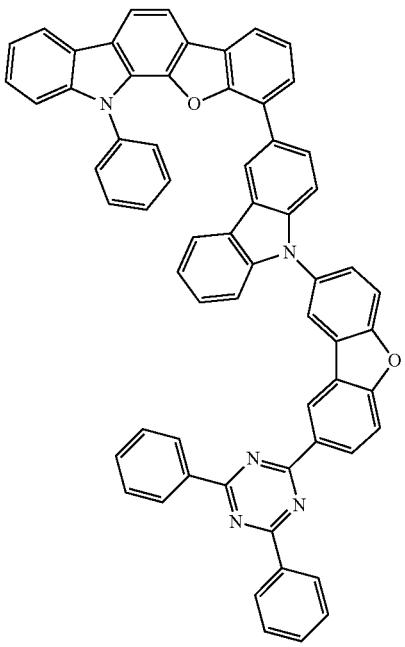
Compound 701
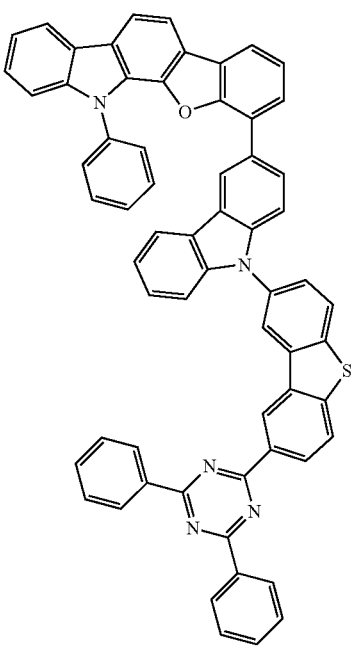

Compound 709
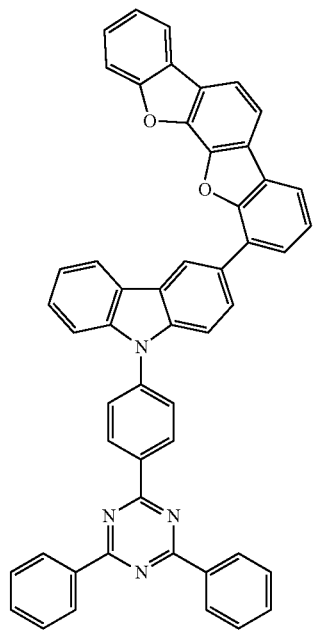
Compound 705
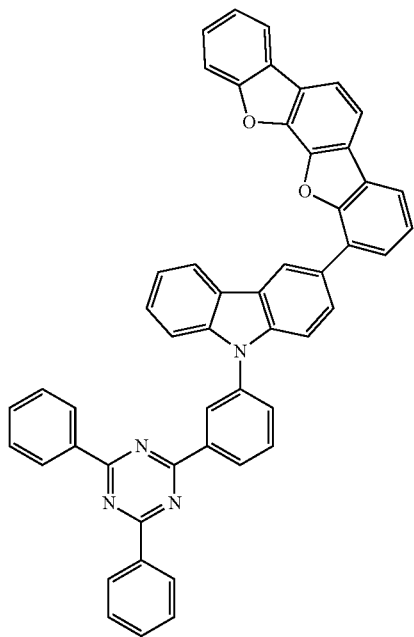
Compound 717
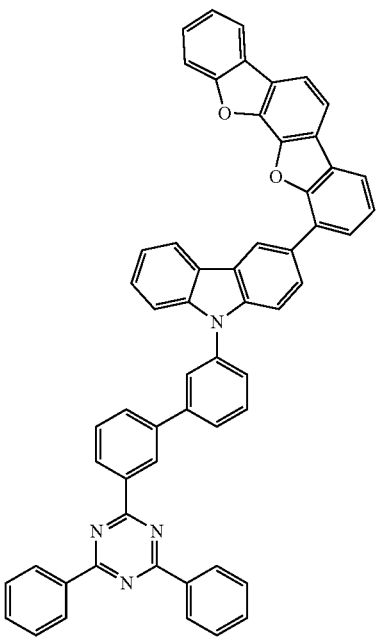
Compound 713
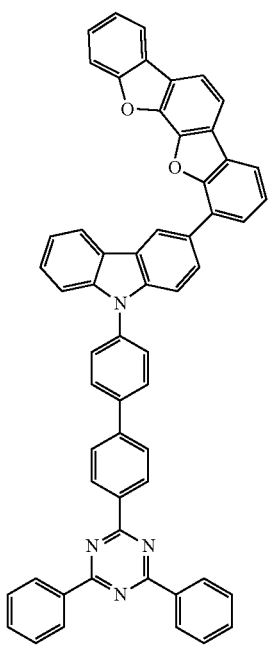

Compound 737
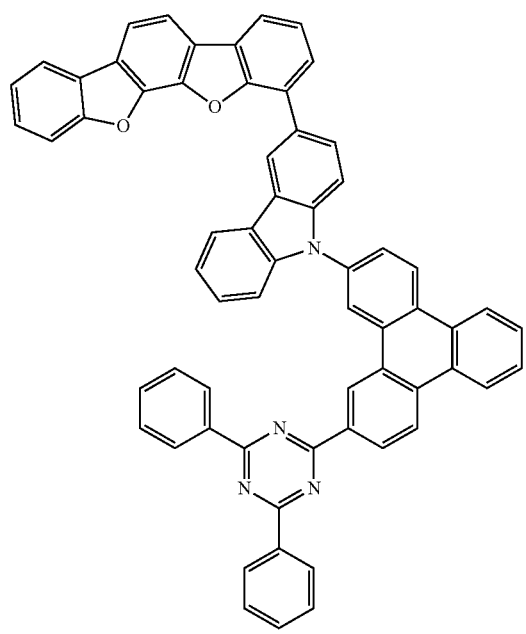
Compound 741
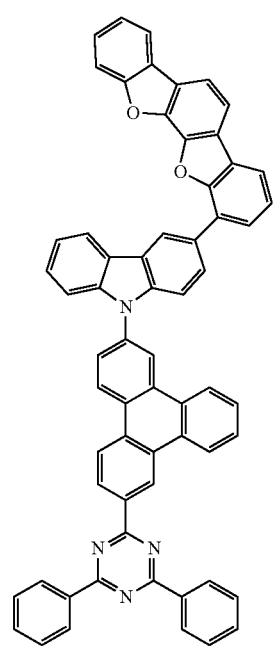
Compound 745
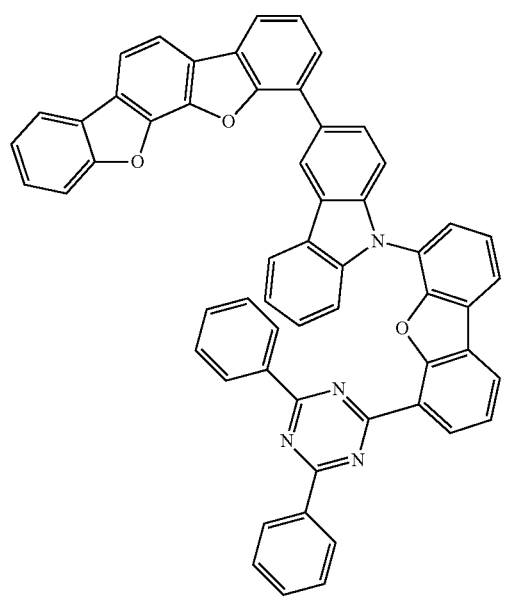
Compound 749
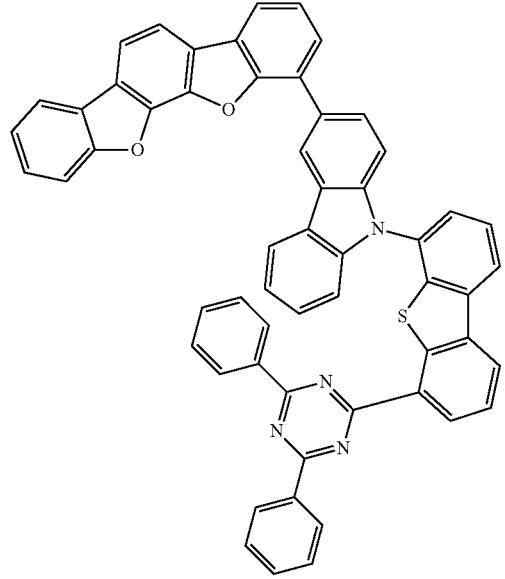

Compound 761
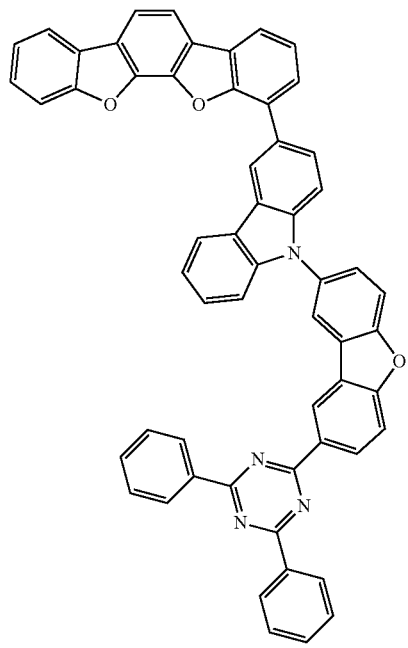
Compound 773
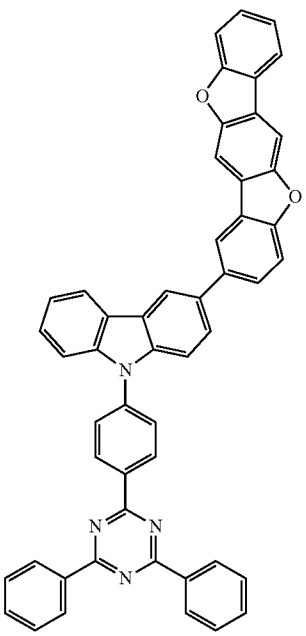
Compound 765
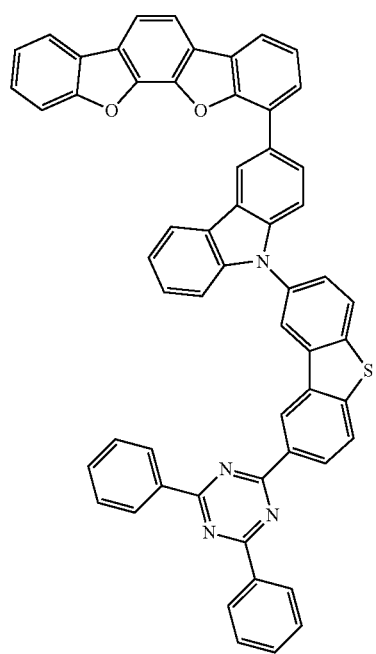
Compound 769
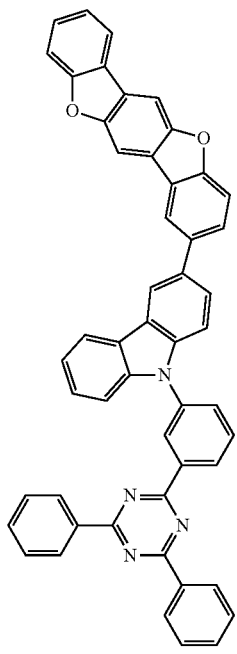

Compound 781
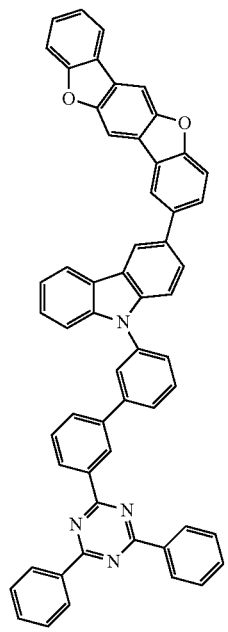
Compound 777
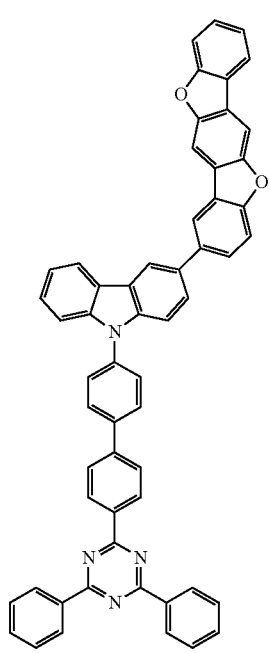
Compound 801
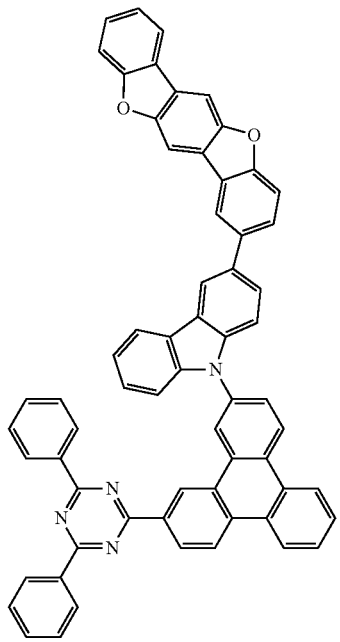
Compound 805
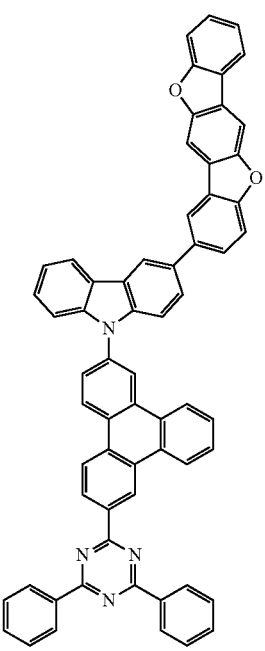

Compound 809
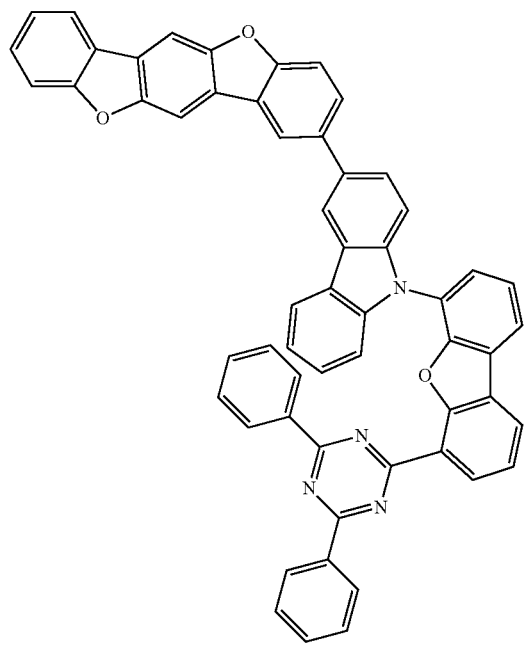
Compound 825
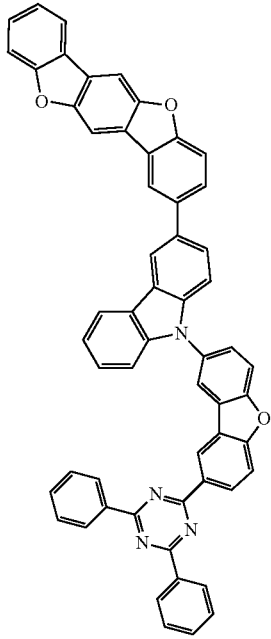
Compound 813
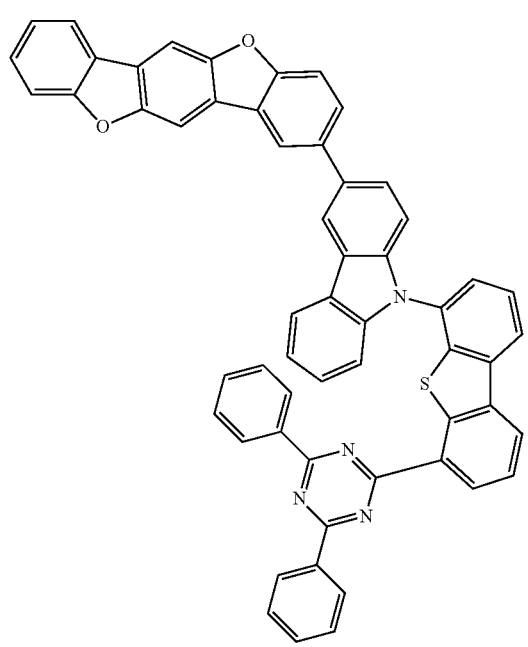
Compound 829
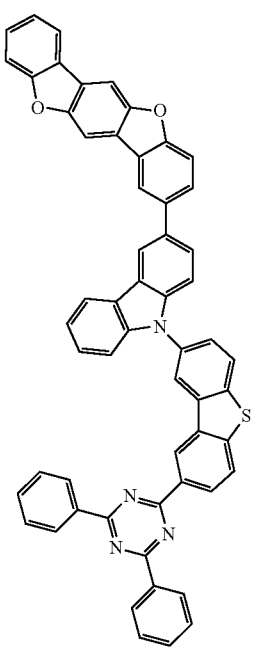

Compound 837
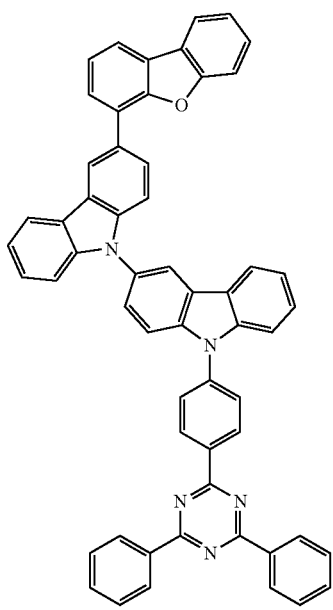
Compound 845
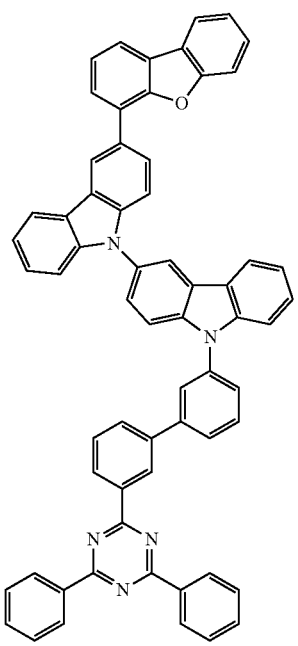
Compound 833
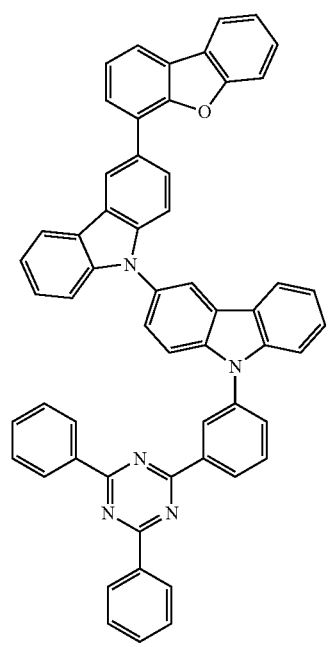
Compound 841
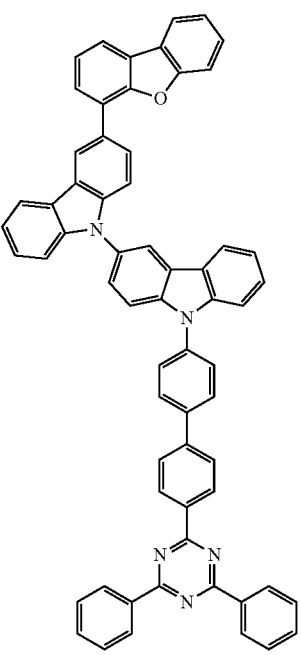

Compound 865
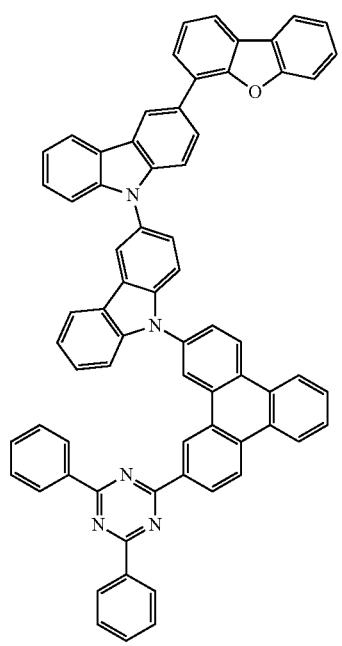
Compound 873
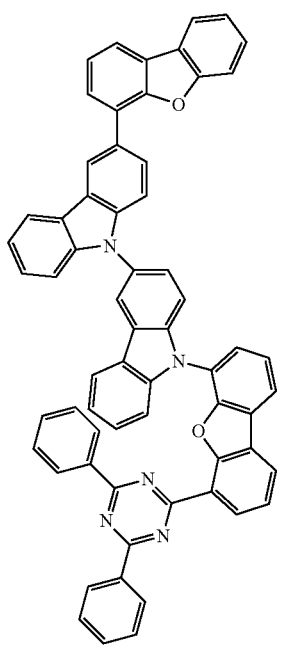
Compound 869
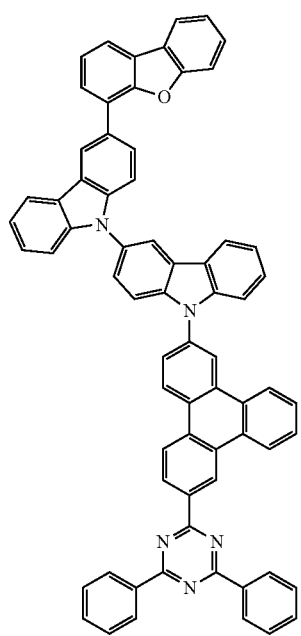
Compound 877
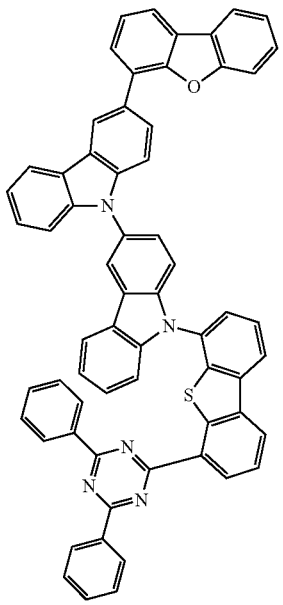

Compound 889
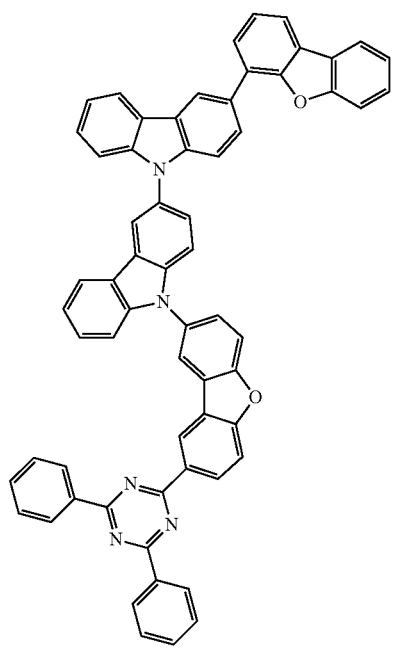
Compound 1029
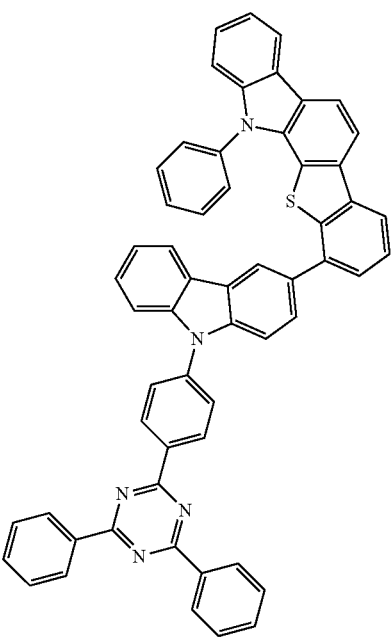
Compound 893
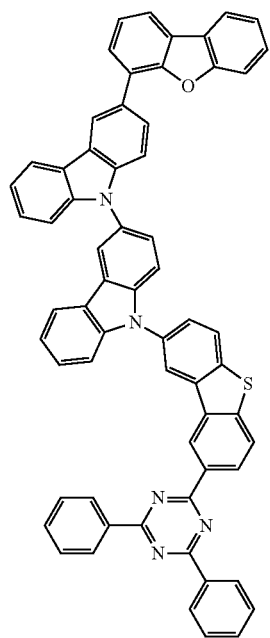
Compound 1025
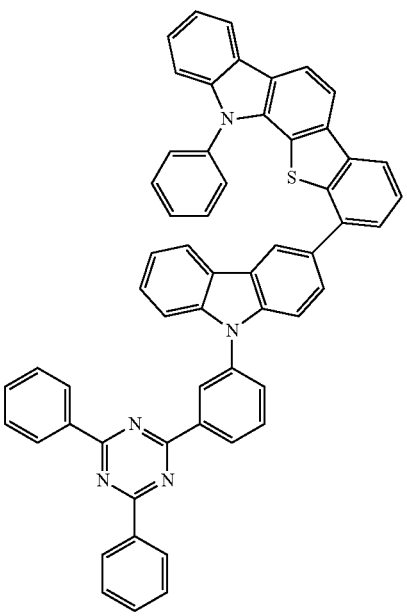

Compound 1037
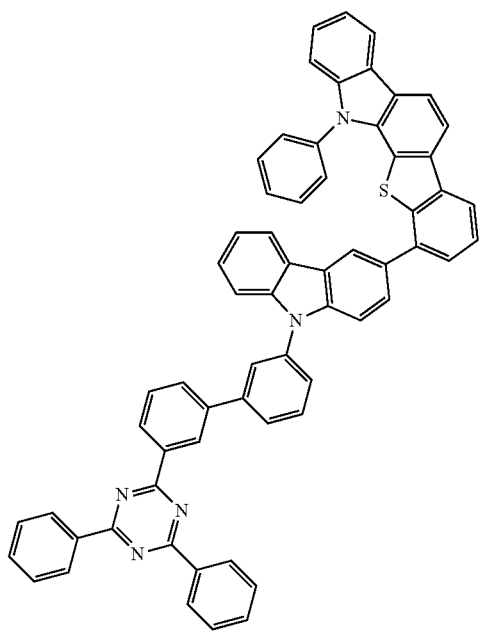
Compound 1033
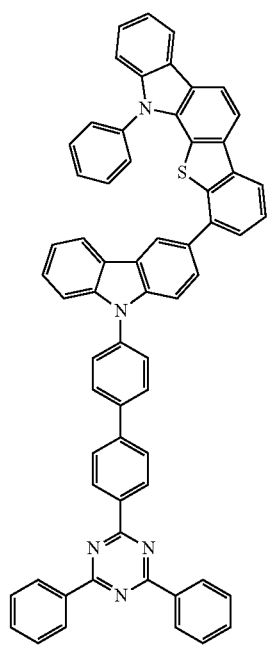
Compound 1057
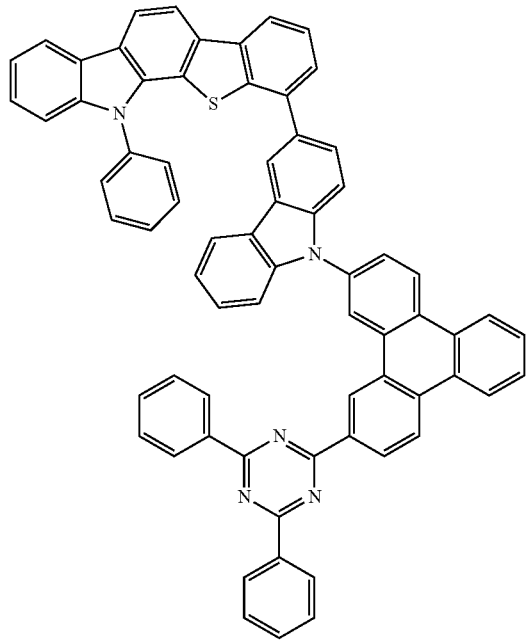
Compound 1061
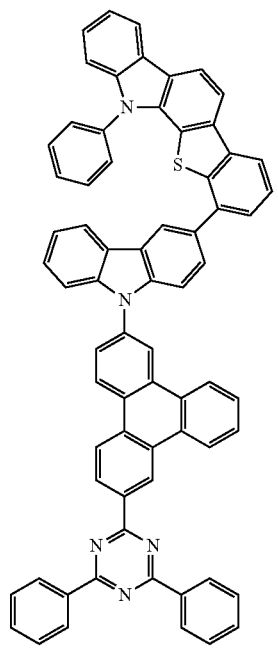

Compound 1065
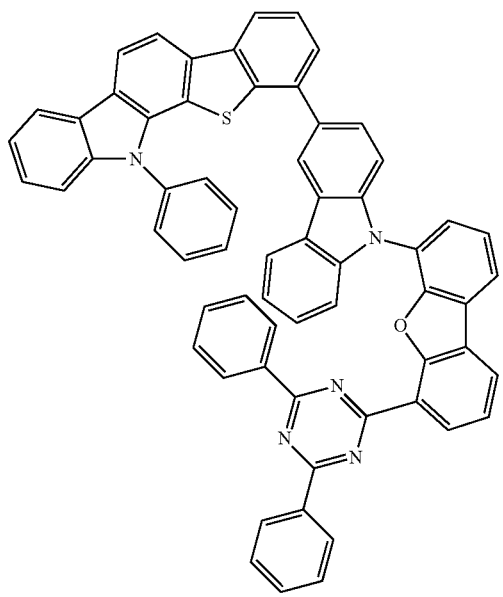
Compound 1081
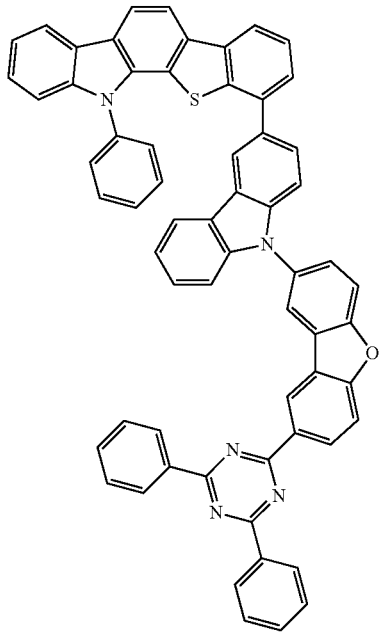
Compound 1069
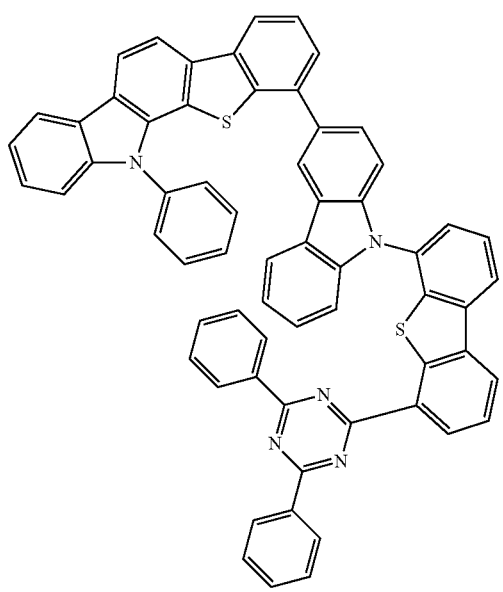
Compound 1085
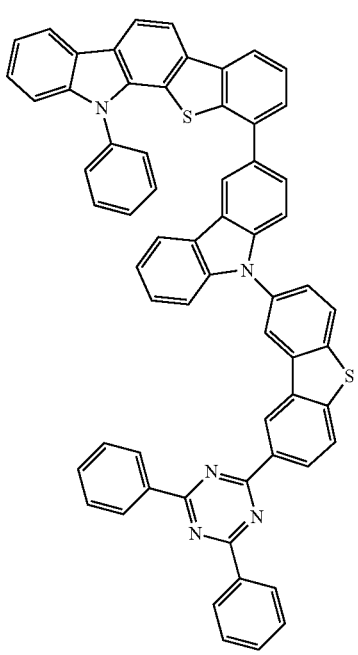

Compound 1093
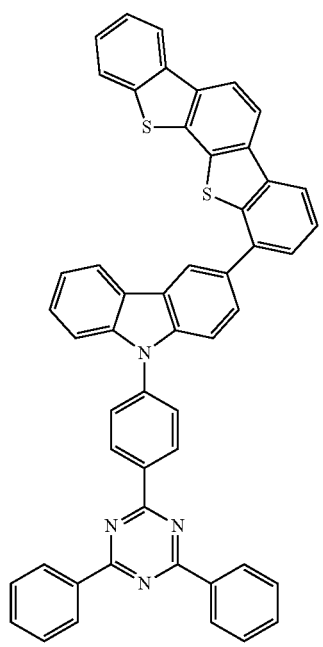
Compound 1111
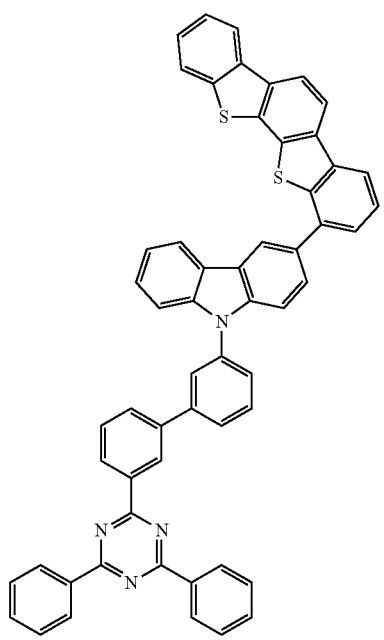
Compound 1089
Compound 1097
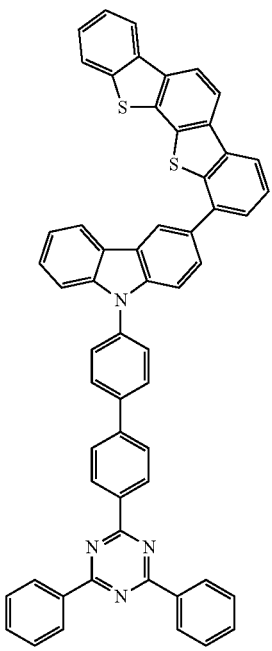

-continued
Compound 1121
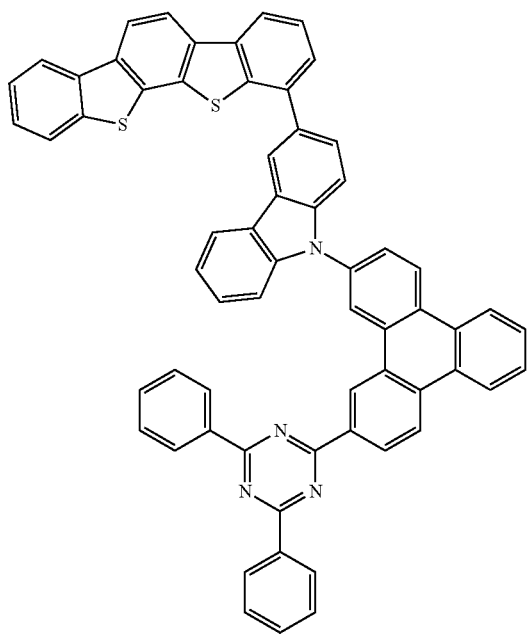
Compound 1125
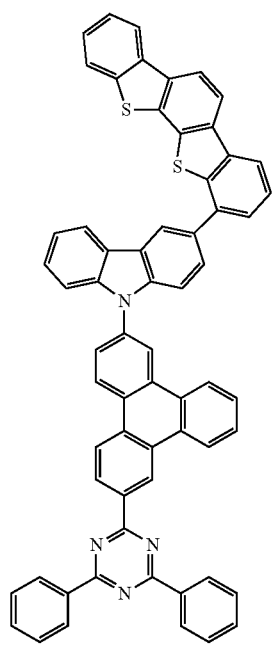
-continued
Compound 1129
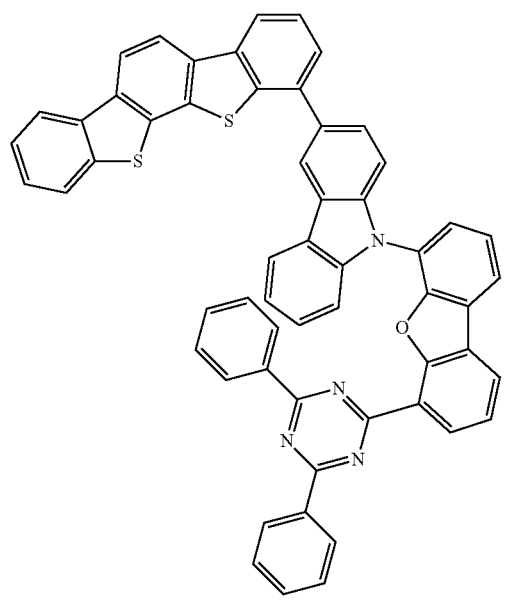
Compound 1133
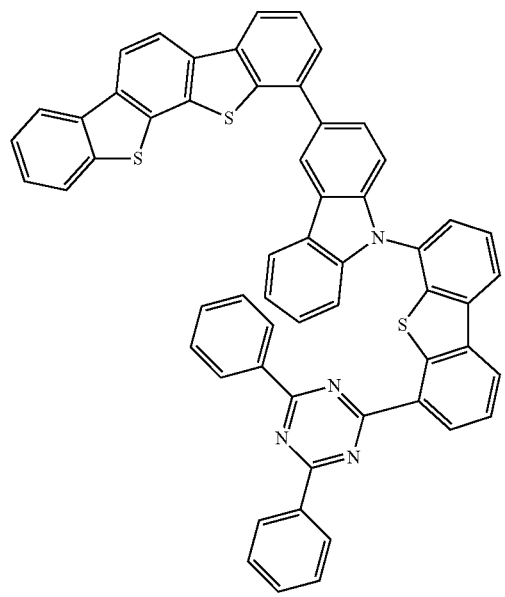

Compound 1145
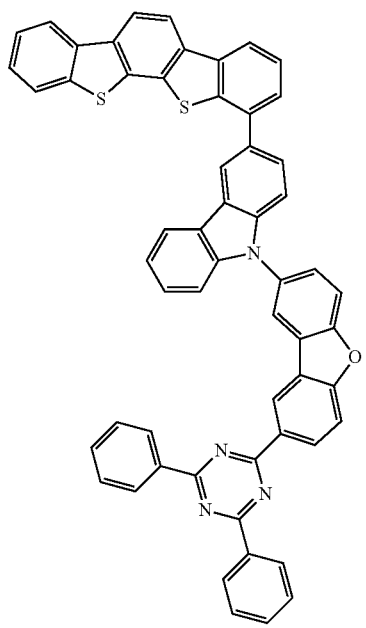
Compound 1157
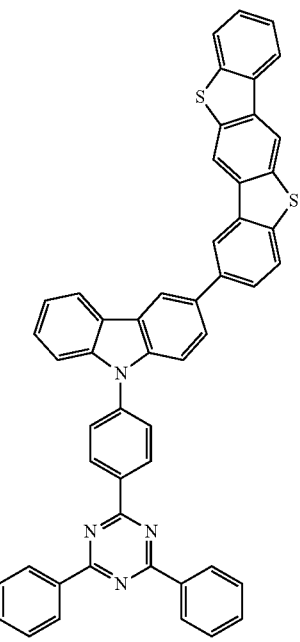
Compound 1149
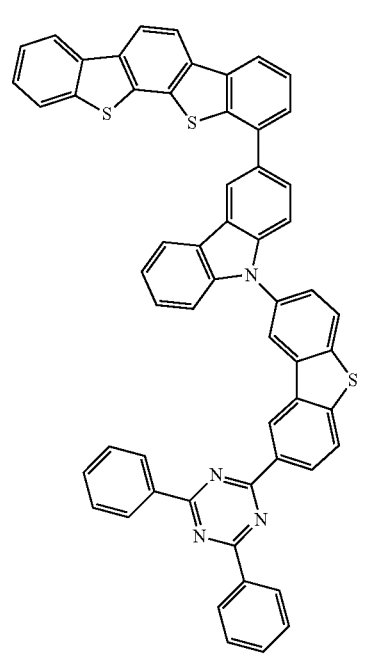
Compound 1153
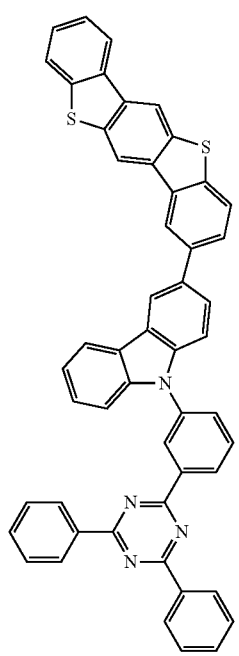

Compound 1165
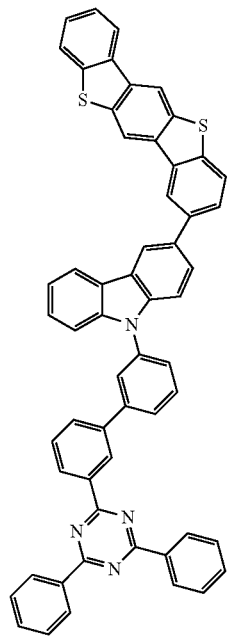
Compound 1185
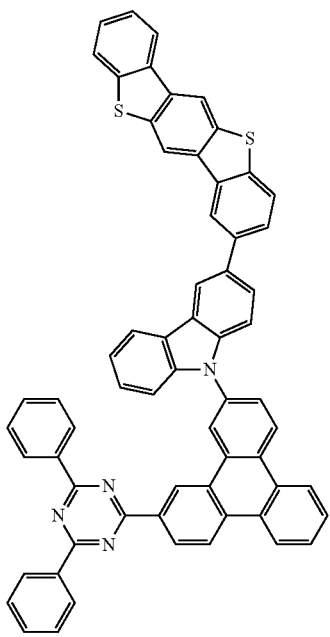
Compound 1161
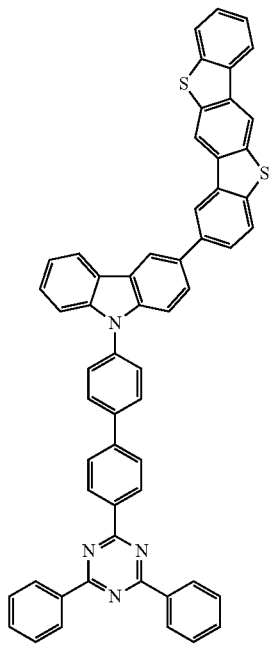
Compound 1189
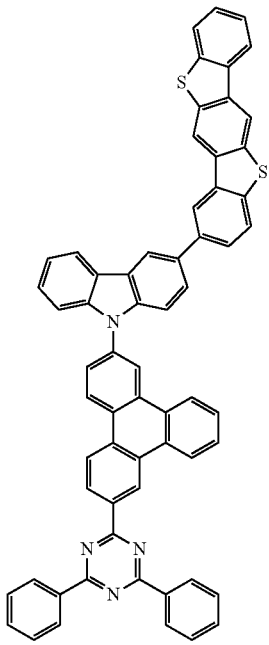

-continued
Compound 1193
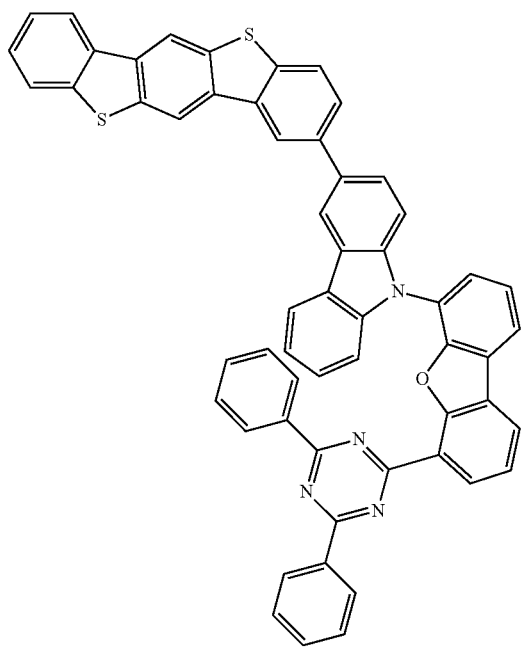
Compound 1197
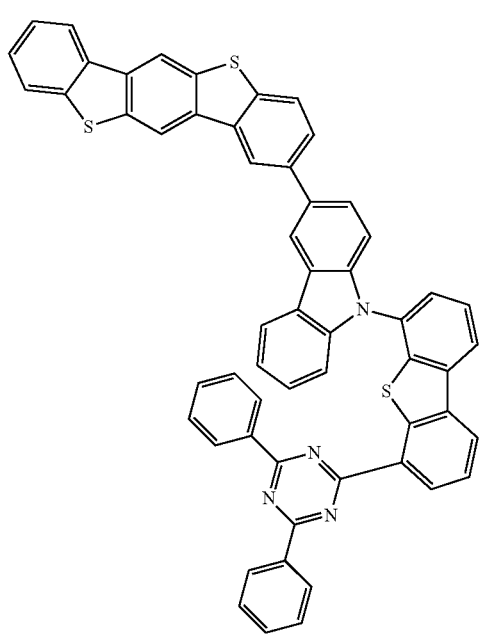
-continued
Compound 1209
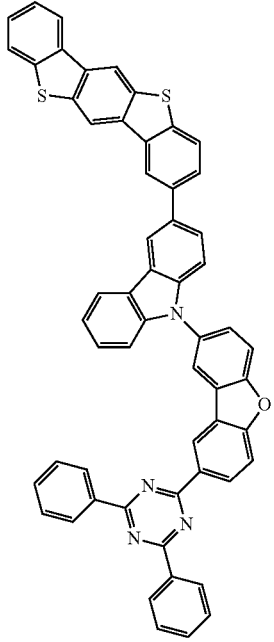
Compound 1213
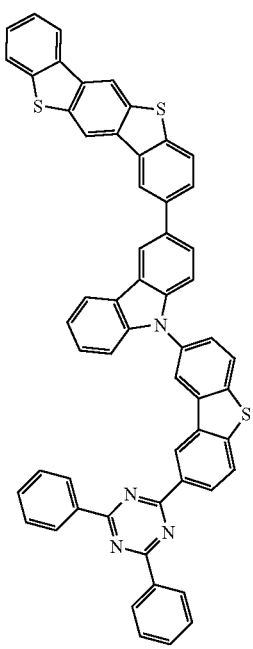

Compound 1221
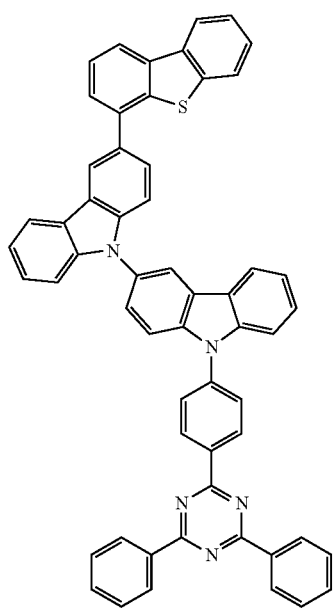
Compound 1229
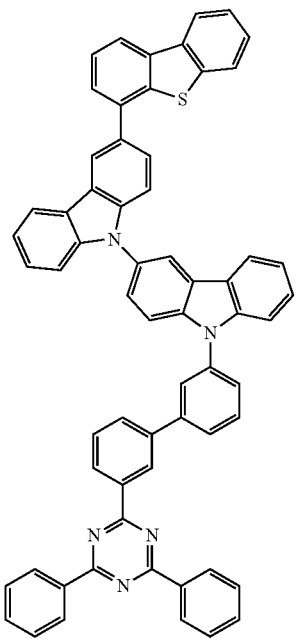
Compound 1217
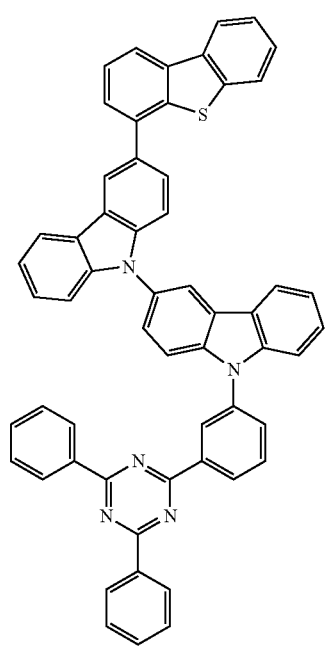
Compound 1225
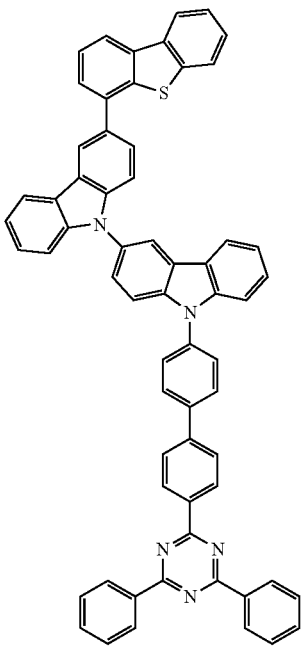

Compound 1249
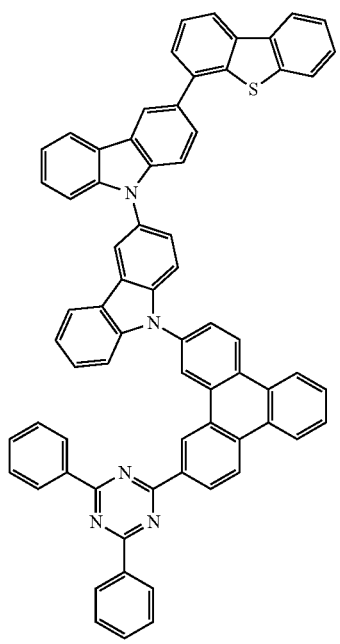
Compound 1253
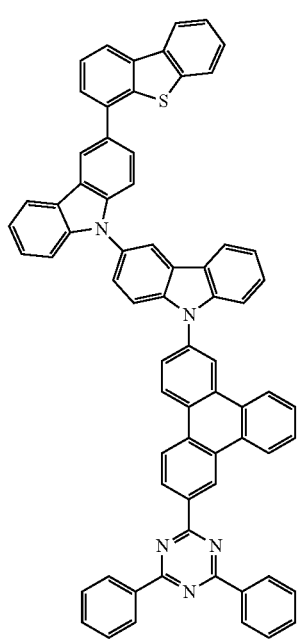
Compound 1257
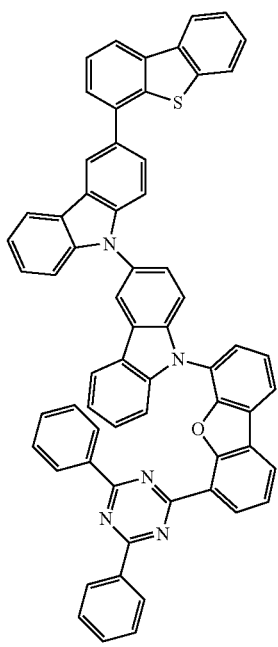
Compound 1261
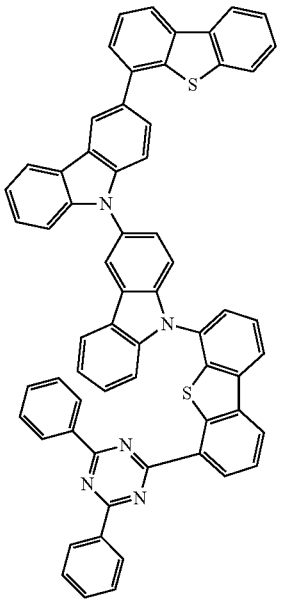

Compound 1173
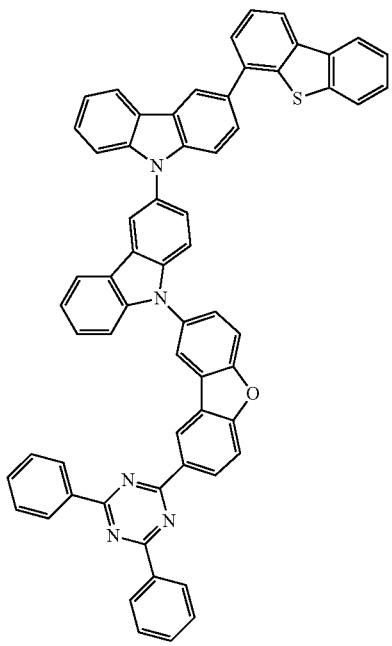
Compound 1477
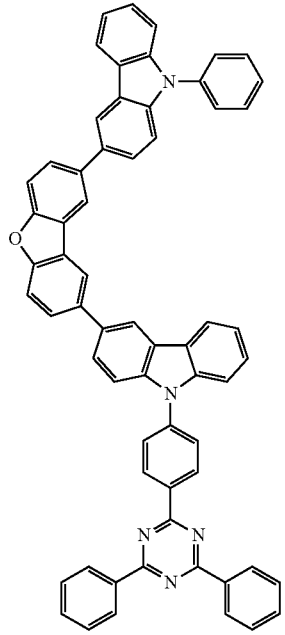
Compound 1177
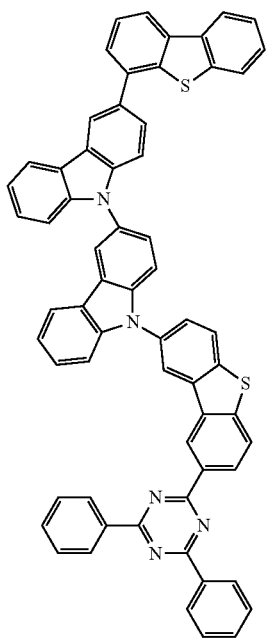
Compound 1473
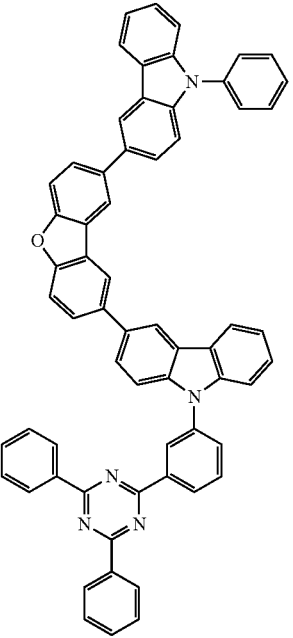

Compound 1485
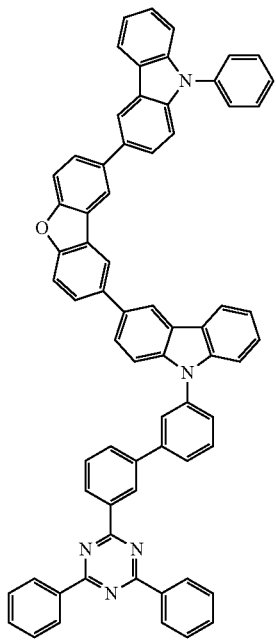
Compound 1505
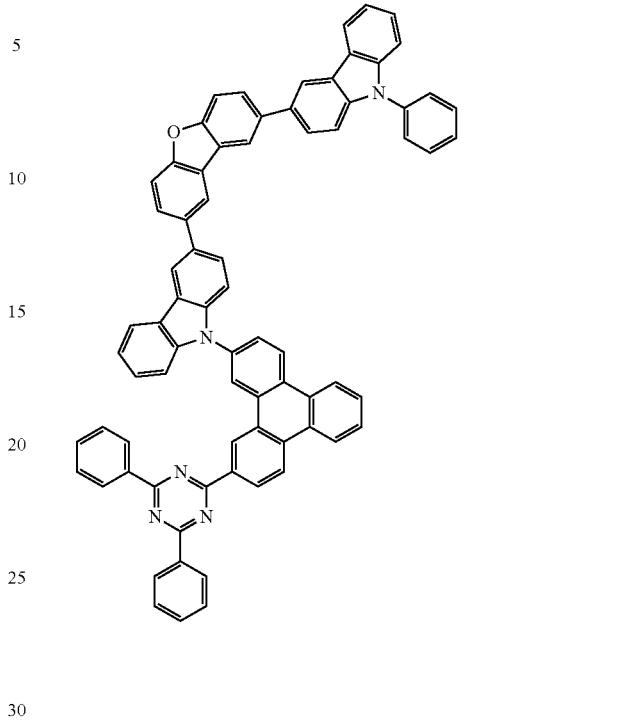
Compound 1481
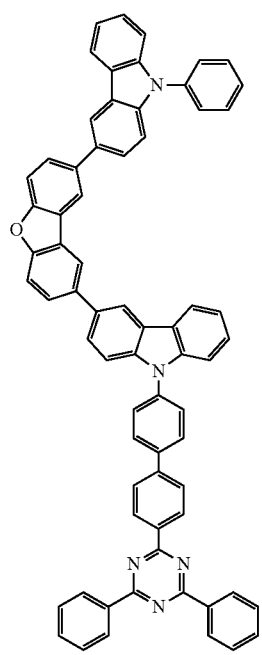
Compound 1509
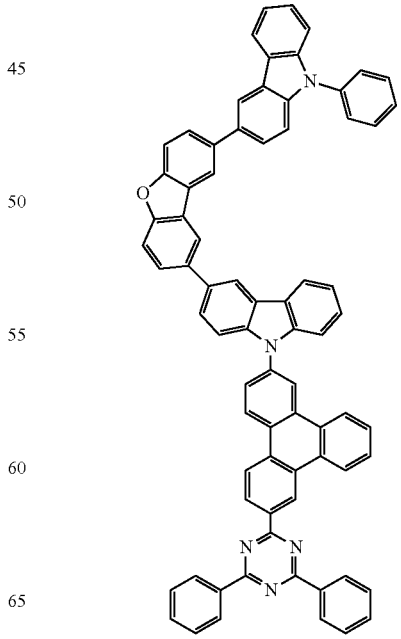

-continued
Compound 1513
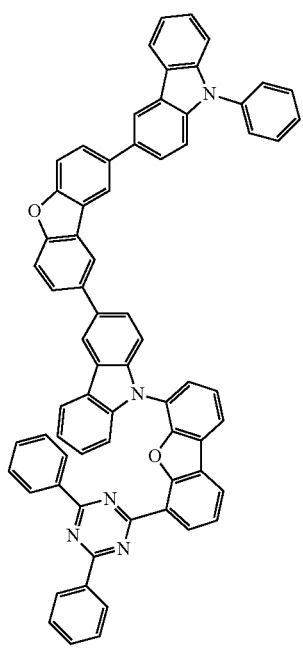
Compound 1529
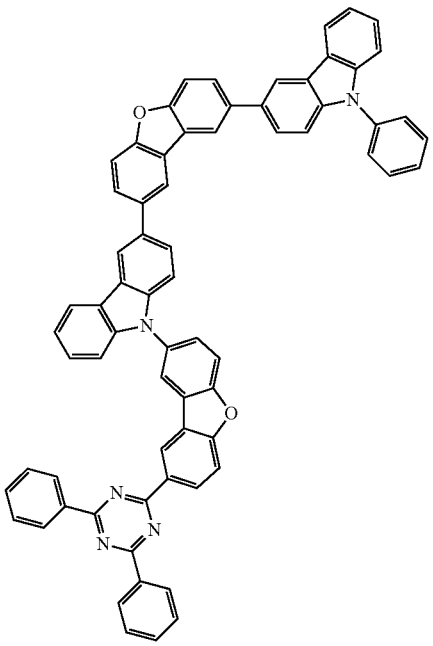
Compound 1517
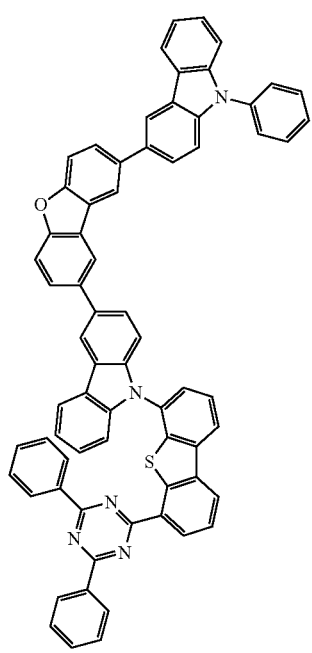
Compound 1533
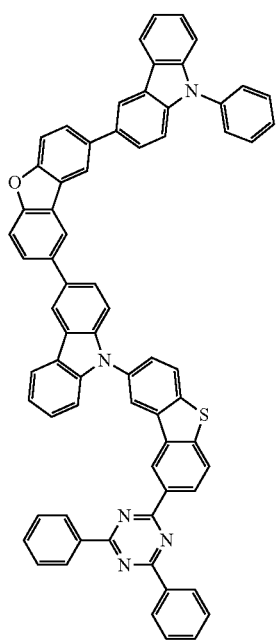

Compound 1605
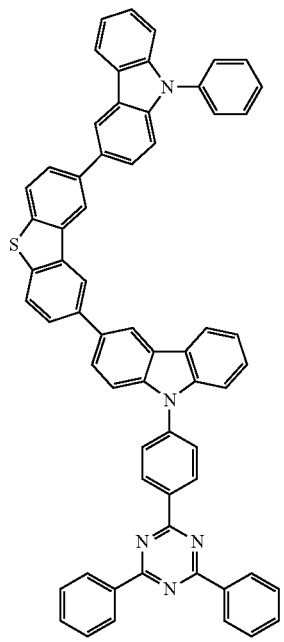
Compound 1613
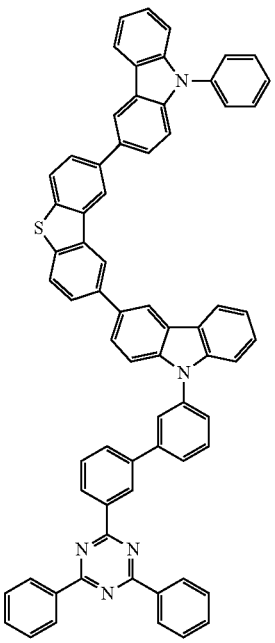
Compound 1601
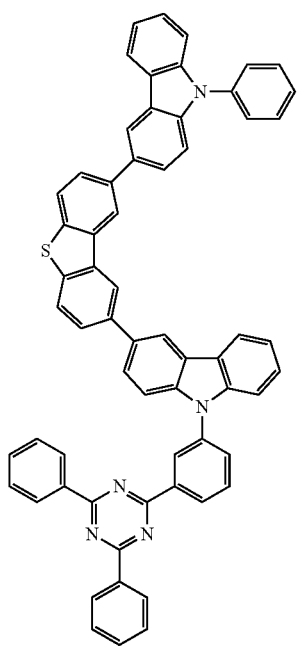
Compound 1609
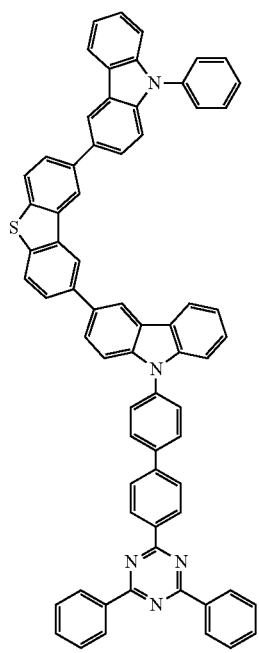

Compound 1633
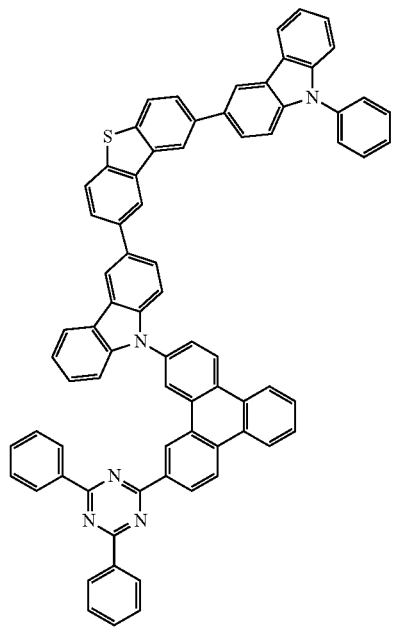
Compound 1641
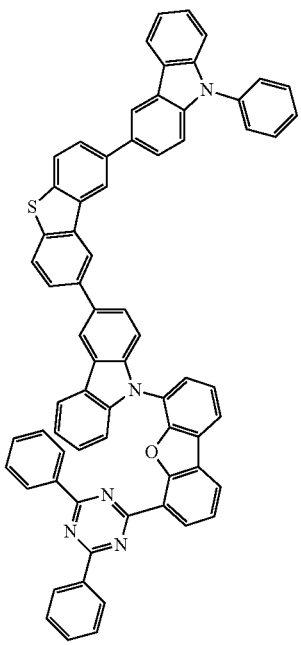
Compound 1637
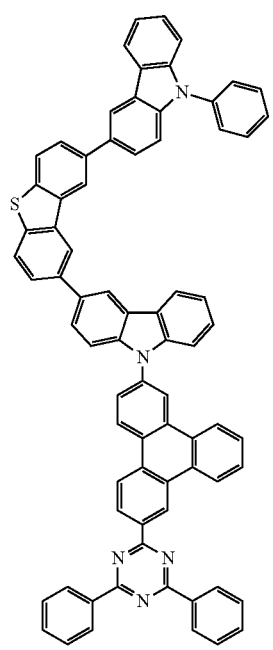
Compound 1645
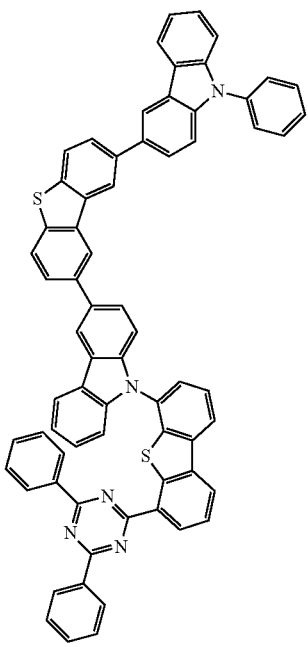

-continued
Compound 1657
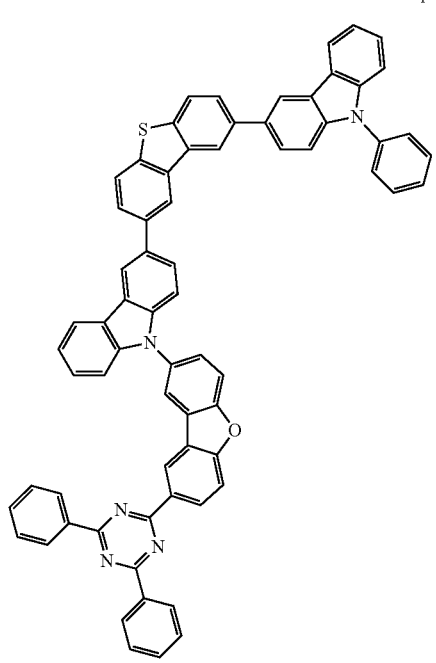
Compound 1669
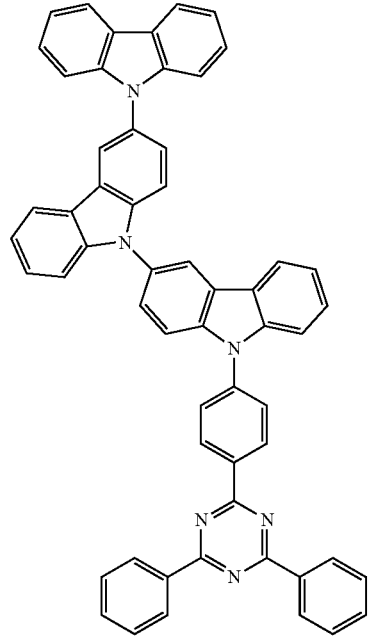
Compound 1661
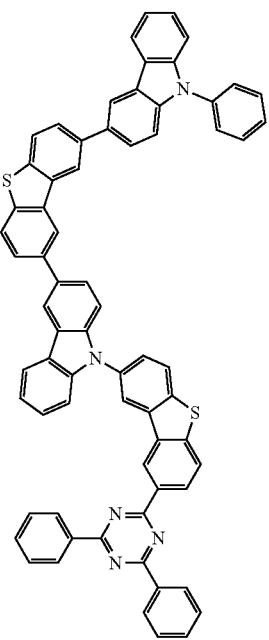
Compound 1665
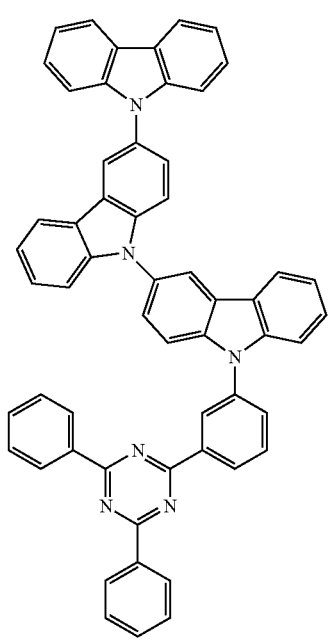

Compound 1677
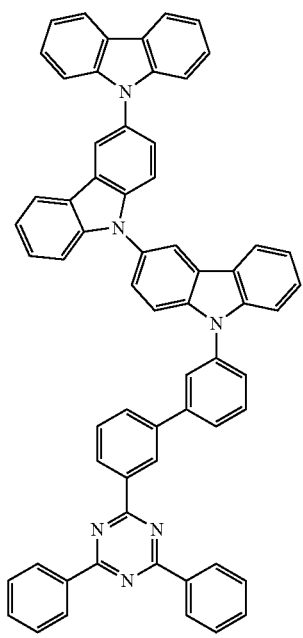
Compound 1697
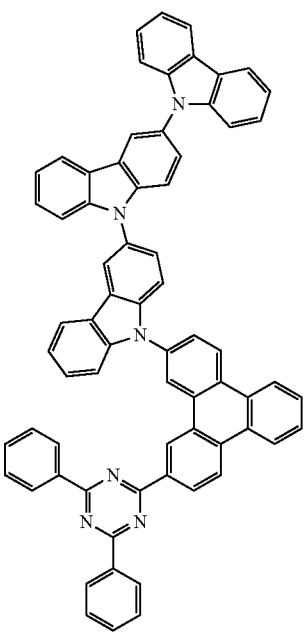
Compound 1673
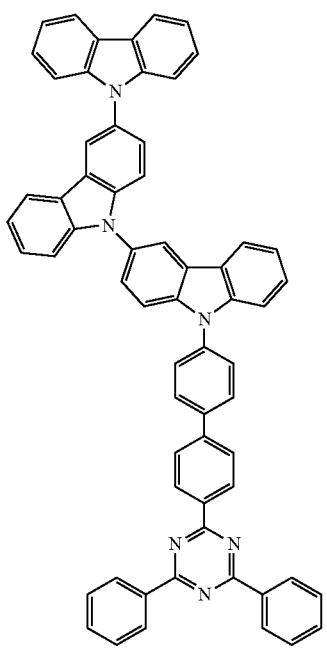
Compound 1701
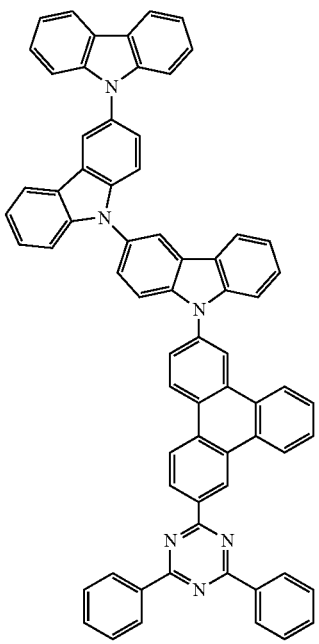

Compound 1705
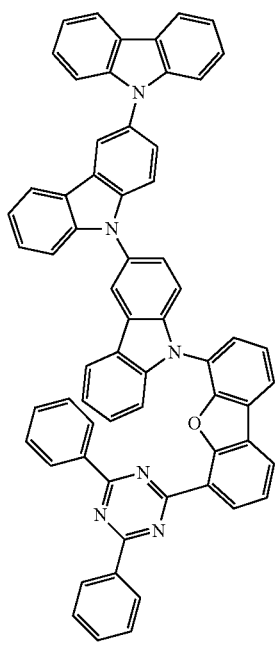
Compound 1721
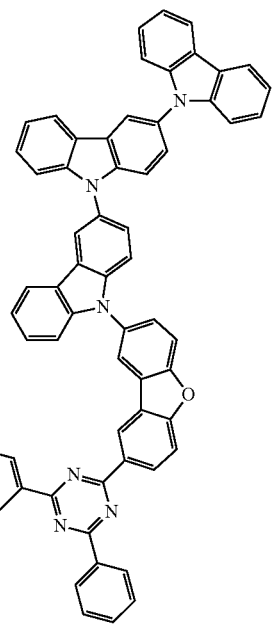
Compound 1709
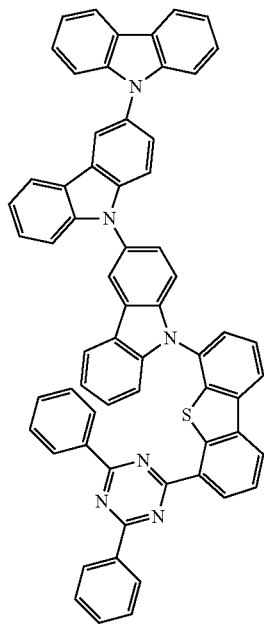
Compound 1725
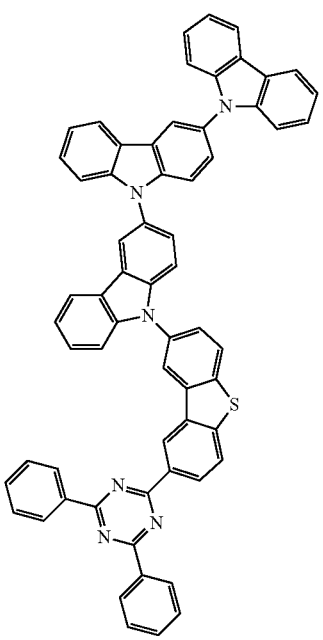

Compound 1797
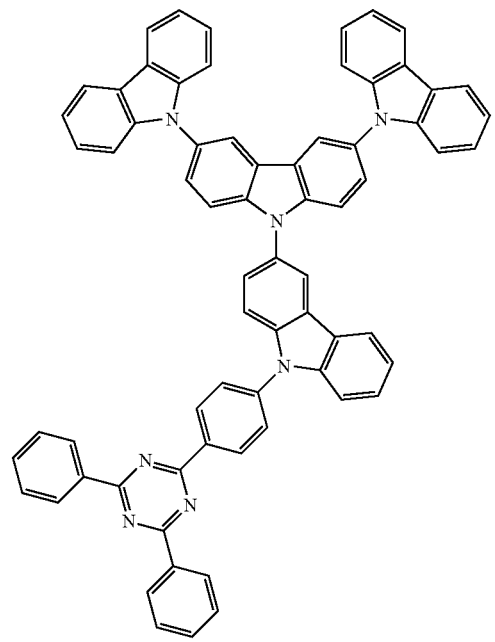
Compound 1805
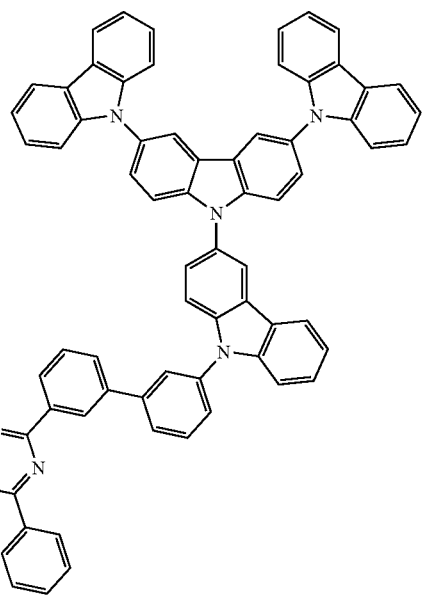
Compound 1793
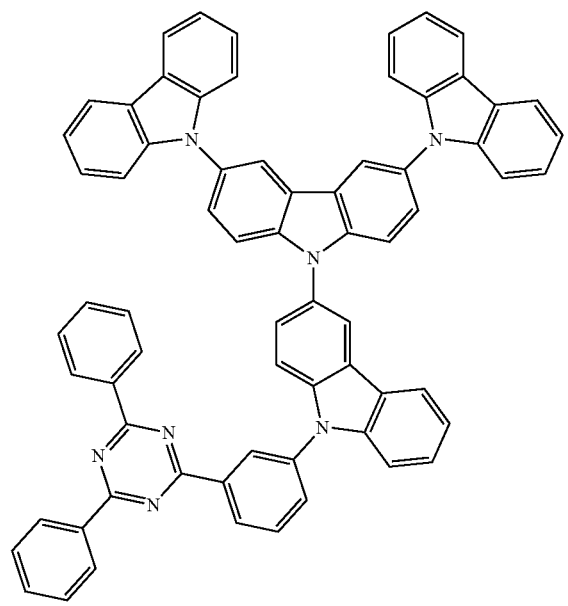
Compound 1801
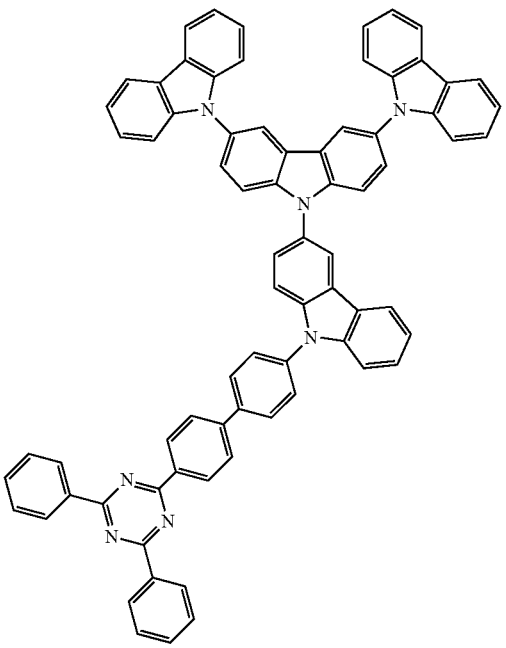

Compound 1833
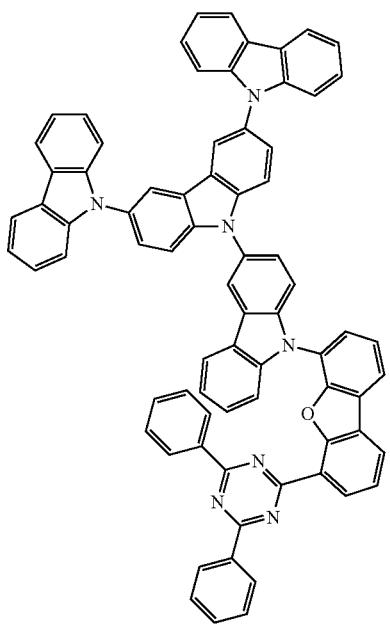
Compound 1853
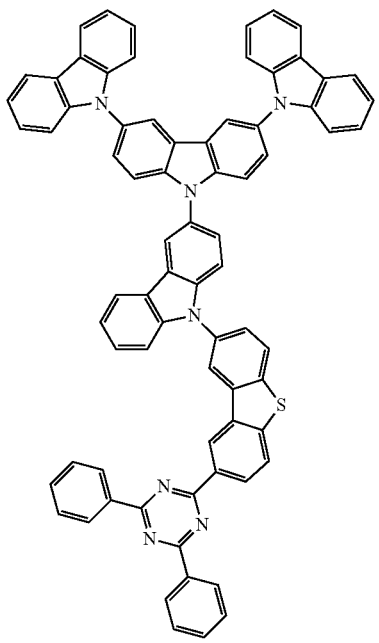
Compouns 1837
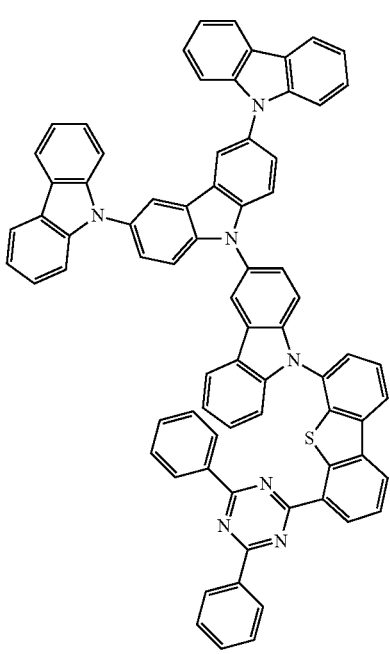
Compound 1849
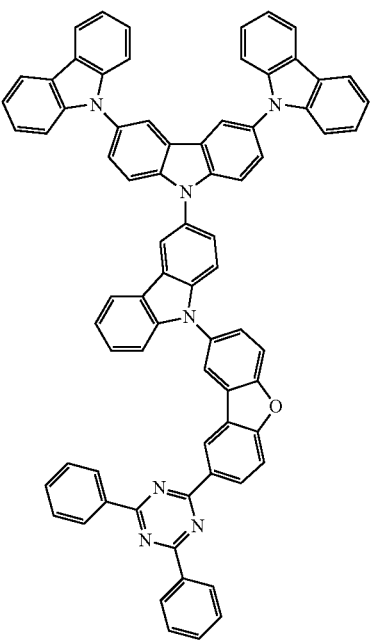

Compound 1861
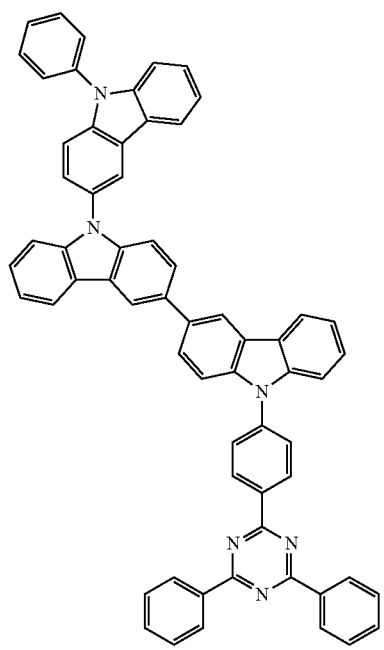
Compound 1857
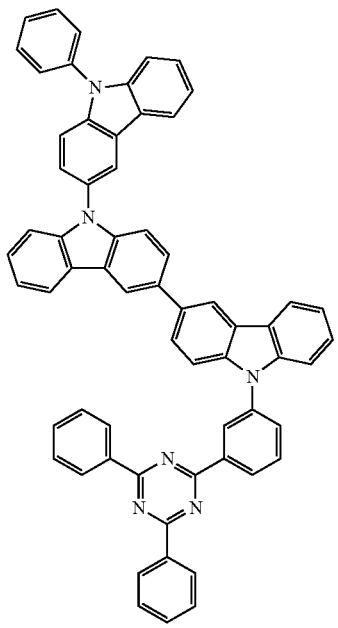
Compound 1869
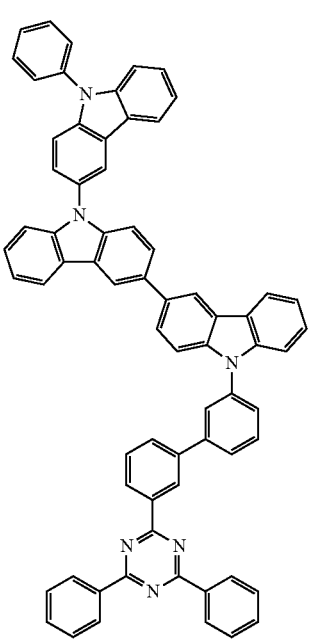
Compound 1865
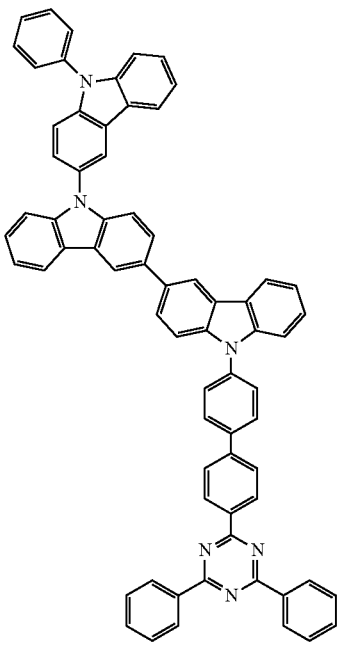

-continued
Compound 1889
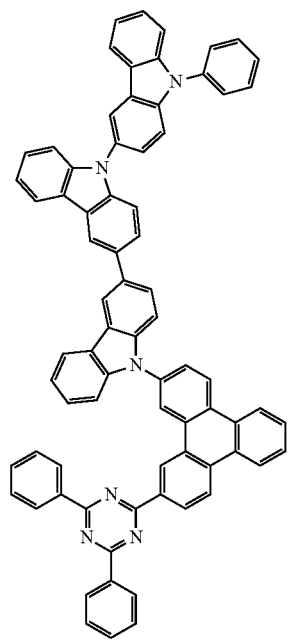
Compound 1897
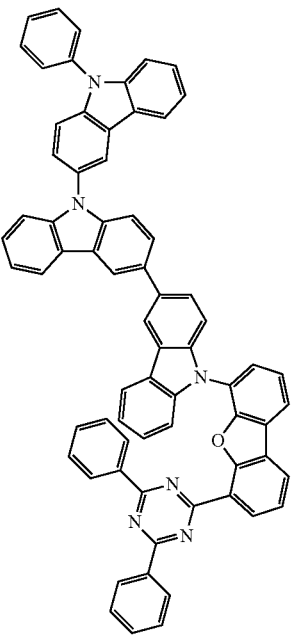
Compouund 1893
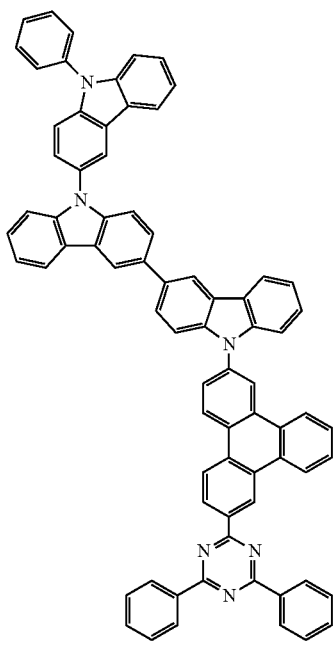
Compound 1901
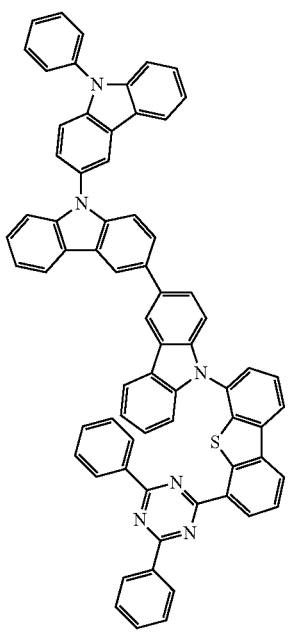

Compound 1913
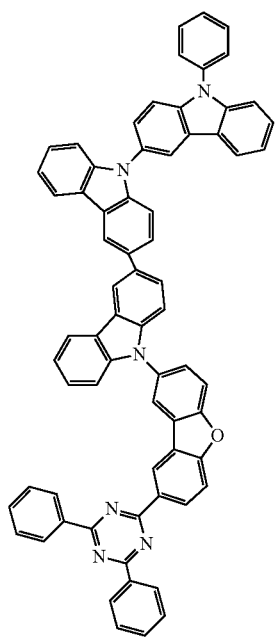
Compound 1989
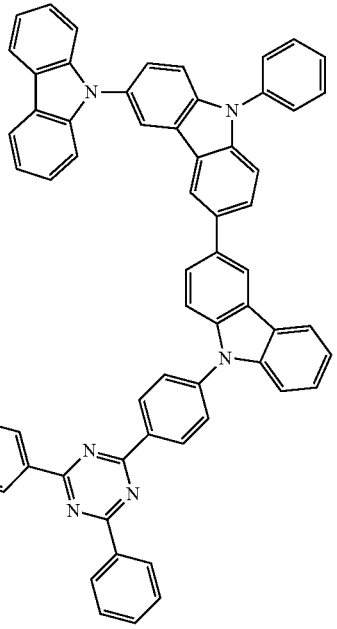
Compound 1917
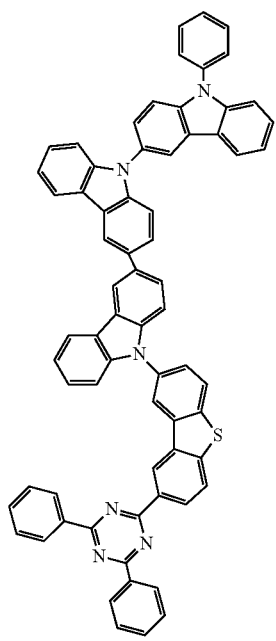
Compound 1985
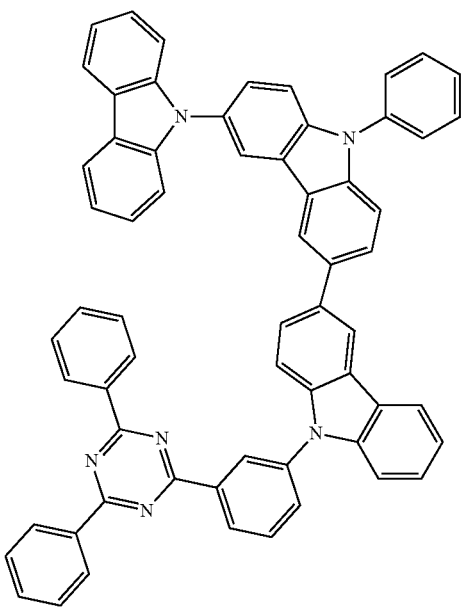

167
-continued
Compound 1997
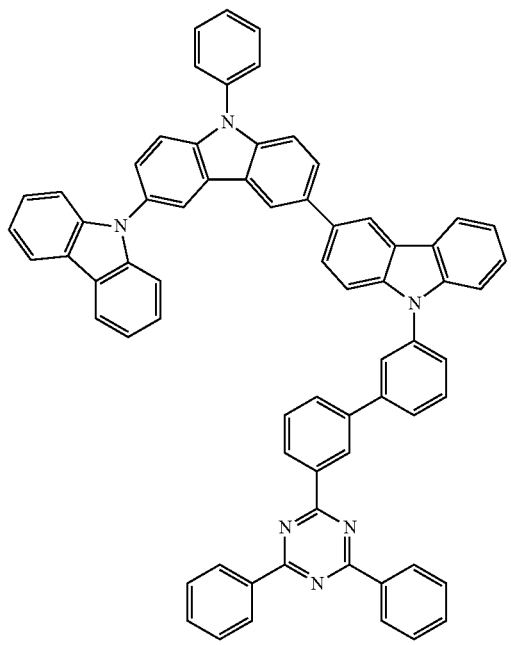
Compound 1993
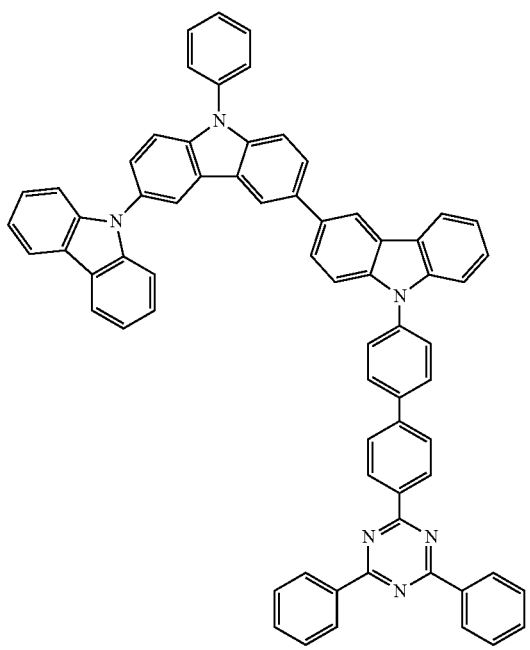
168
-continued
Compound 2017
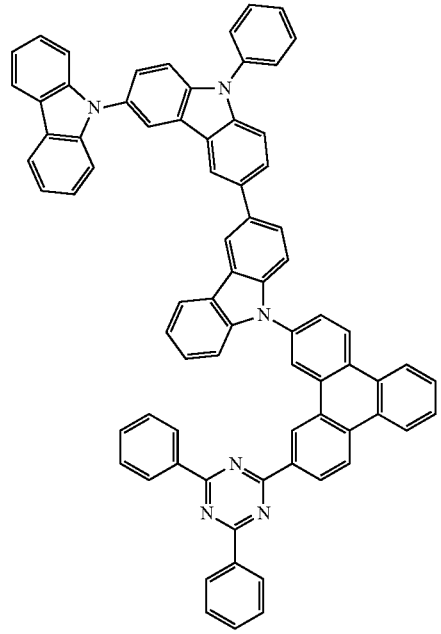
Compound 2021
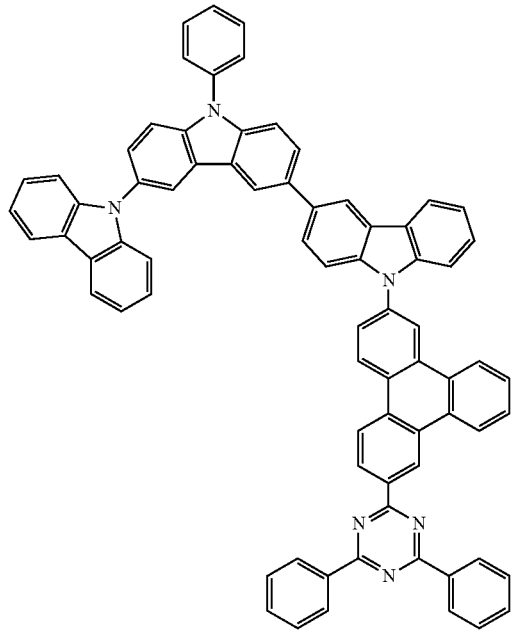

Compound 2025
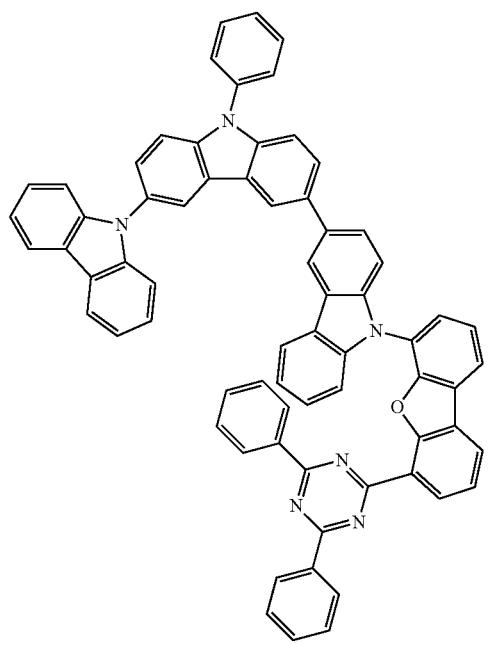
Compound 2029
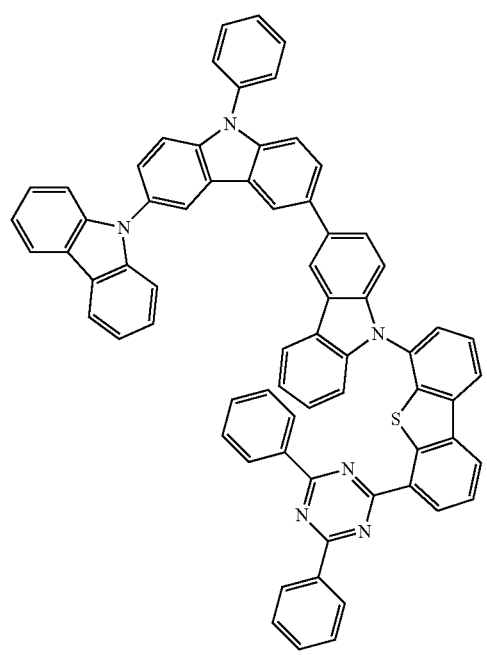
Compound 2041
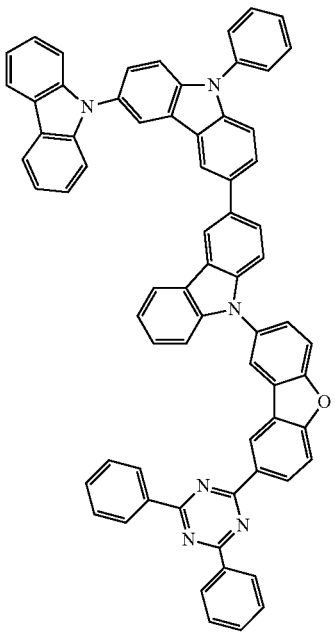
Compound 2045
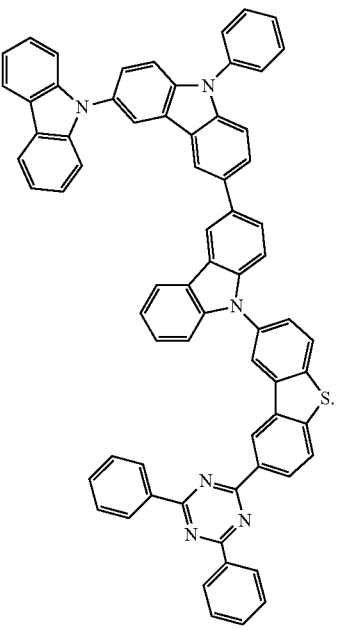
In one embodiment, a first device comprising a first organic light emitting device, further comprising an anode, a cathode; and an emissive layer, disposed between the anode and the cathode, wherein the emissive layer comprises a first emitting compound having the formula:

Formula I

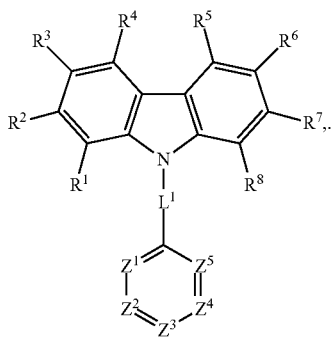

$Z^1$, $Z^2$, $Z^3$, $Z^4$ and $Z^5$ are each independently selected from group consisting of $CR^9$ and N, and any adjacent $R^9$ are optionally joined to form a fused ring. At least one of $Z^1$, $Z^2$, $Z^3$, $Z^4$ and $Z^5$ is N.

$L^1$ is selected from the group consisting of:

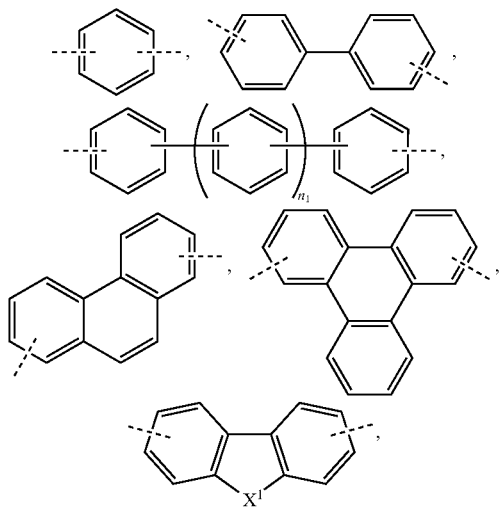

and combinations thereof;
where $X^1$ is O, S, or CRR' and R, R' are optionally joined to form a ring. $n_1$ is an integer from 1 to 20, and $L^1$ can be further substituted by a substituent selected from the group consisting of alkyl, aryl, and heteroaryl. At least one of $R^1$, $R^2$, $R^3$, $R^4$, $R^5$, $R^6$, $R^7$, and $R^8$ comprises an electron donor group.

Any two adjacent $R^1$, $R^2$, $R^3$, $R^4$, $R^5$, $R^6$, $R^7$, and $R^8$ are not joined to form a ring. $R^1$, $R^2$, $R^3$, $R^4$, $R^5$, $R^6$, $R^7$, and $R^8$ do not contain an electron acceptor group, and $R^9$ does not contain an electron donor group.

$R^1$, $R^2$, $R^3$, $R^4$, $R^5$, $R^6$, $R^7$, and $R^8$ are independently selected from the group consisting of hydrogen, deuterium, alkyl, cycloalkyl, arylalkyl, alkoxy, aryloxy, amino, silyl, alkenyl, cycloalkenyl, heteroalkenyl, alkynyl, aryl, heteroaryl, and combinations thereof; and $R^9$, R, and R' are independently selected from the group consisting of hydrogen, deuterium, alkyl, cycloalkyl, heteroalkyl, arylalkyl, silyl, alkenyl, cycloalkenyl, heteroalkenyl, alkynyl, aryl, heteroaryl, and combinations thereof.

In one embodiment, the electron donor group comprises at least one chemical group selected from the group consisting of amino, indole, carbazole, benzothiohpene, benzo- furan, benzoselenophene, dibenzothiophene, dibenzofuran, dibenzoselenophene, and combinations thereof.

In one embodiment, the electron donor group comprises at least one chemical group selected from the group consisting of:

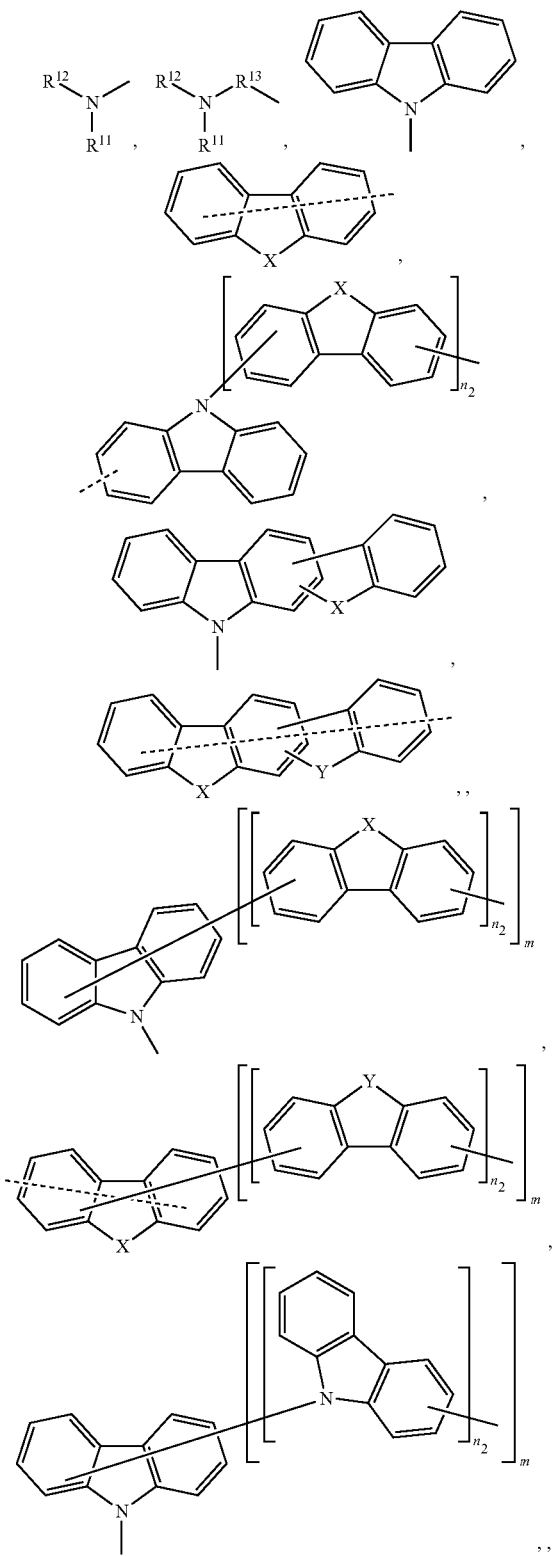

-continued
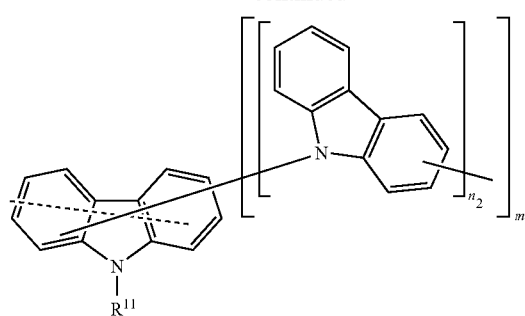
, and
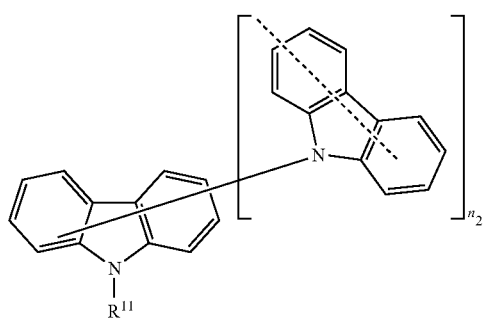
,
where X and Y are selected from the group consisting of O, S, NR$^{14}$, m is an integer from 1 to 20, n$_2$ is an integer from 1 to 20, and where R$^{11}$, R$^{12}$, R$^{13}$ and R$^{14}$ are selected from the group consisting of aryl and heteroaryl.
In one embodiment, the donor group is selected from the group consisting of:
D$^1$
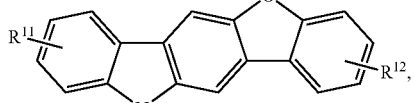
D$^2$
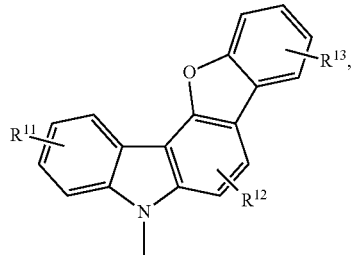
D$^3$
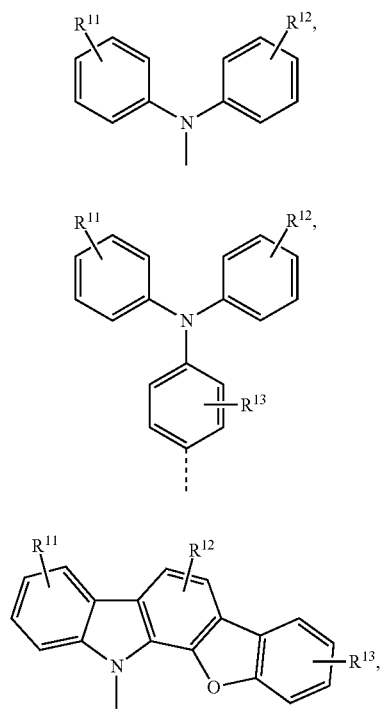
-continued
D$^4$
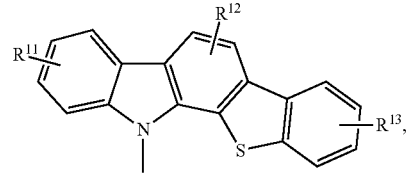
D$^5$
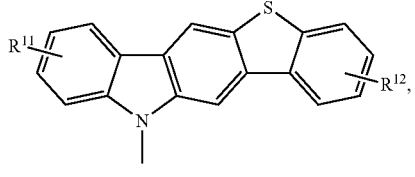
D$^6$
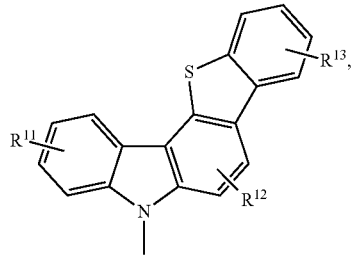
D$^7$
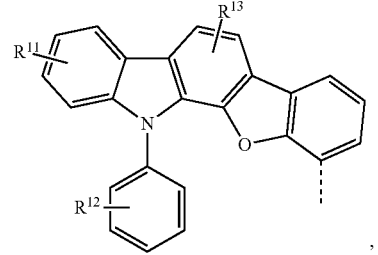
D$^8$
D$^9$
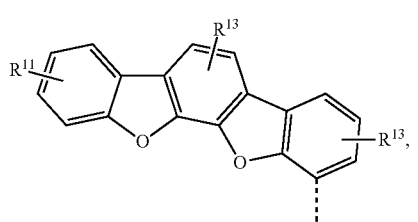
,
D$^{10}$

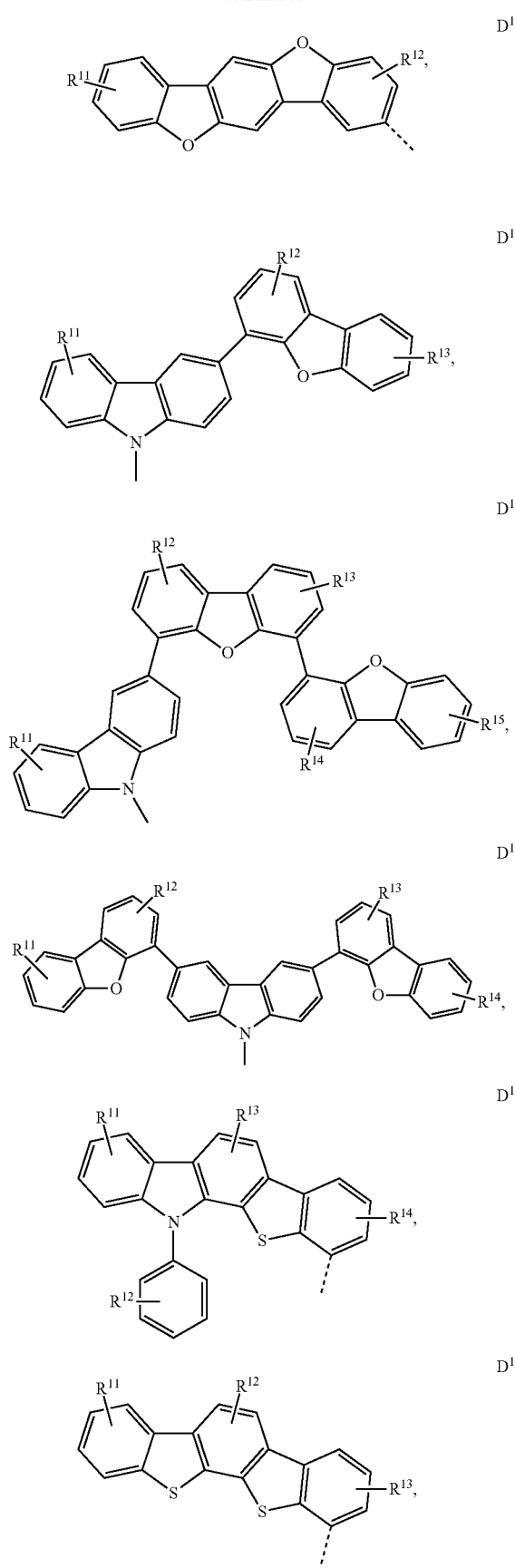
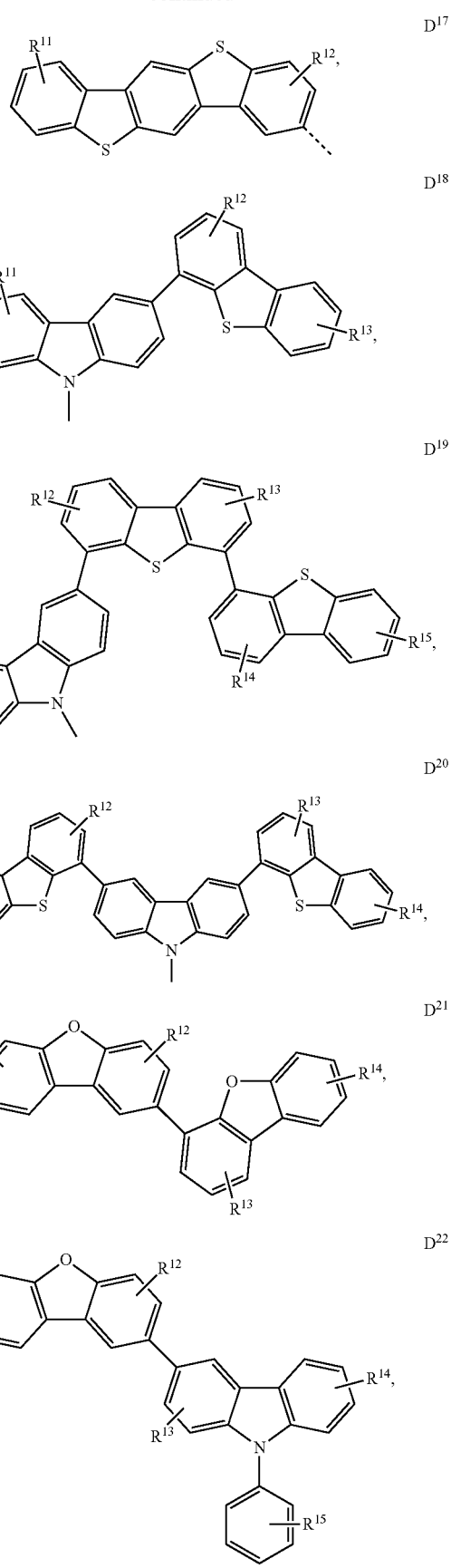

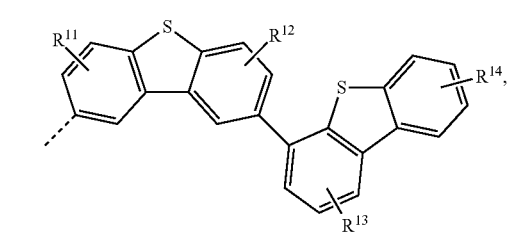 D23
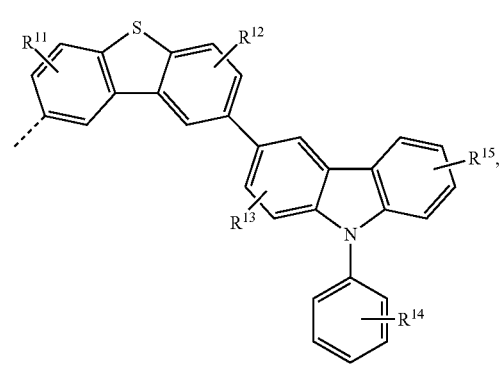 D24
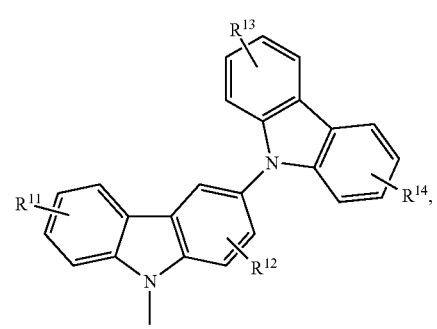 D25
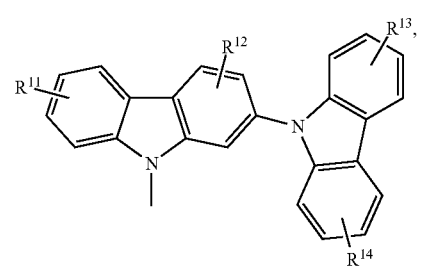 D26
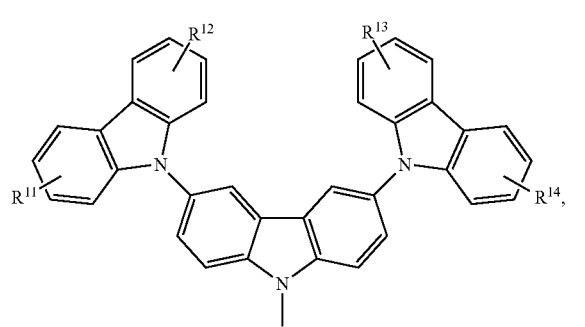 D27
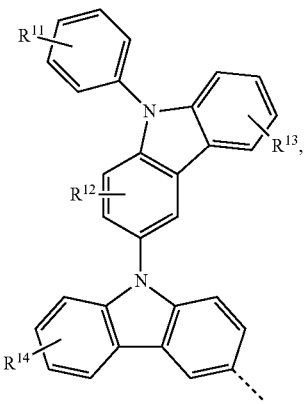 D28
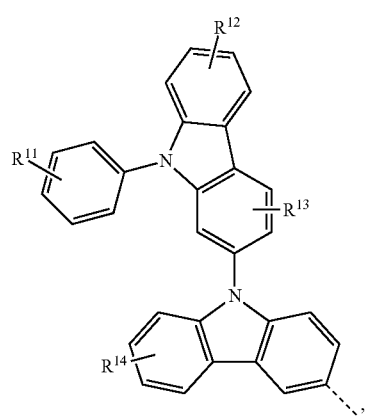 D29
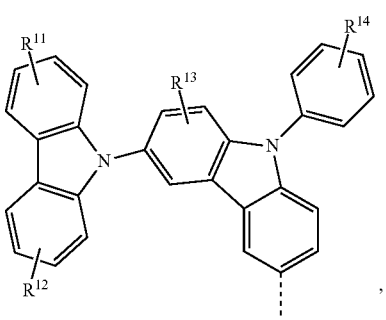 D30
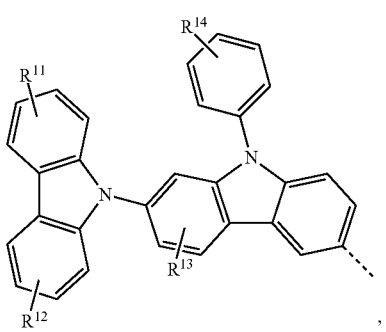 D31

-continued
D32 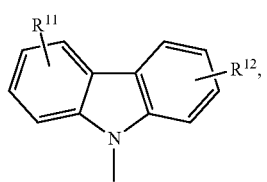
D33 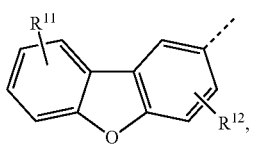
D34 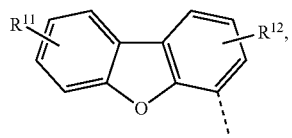
D35 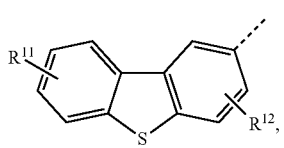
D36 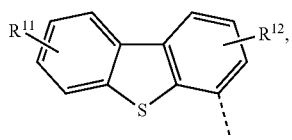
D37 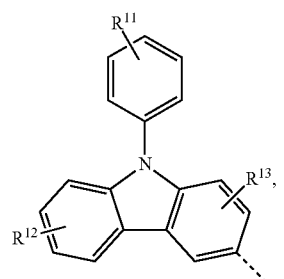
D38 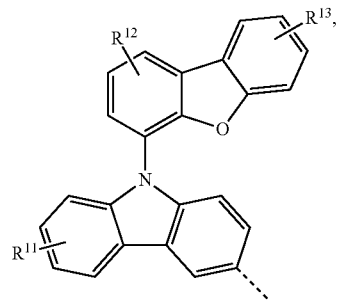
-continued
D39 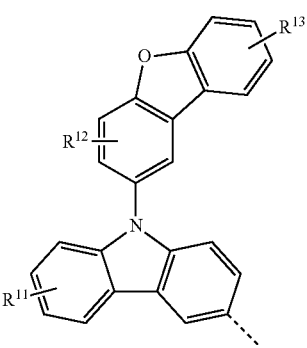, and
D40 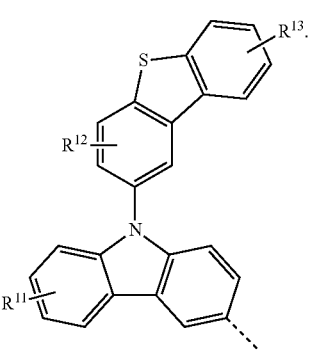
In one embodiment, the first emitting compound having the formula:
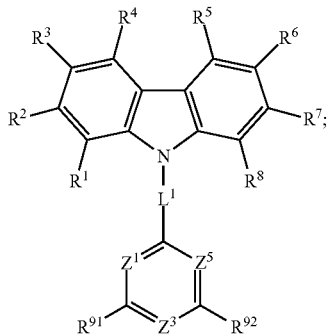
and
wherein $R^{91}$ and $R^{92}$ are independently selected from aryl or heteroaryl, and can be further substituted.
In one embodiment, the electron donor group has a formula selected from the group consisting of:
D101 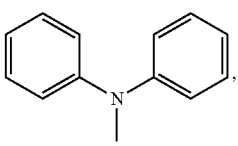

181
-continued
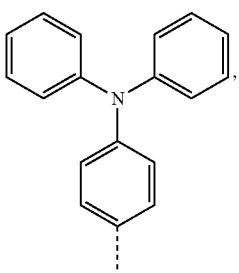 D102
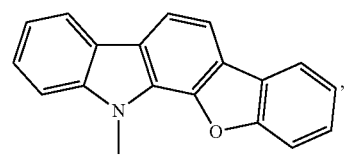 D103
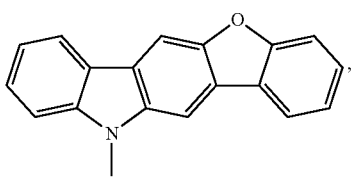 D104
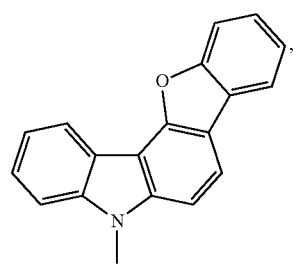 D105
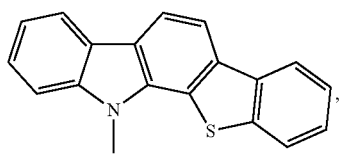 D106
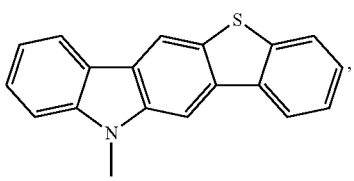 D107
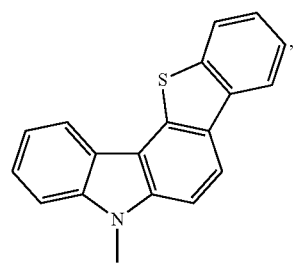 D108
182
-continued
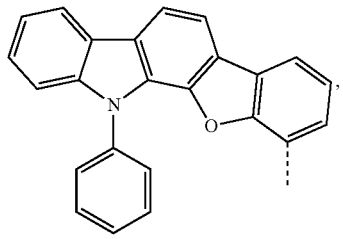 D109
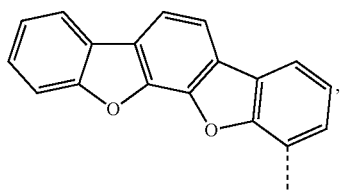 D110
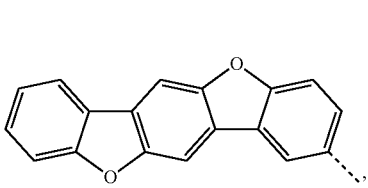 D111
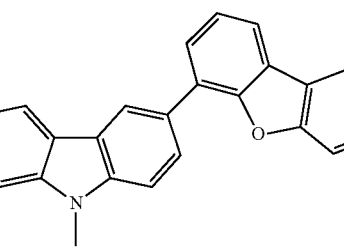 D112
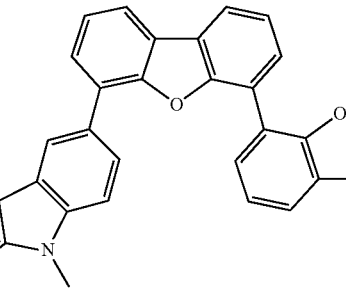 D113
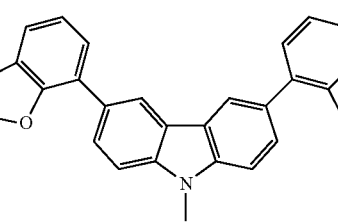 D114

-continued
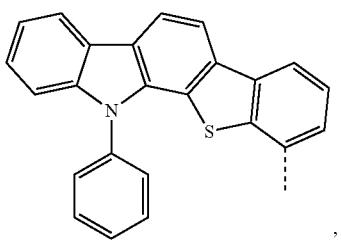
D115
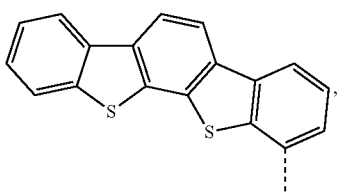
D116
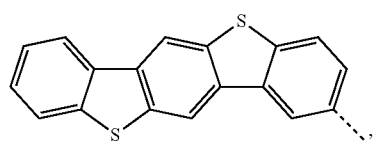
D117
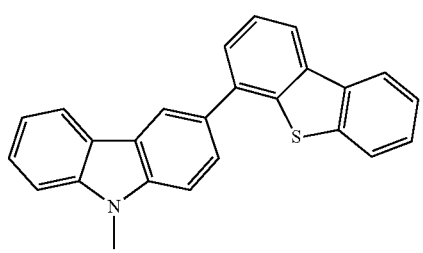
D118
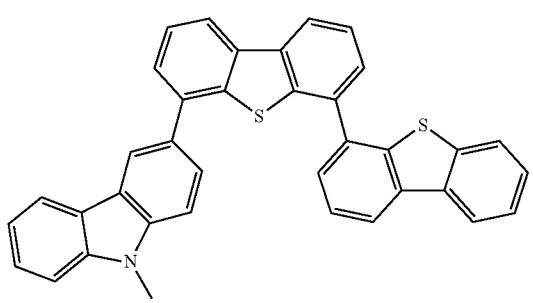
D119
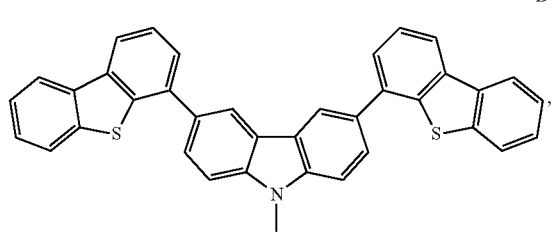
D120
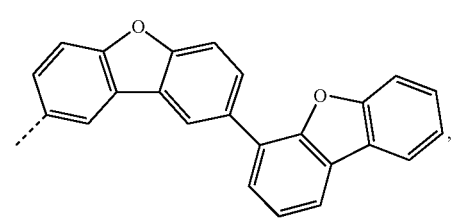
D121
-continued
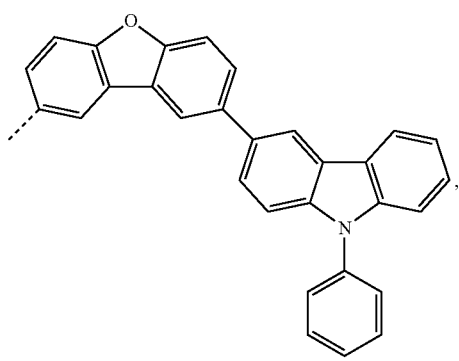
D122
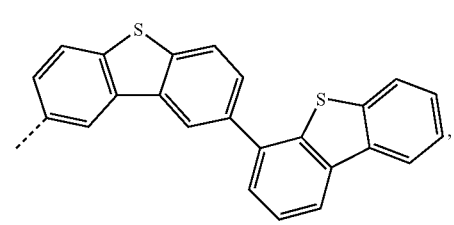
D123
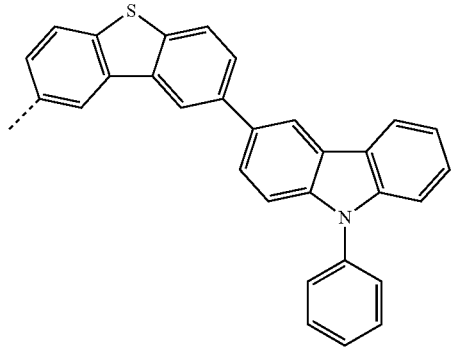
D124
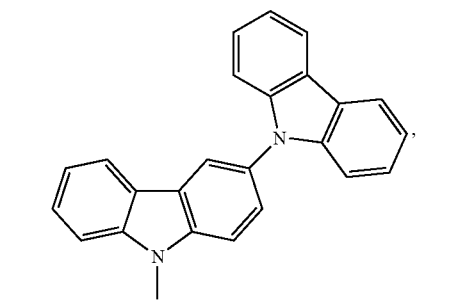
D125
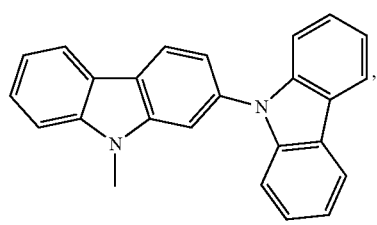
D126

-continued
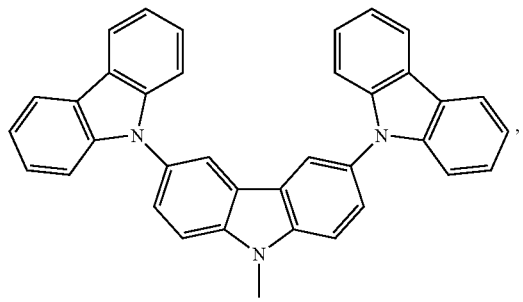 D127
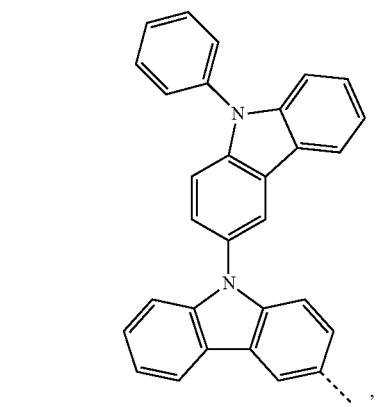 D128
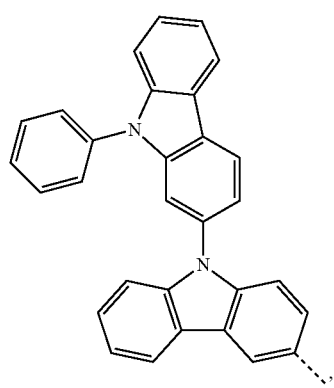 D129
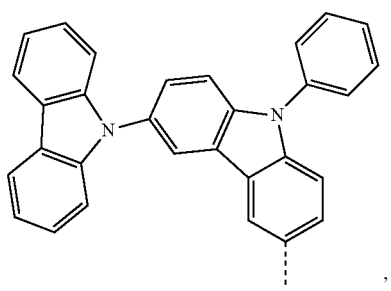 D130
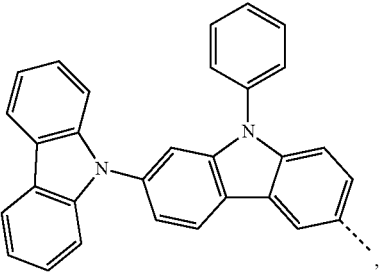 D131
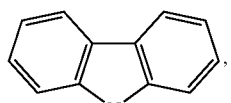 D132
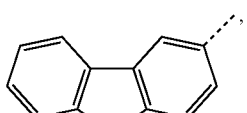 D133
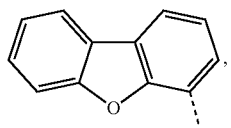 D134
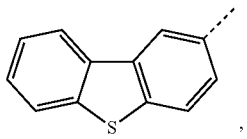 D135
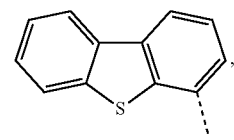 D136
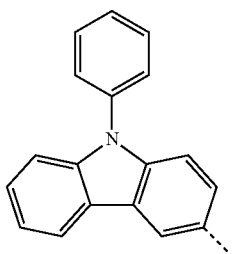 D137
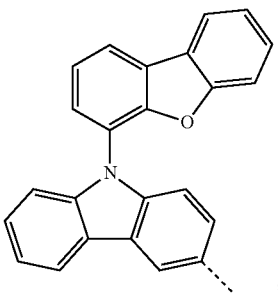 D138

-continued
D<sup>139</sup>
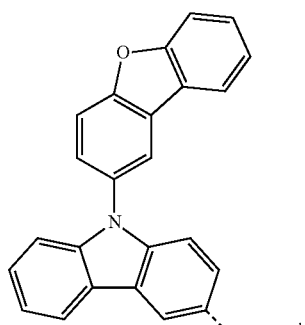
, and
D<sup>140</sup>
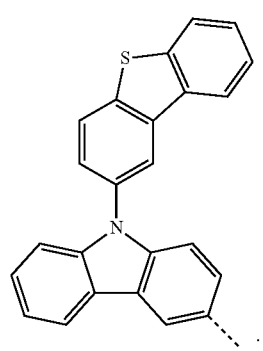
.
In one embodiment, the first emitting compound has a formula selected from the group consisting of:
Compound 1
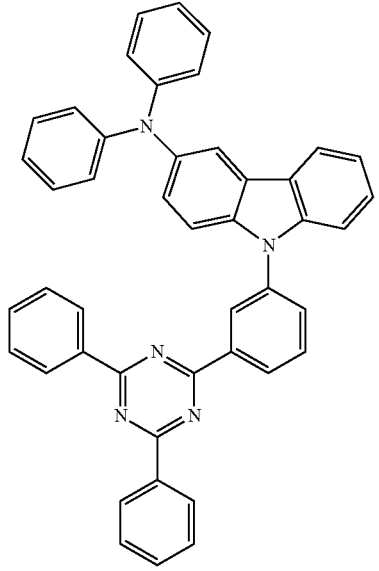
Compound 5
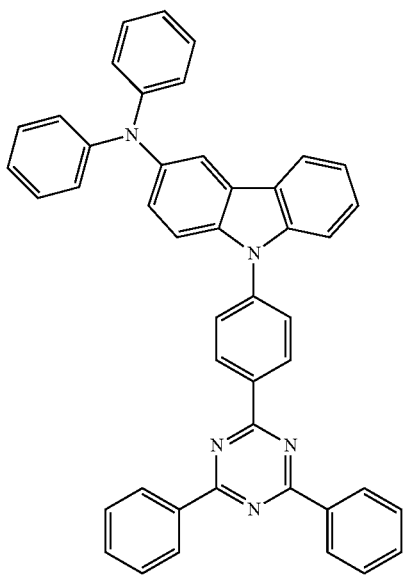
Compound 13
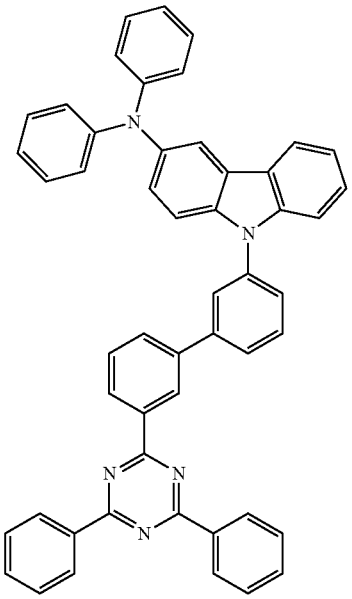

Compound 9
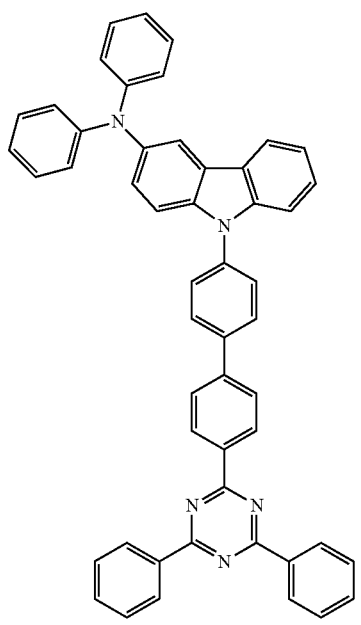
Compound 37
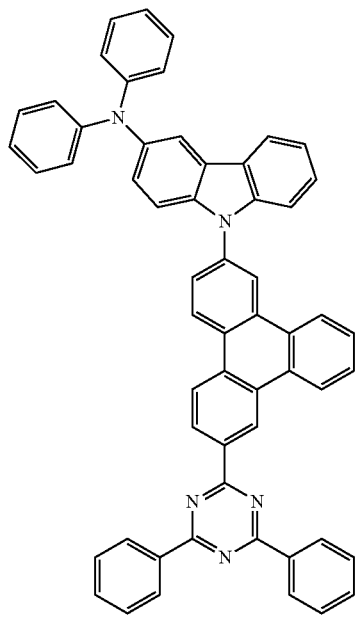
Compound 33
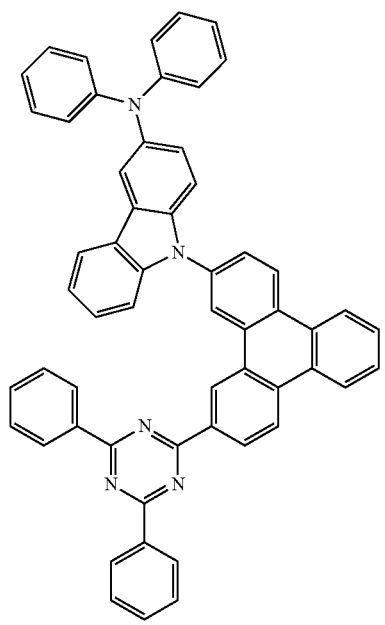
Compound 41
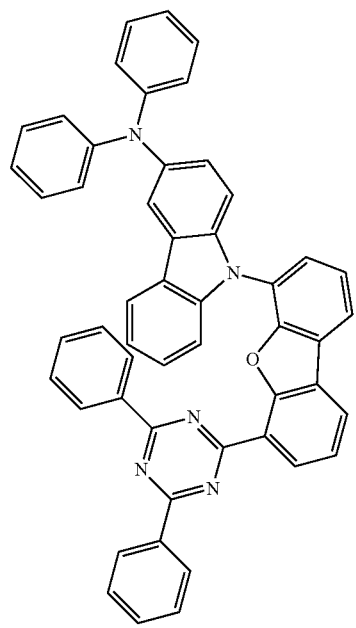

Compound 45
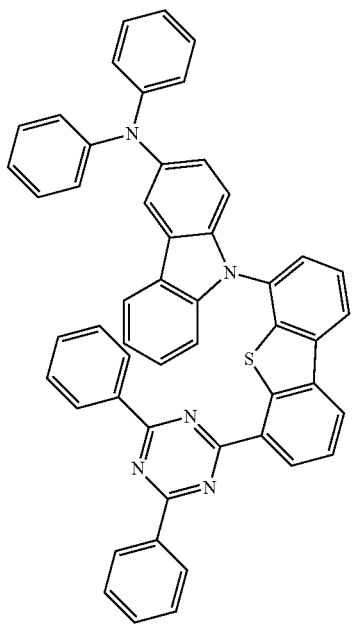
Compound 61
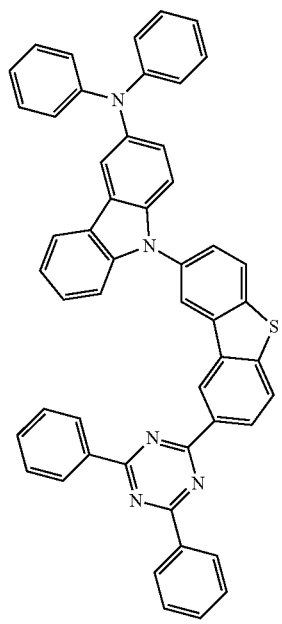
Compound 57
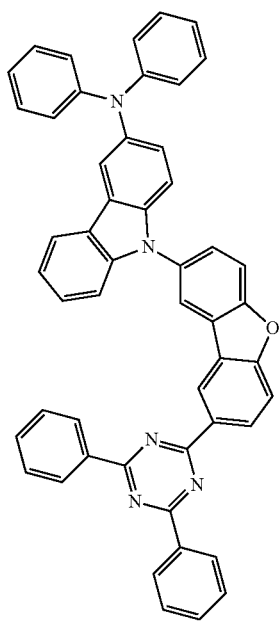
Compound 69
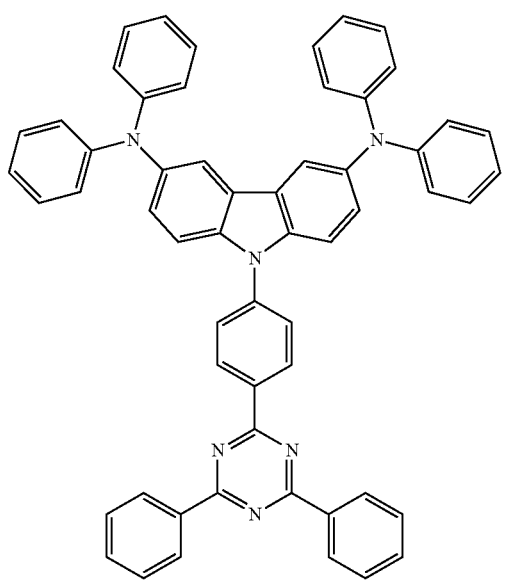

Compound 65
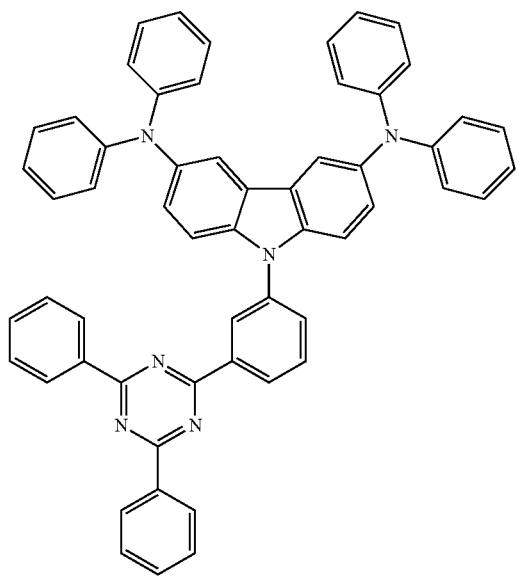
Compound 73
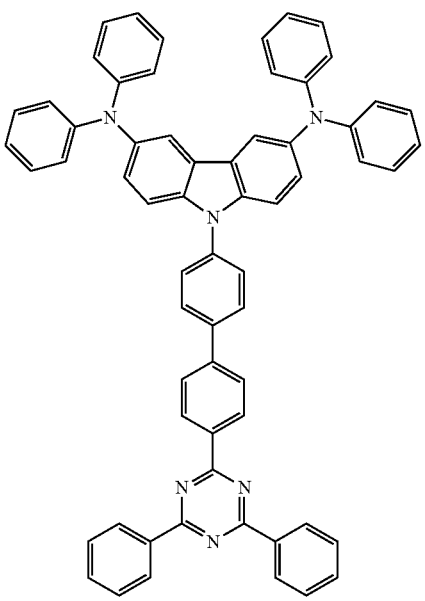
Compound 77
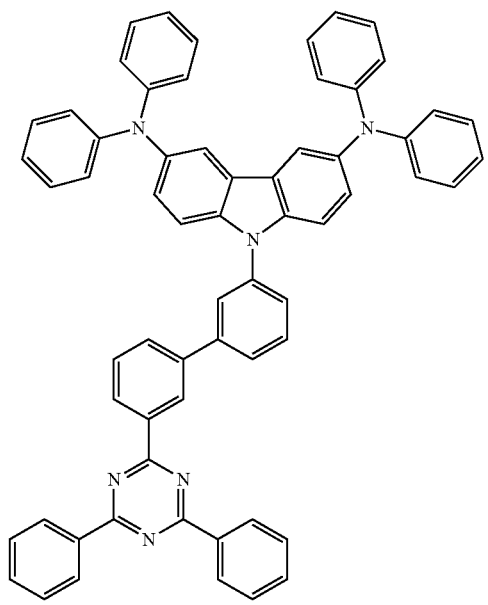
Compound 97
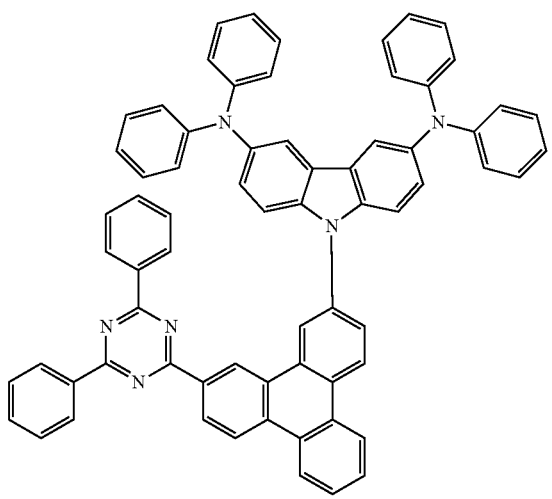

Compound 101
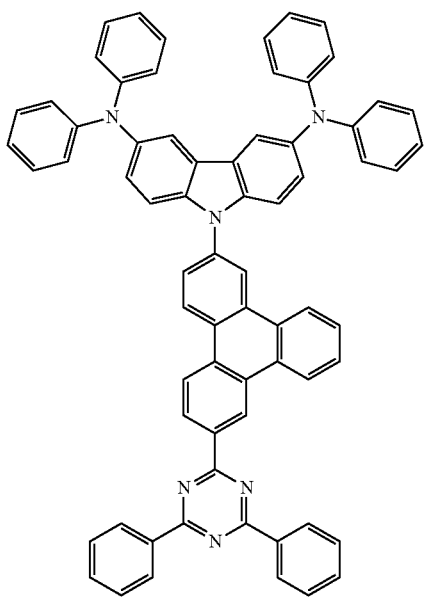
Compound 105
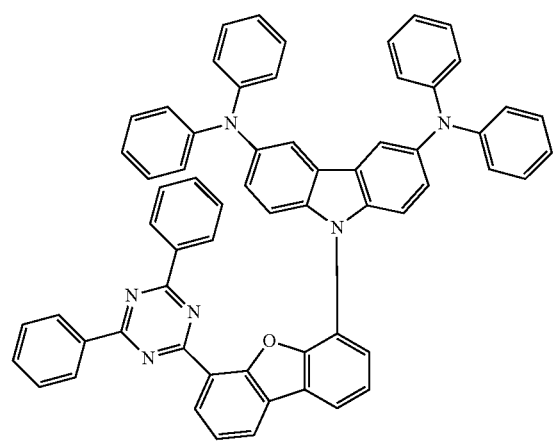
Compound 121
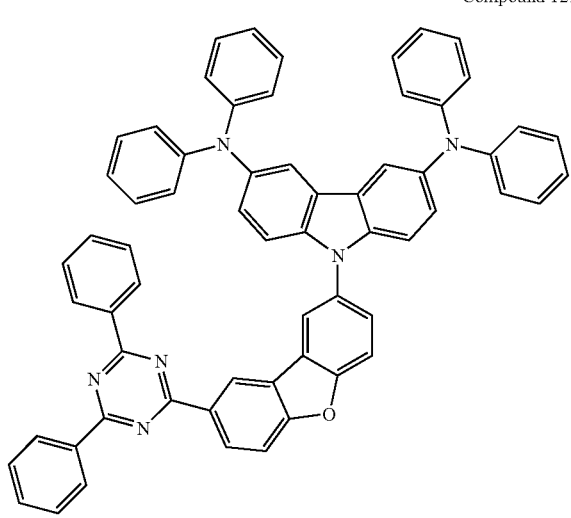
Compound 125
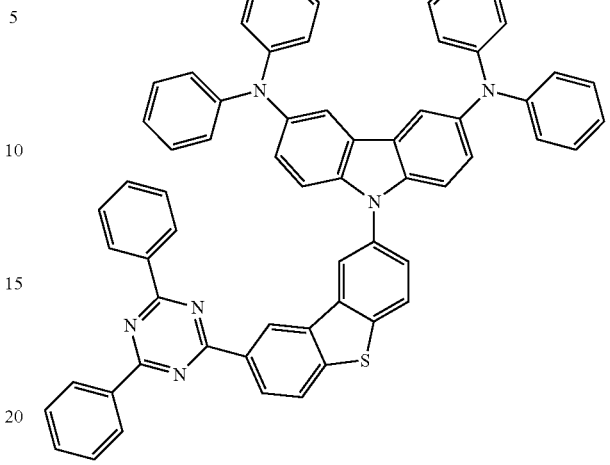
Compound 109
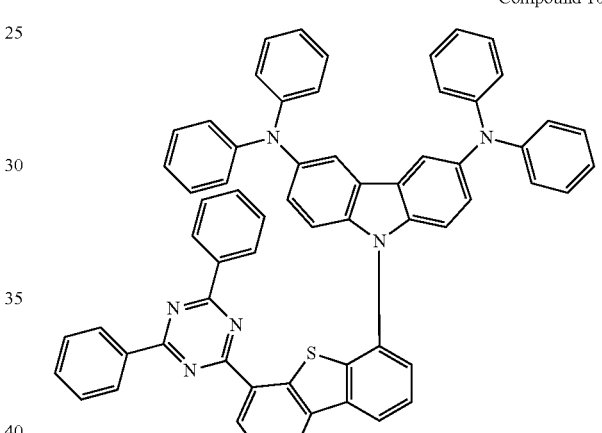
Compound 133
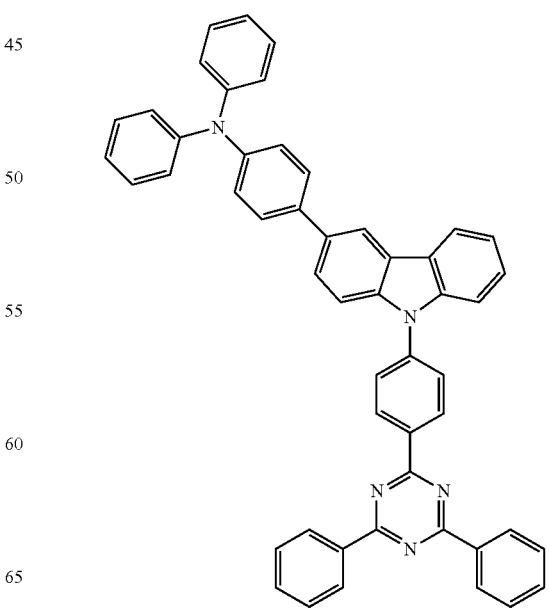

Compound 129
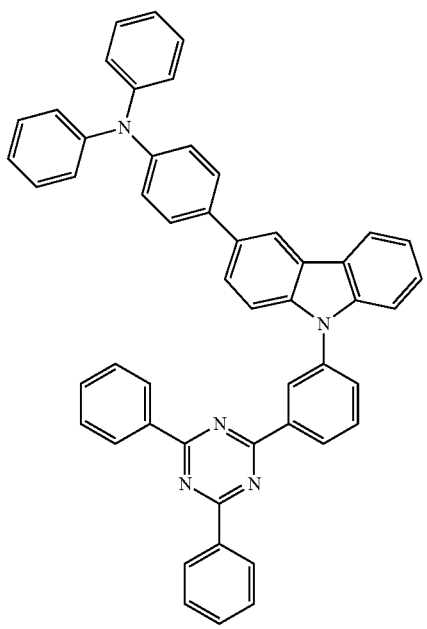
Compound 137
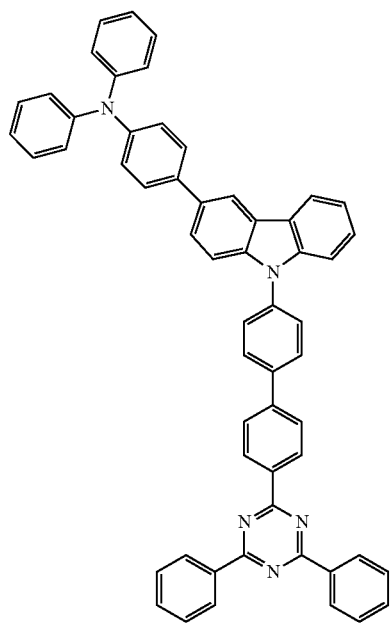
Compound 141
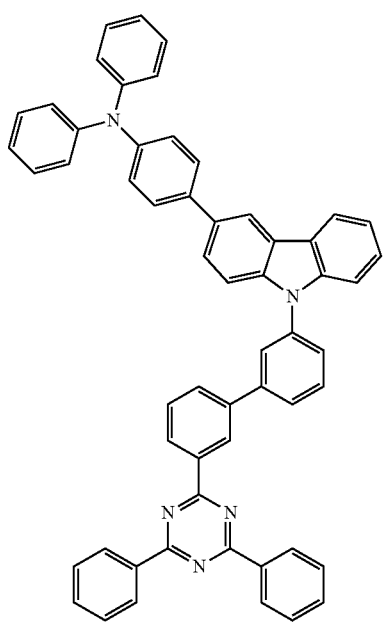
Compound 161
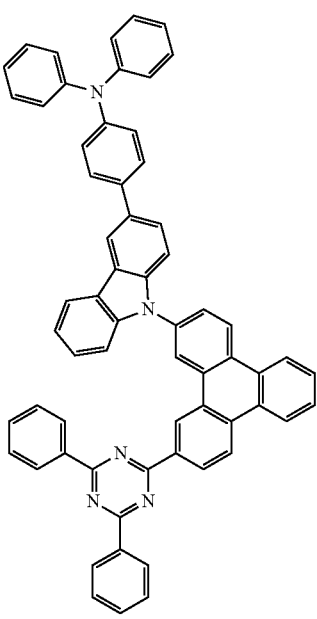

Compound 165
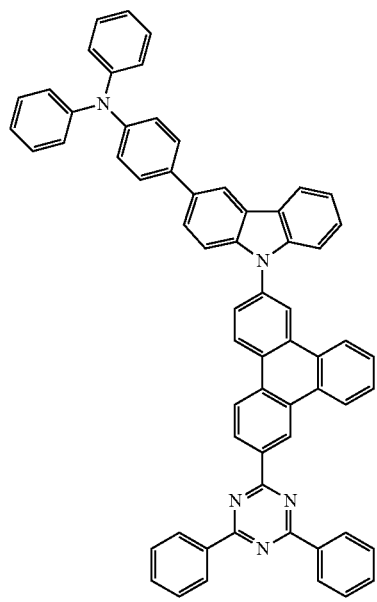
Compound 173
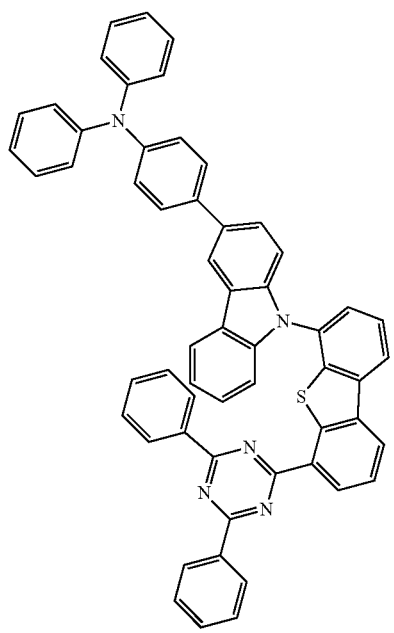
Compound 169
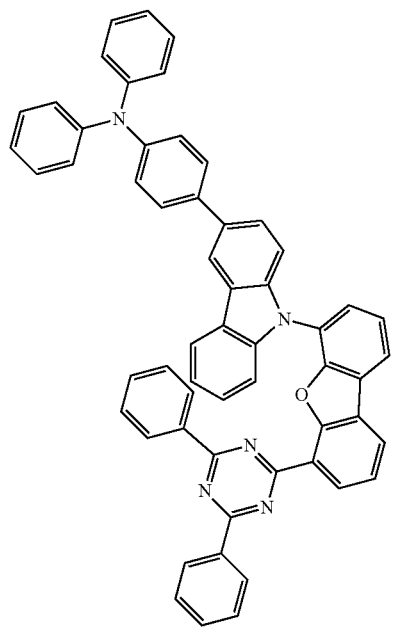
Compound 185
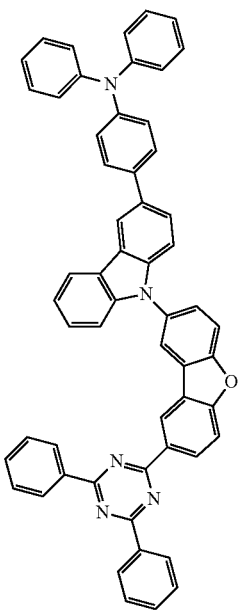

Compound 189
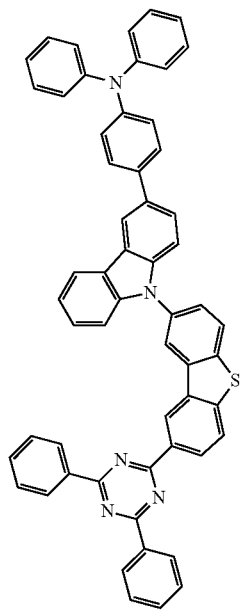
Compound 193
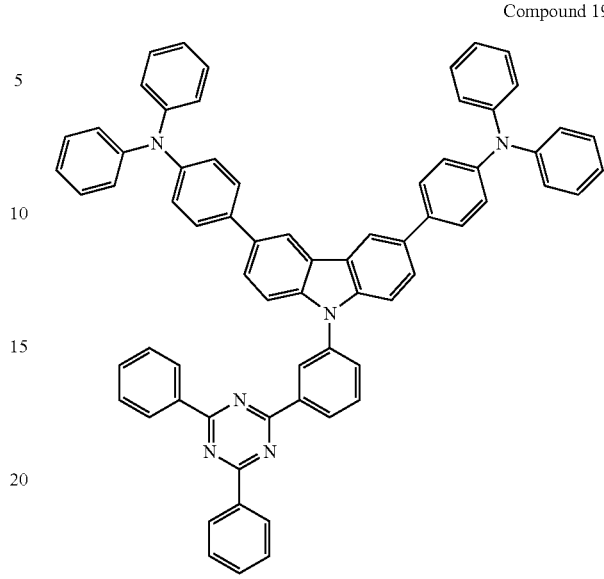
Compound 197
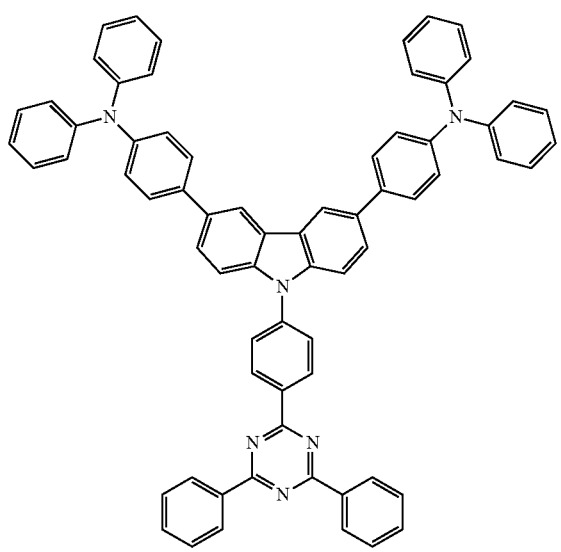
Compound 205
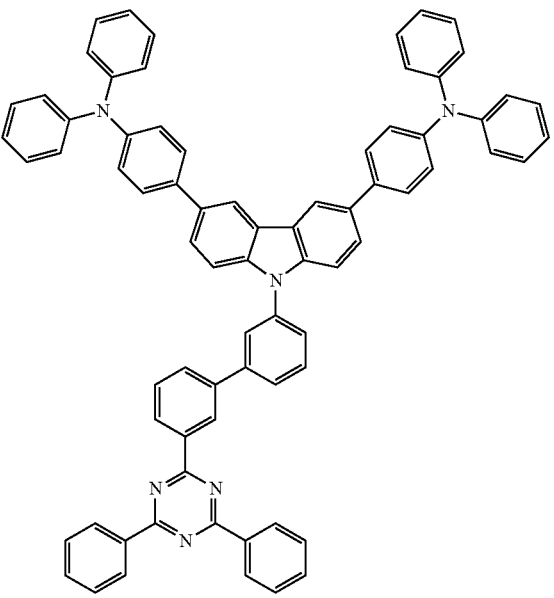

Compound 201
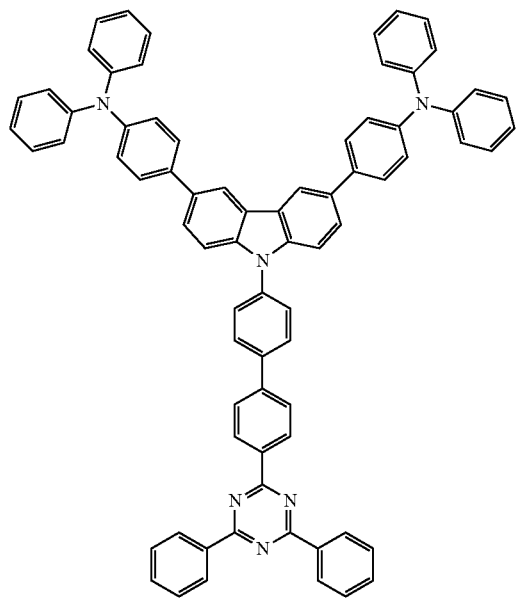
Compound 229
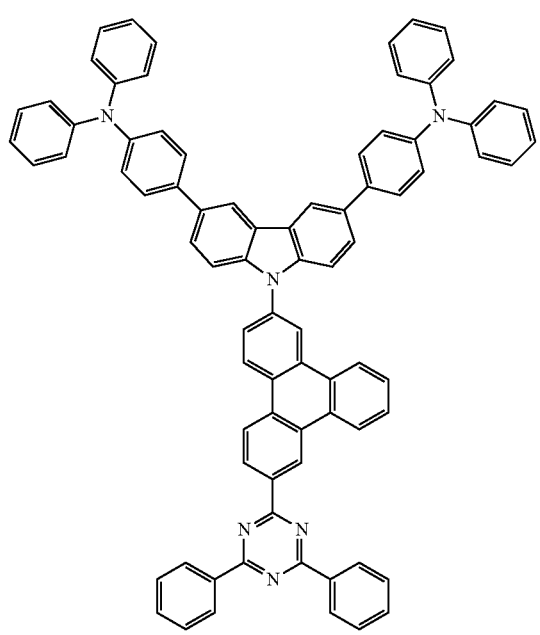
Compound 225
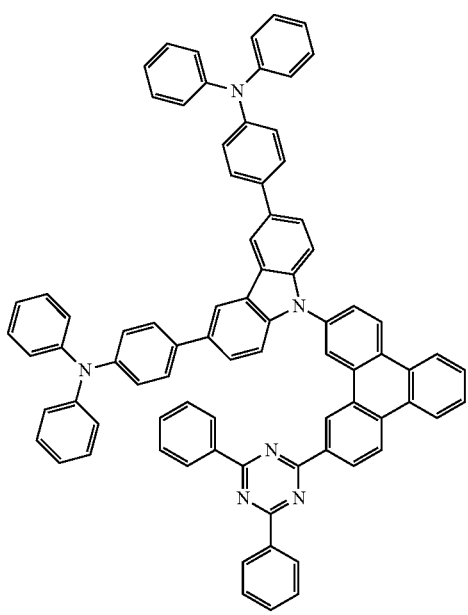
Compound 233
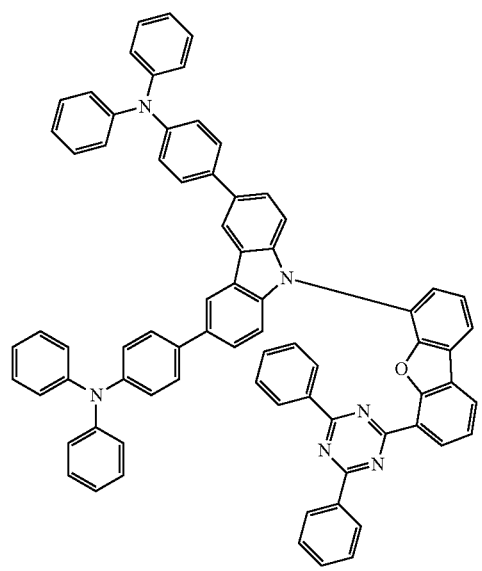

-continued
Compound 237
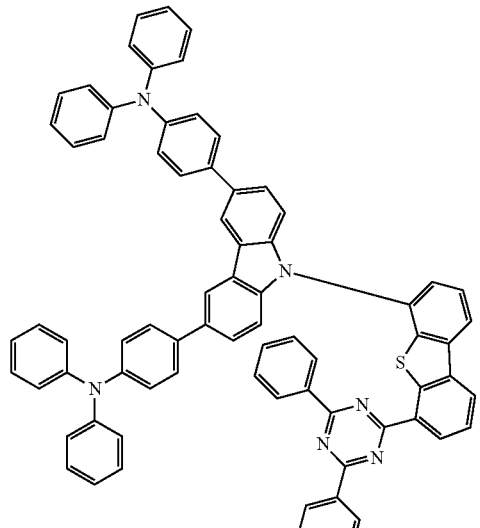
Compound 249
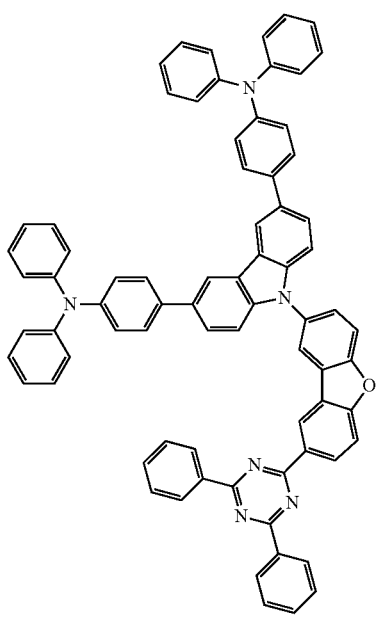
-continued
Compound 253
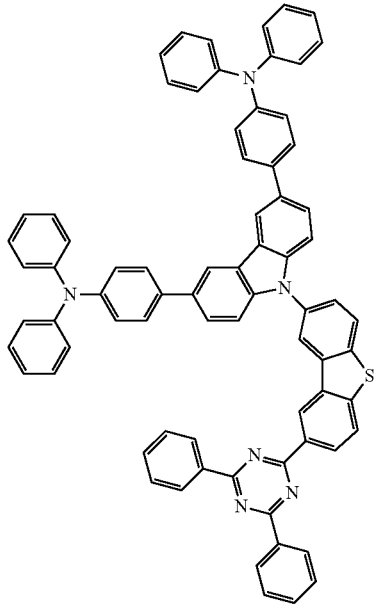
Compound 261
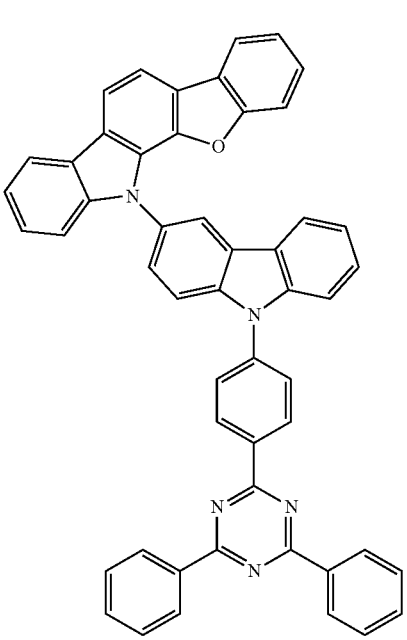

Compound 257
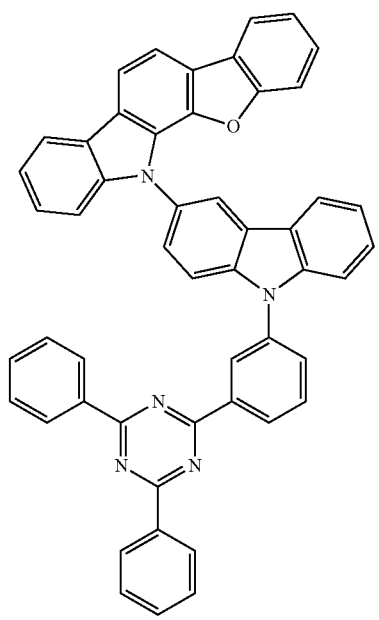
Compound 265
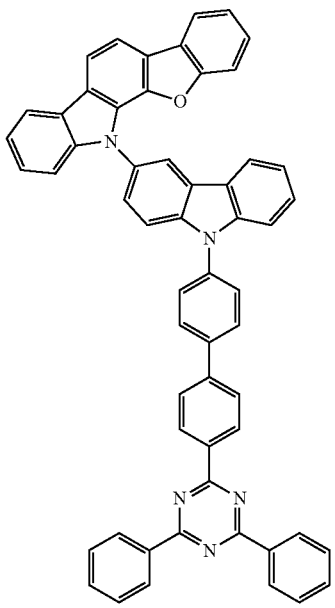
Compound 269
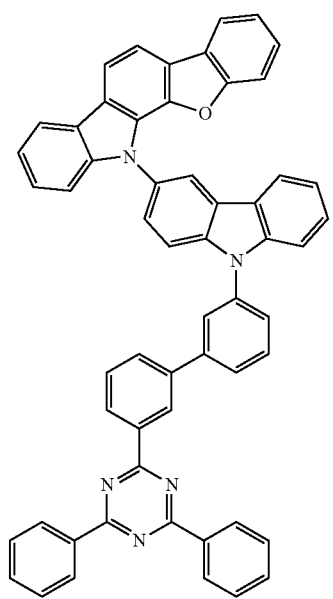
Compound 289
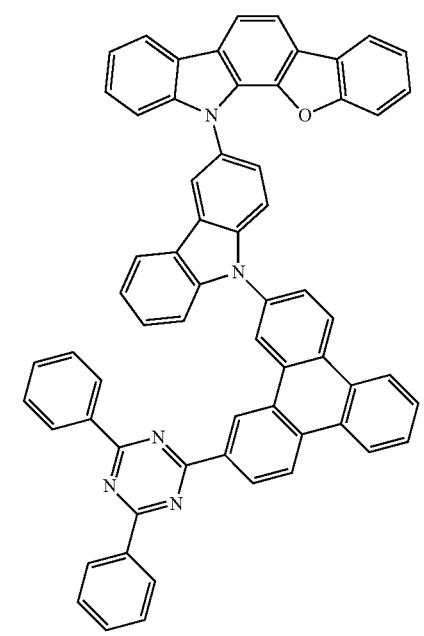

Compound 293
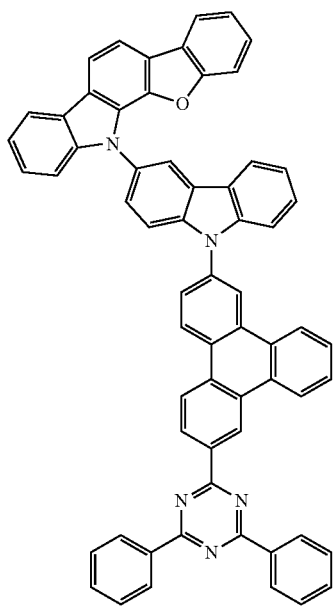
Compound 297
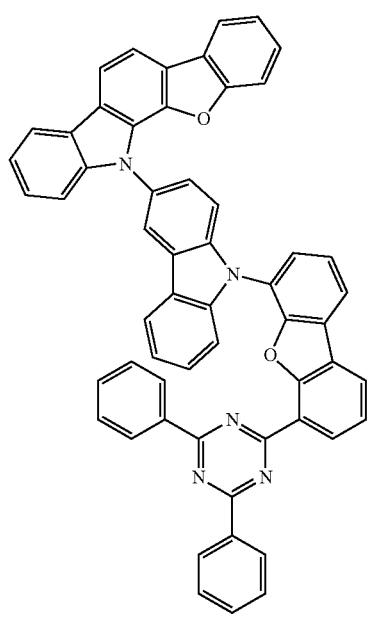
Compound 301
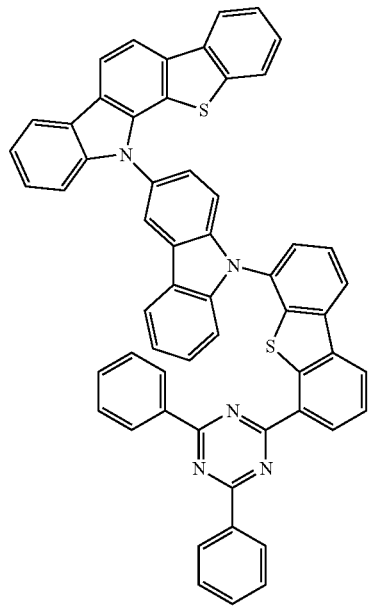
Compound 313
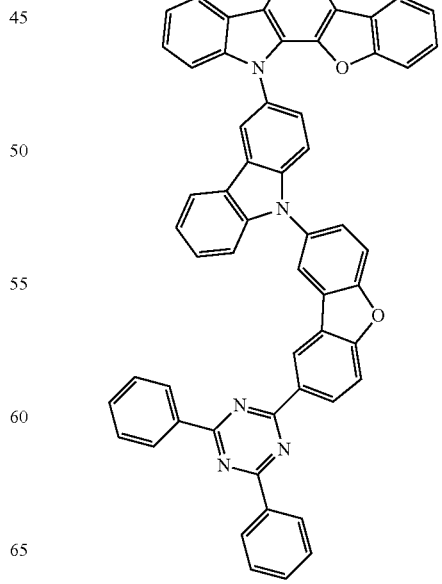

Compound 317
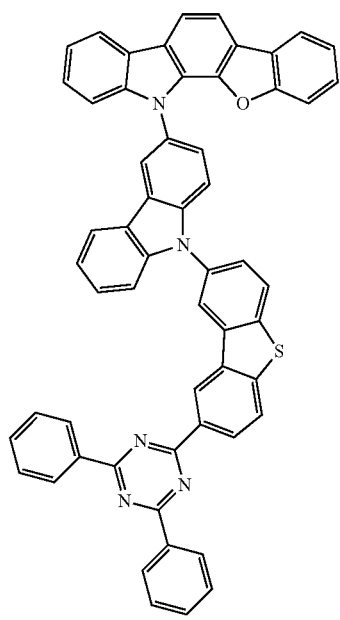
Compound 321
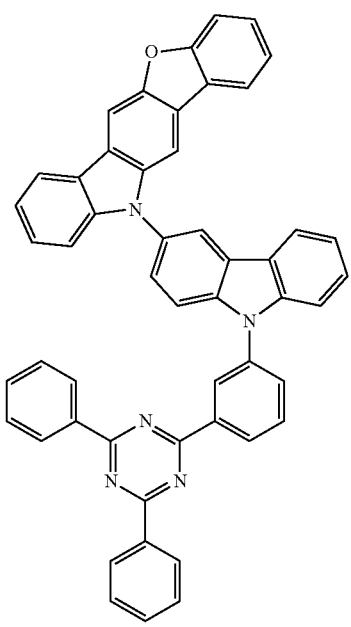
Compound 325
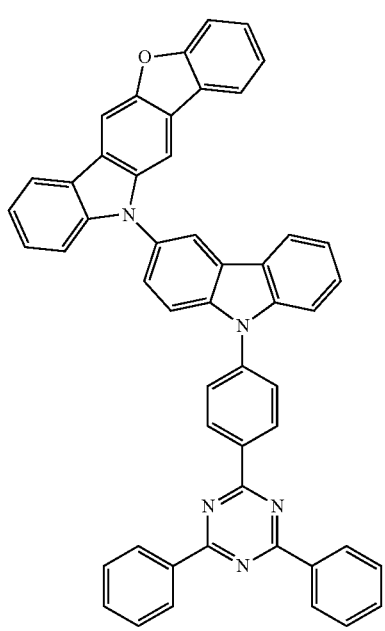
Compound 333
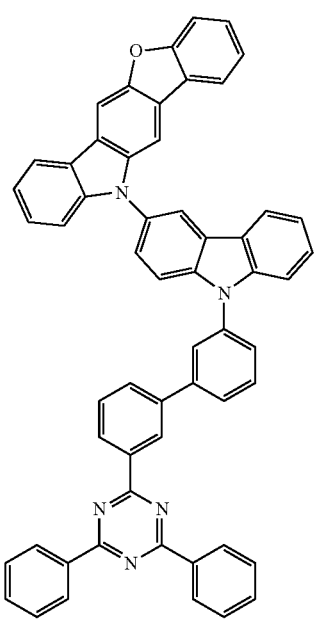

Compound 329
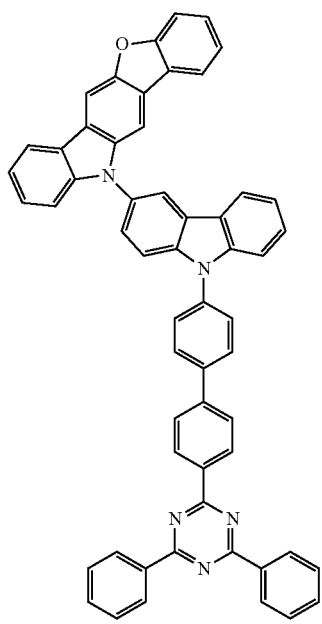
Compound 353
Compound 357
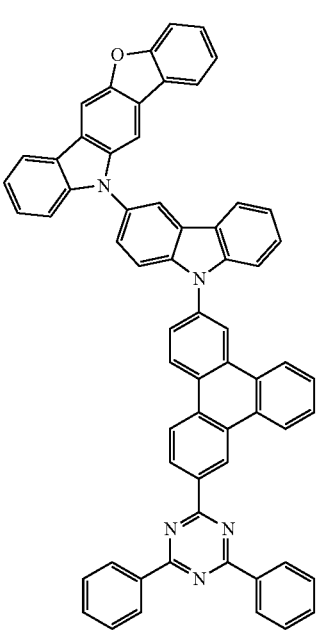
Compound 361
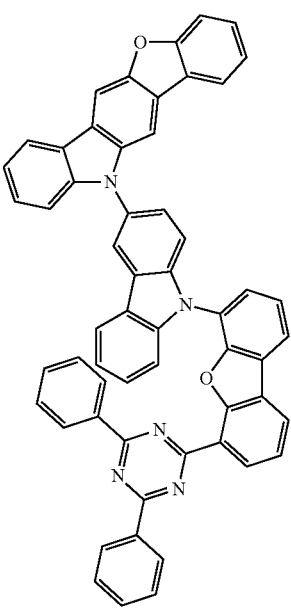

Compound 365
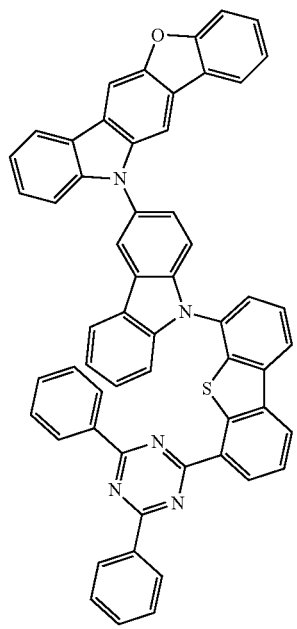
Compound 381
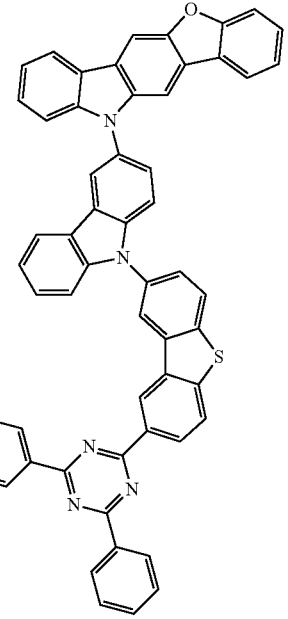
Compound 377
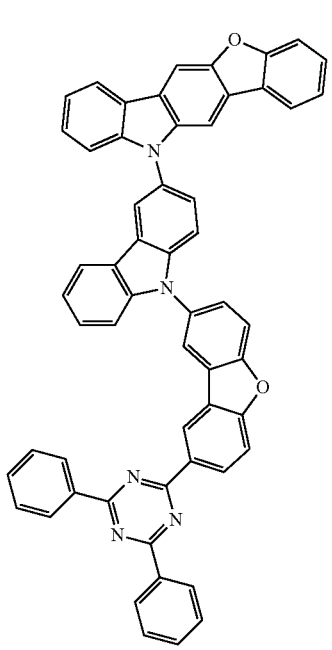
Compound 389
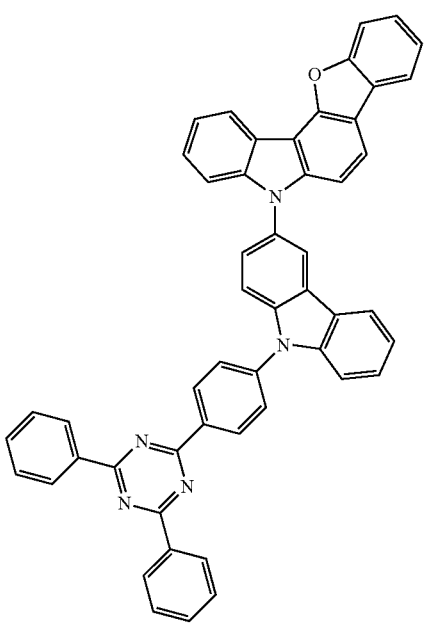

Compound 385
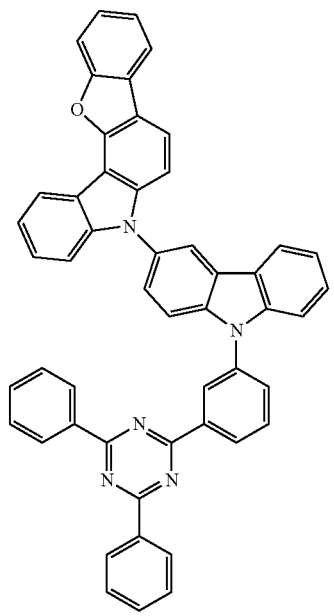
Compound 393
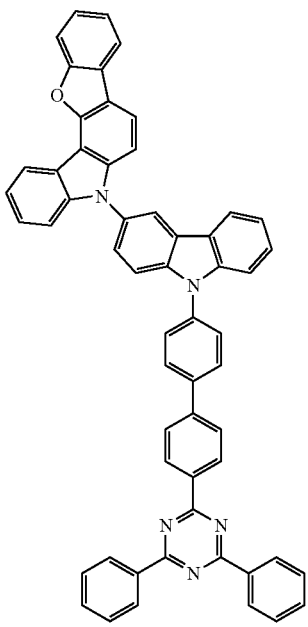
Compound 417
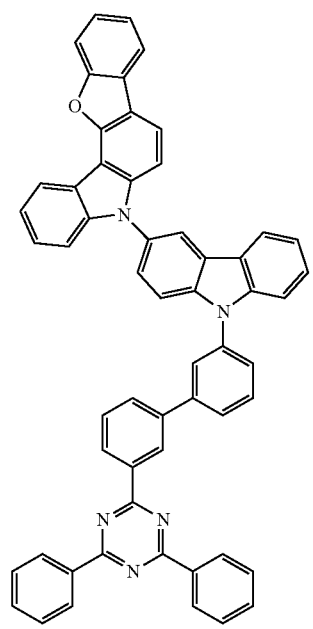
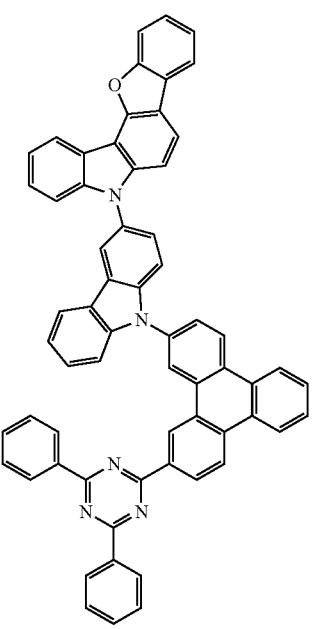

-continued
Compound 421
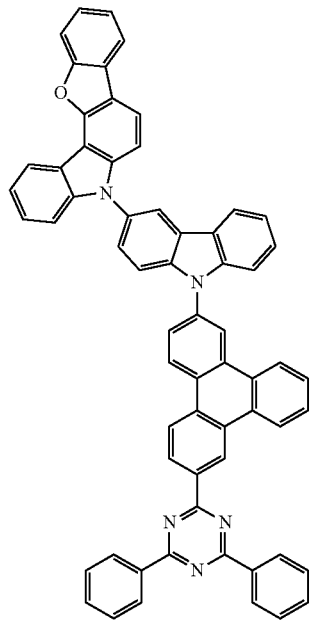
Compound 429
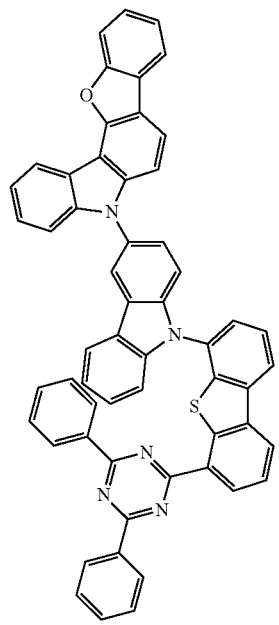
Compound 425
Compound 441
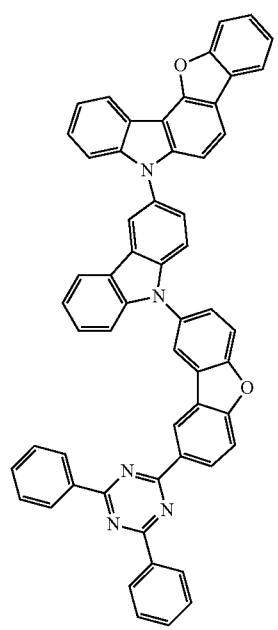

Compound 445
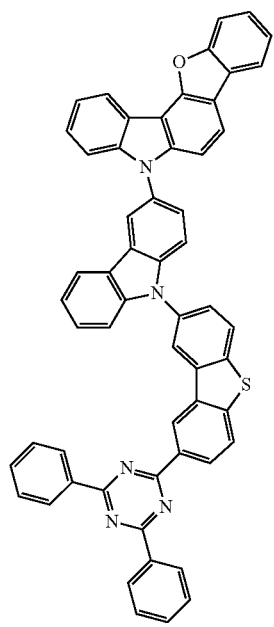
Compound 449
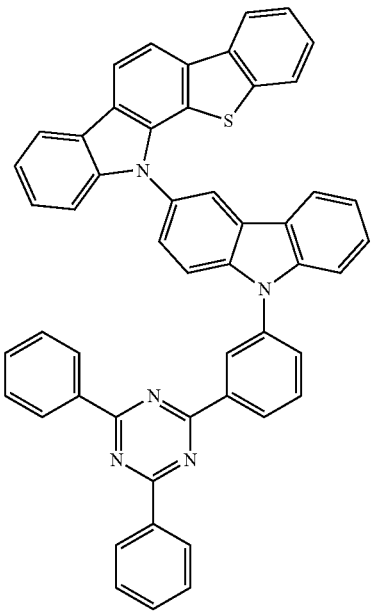
Compound 453
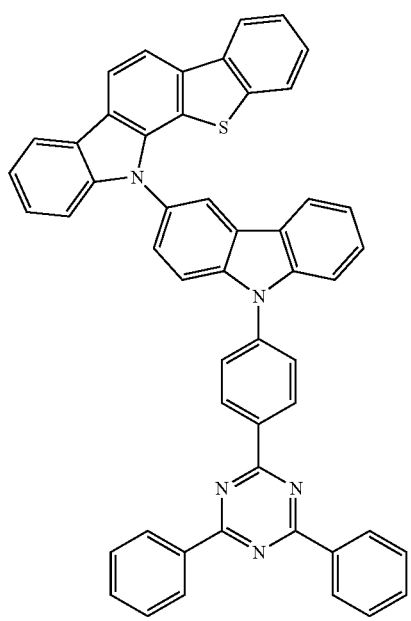
Compound 461
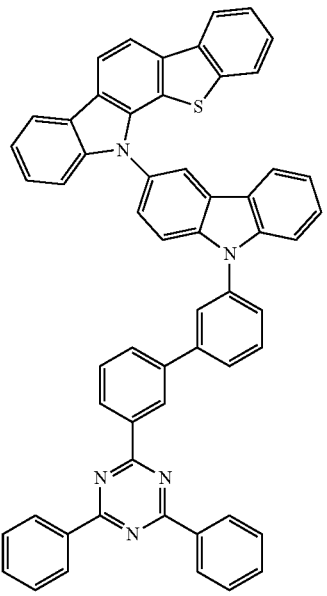

Compound 457
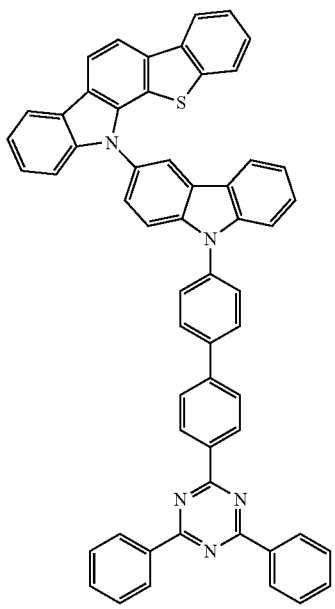
Compound 485
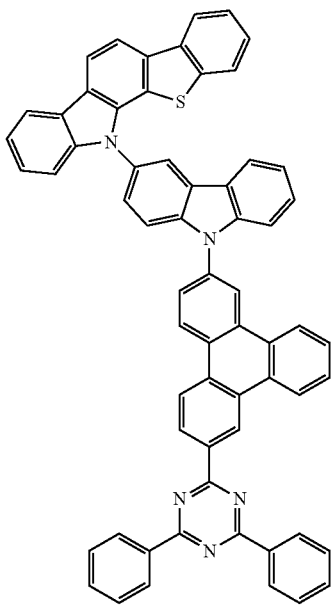
Compound 481
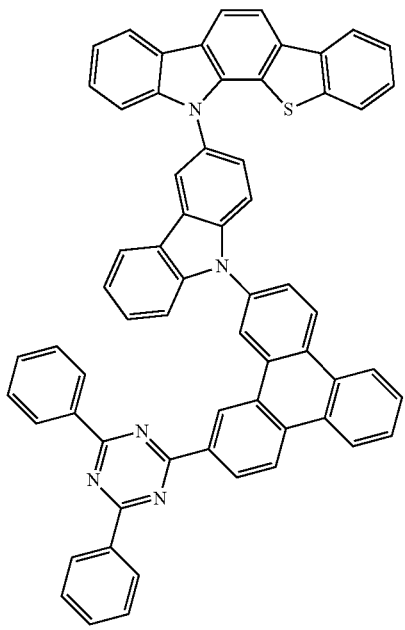
Compound 489
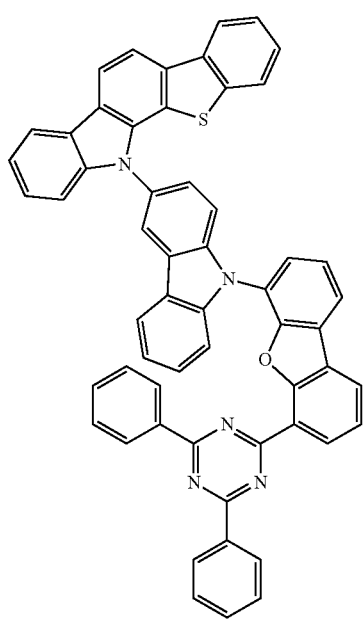

Compound 493
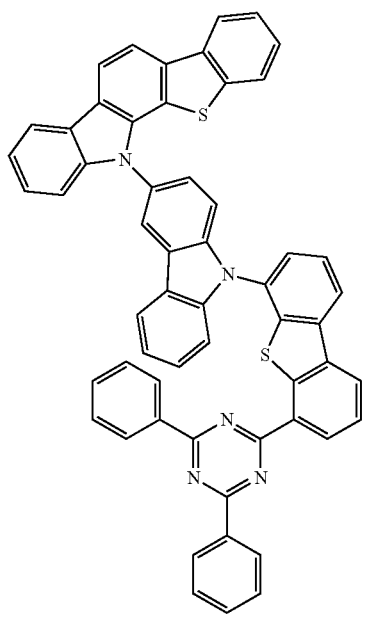
Compound 509
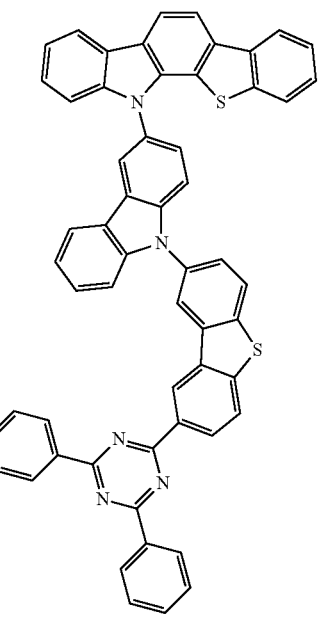
Compound 505
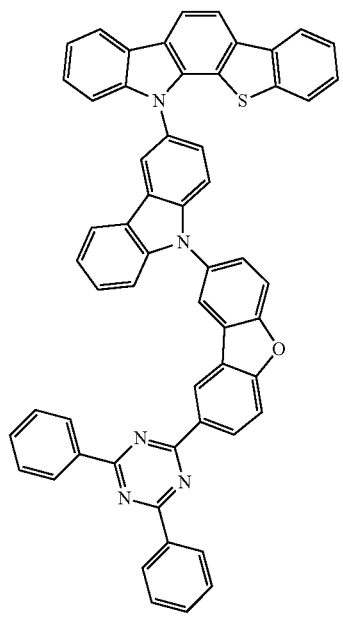
Compound 517
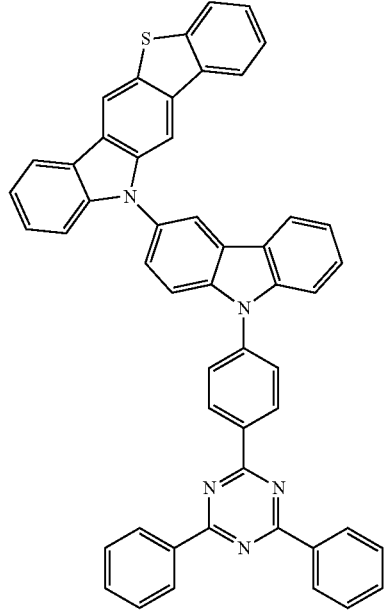

Compound 513
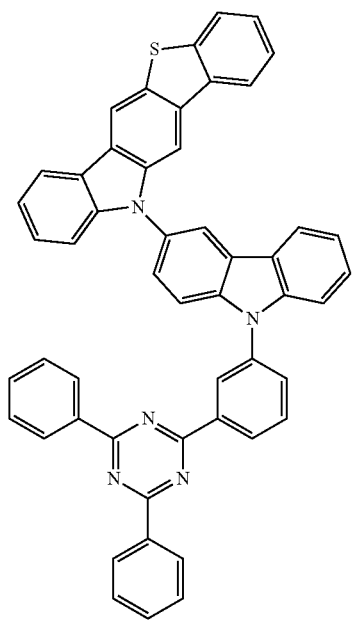
Compound 521
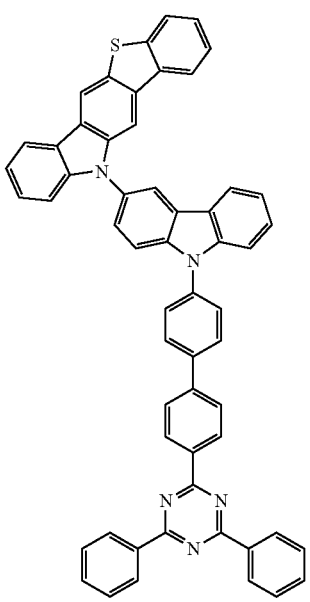
Compound 525
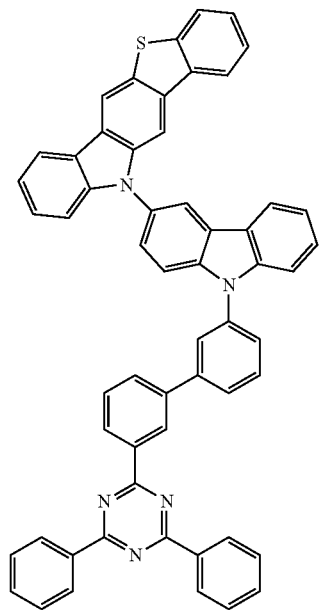
Compound 545
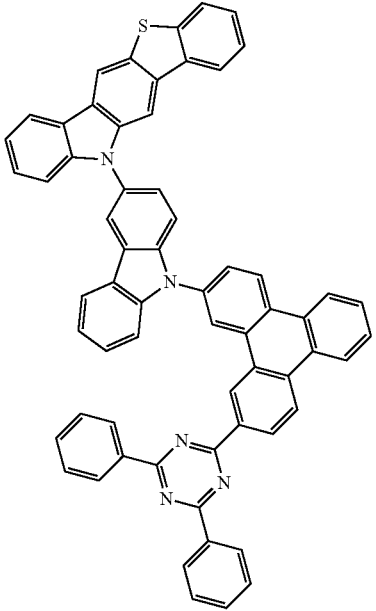

Compound 549
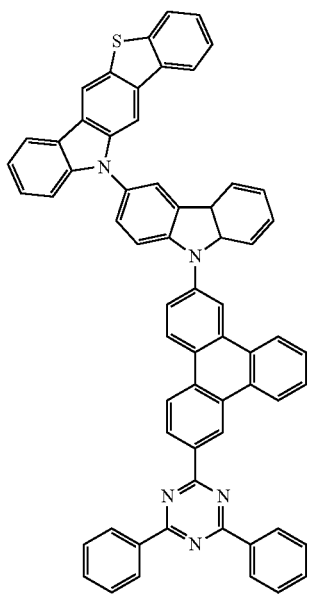
Compound 553
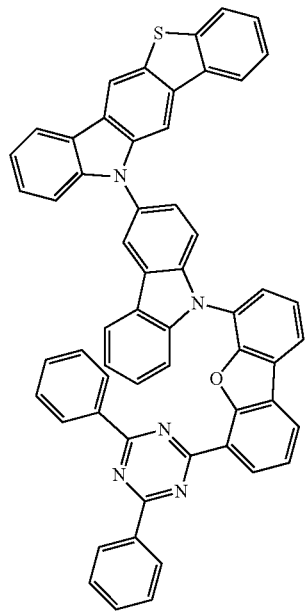
Compound 557
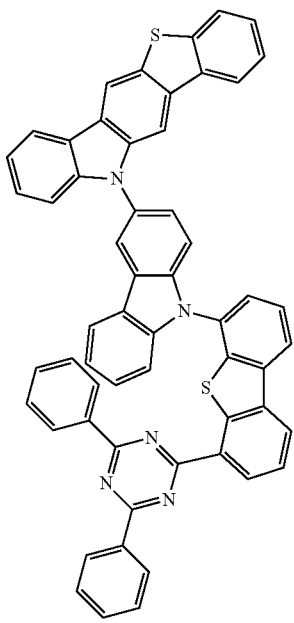
Compound 569
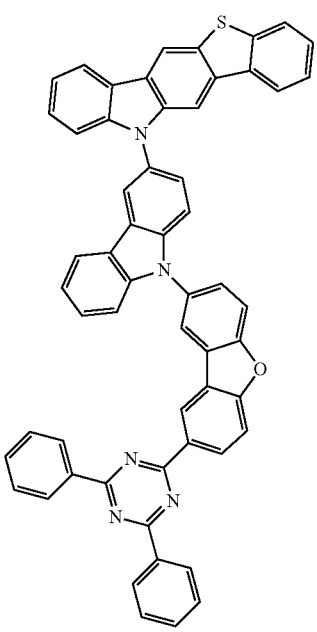

Compound 573
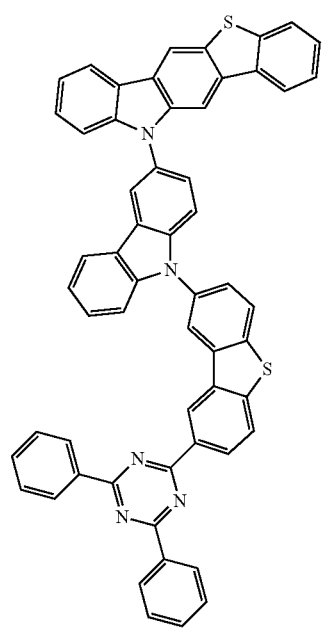
Compound 577
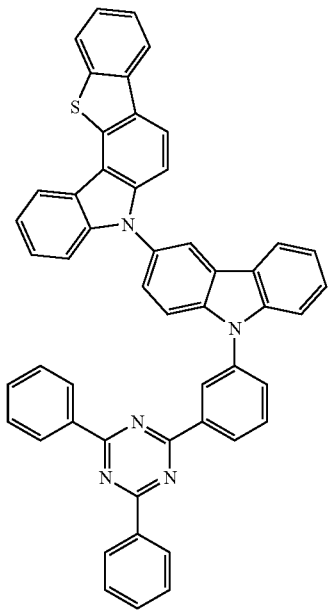
Compound 581
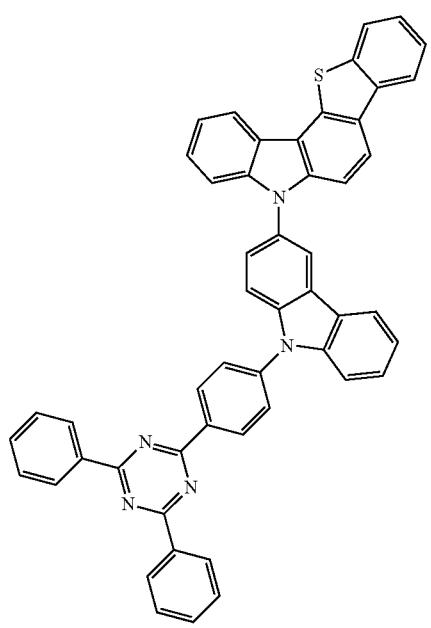
Compound 589
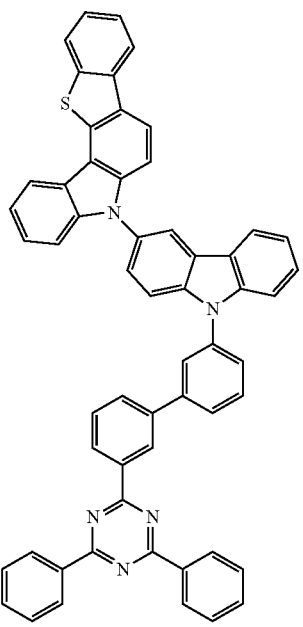

233
-continued
Compound 585
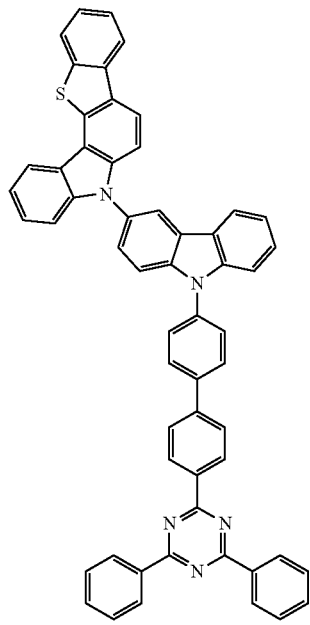
234
-continued
Compound 613
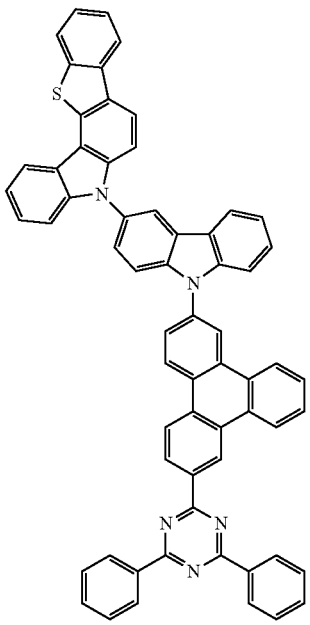
Compound 609
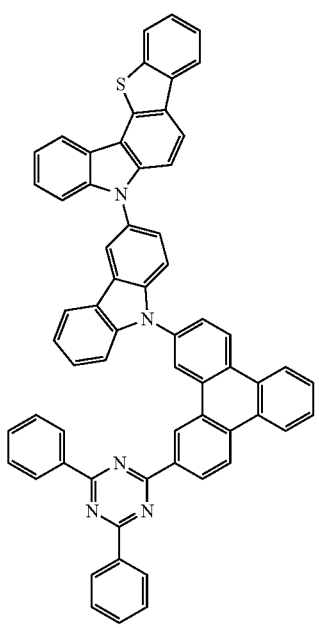
Compound 617
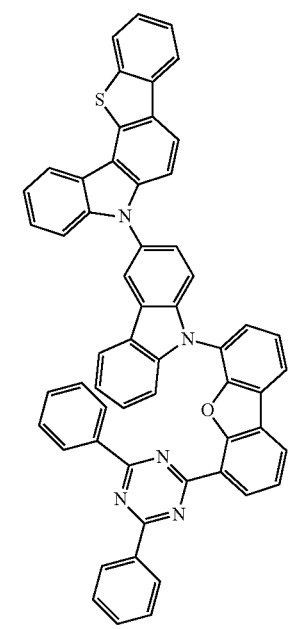

Compound 621
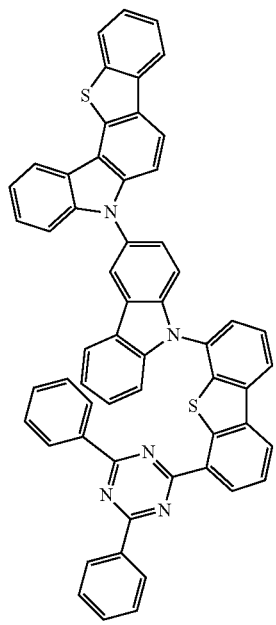
Compound 637
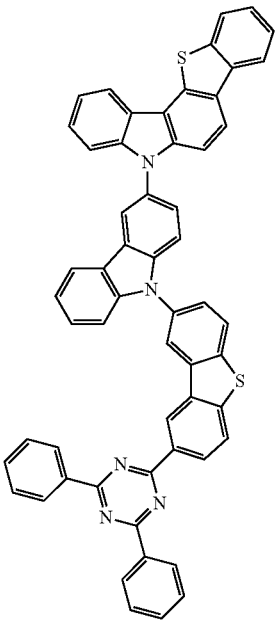
Compound 633
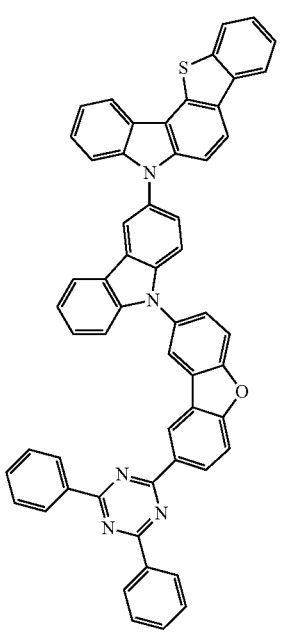
Compound 645
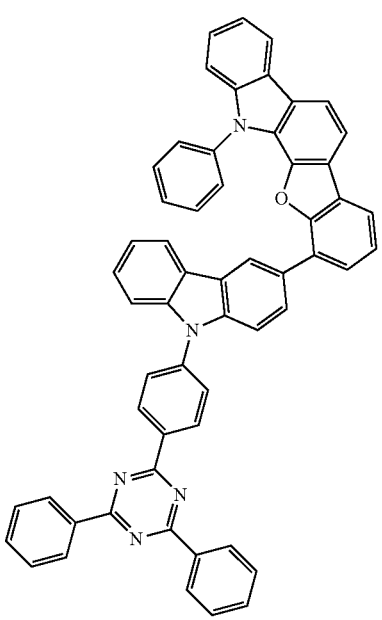

-continued
Compound 641
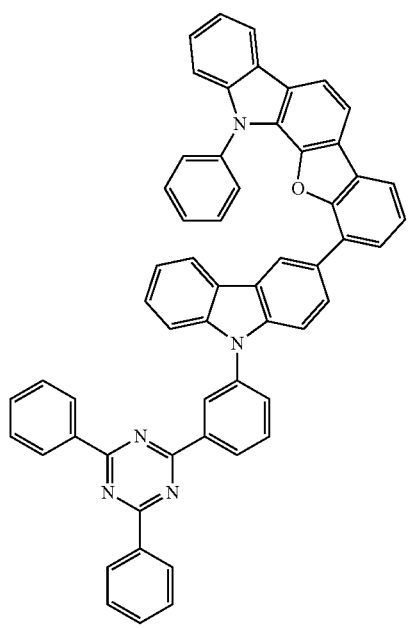
Compound 649
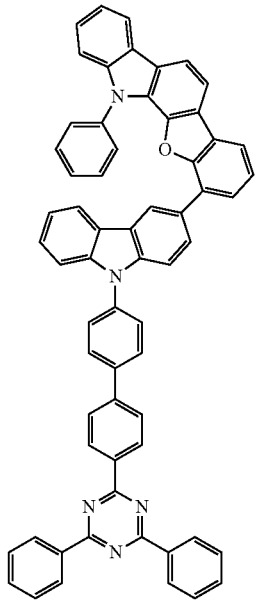
Compound 653
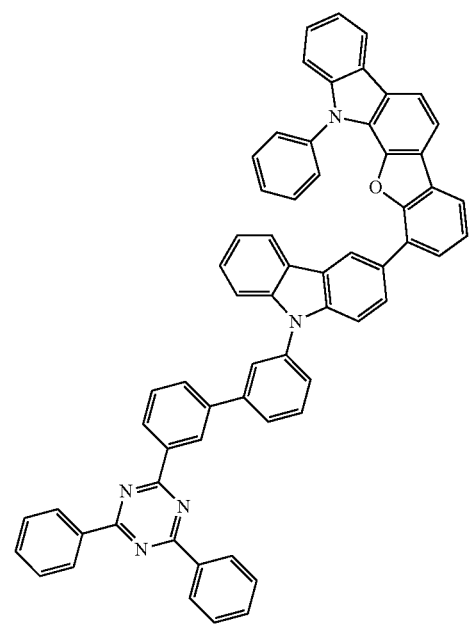
Compound 673
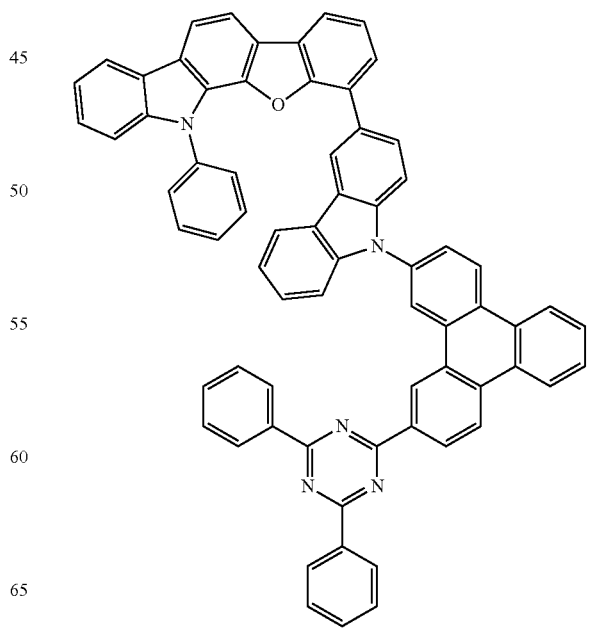

Compound 677
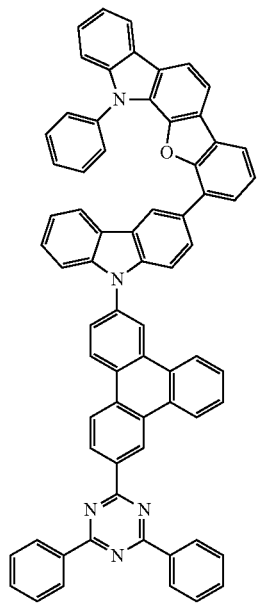
Compound 685
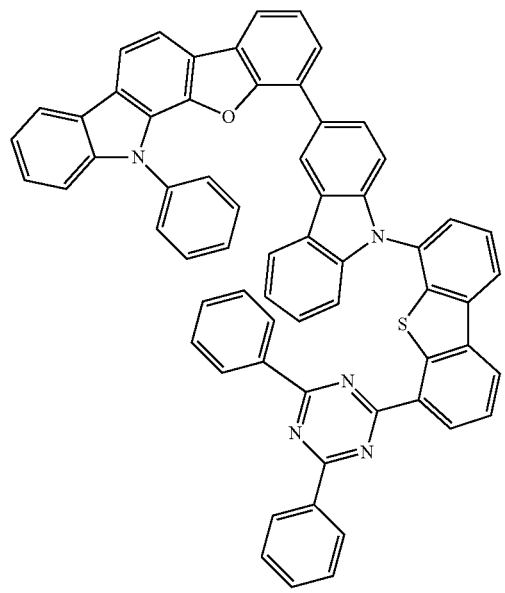
Compound 681
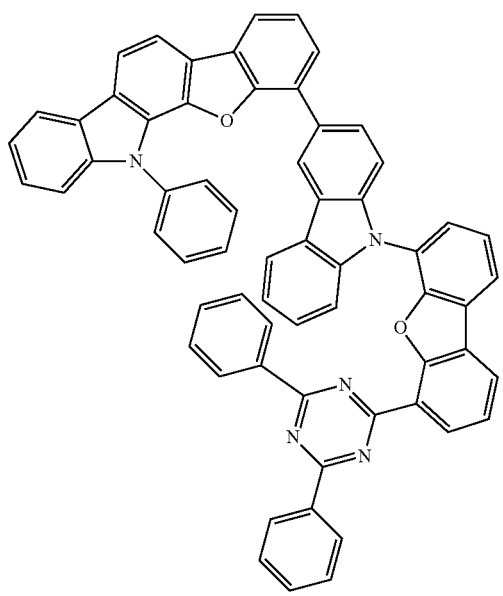
Compound 697
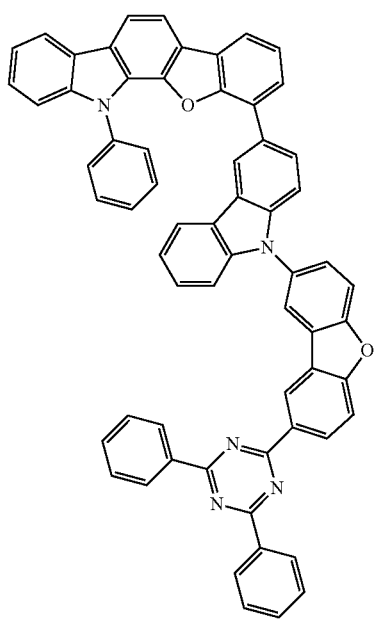

Compound 701
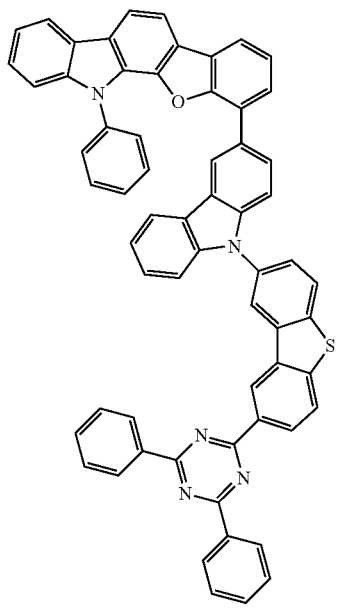
Compound 705
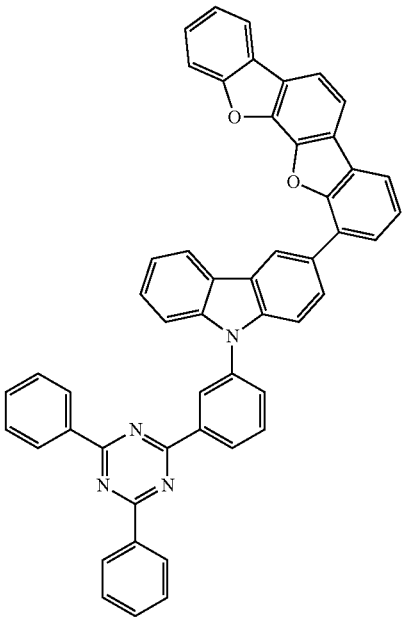
Compound 709
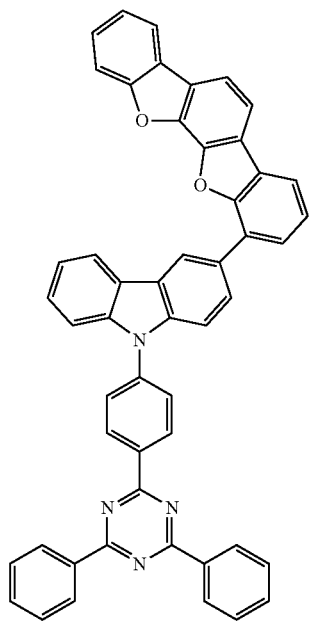
Compound 717
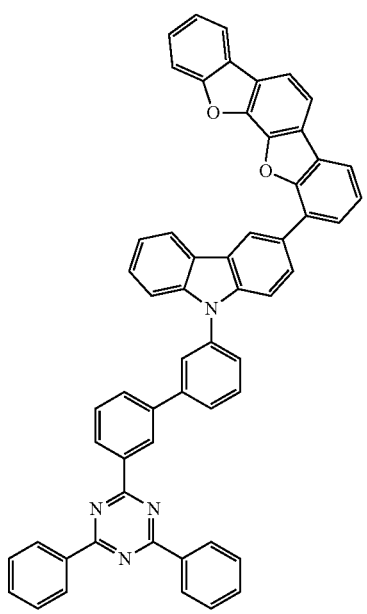

Compound 713
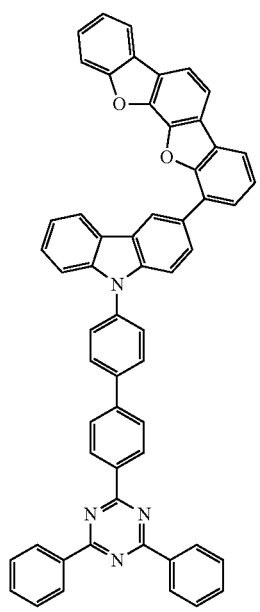
Compound 741
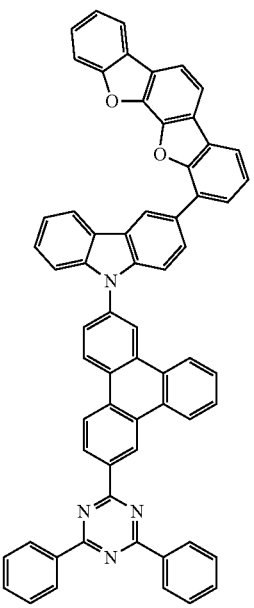
Compound 737
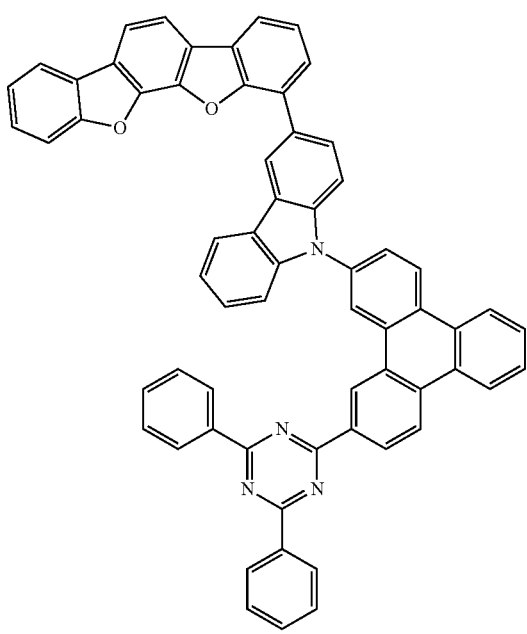
Compound 745
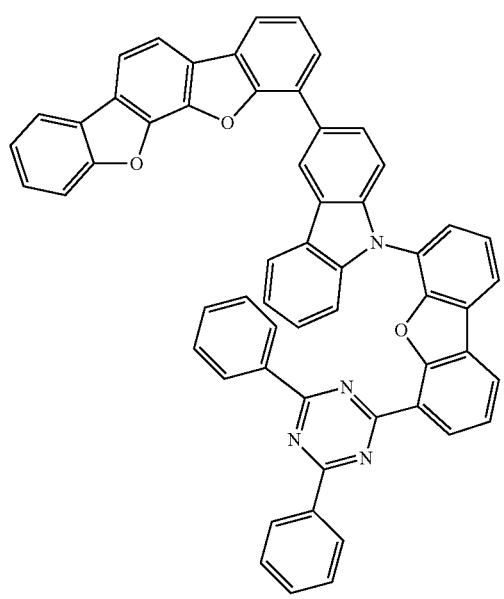

Compound 749
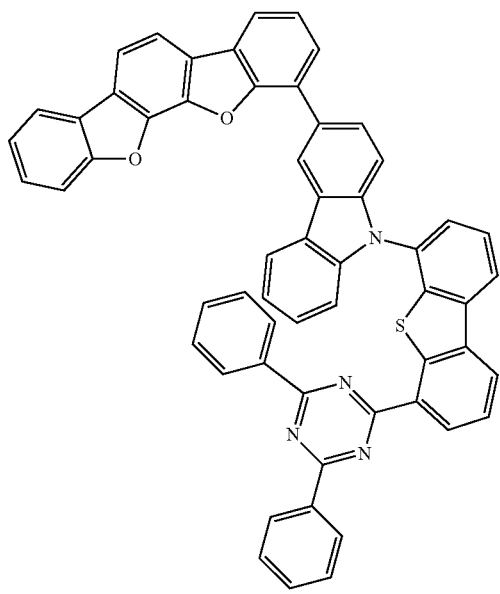
Compound 765
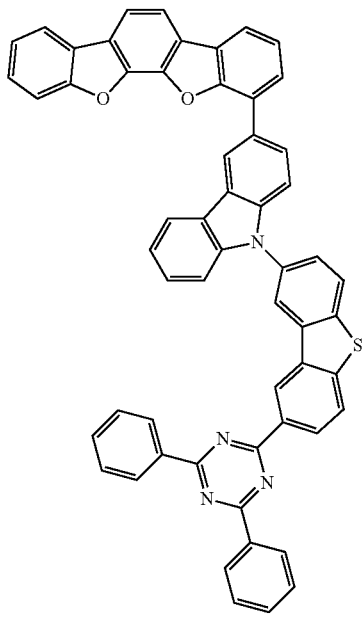
Compound 761
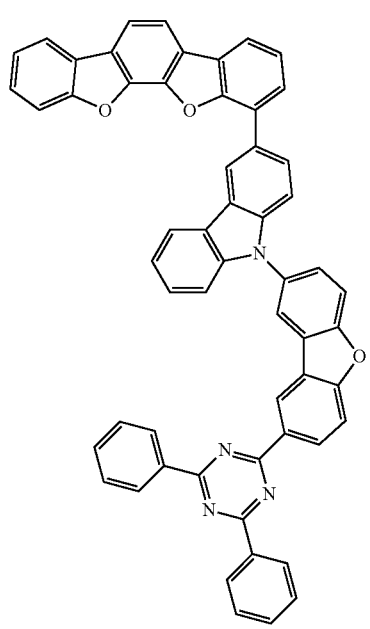
Compound 773
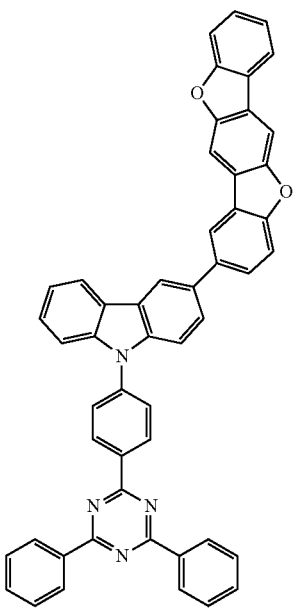

Compound 769
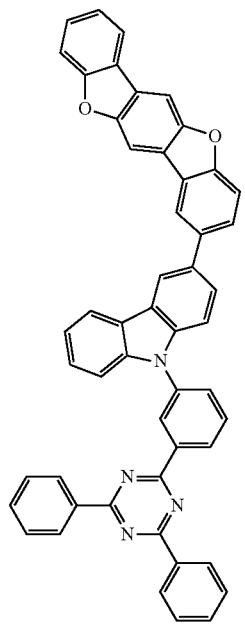
Compound 777
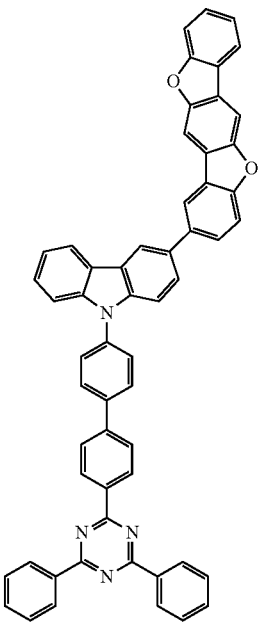
Compound 781
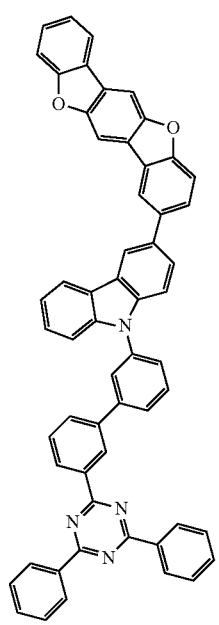
Compound 801
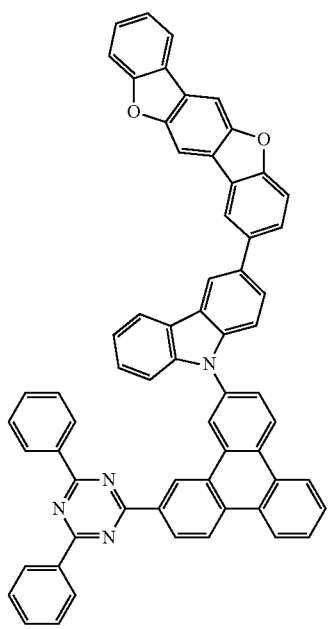

Compound 805
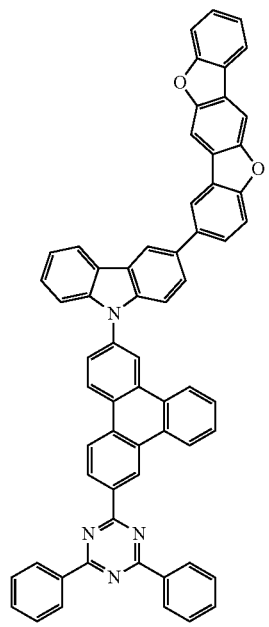
Compound 813
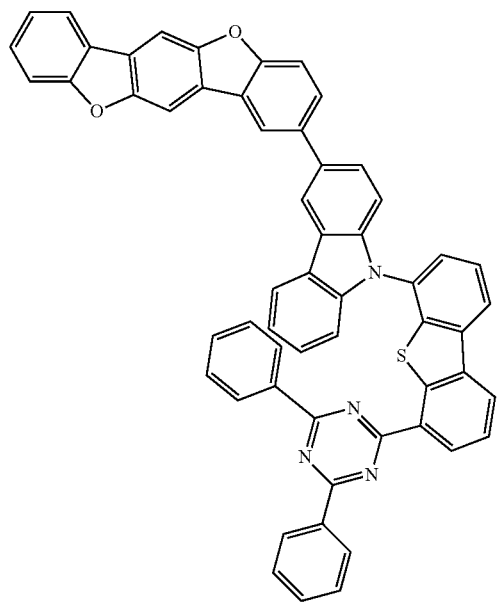
Compound 809
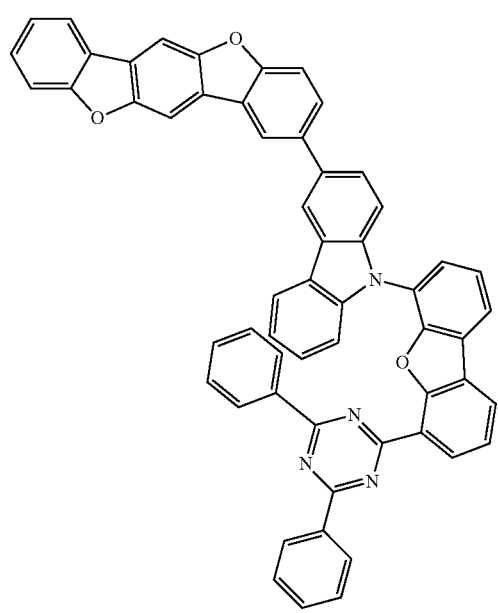
Compound 825
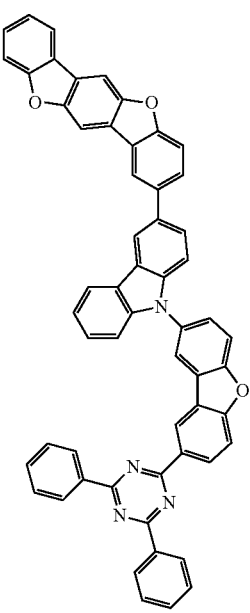

Compound 829
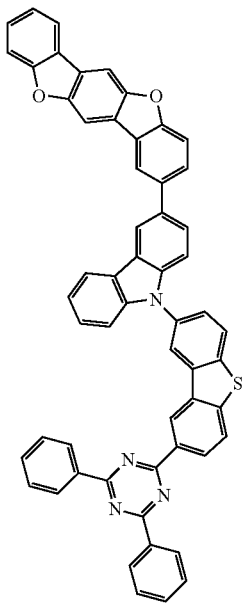
Compound 833
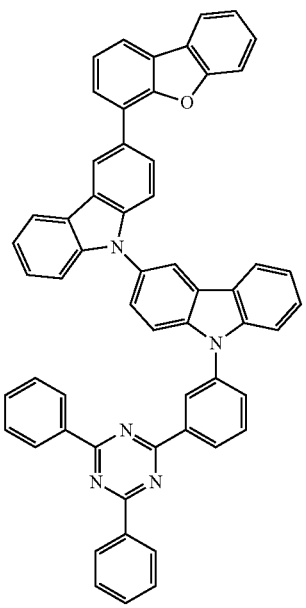
Compound 837
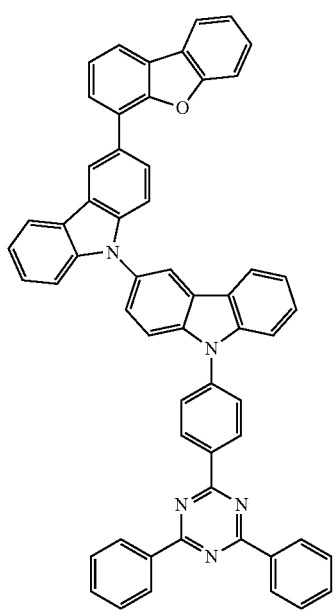
Compound 845
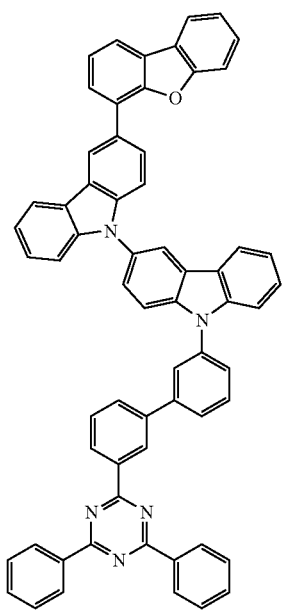

Compound 841
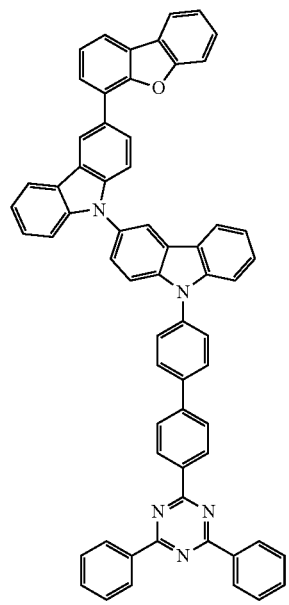
Compound 869
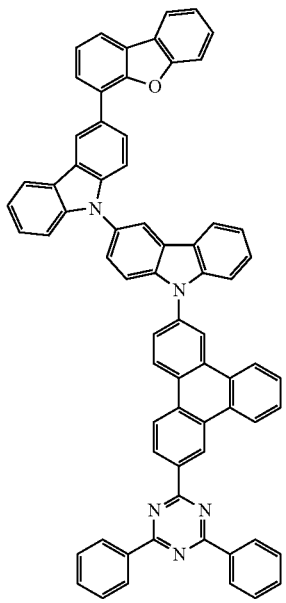
Compound 865
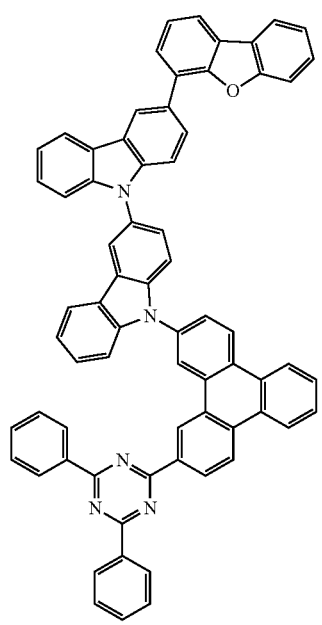
Compound 873
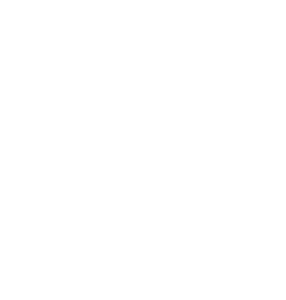
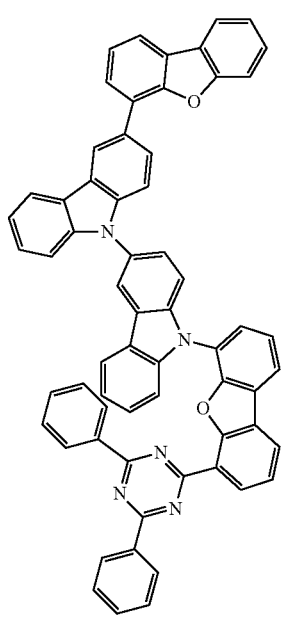

Compound 877
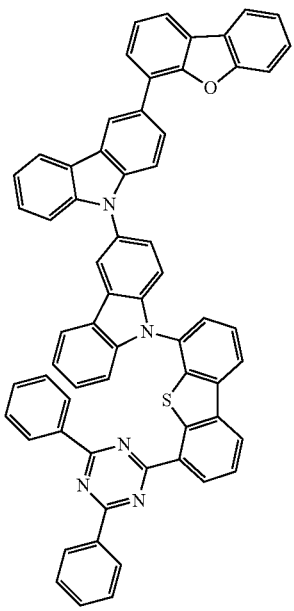
Compound 893
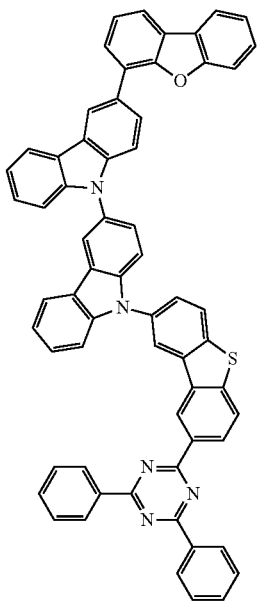
Compound 889
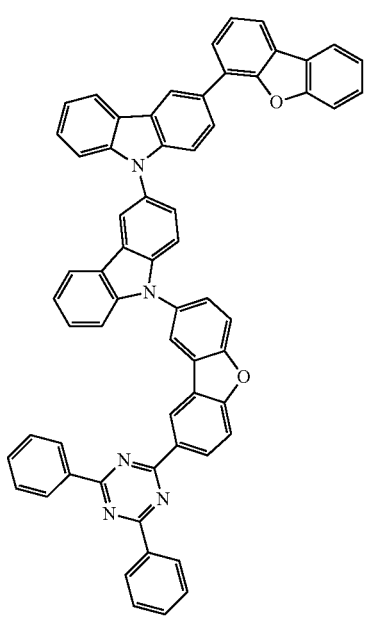
Compound 1029
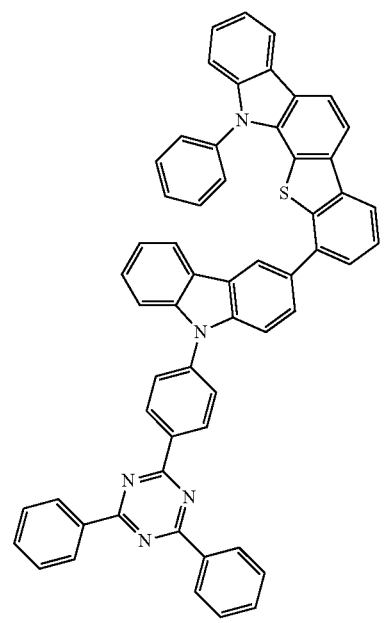

Compound 1025
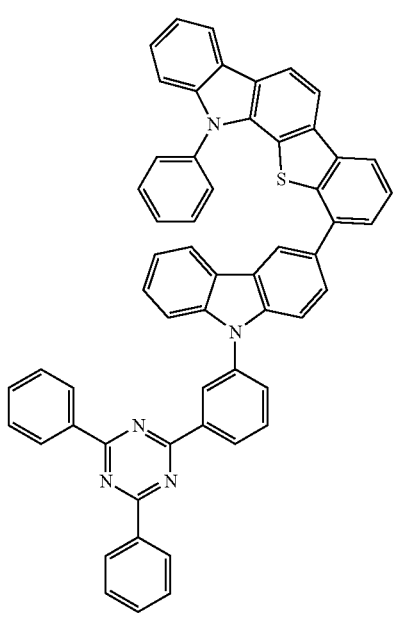
Compound 1033
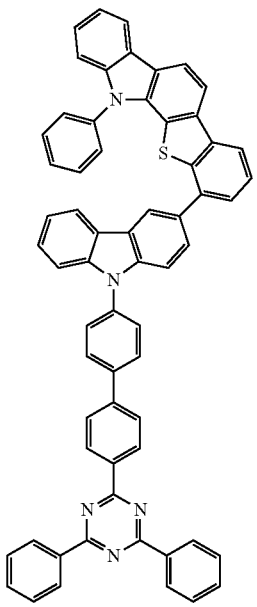
Compound 1037
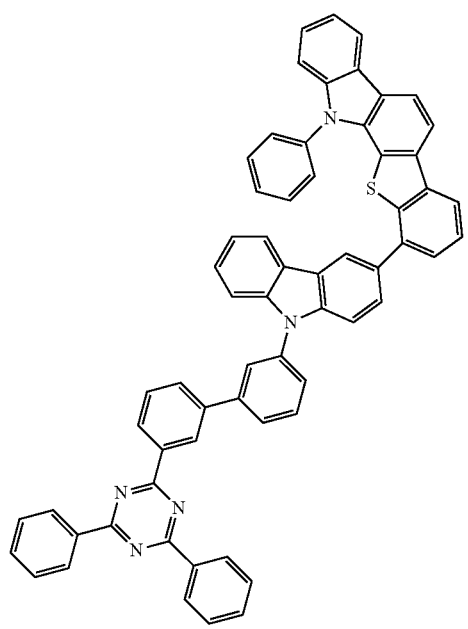
Compound 1057

Compound 1061
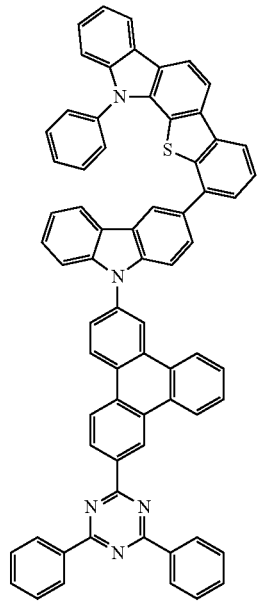
Compound 1065
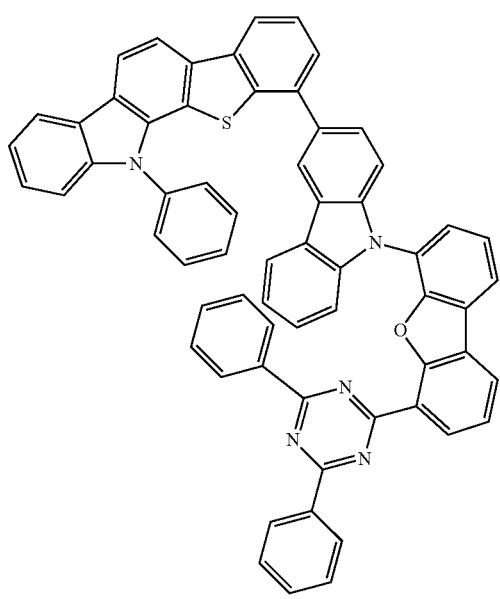
Compound 1069
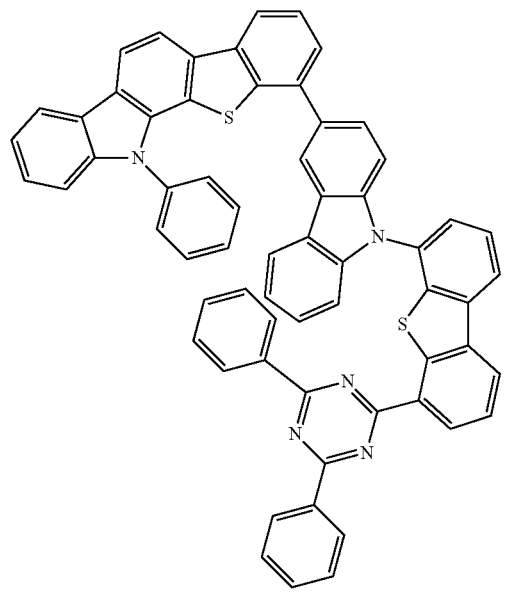
Compound 1081
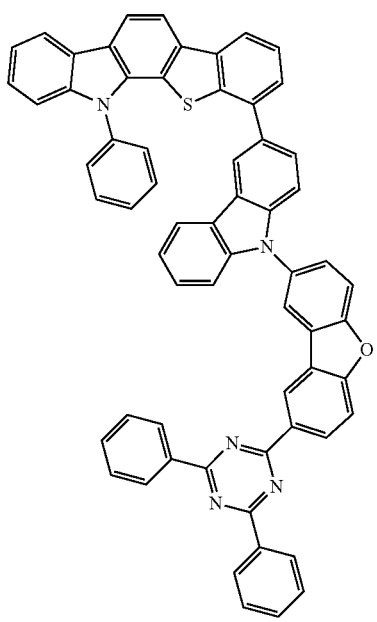

Compound 1085
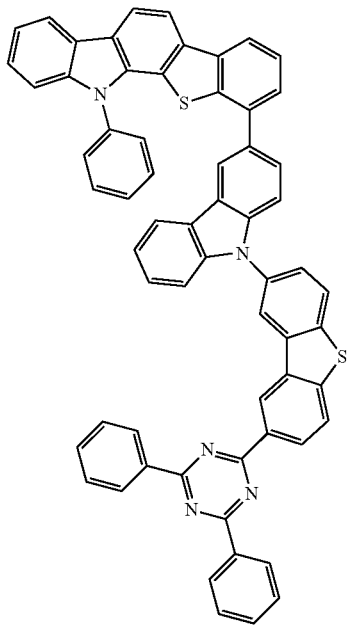
Compound 1089
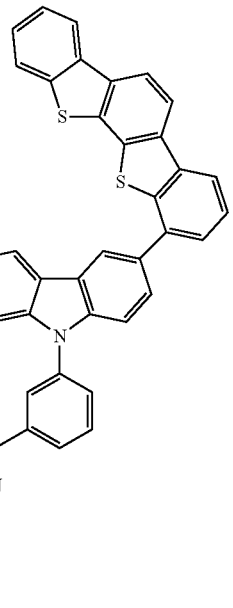
Compound 1093
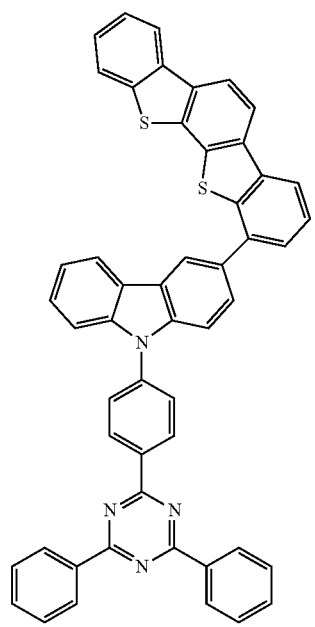
Compound 1111
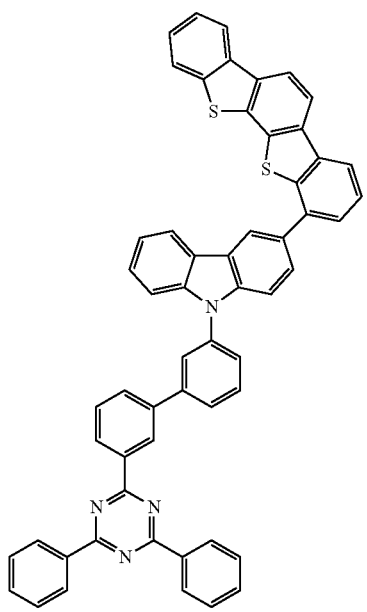

-continued
Compound 1097
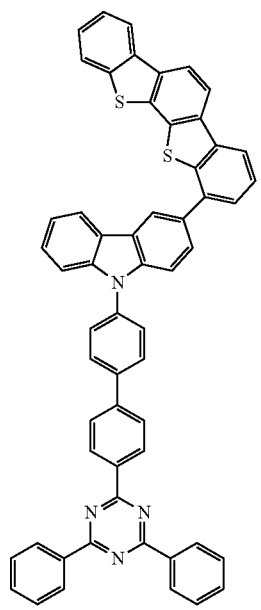
Compound 1121
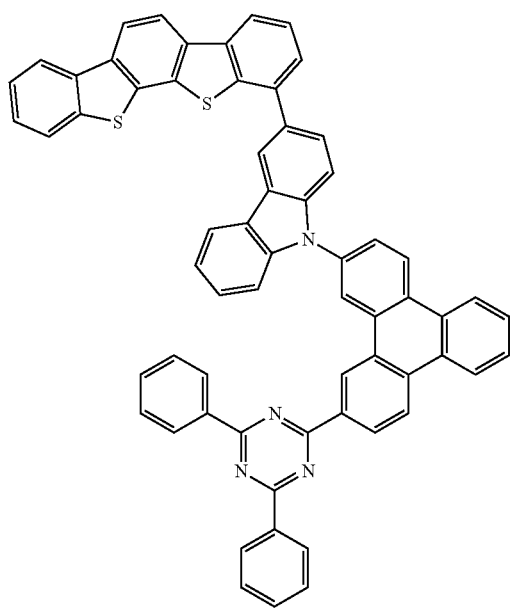
-continued
Compound 1125
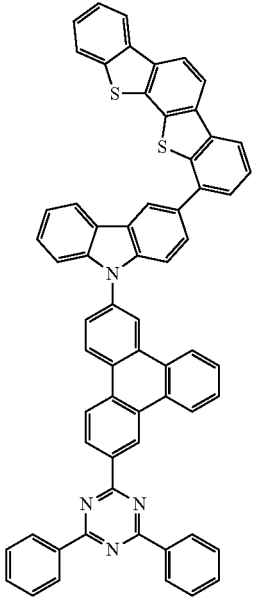
Compound 1129
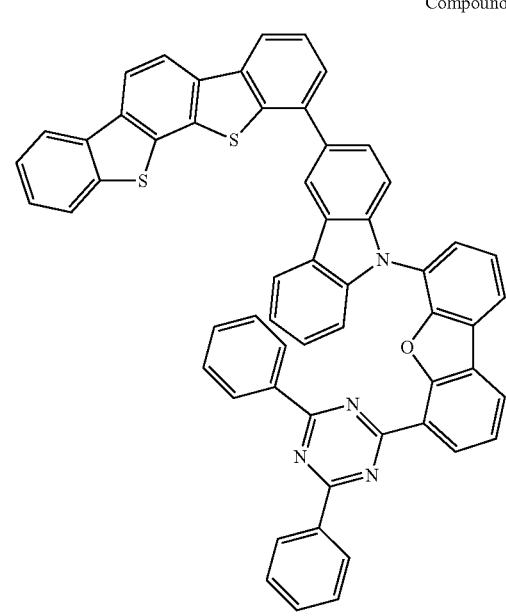

Compound 1133
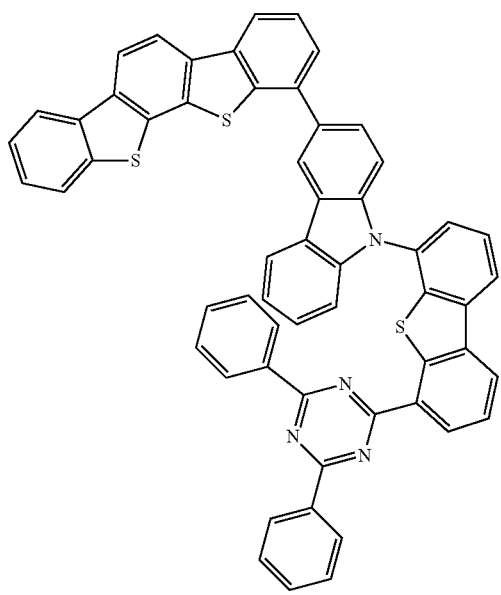
Compound 1149
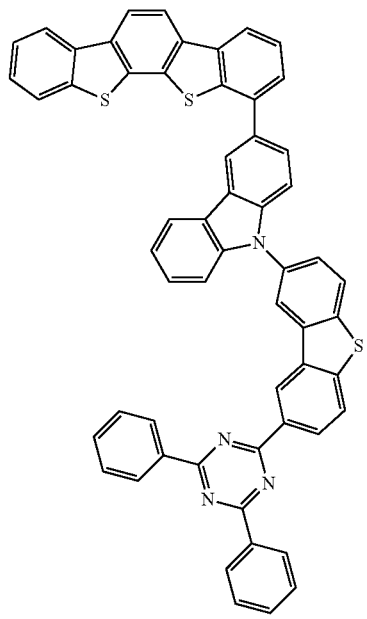
Compound 1145
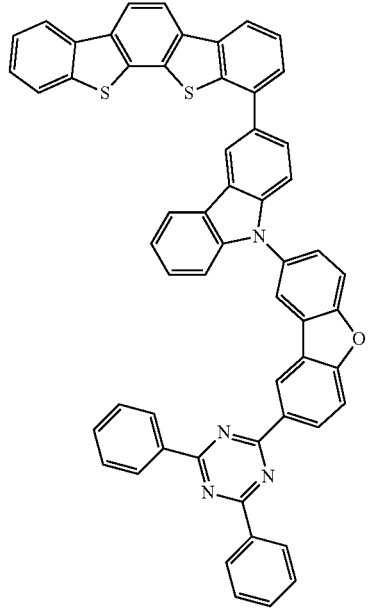
Compound 1157
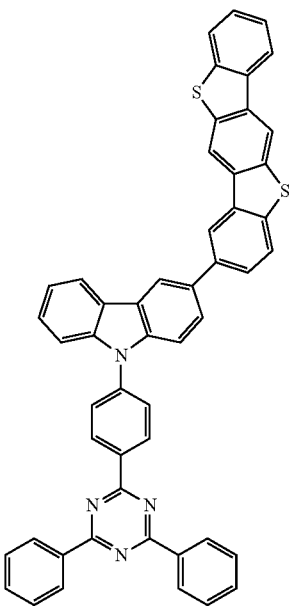

Compound 1153
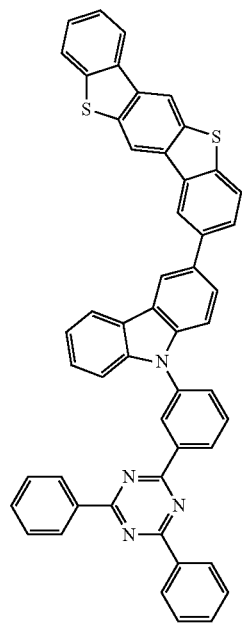
Compound 1161
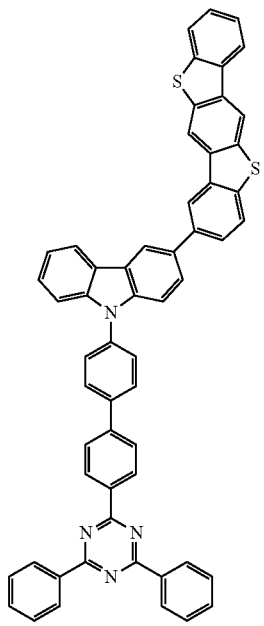
Compound 1165
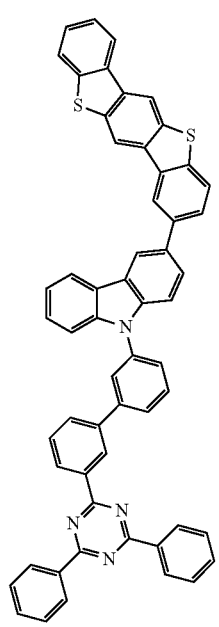
Compound 1185
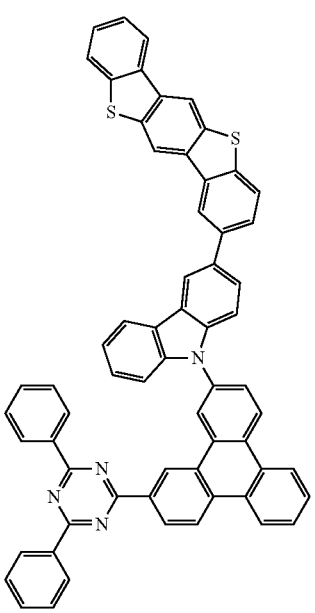

Compound 1189
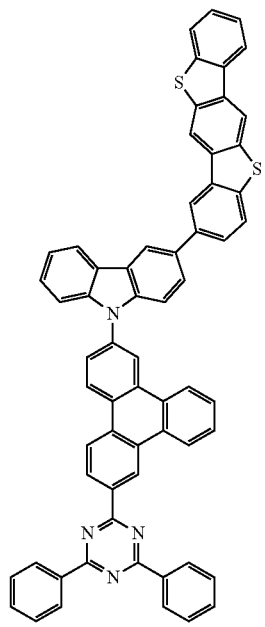
Compound 1197
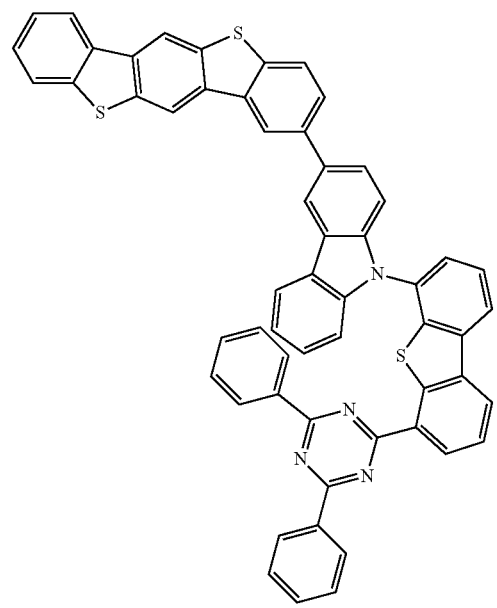
Compound 1193
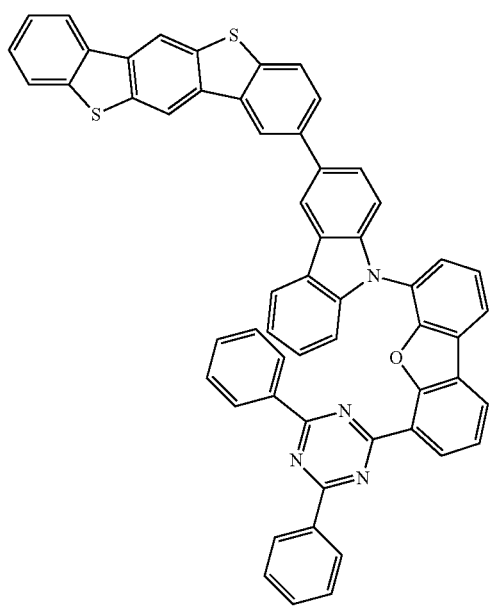
Compound 1209
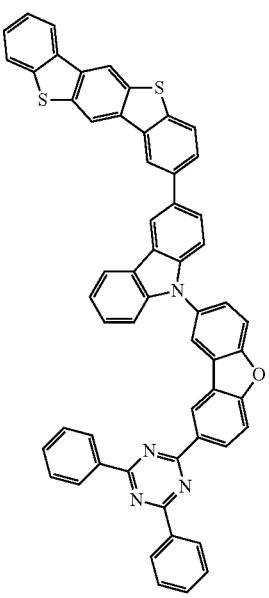

Compound 1213
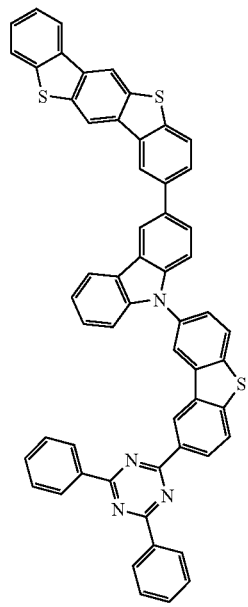
Compound 1217
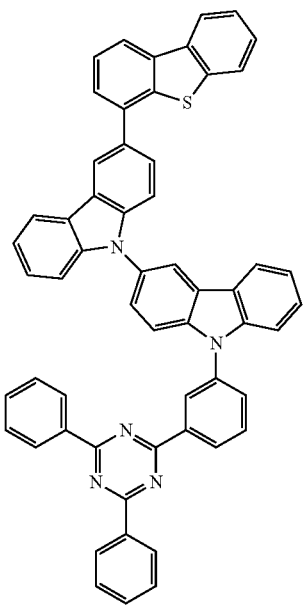
Compound 1221
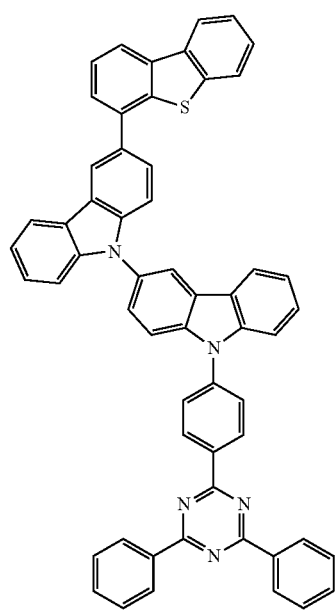
Compound 1229
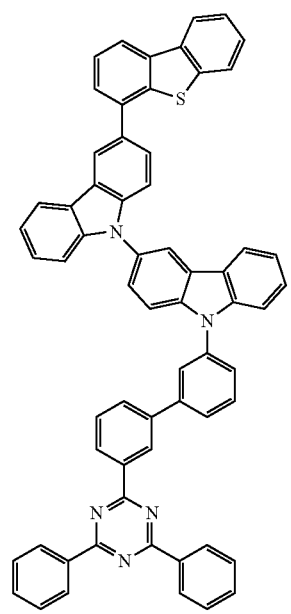

Compound 1225
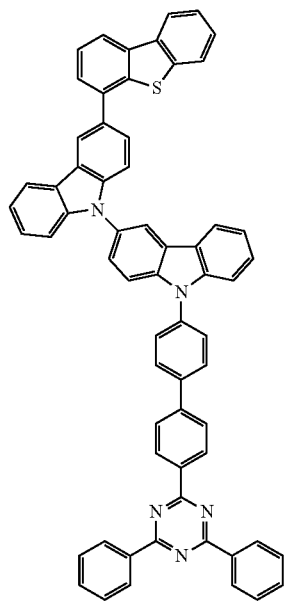
Compound 1253
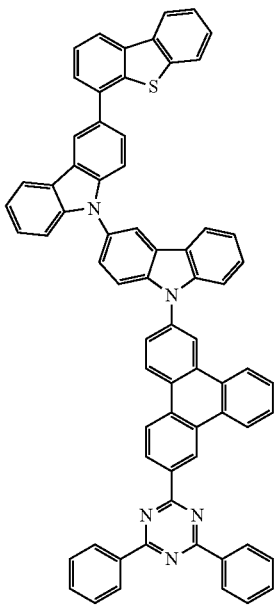
Compoound 1249
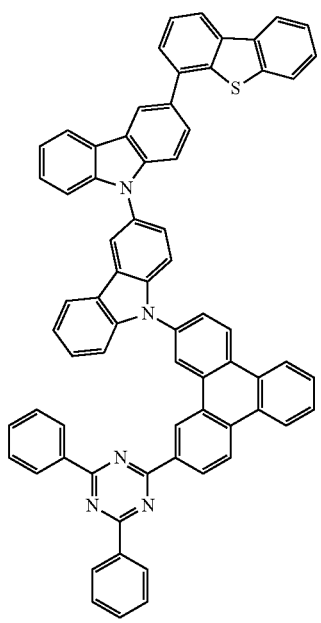
Compound 1257
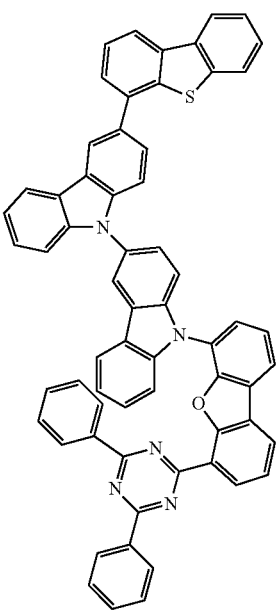

Compound 1261
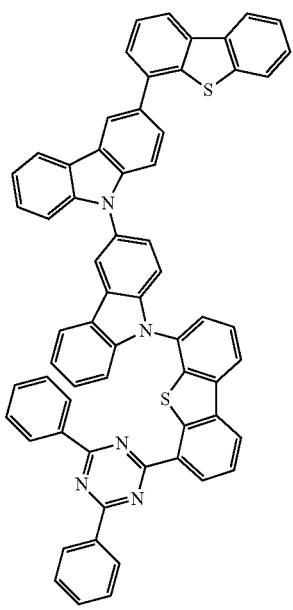
Compound 1177
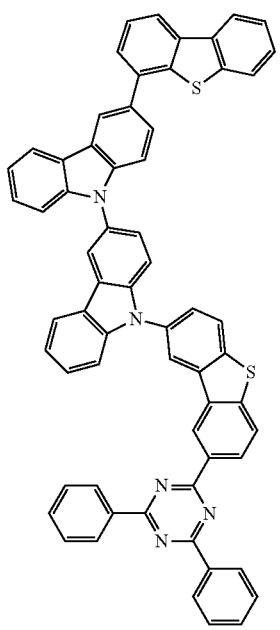
Compound 1173
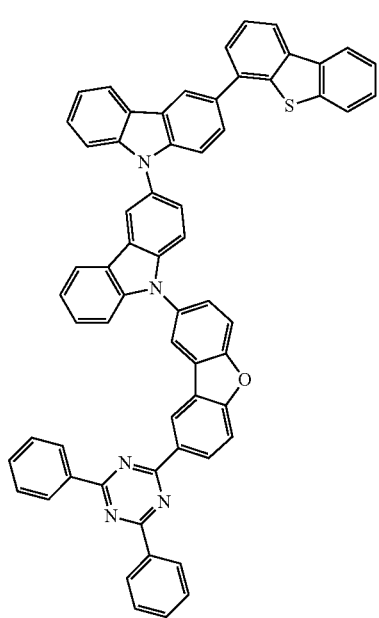
Compound 1477
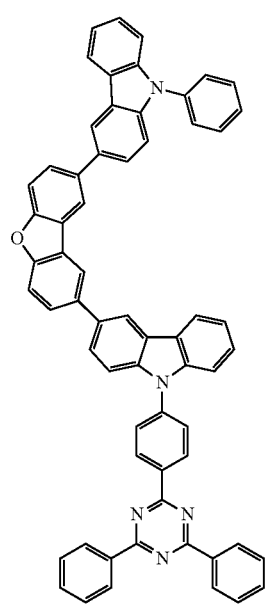

-continued
Compound 1473
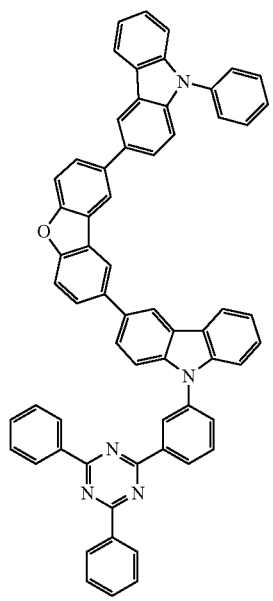
Compound 1481
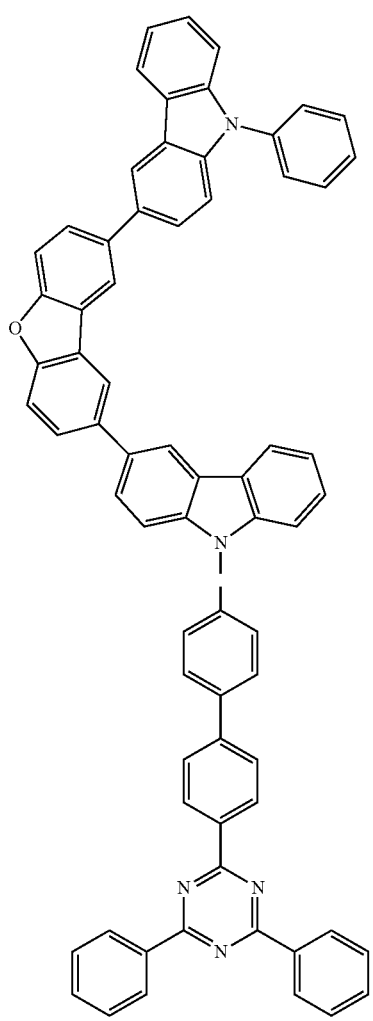
Compound 1485
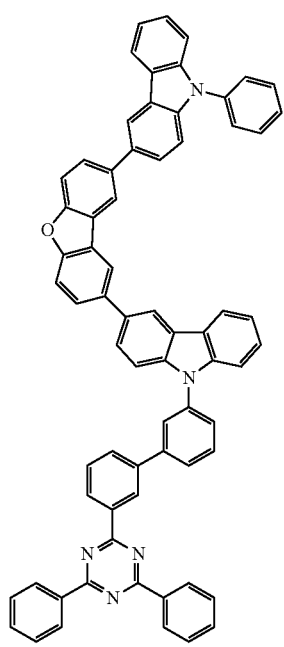
Compound 1505
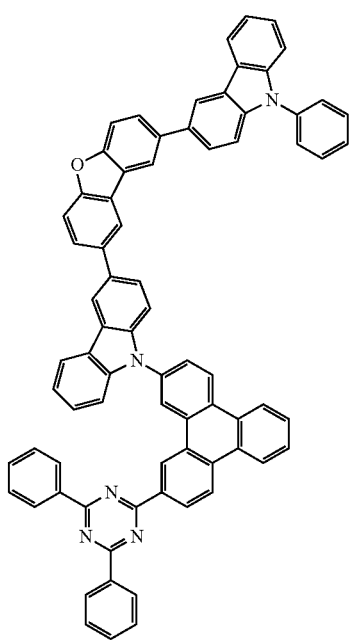

Compound 1509
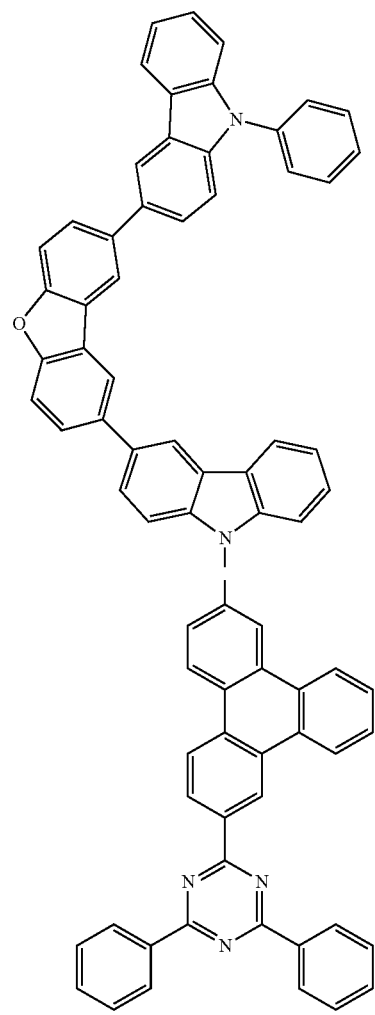
Compound 1513
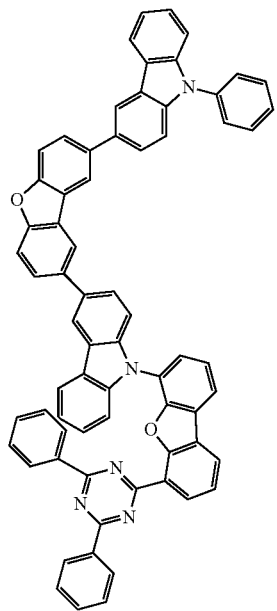
Compound 1517
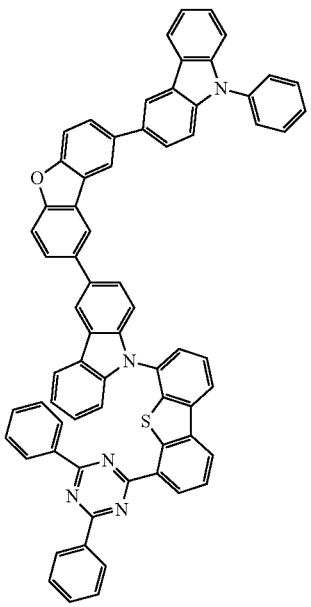
Compound 1529
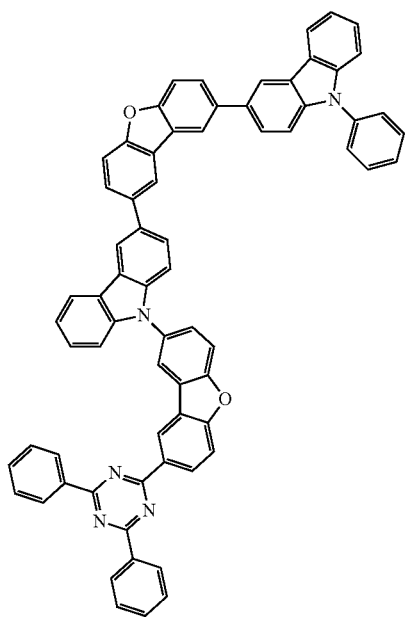

Compound 1533
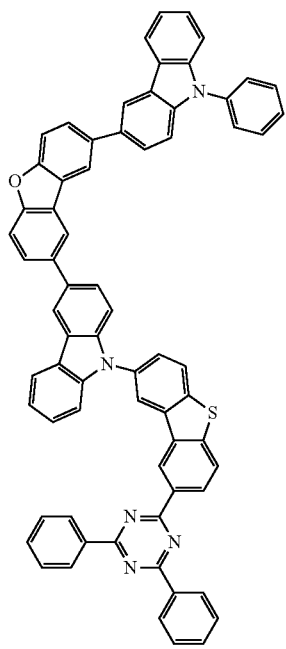
Compound 1601
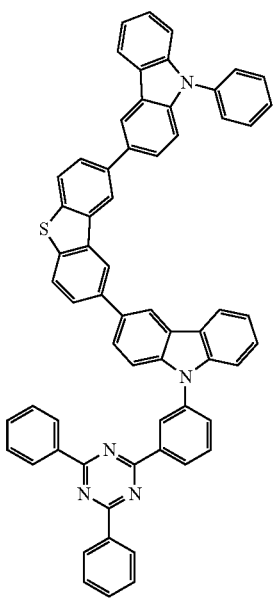
Compound 1605
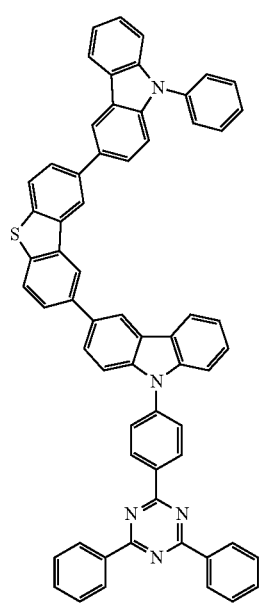
Compound 1613
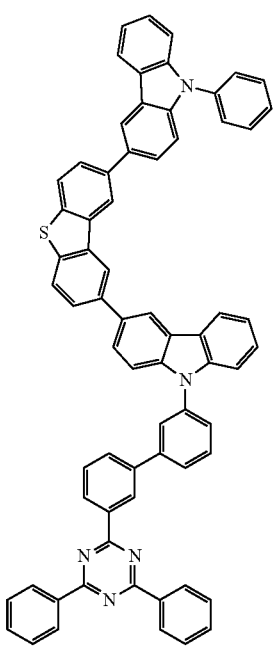

Compound 1609
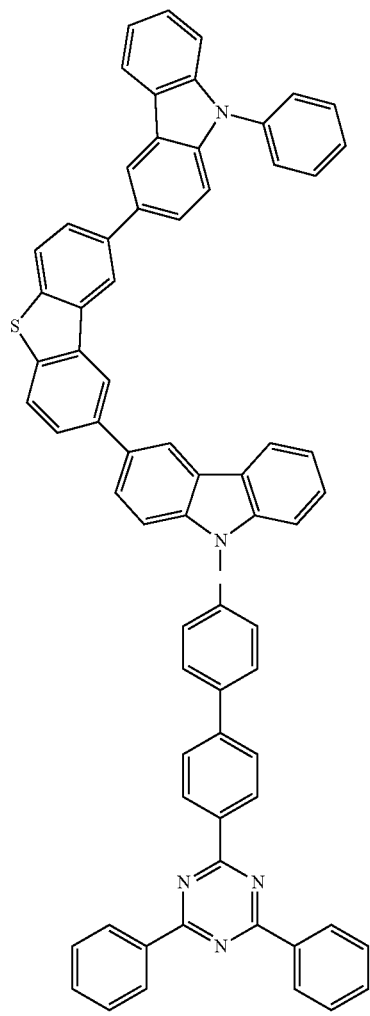
Compound 1637
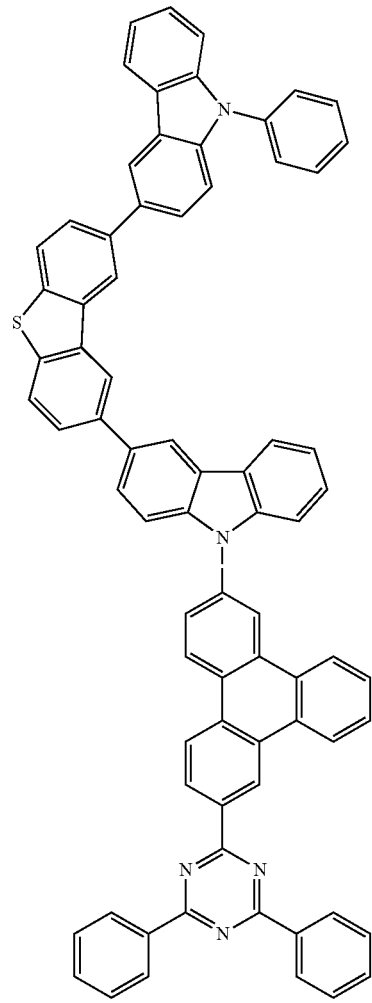
Compound 1633
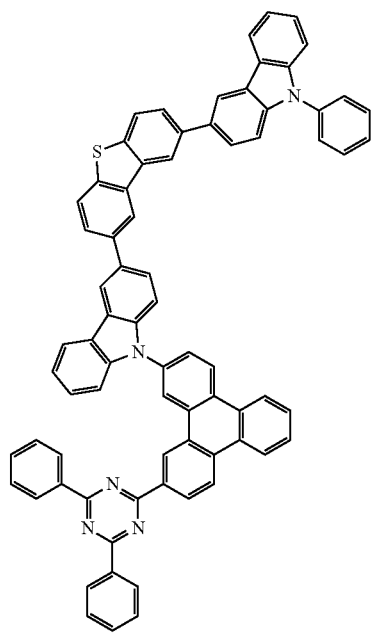
Compound 1641
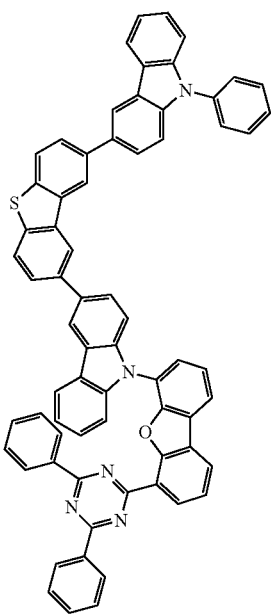

-continued
Compound 1645
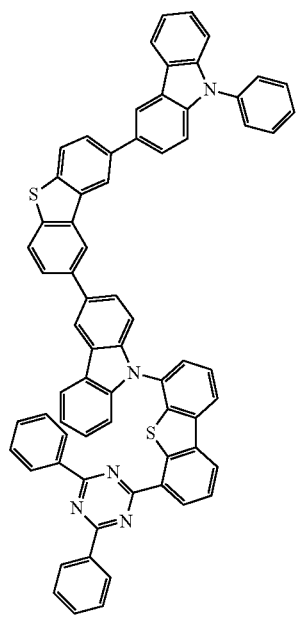
Compound 1661
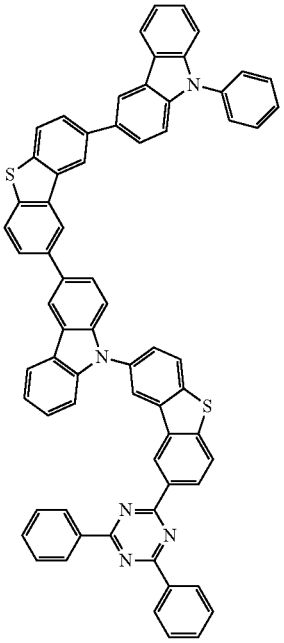
Compound 1657
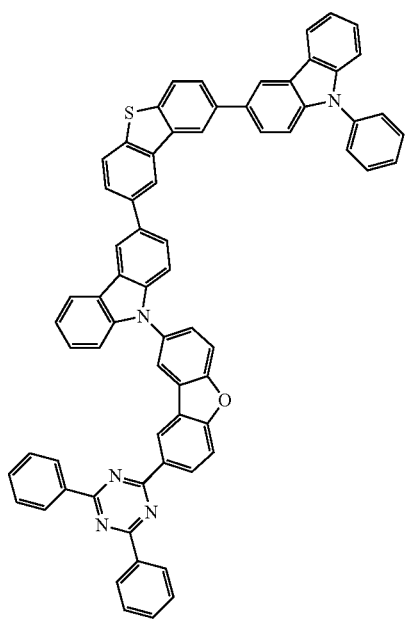
Compound 1669
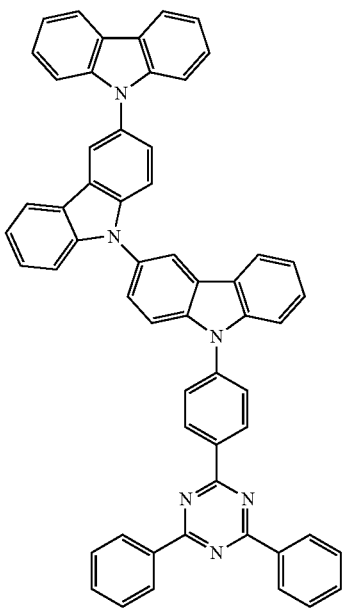

Compound 1665
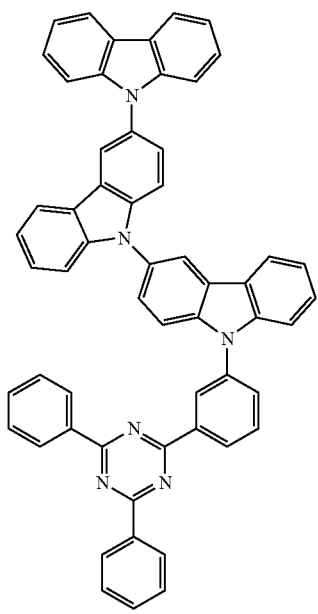
Compound 1673
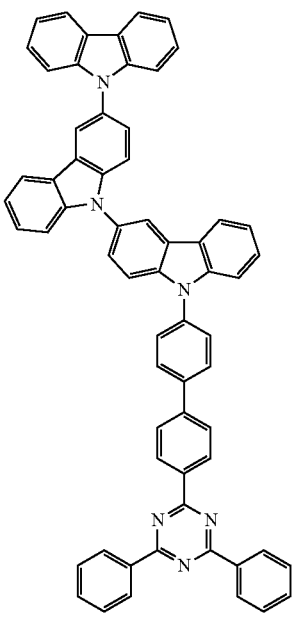
Compound 1677
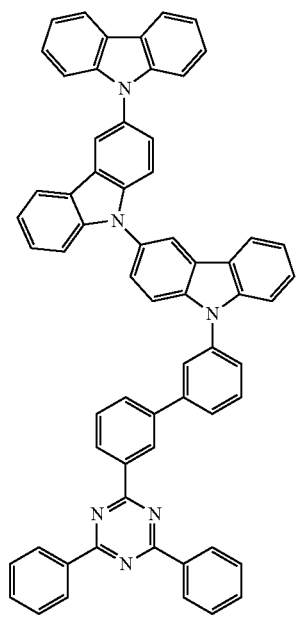
Compound 1697
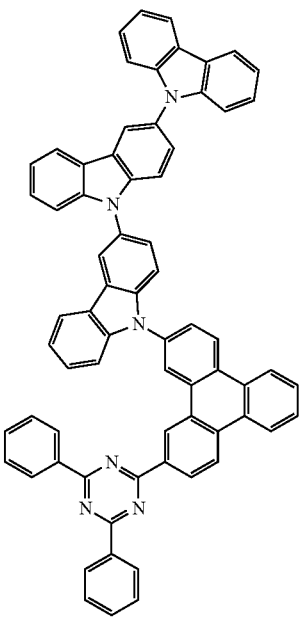

Compound 1701
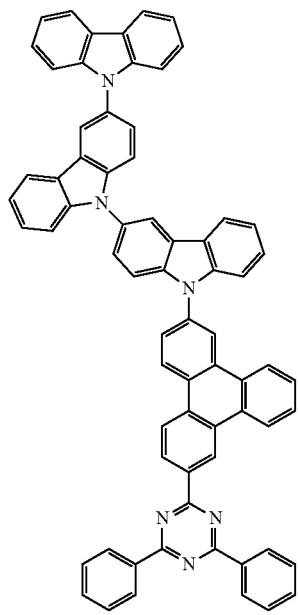
Compound 1705
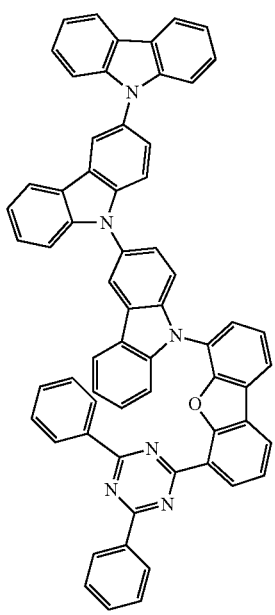
Compound 1709
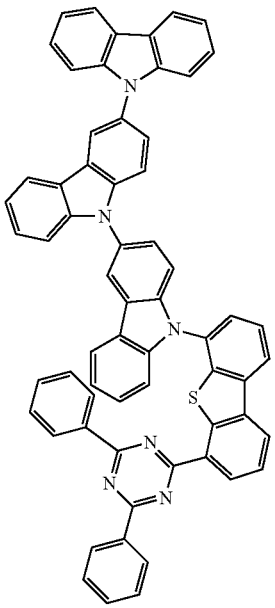
Compound 1721
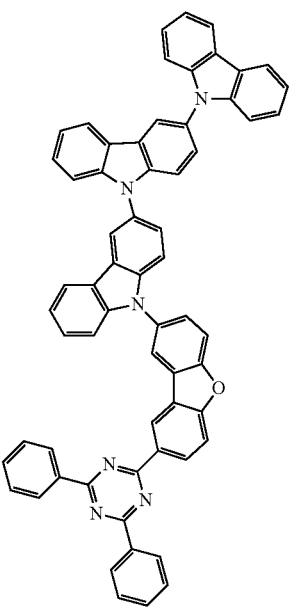

Compound 1725
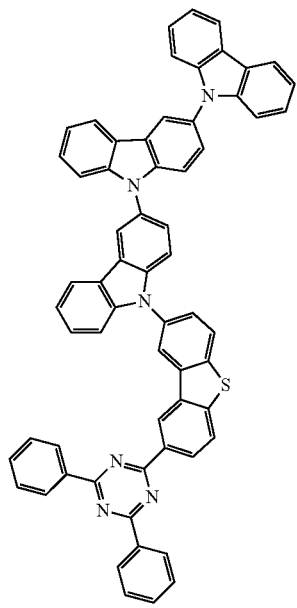
Compound 1793
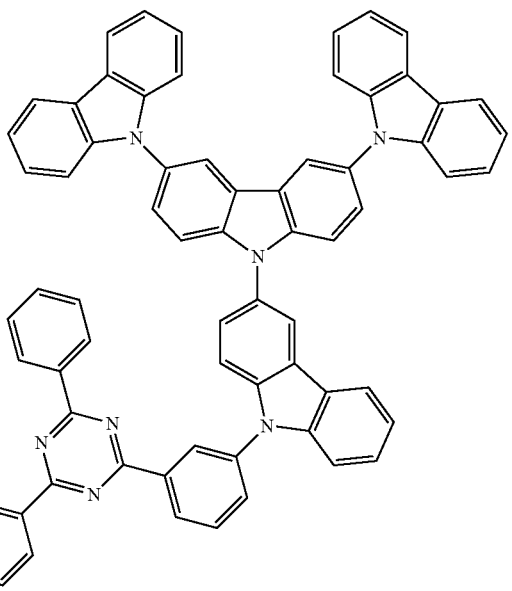
Compound 1797
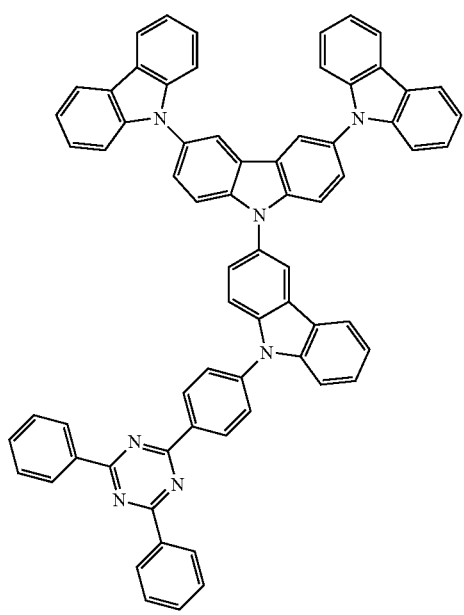
Compound 1805
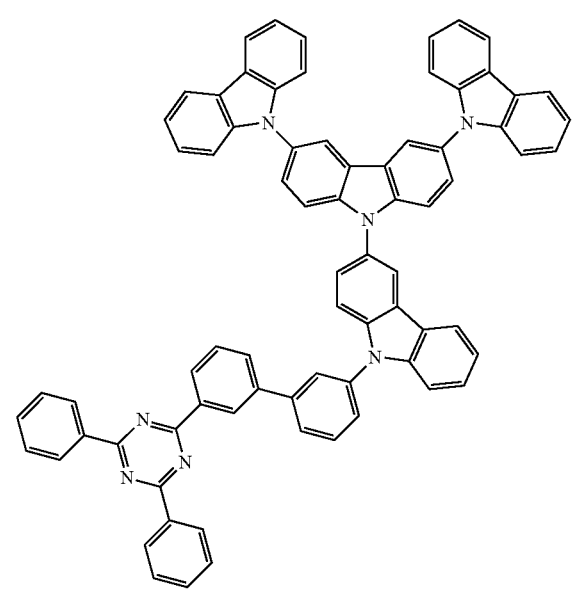

Compound 1801
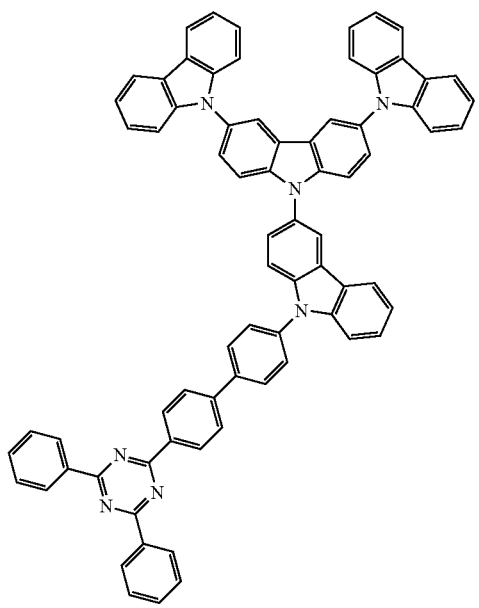
Compound 1837
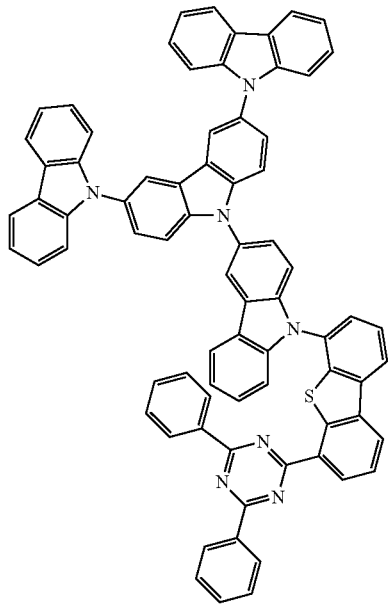
Compound 1833
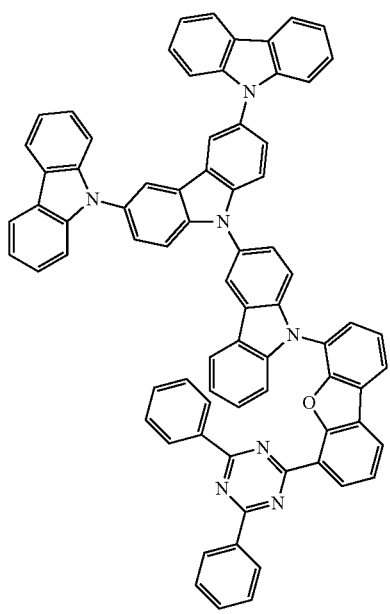
Compound 1853
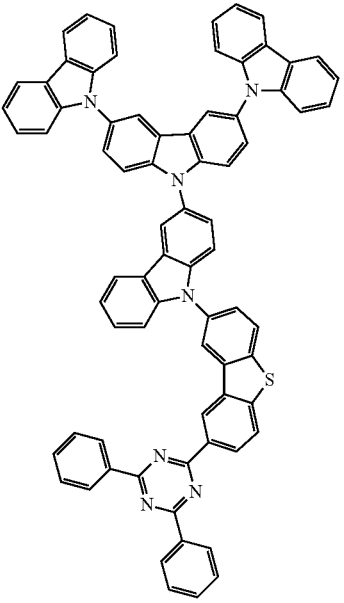

Compound 1849
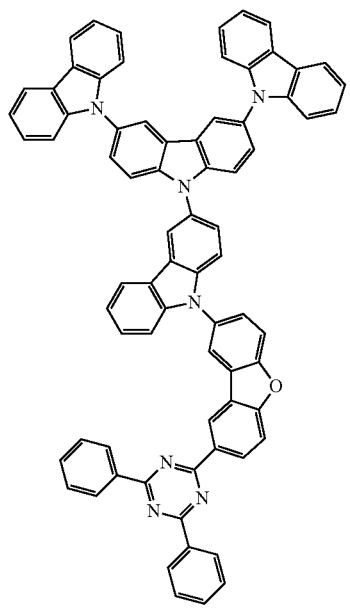
Compound 1857
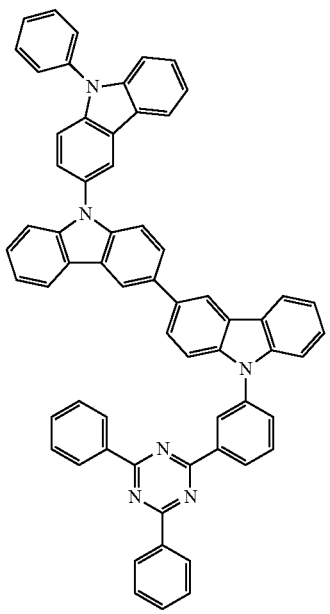
Compound 1861
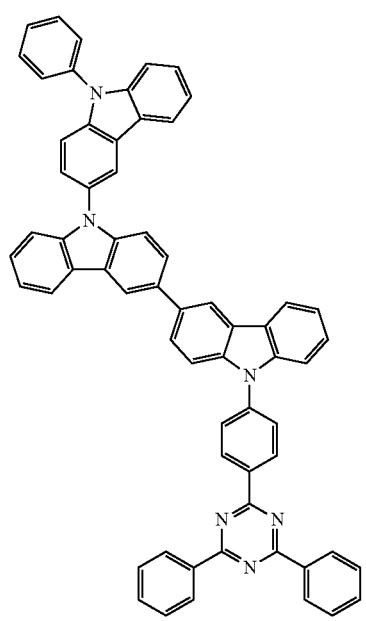
Compound 1869
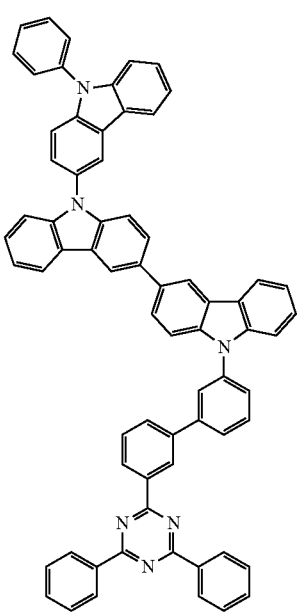

Compound 1865
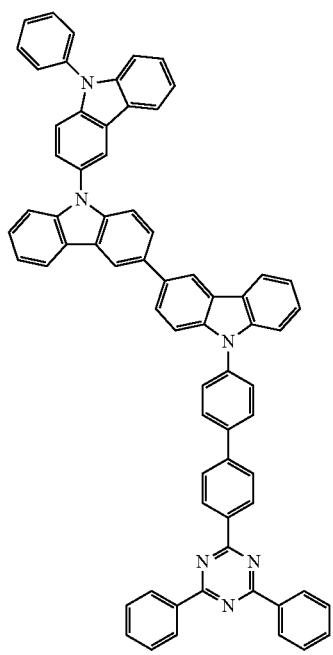
Compound 1889
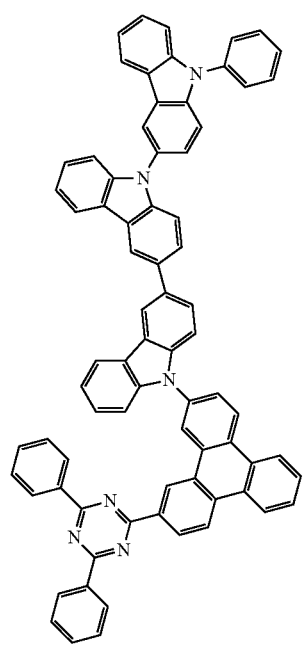
Compound 1893
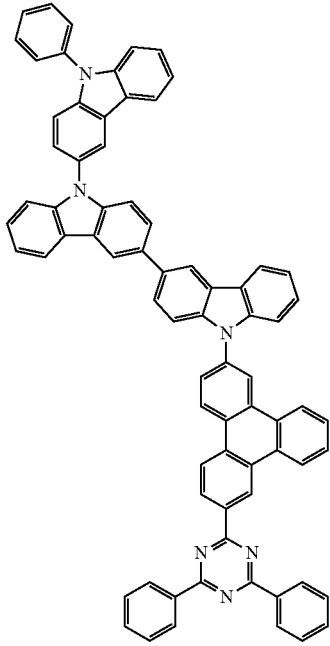
Compound 1897
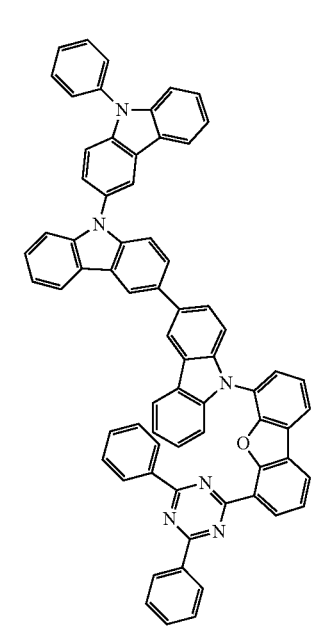

Compound 1901
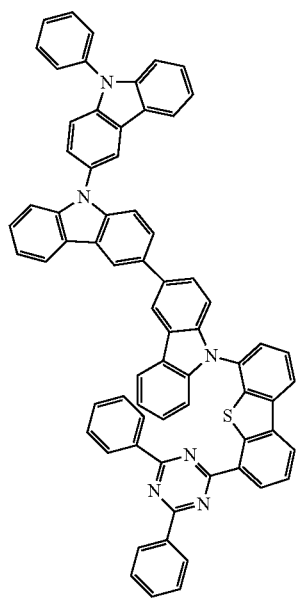
Compound 1913
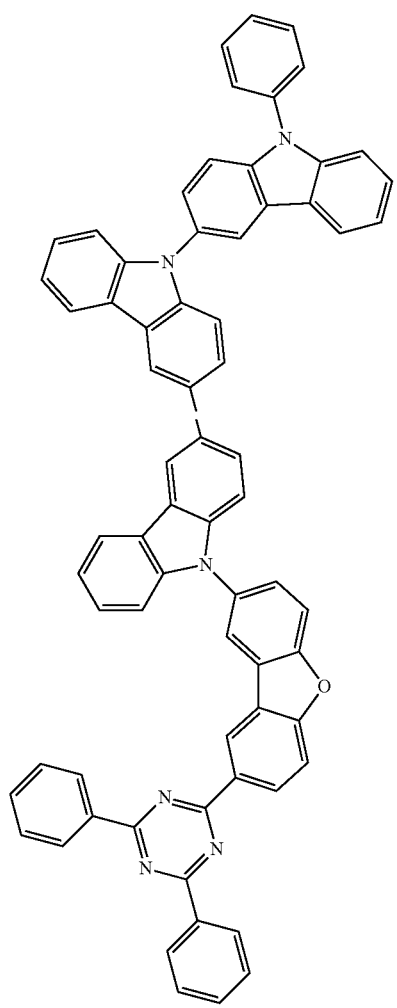
Compound 1917
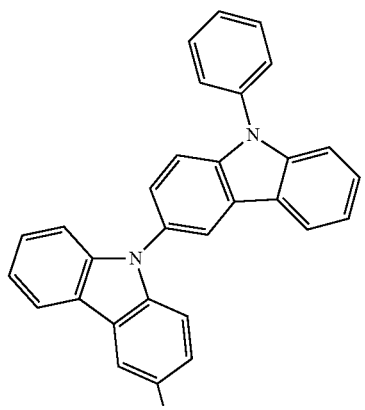
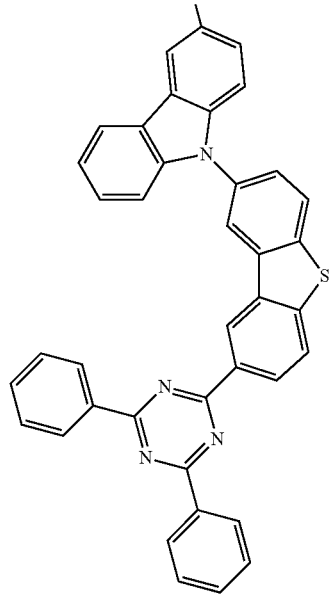
Compound 1989
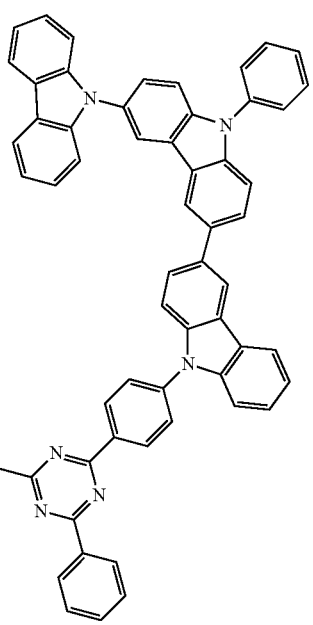

Compound 1985
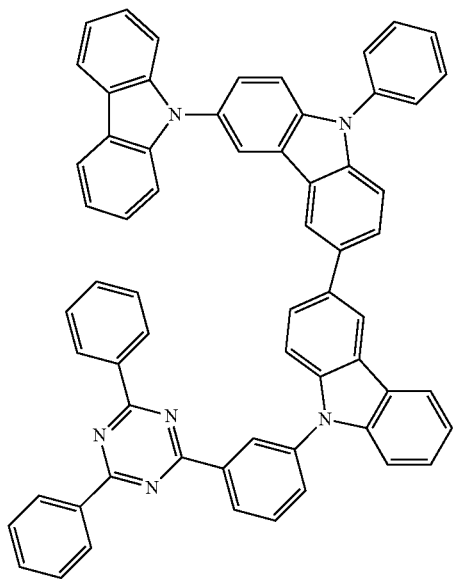
Compound 1993
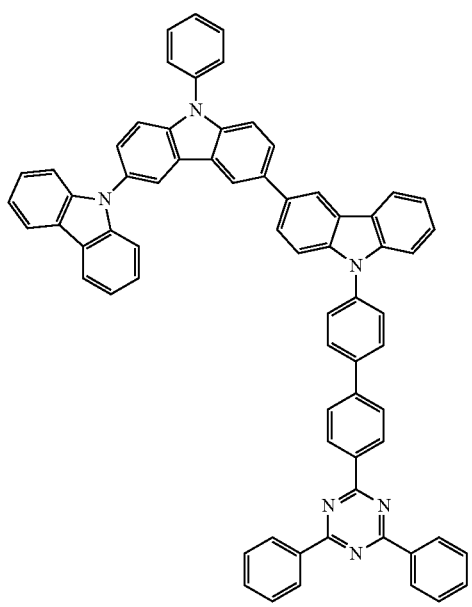
Compound 1997
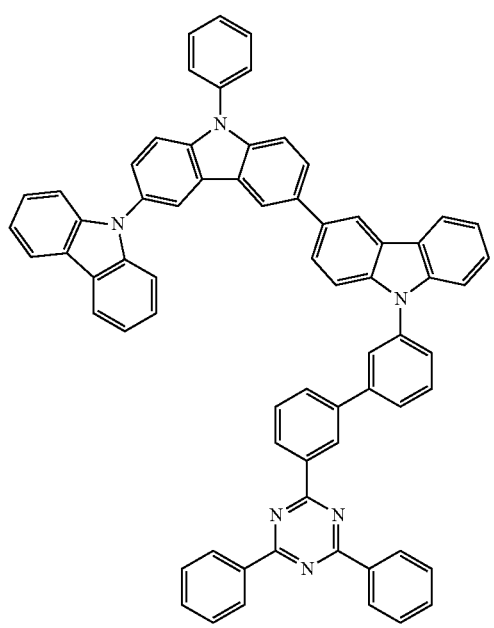
Compound 2017
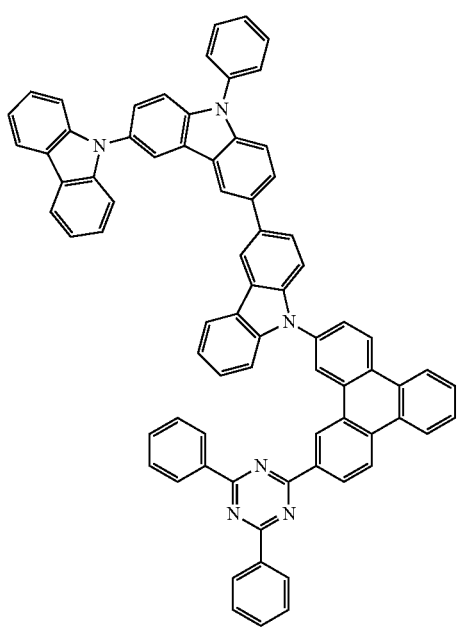

Compound 2021
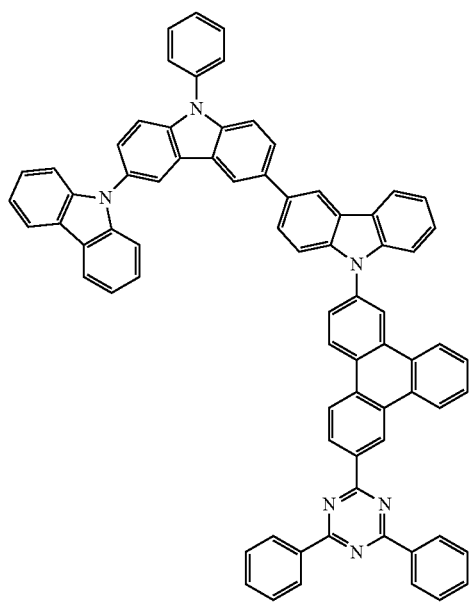
Compound 2029
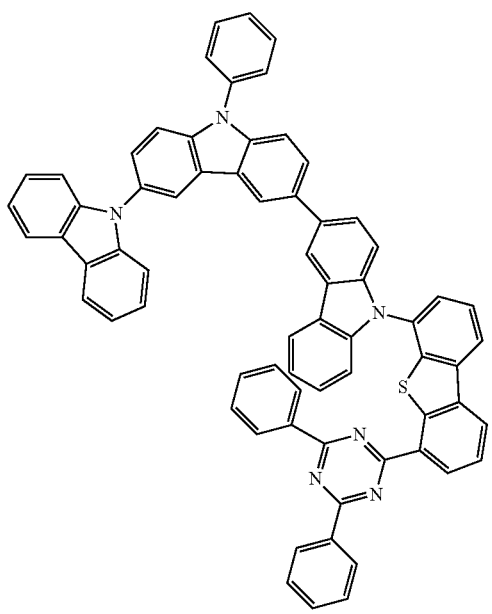
Compound 2025
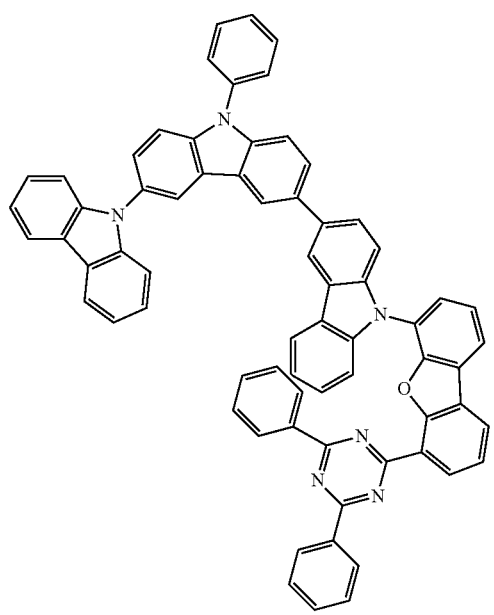
Compound 2041
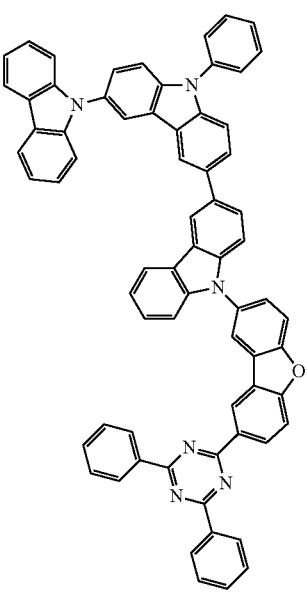

-continued
Compound 2045
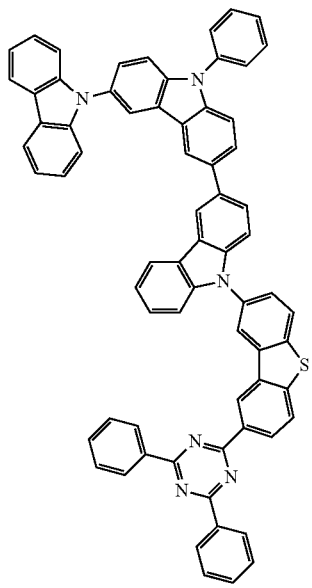
Compound 2113
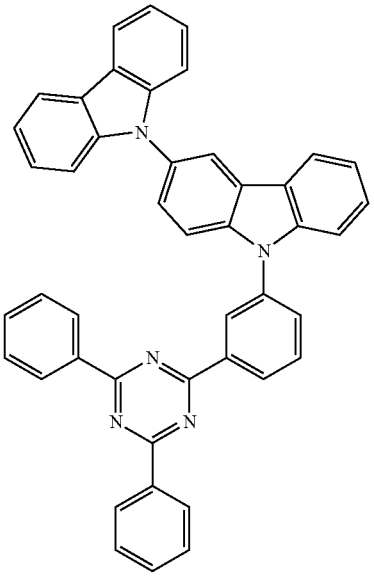
Compound 2117
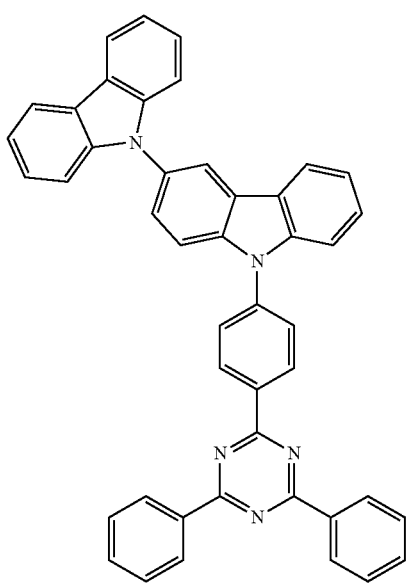
Compound 2125
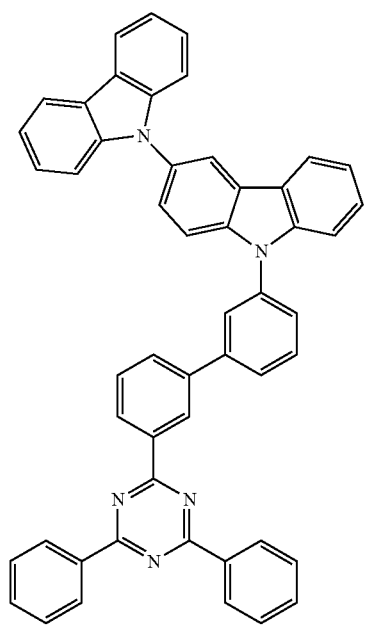

Compound 2121
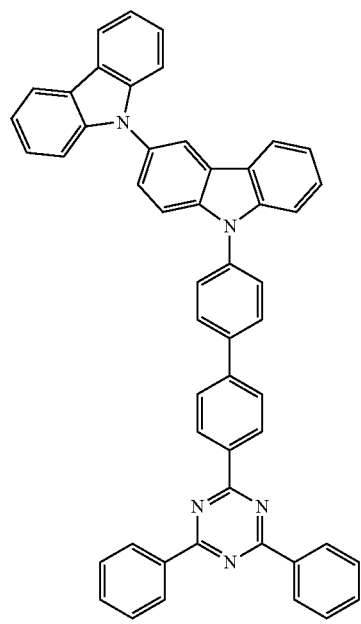
Compound 2149
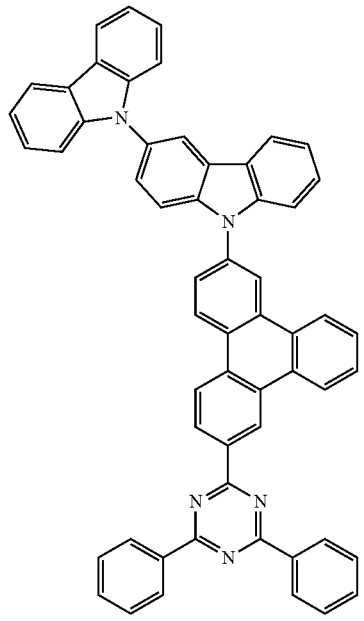
Compound 2145
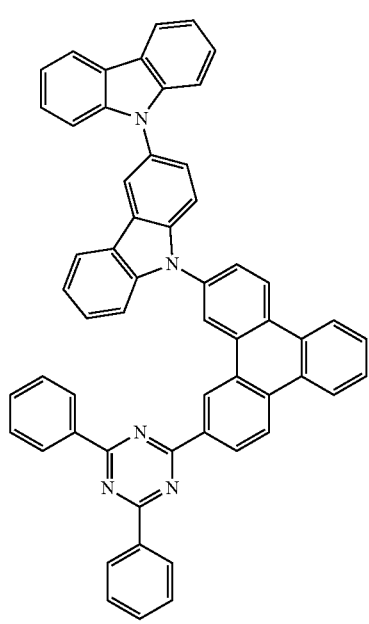
Compound 2153
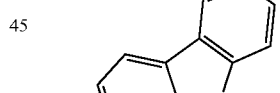

Compound 2157
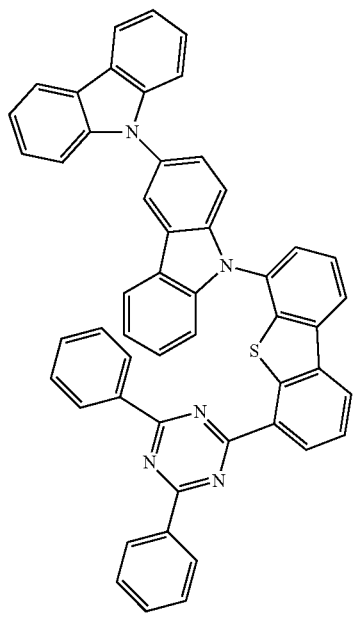
Compound 2169
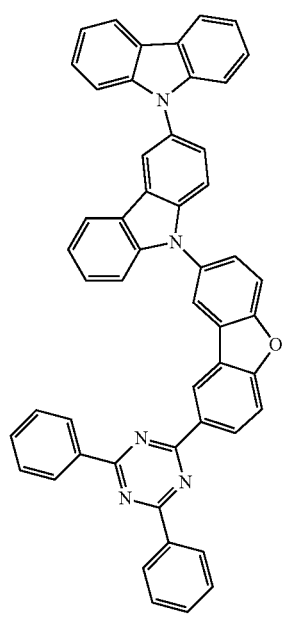
Compound 2173
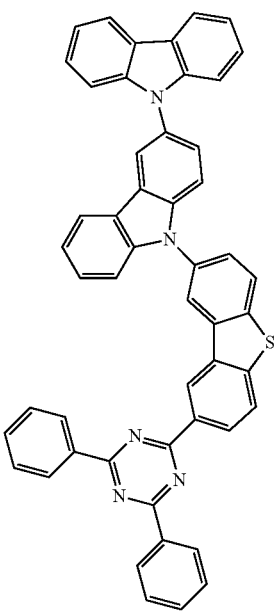
Compound 2181
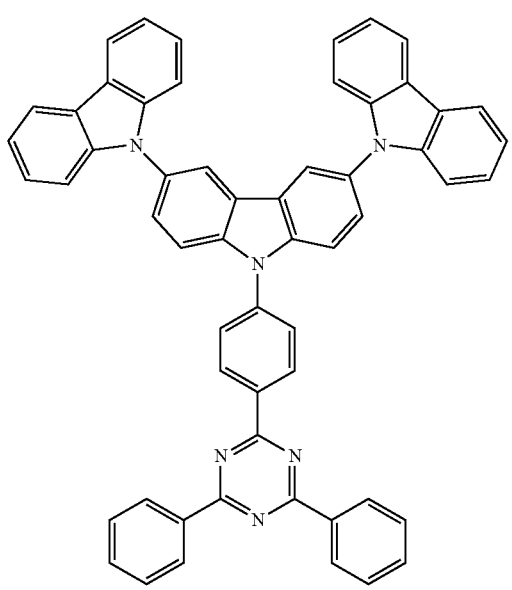

Compound 2177
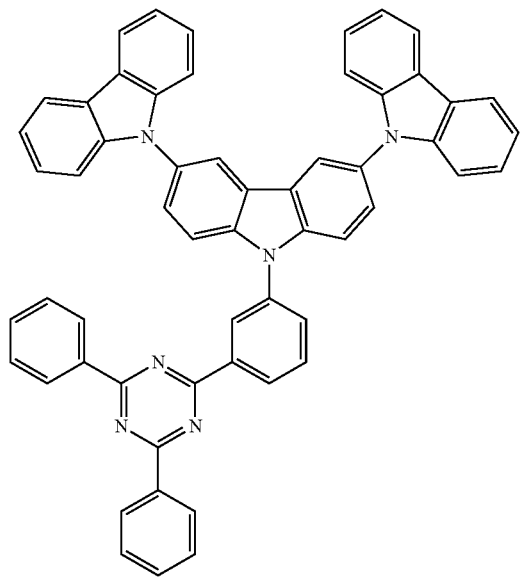
Compound 2185
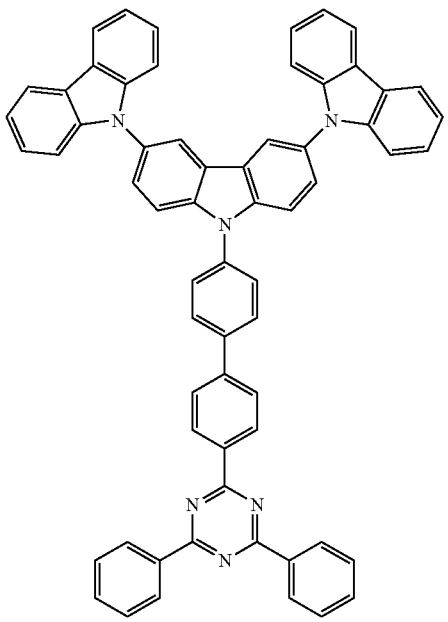
Compound 2189
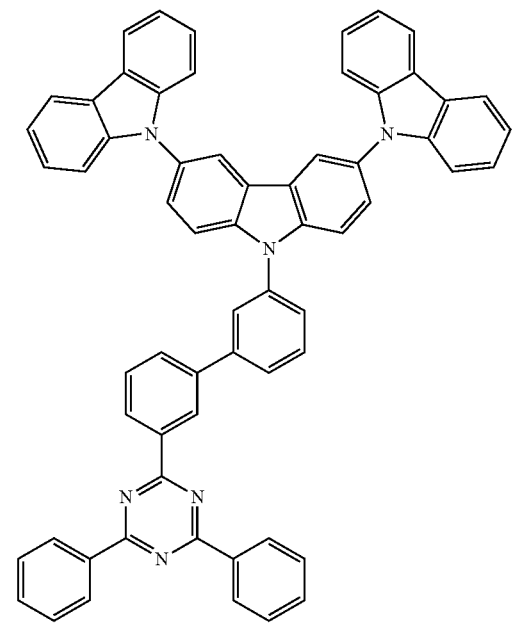
Compound 2209
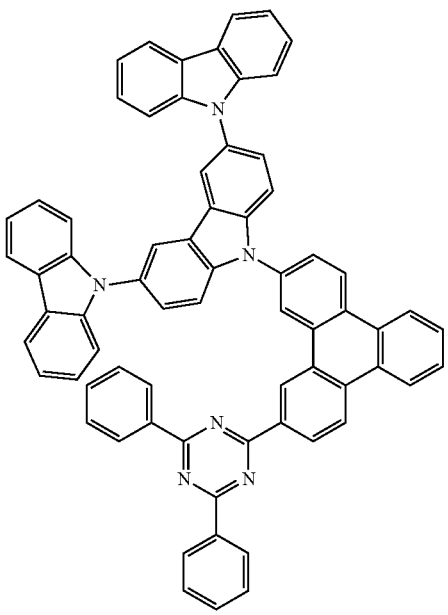

Compound 2213
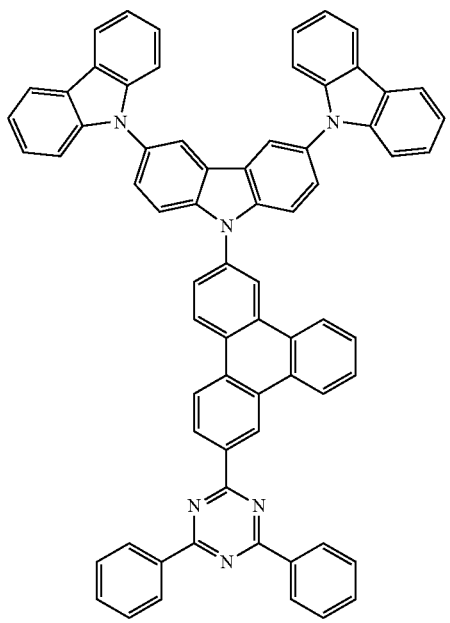
Compound 2217
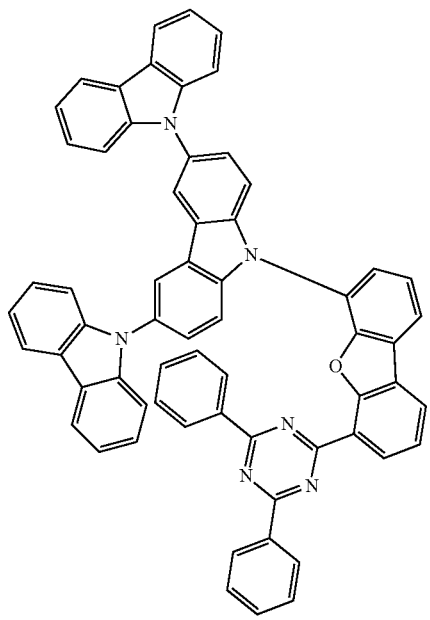
Compound 2221
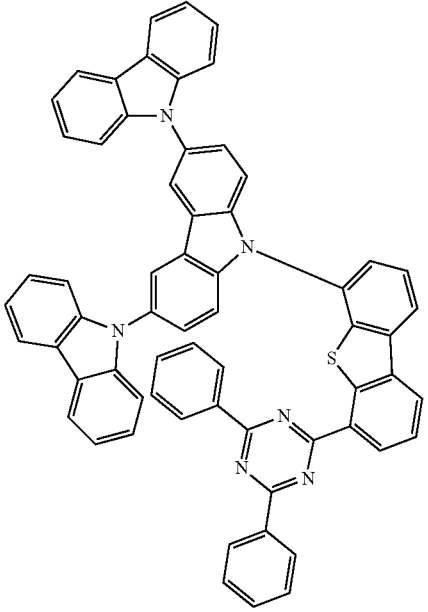
Compound 2221
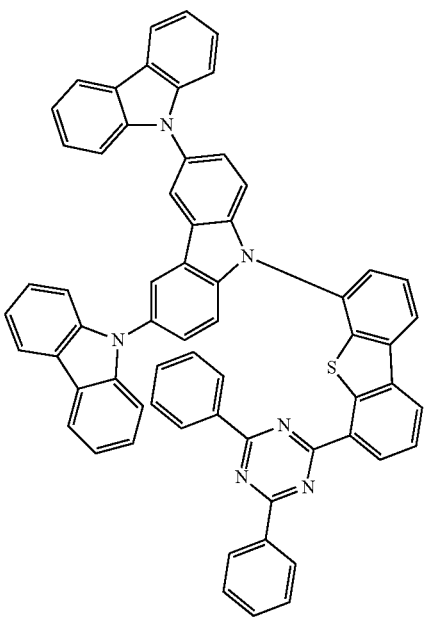

Compound 2233
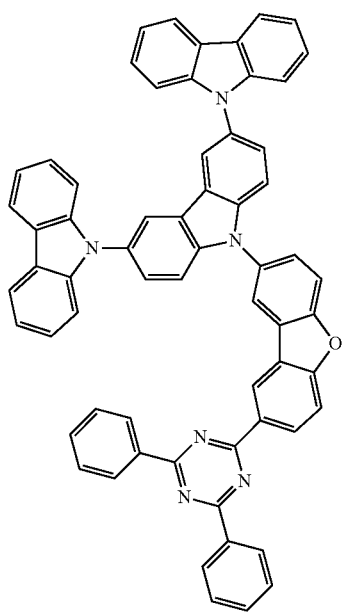
Compound 2245
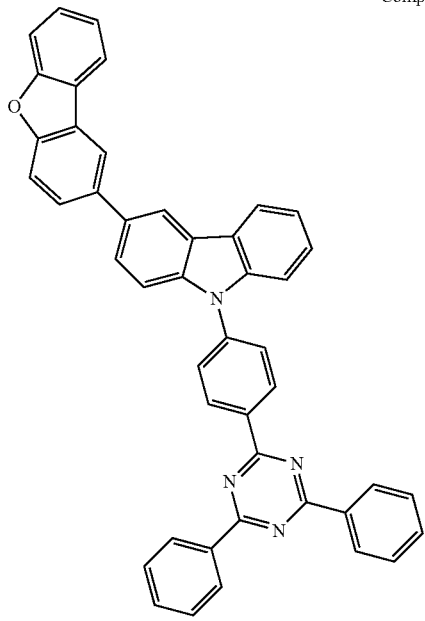
Compound 2237
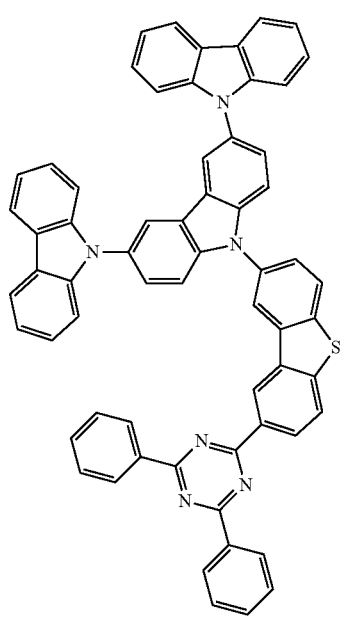
Compound 2241

Compound 2253
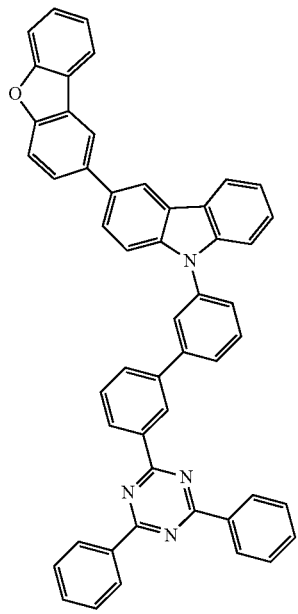
Compound 2273
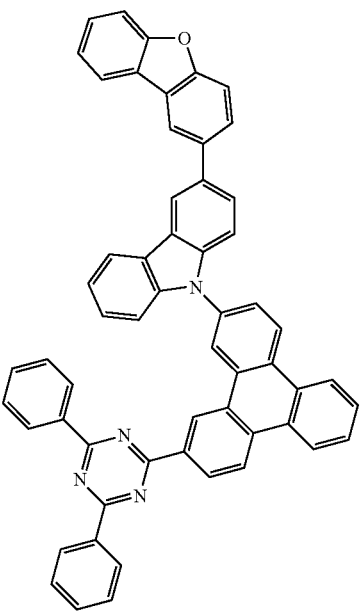
Compound 2249
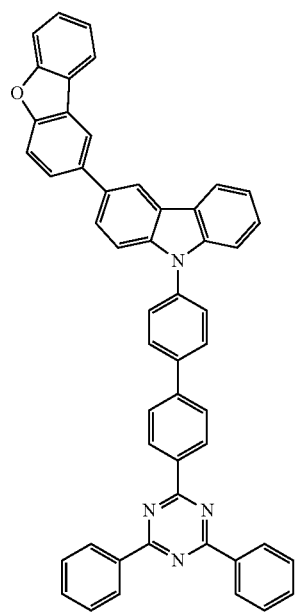
Compound 2277
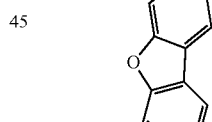

Compound 2281
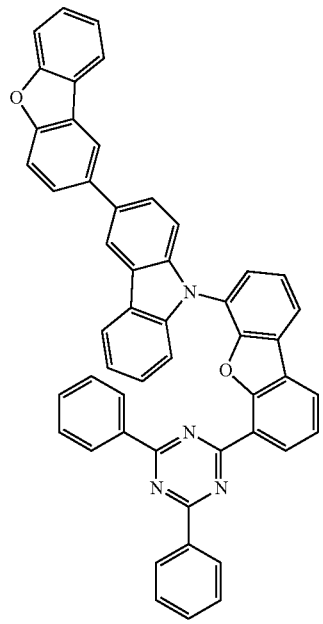
Compound 2297
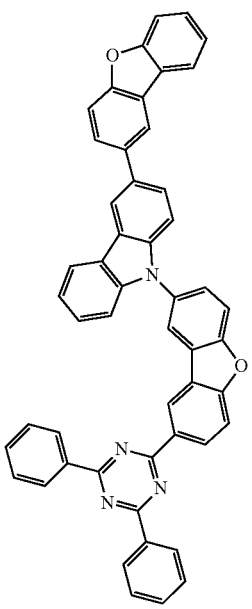
Compound 2285
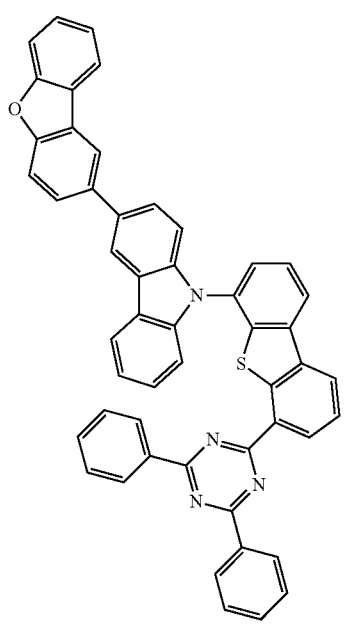
Compound 2301
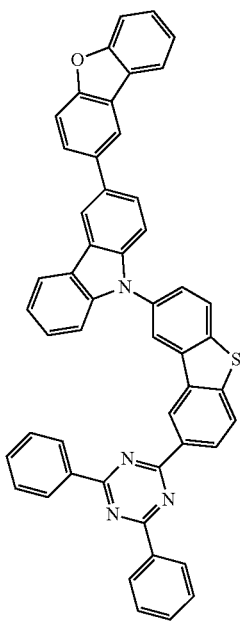

Compound 2373
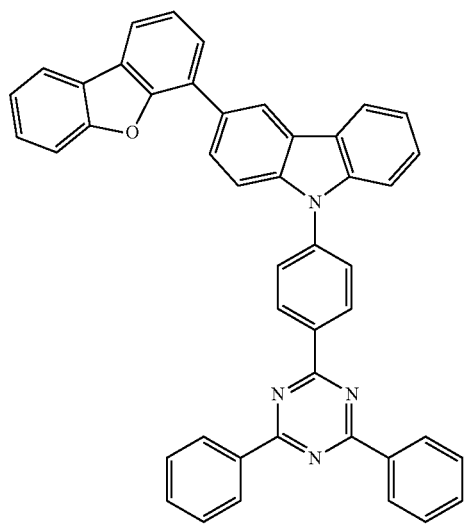
Compound 2369
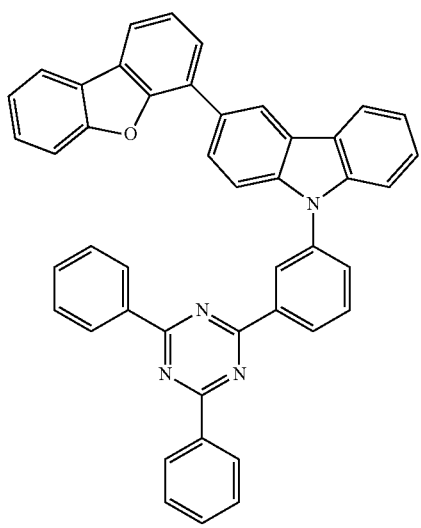
Compound 2381
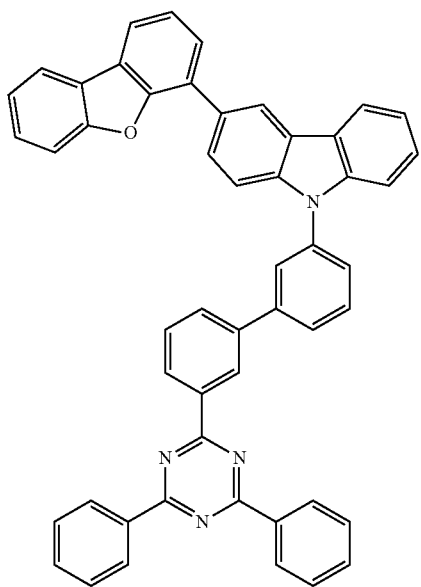
Compound 2277
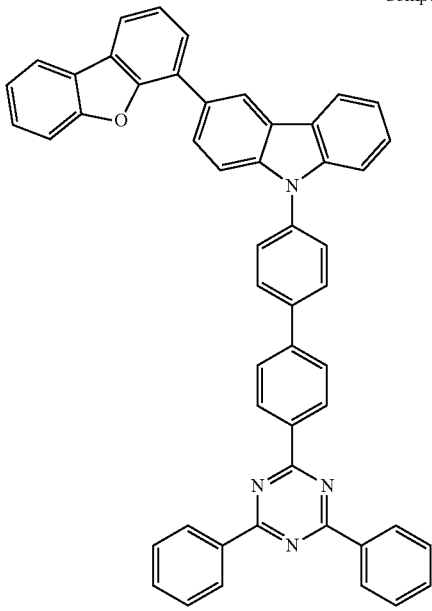
Compound 2401
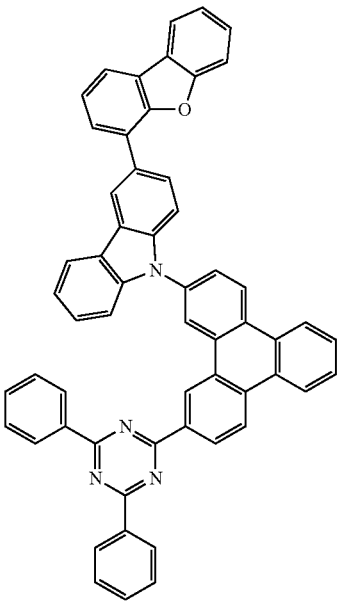

Compound 2405
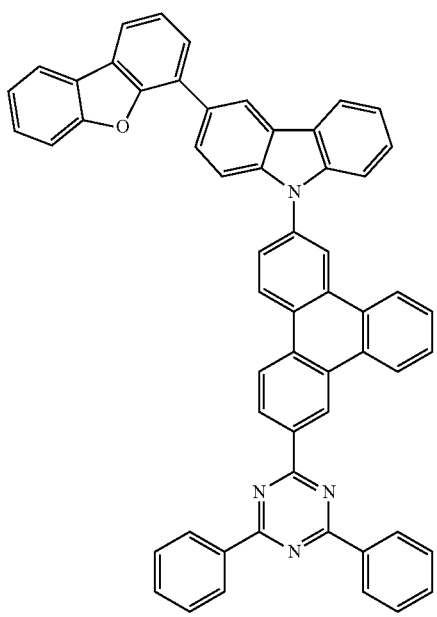
Compound 2413
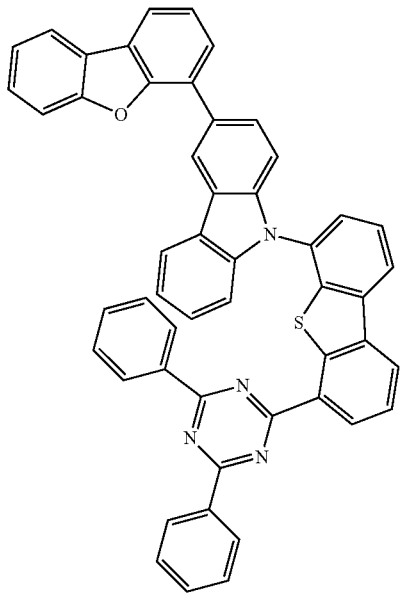
Compound 2409
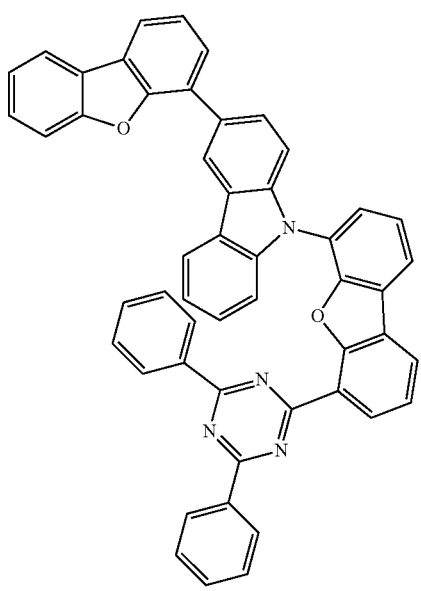
Compound 2425
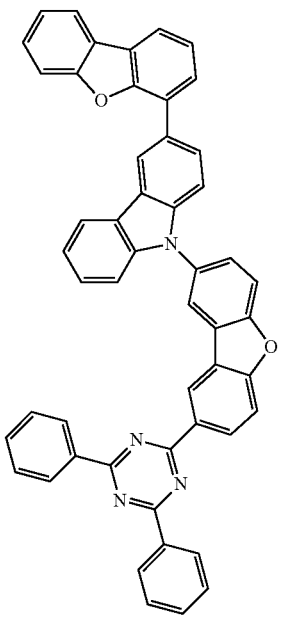

325
-continued
Compound 2429
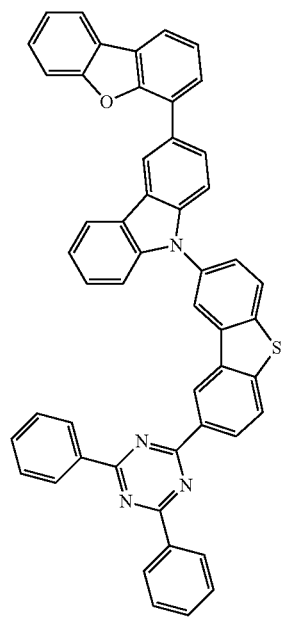
Compound 2503
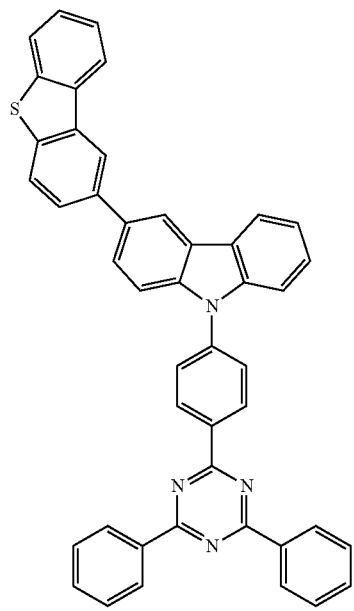
326
-continued
Compound 2497
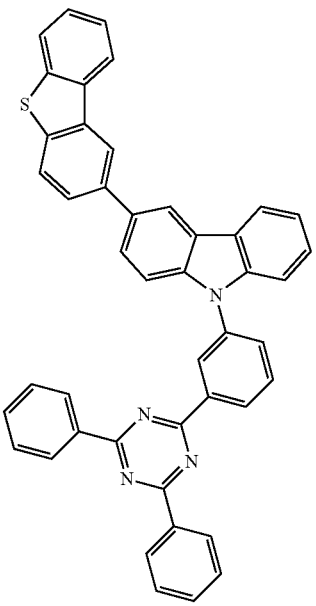
Compound 2511
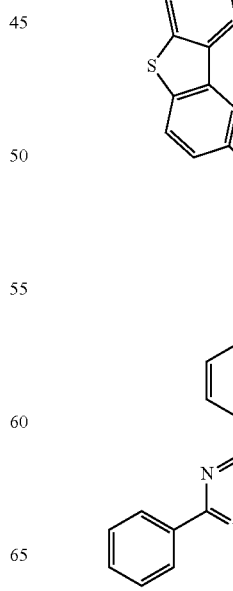

Compound 2507
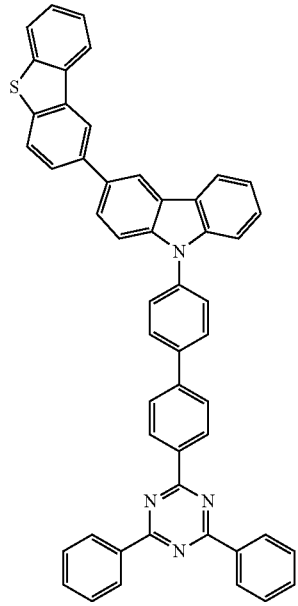
Compound 2533
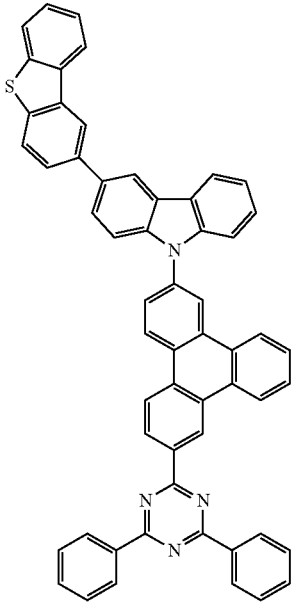
Compound 2529
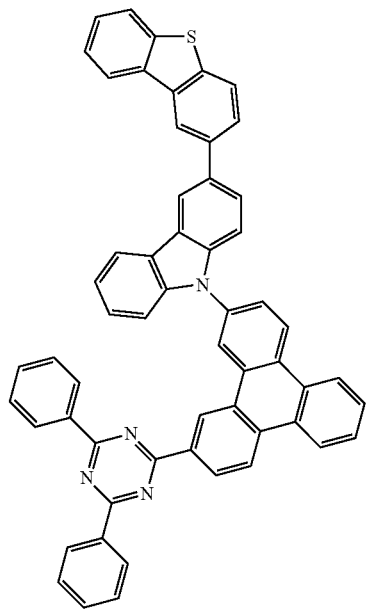
Compound 2537
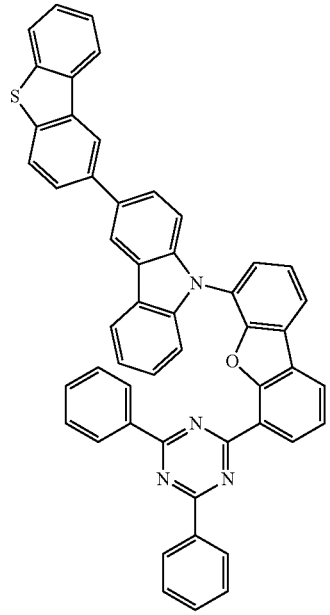

Compound 2541
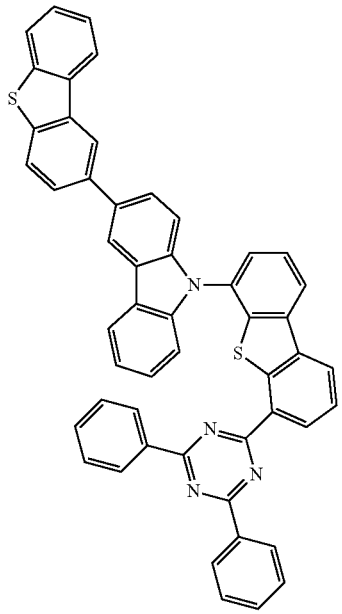
Compound 2557
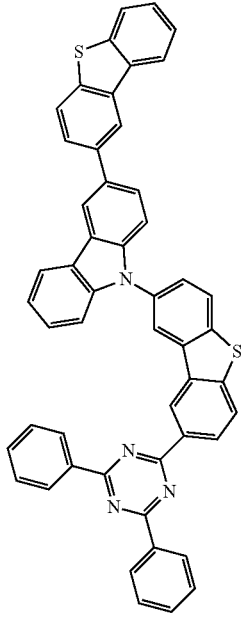
Compound 2553
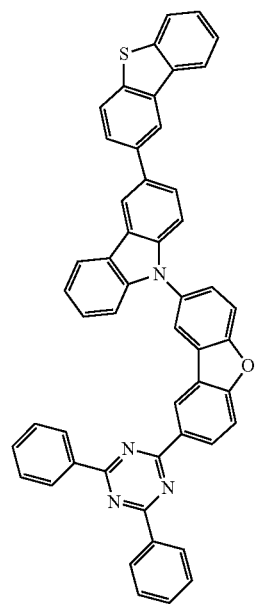
Compound 2629
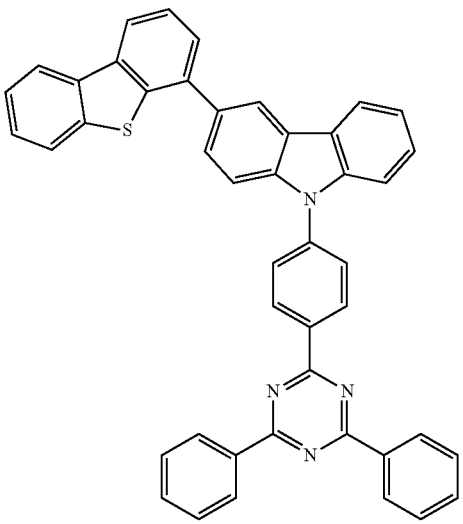

Compound 2625
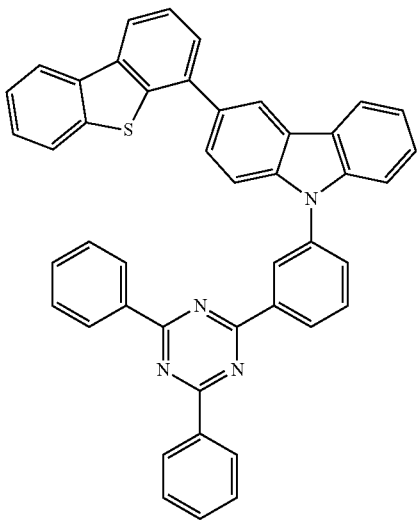
Compound 2633
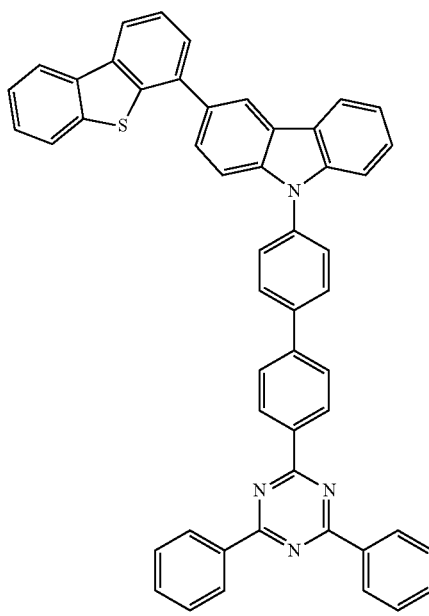
Compound 2637
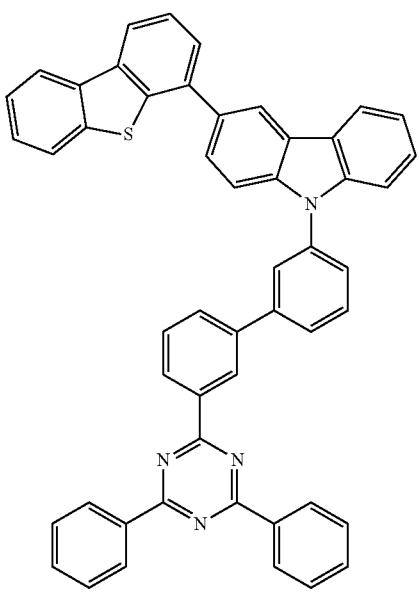
Compound 2657
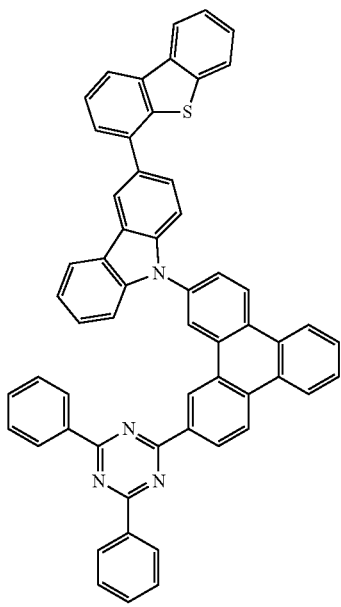

Compound 2661
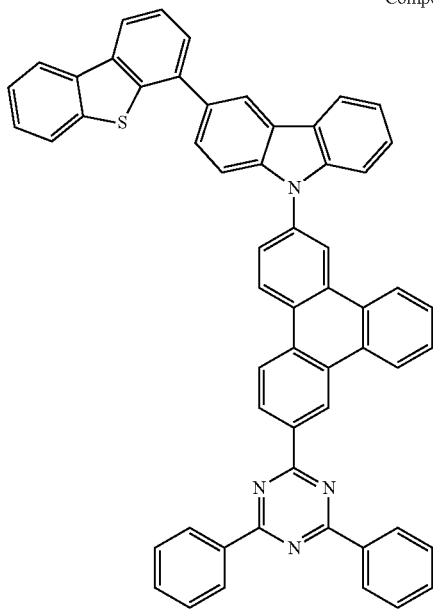
Compound 2669
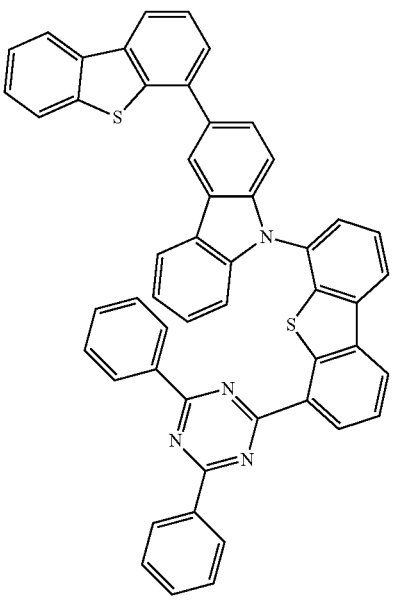
Compound 2665
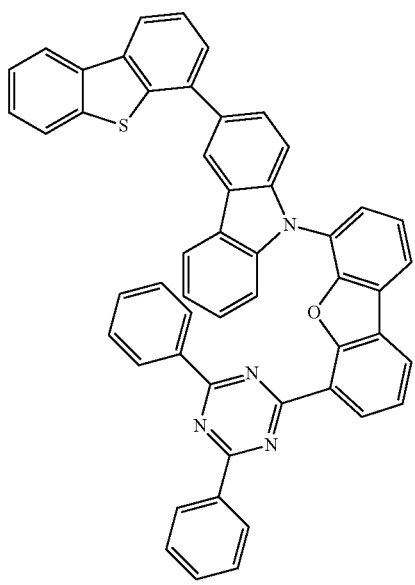
Compound 2681
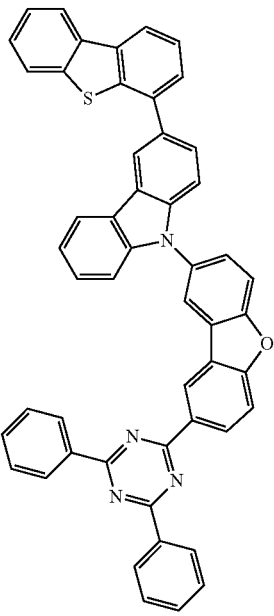

Compound 2685
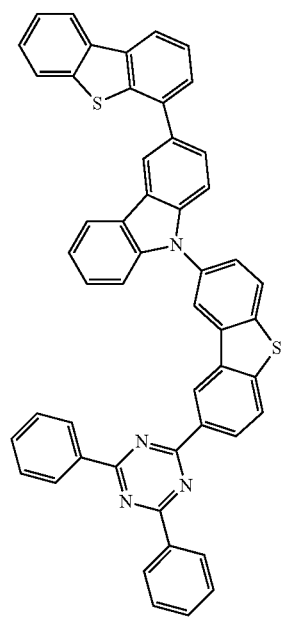
Compound 2753
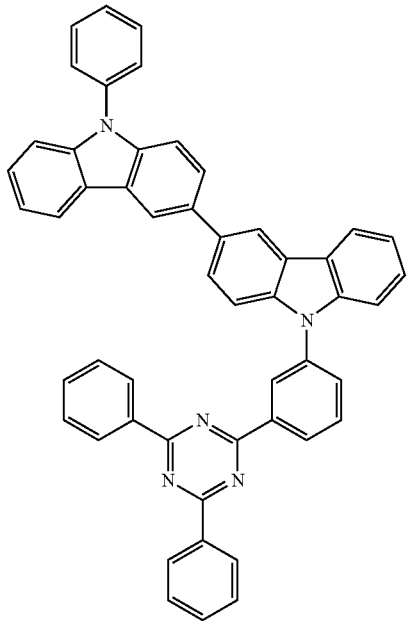
Compound 2757
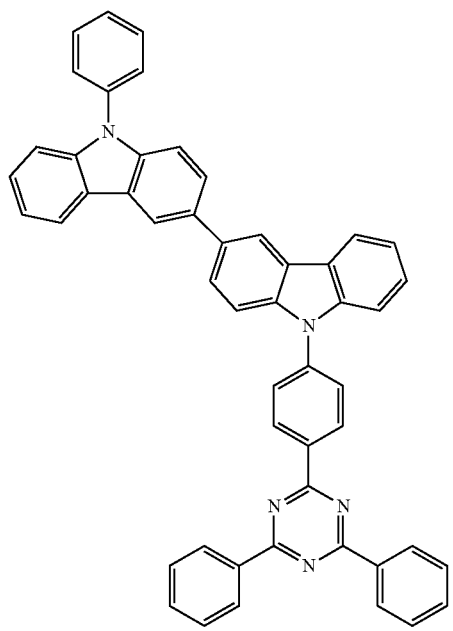
Compound 2765
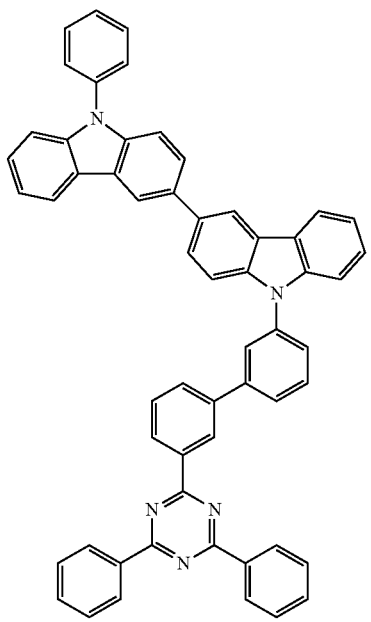

Compound 2761
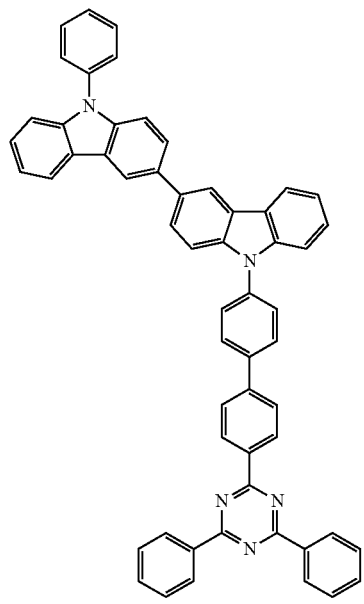
Compound 2789
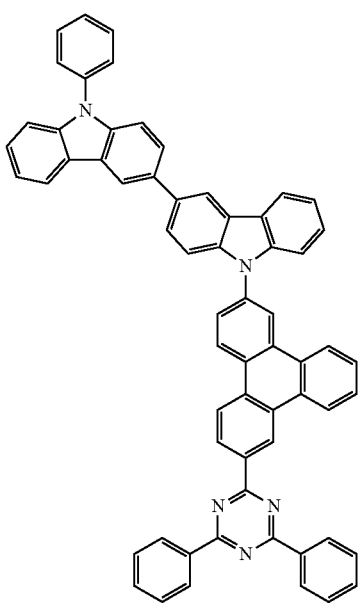
Compound 2785
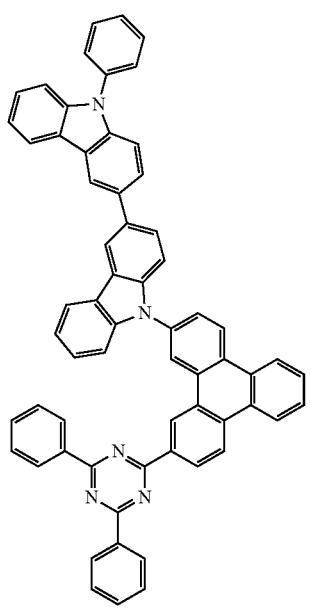
Compound 2793
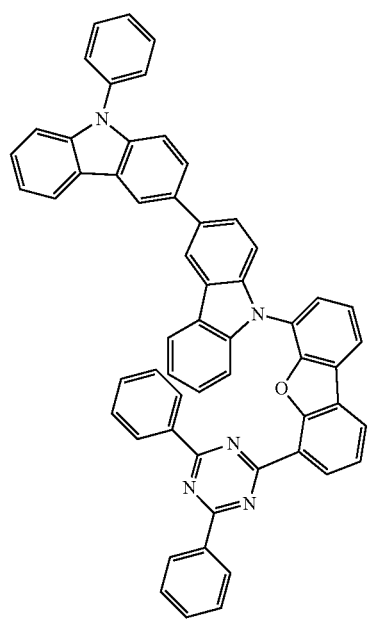

Compound 2797
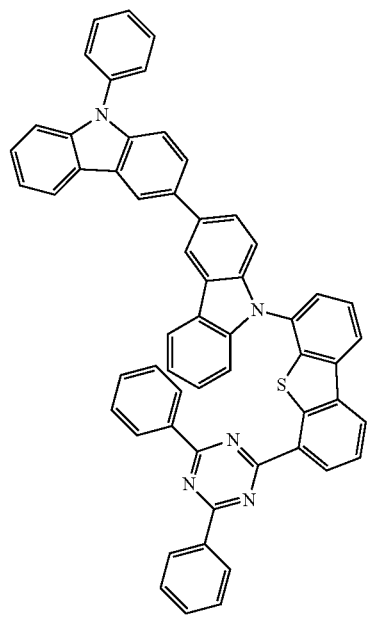
Compound 2813
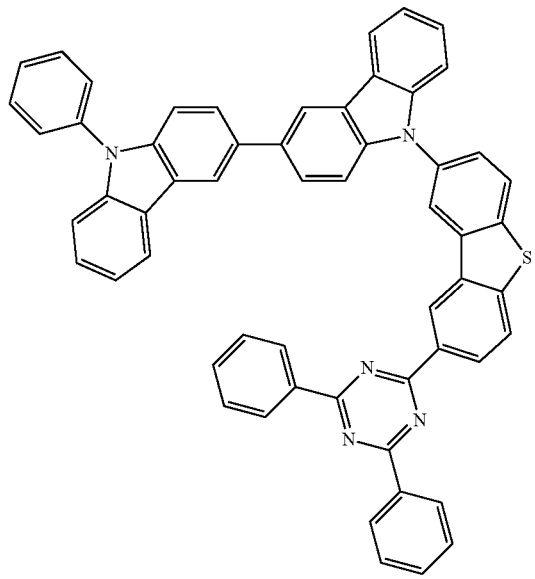
Compound 2809
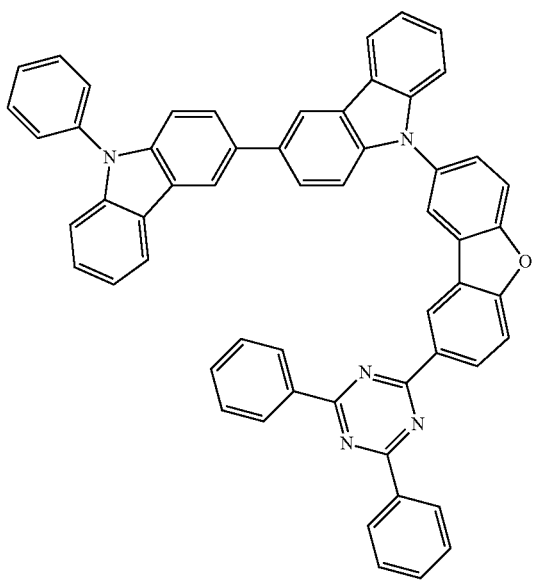
Compound 2885
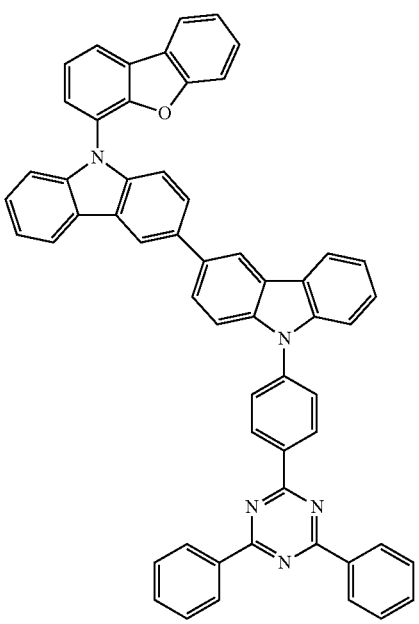

-continued
Compound 2881
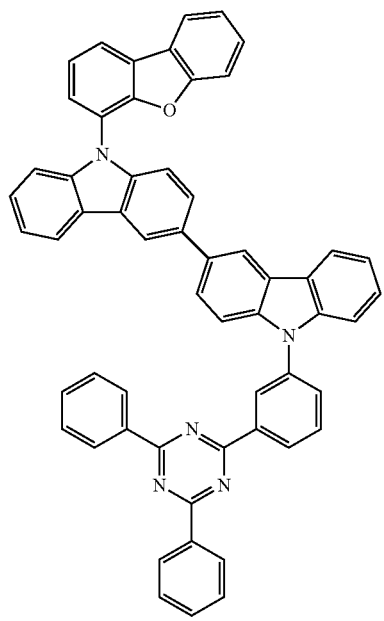
Compound 2889
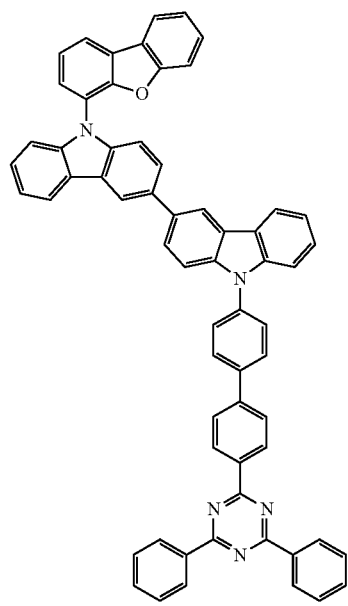
Compound 2893
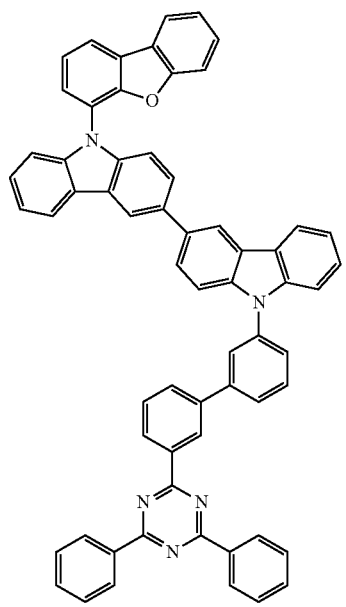
Compound 2913
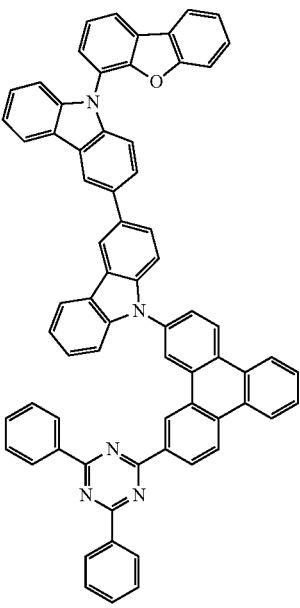

Compound 2917
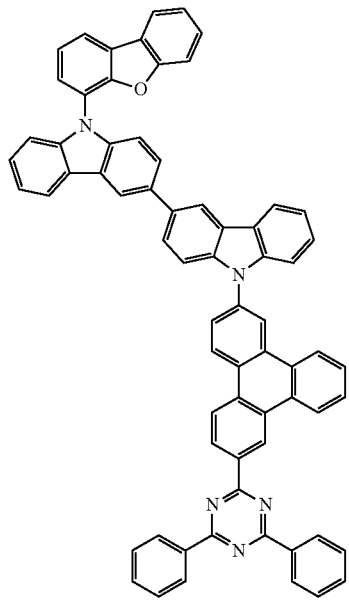
Compound 2925
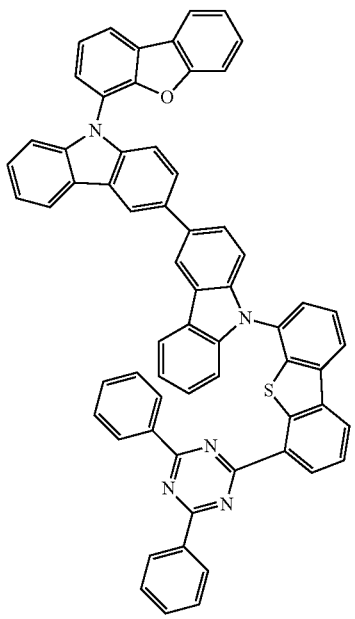
Compound 2921
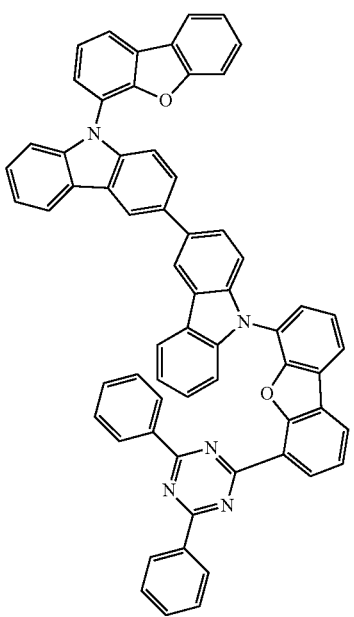
Compound 2937
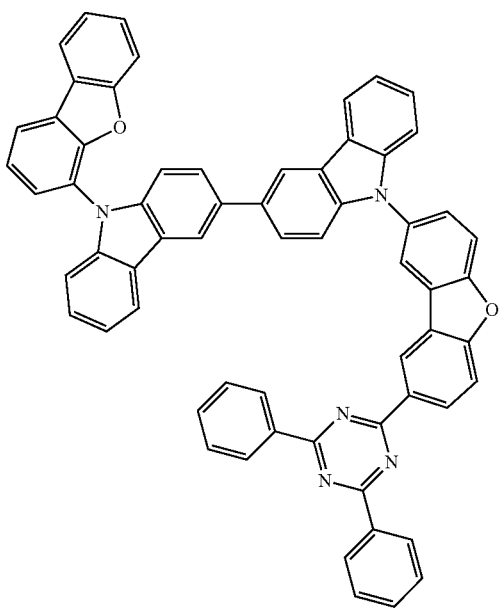

Compound 2941
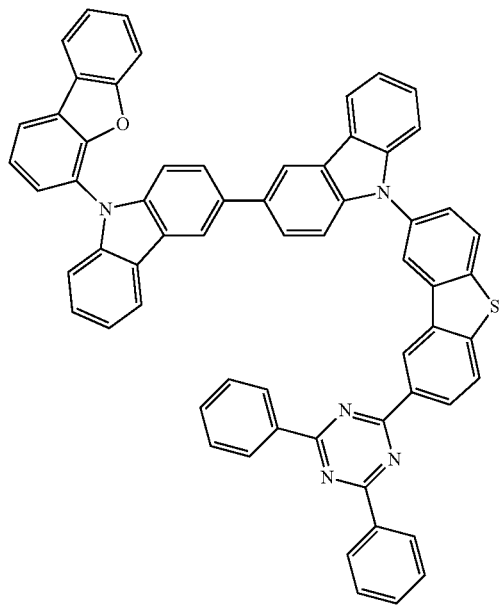
Compound 2945
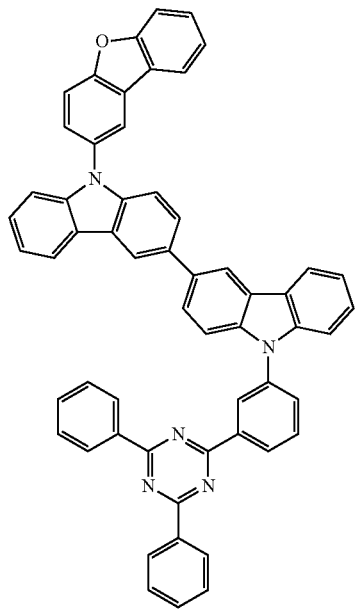
Compound 2949
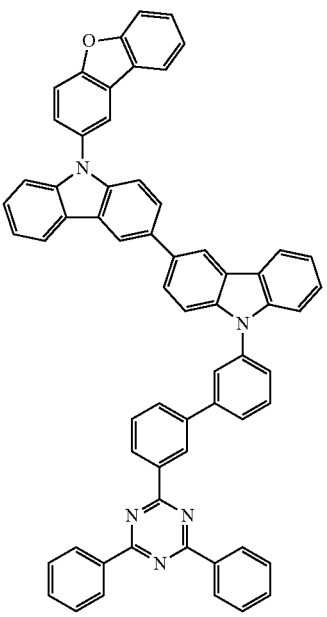
Compound 2957
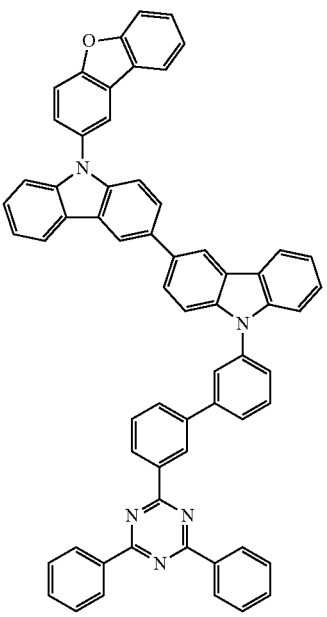

Compound 2953
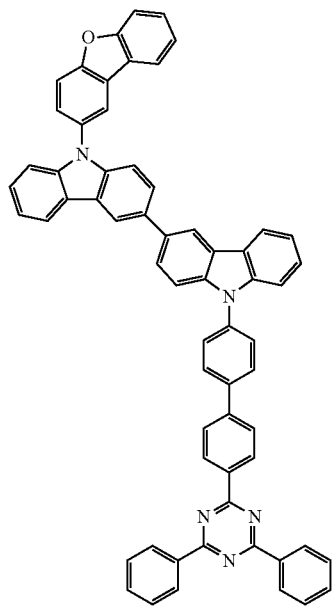
Compound 2981
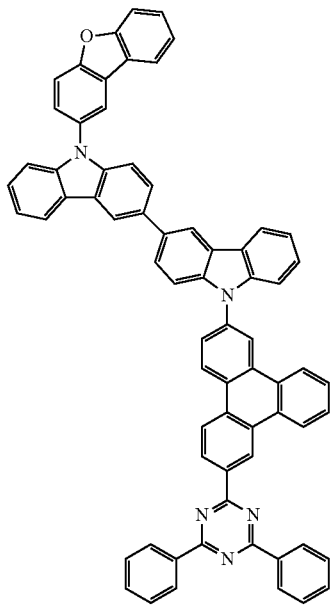
Compound 2977
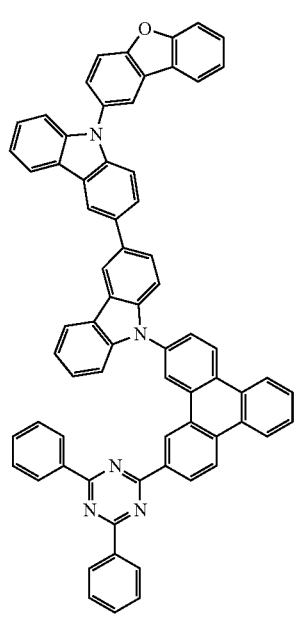
Compound 2985
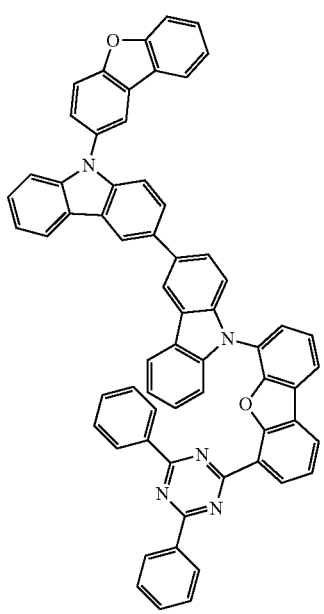

Compound 2989
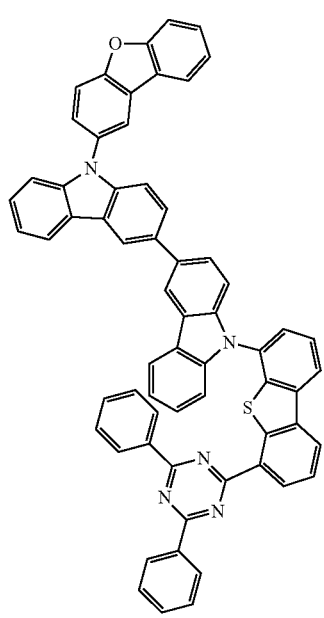
Compound 3005
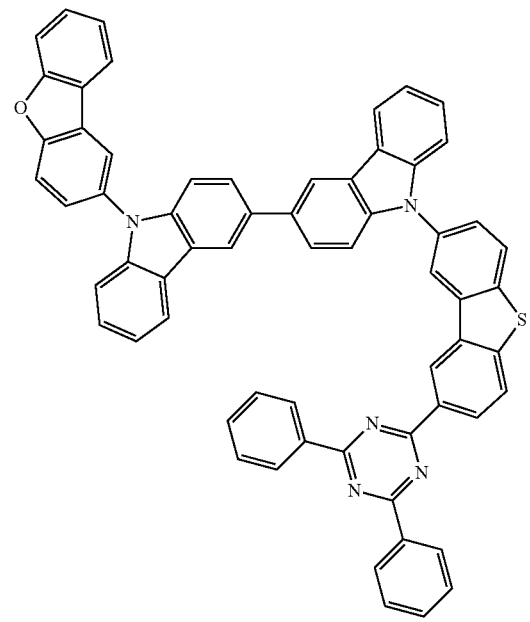
Compound 3001
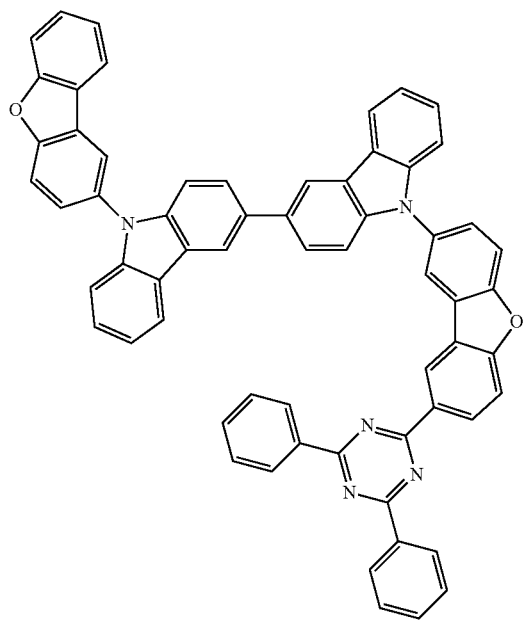
Compound 3013
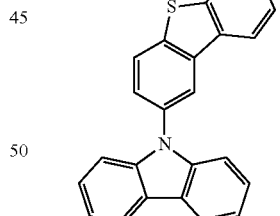

Compound 3009
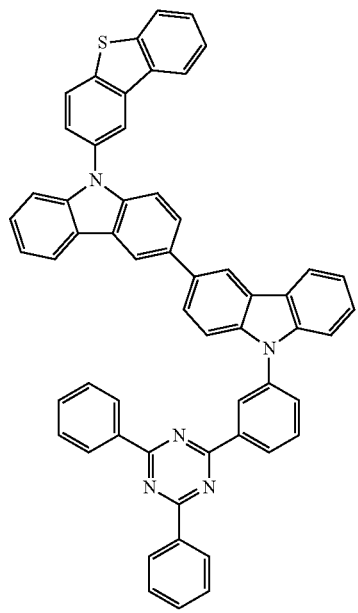
Compound 3017
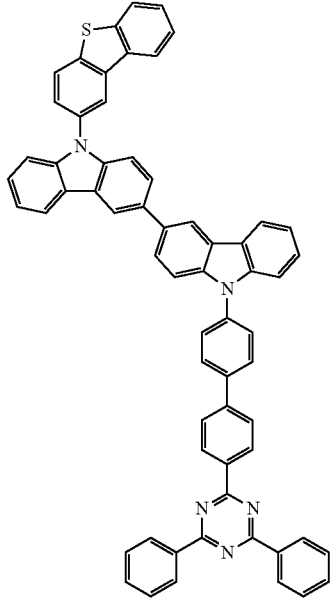
Compound 3021
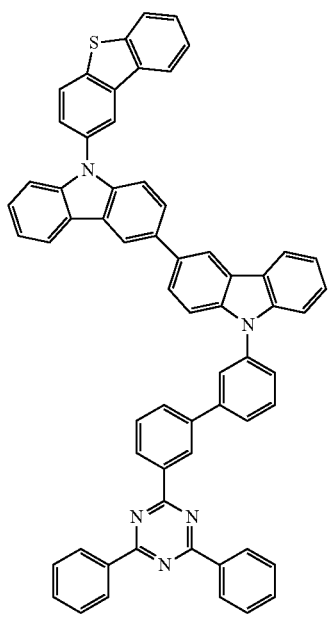
Compound 3041
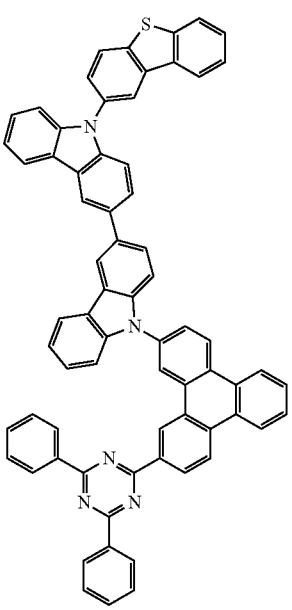

Compound 3045
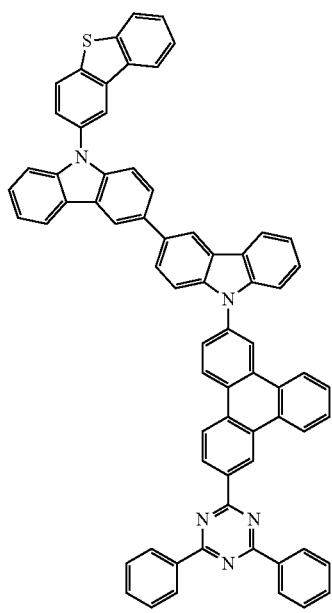
Compound 3049
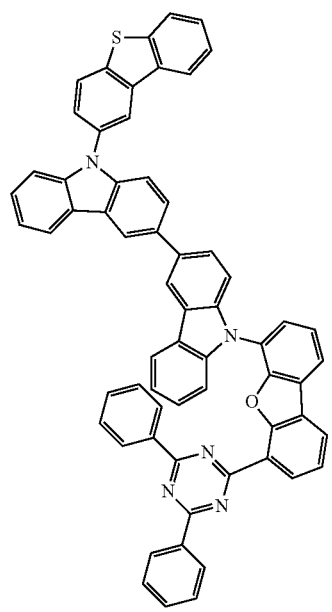
Compound 3053
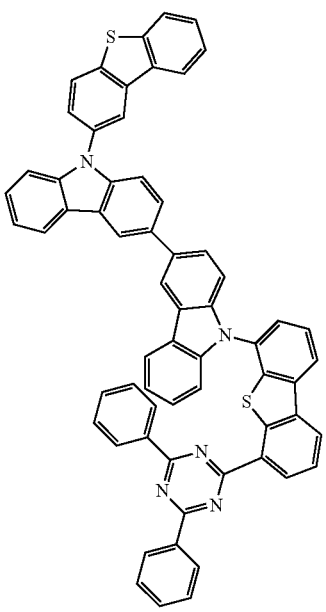
Compound 3065
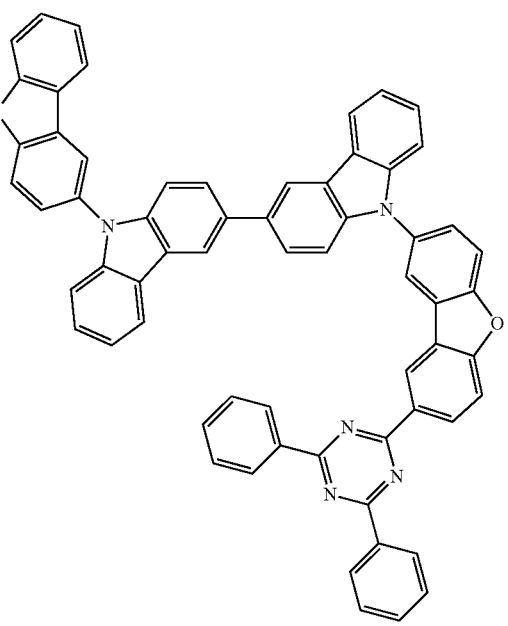

Compound 3069
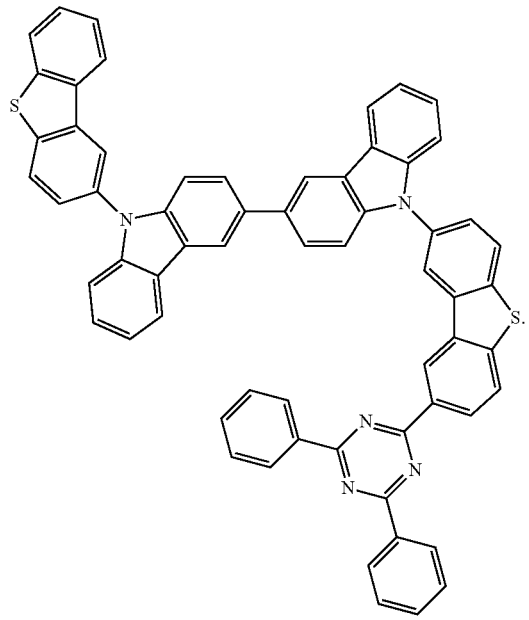
In one embodiment, the compound has the formula according to the table below:
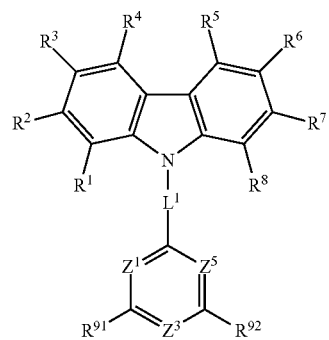
$L^{101}$
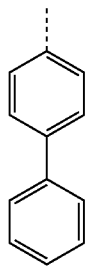
$L^{102}$
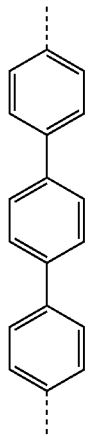
$L^{103}$
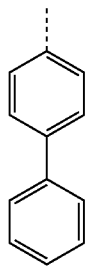
$L^{104}$
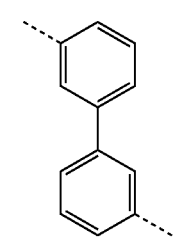
$L^{105}$
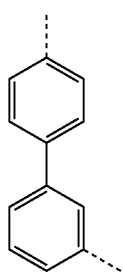
$L^{106}$
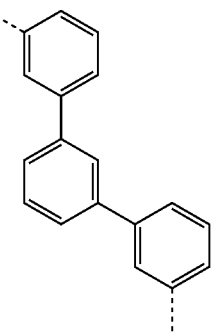
$L^{107}$
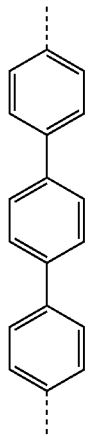

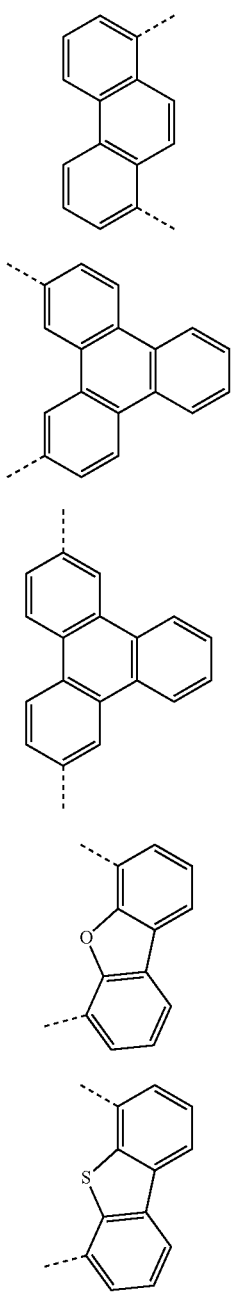
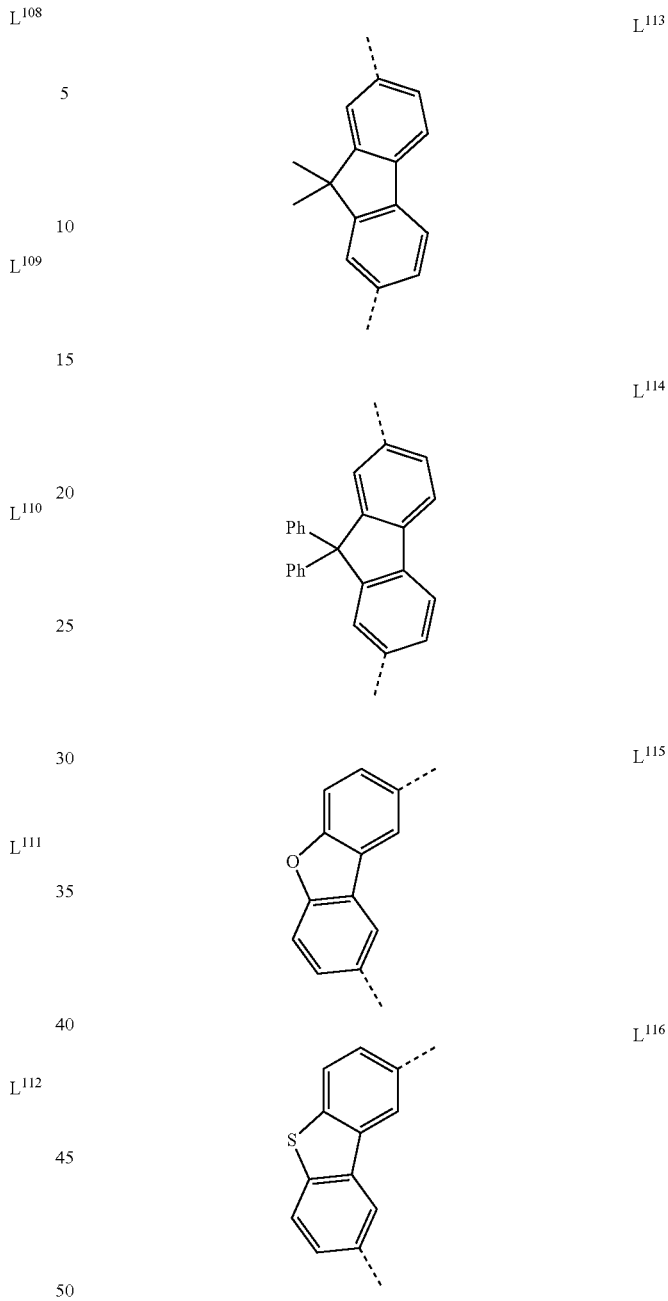
| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1. | H | H | D¹⁰¹ | H | H | H | H | H | L¹⁰¹ | N | N | N | Ph | Ph |
| 2. | H | H | D¹⁰¹ | H | H | H | H | H | L¹⁰¹ | N | N | N | 4-biphenyl | 4-biphenyl |
| 3. | H | H | D¹⁰¹ | H | H | H | H | H | L¹⁰¹ | N | CH | N | Ph | Ph |
| 4. | H | H | D¹⁰¹ | H | H | H | H | H | L¹⁰¹ | N | CH | N | 4-biphenyl | 4-biphenyl |
| 5. | H | H | D¹⁰¹ | H | H | H | H | H | L¹⁰² | N | N | N | Ph | Ph |
| 6. | H | H | D¹⁰¹ | H | H | H | H | H | L¹⁰² | N | N | N | 4-biphenyl | 4-biphenyl |
| 7. | H | H | D¹⁰¹ | H | H | H | H | H | L¹⁰² | N | CH | N | Ph | Ph |
| 8. | H | H | D¹⁰¹ | H | H | H | H | H | L¹⁰² | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 9. | H | H | $D^{101}$ | H | H | H | H | H | $L^{103}$ | N | N | N | Ph | Ph |
| 10. | H | H | $D^{101}$ | H | H | H | H | H | $L^{103}$ | N | N | N | 4-biphenyl | 4-biphenyl |
| 11. | H | H | $D^{101}$ | H | H | H | H | H | $L^{103}$ | N | CH | N | Ph | Ph |
| 12. | H | H | $D^{101}$ | H | H | H | H | H | $L^{103}$ | N | CH | N | 4-biphenyl | 4-biphenyl |
| 13. | H | H | $D^{101}$ | H | H | H | H | H | $L^{104}$ | N | N | N | Ph | Ph |
| 14. | H | H | $D^{101}$ | H | H | H | H | H | $L^{104}$ | N | N | N | 4-biphenyl | 4-biphenyl |
| 15. | H | H | $D^{101}$ | H | H | H | H | H | $L^{104}$ | N | CH | N | Ph | Ph |
| 16. | H | H | $D^{101}$ | H | H | H | H | H | $L^{104}$ | N | CH | N | 4-biphenyl | 4-biphenyl |
| 17. | H | H | $D^{101}$ | H | H | H | H | H | $L^{105}$ | N | N | N | Ph | Ph |
| 18. | H | H | $D^{101}$ | H | H | H | H | H | $L^{105}$ | N | N | N | 4-biphenyl | 4-biphenyl |
| 19. | H | H | $D^{101}$ | H | H | H | H | H | $L^{105}$ | N | CH | N | Ph | Ph |
| 20. | H | H | $D^{101}$ | H | H | H | H | H | $L^{105}$ | N | CH | N | 4-biphenyl | 4-biphenyl |
| 21. | H | H | $D^{101}$ | H | H | H | H | H | $L^{106}$ | N | N | N | Ph | Ph |
| 22. | H | H | $D^{101}$ | H | H | H | H | H | $L^{106}$ | N | N | N | 4-biphenyl | 4-biphenyl |
| 23. | H | H | $D^{101}$ | H | H | H | H | H | $L^{106}$ | N | CH | N | Ph | Ph |
| 24. | H | H | $D^{101}$ | H | H | H | H | H | $L^{106}$ | N | CH | N | 4-biphenyl | 4-biphenyl |
| 25. | H | H | $D^{101}$ | H | H | H | H | H | $L^{107}$ | N | N | N | Ph | Ph |
| 26. | H | H | $D^{101}$ | H | H | H | H | H | $L^{107}$ | N | N | N | 4-biphenyl | 4-biphenyl |
| 27. | H | H | $D^{101}$ | H | H | H | H | H | $L^{107}$ | N | CH | N | Ph | Ph |
| 28. | H | H | $D^{101}$ | H | H | H | H | H | $L^{107}$ | N | CH | N | 4-biphenyl | 4-biphenyl |
| 29. | H | H | $D^{101}$ | H | H | H | H | H | $L^{108}$ | N | N | N | Ph | Ph |
| 30. | H | H | $D^{101}$ | H | H | H | H | H | $L^{108}$ | N | N | N | 4-biphenyl | 4-biphenyl |
| 31. | H | H | $D^{101}$ | H | H | H | H | H | $L^{108}$ | N | CH | N | Ph | Ph |
| 32. | H | H | $D^{101}$ | H | H | H | H | H | $L^{108}$ | N | CH | N | 4-biphenyl | 4-biphenyl |
| 33. | H | H | $D^{101}$ | H | H | H | H | H | $L^{109}$ | N | N | N | Ph | Ph |
| 34. | H | H | $D^{101}$ | H | H | H | H | H | $L^{109}$ | N | N | N | 4-biphenyl | 4-biphenyl |
| 35. | H | H | $D^{101}$ | H | H | H | H | H | $L^{109}$ | N | CH | N | Ph | Ph |
| 36. | H | H | $D^{101}$ | H | H | H | H | H | $L^{109}$ | N | CH | N | 4-biphenyl | 4-biphenyl |
| 37. | H | H | $D^{101}$ | H | H | H | H | H | $L^{110}$ | N | N | N | Ph | Ph |
| 38. | H | H | $D^{101}$ | H | H | H | H | H | $L^{110}$ | N | N | N | 4-biphenyl | 4-biphenyl |
| 39. | H | H | $D^{101}$ | H | H | H | H | H | $L^{110}$ | N | CH | N | Ph | Ph |
| 40. | H | H | $D^{101}$ | H | H | H | H | H | $L^{110}$ | N | CH | N | 4-biphenyl | 4-biphenyl |
| 41. | H | H | $D^{101}$ | H | H | H | H | H | $L^{111}$ | N | N | N | Ph | Ph |
| 42. | H | H | $D^{101}$ | H | H | H | H | H | $L^{111}$ | N | N | N | 4-biphenyl | 4-biphenyl |
| 43. | H | H | $D^{101}$ | H | H | H | H | H | $L^{111}$ | N | CH | N | Ph | Ph |
| 44. | H | H | $D^{101}$ | H | H | H | H | H | $L^{111}$ | N | CH | N | 4-biphenyl | 4-biphenyl |
| 45. | H | H | $D^{101}$ | H | H | H | H | H | $L^{112}$ | N | N | N | Ph | Ph |
| 46. | H | H | $D^{101}$ | H | H | H | H | H | $L^{112}$ | N | N | N | 4-biphenyl | 4-biphenyl |
| 47. | H | H | $D^{101}$ | H | H | H | H | H | $L^{112}$ | N | CH | N | Ph | Ph |
| 48. | H | H | $D^{101}$ | H | H | H | H | H | $L^{112}$ | N | CH | N | 4-biphenyl | 4-biphenyl |
| 49. | H | H | $D^{101}$ | H | H | H | H | H | $L^{113}$ | N | N | N | Ph | Ph |
| 50. | H | H | $D^{101}$ | H | H | H | H | H | $L^{113}$ | N | N | N | 4-biphenyl | 4-biphenyl |
| 51. | H | H | $D^{101}$ | H | H | H | H | H | $L^{113}$ | N | CH | N | Ph | Ph |
| 52. | H | H | $D^{101}$ | H | H | H | H | H | $L^{113}$ | N | CH | N | 4-biphenyl | 4-biphenyl |
| 53. | H | H | $D^{101}$ | H | H | H | H | H | $L^{114}$ | N | N | N | Ph | Ph |
| 54. | H | H | $D^{101}$ | H | H | H | H | H | $L^{114}$ | N | N | N | 4-biphenyl | 4-biphenyl |
| 55. | H | H | $D^{101}$ | H | H | H | H | H | $L^{114}$ | N | CH | N | Ph | Ph |
| 56. | H | H | $D^{101}$ | H | H | H | H | H | $L^{114}$ | N | CH | N | 4-biphenyl | 4-biphenyl |
| 57. | H | H | $D^{101}$ | H | H | H | H | H | $L^{115}$ | N | N | N | Ph | Ph |
| 58. | H | H | $D^{101}$ | H | H | H | H | H | $L^{115}$ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 59. | H | H | D¹⁰¹ | H | H | H | H | H | L¹¹⁵ | N | CH | N | Ph | Ph |
| 60. | H | H | D¹⁰¹ | H | H | H | H | H | L¹¹⁵ | N | CH | N | 4-biphenyl | 4-biphenyl |
| 61. | H | H | D¹⁰¹ | H | H | H | H | H | L¹¹⁶ | N | N | N | Ph | Ph |
| 62. | H | H | D¹⁰¹ | H | H | H | H | H | L¹¹⁶ | N | N | N | 4-biphenyl | 4-biphenyl |
| 63. | H | H | D¹⁰¹ | H | H | H | H | H | L¹¹⁶ | N | CH | N | Ph | Ph |
| 64. | H | H | D¹⁰¹ | H | H | H | H | H | L¹¹⁶ | N | CH | N | 4-biphenyl | 4-biphenyl |
| 65. | H | H | D¹⁰¹ | H | H | D¹⁰¹ | H | H | L¹⁰¹ | N | N | N | Ph | Ph |
| 66. | H | H | D¹⁰¹ | H | H | D¹⁰¹ | H | H | L¹⁰¹ | N | N | N | 4-biphenyl | 4-biphenyl |
| 67. | H | H | D¹⁰¹ | H | H | D¹⁰¹ | H | H | L¹⁰¹ | N | CH | N | Ph | Ph |
| 68. | H | H | D¹⁰¹ | H | H | D¹⁰¹ | H | H | L¹⁰¹ | N | CH | N | 4-biphenyl | 4-biphenyl |
| 69. | H | H | D¹⁰¹ | H | H | D¹⁰¹ | H | H | L¹⁰² | N | N | N | Ph | Ph |
| 70. | H | H | D¹⁰¹ | H | H | D¹⁰¹ | H | H | L¹⁰² | N | N | N | 4-biphenyl | 4-biphenyl |
| 71. | H | H | D¹⁰¹ | H | H | D¹⁰¹ | H | H | L¹⁰² | N | CH | N | Ph | Ph |
| 72. | H | H | D¹⁰¹ | H | H | D¹⁰¹ | H | H | L¹⁰² | N | CH | N | 4-biphenyl | 4-biphenyl |
| 73. | H | H | D¹⁰¹ | H | H | D¹⁰¹ | H | H | L¹⁰³ | N | N | N | Ph | Ph |
| 74. | H | H | D¹⁰¹ | H | H | D¹⁰¹ | H | H | L¹⁰³ | N | N | N | 4-biphenyl | 4-biphenyl |
| 75. | H | H | D¹⁰¹ | H | H | D¹⁰¹ | H | H | L¹⁰³ | N | CH | N | Ph | Ph |
| 76. | H | H | D¹⁰¹ | H | H | D¹⁰¹ | H | H | L¹⁰³ | N | CH | N | 4-biphenyl | 4-biphenyl |
| 77. | H | H | D¹⁰¹ | H | H | D¹⁰¹ | H | H | L¹⁰⁴ | N | N | N | Ph | Ph |
| 78. | H | H | D¹⁰¹ | H | H | D¹⁰¹ | H | H | L¹⁰⁴ | N | N | N | 4-biphenyl | 4-biphenyl |
| 79. | H | H | D¹⁰¹ | H | H | D¹⁰¹ | H | H | L¹⁰⁴ | N | CH | N | Ph | Ph |
| 80. | H | H | D¹⁰¹ | H | H | D¹⁰¹ | H | H | L¹⁰⁴ | N | CH | N | 4-biphenyl | 4-biphenyl |
| 81. | H | H | D¹⁰¹ | H | H | D¹⁰¹ | H | H | L¹⁰⁵ | N | N | N | Ph | Ph |
| 82. | H | H | D¹⁰¹ | H | H | D¹⁰¹ | H | H | L¹⁰⁵ | N | N | N | 4-biphenyl | 4-biphenyl |
| 83. | H | H | D¹⁰¹ | H | H | D¹⁰¹ | H | H | L¹⁰⁵ | N | CH | N | Ph | Ph |
| 84. | H | H | D¹⁰¹ | H | H | D¹⁰¹ | H | H | L¹⁰⁵ | N | CH | N | 4-biphenyl | 4-biphenyl |
| 85. | H | H | D¹⁰¹ | H | H | D¹⁰¹ | H | H | L¹⁰⁶ | N | N | N | Ph | Ph |
| 86. | H | H | D¹⁰¹ | H | H | D¹⁰¹ | H | H | L¹⁰⁶ | N | N | N | 4-biphenyl | 4-biphenyl |
| 87. | H | H | D¹⁰¹ | H | H | D¹⁰¹ | H | H | L¹⁰⁶ | N | CH | N | Ph | Ph |
| 88. | H | H | D¹⁰¹ | H | H | D¹⁰¹ | H | H | L¹⁰⁶ | N | CH | N | 4-biphenyl | 4-biphenyl |
| 89. | H | H | D¹⁰¹ | H | H | D¹⁰¹ | H | H | L¹⁰⁷ | N | N | N | Ph | Ph |
| 90. | H | H | D¹⁰¹ | H | H | D¹⁰¹ | H | H | L¹⁰⁷ | N | N | N | 4-biphenyl | 4-biphenyl |
| 91. | H | H | D¹⁰¹ | H | H | D¹⁰¹ | H | H | L¹⁰⁷ | N | CH | N | Ph | Ph |
| 92. | H | H | D¹⁰¹ | H | H | D¹⁰¹ | H | H | L¹⁰⁷ | N | CH | N | 4-biphenyl | 4-biphenyl |
| 93. | H | H | D¹⁰¹ | H | H | D¹⁰¹ | H | H | L¹⁰⁸ | N | N | N | Ph | Ph |
| 94. | H | H | D¹⁰¹ | H | H | D¹⁰¹ | H | H | L¹⁰⁸ | N | N | N | 4-biphenyl | 4-biphenyl |
| 95. | H | H | D¹⁰¹ | H | H | D¹⁰¹ | H | H | L¹⁰⁸ | N | CH | N | Ph | Ph |
| 96. | H | H | D¹⁰¹ | H | H | D¹⁰¹ | H | H | L¹⁰⁸ | N | CH | N | 4-biphenyl | 4-biphenyl |
| 97. | H | H | D¹⁰¹ | H | H | D¹⁰¹ | H | H | L¹⁰⁹ | N | N | N | Ph | Ph |
| 98. | H | H | D¹⁰¹ | H | H | D¹⁰¹ | H | H | L¹⁰⁹ | N | N | N | 4-biphenyl | 4-biphenyl |
| 99. | H | H | D¹⁰¹ | H | H | D¹⁰¹ | H | H | L¹⁰⁹ | N | CH | N | Ph | Ph |
| 100. | H | H | D¹⁰¹ | H | H | D¹⁰¹ | H | H | L¹⁰⁹ | N | CH | N | 4-biphenyl | 4-biphenyl |
| 101. | H | H | D¹⁰¹ | H | H | D¹⁰¹ | H | H | L¹¹⁰ | N | N | N | Ph | Ph |
| 102. | H | H | D¹⁰¹ | H | H | D¹⁰¹ | H | H | L¹¹⁰ | N | N | N | 4-biphenyl | 4-biphenyl |
| 103. | H | H | D¹⁰¹ | H | H | D¹⁰¹ | H | H | L¹¹⁰ | N | CH | N | Ph | Ph |
| 104. | H | H | D¹⁰¹ | H | H | D¹⁰¹ | H | H | L¹¹⁰ | N | CH | N | 4-biphenyl | 4-biphenyl |
| 105. | H | H | D¹⁰¹ | H | H | D¹⁰¹ | H | H | L¹¹¹ | N | N | N | Ph | Ph |
| 106. | H | H | D¹⁰¹ | H | H | D¹⁰¹ | H | H | L¹¹¹ | N | N | N | 4-biphenyl | 4-biphenyl |
| 107. | H | H | D¹⁰¹ | H | H | D¹⁰¹ | H | H | L¹¹¹ | N | CH | N | Ph | Ph |
| 108. | H | H | D¹⁰¹ | H | H | D¹⁰¹ | H | H | L¹¹¹ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 109. | H | H | D¹⁰¹ | H | H | D¹⁰¹ | H | H | L¹¹² | N | N | N | Ph | Ph |
| 110. | H | H | D¹⁰¹ | H | H | D¹⁰¹ | H | H | L¹¹² | N | N | N | 4-biphenyl | 4-biphenyl |
| 111. | H | H | D¹⁰¹ | H | H | D¹⁰¹ | H | H | L¹¹² | N | CH | N | Ph | Ph |
| 112. | H | H | D¹⁰¹ | H | H | D¹⁰¹ | H | H | L¹¹² | N | CH | N | 4-biphenyl | 4-biphenyl |
| 113. | H | H | D¹⁰¹ | H | H | D¹⁰¹ | H | H | L¹¹³ | N | N | N | Ph | Ph |
| 114. | H | H | D¹⁰¹ | H | H | D¹⁰¹ | H | H | L¹¹³ | N | N | N | 4-biphenyl | 4-biphenyl |
| 115. | H | H | D¹⁰¹ | H | H | D¹⁰¹ | H | H | L¹¹³ | N | CH | N | Ph | Ph |
| 116. | H | H | D¹⁰¹ | H | H | D¹⁰¹ | H | H | L¹¹³ | N | CH | N | 4-biphenyl | 4-biphenyl |
| 117. | H | H | D¹⁰¹ | H | H | D¹⁰¹ | H | H | L¹¹⁴ | N | N | N | Ph | Ph |
| 118. | H | H | D¹⁰¹ | H | H | D¹⁰¹ | H | H | L¹¹⁴ | N | N | N | 4-biphenyl | 4-biphenyl |
| 119. | H | H | D¹⁰¹ | H | H | D¹⁰¹ | H | H | L¹¹⁴ | N | CH | N | Ph | Ph |
| 120. | H | H | D¹⁰¹ | H | H | D¹⁰¹ | H | H | L¹¹⁴ | N | CH | N | 4-biphenyl | 4-biphenyl |
| 121. | H | H | D¹⁰¹ | H | H | D¹⁰¹ | H | H | L¹¹⁵ | N | N | N | Ph | Ph |
| 122. | H | H | D¹⁰¹ | H | H | D¹⁰¹ | H | H | L¹¹⁵ | N | N | N | 4-biphenyl | 4-biphenyl |
| 123. | H | H | D¹⁰¹ | H | H | D¹⁰¹ | H | H | L¹¹⁵ | N | CH | N | Ph | Ph |
| 124. | H | H | D¹⁰¹ | H | H | D¹⁰¹ | H | H | L¹¹⁵ | N | CH | N | 4-biphenyl | 4-biphenyl |
| 125. | H | H | D¹⁰¹ | H | H | D¹⁰¹ | H | H | L¹¹⁶ | N | N | N | Ph | Ph |
| 126. | H | H | D¹⁰¹ | H | H | D¹⁰¹ | H | H | L¹¹⁶ | N | N | N | 4-biphenyl | 4-biphenyl |
| 127. | H | H | D¹⁰¹ | H | H | D¹⁰¹ | H | H | L¹¹⁶ | N | CH | N | Ph | Ph |
| 128. | H | H | D¹⁰¹ | H | H | D¹⁰¹ | H | H | L¹¹⁶ | N | CH | N | 4-biphenyl | 4-biphenyl |
| 129. | H | H | D¹⁰² | H | H | H | H | H | L¹⁰¹ | N | N | N | Ph | Ph |
| 130. | H | H | D¹⁰² | H | H | H | H | H | L¹⁰¹ | N | N | N | 4-biphenyl | 4-biphenyl |
| 131. | H | H | D¹⁰² | H | H | H | H | H | L¹⁰¹ | N | CH | N | Ph | Ph |
| 132. | H | H | D¹⁰² | H | H | H | H | H | L¹⁰¹ | N | CH | N | 4-biphenyl | 4-biphenyl |
| 133. | H | H | D¹⁰² | H | H | H | H | H | L¹⁰² | N | N | N | Ph | Ph |
| 134. | H | H | D¹⁰² | H | H | H | H | H | L¹⁰² | N | N | N | 4-biphenyl | 4-biphenyl |
| 135. | H | H | D¹⁰² | H | H | H | H | H | L¹⁰² | N | CH | N | Ph | Ph |
| 136. | H | H | D¹⁰² | H | H | H | H | H | L¹⁰² | N | CH | N | 4-biphenyl | 4-biphenyl |
| 137. | H | H | D¹⁰² | H | H | H | H | H | L¹⁰³ | N | N | N | Ph | Ph |
| 138. | H | H | D¹⁰² | H | H | H | H | H | L¹⁰³ | N | N | N | 4-biphenyl | 4-biphenyl |
| 139. | H | H | D¹⁰² | H | H | H | H | H | L¹⁰³ | N | CH | N | Ph | Ph |
| 140. | H | H | D¹⁰² | H | H | H | H | H | L¹⁰³ | N | CH | N | 4-biphenyl | 4-biphenyl |
| 141. | H | H | D¹⁰² | H | H | H | H | H | L¹⁰⁴ | N | N | N | Ph | Ph |
| 142. | H | H | D¹⁰² | H | H | H | H | H | L¹⁰⁴ | N | N | N | 4-biphenyl | 4-biphenyl |
| 143. | H | H | D¹⁰² | H | H | H | H | H | L¹⁰⁴ | N | CH | N | Ph | Ph |
| 144. | H | H | D¹⁰² | H | H | H | H | H | L¹⁰⁴ | N | CH | N | 4-biphenyl | 4-biphenyl |
| 145. | H | H | D¹⁰² | H | H | H | H | H | L¹⁰⁵ | N | N | N | Ph | Ph |
| 146. | H | H | D¹⁰² | H | H | H | H | H | L¹⁰⁵ | N | N | N | 4-biphenyl | 4-biphenyl |
| 147. | H | H | D¹⁰² | H | H | H | H | H | L¹⁰⁵ | N | CH | N | Ph | Ph |
| 148. | H | H | D¹⁰² | H | H | H | H | H | L¹⁰⁵ | N | CH | N | 4-biphenyl | 4-biphenyl |
| 149. | H | H | D¹⁰² | H | H | H | H | H | L¹⁰⁶ | N | N | N | Ph | Ph |
| 150. | H | H | D¹⁰² | H | H | H | H | H | L¹⁰⁶ | N | N | N | 4-biphenyl | 4-biphenyl |
| 151. | H | H | D¹⁰² | H | H | H | H | H | L¹⁰⁶ | N | CH | N | Ph | Ph |
| 152. | H | H | D¹⁰² | H | H | H | H | H | L¹⁰⁶ | N | CH | N | 4-biphenyl | 4-biphenyl |
| 153. | H | H | D¹⁰² | H | H | H | H | H | L¹⁰⁷ | N | N | N | Ph | Ph |
| 154. | H | H | D¹⁰² | H | H | H | H | H | L¹⁰⁷ | N | N | N | 4-biphenyl | 4-biphenyl |
| 155. | H | H | D¹⁰² | H | H | H | H | H | L¹⁰⁷ | N | CH | N | Ph | Ph |
| 156. | H | H | D¹⁰² | H | H | H | H | H | L¹⁰⁷ | N | CH | N | 4-biphenyl | 4-biphenyl |
| 157. | H | H | D¹⁰² | H | H | H | H | H | L¹⁰⁸ | N | N | N | Ph | Ph |
| 158. | H | H | D¹⁰² | H | H | H | H | H | L¹⁰⁸ | N | N | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 159. | H | H | D¹⁰² | H | H | H | H | H | L¹⁰⁸ | N | CH | N | Ph | Ph |
| 160. | H | H | D¹⁰² | H | H | H | H | H | L¹⁰⁸ | N | CH | N | 4-biphenyl | 4-biphenyl |
| 161. | H | H | D¹⁰² | H | H | H | H | H | L¹⁰⁹ | N | N | N | Ph | Ph |
| 162. | H | H | D¹⁰² | H | H | H | H | H | L¹⁰⁹ | N | N | N | 4-biphenyl | 4-biphenyl |
| 163. | H | H | D¹⁰² | H | H | H | H | H | L¹⁰⁹ | N | CH | N | Ph | Ph |
| 164. | H | H | D¹⁰² | H | H | H | H | H | L¹⁰⁹ | N | CH | N | 4-biphenyl | 4-biphenyl |
| 165. | H | H | D¹⁰² | H | H | H | H | H | L¹¹⁰ | N | N | N | Ph | Ph |
| 166. | H | H | D¹⁰² | H | H | H | H | H | L¹¹⁰ | N | N | N | 4-biphenyl | 4-biphenyl |
| 167. | H | H | D¹⁰² | H | H | H | H | H | L¹¹⁰ | N | CH | N | Ph | Ph |
| 168. | H | H | D¹⁰² | H | H | H | H | H | L¹¹⁰ | N | CH | N | 4-biphenyl | 4-biphenyl |
| 169. | H | H | D¹⁰² | H | H | H | H | H | L¹¹¹ | N | N | N | Ph | Ph |
| 170. | H | H | D¹⁰² | H | H | H | H | H | L¹¹¹ | N | N | N | 4-biphenyl | 4-biphenyl |
| 171. | H | H | D¹⁰² | H | H | H | H | H | L¹¹¹ | N | CH | N | Ph | Ph |
| 172. | H | H | D¹⁰² | H | H | H | H | H | L¹¹¹ | N | CH | N | 4-biphenyl | 4-biphenyl |
| 173. | H | H | D¹⁰² | H | H | H | H | H | L¹¹² | N | N | N | Ph | Ph |
| 174. | H | H | D¹⁰² | H | H | H | H | H | L¹¹² | N | N | N | 4-biphenyl | 4-biphenyl |
| 175. | H | H | D¹⁰² | H | H | H | H | H | L¹¹² | N | CH | N | Ph | Ph |
| 176. | H | H | D¹⁰² | H | H | H | H | H | L¹¹² | N | CH | N | 4-biphenyl | 4-biphenyl |
| 177. | H | H | D¹⁰² | H | H | H | H | H | L¹¹³ | N | N | N | Ph | Ph |
| 178. | H | H | D¹⁰² | H | H | H | H | H | L¹¹³ | N | N | N | 4-biphenyl | 4-biphenyl |
| 179. | H | H | D¹⁰² | H | H | H | H | H | L¹¹³ | N | CH | N | Ph | Ph |
| 180. | H | H | D¹⁰² | H | H | H | H | H | L¹¹³ | N | CH | N | 4-biphenyl | 4-biphenyl |
| 181. | H | H | D¹⁰² | H | H | H | H | H | L¹¹⁴ | N | N | N | Ph | Ph |
| 182. | H | H | D¹⁰² | H | H | H | H | H | L¹¹⁴ | N | N | N | 4-biphenyl | 4-biphenyl |
| 183. | H | H | D¹⁰² | H | H | H | H | H | L¹¹⁴ | N | CH | N | Ph | Ph |
| 184. | H | H | D¹⁰² | H | H | H | H | H | L¹¹⁴ | N | CH | N | 4-biphenyl | 4-biphenyl |
| 185. | H | H | D¹⁰² | H | H | H | H | H | L¹¹⁵ | N | N | N | Ph | Ph |
| 186. | H | H | D¹⁰² | H | H | H | H | H | L¹¹⁵ | N | N | N | 4-biphenyl | 4-biphenyl |
| 187. | H | H | D¹⁰² | H | H | H | H | H | L¹¹⁵ | N | CH | N | Ph | Ph |
| 188. | H | H | D¹⁰² | H | H | H | H | H | L¹¹⁵ | N | CH | N | 4-biphenyl | 4-biphenyl |
| 189. | H | H | D¹⁰² | H | H | H | H | H | L¹¹⁶ | N | N | N | Ph | Ph |
| 190. | H | H | D¹⁰² | H | H | H | H | H | L¹¹⁶ | N | N | N | 4-biphenyl | 4-biphenyl |
| 191. | H | H | D¹⁰² | H | H | H | H | H | L¹¹⁶ | N | CH | N | Ph | Ph |
| 192. | H | H | D¹⁰² | H | H | H | H | H | L¹¹⁶ | N | CH | N | 4-biphenyl | 4-biphenyl |
| 193. | H | H | D¹⁰² | H | H | D¹⁰² | H | H | L¹⁰¹ | N | N | N | Ph | Ph |
| 194. | H | H | D¹⁰² | H | H | D¹⁰² | H | H | L¹⁰¹ | N | N | N | 4-biphenyl | 4-biphenyl |
| 195. | H | H | D¹⁰² | H | H | D¹⁰² | H | H | L¹⁰¹ | N | CH | N | Ph | Ph |
| 196. | H | H | D¹⁰² | H | H | D¹⁰² | H | H | L¹⁰¹ | N | CH | N | 4-biphenyl | 4-biphenyl |
| 197. | H | H | D¹⁰² | H | H | D¹⁰² | H | H | L¹⁰² | N | N | N | Ph | Ph |
| 198. | H | H | D¹⁰² | H | H | D¹⁰² | H | H | L¹⁰² | N | N | N | 4-biphenyl | 4-biphenyl |
| 199. | H | H | D¹⁰² | H | H | D¹⁰² | H | H | L¹⁰² | N | CH | N | Ph | Ph |
| 200. | H | H | D¹⁰² | H | H | D¹⁰² | H | H | L¹⁰² | N | CH | N | 4-biphenyl | 4-biphenyl |
| 201. | H | H | D¹⁰² | H | H | D¹⁰² | H | H | L¹⁰³ | N | N | N | Ph | Ph |
| 202. | H | H | D¹⁰² | H | H | D¹⁰² | H | H | L¹⁰³ | N | N | N | 4-biphenyl | 4-biphenyl |
| 203. | H | H | D¹⁰² | H | H | D¹⁰² | H | H | L¹⁰³ | N | CH | N | Ph | Ph |
| 204. | H | H | D¹⁰² | H | H | D¹⁰² | H | H | L¹⁰³ | N | CH | N | 4-biphenyl | 4-biphenyl |
| 205. | H | H | D¹⁰² | H | H | D¹⁰² | H | H | L¹⁰⁴ | N | N | N | Ph | Ph |
| 206. | H | H | D¹⁰² | H | H | D¹⁰² | H | H | L¹⁰⁴ | N | N | N | 4-biphenyl | 4-biphenyl |
| 207. | H | H | D¹⁰² | H | H | D¹⁰² | H | H | L¹⁰⁴ | N | CH | N | Ph | Ph |
| 208. | H | H | D¹⁰² | H | H | D¹⁰² | H | H | L¹⁰⁴ | N | CH | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 209. | H | H | D¹⁰² | H | H | D¹⁰² | H | H | L¹⁰⁵ | N | N | N | Ph | Ph |
| 210. | H | H | D¹⁰² | H | H | D¹⁰² | H | H | L¹⁰⁵ | N | N | N | 4-biphenyl | 4-biphenyl |
| 211. | H | H | D¹⁰² | H | H | D¹⁰² | H | H | L¹⁰⁵ | N | CH | N | Ph | Ph |
| 212. | H | H | D¹⁰² | H | H | D¹⁰² | H | H | L¹⁰⁵ | N | CH | N | 4-biphenyl | 4-biphenyl |
| 213. | H | H | D¹⁰² | H | H | D¹⁰² | H | H | L¹⁰⁶ | N | N | N | Ph | Ph |
| 214. | H | H | D¹⁰² | H | H | D¹⁰² | H | H | L¹⁰⁶ | N | N | N | 4-biphenyl | 4-biphenyl |
| 215. | H | H | D¹⁰² | H | H | D¹⁰² | H | H | L¹⁰⁶ | N | CH | N | Ph | Ph |
| 216. | H | H | D¹⁰² | H | H | D¹⁰² | H | H | L¹⁰⁶ | N | CH | N | 4-biphenyl | 4-biphenyl |
| 217. | H | H | D¹⁰² | H | H | D¹⁰² | H | H | L¹⁰⁷ | N | N | N | Ph | Ph |
| 218. | H | H | D¹⁰² | H | H | D¹⁰² | H | H | L¹⁰⁷ | N | N | N | 4-biphenyl | 4-biphenyl |
| 219. | H | H | D¹⁰² | H | H | D¹⁰² | H | H | L¹⁰⁷ | N | CH | N | Ph | Ph |
| 220. | H | H | D¹⁰² | H | H | D¹⁰² | H | H | L¹⁰⁷ | N | CH | N | 4-biphenyl | 4-biphenyl |
| 221. | H | H | D¹⁰² | H | H | D¹⁰² | H | H | L¹⁰⁸ | N | N | N | Ph | Ph |
| 222. | H | H | D¹⁰² | H | H | D¹⁰² | H | H | L¹⁰⁸ | N | N | N | 4-biphenyl | 4-biphenyl |
| 223. | H | H | D¹⁰² | H | H | D¹⁰² | H | H | L¹⁰⁸ | N | CH | N | Ph | Ph |
| 224. | H | H | D¹⁰² | H | H | D¹⁰² | H | H | L¹⁰⁸ | N | CH | N | 4-biphenyl | 4-biphenyl |
| 225. | H | H | D¹⁰² | H | H | D¹⁰² | H | H | L¹⁰⁹ | N | N | N | Ph | Ph |
| 226. | H | H | D¹⁰² | H | H | D¹⁰² | H | H | L¹⁰⁹ | N | N | N | 4-biphenyl | 4-biphenyl |
| 227. | H | H | D¹⁰² | H | H | D¹⁰² | H | H | L¹⁰⁹ | N | CH | N | Ph | Ph |
| 228. | H | H | D¹⁰² | H | H | D¹⁰² | H | H | L¹⁰⁹ | N | CH | N | 4-biphenyl | 4-biphenyl |
| 229. | H | H | D¹⁰² | H | H | D¹⁰² | H | H | L¹¹⁰ | N | N | N | Ph | Ph |
| 230. | H | H | D¹⁰² | H | H | D¹⁰² | H | H | L¹¹⁰ | N | N | N | 4-biphenyl | 4-biphenyl |
| 231. | H | H | D¹⁰² | H | H | D¹⁰² | H | H | L¹¹⁰ | N | CH | N | Ph | Ph |
| 232. | H | H | D¹⁰² | H | H | D¹⁰² | H | H | L¹¹⁰ | N | CH | N | 4-biphenyl | 4-biphenyl |
| 233. | H | H | D¹⁰² | H | H | D¹⁰² | H | H | L¹¹¹ | N | N | N | Ph | Ph |
| 234. | H | H | D¹⁰² | H | H | D¹⁰² | H | H | L¹¹¹ | N | N | N | 4-biphenyl | 4-biphenyl |
| 235. | H | H | D¹⁰² | H | H | D¹⁰² | H | H | L¹¹¹ | N | CH | N | Ph | Ph |
| 236. | H | H | D¹⁰² | H | H | D¹⁰² | H | H | L¹¹¹ | N | CH | N | 4-biphenyl | 4-biphenyl |
| 237. | H | H | D¹⁰² | H | H | D¹⁰² | H | H | L¹¹² | N | N | N | Ph | Ph |
| 238. | H | H | D¹⁰² | H | H | D¹⁰² | H | H | L¹¹² | N | N | N | 4-biphenyl | 4-biphenyl |
| 239. | H | H | D¹⁰² | H | H | D¹⁰² | H | H | L¹¹² | N | CH | N | Ph | Ph |
| 240. | H | H | D¹⁰² | H | H | D¹⁰² | H | H | L¹¹² | N | CH | N | 4-biphenyl | 4-biphenyl |
| 241. | H | H | D¹⁰² | H | H | D¹⁰² | H | H | L¹¹³ | N | N | N | Ph | Ph |
| 242. | H | H | D¹⁰² | H | H | D¹⁰² | H | H | L¹¹³ | N | N | N | 4-biphenyl | 4-biphenyl |
| 243. | H | H | D¹⁰² | H | H | D¹⁰² | H | H | L¹¹³ | N | CH | N | Ph | Ph |
| 244. | H | H | D¹⁰² | H | H | D¹⁰² | H | H | L¹¹³ | N | CH | N | 4-biphenyl | 4-biphenyl |
| 245. | H | H | D¹⁰² | H | H | D¹⁰² | H | H | L¹¹⁴ | N | N | N | Ph | Ph |
| 246. | H | H | D¹⁰² | H | H | D¹⁰² | H | H | L¹¹⁴ | N | N | N | 4-biphenyl | 4-biphenyl |
| 247. | H | H | D¹⁰² | H | H | D¹⁰² | H | H | L¹¹⁴ | N | CH | N | Ph | Ph |
| 248. | H | H | D¹⁰² | H | H | D¹⁰² | H | H | L¹¹⁴ | N | CH | N | 4-biphenyl | 4-biphenyl |
| 249. | H | H | D¹⁰² | H | H | D¹⁰² | H | H | L¹¹⁵ | N | N | N | Ph | Ph |
| 250. | H | H | D¹⁰² | H | H | D¹⁰² | H | H | L¹¹⁵ | N | N | N | 4-biphenyl | 4-biphenyl |
| 251. | H | H | D¹⁰² | H | H | D¹⁰² | H | H | L¹¹⁵ | N | CH | N | Ph | Ph |
| 252. | H | H | D¹⁰² | H | H | D¹⁰² | H | H | L¹¹⁵ | N | CH | N | 4-biphenyl | 4-biphenyl |
| 253. | H | H | D¹⁰² | H | H | D¹⁰² | H | H | L¹¹⁶ | N | N | N | Ph | Ph |
| 254. | H | H | D¹⁰² | H | H | D¹⁰² | H | H | L¹¹⁶ | N | N | N | 4-biphenyl | 4-biphenyl |
| 255. | H | H | D¹⁰² | H | H | D¹⁰² | H | H | L¹¹⁶ | N | CH | N | Ph | Ph |
| 256. | H | H | D¹⁰² | H | H | D¹⁰² | H | H | L¹¹⁶ | N | CH | N | 4-biphenyl | 4-biphenyl |
| 257. | H | H | D¹⁰³ | H | H | H | H | H | L¹⁰¹ | N | N | N | Ph | Ph |
| 258. | H | H | D¹⁰³ | H | H | H | H | H | L¹⁰¹ | N | N | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 259. | H | H | D¹⁰³ | H | H | H | H | H | L¹⁰¹ | N | CH | N | Ph | Ph |
| 260. | H | H | D¹⁰³ | H | H | H | H | H | L¹⁰¹ | N | CH | N | 4-biphenyl | 4-biphenyl |
| 261. | H | H | D¹⁰³ | H | H | H | H | H | L¹⁰² | N | N | N | Ph | Ph |
| 262. | H | H | D¹⁰³ | H | H | H | H | H | L¹⁰² | N | N | N | 4-biphenyl | 4-biphenyl |
| 263. | H | H | D¹⁰³ | H | H | H | H | H | L¹⁰² | N | CH | N | Ph | Ph |
| 264. | H | H | D¹⁰³ | H | H | H | H | H | L¹⁰² | N | CH | N | 4-biphenyl | 4-biphenyl |
| 265. | H | H | D¹⁰³ | H | H | H | H | H | L¹⁰³ | N | N | N | Ph | Ph |
| 266. | H | H | D¹⁰³ | H | H | H | H | H | L¹⁰³ | N | N | N | 4-biphenyl | 4-biphenyl |
| 267. | H | H | D¹⁰³ | H | H | H | H | H | L¹⁰³ | N | CH | N | Ph | Ph |
| 268. | H | H | D¹⁰³ | H | H | H | H | H | L¹⁰³ | N | CH | N | 4-biphenyl | 4-biphenyl |
| 269. | H | H | D¹⁰³ | H | H | H | H | H | L¹⁰⁴ | N | N | N | Ph | Ph |
| 270. | H | H | D¹⁰³ | H | H | H | H | H | L¹⁰⁴ | N | N | N | 4-biphenyl | 4-biphenyl |
| 271. | H | H | D¹⁰³ | H | H | H | H | H | L¹⁰⁴ | N | CH | N | Ph | Ph |
| 272. | H | H | D¹⁰³ | H | H | H | H | H | L¹⁰⁴ | N | CH | N | 4-biphenyl | 4-biphenyl |
| 273. | H | H | D¹⁰³ | H | H | H | H | H | L¹⁰⁵ | N | N | N | Ph | Ph |
| 274. | H | H | D¹⁰³ | H | H | H | H | H | L¹⁰⁵ | N | N | N | 4-biphenyl | 4-biphenyl |
| 275. | H | H | D¹⁰³ | H | H | H | H | H | L¹⁰⁵ | N | CH | N | Ph | Ph |
| 276. | H | H | D¹⁰³ | H | H | H | H | H | L¹⁰⁵ | N | CH | N | 4-biphenyl | 4-biphenyl |
| 277. | H | H | D¹⁰³ | H | H | H | H | H | L¹⁰⁶ | N | N | N | Ph | Ph |
| 278. | H | H | D¹⁰³ | H | H | H | H | H | L¹⁰⁶ | N | N | N | 4-biphenyl | 4-biphenyl |
| 279. | H | H | D¹⁰³ | H | H | H | H | H | L¹⁰⁶ | N | CH | N | Ph | Ph |
| 280. | H | H | D¹⁰³ | H | H | H | H | H | L¹⁰⁶ | N | CH | N | 4-biphenyl | 4-biphenyl |
| 281. | H | H | D¹⁰³ | H | H | H | H | H | L¹⁰⁷ | N | N | N | Ph | Ph |
| 282. | H | H | D¹⁰³ | H | H | H | H | H | L¹⁰⁷ | N | N | N | 4-biphenyl | 4-biphenyl |
| 283. | H | H | D¹⁰³ | H | H | H | H | H | L¹⁰⁷ | N | CH | N | Ph | Ph |
| 284. | H | H | D¹⁰³ | H | H | H | H | H | L¹⁰⁷ | N | CH | N | 4-biphenyl | 4-biphenyl |
| 285. | H | H | D¹⁰³ | H | H | H | H | H | L¹⁰⁸ | N | N | N | Ph | Ph |
| 286. | H | H | D¹⁰³ | H | H | H | H | H | L¹⁰⁸ | N | N | N | 4-biphenyl | 4-biphenyl |
| 287. | H | H | D¹⁰³ | H | H | H | H | H | L¹⁰⁸ | N | CH | N | Ph | Ph |
| 288. | H | H | D¹⁰³ | H | H | H | H | H | L¹⁰⁸ | N | CH | N | 4-biphenyl | 4-biphenyl |
| 289. | H | H | D¹⁰³ | H | H | H | H | H | L¹⁰⁹ | N | N | N | Ph | Ph |
| 290. | H | H | D¹⁰³ | H | H | H | H | H | L¹⁰⁹ | N | N | N | 4-biphenyl | 4-biphenyl |
| 291. | H | H | D¹⁰³ | H | H | H | H | H | L¹⁰⁹ | N | CH | N | Ph | Ph |
| 292. | H | H | D¹⁰³ | H | H | H | H | H | L¹⁰⁹ | N | CH | N | 4-biphenyl | 4-biphenyl |
| 293. | H | H | D¹⁰³ | H | H | H | H | H | L¹¹⁰ | N | N | N | Ph | Ph |
| 294. | H | H | D¹⁰³ | H | H | H | H | H | L¹¹⁰ | N | N | N | 4-biphenyl | 4-biphenyl |
| 295. | H | H | D¹⁰³ | H | H | H | H | H | L¹¹⁰ | N | CH | N | Ph | Ph |
| 296. | H | H | D¹⁰³ | H | H | H | H | H | L¹¹⁰ | N | CH | N | 4-biphenyl | 4-biphenyl |
| 297. | H | H | D¹⁰³ | H | H | H | H | H | L¹¹¹ | N | N | N | Ph | Ph |
| 298. | H | H | D¹⁰³ | H | H | H | H | H | L¹¹¹ | N | N | N | 4-biphenyl | 4-biphenyl |
| 299. | H | H | D¹⁰³ | H | H | H | H | H | L¹¹¹ | N | CH | N | Ph | Ph |
| 300. | H | H | D¹⁰³ | H | H | H | H | H | L¹¹¹ | N | CH | N | 4-biphenyl | 4-biphenyl |
| 301. | H | H | D¹⁰³ | H | H | H | H | H | L¹¹² | N | N | N | Ph | Ph |
| 302. | H | H | D¹⁰³ | H | H | H | H | H | L¹¹² | N | N | N | 4-biphenyl | 4-biphenyl |
| 303. | H | H | D¹⁰³ | H | H | H | H | H | L¹¹² | N | CH | N | Ph | Ph |
| 304. | H | H | D¹⁰³ | H | H | H | H | H | L¹¹² | N | CH | N | 4-biphenyl | 4-biphenyl |
| 305. | H | H | D¹⁰³ | H | H | H | H | H | L¹¹³ | N | N | N | Ph | Ph |
| 306. | H | H | D¹⁰³ | H | H | H | H | H | L¹¹³ | N | N | N | 4-biphenyl | 4-biphenyl |
| 307. | H | H | D¹⁰³ | H | H | H | H | H | L¹¹³ | N | CH | N | Ph | Ph |
| 308. | H | H | D¹⁰³ | H | H | H | H | H | L¹¹³ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 309. | H | H | D¹⁰³ | H | H | H | H | H | L¹¹⁴ | N | N | N | Ph | Ph |
| 310. | H | H | D¹⁰³ | H | H | H | H | H | L¹¹⁴ | N | N | N | 4-biphenyl | 4-biphenyl |
| 311. | H | H | D¹⁰³ | H | H | H | H | H | L¹¹⁴ | N | CH | N | Ph | Ph |
| 312. | H | H | D¹⁰³ | H | H | H | H | H | L¹¹⁴ | N | CH | N | 4-biphenyl | 4-biphenyl |
| 313. | H | H | D¹⁰³ | H | H | H | H | H | L¹¹⁵ | N | N | N | Ph | Ph |
| 314. | H | H | D¹⁰³ | H | H | H | H | H | L¹¹⁵ | N | N | N | 4-biphenyl | 4-biphenyl |
| 315. | H | H | D¹⁰³ | H | H | H | H | H | L¹¹⁵ | N | CH | N | Ph | Ph |
| 316. | H | H | D¹⁰³ | H | H | H | H | H | L¹¹⁵ | N | CH | N | 4-biphenyl | 4-biphenyl |
| 317. | H | H | D¹⁰³ | H | H | H | H | H | L¹¹⁶ | N | N | N | Ph | Ph |
| 318. | H | H | D¹⁰³ | H | H | H | H | H | L¹¹⁶ | N | N | N | 4-biphenyl | 4-biphenyl |
| 319. | H | H | D¹⁰³ | H | H | H | H | H | L¹¹⁶ | N | CH | N | Ph | Ph |
| 320. | H | H | D¹⁰³ | H | H | H | H | H | L¹¹⁶ | N | CH | N | 4-biphenyl | 4-biphenyl |
| 321. | H | H | D¹⁰⁴ | H | H | H | H | H | L¹⁰¹ | N | N | N | Ph | Ph |
| 322. | H | H | D¹⁰⁴ | H | H | H | H | H | L¹⁰¹ | N | N | N | 4-biphenyl | 4-biphenyl |
| 323. | H | H | D¹⁰⁴ | H | H | H | H | H | L¹⁰¹ | N | CH | N | Ph | Ph |
| 324. | H | H | D¹⁰⁴ | H | H | H | H | H | L¹⁰¹ | N | CH | N | 4-biphenyl | 4-biphenyl |
| 325. | H | H | D¹⁰⁴ | H | H | H | H | H | L¹⁰² | N | N | N | Ph | Ph |
| 326. | H | H | D¹⁰⁴ | H | H | H | H | H | L¹⁰² | N | N | N | 4-biphenyl | 4-biphenyl |
| 327. | H | H | D¹⁰⁴ | H | H | H | H | H | L¹⁰² | N | CH | N | Ph | Ph |
| 328. | H | H | D¹⁰⁴ | H | H | H | H | H | L¹⁰² | N | CH | N | 4-biphenyl | 4-biphenyl |
| 329. | H | H | D¹⁰⁴ | H | H | H | H | H | L¹⁰³ | N | N | N | Ph | Ph |
| 330. | H | H | D¹⁰⁴ | H | H | H | H | H | L¹⁰³ | N | N | N | 4-biphenyl | 4-biphenyl |
| 331. | H | H | D¹⁰⁴ | H | H | H | H | H | L¹⁰³ | N | CH | N | Ph | Ph |
| 332. | H | H | D¹⁰⁴ | H | H | H | H | H | L¹⁰³ | N | CH | N | 4-biphenyl | 4-biphenyl |
| 333. | H | H | D¹⁰⁴ | H | H | H | H | H | L¹⁰⁴ | N | N | N | Ph | Ph |
| 334. | H | H | D¹⁰⁴ | H | H | H | H | H | L¹⁰⁴ | N | N | N | 4-biphenyl | 4-biphenyl |
| 335. | H | H | D¹⁰⁴ | H | H | H | H | H | L¹⁰⁴ | N | CH | N | Ph | Ph |
| 336. | H | H | D¹⁰⁴ | H | H | H | H | H | L¹⁰⁴ | N | CH | N | 4-biphenyl | 4-biphenyl |
| 337. | H | H | D¹⁰⁴ | H | H | H | H | H | L¹⁰⁵ | N | N | N | Ph | Ph |
| 338. | H | H | D¹⁰⁴ | H | H | H | H | H | L¹⁰⁵ | N | N | N | 4-biphenyl | 4-biphenyl |
| 339. | H | H | D¹⁰⁴ | H | H | H | H | H | L¹⁰⁵ | N | CH | N | Ph | Ph |
| 340. | H | H | D¹⁰⁴ | H | H | H | H | H | L¹⁰⁵ | N | CH | N | 4-biphenyl | 4-biphenyl |
| 341. | H | H | D¹⁰⁴ | H | H | H | H | H | L¹⁰⁶ | N | N | N | Ph | Ph |
| 342. | H | H | D¹⁰⁴ | H | H | H | H | H | L¹⁰⁶ | N | N | N | 4-biphenyl | 4-biphenyl |
| 343. | H | H | D¹⁰⁴ | H | H | H | H | H | L¹⁰⁶ | N | CH | N | Ph | Ph |
| 344. | H | H | D¹⁰⁴ | H | H | H | H | H | L¹⁰⁶ | N | CH | N | 4-biphenyl | 4-biphenyl |
| 345. | H | H | D¹⁰⁴ | H | H | H | H | H | L¹⁰⁷ | N | N | N | Ph | Ph |
| 346. | H | H | D¹⁰⁴ | H | H | H | H | H | L¹⁰⁷ | N | N | N | 4-biphenyl | 4-biphenyl |
| 347. | H | H | D¹⁰⁴ | H | H | H | H | H | L¹⁰⁷ | N | CH | N | Ph | Ph |
| 348. | H | H | D¹⁰⁴ | H | H | H | H | H | L¹⁰⁷ | N | CH | N | 4-biphenyl | 4-biphenyl |
| 349. | H | H | D¹⁰⁴ | H | H | H | H | H | L¹⁰⁸ | N | N | N | Ph | Ph |
| 350. | H | H | D¹⁰⁴ | H | H | H | H | H | L¹⁰⁸ | N | N | N | 4-biphenyl | 4-biphenyl |
| 351. | H | H | D¹⁰⁴ | H | H | H | H | H | L¹⁰⁸ | N | CH | N | Ph | Ph |
| 352. | H | H | D¹⁰⁴ | H | H | H | H | H | L¹⁰⁸ | N | CH | N | 4-biphenyl | 4-biphenyl |
| 353. | H | H | D¹⁰⁴ | H | H | H | H | H | L¹⁰⁹ | N | N | N | Ph | Ph |
| 354. | H | H | D¹⁰⁴ | H | H | H | H | H | L¹⁰⁹ | N | N | N | 4-biphenyl | 4-biphenyl |
| 355. | H | H | D¹⁰⁴ | H | H | H | H | H | L¹⁰⁹ | N | CH | N | Ph | Ph |
| 356. | H | H | D¹⁰⁴ | H | H | H | H | H | L¹⁰⁹ | N | CH | N | 4-biphenyl | 4-biphenyl |
| 357. | H | H | D¹⁰⁴ | H | H | H | H | H | L¹¹⁰ | N | N | N | Ph | Ph |
| 358. | H | H | D¹⁰⁴ | H | H | H | H | H | L¹¹⁰ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 359. | H | H | $D^{104}$ | H | H | H | H | H | $L^{110}$ | N | CH | N | Ph | Ph |
| 360. | H | H | $D^{104}$ | H | H | H | H | H | $L^{110}$ | N | CH | N | 4-biphenyl | 4-biphenyl |
| 361. | H | H | $D^{104}$ | H | H | H | H | H | $L^{111}$ | N | N | N | Ph | Ph |
| 362. | H | H | $D^{104}$ | H | H | H | H | H | $L^{111}$ | N | N | N | 4-biphenyl | 4-biphenyl |
| 363. | H | H | $D^{104}$ | H | H | H | H | H | $L^{111}$ | N | CH | N | Ph | Ph |
| 364. | H | H | $D^{104}$ | H | H | H | H | H | $L^{111}$ | N | CH | N | 4-biphenyl | 4-biphenyl |
| 365. | H | H | $D^{104}$ | H | H | H | H | H | $L^{112}$ | N | N | N | Ph | Ph |
| 366. | H | H | $D^{104}$ | H | H | H | H | H | $L^{112}$ | N | N | N | 4-biphenyl | 4-biphenyl |
| 367. | H | H | $D^{104}$ | H | H | H | H | H | $L^{112}$ | N | CH | N | Ph | Ph |
| 368. | H | H | $D^{104}$ | H | H | H | H | H | $L^{112}$ | N | CH | N | 4-biphenyl | 4-biphenyl |
| 369. | H | H | $D^{104}$ | H | H | H | H | H | $L^{113}$ | N | N | N | Ph | Ph |
| 370. | H | H | $D^{104}$ | H | H | H | H | H | $L^{113}$ | N | N | N | 4-biphenyl | 4-biphenyl |
| 371. | H | H | $D^{104}$ | H | H | H | H | H | $L^{113}$ | N | CH | N | Ph | Ph |
| 372. | H | H | $D^{104}$ | H | H | H | H | H | $L^{113}$ | N | CH | N | 4-biphenyl | 4-biphenyl |
| 373. | H | H | $D^{104}$ | H | H | H | H | H | $L^{114}$ | N | N | N | Ph | Ph |
| 374. | H | H | $D^{104}$ | H | H | H | H | H | $L^{114}$ | N | N | N | 4-biphenyl | 4-biphenyl |
| 375. | H | H | $D^{104}$ | H | H | H | H | H | $L^{114}$ | N | CH | N | Ph | Ph |
| 376. | H | H | $D^{104}$ | H | H | H | H | H | $L^{114}$ | N | CH | N | 4-biphenyl | 4-biphenyl |
| 377. | H | H | $D^{104}$ | H | H | H | H | H | $L^{115}$ | N | N | N | Ph | Ph |
| 378. | H | H | $D^{104}$ | H | H | H | H | H | $L^{115}$ | N | N | N | 4-biphenyl | 4-biphenyl |
| 379. | H | H | $D^{104}$ | H | H | H | H | H | $L^{115}$ | N | CH | N | Ph | Ph |
| 380. | H | H | $D^{104}$ | H | H | H | H | H | $L^{115}$ | N | CH | N | 4-biphenyl | 4-biphenyl |
| 381. | H | H | $D^{104}$ | H | H | H | H | H | $L^{116}$ | N | N | N | Ph | Ph |
| 382. | H | H | $D^{104}$ | H | H | H | H | H | $L^{116}$ | N | N | N | 4-biphenyl | 4-biphenyl |
| 383. | H | H | $D^{104}$ | H | H | H | H | H | $L^{116}$ | N | CH | N | Ph | Ph |
| 384. | H | H | $D^{104}$ | H | H | H | H | H | $L^{116}$ | N | CH | N | 4-biphenyl | 4-biphenyl |
| 385. | H | H | $D^{105}$ | H | H | H | H | H | $L^{101}$ | N | N | N | Ph | Ph |
| 386. | H | H | $D^{105}$ | H | H | H | H | H | $L^{101}$ | N | N | N | 4-biphenyl | 4-biphenyl |
| 387. | H | H | $D^{105}$ | H | H | H | H | H | $L^{101}$ | N | CH | N | Ph | Ph |
| 388. | H | H | $D^{105}$ | H | H | H | H | H | $L^{101}$ | N | CH | N | 4-biphenyl | 4-biphenyl |
| 389. | H | H | $D^{105}$ | H | H | H | H | H | $L^{102}$ | N | N | N | Ph | Ph |
| 390. | H | H | $D^{105}$ | H | H | H | H | H | $L^{102}$ | N | N | N | 4-biphenyl | 4-biphenyl |
| 391. | H | H | $D^{105}$ | H | H | H | H | H | $L^{102}$ | N | CH | N | Ph | Ph |
| 392. | H | H | $D^{105}$ | H | H | H | H | H | $L^{102}$ | N | CH | N | 4-biphenyl | 4-biphenyl |
| 393. | H | H | $D^{105}$ | H | H | H | H | H | $L^{103}$ | N | N | N | Ph | Ph |
| 394. | H | H | $D^{105}$ | H | H | H | H | H | $L^{103}$ | N | N | N | 4-biphenyl | 4-biphenyl |
| 395. | H | H | $D^{105}$ | H | H | H | H | H | $L^{103}$ | N | CH | N | Ph | Ph |
| 396. | H | H | $D^{105}$ | H | H | H | H | H | $L^{103}$ | N | CH | N | 4-biphenyl | 4-biphenyl |
| 397. | H | H | $D^{105}$ | H | H | H | H | H | $L^{104}$ | N | N | N | Ph | Ph |
| 398. | H | H | $D^{105}$ | H | H | H | H | H | $L^{104}$ | N | N | N | 4-biphenyl | 4-biphenyl |
| 399. | H | H | $D^{105}$ | H | H | H | H | H | $L^{104}$ | N | CH | N | Ph | Ph |
| 400. | H | H | $D^{105}$ | H | H | H | H | H | $L^{104}$ | N | CH | N | 4-biphenyl | 4-biphenyl |
| 401. | H | H | $D^{105}$ | H | H | H | H | H | $L^{105}$ | N | N | N | Ph | Ph |
| 402. | H | H | $D^{105}$ | H | H | H | H | H | $L^{105}$ | N | N | N | 4-biphenyl | 4-biphenyl |
| 403. | H | H | $D^{105}$ | H | H | H | H | H | $L^{105}$ | N | CH | N | Ph | Ph |
| 404. | H | H | $D^{105}$ | H | H | H | H | H | $L^{105}$ | N | CH | N | 4-biphenyl | 4-biphenyl |
| 405. | H | H | $D^{105}$ | H | H | H | H | H | $L^{106}$ | N | N | N | Ph | Ph |
| 406. | H | H | $D^{105}$ | H | H | H | H | H | $L^{106}$ | N | N | N | 4-biphenyl | 4-biphenyl |
| 407. | H | H | $D^{105}$ | H | H | H | H | H | $L^{106}$ | N | CH | N | Ph | Ph |
| 408. | H | H | $D^{105}$ | H | H | H | H | H | $L^{106}$ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 409. | H | H | D¹⁰⁵ | H | H | H | H | H | L¹⁰⁷ | N | N | N | Ph | Ph |
| 410. | H | H | D¹⁰⁵ | H | H | H | H | H | L¹⁰⁷ | N | N | N | 4-biphenyl | 4-biphenyl |
| 411. | H | H | D¹⁰⁵ | H | H | H | H | H | L¹⁰⁷ | N | CH | N | Ph | Ph |
| 412. | H | H | D¹⁰⁵ | H | H | H | H | H | L¹⁰⁷ | N | CH | N | 4-biphenyl | 4-biphenyl |
| 413. | H | H | D¹⁰⁵ | H | H | H | H | H | L¹⁰⁸ | N | N | N | Ph | Ph |
| 414. | H | H | D¹⁰⁵ | H | H | H | H | H | L¹⁰⁸ | N | N | N | 4-biphenyl | 4-biphenyl |
| 415. | H | H | D¹⁰⁵ | H | H | H | H | H | L¹⁰⁸ | N | CH | N | Ph | Ph |
| 416. | H | H | D¹⁰⁵ | H | H | H | H | H | L¹⁰⁸ | N | CH | N | 4-biphenyl | 4-biphenyl |
| 417. | H | H | D¹⁰⁵ | H | H | H | H | H | L¹⁰⁹ | N | N | N | Ph | Ph |
| 418. | H | H | D¹⁰⁵ | H | H | H | H | H | L¹⁰⁹ | N | N | N | 4-biphenyl | 4-biphenyl |
| 419. | H | H | D¹⁰⁵ | H | H | H | H | H | L¹⁰⁹ | N | CH | N | Ph | Ph |
| 420. | H | H | D¹⁰⁵ | H | H | H | H | H | L¹⁰⁹ | N | CH | N | 4-biphenyl | 4-biphenyl |
| 421. | H | H | D¹⁰⁵ | H | H | H | H | H | L¹¹⁰ | N | N | N | Ph | Ph |
| 422. | H | H | D¹⁰⁵ | H | H | H | H | H | L¹¹⁰ | N | N | N | 4-biphenyl | 4-biphenyl |
| 423. | H | H | D¹⁰⁵ | H | H | H | H | H | L¹¹⁰ | N | CH | N | Ph | Ph |
| 424. | H | H | D¹⁰⁵ | H | H | H | H | H | L¹¹⁰ | N | CH | N | 4-biphenyl | 4-biphenyl |
| 425. | H | H | D¹⁰⁵ | H | H | H | H | H | L¹¹¹ | N | N | N | Ph | Ph |
| 426. | H | H | D¹⁰⁵ | H | H | H | H | H | L¹¹¹ | N | N | N | 4-biphenyl | 4-biphenyl |
| 427. | H | H | D¹⁰⁵ | H | H | H | H | H | L¹¹¹ | N | CH | N | Ph | Ph |
| 428. | H | H | D¹⁰⁵ | H | H | H | H | H | L¹¹¹ | N | CH | N | 4-biphenyl | 4-biphenyl |
| 429. | H | H | D¹⁰⁵ | H | H | H | H | H | L¹¹² | N | N | N | Ph | Ph |
| 430. | H | H | D¹⁰⁵ | H | H | H | H | H | L¹¹² | N | N | N | 4-biphenyl | 4-biphenyl |
| 431. | H | H | D¹⁰⁵ | H | H | H | H | H | L¹¹² | N | CH | N | Ph | Ph |
| 432. | H | H | D¹⁰⁵ | H | H | H | H | H | L¹¹² | N | CH | N | 4-biphenyl | 4-biphenyl |
| 433. | H | H | D¹⁰⁵ | H | H | H | H | H | L¹¹³ | N | N | N | Ph | Ph |
| 434. | H | H | D¹⁰⁵ | H | H | H | H | H | L¹¹³ | N | N | N | 4-biphenyl | 4-biphenyl |
| 435. | H | H | D¹⁰⁵ | H | H | H | H | H | L¹¹³ | N | CH | N | Ph | Ph |
| 436. | H | H | D¹⁰⁵ | H | H | H | H | H | L¹¹³ | N | CH | N | 4-biphenyl | 4-biphenyl |
| 437. | H | H | D¹⁰⁵ | H | H | H | H | H | L¹¹⁴ | N | N | N | Ph | Ph |
| 438. | H | H | D¹⁰⁵ | H | H | H | H | H | L¹¹⁴ | N | N | N | 4-biphenyl | 4-biphenyl |
| 439. | H | H | D¹⁰⁵ | H | H | H | H | H | L¹¹⁴ | N | CH | N | Ph | Ph |
| 440. | H | H | D¹⁰⁵ | H | H | H | H | H | L¹¹⁴ | N | CH | N | 4-biphenyl | 4-biphenyl |
| 441. | H | H | D¹⁰⁵ | H | H | H | H | H | L¹¹⁵ | N | N | N | Ph | Ph |
| 442. | H | H | D¹⁰⁵ | H | H | H | H | H | L¹¹⁵ | N | N | N | 4-biphenyl | 4-biphenyl |
| 443. | H | H | D¹⁰⁵ | H | H | H | H | H | L¹¹⁵ | N | CH | N | Ph | Ph |
| 444. | H | H | D¹⁰⁵ | H | H | H | H | H | L¹¹⁵ | N | CH | N | 4-biphenyl | 4-biphenyl |
| 445. | H | H | D¹⁰⁵ | H | H | H | H | H | L¹¹⁶ | N | N | N | Ph | Ph |
| 446. | H | H | D¹⁰⁵ | H | H | H | H | H | L¹¹⁶ | N | N | N | 4-biphenyl | 4-biphenyl |
| 447. | H | H | D¹⁰⁵ | H | H | H | H | H | L¹¹⁶ | N | CH | N | Ph | Ph |
| 448. | H | H | D¹⁰⁵ | H | H | H | H | H | L¹¹⁶ | N | CH | N | 4-biphenyl | 4-biphenyl |
| 449. | H | H | D¹⁰⁶ | H | H | H | H | H | L¹⁰¹ | N | N | N | Ph | Ph |
| 450. | H | H | D¹⁰⁶ | H | H | H | H | H | L¹⁰¹ | N | N | N | 4-biphenyl | 4-biphenyl |
| 451. | H | H | D¹⁰⁶ | H | H | H | H | H | L¹⁰¹ | N | CH | N | Ph | Ph |
| 452. | H | H | D¹⁰⁶ | H | H | H | H | H | L¹⁰¹ | N | CH | N | 4-biphenyl | 4-biphenyl |
| 453. | H | H | D¹⁰⁶ | H | H | H | H | H | L¹⁰² | N | N | N | Ph | Ph |
| 454. | H | H | D¹⁰⁶ | H | H | H | H | H | L¹⁰² | N | N | N | 4-biphenyl | 4-biphenyl |
| 455. | H | H | D¹⁰⁶ | H | H | H | H | H | L¹⁰² | N | CH | N | Ph | Ph |
| 456. | H | H | D¹⁰⁶ | H | H | H | H | H | L¹⁰² | N | CH | N | 4-biphenyl | 4-biphenyl |
| 457. | H | H | D¹⁰⁶ | H | H | H | H | H | L¹⁰³ | N | N | N | Ph | Ph |
| 458. | H | H | D¹⁰⁶ | H | H | H | H | H | L¹⁰³ | N | N | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 459. | H | H | D¹⁰⁶ | H | H | H | H | H | L¹⁰³ | N | CH | N | Ph | Ph |
| 460. | H | H | D¹⁰⁶ | H | H | H | H | H | L¹⁰³ | N | CH | N | 4-biphenyl | 4-biphenyl |
| 461. | H | H | D¹⁰⁶ | H | H | H | H | H | L¹⁰⁴ | N | N | N | Ph | Ph |
| 462. | H | H | D¹⁰⁶ | H | H | H | H | H | L¹⁰⁴ | N | N | N | 4-biphenyl | 4-biphenyl |
| 463. | H | H | D¹⁰⁶ | H | H | H | H | H | L¹⁰⁴ | N | CH | N | Ph | Ph |
| 464. | H | H | D¹⁰⁶ | H | H | H | H | H | L¹⁰⁴ | N | CH | N | 4-biphenyl | 4-biphenyl |
| 465. | H | H | D¹⁰⁶ | H | H | H | H | H | L¹⁰⁵ | N | N | N | Ph | Ph |
| 466. | H | H | D¹⁰⁶ | H | H | H | H | H | L¹⁰⁵ | N | N | N | 4-biphenyl | 4-biphenyl |
| 467. | H | H | D¹⁰⁶ | H | H | H | H | H | L¹⁰⁵ | N | CH | N | Ph | Ph |
| 468. | H | H | D¹⁰⁶ | H | H | H | H | H | L¹⁰⁵ | N | CH | N | 4-biphenyl | 4-biphenyl |
| 469. | H | H | D¹⁰⁶ | H | H | H | H | H | L¹⁰⁶ | N | N | N | Ph | Ph |
| 470. | H | H | D¹⁰⁶ | H | H | H | H | H | L¹⁰⁶ | N | N | N | 4-biphenyl | 4-biphenyl |
| 471. | H | H | D¹⁰⁶ | H | H | H | H | H | L¹⁰⁶ | N | CH | N | Ph | Ph |
| 472. | H | H | D¹⁰⁶ | H | H | H | H | H | L¹⁰⁶ | N | CH | N | 4-biphenyl | 4-biphenyl |
| 473. | H | H | D¹⁰⁶ | H | H | H | H | H | L¹⁰⁷ | N | N | N | Ph | Ph |
| 474. | H | H | D¹⁰⁶ | H | H | H | H | H | L¹⁰⁷ | N | N | N | 4-biphenyl | 4-biphenyl |
| 475. | H | H | D¹⁰⁶ | H | H | H | H | H | L¹⁰⁷ | N | CH | N | Ph | Ph |
| 476. | H | H | D¹⁰⁶ | H | H | H | H | H | L¹⁰⁷ | N | CH | N | 4-biphenyl | 4-biphenyl |
| 477. | H | H | D¹⁰⁶ | H | H | H | H | H | L¹⁰⁸ | N | N | N | Ph | Ph |
| 478. | H | H | D¹⁰⁶ | H | H | H | H | H | L¹⁰⁸ | N | N | N | 4-biphenyl | 4-biphenyl |
| 479. | H | H | D¹⁰⁶ | H | H | H | H | H | L¹⁰⁸ | N | CH | N | Ph | Ph |
| 480. | H | H | D¹⁰⁶ | H | H | H | H | H | L¹⁰⁸ | N | CH | N | 4-biphenyl | 4-biphenyl |
| 481. | H | H | D¹⁰⁶ | H | H | H | H | H | L¹⁰⁹ | N | N | N | Ph | Ph |
| 482. | H | H | D¹⁰⁶ | H | H | H | H | H | L¹⁰⁹ | N | N | N | 4-biphenyl | 4-biphenyl |
| 483. | H | H | D¹⁰⁶ | H | H | H | H | H | L¹⁰⁹ | N | CH | N | Ph | Ph |
| 484. | H | H | D¹⁰⁶ | H | H | H | H | H | L¹⁰⁹ | N | CH | N | 4-biphenyl | 4-biphenyl |
| 485. | H | H | D¹⁰⁶ | H | H | H | H | H | L¹¹⁰ | N | N | N | Ph | Ph |
| 486. | H | H | D¹⁰⁶ | H | H | H | H | H | L¹¹⁰ | N | N | N | 4-biphenyl | 4-biphenyl |
| 487. | H | H | D¹⁰⁶ | H | H | H | H | H | L¹¹⁰ | N | CH | N | Ph | Ph |
| 488. | H | H | D¹⁰⁶ | H | H | H | H | H | L¹¹⁰ | N | CH | N | 4-biphenyl | 4-biphenyl |
| 489. | H | H | D¹⁰⁶ | H | H | H | H | H | L¹¹¹ | N | N | N | Ph | Ph |
| 490. | H | H | D¹⁰⁶ | H | H | H | H | H | L¹¹¹ | N | N | N | 4-biphenyl | 4-biphenyl |
| 491. | H | H | D¹⁰⁶ | H | H | H | H | H | L¹¹¹ | N | CH | N | Ph | Ph |
| 492. | H | H | D¹⁰⁶ | H | H | H | H | H | L¹¹¹ | N | CH | N | 4-biphenyl | 4-biphenyl |
| 493. | H | H | D¹⁰⁶ | H | H | H | H | H | L¹¹² | N | N | N | Ph | Ph |
| 494. | H | H | D¹⁰⁶ | H | H | H | H | H | L¹¹² | N | N | N | 4-biphenyl | 4-biphenyl |
| 495. | H | H | D¹⁰⁶ | H | H | H | H | H | L¹¹² | N | CH | N | Ph | Ph |
| 496. | H | H | D¹⁰⁶ | H | H | H | H | H | L¹¹² | N | CH | N | 4-biphenyl | 4-biphenyl |
| 497. | H | H | D¹⁰⁶ | H | H | H | H | H | L¹¹³ | N | N | N | Ph | Ph |
| 498. | H | H | D¹⁰⁶ | H | H | H | H | H | L¹¹³ | N | N | N | 4-biphenyl | 4-biphenyl |
| 499. | H | H | D¹⁰⁶ | H | H | H | H | H | L¹¹³ | N | CH | N | Ph | Ph |
| 500. | H | H | D¹⁰⁶ | H | H | H | H | H | L¹¹³ | N | CH | N | 4-biphenyl | 4-biphenyl |
| 501. | H | H | D¹⁰⁶ | H | H | H | H | H | L¹¹⁴ | N | N | N | Ph | Ph |
| 502. | H | H | D¹⁰⁶ | H | H | H | H | H | L¹¹⁴ | N | N | N | 4-biphenyl | 4-biphenyl |
| 503. | H | H | D¹⁰⁶ | H | H | H | H | H | L¹¹⁴ | N | CH | N | Ph | Ph |
| 504. | H | H | D¹⁰⁶ | H | H | H | H | H | L¹¹⁴ | N | CH | N | 4-biphenyl | 4-biphenyl |
| 505. | H | H | D¹⁰⁶ | H | H | H | H | H | L¹¹⁵ | N | N | N | Ph | Ph |
| 506. | H | H | D¹⁰⁶ | H | H | H | H | H | L¹¹⁵ | N | N | N | 4-biphenyl | 4-biphenyl |
| 507. | H | H | D¹⁰⁶ | H | H | H | H | H | L¹¹⁵ | N | CH | N | Ph | Ph |
| 508. | H | H | D¹⁰⁶ | H | H | H | H | H | L¹¹⁵ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 509. | H | H | D¹⁰⁶ | H | H | H | H | H | L¹¹⁶ | N | N | N | Ph | Ph |
| 510. | H | H | D¹⁰⁶ | H | H | H | H | H | L¹¹⁶ | N | N | N | 4-biphenyl | 4-biphenyl |
| 511. | H | H | D¹⁰⁶ | H | H | H | H | H | L¹¹⁶ | N | CH | N | Ph | Ph |
| 512. | H | H | D¹⁰⁶ | H | H | H | H | H | L¹¹⁶ | N | CH | N | 4-biphenyl | 4-biphenyl |
| 513. | H | H | D¹⁰⁷ | H | H | H | H | H | L¹⁰¹ | N | N | N | Ph | Ph |
| 514. | H | H | D¹⁰⁷ | H | H | H | H | H | L¹⁰¹ | N | N | N | 4-biphenyl | 4-biphenyl |
| 515. | H | H | D¹⁰⁷ | H | H | H | H | H | L¹⁰¹ | N | CH | N | Ph | Ph |
| 516. | H | H | D¹⁰⁷ | H | H | H | H | H | L¹⁰¹ | N | CH | N | 4-biphenyl | 4-biphenyl |
| 517. | H | H | D¹⁰⁷ | H | H | H | H | H | L¹⁰² | N | N | N | Ph | Ph |
| 518. | H | H | D¹⁰⁷ | H | H | H | H | H | L¹⁰² | N | N | N | 4-biphenyl | 4-biphenyl |
| 519. | H | H | D¹⁰⁷ | H | H | H | H | H | L¹⁰² | N | CH | N | Ph | Ph |
| 520. | H | H | D¹⁰⁷ | H | H | H | H | H | L¹⁰² | N | CH | N | 4-biphenyl | 4-biphenyl |
| 521. | H | H | D¹⁰⁷ | H | H | H | H | H | L¹⁰³ | N | N | N | Ph | Ph |
| 522. | H | H | D¹⁰⁷ | H | H | H | H | H | L¹⁰³ | N | N | N | 4-biphenyl | 4-biphenyl |
| 523. | H | H | D¹⁰⁷ | H | H | H | H | H | L¹⁰³ | N | CH | N | Ph | Ph |
| 524. | H | H | D¹⁰⁷ | H | H | H | H | H | L¹⁰³ | N | CH | N | 4-biphenyl | 4-biphenyl |
| 525. | H | H | D¹⁰⁷ | H | H | H | H | H | L¹⁰⁴ | N | N | N | Ph | Ph |
| 526. | H | H | D¹⁰⁷ | H | H | H | H | H | L¹⁰⁴ | N | N | N | 4-biphenyl | 4-biphenyl |
| 527. | H | H | D¹⁰⁷ | H | H | H | H | H | L¹⁰⁴ | N | CH | N | Ph | Ph |
| 528. | H | H | D¹⁰⁷ | H | H | H | H | H | L¹⁰⁴ | N | CH | N | 4-biphenyl | 4-biphenyl |
| 529. | H | H | D¹⁰⁷ | H | H | H | H | H | L¹⁰⁵ | N | N | N | Ph | Ph |
| 530. | H | H | D¹⁰⁷ | H | H | H | H | H | L¹⁰⁵ | N | N | N | 4-biphenyl | 4-biphenyl |
| 531. | H | H | D¹⁰⁷ | H | H | H | H | H | L¹⁰⁵ | N | CH | N | Ph | Ph |
| 532. | H | H | D¹⁰⁷ | H | H | H | H | H | L¹⁰⁵ | N | CH | N | 4-biphenyl | 4-biphenyl |
| 533. | H | H | D¹⁰⁷ | H | H | H | H | H | L¹⁰⁶ | N | N | N | Ph | Ph |
| 534. | H | H | D¹⁰⁷ | H | H | H | H | H | L¹⁰⁶ | N | N | N | 4-biphenyl | 4-biphenyl |
| 535. | H | H | D¹⁰⁷ | H | H | H | H | H | L¹⁰⁶ | N | CH | N | Ph | Ph |
| 536. | H | H | D¹⁰⁷ | H | H | H | H | H | L¹⁰⁶ | N | CH | N | 4-biphenyl | 4-biphenyl |
| 537. | H | H | D¹⁰⁷ | H | H | H | H | H | L¹⁰⁷ | N | N | N | Ph | Ph |
| 538. | H | H | D¹⁰⁷ | H | H | H | H | H | L¹⁰⁷ | N | N | N | 4-biphenyl | 4-biphenyl |
| 539. | H | H | D¹⁰⁷ | H | H | H | H | H | L¹⁰⁷ | N | CH | N | Ph | Ph |
| 540. | H | H | D¹⁰⁷ | H | H | H | H | H | L¹⁰⁷ | N | CH | N | 4-biphenyl | 4-biphenyl |
| 541. | H | H | D¹⁰⁷ | H | H | H | H | H | L¹⁰⁸ | N | N | N | Ph | Ph |
| 542. | H | H | D¹⁰⁷ | H | H | H | H | H | L¹⁰⁸ | N | N | N | 4-biphenyl | 4-biphenyl |
| 543. | H | H | D¹⁰⁷ | H | H | H | H | H | L¹⁰⁸ | N | CH | N | Ph | Ph |
| 544. | H | H | D¹⁰⁷ | H | H | H | H | H | L¹⁰⁸ | N | CH | N | 4-biphenyl | 4-biphenyl |
| 545. | H | H | D¹⁰⁷ | H | H | H | H | H | L¹⁰⁹ | N | N | N | Ph | Ph |
| 546. | H | H | D¹⁰⁷ | H | H | H | H | H | L¹⁰⁹ | N | N | N | 4-biphenyl | 4-biphenyl |
| 547. | H | H | D¹⁰⁷ | H | H | H | H | H | L¹⁰⁹ | N | CH | N | Ph | Ph |
| 548. | H | H | D¹⁰⁷ | H | H | H | H | H | L¹⁰⁹ | N | CH | N | 4-biphenyl | 4-biphenyl |
| 549. | H | H | D¹⁰⁷ | H | H | H | H | H | L¹¹⁰ | N | N | N | Ph | Ph |
| 550. | H | H | D¹⁰⁷ | H | H | H | H | H | L¹¹⁰ | N | N | N | 4-biphenyl | 4-biphenyl |
| 551. | H | H | D¹⁰⁷ | H | H | H | H | H | L¹¹⁰ | N | CH | N | Ph | Ph |
| 552. | H | H | D¹⁰⁷ | H | H | H | H | H | L¹¹⁰ | N | CH | N | 4-biphenyl | 4-biphenyl |
| 553. | H | H | D¹⁰⁷ | H | H | H | H | H | L¹¹¹ | N | N | N | Ph | Ph |
| 554. | H | H | D¹⁰⁷ | H | H | H | H | H | L¹¹¹ | N | N | N | 4-biphenyl | 4-biphenyl |
| 555. | H | H | D¹⁰⁷ | H | H | H | H | H | L¹¹¹ | N | CH | N | Ph | Ph |
| 556. | H | H | D¹⁰⁷ | H | H | H | H | H | L¹¹¹ | N | CH | N | 4-biphenyl | 4-biphenyl |
| 557. | H | H | D¹⁰⁷ | H | H | H | H | H | L¹¹² | N | N | N | Ph | Ph |
| 558. | H | H | D¹⁰⁷ | H | H | H | H | H | L¹¹² | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 559. | H | H | D¹⁰⁷ | H | H | H | H | H | L¹¹² | N | CH | N | Ph | Ph |
| 560. | H | H | D¹⁰⁷ | H | H | H | H | H | L¹¹² | N | CH | N | 4-biphenyl | 4-biphenyl |
| 561. | H | H | D¹⁰⁷ | H | H | H | H | H | L¹¹³ | N | N | N | Ph | Ph |
| 562. | H | H | D¹⁰⁷ | H | H | H | H | H | L¹¹³ | N | N | N | 4-biphenyl | 4-biphenyl |
| 563. | H | H | D¹⁰⁷ | H | H | H | H | H | L¹¹³ | N | CH | N | Ph | Ph |
| 564. | H | H | D¹⁰⁷ | H | H | H | H | H | L¹¹³ | N | CH | N | 4-biphenyl | 4-biphenyl |
| 565. | H | H | D¹⁰⁷ | H | H | H | H | H | L¹¹⁴ | N | N | N | Ph | Ph |
| 566. | H | H | D¹⁰⁷ | H | H | H | H | H | L¹¹⁴ | N | N | N | 4-biphenyl | 4-biphenyl |
| 567. | H | H | D¹⁰⁷ | H | H | H | H | H | L¹¹⁴ | N | CH | N | Ph | Ph |
| 568. | H | H | D¹⁰⁷ | H | H | H | H | H | L¹¹⁴ | N | CH | N | 4-biphenyl | 4-biphenyl |
| 569. | H | H | D¹⁰⁷ | H | H | H | H | H | L¹¹⁵ | N | N | N | Ph | Ph |
| 570. | H | H | D¹⁰⁷ | H | H | H | H | H | L¹¹⁵ | N | N | N | 4-biphenyl | 4-biphenyl |
| 571. | H | H | D¹⁰⁷ | H | H | H | H | H | L¹¹⁵ | N | CH | N | Ph | Ph |
| 572. | H | H | D¹⁰⁷ | H | H | H | H | H | L¹¹⁵ | N | CH | N | 4-biphenyl | 4-biphenyl |
| 573. | H | H | D¹⁰⁷ | H | H | H | H | H | L¹¹⁶ | N | N | N | Ph | Ph |
| 574. | H | H | D¹⁰⁷ | H | H | H | H | H | L¹¹⁶ | N | N | N | 4-biphenyl | 4-biphenyl |
| 575. | H | H | D¹⁰⁷ | H | H | H | H | H | L¹¹⁶ | N | CH | N | Ph | Ph |
| 576. | H | H | D¹⁰⁷ | H | H | H | H | H | L¹¹⁶ | N | CH | N | 4-biphenyl | 4-biphenyl |
| 577. | H | H | D¹⁰⁸ | H | H | H | H | H | L¹⁰¹ | N | N | N | Ph | Ph |
| 578. | H | H | D¹⁰⁸ | H | H | H | H | H | L¹⁰¹ | N | N | N | 4-biphenyl | 4-biphenyl |
| 579. | H | H | D¹⁰⁸ | H | H | H | H | H | L¹⁰¹ | N | CH | N | Ph | Ph |
| 580. | H | H | D¹⁰⁸ | H | H | H | H | H | L¹⁰¹ | N | CH | N | 4-biphenyl | 4-biphenyl |
| 581. | H | H | D¹⁰⁸ | H | H | H | H | H | L¹⁰² | N | N | N | Ph | Ph |
| 582. | H | H | D¹⁰⁸ | H | H | H | H | H | L¹⁰² | N | N | N | 4-biphenyl | 4-biphenyl |
| 583. | H | H | D¹⁰⁸ | H | H | H | H | H | L¹⁰² | N | CH | N | Ph | Ph |
| 584. | H | H | D¹⁰⁸ | H | H | H | H | H | L¹⁰² | N | CH | N | 4-biphenyl | 4-biphenyl |
| 585. | H | H | D¹⁰⁸ | H | H | H | H | H | L¹⁰³ | N | N | N | Ph | Ph |
| 586. | H | H | D¹⁰⁸ | H | H | H | H | H | L¹⁰³ | N | N | N | 4-biphenyl | 4-biphenyl |
| 587. | H | H | D¹⁰⁸ | H | H | H | H | H | L¹⁰³ | N | CH | N | Ph | Ph |
| 588. | H | H | D¹⁰⁸ | H | H | H | H | H | L¹⁰³ | N | CH | N | 4-biphenyl | 4-biphenyl |
| 589. | H | H | D¹⁰⁸ | H | H | H | H | H | L¹⁰⁴ | N | N | N | Ph | Ph |
| 590. | H | H | D¹⁰⁸ | H | H | H | H | H | L¹⁰⁴ | N | N | N | 4-biphenyl | 4-biphenyl |
| 591. | H | H | D¹⁰⁸ | H | H | H | H | H | L¹⁰⁴ | N | CH | N | Ph | Ph |
| 592. | H | H | D¹⁰⁸ | H | H | H | H | H | L¹⁰⁴ | N | CH | N | 4-biphenyl | 4-biphenyl |
| 593. | H | H | D¹⁰⁸ | H | H | H | H | H | L¹⁰⁵ | N | N | N | Ph | Ph |
| 594. | H | H | D¹⁰⁸ | H | H | H | H | H | L¹⁰⁵ | N | N | N | 4-biphenyl | 4-biphenyl |
| 595. | H | H | D¹⁰⁸ | H | H | H | H | H | L¹⁰⁵ | N | CH | N | Ph | Ph |
| 596. | H | H | D¹⁰⁸ | H | H | H | H | H | L¹⁰⁵ | N | CH | N | 4-biphenyl | 4-biphenyl |
| 597. | H | H | D¹⁰⁸ | H | H | H | H | H | L¹⁰⁶ | N | N | N | Ph | Ph |
| 598. | H | H | D¹⁰⁸ | H | H | H | H | H | L¹⁰⁶ | N | N | N | 4-biphenyl | 4-biphenyl |
| 599. | H | H | D¹⁰⁸ | H | H | H | H | H | L¹⁰⁶ | N | CH | N | Ph | Ph |
| 600. | H | H | D¹⁰⁸ | H | H | H | H | H | L¹⁰⁶ | N | CH | N | 4-biphenyl | 4-biphenyl |
| 601. | H | H | D¹⁰⁸ | H | H | H | H | H | L¹⁰⁷ | N | N | N | Ph | Ph |
| 602. | H | H | D¹⁰⁸ | H | H | H | H | H | L¹⁰⁷ | N | N | N | 4-biphenyl | 4-biphenyl |
| 603. | H | H | D¹⁰⁸ | H | H | H | H | H | L¹⁰⁷ | N | CH | N | Ph | Ph |
| 604. | H | H | D¹⁰⁸ | H | H | H | H | H | L¹⁰⁷ | N | CH | N | 4-biphenyl | 4-biphenyl |
| 605. | H | H | D¹⁰⁸ | H | H | H | H | H | L¹⁰⁸ | N | N | N | Ph | Ph |
| 606. | H | H | D¹⁰⁸ | H | H | H | H | H | L¹⁰⁸ | N | N | N | 4-biphenyl | 4-biphenyl |
| 607. | H | H | D¹⁰⁸ | H | H | H | H | H | L¹⁰⁸ | N | CH | N | Ph | Ph |
| 608. | H | H | D¹⁰⁸ | H | H | H | H | H | L¹⁰⁸ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 609. | H | H | D¹⁰⁸ | H | H | H | H | H | L¹⁰⁹ | N | N | N | Ph | Ph |
| 610. | H | H | D¹⁰⁸ | H | H | H | H | H | L¹⁰⁹ | N | N | N | 4-biphenyl | 4-biphenyl |
| 611. | H | H | D¹⁰⁸ | H | H | H | H | H | L¹⁰⁹ | N | CH | N | Ph | Ph |
| 612. | H | H | D¹⁰⁸ | H | H | H | H | H | L¹⁰⁹ | N | CH | N | 4-biphenyl | 4-biphenyl |
| 613. | H | H | D¹⁰⁸ | H | H | H | H | H | L¹¹⁰ | N | N | N | Ph | Ph |
| 614. | H | H | D¹⁰⁸ | H | H | H | H | H | L¹¹⁰ | N | N | N | 4-biphenyl | 4-biphenyl |
| 615. | H | H | D¹⁰⁸ | H | H | H | H | H | L¹¹⁰ | N | CH | N | Ph | Ph |
| 616. | H | H | D¹⁰⁸ | H | H | H | H | H | L¹¹⁰ | N | CH | N | 4-biphenyl | 4-biphenyl |
| 617. | H | H | D¹⁰⁸ | H | H | H | H | H | L¹¹¹ | N | N | N | Ph | Ph |
| 618. | H | H | D¹⁰⁸ | H | H | H | H | H | L¹¹¹ | N | N | N | 4-biphenyl | 4-biphenyl |
| 619. | H | H | D¹⁰⁸ | H | H | H | H | H | L¹¹¹ | N | CH | N | Ph | Ph |
| 620. | H | H | D¹⁰⁸ | H | H | H | H | H | L¹¹¹ | N | CH | N | 4-biphenyl | 4-biphenyl |
| 621. | H | H | D¹⁰⁸ | H | H | H | H | H | L¹¹² | N | N | N | Ph | Ph |
| 622. | H | H | D¹⁰⁸ | H | H | H | H | H | L¹¹² | N | N | N | 4-biphenyl | 4-biphenyl |
| 623. | H | H | D¹⁰⁸ | H | H | H | H | H | L¹¹² | N | CH | N | Ph | Ph |
| 624. | H | H | D¹⁰⁸ | H | H | H | H | H | L¹¹² | N | CH | N | 4-biphenyl | 4-biphenyl |
| 625. | H | H | D¹⁰⁸ | H | H | H | H | H | L¹¹³ | N | N | N | Ph | Ph |
| 626. | H | H | D¹⁰⁸ | H | H | H | H | H | L¹¹³ | N | N | N | 4-biphenyl | 4-biphenyl |
| 627. | H | H | D¹⁰⁸ | H | H | H | H | H | L¹¹³ | N | CH | N | Ph | Ph |
| 628. | H | H | D¹⁰⁸ | H | H | H | H | H | L¹¹³ | N | CH | N | 4-biphenyl | 4-biphenyl |
| 629. | H | H | D¹⁰⁸ | H | H | H | H | H | L¹¹⁴ | N | N | N | Ph | Ph |
| 630. | H | H | D¹⁰⁸ | H | H | H | H | H | L¹¹⁴ | N | N | N | 4-biphenyl | 4-biphenyl |
| 631. | H | H | D¹⁰⁸ | H | H | H | H | H | L¹¹⁴ | N | CH | N | Ph | Ph |
| 632. | H | H | D¹⁰⁸ | H | H | H | H | H | L¹¹⁴ | N | CH | N | 4-biphenyl | 4-biphenyl |
| 633. | H | H | D¹⁰⁸ | H | H | H | H | H | L¹¹⁵ | N | N | N | Ph | Ph |
| 634. | H | H | D¹⁰⁸ | H | H | H | H | H | L¹¹⁵ | N | N | N | 4-biphenyl | 4-biphenyl |
| 635. | H | H | D¹⁰⁸ | H | H | H | H | H | L¹¹⁵ | N | CH | N | Ph | Ph |
| 636. | H | H | D¹⁰⁸ | H | H | H | H | H | L¹¹⁵ | N | CH | N | 4-biphenyl | 4-biphenyl |
| 637. | H | H | D¹⁰⁸ | H | H | H | H | H | L¹¹⁶ | N | N | N | Ph | Ph |
| 638. | H | H | D¹⁰⁸ | H | H | H | H | H | L¹¹⁶ | N | N | N | 4-biphenyl | 4-biphenyl |
| 639. | H | H | D¹⁰⁸ | H | H | H | H | H | L¹¹⁶ | N | CH | N | Ph | Ph |
| 640. | H | H | D¹⁰⁸ | H | H | H | H | H | L¹¹⁶ | N | CH | N | 4-biphenyl | 4-biphenyl |
| 641. | H | H | D¹⁰⁹ | H | H | H | H | H | L¹⁰¹ | N | N | N | Ph | Ph |
| 642. | H | H | D¹⁰⁹ | H | H | H | H | H | L¹⁰¹ | N | N | N | 4-biphenyl | 4-biphenyl |
| 643. | H | H | D¹⁰⁹ | H | H | H | H | H | L¹⁰¹ | N | CH | N | Ph | Ph |
| 644. | H | H | D¹⁰⁹ | H | H | H | H | H | L¹⁰¹ | N | CH | N | 4-biphenyl | 4-biphenyl |
| 645. | H | H | D¹⁰⁹ | H | H | H | H | H | L¹⁰² | N | N | N | Ph | Ph |
| 646. | H | H | D¹⁰⁹ | H | H | H | H | H | L¹⁰² | N | N | N | 4-biphenyl | 4-biphenyl |
| 647. | H | H | D¹⁰⁹ | H | H | H | H | H | L¹⁰² | N | CH | N | Ph | Ph |
| 648. | H | H | D¹⁰⁹ | H | H | H | H | H | L¹⁰² | N | CH | N | 4-biphenyl | 4-biphenyl |
| 649. | H | H | D¹⁰⁹ | H | H | H | H | H | L¹⁰³ | N | N | N | Ph | Ph |
| 650. | H | H | D¹⁰⁹ | H | H | H | H | H | L¹⁰³ | N | N | N | 4-biphenyl | 4-biphenyl |
| 651. | H | H | D¹⁰⁹ | H | H | H | H | H | L¹⁰³ | N | CH | N | Ph | Ph |
| 652. | H | H | D¹⁰⁹ | H | H | H | H | H | L¹⁰³ | N | CH | N | 4-biphenyl | 4-biphenyl |
| 653. | H | H | D¹⁰⁹ | H | H | H | H | H | L¹⁰⁴ | N | N | N | Ph | Ph |
| 654. | H | H | D¹⁰⁹ | H | H | H | H | H | L¹⁰⁴ | N | N | N | 4-biphenyl | 4-biphenyl |
| 655. | H | H | D¹⁰⁹ | H | H | H | H | H | L¹⁰⁴ | N | CH | N | Ph | Ph |
| 656. | H | H | D¹⁰⁹ | H | H | H | H | H | L¹⁰⁴ | N | CH | N | 4-biphenyl | 4-biphenyl |
| 657. | H | H | D¹⁰⁹ | H | H | H | H | H | L¹⁰⁵ | N | N | N | Ph | Ph |
| 658. | H | H | D¹⁰⁹ | H | H | H | H | H | L¹⁰⁵ | N | N | N | 4-biphenyl | 4-biphenyl |

-continued

| Compound number | $R^1$ | $R^2$ | $R^3$ | $R^4$ | $R^5$ | $R^6$ | $R^7$ | $R^8$ | $L^1$ | $Z^1$ | $Z^3$ | $Z^5$ | $R^{91}$ | $R^{92}$ |
|---|---|---|---|---|---|---|---|---|---|---|---|---|---|---|
| 659. | H | H | $D^{109}$ | H | H | H | H | H | $L^{105}$ | N | CH | N | Ph | Ph |
| 660. | H | H | $D^{109}$ | H | H | H | H | H | $L^{105}$ | N | CH | N | 4-biphenyl | 4-biphenyl |
| 661. | H | H | $D^{109}$ | H | H | H | H | H | $L^{106}$ | N | N | N | Ph | Ph |
| 662. | H | H | $D^{109}$ | H | H | H | H | H | $L^{106}$ | N | N | N | 4-biphenyl | 4-biphenyl |
| 663. | H | H | $D^{109}$ | H | H | H | H | H | $L^{106}$ | N | CH | N | Ph | Ph |
| 664. | H | H | $D^{109}$ | H | H | H | H | H | $L^{106}$ | N | CH | N | 4-biphenyl | 4-biphenyl |
| 665. | H | H | $D^{109}$ | H | H | H | H | H | $L^{107}$ | N | N | N | Ph | Ph |
| 666. | H | H | $D^{109}$ | H | H | H | H | H | $L^{107}$ | N | N | N | 4-biphenyl | 4-biphenyl |
| 667. | H | H | $D^{109}$ | H | H | H | H | H | $L^{107}$ | N | CH | N | Ph | Ph |
| 668. | H | H | $D^{109}$ | H | H | H | H | H | $L^{107}$ | N | CH | N | 4-biphenyl | 4-biphenyl |
| 669. | H | H | $D^{109}$ | H | H | H | H | H | $L^{108}$ | N | N | N | Ph | Ph |
| 670. | H | H | $D^{109}$ | H | H | H | H | H | $L^{108}$ | N | N | N | 4-biphenyl | 4-biphenyl |
| 671. | H | H | $D^{109}$ | H | H | H | H | H | $L^{108}$ | N | CH | N | Ph | Ph |
| 672. | H | H | $D^{109}$ | H | H | H | H | H | $L^{108}$ | N | CH | N | 4-biphenyl | 4-biphenyl |
| 673. | H | H | $D^{109}$ | H | H | H | H | H | $L^{109}$ | N | N | N | Ph | Ph |
| 674. | H | H | $D^{109}$ | H | H | H | H | H | $L^{109}$ | N | N | N | 4-biphenyl | 4-biphenyl |
| 675. | H | H | $D^{109}$ | H | H | H | H | H | $L^{109}$ | N | CH | N | Ph | Ph |
| 676. | H | H | $D^{109}$ | H | H | H | H | H | $L^{109}$ | N | CH | N | 4-biphenyl | 4-biphenyl |
| 677. | H | H | $D^{109}$ | H | H | H | H | H | $L^{110}$ | N | N | N | Ph | Ph |
| 678. | H | H | $D^{109}$ | H | H | H | H | H | $L^{110}$ | N | N | N | 4-biphenyl | 4-biphenyl |
| 679. | H | H | $D^{109}$ | H | H | H | H | H | $L^{110}$ | N | CH | N | Ph | Ph |
| 680. | H | H | $D^{109}$ | H | H | H | H | H | $L^{110}$ | N | CH | N | 4-biphenyl | 4-biphenyl |
| 681. | H | H | $D^{109}$ | H | H | H | H | H | $L^{111}$ | N | N | N | Ph | Ph |
| 682. | H | H | $D^{109}$ | H | H | H | H | H | $L^{111}$ | N | N | N | 4-biphenyl | 4-biphenyl |
| 683. | H | H | $D^{109}$ | H | H | H | H | H | $L^{111}$ | N | CH | N | Ph | Ph |
| 684. | H | H | $D^{109}$ | H | H | H | H | H | $L^{111}$ | N | CH | N | 4-biphenyl | 4-biphenyl |
| 685. | H | H | $D^{109}$ | H | H | H | H | H | $L^{112}$ | N | N | N | Ph | Ph |
| 686. | H | H | $D^{109}$ | H | H | H | H | H | $L^{112}$ | N | N | N | 4-biphenyl | 4-biphenyl |
| 687. | H | H | $D^{109}$ | H | H | H | H | H | $L^{112}$ | N | CH | N | Ph | Ph |
| 688. | H | H | $D^{109}$ | H | H | H | H | H | $L^{112}$ | N | CH | N | 4-biphenyl | 4-biphenyl |
| 689. | H | H | $D^{109}$ | H | H | H | H | H | $L^{113}$ | N | N | N | Ph | Ph |
| 690. | H | H | $D^{109}$ | H | H | H | H | H | $L^{113}$ | N | N | N | 4-biphenyl | 4-biphenyl |
| 691. | H | H | $D^{109}$ | H | H | H | H | H | $L^{113}$ | N | CH | N | Ph | Ph |
| 692. | H | H | $D^{109}$ | H | H | H | H | H | $L^{113}$ | N | CH | N | 4-biphenyl | 4-biphenyl |
| 693. | H | H | $D^{109}$ | H | H | H | H | H | $L^{114}$ | N | N | N | Ph | Ph |
| 694. | H | H | $D^{109}$ | H | H | H | H | H | $L^{114}$ | N | N | N | 4-biphenyl | 4-biphenyl |
| 695. | H | H | $D^{109}$ | H | H | H | H | H | $L^{114}$ | N | CH | N | Ph | Ph |
| 696. | H | H | $D^{109}$ | H | H | H | H | H | $L^{114}$ | N | CH | N | 4-biphenyl | 4-biphenyl |
| 697. | H | H | $D^{109}$ | H | H | H | H | H | $L^{115}$ | N | N | N | Ph | Ph |
| 698. | H | H | $D^{109}$ | H | H | H | H | H | $L^{115}$ | N | N | N | 4-biphenyl | 4-biphenyl |
| 699. | H | H | $D^{109}$ | H | H | H | H | H | $L^{115}$ | N | CH | N | Ph | Ph |
| 700. | H | H | $D^{109}$ | H | H | H | H | H | $L^{115}$ | N | CH | N | 4-biphenyl | 4-biphenyl |
| 701. | H | H | $D^{109}$ | H | H | H | H | H | $L^{116}$ | N | N | N | Ph | Ph |
| 702. | H | H | $D^{109}$ | H | H | H | H | H | $L^{116}$ | N | N | N | 4-biphenyl | 4-biphenyl |
| 703. | H | H | $D^{109}$ | H | H | H | H | H | $L^{116}$ | N | CH | N | Ph | Ph |
| 704. | H | H | $D^{109}$ | H | H | H | H | H | $L^{116}$ | N | CH | N | 4-biphenyl | 4-biphenyl |
| 705. | H | H | $D^{110}$ | H | H | H | H | H | $L^{101}$ | N | N | N | Ph | Ph |
| 706. | H | H | $D^{110}$ | H | H | H | H | H | $L^{101}$ | N | N | N | 4-biphenyl | 4-biphenyl |
| 707. | H | H | $D^{110}$ | H | H | H | H | H | $L^{101}$ | N | CH | N | Ph | Ph |
| 708. | H | H | $D^{110}$ | H | H | H | H | H | $L^{101}$ | N | CH | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 709. | H | H | D¹¹⁰ | H | H | H | H | H | L¹⁰² | N | N | N | Ph | Ph |
| 710. | H | H | D¹¹⁰ | H | H | H | H | H | L¹⁰² | N | N | N | 4-biphenyl | 4-biphenyl |
| 711. | H | H | D¹¹⁰ | H | H | H | H | H | L¹⁰² | N | CH | N | Ph | Ph |
| 712. | H | H | D¹¹⁰ | H | H | H | H | H | L¹⁰² | N | CH | N | 4-biphenyl | 4-biphenyl |
| 713. | H | H | D¹¹⁰ | H | H | H | H | H | L¹⁰³ | N | N | N | Ph | Ph |
| 714. | H | H | D¹¹⁰ | H | H | H | H | H | L¹⁰³ | N | N | N | 4-biphenyl | 4-biphenyl |
| 715. | H | H | D¹¹⁰ | H | H | H | H | H | L¹⁰³ | N | CH | N | Ph | Ph |
| 716. | H | H | D¹¹⁰ | H | H | H | H | H | L¹⁰³ | N | CH | N | 4-biphenyl | 4-biphenyl |
| 717. | H | H | D¹¹⁰ | H | H | H | H | H | L¹⁰⁴ | N | N | N | Ph | Ph |
| 718. | H | H | D¹¹⁰ | H | H | H | H | H | L¹⁰⁴ | N | N | N | 4-biphenyl | 4-biphenyl |
| 719. | H | H | D¹¹⁰ | H | H | H | H | H | L¹⁰⁴ | N | CH | N | Ph | Ph |
| 720. | H | H | D¹¹⁰ | H | H | H | H | H | L¹⁰⁴ | N | CH | N | 4-biphenyl | 4-biphenyl |
| 721. | H | H | D¹¹⁰ | H | H | H | H | H | L¹⁰⁵ | N | N | N | Ph | Ph |
| 722. | H | H | D¹¹⁰ | H | H | H | H | H | L¹⁰⁵ | N | N | N | 4-biphenyl | 4-biphenyl |
| 723. | H | H | D¹¹⁰ | H | H | H | H | H | L¹⁰⁵ | N | CH | N | Ph | Ph |
| 724. | H | H | D¹¹⁰ | H | H | H | H | H | L¹⁰⁵ | N | CH | N | 4-biphenyl | 4-biphenyl |
| 725. | H | H | D¹¹⁰ | H | H | H | H | H | L¹⁰⁶ | N | N | N | Ph | Ph |
| 726. | H | H | D¹¹⁰ | H | H | H | H | H | L¹⁰⁶ | N | N | N | 4-biphenyl | 4-biphenyl |
| 727. | H | H | D¹¹⁰ | H | H | H | H | H | L¹⁰⁶ | N | CH | N | Ph | Ph |
| 728. | H | H | D¹¹⁰ | H | H | H | H | H | L¹⁰⁶ | N | CH | N | 4-biphenyl | 4-biphenyl |
| 729. | H | H | D¹¹⁰ | H | H | H | H | H | L¹⁰⁷ | N | N | N | Ph | Ph |
| 730. | H | H | D¹¹⁰ | H | H | H | H | H | L¹⁰⁷ | N | N | N | 4-biphenyl | 4-biphenyl |
| 731. | H | H | D¹¹⁰ | H | H | H | H | H | L¹⁰⁷ | N | CH | N | Ph | Ph |
| 732. | H | H | D¹¹⁰ | H | H | H | H | H | L¹⁰⁷ | N | CH | N | 4-biphenyl | 4-biphenyl |
| 733. | H | H | D¹¹⁰ | H | H | H | H | H | L¹⁰⁸ | N | N | N | Ph | Ph |
| 734. | H | H | D¹¹⁰ | H | H | H | H | H | L¹⁰⁸ | N | N | N | 4-biphenyl | 4-biphenyl |
| 735. | H | H | D¹¹⁰ | H | H | H | H | H | L¹⁰⁸ | N | CH | N | Ph | Ph |
| 736. | H | H | D¹¹⁰ | H | H | H | H | H | L¹⁰⁸ | N | CH | N | 4-biphenyl | 4-biphenyl |
| 737. | H | H | D¹¹⁰ | H | H | H | H | H | L¹⁰⁹ | N | N | N | Ph | Ph |
| 738. | H | H | D¹¹⁰ | H | H | H | H | H | L¹⁰⁹ | N | N | N | 4-biphenyl | 4-biphenyl |
| 739. | H | H | D¹¹⁰ | H | H | H | H | H | L¹⁰⁹ | N | CH | N | Ph | Ph |
| 740. | H | H | D¹¹⁰ | H | H | H | H | H | L¹⁰⁹ | N | CH | N | 4-biphenyl | 4-biphenyl |
| 741. | H | H | D¹¹⁰ | H | H | H | H | H | L¹¹⁰ | N | N | N | Ph | Ph |
| 742. | H | H | D¹¹⁰ | H | H | H | H | H | L¹¹⁰ | N | N | N | 4-biphenyl | 4-biphenyl |
| 743. | H | H | D¹¹⁰ | H | H | H | H | H | L¹¹⁰ | N | CH | N | Ph | Ph |
| 744. | H | H | D¹¹⁰ | H | H | H | H | H | L¹¹⁰ | N | CH | N | 4-biphenyl | 4-biphenyl |
| 745. | H | H | D¹¹⁰ | H | H | H | H | H | L¹¹¹ | N | N | N | Ph | Ph |
| 746. | H | H | D¹¹⁰ | H | H | H | H | H | L¹¹¹ | N | N | N | 4-biphenyl | 4-biphenyl |
| 747. | H | H | D¹¹⁰ | H | H | H | H | H | L¹¹¹ | N | CH | N | Ph | Ph |
| 748. | H | H | D¹¹⁰ | H | H | H | H | H | L¹¹¹ | N | CH | N | 4-biphenyl | 4-biphenyl |
| 749. | H | H | D¹¹⁰ | H | H | H | H | H | L¹¹² | N | N | N | Ph | Ph |
| 750. | H | H | D¹¹⁰ | H | H | H | H | H | L¹¹² | N | N | N | 4-biphenyl | 4-biphenyl |
| 751. | H | H | D¹¹⁰ | H | H | H | H | H | L¹¹² | N | CH | N | Ph | Ph |
| 752. | H | H | D¹¹⁰ | H | H | H | H | H | L¹¹² | N | CH | N | 4-biphenyl | 4-biphenyl |
| 753. | H | H | D¹¹⁰ | H | H | H | H | H | L¹¹³ | N | N | N | Ph | Ph |
| 754. | H | H | D¹¹⁰ | H | H | H | H | H | L¹¹³ | N | N | N | 4-biphenyl | 4-biphenyl |
| 755. | H | H | D¹¹⁰ | H | H | H | H | H | L¹¹³ | N | CH | N | Ph | Ph |
| 756. | H | H | D¹¹⁰ | H | H | H | H | H | L¹¹³ | N | CH | N | 4-biphenyl | 4-biphenyl |
| 757. | H | H | D¹¹⁰ | H | H | H | H | H | L¹¹⁴ | N | N | N | Ph | Ph |
| 758. | H | H | D¹¹⁰ | H | H | H | H | H | L¹¹⁴ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 759. | H | H | D¹¹⁰ | H | H | H | H | H | L¹¹⁴ | N | CH | N | Ph | Ph |
| 760. | H | H | D¹¹⁰ | H | H | H | H | H | L¹¹⁴ | N | CH | N | 4-biphenyl | 4-biphenyl |
| 761. | H | H | D¹¹⁰ | H | H | H | H | H | L¹¹⁵ | N | N | N | Ph | Ph |
| 762. | H | H | D¹¹⁰ | H | H | H | H | H | L¹¹⁵ | N | N | N | 4-biphenyl | 4-biphenyl |
| 763. | H | H | D¹¹⁰ | H | H | H | H | H | L¹¹⁵ | N | CH | N | Ph | Ph |
| 764. | H | H | D¹¹⁰ | H | H | H | H | H | L¹¹⁵ | N | CH | N | 4-biphenyl | 4-biphenyl |
| 765. | H | H | D¹¹⁰ | H | H | H | H | H | L¹¹⁶ | N | N | N | Ph | Ph |
| 766. | H | H | D¹¹⁰ | H | H | H | H | H | L¹¹⁶ | N | N | N | 4-biphenyl | 4-biphenyl |
| 767. | H | H | D¹¹⁰ | H | H | H | H | H | L¹¹⁶ | N | CH | N | Ph | Ph |
| 768. | H | H | D¹¹⁰ | H | H | H | H | H | L¹¹⁶ | N | CH | N | 4-biphenyl | 4-biphenyl |
| 769. | H | H | D¹¹¹ | H | H | H | H | H | L¹⁰¹ | N | N | N | Ph | Ph |
| 770. | H | H | D¹¹¹ | H | H | H | H | H | L¹⁰¹ | N | N | N | 4-biphenyl | 4-biphenyl |
| 771. | H | H | D¹¹¹ | H | H | H | H | H | L¹⁰¹ | N | CH | N | Ph | Ph |
| 772. | H | H | D¹¹¹ | H | H | H | H | H | L¹⁰¹ | N | CH | N | 4-biphenyl | 4-biphenyl |
| 773. | H | H | D¹¹¹ | H | H | H | H | H | L¹⁰² | N | N | N | Ph | Ph |
| 774. | H | H | D¹¹¹ | H | H | H | H | H | L¹⁰² | N | N | N | 4-biphenyl | 4-biphenyl |
| 775. | H | H | D¹¹¹ | H | H | H | H | H | L¹⁰² | N | CH | N | Ph | Ph |
| 776. | H | H | D¹¹¹ | H | H | H | H | H | L¹⁰² | N | CH | N | 4-biphenyl | 4-biphenyl |
| 777. | H | H | D¹¹¹ | H | H | H | H | H | L¹⁰³ | N | N | N | Ph | Ph |
| 778. | H | H | D¹¹¹ | H | H | H | H | H | L¹⁰³ | N | N | N | 4-biphenyl | 4-biphenyl |
| 779. | H | H | D¹¹¹ | H | H | H | H | H | L¹⁰³ | N | CH | N | Ph | Ph |
| 780. | H | H | D¹¹¹ | H | H | H | H | H | L¹⁰³ | N | CH | N | 4-biphenyl | 4-biphenyl |
| 781. | H | H | D¹¹¹ | H | H | H | H | H | L¹⁰⁴ | N | N | N | Ph | Ph |
| 782. | H | H | D¹¹¹ | H | H | H | H | H | L¹⁰⁴ | N | N | N | 4-biphenyl | 4-biphenyl |
| 783. | H | H | D¹¹¹ | H | H | H | H | H | L¹⁰⁴ | N | CH | N | Ph | Ph |
| 784. | H | H | D¹¹¹ | H | H | H | H | H | L¹⁰⁴ | N | CH | N | 4-biphenyl | 4-biphenyl |
| 785. | H | H | D¹¹¹ | H | H | H | H | H | L¹⁰⁵ | N | N | N | Ph | Ph |
| 786. | H | H | D¹¹¹ | H | H | H | H | H | L¹⁰⁵ | N | N | N | 4-biphenyl | 4-biphenyl |
| 787. | H | H | D¹¹¹ | H | H | H | H | H | L¹⁰⁵ | N | CH | N | Ph | Ph |
| 788. | H | H | D¹¹¹ | H | H | H | H | H | L¹⁰⁵ | N | CH | N | 4-biphenyl | 4-biphenyl |
| 789. | H | H | D¹¹¹ | H | H | H | H | H | L¹⁰⁶ | N | N | N | Ph | Ph |
| 790. | H | H | D¹¹¹ | H | H | H | H | H | L¹⁰⁶ | N | N | N | 4-biphenyl | 4-biphenyl |
| 791. | H | H | D¹¹¹ | H | H | H | H | H | L¹⁰⁶ | N | CH | N | Ph | Ph |
| 792. | H | H | D¹¹¹ | H | H | H | H | H | L¹⁰⁶ | N | CH | N | 4-biphenyl | 4-biphenyl |
| 793. | H | H | D¹¹¹ | H | H | H | H | H | L¹⁰⁷ | N | N | N | Ph | Ph |
| 794. | H | H | D¹¹¹ | H | H | H | H | H | L¹⁰⁷ | N | N | N | 4-biphenyl | 4-biphenyl |
| 795. | H | H | D¹¹¹ | H | H | H | H | H | L¹⁰⁷ | N | CH | N | Ph | Ph |
| 796. | H | H | D¹¹¹ | H | H | H | H | H | L¹⁰⁷ | N | CH | N | 4-biphenyl | 4-biphenyl |
| 797. | H | H | D¹¹¹ | H | H | H | H | H | L¹⁰⁸ | N | N | N | Ph | Ph |
| 798. | H | H | D¹¹¹ | H | H | H | H | H | L¹⁰⁸ | N | N | N | 4-biphenyl | 4-biphenyl |
| 799. | H | H | D¹¹¹ | H | H | H | H | H | L¹⁰⁸ | N | CH | N | Ph | Ph |
| 800. | H | H | D¹¹¹ | H | H | H | H | H | L¹⁰⁸ | N | CH | N | 4-biphenyl | 4-biphenyl |
| 801. | H | H | D¹¹¹ | H | H | H | H | H | L¹⁰⁹ | N | N | N | Ph | Ph |
| 802. | H | H | D¹¹¹ | H | H | H | H | H | L¹⁰⁹ | N | N | N | 4-biphenyl | 4-biphenyl |
| 803. | H | H | D¹¹¹ | H | H | H | H | H | L¹⁰⁹ | N | CH | N | Ph | Ph |
| 804. | H | H | D¹¹¹ | H | H | H | H | H | L¹⁰⁹ | N | CH | N | 4-biphenyl | 4-biphenyl |
| 805. | H | H | D¹¹¹ | H | H | H | H | H | L¹¹⁰ | N | N | N | Ph | Ph |
| 806. | H | H | D¹¹¹ | H | H | H | H | H | L¹¹⁰ | N | N | N | 4-biphenyl | 4-biphenyl |
| 807. | H | H | D¹¹¹ | H | H | H | H | H | L¹¹⁰ | N | CH | N | Ph | Ph |
| 808. | H | H | D¹¹¹ | H | H | H | H | H | L¹¹⁰ | N | CH | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 809. | H | H | D¹¹¹ | H | H | H | H | H | L¹¹¹ | N | N | N | Ph | Ph |
| 810. | H | H | D¹¹¹ | H | H | H | H | H | L¹¹¹ | N | N | N | 4-biphenyl | 4-biphenyl |
| 811. | H | H | D¹¹¹ | H | H | H | H | H | L¹¹¹ | N | CH | N | Ph | Ph |
| 812. | H | H | D¹¹¹ | H | H | H | H | H | L¹¹¹ | N | CH | N | 4-biphenyl | 4-biphenyl |
| 813. | H | H | D¹¹¹ | H | H | H | H | H | L¹¹² | N | N | N | Ph | Ph |
| 814. | H | H | D¹¹¹ | H | H | H | H | H | L¹¹² | N | N | N | 4-biphenyl | 4-biphenyl |
| 815. | H | H | D¹¹¹ | H | H | H | H | H | L¹¹² | N | CH | N | Ph | Ph |
| 816. | H | H | D¹¹¹ | H | H | H | H | H | L¹¹² | N | CH | N | 4-biphenyl | 4-biphenyl |
| 817. | H | H | D¹¹¹ | H | H | H | H | H | L¹¹³ | N | N | N | Ph | Ph |
| 818. | H | H | D¹¹¹ | H | H | H | H | H | L¹¹³ | N | N | N | 4-biphenyl | 4-biphenyl |
| 819. | H | H | D¹¹¹ | H | H | H | H | H | L¹¹³ | N | CH | N | Ph | Ph |
| 820. | H | H | D¹¹¹ | H | H | H | H | H | L¹¹³ | N | CH | N | 4-biphenyl | 4-biphenyl |
| 821. | H | H | D¹¹¹ | H | H | H | H | H | L¹¹⁴ | N | N | N | Ph | Ph |
| 822. | H | H | D¹¹¹ | H | H | H | H | H | L¹¹⁴ | N | N | N | 4-biphenyl | 4-biphenyl |
| 823. | H | H | D¹¹¹ | H | H | H | H | H | L¹¹⁴ | N | CH | N | Ph | Ph |
| 824. | H | H | D¹¹¹ | H | H | H | H | H | L¹¹⁴ | N | CH | N | 4-biphenyl | 4-biphenyl |
| 825. | H | H | D¹¹¹ | H | H | H | H | H | L¹¹⁵ | N | N | N | Ph | Ph |
| 826. | H | H | D¹¹¹ | H | H | H | H | H | L¹¹⁵ | N | N | N | 4-biphenyl | 4-biphenyl |
| 827. | H | H | D¹¹¹ | H | H | H | H | H | L¹¹⁵ | N | CH | N | Ph | Ph |
| 828. | H | H | D¹¹¹ | H | H | H | H | H | L¹¹⁵ | N | CH | N | 4-biphenyl | 4-biphenyl |
| 829. | H | H | D¹¹¹ | H | H | H | H | H | L¹¹⁶ | N | N | N | Ph | Ph |
| 830. | H | H | D¹¹¹ | H | H | H | H | H | L¹¹⁶ | N | N | N | 4-biphenyl | 4-biphenyl |
| 831. | H | H | D¹¹¹ | H | H | H | H | H | L¹¹⁶ | N | CH | N | Ph | Ph |
| 832. | H | H | D¹¹¹ | H | H | H | H | H | L¹¹⁶ | N | CH | N | 4-biphenyl | 4-biphenyl |
| 833. | H | H | D¹¹² | H | H | H | H | H | L¹⁰¹ | N | N | N | Ph | Ph |
| 834. | H | H | D¹¹² | H | H | H | H | H | L¹⁰¹ | N | N | N | 4-biphenyl | 4-biphenyl |
| 835. | H | H | D¹¹² | H | H | H | H | H | L¹⁰¹ | N | CH | N | Ph | Ph |
| 836. | H | H | D¹¹² | H | H | H | H | H | L¹⁰¹ | N | CH | N | 4-biphenyl | 4-biphenyl |
| 837. | H | H | D¹¹² | H | H | H | H | H | L¹⁰² | N | N | N | Ph | Ph |
| 838. | H | H | D¹¹² | H | H | H | H | H | L¹⁰² | N | N | N | 4-biphenyl | 4-biphenyl |
| 839. | H | H | D¹¹² | H | H | H | H | H | L¹⁰² | N | CH | N | Ph | Ph |
| 840. | H | H | D¹¹² | H | H | H | H | H | L¹⁰² | N | CH | N | 4-biphenyl | 4-biphenyl |
| 841. | H | H | D¹¹² | H | H | H | H | H | L¹⁰³ | N | N | N | Ph | Ph |
| 842. | H | H | D¹¹² | H | H | H | H | H | L¹⁰³ | N | N | N | 4-biphenyl | 4-biphenyl |
| 843. | H | H | D¹¹² | H | H | H | H | H | L¹⁰³ | N | CH | N | Ph | Ph |
| 844. | H | H | D¹¹² | H | H | H | H | H | L¹⁰³ | N | CH | N | 4-biphenyl | 4-biphenyl |
| 845. | H | H | D¹¹² | H | H | H | H | H | L¹⁰⁴ | N | N | N | Ph | Ph |
| 846. | H | H | D¹¹² | H | H | H | H | H | L¹⁰⁴ | N | N | N | 4-biphenyl | 4-biphenyl |
| 847. | H | H | D¹¹² | H | H | H | H | H | L¹⁰⁴ | N | CH | N | Ph | Ph |
| 848. | H | H | D¹¹² | H | H | H | H | H | L¹⁰⁴ | N | CH | N | 4-biphenyl | 4-biphenyl |
| 849. | H | H | D¹¹² | H | H | H | H | H | L¹⁰⁵ | N | N | N | Ph | Ph |
| 850. | H | H | D¹¹² | H | H | H | H | H | L¹⁰⁵ | N | N | N | 4-biphenyl | 4-biphenyl |
| 851. | H | H | D¹¹² | H | H | H | H | H | L¹⁰⁵ | N | CH | N | Ph | Ph |
| 852. | H | H | D¹¹² | H | H | H | H | H | L¹⁰⁵ | N | CH | N | 4-biphenyl | 4-biphenyl |
| 853. | H | H | D¹¹² | H | H | H | H | H | L¹⁰⁶ | N | N | N | Ph | Ph |
| 854. | H | H | D¹¹² | H | H | H | H | H | L¹⁰⁶ | N | N | N | 4-biphenyl | 4-biphenyl |
| 855. | H | H | D¹¹² | H | H | H | H | H | L¹⁰⁶ | N | CH | N | Ph | Ph |
| 856. | H | H | D¹¹² | H | H | H | H | H | L¹⁰⁶ | N | CH | N | 4-biphenyl | 4-biphenyl |
| 857. | H | H | D¹¹² | H | H | H | H | H | L¹⁰⁷ | N | N | N | Ph | Ph |
| 858. | H | H | D¹¹² | H | H | H | H | H | L¹⁰⁷ | N | N | N | 4-biphenyl | 4-biphenyl |

-continued

| Compound number | $R^1$ | $R^2$ | $R^3$ | $R^4$ | $R^5$ | $R^6$ | $R^7$ | $R^8$ | $L^1$ | $Z^1$ | $Z^3$ | $Z^5$ | $R^{91}$ | $R^{92}$ |
|---|---|---|---|---|---|---|---|---|---|---|---|---|---|---|
| 859. | H | H | $D^{112}$ | H | H | H | H | H | $L^{107}$ | N | CH | N | Ph | Ph |
| 860. | H | H | $D^{112}$ | H | H | H | H | H | $L^{107}$ | N | CH | N | 4-biphenyl | 4-biphenyl |
| 861. | H | H | $D^{112}$ | H | H | H | H | H | $L^{108}$ | N | N | N | Ph | Ph |
| 862. | H | H | $D^{112}$ | H | H | H | H | H | $L^{108}$ | N | N | N | 4-biphenyl | 4-biphenyl |
| 863. | H | H | $D^{112}$ | H | H | H | H | H | $L^{108}$ | N | CH | N | Ph | Ph |
| 864. | H | H | $D^{112}$ | H | H | H | H | H | $L^{108}$ | N | CH | N | 4-biphenyl | 4-biphenyl |
| 865. | H | H | $D^{112}$ | H | H | H | H | H | $L^{109}$ | N | N | N | Ph | Ph |
| 866. | H | H | $D^{112}$ | H | H | H | H | H | $L^{109}$ | N | N | N | 4-biphenyl | 4-biphenyl |
| 867. | H | H | $D^{112}$ | H | H | H | H | H | $L^{109}$ | N | CH | N | Ph | Ph |
| 868. | H | H | $D^{112}$ | H | H | H | H | H | $L^{109}$ | N | CH | N | 4-biphenyl | 4-biphenyl |
| 869. | H | H | $D^{112}$ | H | H | H | H | H | $L^{110}$ | N | N | N | Ph | Ph |
| 870. | H | H | $D^{112}$ | H | H | H | H | H | $L^{110}$ | N | N | N | 4-biphenyl | 4-biphenyl |
| 871. | H | H | $D^{112}$ | H | H | H | H | H | $L^{110}$ | N | CH | N | Ph | Ph |
| 872. | H | H | $D^{112}$ | H | H | H | H | H | $L^{110}$ | N | CH | N | 4-biphenyl | 4-biphenyl |
| 873. | H | H | $D^{112}$ | H | H | H | H | H | $L^{111}$ | N | N | N | Ph | Ph |
| 874. | H | H | $D^{112}$ | H | H | H | H | H | $L^{111}$ | N | N | N | 4-biphenyl | 4-biphenyl |
| 875. | H | H | $D^{112}$ | H | H | H | H | H | $L^{111}$ | N | CH | N | Ph | Ph |
| 876. | H | H | $D^{112}$ | H | H | H | H | H | $L^{111}$ | N | CH | N | 4-biphenyl | 4-biphenyl |
| 877. | H | H | $D^{112}$ | H | H | H | H | H | $L^{112}$ | N | N | N | Ph | Ph |
| 878. | H | H | $D^{112}$ | H | H | H | H | H | $L^{112}$ | N | N | N | 4-biphenyl | 4-biphenyl |
| 879. | H | H | $D^{112}$ | H | H | H | H | H | $L^{112}$ | N | CH | N | Ph | Ph |
| 880. | H | H | $D^{112}$ | H | H | H | H | H | $L^{112}$ | N | CH | N | 4-biphenyl | 4-biphenyl |
| 881. | H | H | $D^{112}$ | H | H | H | H | H | $L^{113}$ | N | N | N | Ph | Ph |
| 882. | H | H | $D^{112}$ | H | H | H | H | H | $L^{113}$ | N | N | N | 4-biphenyl | 4-biphenyl |
| 883. | H | H | $D^{112}$ | H | H | H | H | H | $L^{113}$ | N | CH | N | Ph | Ph |
| 884. | H | H | $D^{112}$ | H | H | H | H | H | $L^{113}$ | N | CH | N | 4-biphenyl | 4-biphenyl |
| 885. | H | H | $D^{112}$ | H | H | H | H | H | $L^{114}$ | N | N | N | Ph | Ph |
| 886. | H | H | $D^{112}$ | H | H | H | H | H | $L^{114}$ | N | N | N | 4-biphenyl | 4-biphenyl |
| 887. | H | H | $D^{112}$ | H | H | H | H | H | $L^{114}$ | N | CH | N | Ph | Ph |
| 888. | H | H | $D^{112}$ | H | H | H | H | H | $L^{114}$ | N | CH | N | 4-biphenyl | 4-biphenyl |
| 889. | H | H | $D^{112}$ | H | H | H | H | H | $L^{115}$ | N | N | N | Ph | Ph |
| 890. | H | H | $D^{112}$ | H | H | H | H | H | $L^{115}$ | N | N | N | 4-biphenyl | 4-biphenyl |
| 891. | H | H | $D^{112}$ | H | H | H | H | H | $L^{115}$ | N | CH | N | Ph | Ph |
| 892. | H | H | $D^{112}$ | H | H | H | H | H | $L^{115}$ | N | CH | N | 4-biphenyl | 4-biphenyl |
| 893. | H | H | $D^{112}$ | H | H | H | H | H | $L^{116}$ | N | N | N | Ph | Ph |
| 894. | H | H | $D^{112}$ | H | H | H | H | H | $L^{116}$ | N | N | N | 4-biphenyl | 4-biphenyl |
| 895. | H | H | $D^{112}$ | H | H | H | H | H | $L^{116}$ | N | CH | N | Ph | Ph |
| 896. | H | H | $D^{112}$ | H | H | H | H | H | $L^{116}$ | N | CH | N | 4-biphenyl | 4-biphenyl |
| 897. | H | H | $D^{113}$ | H | H | H | H | H | $L^{101}$ | N | N | N | Ph | Ph |
| 898. | H | H | $D^{113}$ | H | H | H | H | H | $L^{101}$ | N | N | N | 4-biphenyl | 4-biphenyl |
| 899. | H | H | $D^{113}$ | H | H | H | H | H | $L^{101}$ | N | CH | N | Ph | Ph |
| 900. | H | H | $D^{113}$ | H | H | H | H | H | $L^{101}$ | N | CH | N | 4-biphenyl | 4-biphenyl |
| 901. | H | H | $D^{113}$ | H | H | H | H | H | $L^{102}$ | N | N | N | Ph | Ph |
| 902. | H | H | $D^{113}$ | H | H | H | H | H | $L^{102}$ | N | N | N | 4-biphenyl | 4-biphenyl |
| 903. | H | H | $D^{113}$ | H | H | H | H | H | $L^{102}$ | N | CH | N | Ph | Ph |
| 904. | H | H | $D^{113}$ | H | H | H | H | H | $L^{102}$ | N | CH | N | 4-biphenyl | 4-biphenyl |
| 905. | H | H | $D^{113}$ | H | H | H | H | H | $L^{103}$ | N | N | N | Ph | Ph |
| 906. | H | H | $D^{113}$ | H | H | H | H | H | $L^{103}$ | N | N | N | 4-biphenyl | 4-biphenyl |
| 907. | H | H | $D^{113}$ | H | H | H | H | H | $L^{103}$ | N | CH | N | Ph | Ph |
| 908. | H | H | $D^{113}$ | H | H | H | H | H | $L^{103}$ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 909. | H | H | D¹¹³ | H | H | H | H | H | L¹⁰⁴ | N | N | N | Ph | Ph |
| 910. | H | H | D¹¹³ | H | H | H | H | H | L¹⁰⁴ | N | N | N | 4-biphenyl | 4-biphenyl |
| 911. | H | H | D¹¹³ | H | H | H | H | H | L¹⁰⁴ | N | CH | N | Ph | Ph |
| 912. | H | H | D¹¹³ | H | H | H | H | H | L¹⁰⁴ | N | CH | N | 4-biphenyl | 4-biphenyl |
| 913. | H | H | D¹¹³ | H | H | H | H | H | L¹⁰⁵ | N | N | N | Ph | Ph |
| 914. | H | H | D¹¹³ | H | H | H | H | H | L¹⁰⁵ | N | N | N | 4-biphenyl | 4-biphenyl |
| 915. | H | H | D¹¹³ | H | H | H | H | H | L¹⁰⁵ | N | CH | N | Ph | Ph |
| 916. | H | H | D¹¹³ | H | H | H | H | H | L¹⁰⁵ | N | CH | N | 4-biphenyl | 4-biphenyl |
| 917. | H | H | D¹¹³ | H | H | H | H | H | L¹⁰⁶ | N | N | N | Ph | Ph |
| 918. | H | H | D¹¹³ | H | H | H | H | H | L¹⁰⁶ | N | N | N | 4-biphenyl | 4-biphenyl |
| 919. | H | H | D¹¹³ | H | H | H | H | H | L¹⁰⁶ | N | CH | N | Ph | Ph |
| 920. | H | H | D¹¹³ | H | H | H | H | H | L¹⁰⁶ | N | CH | N | 4-biphenyl | 4-biphenyl |
| 921. | H | H | D¹¹³ | H | H | H | H | H | L¹⁰⁷ | N | N | N | Ph | Ph |
| 922. | H | H | D¹¹³ | H | H | H | H | H | L¹⁰⁷ | N | N | N | 4-biphenyl | 4-biphenyl |
| 923. | H | H | D¹¹³ | H | H | H | H | H | L¹⁰⁷ | N | CH | N | Ph | Ph |
| 924. | H | H | D¹¹³ | H | H | H | H | H | L¹⁰⁷ | N | CH | N | 4-biphenyl | 4-biphenyl |
| 925. | H | H | D¹¹³ | H | H | H | H | H | L¹⁰⁸ | N | N | N | Ph | Ph |
| 926. | H | H | D¹¹³ | H | H | H | H | H | L¹⁰⁸ | N | N | N | 4-biphenyl | 4-biphenyl |
| 927. | H | H | D¹¹³ | H | H | H | H | H | L¹⁰⁸ | N | CH | N | Ph | Ph |
| 928. | H | H | D¹¹³ | H | H | H | H | H | L¹⁰⁸ | N | CH | N | 4-biphenyl | 4-biphenyl |
| 929. | H | H | D¹¹³ | H | H | H | H | H | L¹⁰⁹ | N | N | N | Ph | Ph |
| 930. | H | H | D¹¹³ | H | H | H | H | H | L¹⁰⁹ | N | N | N | 4-biphenyl | 4-biphenyl |
| 931. | H | H | D¹¹³ | H | H | H | H | H | L¹⁰⁹ | N | CH | N | Ph | Ph |
| 932. | H | H | D¹¹³ | H | H | H | H | H | L¹⁰⁹ | N | CH | N | 4-biphenyl | 4-biphenyl |
| 933. | H | H | D¹¹³ | H | H | H | H | H | L¹¹⁰ | N | N | N | Ph | Ph |
| 934. | H | H | D¹¹³ | H | H | H | H | H | L¹¹⁰ | N | N | N | 4-biphenyl | 4-biphenyl |
| 935. | H | H | D¹¹³ | H | H | H | H | H | L¹¹⁰ | N | CH | N | Ph | Ph |
| 936. | H | H | D¹¹³ | H | H | H | H | H | L¹¹⁰ | N | CH | N | 4-biphenyl | 4-biphenyl |
| 937. | H | H | D¹¹³ | H | H | H | H | H | L¹¹¹ | N | N | N | Ph | Ph |
| 938. | H | H | D¹¹³ | H | H | H | H | H | L¹¹¹ | N | N | N | 4-biphenyl | 4-biphenyl |
| 939. | H | H | D¹¹³ | H | H | H | H | H | L¹¹¹ | N | CH | N | Ph | Ph |
| 940. | H | H | D¹¹³ | H | H | H | H | H | L¹¹¹ | N | CH | N | 4-biphenyl | 4-biphenyl |
| 941. | H | H | D¹¹³ | H | H | H | H | H | L¹¹² | N | N | N | Ph | Ph |
| 942. | H | H | D¹¹³ | H | H | H | H | H | L¹¹² | N | N | N | 4-biphenyl | 4-biphenyl |
| 943. | H | H | D¹¹³ | H | H | H | H | H | L¹¹² | N | CH | N | Ph | Ph |
| 944. | H | H | D¹¹³ | H | H | H | H | H | L¹¹² | N | CH | N | 4-biphenyl | 4-biphenyl |
| 945. | H | H | D¹¹³ | H | H | H | H | H | L¹¹³ | N | N | N | Ph | Ph |
| 946. | H | H | D¹¹³ | H | H | H | H | H | L¹¹³ | N | N | N | 4-biphenyl | 4-biphenyl |
| 947. | H | H | D¹¹³ | H | H | H | H | H | L¹¹³ | N | CH | N | Ph | Ph |
| 948. | H | H | D¹¹³ | H | H | H | H | H | L¹¹³ | N | CH | N | 4-biphenyl | 4-biphenyl |
| 949. | H | H | D¹¹³ | H | H | H | H | H | L¹¹⁴ | N | N | N | Ph | Ph |
| 950. | H | H | D¹¹³ | H | H | H | H | H | L¹¹⁴ | N | N | N | 4-biphenyl | 4-biphenyl |
| 951. | H | H | D¹¹³ | H | H | H | H | H | L¹¹⁴ | N | CH | N | Ph | Ph |
| 952. | H | H | D¹¹³ | H | H | H | H | H | L¹¹⁴ | N | CH | N | 4-biphenyl | 4-biphenyl |
| 953. | H | H | D¹¹³ | H | H | H | H | H | L¹¹⁵ | N | N | N | Ph | Ph |
| 954. | H | H | D¹¹³ | H | H | H | H | H | L¹¹⁵ | N | N | N | 4-biphenyl | 4-biphenyl |
| 955. | H | H | D¹¹³ | H | H | H | H | H | L¹¹⁵ | N | CH | N | Ph | Ph |
| 956. | H | H | D¹¹³ | H | H | H | H | H | L¹¹⁵ | N | CH | N | 4-biphenyl | 4-biphenyl |
| 957. | H | H | D¹¹³ | H | H | H | H | H | L¹¹⁶ | N | N | N | Ph | Ph |
| 958. | H | H | D¹¹³ | H | H | H | H | H | L¹¹⁶ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 959. | H | H | D¹¹³ | H | H | H | H | H | L¹¹⁶ | N | CH | N | Ph | Ph |
| 960. | H | H | D¹¹³ | H | H | H | H | H | L¹¹⁶ | N | CH | N | 4-biphenyl | 4-biphenyl |
| 961. | H | H | D¹¹⁴ | H | H | H | H | H | L¹⁰¹ | N | N | N | Ph | Ph |
| 962. | H | H | D¹¹⁴ | H | H | H | H | H | L¹⁰¹ | N | N | N | 4-biphenyl | 4-biphenyl |
| 963. | H | H | D¹¹⁴ | H | H | H | H | H | L¹⁰¹ | N | CH | N | Ph | Ph |
| 964. | H | H | D¹¹⁴ | H | H | H | H | H | L¹⁰¹ | N | CH | N | 4-biphenyl | 4-biphenyl |
| 965. | H | H | D¹¹⁴ | H | H | H | H | H | L¹⁰² | N | N | N | Ph | Ph |
| 966. | H | H | D¹¹⁴ | H | H | H | H | H | L¹⁰² | N | N | N | 4-biphenyl | 4-biphenyl |
| 967. | H | H | D¹¹⁴ | H | H | H | H | H | L¹⁰² | N | CH | N | Ph | Ph |
| 968. | H | H | D¹¹⁴ | H | H | H | H | H | L¹⁰² | N | CH | N | 4-biphenyl | 4-biphenyl |
| 969. | H | H | D¹¹⁴ | H | H | H | H | H | L¹⁰³ | N | N | N | Ph | Ph |
| 970. | H | H | D¹¹⁴ | H | H | H | H | H | L¹⁰³ | N | N | N | 4-biphenyl | 4-biphenyl |
| 971. | H | H | D¹¹⁴ | H | H | H | H | H | L¹⁰³ | N | CH | N | Ph | Ph |
| 972. | H | H | D¹¹⁴ | H | H | H | H | H | L¹⁰³ | N | CH | N | 4-biphenyl | 4-biphenyl |
| 973. | H | H | D¹¹⁴ | H | H | H | H | H | L¹⁰⁴ | N | N | N | Ph | Ph |
| 974. | H | H | D¹¹⁴ | H | H | H | H | H | L¹⁰⁴ | N | N | N | 4-biphenyl | 4-biphenyl |
| 975. | H | H | D¹¹⁴ | H | H | H | H | H | L¹⁰⁴ | N | CH | N | Ph | Ph |
| 976. | H | H | D¹¹⁴ | H | H | H | H | H | L¹⁰⁴ | N | CH | N | 4-biphenyl | 4-biphenyl |
| 977. | H | H | D¹¹⁴ | H | H | H | H | H | L¹⁰⁵ | N | N | N | Ph | Ph |
| 978. | H | H | D¹¹⁴ | H | H | H | H | H | L¹⁰⁵ | N | N | N | 4-biphenyl | 4-biphenyl |
| 979. | H | H | D¹¹⁴ | H | H | H | H | H | L¹⁰⁵ | N | CH | N | Ph | Ph |
| 980. | H | H | D¹¹⁴ | H | H | H | H | H | L¹⁰⁵ | N | CH | N | 4-biphenyl | 4-biphenyl |
| 981. | H | H | D¹¹⁴ | H | H | H | H | H | L¹⁰⁶ | N | N | N | Ph | Ph |
| 982. | H | H | D¹¹⁴ | H | H | H | H | H | L¹⁰⁶ | N | N | N | 4-biphenyl | 4-biphenyl |
| 983. | H | H | D¹¹⁴ | H | H | H | H | H | L¹⁰⁶ | N | CH | N | Ph | Ph |
| 984. | H | H | D¹¹⁴ | H | H | H | H | H | L¹⁰⁶ | N | CH | N | 4-biphenyl | 4-biphenyl |
| 985. | H | H | D¹¹⁴ | H | H | H | H | H | L¹⁰⁷ | N | N | N | Ph | Ph |
| 986. | H | H | D¹¹⁴ | H | H | H | H | H | L¹⁰⁷ | N | N | N | 4-biphenyl | 4-biphenyl |
| 987. | H | H | D¹¹⁴ | H | H | H | H | H | L¹⁰⁷ | N | CH | N | Ph | Ph |
| 988. | H | H | D¹¹⁴ | H | H | H | H | H | L¹⁰⁷ | N | CH | N | 4-biphenyl | 4-biphenyl |
| 989. | H | H | D¹¹⁴ | H | H | H | H | H | L¹⁰⁸ | N | N | N | Ph | Ph |
| 990. | H | H | D¹¹⁴ | H | H | H | H | H | L¹⁰⁸ | N | N | N | 4-biphenyl | 4-biphenyl |
| 991. | H | H | D¹¹⁴ | H | H | H | H | H | L¹⁰⁸ | N | CH | N | Ph | Ph |
| 992. | H | H | D¹¹⁴ | H | H | H | H | H | L¹⁰⁸ | N | CH | N | 4-biphenyl | 4-biphenyl |
| 993. | H | H | D¹¹⁴ | H | H | H | H | H | L¹⁰⁹ | N | N | N | Ph | Ph |
| 994. | H | H | D¹¹⁴ | H | H | H | H | H | L¹⁰⁹ | N | N | N | 4-biphenyl | 4-biphenyl |
| 995. | H | H | D¹¹⁴ | H | H | H | H | H | L¹⁰⁹ | N | CH | N | Ph | Ph |
| 996. | H | H | D¹¹⁴ | H | H | H | H | H | L¹⁰⁹ | N | CH | N | 4-biphenyl | 4-biphenyl |
| 997. | H | H | D¹¹⁴ | H | H | H | H | H | L¹¹⁰ | N | N | N | Ph | Ph |
| 998. | H | H | D¹¹⁴ | H | H | H | H | H | L¹¹⁰ | N | N | N | 4-biphenyl | 4-biphenyl |
| 999. | H | H | D¹¹⁴ | H | H | H | H | H | L¹¹⁰ | N | CH | N | Ph | Ph |
| 1000. | H | H | D¹¹⁴ | H | H | H | H | H | L¹¹⁰ | N | CH | N | 4-biphenyl | 4-biphenyl |
| 1001. | H | H | D¹¹⁴ | H | H | H | H | H | L¹¹¹ | N | N | N | Ph | Ph |
| 1002. | H | H | D¹¹⁴ | H | H | H | H | H | L¹¹¹ | N | N | N | 4-biphenyl | 4-biphenyl |
| 1003. | H | H | D¹¹⁴ | H | H | H | H | H | L¹¹¹ | N | CH | N | Ph | Ph |
| 1004. | H | H | D¹¹⁴ | H | H | H | H | H | L¹¹¹ | N | CH | N | 4-biphenyl | 4-biphenyl |
| 1005. | H | H | D¹¹⁴ | H | H | H | H | H | L¹¹² | N | N | N | Ph | Ph |
| 1006. | H | H | D¹¹⁴ | H | H | H | H | H | L¹¹² | N | N | N | 4-biphenyl | 4-biphenyl |
| 1007. | H | H | D¹¹⁴ | H | H | H | H | H | L¹¹² | N | CH | N | Ph | Ph |
| 1008. | H | H | D¹¹⁴ | H | H | H | H | H | L¹¹² | N | CH | N | 4-biphenyl | 4-biphenyl |

| Compound number | $R^1$ | $R^2$ | $R^3$ | $R^4$ | $R^5$ | $R^6$ | $R^7$ | $R^8$ | $L^1$ | $Z^1$ | $Z^3$ | $Z^5$ | $R^{91}$ | $R^{92}$ |
|---|---|---|---|---|---|---|---|---|---|---|---|---|---|---|
| 1009. | H | H | $D^{114}$ | H | H | H | H | H | $L^{113}$ | N | N | N | Ph | Ph |
| 1010. | H | H | $D^{114}$ | H | H | H | H | H | $L^{113}$ | N | N | N | 4-biphenyl | 4-biphenyl |
| 1011. | H | H | $D^{114}$ | H | H | H | H | H | $L^{113}$ | N | CH | N | Ph | Ph |
| 1012. | H | H | $D^{114}$ | H | H | H | H | H | $L^{113}$ | N | CH | N | 4-biphenyl | 4-biphenyl |
| 1013. | H | H | $D^{114}$ | H | H | H | H | H | $L^{114}$ | N | N | N | Ph | Ph |
| 1014. | H | H | $D^{114}$ | H | H | H | H | H | $L^{114}$ | N | N | N | 4-biphenyl | 4-biphenyl |
| 1015. | H | H | $D^{114}$ | H | H | H | H | H | $L^{114}$ | N | CH | N | Ph | Ph |
| 1016. | H | H | $D^{114}$ | H | H | H | H | H | $L^{114}$ | N | CH | N | 4-biphenyl | 4-biphenyl |
| 1017. | H | H | $D^{114}$ | H | H | H | H | H | $L^{115}$ | N | N | N | Ph | Ph |
| 1018. | H | H | $D^{114}$ | H | H | H | H | H | $L^{115}$ | N | N | N | 4-biphenyl | 4-biphenyl |
| 1019. | H | H | $D^{114}$ | H | H | H | H | H | $L^{115}$ | N | CH | N | Ph | Ph |
| 1020. | H | H | $D^{114}$ | H | H | H | H | H | $L^{115}$ | N | CH | N | 4-biphenyl | 4-biphenyl |
| 1021. | H | H | $D^{114}$ | H | H | H | H | H | $L^{116}$ | N | N | N | Ph | Ph |
| 1022. | H | H | $D^{114}$ | H | H | H | H | H | $L^{116}$ | N | N | N | 4-biphenyl | 4-biphenyl |
| 1023. | H | H | $D^{114}$ | H | H | H | H | H | $L^{116}$ | N | CH | N | Ph | Ph |
| 1024. | H | H | $D^{114}$ | H | H | H | H | H | $L^{116}$ | N | CH | N | 4-biphenyl | 4-biphenyl |
| 1025. | H | H | $D^{115}$ | H | H | H | H | H | $L^{101}$ | N | N | N | Ph | Ph |
| 1026. | H | H | $D^{115}$ | H | H | H | H | H | $L^{101}$ | N | N | N | 4-biphenyl | 4-biphenyl |
| 1027. | H | H | $D^{115}$ | H | H | H | H | H | $L^{101}$ | N | CH | N | Ph | Ph |
| 1028. | H | H | $D^{115}$ | H | H | H | H | H | $L^{101}$ | N | CH | N | 4-biphenyl | 4-biphenyl |
| 1029. | H | H | $D^{115}$ | H | H | H | H | H | $L^{102}$ | N | N | N | Ph | Ph |
| 1030. | H | H | $D^{115}$ | H | H | H | H | H | $L^{102}$ | N | N | N | 4-biphenyl | 4-biphenyl |
| 1031. | H | H | $D^{115}$ | H | H | H | H | H | $L^{102}$ | N | CH | N | Ph | Ph |
| 1032. | H | H | $D^{115}$ | H | H | H | H | H | $L^{102}$ | N | CH | N | 4-biphenyl | 4-biphenyl |
| 1033. | H | H | $D^{115}$ | H | H | H | H | H | $L^{103}$ | N | N | N | Ph | Ph |
| 1034. | H | H | $D^{115}$ | H | H | H | H | H | $L^{103}$ | N | N | N | 4-biphenyl | 4-biphenyl |
| 1035. | H | H | $D^{115}$ | H | H | H | H | H | $L^{103}$ | N | CH | N | Ph | Ph |
| 1036. | H | H | $D^{115}$ | H | H | H | H | H | $L^{103}$ | N | CH | N | 4-biphenyl | 4-biphenyl |
| 1037. | H | H | $D^{115}$ | H | H | H | H | H | $L^{104}$ | N | N | N | Ph | Ph |
| 1038. | H | H | $D^{115}$ | H | H | H | H | H | $L^{104}$ | N | N | N | 4-biphenyl | 4-biphenyl |
| 1039. | H | H | $D^{115}$ | H | H | H | H | H | $L^{104}$ | N | CH | N | Ph | Ph |
| 1040. | H | H | $D^{115}$ | H | H | H | H | H | $L^{104}$ | N | CH | N | 4-biphenyl | 4-biphenyl |
| 1041. | H | H | $D^{115}$ | H | H | H | H | H | $L^{105}$ | N | N | N | Ph | Ph |
| 1042. | H | H | $D^{115}$ | H | H | H | H | H | $L^{105}$ | N | N | N | 4-biphenyl | 4-biphenyl |
| 1043. | H | H | $D^{115}$ | H | H | H | H | H | $L^{105}$ | N | CH | N | Ph | Ph |
| 1044. | H | H | $D^{115}$ | H | H | H | H | H | $L^{105}$ | N | CH | N | 4-biphenyl | 4-biphenyl |
| 1045. | H | H | $D^{115}$ | H | H | H | H | H | $L^{106}$ | N | N | N | Ph | Ph |
| 1046. | H | H | $D^{115}$ | H | H | H | H | H | $L^{106}$ | N | N | N | 4-biphenyl | 4-biphenyl |
| 1047. | H | H | $D^{115}$ | H | H | H | H | H | $L^{106}$ | N | CH | N | Ph | Ph |
| 1048. | H | H | $D^{115}$ | H | H | H | H | H | $L^{106}$ | N | CH | N | 4-biphenyl | 4-biphenyl |
| 1049. | H | H | $D^{115}$ | H | H | H | H | H | $L^{107}$ | N | N | N | Ph | Ph |
| 1050. | H | H | $D^{115}$ | H | H | H | H | H | $L^{107}$ | N | N | N | 4-biphenyl | 4-biphenyl |
| 1051. | H | H | $D^{115}$ | H | H | H | H | H | $L^{107}$ | N | CH | N | Ph | Ph |
| 1052. | H | H | $D^{115}$ | H | H | H | H | H | $L^{107}$ | N | CH | N | 4-biphenyl | 4-biphenyl |
| 1053. | H | H | $D^{115}$ | H | H | H | H | H | $L^{108}$ | N | N | N | Ph | Ph |
| 1054. | H | H | $D^{115}$ | H | H | H | H | H | $L^{108}$ | N | N | N | 4-biphenyl | 4-biphenyl |
| 1055. | H | H | $D^{115}$ | H | H | H | H | H | $L^{108}$ | N | CH | N | Ph | Ph |
| 1056. | H | H | $D^{115}$ | H | H | H | H | H | $L^{108}$ | N | CH | N | 4-biphenyl | 4-biphenyl |
| 1057. | H | H | $D^{115}$ | H | H | H | H | H | $L^{109}$ | N | N | N | Ph | Ph |
| 1058. | H | H | $D^{115}$ | H | H | H | H | H | $L^{109}$ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1059. | H | H | D¹¹⁵ | H | H | H | H | H | L¹⁰⁹ | N | CH | N | Ph | Ph |
| 1060. | H | H | D¹¹⁵ | H | H | H | H | H | L¹⁰⁹ | N | CH | N | 4-biphenyl | 4-biphenyl |
| 1061. | H | H | D¹¹⁵ | H | H | H | H | H | L¹¹⁰ | N | N | N | Ph | Ph |
| 1062. | H | H | D¹¹⁵ | H | H | H | H | H | L¹¹⁰ | N | N | N | 4-biphenyl | 4-biphenyl |
| 1063. | H | H | D¹¹⁵ | H | H | H | H | H | L¹¹⁰ | N | CH | N | Ph | Ph |
| 1064. | H | H | D¹¹⁵ | H | H | H | H | H | L¹¹⁰ | N | CH | N | 4-biphenyl | 4-biphenyl |
| 1065. | H | H | D¹¹⁵ | H | H | H | H | H | L¹¹¹ | N | N | N | Ph | Ph |
| 1066. | H | H | D¹¹⁵ | H | H | H | H | H | L¹¹¹ | N | N | N | 4-biphenyl | 4-biphenyl |
| 1067. | H | H | D¹¹⁵ | H | H | H | H | H | L¹¹¹ | N | CH | N | Ph | Ph |
| 1068. | H | H | D¹¹⁵ | H | H | H | H | H | L¹¹¹ | N | CH | N | 4-biphenyl | 4-biphenyl |
| 1069. | H | H | D¹¹⁵ | H | H | H | H | H | L¹¹² | N | N | N | Ph | Ph |
| 1070. | H | H | D¹¹⁵ | H | H | H | H | H | L¹¹² | N | N | N | 4-biphenyl | 4-biphenyl |
| 1071. | H | H | D¹¹⁵ | H | H | H | H | H | L¹¹² | N | CH | N | Ph | Ph |
| 1072. | H | H | D¹¹⁵ | H | H | H | H | H | L¹¹² | N | CH | N | 4-biphenyl | 4-biphenyl |
| 1073. | H | H | D¹¹⁵ | H | H | H | H | H | L¹¹³ | N | N | N | Ph | Ph |
| 1074. | H | H | D¹¹⁵ | H | H | H | H | H | L¹¹³ | N | N | N | 4-biphenyl | 4-biphenyl |
| 1075. | H | H | D¹¹⁵ | H | H | H | H | H | L¹¹³ | N | CH | N | Ph | Ph |
| 1076. | H | H | D¹¹⁵ | H | H | H | H | H | L¹¹³ | N | CH | N | 4-biphenyl | 4-biphenyl |
| 1077. | H | H | D¹¹⁵ | H | H | H | H | H | L¹¹⁴ | N | N | N | Ph | Ph |
| 1078. | H | H | D¹¹⁵ | H | H | H | H | H | L¹¹⁴ | N | N | N | 4-biphenyl | 4-biphenyl |
| 1079. | H | H | D¹¹⁵ | H | H | H | H | H | L¹¹⁴ | N | CH | N | Ph | Ph |
| 1080. | H | H | D¹¹⁵ | H | H | H | H | H | L¹¹⁴ | N | CH | N | 4-biphenyl | 4-biphenyl |
| 1081. | H | H | D¹¹⁵ | H | H | H | H | H | L¹¹⁵ | N | N | N | Ph | Ph |
| 1082. | H | H | D¹¹⁵ | H | H | H | H | H | L¹¹⁵ | N | N | N | 4-biphenyl | 4-biphenyl |
| 1083. | H | H | D¹¹⁵ | H | H | H | H | H | L¹¹⁵ | N | CH | N | Ph | Ph |
| 1084. | H | H | D¹¹⁵ | H | H | H | H | H | L¹¹⁵ | N | CH | N | 4-biphenyl | 4-biphenyl |
| 1085. | H | H | D¹¹⁵ | H | H | H | H | H | L¹¹⁶ | N | N | N | Ph | Ph |
| 1086. | H | H | D¹¹⁵ | H | H | H | H | H | L¹¹⁶ | N | N | N | 4-biphenyl | 4-biphenyl |
| 1087. | H | H | D¹¹⁵ | H | H | H | H | H | L¹¹⁶ | N | CH | N | Ph | Ph |
| 1088. | H | H | D¹¹⁵ | H | H | H | H | H | L¹¹⁶ | N | CH | N | 4-biphenyl | 4-biphenyl |
| 1089. | H | H | D¹¹⁶ | H | H | H | H | H | L¹⁰¹ | N | N | N | Ph | Ph |
| 1090. | H | H | D¹¹⁶ | H | H | H | H | H | L¹⁰¹ | N | N | N | 4-biphenyl | 4-biphenyl |
| 1091. | H | H | D¹¹⁶ | H | H | H | H | H | L¹⁰¹ | N | CH | N | Ph | Ph |
| 1092. | H | H | D¹¹⁶ | H | H | H | H | H | L¹⁰¹ | N | CH | N | 4-biphenyl | 4-biphenyl |
| 1093. | H | H | D¹¹⁶ | H | H | H | H | H | L¹⁰² | N | N | N | Ph | Ph |
| 1094. | H | H | D¹¹⁶ | H | H | H | H | H | L¹⁰² | N | N | N | 4-biphenyl | 4-biphenyl |
| 1095. | H | H | D¹¹⁶ | H | H | H | H | H | L¹⁰² | N | CH | N | Ph | Ph |
| 1096. | H | H | D¹¹⁶ | H | H | H | H | H | L¹⁰² | N | CH | N | 4-biphenyl | 4-biphenyl |
| 1097. | H | H | D¹¹⁶ | H | H | H | H | H | L¹⁰³ | N | N | N | Ph | Ph |
| 1098. | H | H | D¹¹⁶ | H | H | H | H | H | L¹⁰³ | N | N | N | 4-biphenyl | 4-biphenyl |
| 1099. | H | H | D¹¹⁶ | H | H | H | H | H | L¹⁰³ | N | CH | N | Ph | Ph |
| 1100. | H | H | D¹¹⁶ | H | H | H | H | H | L¹⁰³ | N | CH | N | 4-biphenyl | 4-biphenyl |
| 1101. | H | H | D¹¹⁶ | H | H | H | H | H | L¹⁰⁴ | N | N | N | Ph | Ph |
| 1102. | H | H | D¹¹⁶ | H | H | H | H | H | L¹⁰⁴ | N | N | N | 4-biphenyl | 4-biphenyl |
| 1103. | H | H | D¹¹⁶ | H | H | H | H | H | L¹⁰⁴ | N | CH | N | Ph | Ph |
| 1104. | H | H | D¹¹⁶ | H | H | H | H | H | L¹⁰⁴ | N | CH | N | 4-biphenyl | 4-biphenyl |
| 1105. | H | H | D¹¹⁶ | H | H | H | H | H | L¹⁰⁵ | N | N | N | Ph | Ph |
| 1106. | H | H | D¹¹⁶ | H | H | H | H | H | L¹⁰⁵ | N | N | N | 4-biphenyl | 4-biphenyl |
| 1107. | H | H | D¹¹⁶ | H | H | H | H | H | L¹⁰⁵ | N | CH | N | Ph | Ph |
| 1108. | H | H | D¹¹⁶ | H | H | H | H | H | L¹⁰⁵ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1109. | H | H | D¹¹⁶ | H | H | H | H | H | L¹⁰⁶ | N | N | N | Ph | Ph |
| 1110. | H | H | D¹¹⁶ | H | H | H | H | H | L¹⁰⁶ | N | N | N | 4-biphenyl | 4-biphenyl |
| 1111. | H | H | D¹¹⁶ | H | H | H | H | H | L¹⁰⁶ | N | CH | N | Ph | Ph |
| 1112. | H | H | D¹¹⁶ | H | H | H | H | H | L¹⁰⁶ | N | CH | N | 4-biphenyl | 4-biphenyl |
| 1113. | H | H | D¹¹⁶ | H | H | H | H | H | L¹⁰⁷ | N | N | N | Ph | Ph |
| 1114. | H | H | D¹¹⁶ | H | H | H | H | H | L¹⁰⁷ | N | N | N | 4-biphenyl | 4-biphenyl |
| 1115. | H | H | D¹¹⁶ | H | H | H | H | H | L¹⁰⁷ | N | CH | N | Ph | Ph |
| 1116. | H | H | D¹¹⁶ | H | H | H | H | H | L¹⁰⁷ | N | CH | N | 4-biphenyl | 4-biphenyl |
| 1117. | H | H | D¹¹⁶ | H | H | H | H | H | L¹⁰⁸ | N | N | N | Ph | Ph |
| 1118. | H | H | D¹¹⁶ | H | H | H | H | H | L¹⁰⁸ | N | N | N | 4-biphenyl | 4-biphenyl |
| 1119. | H | H | D¹¹⁶ | H | H | H | H | H | L¹⁰⁸ | N | CH | N | Ph | Ph |
| 1120. | H | H | D¹¹⁶ | H | H | H | H | H | L¹⁰⁸ | N | CH | N | 4-biphenyl | 4-biphenyl |
| 1121. | H | H | D¹¹⁶ | H | H | H | H | H | L¹⁰⁹ | N | N | N | Ph | Ph |
| 1122. | H | H | D¹¹⁶ | H | H | H | H | H | L¹⁰⁹ | N | N | N | 4-biphenyl | 4-biphenyl |
| 1123. | H | H | D¹¹⁶ | H | H | H | H | H | L¹⁰⁹ | N | CH | N | Ph | Ph |
| 1124. | H | H | D¹¹⁶ | H | H | H | H | H | L¹⁰⁹ | N | CH | N | 4-biphenyl | 4-biphenyl |
| 1125. | H | H | D¹¹⁶ | H | H | H | H | H | L¹¹⁰ | N | N | N | Ph | Ph |
| 1126. | H | H | D¹¹⁶ | H | H | H | H | H | L¹¹⁰ | N | N | N | 4-biphenyl | 4-biphenyl |
| 1127. | H | H | D¹¹⁶ | H | H | H | H | H | L¹¹⁰ | N | CH | N | Ph | Ph |
| 1128. | H | H | D¹¹⁶ | H | H | H | H | H | L¹¹⁰ | N | CH | N | 4-biphenyl | 4-biphenyl |
| 1129. | H | H | D¹¹⁶ | H | H | H | H | H | L¹¹¹ | N | N | N | Ph | Ph |
| 1130. | H | H | D¹¹⁶ | H | H | H | H | H | L¹¹¹ | N | N | N | 4-biphenyl | 4-biphenyl |
| 1131. | H | H | D¹¹⁶ | H | H | H | H | H | L¹¹¹ | N | CH | N | Ph | Ph |
| 1132. | H | H | D¹¹⁶ | H | H | H | H | H | L¹¹¹ | N | CH | N | 4-biphenyl | 4-biphenyl |
| 1133. | H | H | D¹¹⁶ | H | H | H | H | H | L¹¹² | N | N | N | Ph | Ph |
| 1134. | H | H | D¹¹⁶ | H | H | H | H | H | L¹¹² | N | N | N | 4-biphenyl | 4-biphenyl |
| 1135. | H | H | D¹¹⁶ | H | H | H | H | H | L¹¹² | N | CH | N | Ph | Ph |
| 1136. | H | H | D¹¹⁶ | H | H | H | H | H | L¹¹² | N | CH | N | 4-biphenyl | 4-biphenyl |
| 1137. | H | H | D¹¹⁶ | H | H | H | H | H | L¹¹³ | N | N | N | Ph | Ph |
| 1138. | H | H | D¹¹⁶ | H | H | H | H | H | L¹¹³ | N | N | N | 4-biphenyl | 4-biphenyl |
| 1139. | H | H | D¹¹⁶ | H | H | H | H | H | L¹¹³ | N | CH | N | Ph | Ph |
| 1140. | H | H | D¹¹⁶ | H | H | H | H | H | L¹¹³ | N | CH | N | 4-biphenyl | 4-biphenyl |
| 1141. | H | H | D¹¹⁶ | H | H | H | H | H | L¹¹⁴ | N | N | N | Ph | Ph |
| 1142. | H | H | D¹¹⁶ | H | H | H | H | H | L¹¹⁴ | N | N | N | 4-biphenyl | 4-biphenyl |
| 1143. | H | H | D¹¹⁶ | H | H | H | H | H | L¹¹⁴ | N | CH | N | Ph | Ph |
| 1144. | H | H | D¹¹⁶ | H | H | H | H | H | L¹¹⁴ | N | CH | N | 4-biphenyl | 4-biphenyl |
| 1145. | H | H | D¹¹⁶ | H | H | H | H | H | L¹¹⁵ | N | N | N | Ph | Ph |
| 1146. | H | H | D¹¹⁶ | H | H | H | H | H | L¹¹⁵ | N | N | N | 4-biphenyl | 4-biphenyl |
| 1147. | H | H | D¹¹⁶ | H | H | H | H | H | L¹¹⁵ | N | CH | N | Ph | Ph |
| 1148. | H | H | D¹¹⁶ | H | H | H | H | H | L¹¹⁵ | N | CH | N | 4-biphenyl | 4-biphenyl |
| 1149. | H | H | D¹¹⁶ | H | H | H | H | H | L¹¹⁶ | N | N | N | Ph | Ph |
| 1150. | H | H | D¹¹⁶ | H | H | H | H | H | L¹¹⁶ | N | N | N | 4-biphenyl | 4-biphenyl |
| 1151. | H | H | D¹¹⁶ | H | H | H | H | H | L¹¹⁶ | N | CH | N | Ph | Ph |
| 1152. | H | H | D¹¹⁶ | H | H | H | H | H | L¹¹⁶ | N | CH | N | 4-biphenyl | 4-biphenyl |
| 1153. | H | H | D¹¹⁷ | H | H | H | H | H | L¹⁰¹ | N | N | N | Ph | Ph |
| 1154. | H | H | D¹¹⁷ | H | H | H | H | H | L¹⁰¹ | N | N | N | 4-biphenyl | 4-biphenyl |
| 1155. | H | H | D¹¹⁷ | H | H | H | H | H | L¹⁰¹ | N | CH | N | Ph | Ph |
| 1156. | H | H | D¹¹⁷ | H | H | H | H | H | L¹⁰¹ | N | CH | N | 4-biphenyl | 4-biphenyl |
| 1157. | H | H | D¹¹⁷ | H | H | H | H | H | L¹⁰² | N | N | N | Ph | Ph |
| 1158. | H | H | D¹¹⁷ | H | H | H | H | H | L¹⁰² | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1159. | H | H | D¹¹⁷ | H | H | H | H | H | L¹⁰² | N | CH | N | Ph | Ph |
| 1160. | H | H | D¹¹⁷ | H | H | H | H | H | L¹⁰² | N | CH | N | 4-biphenyl | 4-biphenyl |
| 1161. | H | H | D¹¹⁷ | H | H | H | H | H | L¹⁰³ | N | N | N | Ph | Ph |
| 1162. | H | H | D¹¹⁷ | H | H | H | H | H | L¹⁰³ | N | N | N | 4-biphenyl | 4-biphenyl |
| 1163. | H | H | D¹¹⁷ | H | H | H | H | H | L¹⁰³ | N | CH | N | Ph | Ph |
| 1164. | H | H | D¹¹⁷ | H | H | H | H | H | L¹⁰³ | N | CH | N | 4-biphenyl | 4-biphenyl |
| 1165. | H | H | D¹¹⁷ | H | H | H | H | H | L¹⁰⁴ | N | N | N | Ph | Ph |
| 1166. | H | H | D¹¹⁷ | H | H | H | H | H | L¹⁰⁴ | N | N | N | 4-biphenyl | 4-biphenyl |
| 1167. | H | H | D¹¹⁷ | H | H | H | H | H | L¹⁰⁴ | N | CH | N | Ph | Ph |
| 1168. | H | H | D¹¹⁷ | H | H | H | H | H | L¹⁰⁴ | N | CH | N | 4-biphenyl | 4-biphenyl |
| 1169. | H | H | D¹¹⁷ | H | H | H | H | H | L¹⁰⁵ | N | N | N | Ph | Ph |
| 1170. | H | H | D¹¹⁷ | H | H | H | H | H | L¹⁰⁵ | N | N | N | 4-biphenyl | 4-biphenyl |
| 1171. | H | H | D¹¹⁷ | H | H | H | H | H | L¹⁰⁵ | N | CH | N | Ph | Ph |
| 1172. | H | H | D¹¹⁷ | H | H | H | H | H | L¹⁰⁵ | N | CH | N | 4-biphenyl | 4-biphenyl |
| 1173. | H | H | D¹¹⁷ | H | H | H | H | H | L¹⁰⁶ | N | N | N | Ph | Ph |
| 1174. | H | H | D¹¹⁷ | H | H | H | H | H | L¹⁰⁶ | N | N | N | 4-biphenyl | 4-biphenyl |
| 1175. | H | H | D¹¹⁷ | H | H | H | H | H | L¹⁰⁶ | N | CH | N | Ph | Ph |
| 1176. | H | H | D¹¹⁷ | H | H | H | H | H | L¹⁰⁶ | N | CH | N | 4-biphenyl | 4-biphenyl |
| 1177. | H | H | D¹¹⁷ | H | H | H | H | H | L¹⁰⁷ | N | N | N | Ph | Ph |
| 1178. | H | H | D¹¹⁷ | H | H | H | H | H | L¹⁰⁷ | N | N | N | 4-biphenyl | 4-biphenyl |
| 1179. | H | H | D¹¹⁷ | H | H | H | H | H | L¹⁰⁷ | N | CH | N | Ph | Ph |
| 1180. | H | H | D¹¹⁷ | H | H | H | H | H | L¹⁰⁷ | N | CH | N | 4-biphenyl | 4-biphenyl |
| 1181. | H | H | D¹¹⁷ | H | H | H | H | H | L¹⁰⁸ | N | N | N | Ph | Ph |
| 1182. | H | H | D¹¹⁷ | H | H | H | H | H | L¹⁰⁸ | N | N | N | 4-biphenyl | 4-biphenyl |
| 1183. | H | H | D¹¹⁷ | H | H | H | H | H | L¹⁰⁸ | N | CH | N | Ph | Ph |
| 1184. | H | H | D¹¹⁷ | H | H | H | H | H | L¹⁰⁸ | N | CH | N | 4-biphenyl | 4-biphenyl |
| 1185. | H | H | D¹¹⁷ | H | H | H | H | H | L¹⁰⁹ | N | N | N | Ph | Ph |
| 1186. | H | H | D¹¹⁷ | H | H | H | H | H | L¹⁰⁹ | N | N | N | 4-biphenyl | 4-biphenyl |
| 1187. | H | H | D¹¹⁷ | H | H | H | H | H | L¹⁰⁹ | N | CH | N | Ph | Ph |
| 1188. | H | H | D¹¹⁷ | H | H | H | H | H | L¹⁰⁹ | N | CH | N | 4-biphenyl | 4-biphenyl |
| 1189. | H | H | D¹¹⁷ | H | H | H | H | H | L¹¹⁰ | N | N | N | Ph | Ph |
| 1190. | H | H | D¹¹⁷ | H | H | H | H | H | L¹¹⁰ | N | N | N | 4-biphenyl | 4-biphenyl |
| 1191. | H | H | D¹¹⁷ | H | H | H | H | H | L¹¹⁰ | N | CH | N | Ph | Ph |
| 1192. | H | H | D¹¹⁷ | H | H | H | H | H | L¹¹⁰ | N | CH | N | 4-biphenyl | 4-biphenyl |
| 1193. | H | H | D¹¹⁷ | H | H | H | H | H | L¹¹¹ | N | N | N | Ph | Ph |
| 1194. | H | H | D¹¹⁷ | H | H | H | H | H | L¹¹¹ | N | N | N | 4-biphenyl | 4-biphenyl |
| 1195. | H | H | D¹¹⁷ | H | H | H | H | H | L¹¹¹ | N | CH | N | Ph | Ph |
| 1196. | H | H | D¹¹⁷ | H | H | H | H | H | L¹¹¹ | N | CH | N | 4-biphenyl | 4-biphenyl |
| 1197. | H | H | D¹¹⁷ | H | H | H | H | H | L¹¹² | N | N | N | Ph | Ph |
| 1198. | H | H | D¹¹⁷ | H | H | H | H | H | L¹¹² | N | N | N | 4-biphenyl | 4-biphenyl |
| 1199. | H | H | D¹¹⁷ | H | H | H | H | H | L¹¹² | N | CH | N | Ph | Ph |
| 1200. | H | H | D¹¹⁷ | H | H | H | H | H | L¹¹² | N | CH | N | 4-biphenyl | 4-biphenyl |
| 1201. | H | H | D¹¹⁷ | H | H | H | H | H | L¹¹³ | N | N | N | Ph | Ph |
| 1202. | H | H | D¹¹⁷ | H | H | H | H | H | L¹¹³ | N | N | N | 4-biphenyl | 4-biphenyl |
| 1203. | H | H | D¹¹⁷ | H | H | H | H | H | L¹¹³ | N | CH | N | Ph | Ph |
| 1204. | H | H | D¹¹⁷ | H | H | H | H | H | L¹¹³ | N | CH | N | 4-biphenyl | 4-biphenyl |
| 1205. | H | H | D¹¹⁷ | H | H | H | H | H | L¹¹⁴ | N | N | N | Ph | Ph |
| 1206. | H | H | D¹¹⁷ | H | H | H | H | H | L¹¹⁴ | N | N | N | 4-biphenyl | 4-biphenyl |
| 1207. | H | H | D¹¹⁷ | H | H | H | H | H | L¹¹⁴ | N | CH | N | Ph | Ph |
| 1208. | H | H | D¹¹⁷ | H | H | H | H | H | L¹¹⁴ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1209. | H | H | D¹¹⁷ | H | H | H | H | H | L¹¹⁵ | N | N | N | Ph | Ph |
| 1210. | H | H | D¹¹⁷ | H | H | H | H | H | L¹¹⁵ | N | N | N | 4-biphenyl | 4-biphenyl |
| 1211. | H | H | D¹¹⁷ | H | H | H | H | H | L¹¹⁵ | N | CH | N | Ph | Ph |
| 1212. | H | H | D¹¹⁷ | H | H | H | H | H | L¹¹⁵ | N | CH | N | 4-biphenyl | 4-biphenyl |
| 1213. | H | H | D¹¹⁷ | H | H | H | H | H | L¹¹⁶ | N | N | N | Ph | Ph |
| 1214. | H | H | D¹¹⁷ | H | H | H | H | H | L¹¹⁶ | N | N | N | 4-biphenyl | 4-biphenyl |
| 1215. | H | H | D¹¹⁷ | H | H | H | H | H | L¹¹⁶ | N | CH | N | Ph | Ph |
| 1216. | H | H | D¹¹⁷ | H | H | H | H | H | L¹¹⁶ | N | CH | N | 4-biphenyl | 4-biphenyl |
| 1217. | H | H | D¹¹⁸ | H | H | H | H | H | L¹⁰¹ | N | N | N | Ph | Ph |
| 1218. | H | H | D¹¹⁸ | H | H | H | H | H | L¹⁰¹ | N | N | N | 4-biphenyl | 4-biphenyl |
| 1219. | H | H | D¹¹⁸ | H | H | H | H | H | L¹⁰¹ | N | CH | N | Ph | Ph |
| 1220. | H | H | D¹¹⁸ | H | H | H | H | H | L¹⁰¹ | N | CH | N | 4-biphenyl | 4-biphenyl |
| 1221. | H | H | D¹¹⁸ | H | H | H | H | H | L¹⁰² | N | N | N | Ph | Ph |
| 1222. | H | H | D¹¹⁸ | H | H | H | H | H | L¹⁰² | N | N | N | 4-biphenyl | 4-biphenyl |
| 1223. | H | H | D¹¹⁸ | H | H | H | H | H | L¹⁰² | N | CH | N | Ph | Ph |
| 1224. | H | H | D¹¹⁸ | H | H | H | H | H | L¹⁰² | N | CH | N | 4-biphenyl | 4-biphenyl |
| 1225. | H | H | D¹¹⁸ | H | H | H | H | H | L¹⁰³ | N | N | N | Ph | Ph |
| 1226. | H | H | D¹¹⁸ | H | H | H | H | H | L¹⁰³ | N | N | N | 4-biphenyl | 4-biphenyl |
| 1227. | H | H | D¹¹⁸ | H | H | H | H | H | L¹⁰³ | N | CH | N | Ph | Ph |
| 1228. | H | H | D¹¹⁸ | H | H | H | H | H | L¹⁰³ | N | CH | N | 4-biphenyl | 4-biphenyl |
| 1229. | H | H | D¹¹⁸ | H | H | H | H | H | L¹⁰⁴ | N | N | N | Ph | Ph |
| 1230. | H | H | D¹¹⁸ | H | H | H | H | H | L¹⁰⁴ | N | N | N | 4-biphenyl | 4-biphenyl |
| 1231. | H | H | D¹¹⁸ | H | H | H | H | H | L¹⁰⁴ | N | CH | N | Ph | Ph |
| 1232. | H | H | D¹¹⁸ | H | H | H | H | H | L¹⁰⁴ | N | CH | N | 4-biphenyl | 4-biphenyl |
| 1233. | H | H | D¹¹⁸ | H | H | H | H | H | L¹⁰⁵ | N | N | N | Ph | Ph |
| 1234. | H | H | D¹¹⁸ | H | H | H | H | H | L¹⁰⁵ | N | N | N | 4-biphenyl | 4-biphenyl |
| 1235. | H | H | D¹¹⁸ | H | H | H | H | H | L¹⁰⁵ | N | CH | N | Ph | Ph |
| 1236. | H | H | D¹¹⁸ | H | H | H | H | H | L¹⁰⁵ | N | CH | N | 4-biphenyl | 4-biphenyl |
| 1237. | H | H | D¹¹⁸ | H | H | H | H | H | L¹⁰⁶ | N | N | N | Ph | Ph |
| 1238. | H | H | D¹¹⁸ | H | H | H | H | H | L¹⁰⁶ | N | N | N | 4-biphenyl | 4-biphenyl |
| 1239. | H | H | D¹¹⁸ | H | H | H | H | H | L¹⁰⁶ | N | CH | N | Ph | Ph |
| 1240. | H | H | D¹¹⁸ | H | H | H | H | H | L¹⁰⁶ | N | CH | N | 4-biphenyl | 4-biphenyl |
| 1241. | H | H | D¹¹⁸ | H | H | H | H | H | L¹⁰⁷ | N | N | N | Ph | Ph |
| 1242. | H | H | D¹¹⁸ | H | H | H | H | H | L¹⁰⁷ | N | N | N | 4-biphenyl | 4-biphenyl |
| 1243. | H | H | D¹¹⁸ | H | H | H | H | H | L¹⁰⁷ | N | CH | N | Ph | Ph |
| 1244. | H | H | D¹¹⁸ | H | H | H | H | H | L¹⁰⁷ | N | CH | N | 4-biphenyl | 4-biphenyl |
| 1245. | H | H | D¹¹⁸ | H | H | H | H | H | L¹⁰⁸ | N | N | N | Ph | Ph |
| 1246. | H | H | D¹¹⁸ | H | H | H | H | H | L¹⁰⁸ | N | N | N | 4-biphenyl | 4-biphenyl |
| 1247. | H | H | D¹¹⁸ | H | H | H | H | H | L¹⁰⁸ | N | CH | N | Ph | Ph |
| 1248. | H | H | D¹¹⁸ | H | H | H | H | H | L¹⁰⁸ | N | CH | N | 4-biphenyl | 4-biphenyl |
| 1249. | H | H | D¹¹⁸ | H | H | H | H | H | L¹⁰⁹ | N | N | N | Ph | Ph |
| 1250. | H | H | D¹¹⁸ | H | H | H | H | H | L¹⁰⁹ | N | N | N | 4-biphenyl | 4-biphenyl |
| 1251. | H | H | D¹¹⁸ | H | H | H | H | H | L¹⁰⁹ | N | CH | N | Ph | Ph |
| 1252. | H | H | D¹¹⁸ | H | H | H | H | H | L¹⁰⁹ | N | CH | N | 4-biphenyl | 4-biphenyl |
| 1253. | H | H | D¹¹⁸ | H | H | H | H | H | L¹¹⁰ | N | N | N | Ph | Ph |
| 1254. | H | H | D¹¹⁸ | H | H | H | H | H | L¹¹⁰ | N | N | N | 4-biphenyl | 4-biphenyl |
| 1255. | H | H | D¹¹⁸ | H | H | H | H | H | L¹¹⁰ | N | CH | N | Ph | Ph |
| 1256. | H | H | D¹¹⁸ | H | H | H | H | H | L¹¹⁰ | N | CH | N | 4-biphenyl | 4-biphenyl |
| 1257. | H | H | D¹¹⁸ | H | H | H | H | H | L¹¹¹ | N | N | N | Ph | Ph |
| 1258. | H | H | D¹¹⁸ | H | H | H | H | H | L¹¹¹ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1259. | H | H | D¹¹⁸ | H | H | H | H | H | L¹¹¹ | N | CH | N | Ph | Ph |
| 1260. | H | H | D¹¹⁸ | H | H | H | H | H | L¹¹¹ | N | CH | N | 4-biphenyl | 4-biphenyl |
| 1261. | H | H | D¹¹⁸ | H | H | H | H | H | L¹¹² | N | N | N | Ph | Ph |
| 1262. | H | H | D¹¹⁸ | H | H | H | H | H | L¹¹² | N | N | N | 4-biphenyl | 4-biphenyl |
| 1263. | H | H | D¹¹⁸ | H | H | H | H | H | L¹¹² | N | CH | N | Ph | Ph |
| 1264. | H | H | D¹¹⁸ | H | H | H | H | H | L¹¹² | N | CH | N | 4-biphenyl | 4-biphenyl |
| 1265. | H | H | D¹¹⁸ | H | H | H | H | H | L¹¹³ | N | N | N | Ph | Ph |
| 1266. | H | H | D¹¹⁸ | H | H | H | H | H | L¹¹³ | N | N | N | 4-biphenyl | 4-biphenyl |
| 1267. | H | H | D¹¹⁸ | H | H | H | H | H | L¹¹³ | N | CH | N | Ph | Ph |
| 1268. | H | H | D¹¹⁸ | H | H | H | H | H | L¹¹³ | N | CH | N | 4-biphenyl | 4-biphenyl |
| 1269. | H | H | D¹¹⁸ | H | H | H | H | H | L¹¹⁴ | N | N | N | Ph | Ph |
| 1270. | H | H | D¹¹⁸ | H | H | H | H | H | L¹¹⁴ | N | N | N | 4-biphenyl | 4-biphenyl |
| 1271. | H | H | D¹¹⁸ | H | H | H | H | H | L¹¹⁴ | N | CH | N | Ph | Ph |
| 1272. | H | H | D¹¹⁸ | H | H | H | H | H | L¹¹⁴ | N | CH | N | 4-biphenyl | 4-biphenyl |
| 1273. | H | H | D¹¹⁸ | H | H | H | H | H | L¹¹⁵ | N | N | N | Ph | Ph |
| 1274. | H | H | D¹¹⁸ | H | H | H | H | H | L¹¹⁵ | N | N | N | 4-biphenyl | 4-biphenyl |
| 1275. | H | H | D¹¹⁸ | H | H | H | H | H | L¹¹⁵ | N | CH | N | Ph | Ph |
| 1276. | H | H | D¹¹⁸ | H | H | H | H | H | L¹¹⁵ | N | CH | N | 4-biphenyl | 4-biphenyl |
| 1277. | H | H | D¹¹⁸ | H | H | H | H | H | L¹¹⁶ | N | N | N | Ph | Ph |
| 1278. | H | H | D¹¹⁸ | H | H | H | H | H | L¹¹⁶ | N | N | N | 4-biphenyl | 4-biphenyl |
| 1279. | H | H | D¹¹⁸ | H | H | H | H | H | L¹¹⁶ | N | CH | N | Ph | Ph |
| 1280. | H | H | D¹¹⁸ | H | H | H | H | H | L¹¹⁶ | N | CH | N | 4-biphenyl | 4-biphenyl |
| 1281. | H | H | D¹¹⁹ | H | H | H | H | H | L¹⁰¹ | N | N | N | Ph | Ph |
| 1282. | H | H | D¹¹⁹ | H | H | H | H | H | L¹⁰¹ | N | N | N | 4-biphenyl | 4-biphenyl |
| 1283. | H | H | D¹¹⁹ | H | H | H | H | H | L¹⁰¹ | N | CH | N | Ph | Ph |
| 1284. | H | H | D¹¹⁹ | H | H | H | H | H | L¹⁰¹ | N | CH | N | 4-biphenyl | 4-biphenyl |
| 1285. | H | H | D¹¹⁹ | H | H | H | H | H | L¹⁰² | N | N | N | Ph | Ph |
| 1286. | H | H | D¹¹⁹ | H | H | H | H | H | L¹⁰² | N | N | N | 4-biphenyl | 4-biphenyl |
| 1287. | H | H | D¹¹⁹ | H | H | H | H | H | L¹⁰² | N | CH | N | Ph | Ph |
| 1288. | H | H | D¹¹⁹ | H | H | H | H | H | L¹⁰² | N | CH | N | 4-biphenyl | 4-biphenyl |
| 1289. | H | H | D¹¹⁹ | H | H | H | H | H | L¹⁰³ | N | N | N | Ph | Ph |
| 1290. | H | H | D¹¹⁹ | H | H | H | H | H | L¹⁰³ | N | N | N | 4-biphenyl | 4-biphenyl |
| 1291. | H | H | D¹¹⁹ | H | H | H | H | H | L¹⁰³ | N | CH | N | Ph | Ph |
| 1292. | H | H | D¹¹⁹ | H | H | H | H | H | L¹⁰³ | N | CH | N | 4-biphenyl | 4-biphenyl |
| 1293. | H | H | D¹¹⁹ | H | H | H | H | H | L¹⁰⁴ | N | N | N | Ph | Ph |
| 1294. | H | H | D¹¹⁹ | H | H | H | H | H | L¹⁰⁴ | N | N | N | 4-biphenyl | 4-biphenyl |
| 1295. | H | H | D¹¹⁹ | H | H | H | H | H | L¹⁰⁴ | N | CH | N | Ph | Ph |
| 1296. | H | H | D¹¹⁹ | H | H | H | H | H | L¹⁰⁴ | N | CH | N | 4-biphenyl | 4-biphenyl |
| 1297. | H | H | D¹¹⁹ | H | H | H | H | H | L¹⁰⁵ | N | N | N | Ph | Ph |
| 1298. | H | H | D¹¹⁹ | H | H | H | H | H | L¹⁰⁵ | N | N | N | 4-biphenyl | 4-biphenyl |
| 1299. | H | H | D¹¹⁹ | H | H | H | H | H | L¹⁰⁵ | N | CH | N | Ph | Ph |
| 1300. | H | H | D¹¹⁹ | H | H | H | H | H | L¹⁰⁵ | N | CH | N | 4-biphenyl | 4-biphenyl |
| 1301. | H | H | D¹¹⁹ | H | H | H | H | H | L¹⁰⁶ | N | N | N | Ph | Ph |
| 1302. | H | H | D¹¹⁹ | H | H | H | H | H | L¹⁰⁶ | N | N | N | 4-biphenyl | 4-biphenyl |
| 1303. | H | H | D¹¹⁹ | H | H | H | H | H | L¹⁰⁶ | N | CH | N | Ph | Ph |
| 1304. | H | H | D¹¹⁹ | H | H | H | H | H | L¹⁰⁶ | N | CH | N | 4-biphenyl | 4-biphenyl |
| 1305. | H | H | D¹¹⁹ | H | H | H | H | H | L¹⁰⁷ | N | N | N | Ph | Ph |
| 1306. | H | H | D¹¹⁹ | H | H | H | H | H | L¹⁰⁷ | N | N | N | 4-biphenyl | 4-biphenyl |
| 1307. | H | H | D¹¹⁹ | H | H | H | H | H | L¹⁰⁷ | N | CH | N | Ph | Ph |
| 1308. | H | H | D¹¹⁹ | H | H | H | H | H | L¹⁰⁷ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1309. | H | H | D¹¹⁹ | H | H | H | H | H | L¹⁰⁸ | N | N | N | Ph | Ph |
| 1310. | H | H | D¹¹⁹ | H | H | H | H | H | L¹⁰⁸ | N | N | N | 4-biphenyl | 4-biphenyl |
| 1311. | H | H | D¹¹⁹ | H | H | H | H | H | L¹⁰⁸ | N | CH | N | Ph | Ph |
| 1312. | H | H | D¹¹⁹ | H | H | H | H | H | L¹⁰⁸ | N | CH | N | 4-biphenyl | 4-biphenyl |
| 1313. | H | H | D¹¹⁹ | H | H | H | H | H | L¹⁰⁹ | N | N | N | Ph | Ph |
| 1314. | H | H | D¹¹⁹ | H | H | H | H | H | L¹⁰⁹ | N | N | N | 4-biphenyl | 4-biphenyl |
| 1315. | H | H | D¹¹⁹ | H | H | H | H | H | L¹⁰⁹ | N | CH | N | Ph | Ph |
| 1316. | H | H | D¹¹⁹ | H | H | H | H | H | L¹⁰⁹ | N | CH | N | 4-biphenyl | 4-biphenyl |
| 1317. | H | H | D¹¹⁹ | H | H | H | H | H | L¹¹⁰ | N | N | N | Ph | Ph |
| 1318. | H | H | D¹¹⁹ | H | H | H | H | H | L¹¹⁰ | N | N | N | 4-biphenyl | 4-biphenyl |
| 1319. | H | H | D¹¹⁹ | H | H | H | H | H | L¹¹⁰ | N | CH | N | Ph | Ph |
| 1320. | H | H | D¹¹⁹ | H | H | H | H | H | L¹¹⁰ | N | CH | N | 4-biphenyl | 4-biphenyl |
| 1321. | H | H | D¹¹⁹ | H | H | H | H | H | L¹¹¹ | N | N | N | Ph | Ph |
| 1322. | H | H | D¹¹⁹ | H | H | H | H | H | L¹¹¹ | N | N | N | 4-biphenyl | 4-biphenyl |
| 1323. | H | H | D¹¹⁹ | H | H | H | H | H | L¹¹¹ | N | CH | N | Ph | Ph |
| 1324. | H | H | D¹¹⁹ | H | H | H | H | H | L¹¹¹ | N | CH | N | 4-biphenyl | 4-biphenyl |
| 1325. | H | H | D¹¹⁹ | H | H | H | H | H | L¹¹² | N | N | N | Ph | Ph |
| 1326. | H | H | D¹¹⁹ | H | H | H | H | H | L¹¹² | N | N | N | 4-biphenyl | 4-biphenyl |
| 1327. | H | H | D¹¹⁹ | H | H | H | H | H | L¹¹² | N | CH | N | Ph | Ph |
| 1328. | H | H | D¹¹⁹ | H | H | H | H | H | L¹¹² | N | CH | N | 4-biphenyl | 4-biphenyl |
| 1329. | H | H | D¹¹⁹ | H | H | H | H | H | L¹¹³ | N | N | N | Ph | Ph |
| 1330. | H | H | D¹¹⁹ | H | H | H | H | H | L¹¹³ | N | N | N | 4-biphenyl | 4-biphenyl |
| 1331. | H | H | D¹¹⁹ | H | H | H | H | H | L¹¹³ | N | CH | N | Ph | Ph |
| 1332. | H | H | D¹¹⁹ | H | H | H | H | H | L¹¹³ | N | CH | N | 4-biphenyl | 4-biphenyl |
| 1333. | H | H | D¹¹⁹ | H | H | H | H | H | L¹¹⁴ | N | N | N | Ph | Ph |
| 1334. | H | H | D¹¹⁹ | H | H | H | H | H | L¹¹⁴ | N | N | N | 4-biphenyl | 4-biphenyl |
| 1335. | H | H | D¹¹⁹ | H | H | H | H | H | L¹¹⁴ | N | CH | N | Ph | Ph |
| 1336. | H | H | D¹¹⁹ | H | H | H | H | H | L¹¹⁴ | N | CH | N | 4-biphenyl | 4-biphenyl |
| 1337. | H | H | D¹¹⁹ | H | H | H | H | H | L¹¹⁵ | N | N | N | Ph | Ph |
| 1338. | H | H | D¹¹⁹ | H | H | H | H | H | L¹¹⁵ | N | N | N | 4-biphenyl | 4-biphenyl |
| 1339. | H | H | D¹¹⁹ | H | H | H | H | H | L¹¹⁵ | N | CH | N | Ph | Ph |
| 1340. | H | H | D¹¹⁹ | H | H | H | H | H | L¹¹⁵ | N | CH | N | 4-biphenyl | 4-biphenyl |
| 1341. | H | H | D¹¹⁹ | H | H | H | H | H | L¹¹⁶ | N | N | N | Ph | Ph |
| 1342. | H | H | D¹¹⁹ | H | H | H | H | H | L¹¹⁶ | N | N | N | 4-biphenyl | 4-biphenyl |
| 1343. | H | H | D¹¹⁹ | H | H | H | H | H | L¹¹⁶ | N | CH | N | Ph | Ph |
| 1344. | H | H | D¹¹⁹ | H | H | H | H | H | L¹¹⁶ | N | CH | N | 4-biphenyl | 4-biphenyl |
| 1345. | H | H | D¹²⁰ | H | H | H | H | H | L¹⁰¹ | N | N | N | Ph | Ph |
| 1346. | H | H | D¹²⁰ | H | H | H | H | H | L¹⁰¹ | N | N | N | 4-biphenyl | 4-biphenyl |
| 1347. | H | H | D¹²⁰ | H | H | H | H | H | L¹⁰¹ | N | CH | N | Ph | Ph |
| 1348. | H | H | D¹²⁰ | H | H | H | H | H | L¹⁰¹ | N | CH | N | 4-biphenyl | 4-biphenyl |
| 1349. | H | H | D¹²⁰ | H | H | H | H | H | L¹⁰² | N | N | N | Ph | Ph |
| 1350. | H | H | D¹²⁰ | H | H | H | H | H | L¹⁰² | N | N | N | 4-biphenyl | 4-biphenyl |
| 1351. | H | H | D¹²⁰ | H | H | H | H | H | L¹⁰² | N | CH | N | Ph | Ph |
| 1352. | H | H | D¹²⁰ | H | H | H | H | H | L¹⁰² | N | CH | N | 4-biphenyl | 4-biphenyl |
| 1353. | H | H | D¹²⁰ | H | H | H | H | H | L¹⁰³ | N | N | N | Ph | Ph |
| 1354. | H | H | D¹²⁰ | H | H | H | H | H | L¹⁰³ | N | N | N | 4-biphenyl | 4-biphenyl |
| 1355. | H | H | D¹²⁰ | H | H | H | H | H | L¹⁰³ | N | CH | N | Ph | Ph |
| 1356. | H | H | D¹²⁰ | H | H | H | H | H | L¹⁰³ | N | CH | N | 4-biphenyl | 4-biphenyl |
| 1357. | H | H | D¹²⁰ | H | H | H | H | H | L¹⁰⁴ | N | N | N | Ph | Ph |
| 1358. | H | H | D¹²⁰ | H | H | H | H | H | L¹⁰⁴ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1359. | H | H | D¹²⁰ | H | H | H | H | H | L¹⁰⁴ | N | CH | N | Ph | Ph |
| 1360. | H | H | D¹²⁰ | H | H | H | H | H | L¹⁰⁴ | N | CH | N | 4-biphenyl | 4-biphenyl |
| 1361. | H | H | D¹²⁰ | H | H | H | H | H | L¹⁰⁵ | N | N | N | Ph | Ph |
| 1362. | H | H | D¹²⁰ | H | H | H | H | H | L¹⁰⁵ | N | N | N | 4-biphenyl | 4-biphenyl |
| 1363. | H | H | D¹²⁰ | H | H | H | H | H | L¹⁰⁵ | N | CH | N | Ph | Ph |
| 1364. | H | H | D¹²⁰ | H | H | H | H | H | L¹⁰⁵ | N | CH | N | 4-biphenyl | 4-biphenyl |
| 1365. | H | H | D¹²⁰ | H | H | H | H | H | L¹⁰⁶ | N | N | N | Ph | Ph |
| 1366. | H | H | D¹²⁰ | H | H | H | H | H | L¹⁰⁶ | N | N | N | 4-biphenyl | 4-biphenyl |
| 1367. | H | H | D¹²⁰ | H | H | H | H | H | L¹⁰⁶ | N | CH | N | Ph | Ph |
| 1368. | H | H | D¹²⁰ | H | H | H | H | H | L¹⁰⁶ | N | CH | N | 4-biphenyl | 4-biphenyl |
| 1369. | H | H | D¹²⁰ | H | H | H | H | H | L¹⁰⁷ | N | N | N | Ph | Ph |
| 1370. | H | H | D¹²⁰ | H | H | H | H | H | L¹⁰⁷ | N | N | N | 4-biphenyl | 4-biphenyl |
| 1371. | H | H | D¹²⁰ | H | H | H | H | H | L¹⁰⁷ | N | CH | N | Ph | Ph |
| 1372. | H | H | D¹²⁰ | H | H | H | H | H | L¹⁰⁷ | N | CH | N | 4-biphenyl | 4-biphenyl |
| 1373. | H | H | D¹²⁰ | H | H | H | H | H | L¹⁰⁸ | N | N | N | Ph | Ph |
| 1374. | H | H | D¹²⁰ | H | H | H | H | H | L¹⁰⁸ | N | N | N | 4-biphenyl | 4-biphenyl |
| 1375. | H | H | D¹²⁰ | H | H | H | H | H | L¹⁰⁸ | N | CH | N | Ph | Ph |
| 1376. | H | H | D¹²⁰ | H | H | H | H | H | L¹⁰⁸ | N | CH | N | 4-biphenyl | 4-biphenyl |
| 1377. | H | H | D¹²⁰ | H | H | H | H | H | L¹⁰⁹ | N | N | N | Ph | Ph |
| 1378. | H | H | D¹²⁰ | H | H | H | H | H | L¹⁰⁹ | N | N | N | 4-biphenyl | 4-biphenyl |
| 1379. | H | H | D¹²⁰ | H | H | H | H | H | L¹⁰⁹ | N | CH | N | Ph | Ph |
| 1380. | H | H | D¹²⁰ | H | H | H | H | H | L¹⁰⁹ | N | CH | N | 4-biphenyl | 4-biphenyl |
| 1381. | H | H | D¹²⁰ | H | H | H | H | H | L¹¹⁰ | N | N | N | Ph | Ph |
| 1382. | H | H | D¹²⁰ | H | H | H | H | H | L¹¹⁰ | N | N | N | 4-biphenyl | 4-biphenyl |
| 1383. | H | H | D¹²⁰ | H | H | H | H | H | L¹¹⁰ | N | CH | N | Ph | Ph |
| 1384. | H | H | D¹²⁰ | H | H | H | H | H | L¹¹⁰ | N | CH | N | 4-biphenyl | 4-biphenyl |
| 1385. | H | H | D¹²⁰ | H | H | H | H | H | L¹¹¹ | N | N | N | Ph | Ph |
| 1386. | H | H | D¹²⁰ | H | H | H | H | H | L¹¹¹ | N | N | N | 4-biphenyl | 4-biphenyl |
| 1387. | H | H | D¹²⁰ | H | H | H | H | H | L¹¹¹ | N | CH | N | Ph | Ph |
| 1388. | H | H | D¹²⁰ | H | H | H | H | H | L¹¹¹ | N | CH | N | 4-biphenyl | 4-biphenyl |
| 1389. | H | H | D¹²⁰ | H | H | H | H | H | L¹¹² | N | N | N | Ph | Ph |
| 1390. | H | H | D¹²⁰ | H | H | H | H | H | L¹¹² | N | N | N | 4-biphenyl | 4-biphenyl |
| 1391. | H | H | D¹²⁰ | H | H | H | H | H | L¹¹² | N | CH | N | Ph | Ph |
| 1392. | H | H | D¹²⁰ | H | H | H | H | H | L¹¹² | N | CH | N | 4-biphenyl | 4-biphenyl |
| 1393. | H | H | D¹²⁰ | H | H | H | H | H | L¹¹³ | N | N | N | Ph | Ph |
| 1394. | H | H | D¹²⁰ | H | H | H | H | H | L¹¹³ | N | N | N | 4-biphenyl | 4-biphenyl |
| 1395. | H | H | D¹²⁰ | H | H | H | H | H | L¹¹³ | N | CH | N | Ph | Ph |
| 1396. | H | H | D¹²⁰ | H | H | H | H | H | L¹¹³ | N | CH | N | 4-biphenyl | 4-biphenyl |
| 1397. | H | H | D¹²⁰ | H | H | H | H | H | L¹¹⁴ | N | N | N | Ph | Ph |
| 1398. | H | H | D¹²⁰ | H | H | H | H | H | L¹¹⁴ | N | N | N | 4-biphenyl | 4-biphenyl |
| 1399. | H | H | D¹²⁰ | H | H | H | H | H | L¹¹⁴ | N | CH | N | Ph | Ph |
| 1400. | H | H | D¹²⁰ | H | H | H | H | H | L¹¹⁴ | N | CH | N | 4-biphenyl | 4-biphenyl |
| 1401. | H | H | D¹²⁰ | H | H | H | H | H | L¹¹⁵ | N | N | N | Ph | Ph |
| 1402. | H | H | D¹²⁰ | H | H | H | H | H | L¹¹⁵ | N | N | N | 4-biphenyl | 4-biphenyl |
| 1403. | H | H | D¹²⁰ | H | H | H | H | H | L¹¹⁵ | N | CH | N | Ph | Ph |
| 1404. | H | H | D¹²⁰ | H | H | H | H | H | L¹¹⁵ | N | CH | N | 4-biphenyl | 4-biphenyl |
| 1405. | H | H | D¹²⁰ | H | H | H | H | H | L¹¹⁶ | N | N | N | Ph | Ph |
| 1406. | H | H | D¹²⁰ | H | H | H | H | H | L¹¹⁶ | N | N | N | 4-biphenyl | 4-biphenyl |
| 1407. | H | H | D¹²⁰ | H | H | H | H | H | L¹¹⁶ | N | CH | N | Ph | Ph |
| 1408. | H | H | D¹²⁰ | H | H | H | H | H | L¹¹⁶ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1409. | H | H | D¹²¹ | H | H | H | H | H | L¹⁰¹ | N | N | N | Ph | Ph |
| 1410. | H | H | D¹²¹ | H | H | H | H | H | L¹⁰¹ | N | N | N | 4-biphenyl | 4-biphenyl |
| 1411. | H | H | D¹²¹ | H | H | H | H | H | L¹⁰¹ | N | CH | N | Ph | Ph |
| 1412. | H | H | D¹²¹ | H | H | H | H | H | L¹⁰¹ | N | CH | N | 4-biphenyl | 4-biphenyl |
| 1413. | H | H | D¹²¹ | H | H | H | H | H | L¹⁰² | N | N | N | Ph | Ph |
| 1414. | H | H | D¹²¹ | H | H | H | H | H | L¹⁰² | N | N | N | 4-biphenyl | 4-biphenyl |
| 1415. | H | H | D¹²¹ | H | H | H | H | H | L¹⁰² | N | CH | N | Ph | Ph |
| 1416. | H | H | D¹²¹ | H | H | H | H | H | L¹⁰² | N | CH | N | 4-biphenyl | 4-biphenyl |
| 1417. | H | H | D¹²¹ | H | H | H | H | H | L¹⁰³ | N | N | N | Ph | Ph |
| 1418. | H | H | D¹²¹ | H | H | H | H | H | L¹⁰³ | N | N | N | 4-biphenyl | 4-biphenyl |
| 1419. | H | H | D¹²¹ | H | H | H | H | H | L¹⁰³ | N | CH | N | Ph | Ph |
| 1420. | H | H | D¹²¹ | H | H | H | H | H | L¹⁰³ | N | CH | N | 4-biphenyl | 4-biphenyl |
| 1421. | H | H | D¹²¹ | H | H | H | H | H | L¹⁰⁴ | N | N | N | Ph | Ph |
| 1422. | H | H | D¹²¹ | H | H | H | H | H | L¹⁰⁴ | N | N | N | 4-biphenyl | 4-biphenyl |
| 1423. | H | H | D¹²¹ | H | H | H | H | H | L¹⁰⁴ | N | CH | N | Ph | Ph |
| 1424. | H | H | D¹²¹ | H | H | H | H | H | L¹⁰⁴ | N | CH | N | 4-biphenyl | 4-biphenyl |
| 1425. | H | H | D¹²¹ | H | H | H | H | H | L¹⁰⁵ | N | N | N | Ph | Ph |
| 1426. | H | H | D¹²¹ | H | H | H | H | H | L¹⁰⁵ | N | N | N | 4-biphenyl | 4-biphenyl |
| 1427. | H | H | D¹²¹ | H | H | H | H | H | L¹⁰⁵ | N | CH | N | Ph | Ph |
| 1428. | H | H | D¹²¹ | H | H | H | H | H | L¹⁰⁵ | N | CH | N | 4-biphenyl | 4-biphenyl |
| 1429. | H | H | D¹²¹ | H | H | H | H | H | L¹⁰⁶ | N | N | N | Ph | Ph |
| 1430. | H | H | D¹²¹ | H | H | H | H | H | L¹⁰⁶ | N | N | N | 4-biphenyl | 4-biphenyl |
| 1431. | H | H | D¹²¹ | H | H | H | H | H | L¹⁰⁶ | N | CH | N | Ph | Ph |
| 1432. | H | H | D¹²¹ | H | H | H | H | H | L¹⁰⁶ | N | CH | N | 4-biphenyl | 4-biphenyl |
| 1433. | H | H | D¹²¹ | H | H | H | H | H | L¹⁰⁷ | N | N | N | Ph | Ph |
| 1434. | H | H | D¹²¹ | H | H | H | H | H | L¹⁰⁷ | N | N | N | 4-biphenyl | 4-biphenyl |
| 1435. | H | H | D¹²¹ | H | H | H | H | H | L¹⁰⁷ | N | CH | N | Ph | Ph |
| 1436. | H | H | D¹²¹ | H | H | H | H | H | L¹⁰⁷ | N | CH | N | 4-biphenyl | 4-biphenyl |
| 1437. | H | H | D¹²¹ | H | H | H | H | H | L¹⁰⁸ | N | N | N | Ph | Ph |
| 1438. | H | H | D¹²¹ | H | H | H | H | H | L¹⁰⁸ | N | N | N | 4-biphenyl | 4-biphenyl |
| 1439. | H | H | D¹²¹ | H | H | H | H | H | L¹⁰⁸ | N | CH | N | Ph | Ph |
| 1440. | H | H | D¹²¹ | H | H | H | H | H | L¹⁰⁸ | N | CH | N | 4-biphenyl | 4-biphenyl |
| 1441. | H | H | D¹²¹ | H | H | H | H | H | L¹⁰⁹ | N | N | N | Ph | Ph |
| 1442. | H | H | D¹²¹ | H | H | H | H | H | L¹⁰⁹ | N | N | N | 4-biphenyl | 4-biphenyl |
| 1443. | H | H | D¹²¹ | H | H | H | H | H | L¹⁰⁹ | N | CH | N | Ph | Ph |
| 1444. | H | H | D¹²¹ | H | H | H | H | H | L¹⁰⁹ | N | CH | N | 4-biphenyl | 4-biphenyl |
| 1445. | H | H | D¹²¹ | H | H | H | H | H | L¹¹⁰ | N | N | N | Ph | Ph |
| 1446. | H | H | D¹²¹ | H | H | H | H | H | L¹¹⁰ | N | N | N | 4-biphenyl | 4-biphenyl |
| 1447. | H | H | D¹²¹ | H | H | H | H | H | L¹¹⁰ | N | CH | N | Ph | Ph |
| 1448. | H | H | D¹²¹ | H | H | H | H | H | L¹¹⁰ | N | CH | N | 4-biphenyl | 4-biphenyl |
| 1449. | H | H | D¹²¹ | H | H | H | H | H | L¹¹¹ | N | N | N | Ph | Ph |
| 1450. | H | H | D¹²¹ | H | H | H | H | H | L¹¹¹ | N | N | N | 4-biphenyl | 4-biphenyl |
| 1451. | H | H | D¹²¹ | H | H | H | H | H | L¹¹¹ | N | CH | N | Ph | Ph |
| 1452. | H | H | D¹²¹ | H | H | H | H | H | L¹¹¹ | N | CH | N | 4-biphenyl | 4-biphenyl |
| 1453. | H | H | D¹²¹ | H | H | H | H | H | L¹¹² | N | N | N | Ph | Ph |
| 1454. | H | H | D¹²¹ | H | H | H | H | H | L¹¹² | N | N | N | 4-biphenyl | 4-biphenyl |
| 1455. | H | H | D¹²¹ | H | H | H | H | H | L¹¹² | N | CH | N | Ph | Ph |
| 1456. | H | H | D¹²¹ | H | H | H | H | H | L¹¹² | N | CH | N | 4-biphenyl | 4-biphenyl |
| 1457. | H | H | D¹²¹ | H | H | H | H | H | L¹¹³ | N | N | N | Ph | Ph |
| 1458. | H | H | D¹²¹ | H | H | H | H | H | L¹¹³ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1459. | H | H | D¹²¹ | H | H | H | H | H | L¹¹³ | N | CH | N | Ph | Ph |
| 1460. | H | H | D¹²¹ | H | H | H | H | H | L¹¹³ | N | CH | N | 4-biphenyl | 4-biphenyl |
| 1461. | H | H | D¹²¹ | H | H | H | H | H | L¹¹⁴ | N | N | N | Ph | Ph |
| 1462. | H | H | D¹²¹ | H | H | H | H | H | L¹¹⁴ | N | N | N | 4-biphenyl | 4-biphenyl |
| 1463. | H | H | D¹²¹ | H | H | H | H | H | L¹¹⁴ | N | CH | N | Ph | Ph |
| 1464. | H | H | D¹²¹ | H | H | H | H | H | L¹¹⁴ | N | CH | N | 4-biphenyl | 4-biphenyl |
| 1465. | H | H | D¹²¹ | H | H | H | H | H | L¹¹⁵ | N | N | N | Ph | Ph |
| 1466. | H | H | D¹²¹ | H | H | H | H | H | L¹¹⁵ | N | N | N | 4-biphenyl | 4-biphenyl |
| 1467. | H | H | D¹²¹ | H | H | H | H | H | L¹¹⁵ | N | CH | N | Ph | Ph |
| 1468. | H | H | D¹²¹ | H | H | H | H | H | L¹¹⁵ | N | CH | N | 4-biphenyl | 4-biphenyl |
| 1469. | H | H | D¹²¹ | H | H | H | H | H | L¹¹⁶ | N | N | N | Ph | Ph |
| 1470. | H | H | D¹²¹ | H | H | H | H | H | L¹¹⁶ | N | N | N | 4-biphenyl | 4-biphenyl |
| 1471. | H | H | D¹²¹ | H | H | H | H | H | L¹¹⁶ | N | CH | N | Ph | Ph |
| 1472. | H | H | D¹²¹ | H | H | H | H | H | L¹¹⁶ | N | CH | N | 4-biphenyl | 4-biphenyl |
| 1473. | H | H | D¹²² | H | H | H | H | H | L¹⁰¹ | N | N | N | Ph | Ph |
| 1474. | H | H | D¹²² | H | H | H | H | H | L¹⁰¹ | N | N | N | 4-biphenyl | 4-biphenyl |
| 1475. | H | H | D¹²² | H | H | H | H | H | L¹⁰¹ | N | CH | N | Ph | Ph |
| 1476. | H | H | D¹²² | H | H | H | H | H | L¹⁰¹ | N | CH | N | 4-biphenyl | 4-biphenyl |
| 1477. | H | H | D¹²² | H | H | H | H | H | L¹⁰² | N | N | N | Ph | Ph |
| 1478. | H | H | D¹²² | H | H | H | H | H | L¹⁰² | N | N | N | 4-biphenyl | 4-biphenyl |
| 1479. | H | H | D¹²² | H | H | H | H | H | L¹⁰² | N | CH | N | Ph | Ph |
| 1480. | H | H | D¹²² | H | H | H | H | H | L¹⁰² | N | CH | N | 4-biphenyl | 4-biphenyl |
| 1481. | H | H | D¹²² | H | H | H | H | H | L¹⁰³ | N | N | N | Ph | Ph |
| 1482. | H | H | D¹²² | H | H | H | H | H | L¹⁰³ | N | N | N | 4-biphenyl | 4-biphenyl |
| 1483. | H | H | D¹²² | H | H | H | H | H | L¹⁰³ | N | CH | N | Ph | Ph |
| 1484. | H | H | D¹²² | H | H | H | H | H | L¹⁰³ | N | CH | N | 4-biphenyl | 4-biphenyl |
| 1485. | H | H | D¹²² | H | H | H | H | H | L¹⁰⁴ | N | N | N | Ph | Ph |
| 1486. | H | H | D¹²² | H | H | H | H | H | L¹⁰⁴ | N | N | N | 4-biphenyl | 4-biphenyl |
| 1487. | H | H | D¹²² | H | H | H | H | H | L¹⁰⁴ | N | CH | N | Ph | Ph |
| 1488. | H | H | D¹²² | H | H | H | H | H | L¹⁰⁴ | N | CH | N | 4-biphenyl | 4-biphenyl |
| 1489. | H | H | D¹²² | H | H | H | H | H | L¹⁰⁵ | N | N | N | Ph | Ph |
| 1490. | H | H | D¹²² | H | H | H | H | H | L¹⁰⁵ | N | N | N | 4-biphenyl | 4-biphenyl |
| 1491. | H | H | D¹²² | H | H | H | H | H | L¹⁰⁵ | N | CH | N | Ph | Ph |
| 1492. | H | H | D¹²² | H | H | H | H | H | L¹⁰⁵ | N | CH | N | 4-biphenyl | 4-biphenyl |
| 1493. | H | H | D¹²² | H | H | H | H | H | L¹⁰⁶ | N | N | N | Ph | Ph |
| 1494. | H | H | D¹²² | H | H | H | H | H | L¹⁰⁶ | N | N | N | 4-biphenyl | 4-biphenyl |
| 1495. | H | H | D¹²² | H | H | H | H | H | L¹⁰⁶ | N | CH | N | Ph | Ph |
| 1496. | H | H | D¹²² | H | H | H | H | H | L¹⁰⁶ | N | CH | N | 4-biphenyl | 4-biphenyl |
| 1497. | H | H | D¹²² | H | H | H | H | H | L¹⁰⁷ | N | N | N | Ph | Ph |
| 1498. | H | H | D¹²² | H | H | H | H | H | L¹⁰⁷ | N | N | N | 4-biphenyl | 4-biphenyl |
| 1499. | H | H | D¹²² | H | H | H | H | H | L¹⁰⁷ | N | CH | N | Ph | Ph |
| 1500. | H | H | D¹²² | H | H | H | H | H | L¹⁰⁷ | N | CH | N | 4-biphenyl | 4-biphenyl |
| 1501. | H | H | D¹²² | H | H | H | H | H | L¹⁰⁸ | N | N | N | Ph | Ph |
| 1502. | H | H | D¹²² | H | H | H | H | H | L¹⁰⁸ | N | N | N | 4-biphenyl | 4-biphenyl |
| 1503. | H | H | D¹²² | H | H | H | H | H | L¹⁰⁸ | N | CH | N | Ph | Ph |
| 1504. | H | H | D¹²² | H | H | H | H | H | L¹⁰⁸ | N | CH | N | 4-biphenyl | 4-biphenyl |
| 1505. | H | H | D¹²² | H | H | H | H | H | L¹⁰⁹ | N | N | N | Ph | Ph |
| 1506. | H | H | D¹²² | H | H | H | H | H | L¹⁰⁹ | N | N | N | 4-biphenyl | 4-biphenyl |
| 1507. | H | H | D¹²² | H | H | H | H | H | L¹⁰⁹ | N | CH | N | Ph | Ph |
| 1508. | H | H | D¹²² | H | H | H | H | H | L¹⁰⁹ | N | CH | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1509. | H | H | D¹²² | H | H | H | H | H | L¹¹⁰ | N | N | N | Ph | Ph |
| 1510. | H | H | D¹²² | H | H | H | H | H | L¹¹⁰ | N | N | N | 4-biphenyl | 4-biphenyl |
| 1511. | H | H | D¹²² | H | H | H | H | H | L¹¹⁰ | N | CH | N | Ph | Ph |
| 1512. | H | H | D¹²² | H | H | H | H | H | L¹¹⁰ | N | CH | N | 4-biphenyl | 4-biphenyl |
| 1513. | H | H | D¹²² | H | H | H | H | H | L¹¹¹ | N | N | N | Ph | Ph |
| 1514. | H | H | D¹²² | H | H | H | H | H | L¹¹¹ | N | N | N | 4-biphenyl | 4-biphenyl |
| 1515. | H | H | D¹²² | H | H | H | H | H | L¹¹¹ | N | CH | N | Ph | Ph |
| 1516. | H | H | D¹²² | H | H | H | H | H | L¹¹¹ | N | CH | N | 4-biphenyl | 4-biphenyl |
| 1517. | H | H | D¹²² | H | H | H | H | H | L¹¹² | N | N | N | Ph | Ph |
| 1518. | H | H | D¹²² | H | H | H | H | H | L¹¹² | N | N | N | 4-biphenyl | 4-biphenyl |
| 1519. | H | H | D¹²² | H | H | H | H | H | L¹¹² | N | CH | N | Ph | Ph |
| 1520. | H | H | D¹²² | H | H | H | H | H | L¹¹² | N | CH | N | 4-biphenyl | 4-biphenyl |
| 1521. | H | H | D¹²² | H | H | H | H | H | L¹¹³ | N | N | N | Ph | Ph |
| 1522. | H | H | D¹²² | H | H | H | H | H | L¹¹³ | N | N | N | 4-biphenyl | 4-biphenyl |
| 1523. | H | H | D¹²² | H | H | H | H | H | L¹¹³ | N | CH | N | Ph | Ph |
| 1524. | H | H | D¹²² | H | H | H | H | H | L¹¹³ | N | CH | N | 4-biphenyl | 4-biphenyl |
| 1525. | H | H | D¹²² | H | H | H | H | H | L¹¹⁴ | N | N | N | Ph | Ph |
| 1526. | H | H | D¹²² | H | H | H | H | H | L¹¹⁴ | N | N | N | 4-biphenyl | 4-biphenyl |
| 1527. | H | H | D¹²² | H | H | H | H | H | L¹¹⁴ | N | CH | N | Ph | Ph |
| 1528. | H | H | D¹²² | H | H | H | H | H | L¹¹⁴ | N | CH | N | 4-biphenyl | 4-biphenyl |
| 1529. | H | H | D¹²² | H | H | H | H | H | L¹¹⁵ | N | N | N | Ph | Ph |
| 1530. | H | H | D¹²² | H | H | H | H | H | L¹¹⁵ | N | N | N | 4-biphenyl | 4-biphenyl |
| 1531. | H | H | D¹²² | H | H | H | H | H | L¹¹⁵ | N | CH | N | Ph | Ph |
| 1532. | H | H | D¹²² | H | H | H | H | H | L¹¹⁵ | N | CH | N | 4-biphenyl | 4-biphenyl |
| 1533. | H | H | D¹²² | H | H | H | H | H | L¹¹⁶ | N | N | N | Ph | Ph |
| 1534. | H | H | D¹²² | H | H | H | H | H | L¹¹⁶ | N | N | N | 4-biphenyl | 4-biphenyl |
| 1535. | H | H | D¹²² | H | H | H | H | H | L¹¹⁶ | N | CH | N | Ph | Ph |
| 1536. | H | H | D¹²² | H | H | H | H | H | L¹¹⁶ | N | CH | N | 4-biphenyl | 4-biphenyl |
| 1537. | H | H | D¹²³ | H | H | H | H | H | L¹⁰¹ | N | N | N | Ph | Ph |
| 1538. | H | H | D¹²³ | H | H | H | H | H | L¹⁰¹ | N | N | N | 4-biphenyl | 4-biphenyl |
| 1539. | H | H | D¹²³ | H | H | H | H | H | L¹⁰¹ | N | CH | N | Ph | Ph |
| 1540. | H | H | D¹²³ | H | H | H | H | H | L¹⁰¹ | N | CH | N | 4-biphenyl | 4-biphenyl |
| 1541. | H | H | D¹²³ | H | H | H | H | H | L¹⁰² | N | N | N | Ph | Ph |
| 1542. | H | H | D¹²³ | H | H | H | H | H | L¹⁰² | N | N | N | 4-biphenyl | 4-biphenyl |
| 1543. | H | H | D¹²³ | H | H | H | H | H | L¹⁰² | N | CH | N | Ph | Ph |
| 1544. | H | H | D¹²³ | H | H | H | H | H | L¹⁰² | N | CH | N | 4-biphenyl | 4-biphenyl |
| 1545. | H | H | D¹²³ | H | H | H | H | H | L¹⁰³ | N | N | N | Ph | Ph |
| 1546. | H | H | D¹²³ | H | H | H | H | H | L¹⁰³ | N | N | N | 4-biphenyl | 4-biphenyl |
| 1547. | H | H | D¹²³ | H | H | H | H | H | L¹⁰³ | N | CH | N | Ph | Ph |
| 1548. | H | H | D¹²³ | H | H | H | H | H | L¹⁰³ | N | CH | N | 4-biphenyl | 4-biphenyl |
| 1549. | H | H | D¹²³ | H | H | H | H | H | L¹⁰⁴ | N | N | N | Ph | Ph |
| 1550. | H | H | D¹²³ | H | H | H | H | H | L¹⁰⁴ | N | N | N | 4-biphenyl | 4-biphenyl |
| 1551. | H | H | D¹²³ | H | H | H | H | H | L¹⁰⁴ | N | CH | N | Ph | Ph |
| 1552. | H | H | D¹²³ | H | H | H | H | H | L¹⁰⁴ | N | CH | N | 4-biphenyl | 4-biphenyl |
| 1553. | H | H | D¹²³ | H | H | H | H | H | L¹⁰⁵ | N | N | N | Ph | Ph |
| 1554. | H | H | D¹²³ | H | H | H | H | H | L¹⁰⁵ | N | N | N | 4-biphenyl | 4-biphenyl |
| 1555. | H | H | D¹²³ | H | H | H | H | H | L¹⁰⁵ | N | CH | N | Ph | Ph |
| 1556. | H | H | D¹²³ | H | H | H | H | H | L¹⁰⁵ | N | CH | N | 4-biphenyl | 4-biphenyl |
| 1557. | H | H | D¹²³ | H | H | H | H | H | L¹⁰⁶ | N | N | N | Ph | Ph |
| 1558. | H | H | D¹²³ | H | H | H | H | H | L¹⁰⁶ | N | N | N | 4-biphenyl | 4-biphenyl |

| Compound number | R$^1$ | R$^2$ | R$^3$ | R$^4$ | R$^5$ | R$^6$ | R$^7$ | R$^8$ | L$^1$ | Z$^1$ | Z$^3$ | Z$^5$ | R$^{91}$ | R$^{92}$ |
|---|---|---|---|---|---|---|---|---|---|---|---|---|---|---|
| 1559. | H | H | D$^{123}$ | H | H | H | H | H | L$^{106}$ | N | CH | N | Ph | Ph |
| 1560. | H | H | D$^{123}$ | H | H | H | H | H | L$^{106}$ | N | CH | N | 4-biphenyl | 4-biphenyl |
| 1561. | H | H | D$^{123}$ | H | H | H | H | H | L$^{107}$ | N | N | N | Ph | Ph |
| 1562. | H | H | D$^{123}$ | H | H | H | H | H | L$^{107}$ | N | N | N | 4-biphenyl | 4-biphenyl |
| 1563. | H | H | D$^{123}$ | H | H | H | H | H | L$^{107}$ | N | CH | N | Ph | Ph |
| 1564. | H | H | D$^{123}$ | H | H | H | H | H | L$^{107}$ | N | CH | N | 4-biphenyl | 4-biphenyl |
| 1565. | H | H | D$^{123}$ | H | H | H | H | H | L$^{108}$ | N | N | N | Ph | Ph |
| 1566. | H | H | D$^{123}$ | H | H | H | H | H | L$^{108}$ | N | N | N | 4-biphenyl | 4-biphenyl |
| 1567. | H | H | D$^{123}$ | H | H | H | H | H | L$^{108}$ | N | CH | N | Ph | Ph |
| 1568. | H | H | D$^{123}$ | H | H | H | H | H | L$^{108}$ | N | CH | N | 4-biphenyl | 4-biphenyl |
| 1569. | H | H | D$^{123}$ | H | H | H | H | H | L$^{109}$ | N | N | N | Ph | Ph |
| 1570. | H | H | D$^{123}$ | H | H | H | H | H | L$^{109}$ | N | N | N | 4-biphenyl | 4-biphenyl |
| 1571. | H | H | D$^{123}$ | H | H | H | H | H | L$^{109}$ | N | CH | N | Ph | Ph |
| 1572. | H | H | D$^{123}$ | H | H | H | H | H | L$^{109}$ | N | CH | N | 4-biphenyl | 4-biphenyl |
| 1573. | H | H | D$^{123}$ | H | H | H | H | H | L$^{110}$ | N | N | N | Ph | Ph |
| 1574. | H | H | D$^{123}$ | H | H | H | H | H | L$^{110}$ | N | N | N | 4-biphenyl | 4-biphenyl |
| 1575. | H | H | D$^{123}$ | H | H | H | H | H | L$^{110}$ | N | CH | N | Ph | Ph |
| 1576. | H | H | D$^{123}$ | H | H | H | H | H | L$^{110}$ | N | CH | N | 4-biphenyl | 4-biphenyl |
| 1577. | H | H | D$^{123}$ | H | H | H | H | H | L$^{111}$ | N | N | N | Ph | Ph |
| 1578. | H | H | D$^{123}$ | H | H | H | H | H | L$^{111}$ | N | N | N | 4-biphenyl | 4-biphenyl |
| 1579. | H | H | D$^{123}$ | H | H | H | H | H | L$^{111}$ | N | CH | N | Ph | Ph |
| 1580. | H | H | D$^{123}$ | H | H | H | H | H | L$^{111}$ | N | CH | N | 4-biphenyl | 4-biphenyl |
| 1581. | H | H | D$^{123}$ | H | H | H | H | H | L$^{112}$ | N | N | N | Ph | Ph |
| 1582. | H | H | D$^{123}$ | H | H | H | H | H | L$^{112}$ | N | N | N | 4-biphenyl | 4-biphenyl |
| 1583. | H | H | D$^{123}$ | H | H | H | H | H | L$^{112}$ | N | CH | N | Ph | Ph |
| 1584. | H | H | D$^{123}$ | H | H | H | H | H | L$^{112}$ | N | CH | N | 4-biphenyl | 4-biphenyl |
| 1585. | H | H | D$^{123}$ | H | H | H | H | H | L$^{113}$ | N | N | N | Ph | Ph |
| 1586. | H | H | D$^{123}$ | H | H | H | H | H | L$^{113}$ | N | N | N | 4-biphenyl | 4-biphenyl |
| 1587. | H | H | D$^{123}$ | H | H | H | H | H | L$^{113}$ | N | CH | N | Ph | Ph |
| 1588. | H | H | D$^{123}$ | H | H | H | H | H | L$^{113}$ | N | CH | N | 4-biphenyl | 4-biphenyl |
| 1589. | H | H | D$^{123}$ | H | H | H | H | H | L$^{114}$ | N | N | N | Ph | Ph |
| 1590. | H | H | D$^{123}$ | H | H | H | H | H | L$^{114}$ | N | N | N | 4-biphenyl | 4-biphenyl |
| 1591. | H | H | D$^{123}$ | H | H | H | H | H | L$^{114}$ | N | CH | N | Ph | Ph |
| 1592. | H | H | D$^{123}$ | H | H | H | H | H | L$^{114}$ | N | CH | N | 4-biphenyl | 4-biphenyl |
| 1593. | H | H | D$^{123}$ | H | H | H | H | H | L$^{115}$ | N | N | N | Ph | Ph |
| 1594. | H | H | D$^{123}$ | H | H | H | H | H | L$^{115}$ | N | N | N | 4-biphenyl | 4-biphenyl |
| 1595. | H | H | D$^{123}$ | H | H | H | H | H | L$^{115}$ | N | CH | N | Ph | Ph |
| 1596. | H | H | D$^{123}$ | H | H | H | H | H | L$^{115}$ | N | CH | N | 4-biphenyl | 4-biphenyl |
| 1597. | H | H | D$^{123}$ | H | H | H | H | H | L$^{116}$ | N | N | N | Ph | Ph |
| 1598. | H | H | D$^{123}$ | H | H | H | H | H | L$^{116}$ | N | N | N | 4-biphenyl | 4-biphenyl |
| 1599. | H | H | D$^{123}$ | H | H | H | H | H | L$^{116}$ | N | CH | N | Ph | Ph |
| 1600. | H | H | D$^{123}$ | H | H | H | H | H | L$^{116}$ | N | CH | N | 4-biphenyl | 4-biphenyl |
| 1601. | H | H | D$^{124}$ | H | H | H | H | H | L$^{101}$ | N | N | N | Ph | Ph |
| 1602. | H | H | D$^{124}$ | H | H | H | H | H | L$^{101}$ | N | N | N | 4-biphenyl | 4-biphenyl |
| 1603. | H | H | D$^{124}$ | H | H | H | H | H | L$^{101}$ | N | CH | N | Ph | Ph |
| 1604. | H | H | D$^{124}$ | H | H | H | H | H | L$^{101}$ | N | CH | N | 4-biphenyl | 4-biphenyl |
| 1605. | H | H | D$^{124}$ | H | H | H | H | H | L$^{102}$ | N | N | N | Ph | Ph |
| 1606. | H | H | D$^{124}$ | H | H | H | H | H | L$^{102}$ | N | N | N | 4-biphenyl | 4-biphenyl |
| 1607. | H | H | D$^{124}$ | H | H | H | H | H | L$^{102}$ | N | CH | N | Ph | Ph |
| 1608. | H | H | D$^{124}$ | H | H | H | H | H | L$^{102}$ | N | CH | N | 4-biphenyl | 4-biphenyl |

-continued

| Compound number | $R^1$ | $R^2$ | $R^3$ | $R^4$ | $R^5$ | $R^6$ | $R^7$ | $R^8$ | $L^1$ | $Z^1$ | $Z^3$ | $Z^5$ | $R^{91}$ | $R^{92}$ |
|---|---|---|---|---|---|---|---|---|---|---|---|---|---|---|
| 1609. | H | H | $D^{124}$ | H | H | H | H | H | $L^{103}$ | N | N | N | Ph | Ph |
| 1610. | H | H | $D^{124}$ | H | H | H | H | H | $L^{103}$ | N | N | N | 4-biphenyl | 4-biphenyl |
| 1611. | H | H | $D^{124}$ | H | H | H | H | H | $L^{103}$ | N | CH | N | Ph | Ph |
| 1612. | H | H | $D^{124}$ | H | H | H | H | H | $L^{103}$ | N | CH | N | 4-biphenyl | 4-biphenyl |
| 1613. | H | H | $D^{124}$ | H | H | H | H | H | $L^{104}$ | N | N | N | Ph | Ph |
| 1614. | H | H | $D^{124}$ | H | H | H | H | H | $L^{104}$ | N | N | N | 4-biphenyl | 4-biphenyl |
| 1615. | H | H | $D^{124}$ | H | H | H | H | H | $L^{104}$ | N | CH | N | Ph | Ph |
| 1616. | H | H | $D^{124}$ | H | H | H | H | H | $L^{104}$ | N | CH | N | 4-biphenyl | 4-biphenyl |
| 1617. | H | H | $D^{124}$ | H | H | H | H | H | $L^{105}$ | N | N | N | Ph | Ph |
| 1618. | H | H | $D^{124}$ | H | H | H | H | H | $L^{105}$ | N | N | N | 4-biphenyl | 4-biphenyl |
| 1619. | H | H | $D^{124}$ | H | H | H | H | H | $L^{105}$ | N | CH | N | Ph | Ph |
| 1620. | H | H | $D^{124}$ | H | H | H | H | H | $L^{105}$ | N | CH | N | 4-biphenyl | 4-biphenyl |
| 1621. | H | H | $D^{124}$ | H | H | H | H | H | $L^{106}$ | N | N | N | Ph | Ph |
| 1622. | H | H | $D^{124}$ | H | H | H | H | H | $L^{106}$ | N | N | N | 4-biphenyl | 4-biphenyl |
| 1623. | H | H | $D^{124}$ | H | H | H | H | H | $L^{106}$ | N | CH | N | Ph | Ph |
| 1624. | H | H | $D^{124}$ | H | H | H | H | H | $L^{106}$ | N | CH | N | 4-biphenyl | 4-biphenyl |
| 1625. | H | H | $D^{124}$ | H | H | H | H | H | $L^{107}$ | N | N | N | Ph | Ph |
| 1626. | H | H | $D^{124}$ | H | H | H | H | H | $L^{107}$ | N | N | N | 4-biphenyl | 4-biphenyl |
| 1627. | H | H | $D^{124}$ | H | H | H | H | H | $L^{107}$ | N | CH | N | Ph | Ph |
| 1628. | H | H | $D^{124}$ | H | H | H | H | H | $L^{107}$ | N | CH | N | 4-biphenyl | 4-biphenyl |
| 1629. | H | H | $D^{124}$ | H | H | H | H | H | $L^{108}$ | N | N | N | Ph | Ph |
| 1630. | H | H | $D^{124}$ | H | H | H | H | H | $L^{108}$ | N | N | N | 4-biphenyl | 4-biphenyl |
| 1631. | H | H | $D^{124}$ | H | H | H | H | H | $L^{108}$ | N | CH | N | Ph | Ph |
| 1632. | H | H | $D^{124}$ | H | H | H | H | H | $L^{108}$ | N | CH | N | 4-biphenyl | 4-biphenyl |
| 1633. | H | H | $D^{124}$ | H | H | H | H | H | $L^{109}$ | N | N | N | Ph | Ph |
| 1634. | H | H | $D^{124}$ | H | H | H | H | H | $L^{109}$ | N | N | N | 4-biphenyl | 4-biphenyl |
| 1635. | H | H | $D^{124}$ | H | H | H | H | H | $L^{109}$ | N | CH | N | Ph | Ph |
| 1636. | H | H | $D^{124}$ | H | H | H | H | H | $L^{109}$ | N | CH | N | 4-biphenyl | 4-biphenyl |
| 1637. | H | H | $D^{124}$ | H | H | H | H | H | $L^{110}$ | N | N | N | Ph | Ph |
| 1638. | H | H | $D^{124}$ | H | H | H | H | H | $L^{110}$ | N | N | N | 4-biphenyl | 4-biphenyl |
| 1639. | H | H | $D^{124}$ | H | H | H | H | H | $L^{110}$ | N | CH | N | Ph | Ph |
| 1640. | H | H | $D^{124}$ | H | H | H | H | H | $L^{110}$ | N | CH | N | 4-biphenyl | 4-biphenyl |
| 1641. | H | H | $D^{124}$ | H | H | H | H | H | $L^{111}$ | N | N | N | Ph | Ph |
| 1642. | H | H | $D^{124}$ | H | H | H | H | H | $L^{111}$ | N | N | N | 4-biphenyl | 4-biphenyl |
| 1643. | H | H | $D^{124}$ | H | H | H | H | H | $L^{111}$ | N | CH | N | Ph | Ph |
| 1644. | H | H | $D^{124}$ | H | H | H | H | H | $L^{111}$ | N | CH | N | 4-biphenyl | 4-biphenyl |
| 1645. | H | H | $D^{124}$ | H | H | H | H | H | $L^{112}$ | N | N | N | Ph | Ph |
| 1646. | H | H | $D^{124}$ | H | H | H | H | H | $L^{112}$ | N | N | N | 4-biphenyl | 4-biphenyl |
| 1647. | H | H | $D^{124}$ | H | H | H | H | H | $L^{112}$ | N | CH | N | Ph | Ph |
| 1648. | H | H | $D^{124}$ | H | H | H | H | H | $L^{112}$ | N | CH | N | 4-biphenyl | 4-biphenyl |
| 1649. | H | H | $D^{124}$ | H | H | H | H | H | $L^{113}$ | N | N | N | Ph | Ph |
| 1650. | H | H | $D^{124}$ | H | H | H | H | H | $L^{113}$ | N | N | N | 4-biphenyl | 4-biphenyl |
| 1651. | H | H | $D^{124}$ | H | H | H | H | H | $L^{113}$ | N | CH | N | Ph | Ph |
| 1652. | H | H | $D^{124}$ | H | H | H | H | H | $L^{113}$ | N | CH | N | 4-biphenyl | 4-biphenyl |
| 1653. | H | H | $D^{124}$ | H | H | H | H | H | $L^{114}$ | N | N | N | Ph | Ph |
| 1654. | H | H | $D^{124}$ | H | H | H | H | H | $L^{114}$ | N | N | N | 4-biphenyl | 4-biphenyl |
| 1655. | H | H | $D^{124}$ | H | H | H | H | H | $L^{114}$ | N | CH | N | Ph | Ph |
| 1656. | H | H | $D^{124}$ | H | H | H | H | H | $L^{114}$ | N | CH | N | 4-biphenyl | 4-biphenyl |
| 1657. | H | H | $D^{124}$ | H | H | H | H | H | $L^{115}$ | N | N | N | Ph | Ph |
| 1658. | H | H | $D^{124}$ | H | H | H | H | H | $L^{115}$ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1659. | H | H | D¹²⁴ | H | H | H | H | H | L¹¹⁵ | N | CH | N | Ph | Ph |
| 1660. | H | H | D¹²⁴ | H | H | H | H | H | L¹¹⁵ | N | CH | N | 4-biphenyl | 4-biphenyl |
| 1661. | H | H | D¹²⁴ | H | H | H | H | H | L¹¹⁶ | N | N | N | Ph | Ph |
| 1662. | H | H | D¹²⁴ | H | H | H | H | H | L¹¹⁶ | N | N | N | 4-biphenyl | 4-biphenyl |
| 1663. | H | H | D¹²⁴ | H | H | H | H | H | L¹¹⁶ | N | CH | N | Ph | Ph |
| 1664. | H | H | D¹²⁴ | H | H | H | H | H | L¹¹⁶ | N | CH | N | 4-biphenyl | 4-biphenyl |
| 1665. | H | H | D¹²⁵ | H | H | H | H | H | L¹⁰¹ | N | N | N | Ph | Ph |
| 1666. | H | H | D¹²⁵ | H | H | H | H | H | L¹⁰¹ | N | N | N | 4-biphenyl | 4-biphenyl |
| 1667. | H | H | D¹²⁵ | H | H | H | H | H | L¹⁰¹ | N | CH | N | Ph | Ph |
| 1668. | H | H | D¹²⁵ | H | H | H | H | H | L¹⁰¹ | N | CH | N | 4-biphenyl | 4-biphenyl |
| 1669. | H | H | D¹²⁵ | H | H | H | H | H | L¹⁰² | N | N | N | Ph | Ph |
| 1670. | H | H | D¹²⁵ | H | H | H | H | H | L¹⁰² | N | N | N | 4-biphenyl | 4-biphenyl |
| 1671. | H | H | D¹²⁵ | H | H | H | H | H | L¹⁰² | N | CH | N | Ph | Ph |
| 1672. | H | H | D¹²⁵ | H | H | H | H | H | L¹⁰² | N | CH | N | 4-biphenyl | 4-biphenyl |
| 1673. | H | H | D¹²⁵ | H | H | H | H | H | L¹⁰³ | N | N | N | Ph | Ph |
| 1674. | H | H | D¹²⁵ | H | H | H | H | H | L¹⁰³ | N | N | N | 4-biphenyl | 4-biphenyl |
| 1675. | H | H | D¹²⁵ | H | H | H | H | H | L¹⁰³ | N | CH | N | Ph | Ph |
| 1676. | H | H | D¹²⁵ | H | H | H | H | H | L¹⁰³ | N | CH | N | 4-biphenyl | 4-biphenyl |
| 1677. | H | H | D¹²⁵ | H | H | H | H | H | L¹⁰⁴ | N | N | N | Ph | Ph |
| 1678. | H | H | D¹²⁵ | H | H | H | H | H | L¹⁰⁴ | N | N | N | 4-biphenyl | 4-biphenyl |
| 1679. | H | H | D¹²⁵ | H | H | H | H | H | L¹⁰⁴ | N | CH | N | Ph | Ph |
| 1680. | H | H | D¹²⁵ | H | H | H | H | H | L¹⁰⁴ | N | CH | N | 4-biphenyl | 4-biphenyl |
| 1681. | H | H | D¹²⁵ | H | H | H | H | H | L¹⁰⁵ | N | N | N | Ph | Ph |
| 1682. | H | H | D¹²⁵ | H | H | H | H | H | L¹⁰⁵ | N | N | N | 4-biphenyl | 4-biphenyl |
| 1683. | H | H | D¹²⁵ | H | H | H | H | H | L¹⁰⁵ | N | CH | N | Ph | Ph |
| 1684. | H | H | D¹²⁵ | H | H | H | H | H | L¹⁰⁵ | N | CH | N | 4-biphenyl | 4-biphenyl |
| 1685. | H | H | D¹²⁵ | H | H | H | H | H | L¹⁰⁶ | N | N | N | Ph | Ph |
| 1686. | H | H | D¹²⁵ | H | H | H | H | H | L¹⁰⁶ | N | N | N | 4-biphenyl | 4-biphenyl |
| 1687. | H | H | D¹²⁵ | H | H | H | H | H | L¹⁰⁶ | N | CH | N | Ph | Ph |
| 1688. | H | H | D¹²⁵ | H | H | H | H | H | L¹⁰⁶ | N | CH | N | 4-biphenyl | 4-biphenyl |
| 1689. | H | H | D¹²⁵ | H | H | H | H | H | L¹⁰⁷ | N | N | N | Ph | Ph |
| 1690. | H | H | D¹²⁵ | H | H | H | H | H | L¹⁰⁷ | N | N | N | 4-biphenyl | 4-biphenyl |
| 1691. | H | H | D¹²⁵ | H | H | H | H | H | L¹⁰⁷ | N | CH | N | Ph | Ph |
| 1692. | H | H | D¹²⁵ | H | H | H | H | H | L¹⁰⁷ | N | CH | N | 4-biphenyl | 4-biphenyl |
| 1693. | H | H | D¹²⁵ | H | H | H | H | H | L¹⁰⁸ | N | N | N | Ph | Ph |
| 1694. | H | H | D¹²⁵ | H | H | H | H | H | L¹⁰⁸ | N | N | N | 4-biphenyl | 4-biphenyl |
| 1695. | H | H | D¹²⁵ | H | H | H | H | H | L¹⁰⁸ | N | CH | N | Ph | Ph |
| 1696. | H | H | D¹²⁵ | H | H | H | H | H | L¹⁰⁸ | N | CH | N | 4-biphenyl | 4-biphenyl |
| 1697. | H | H | D¹²⁵ | H | H | H | H | H | L¹⁰⁹ | N | N | N | Ph | Ph |
| 1698. | H | H | D¹²⁵ | H | H | H | H | H | L¹⁰⁹ | N | N | N | 4-biphenyl | 4-biphenyl |
| 1699. | H | H | D¹²⁵ | H | H | H | H | H | L¹⁰⁹ | N | CH | N | Ph | Ph |
| 1700. | H | H | D¹²⁵ | H | H | H | H | H | L¹⁰⁹ | N | CH | N | 4-biphenyl | 4-biphenyl |
| 1701. | H | H | D¹²⁵ | H | H | H | H | H | L¹¹⁰ | N | N | N | Ph | Ph |
| 1702. | H | H | D¹²⁵ | H | H | H | H | H | L¹¹⁰ | N | N | N | 4-biphenyl | 4-biphenyl |
| 1703. | H | H | D¹²⁵ | H | H | H | H | H | L¹¹⁰ | N | CH | N | Ph | Ph |
| 1704. | H | H | D¹²⁵ | H | H | H | H | H | L¹¹⁰ | N | CH | N | 4-biphenyl | 4-biphenyl |
| 1705. | H | H | D¹²⁵ | H | H | H | H | H | L¹¹¹ | N | N | N | Ph | Ph |
| 1706. | H | H | D¹²⁵ | H | H | H | H | H | L¹¹¹ | N | N | N | 4-biphenyl | 4-biphenyl |
| 1707. | H | H | D¹²⁵ | H | H | H | H | H | L¹¹¹ | N | CH | N | Ph | Ph |
| 1708. | H | H | D¹²⁵ | H | H | H | H | H | L¹¹¹ | N | CH | N | 4-biphenyl | 4-biphenyl |

-continued

| Compound number | R$^1$ | R$^2$ | R$^3$ | R$^4$ | R$^5$ | R$^6$ | R$^7$ | R$^8$ | L$^1$ | Z$^1$ | Z$^3$ | Z$^5$ | R$^{91}$ | R$^{92}$ |
|---|---|---|---|---|---|---|---|---|---|---|---|---|---|---|
| 1709. | H | H | D$^{125}$ | H | H | H | H | H | L$^{112}$ | N | N | N | Ph | Ph |
| 1710. | H | H | D$^{125}$ | H | H | H | H | H | L$^{112}$ | N | N | N | 4-biphenyl | 4-biphenyl |
| 1711. | H | H | D$^{125}$ | H | H | H | H | H | L$^{112}$ | N | CH | N | Ph | Ph |
| 1712. | H | H | D$^{125}$ | H | H | H | H | H | L$^{112}$ | N | CH | N | 4-biphenyl | 4-biphenyl |
| 1713. | H | H | D$^{125}$ | H | H | H | H | H | L$^{113}$ | N | N | N | Ph | Ph |
| 1714. | H | H | D$^{125}$ | H | H | H | H | H | L$^{113}$ | N | N | N | 4-biphenyl | 4-biphenyl |
| 1715. | H | H | D$^{125}$ | H | H | H | H | H | L$^{113}$ | N | CH | N | Ph | Ph |
| 1716. | H | H | D$^{125}$ | H | H | H | H | H | L$^{113}$ | N | CH | N | 4-biphenyl | 4-biphenyl |
| 1717. | H | H | D$^{125}$ | H | H | H | H | H | L$^{114}$ | N | N | N | Ph | Ph |
| 1718. | H | H | D$^{125}$ | H | H | H | H | H | L$^{114}$ | N | N | N | 4-biphenyl | 4-biphenyl |
| 1719. | H | H | D$^{125}$ | H | H | H | H | H | L$^{114}$ | N | CH | N | Ph | Ph |
| 1720. | H | H | D$^{125}$ | H | H | H | H | H | L$^{114}$ | N | CH | N | 4-biphenyl | 4-biphenyl |
| 1721. | H | H | D$^{125}$ | H | H | H | H | H | L$^{115}$ | N | N | N | Ph | Ph |
| 1722. | H | H | D$^{125}$ | H | H | H | H | H | L$^{115}$ | N | N | N | 4-biphenyl | 4-biphenyl |
| 1723. | H | H | D$^{125}$ | H | H | H | H | H | L$^{115}$ | N | CH | N | Ph | Ph |
| 1724. | H | H | D$^{125}$ | H | H | H | H | H | L$^{115}$ | N | CH | N | 4-biphenyl | 4-biphenyl |
| 1725. | H | H | D$^{125}$ | H | H | H | H | H | L$^{116}$ | N | N | N | Ph | Ph |
| 1726. | H | H | D$^{125}$ | H | H | H | H | H | L$^{116}$ | N | N | N | 4-biphenyl | 4-biphenyl |
| 1727. | H | H | D$^{125}$ | H | H | H | H | H | L$^{116}$ | N | CH | N | Ph | Ph |
| 1728. | H | H | D$^{125}$ | H | H | H | H | H | L$^{116}$ | N | CH | N | 4-biphenyl | 4-biphenyl |
| 1729. | H | H | D$^{126}$ | H | H | H | H | H | L$^{101}$ | N | N | N | Ph | Ph |
| 1730. | H | H | D$^{126}$ | H | H | H | H | H | L$^{101}$ | N | N | N | 4-biphenyl | 4-biphenyl |
| 1731. | H | H | D$^{126}$ | H | H | H | H | H | L$^{101}$ | N | CH | N | Ph | Ph |
| 1732. | H | H | D$^{126}$ | H | H | H | H | H | L$^{101}$ | N | CH | N | 4-biphenyl | 4-biphenyl |
| 1733. | H | H | D$^{126}$ | H | H | H | H | H | L$^{102}$ | N | N | N | Ph | Ph |
| 1734. | H | H | D$^{126}$ | H | H | H | H | H | L$^{102}$ | N | N | N | 4-biphenyl | 4-biphenyl |
| 1735. | H | H | D$^{126}$ | H | H | H | H | H | L$^{102}$ | N | CH | N | Ph | Ph |
| 1736. | H | H | D$^{126}$ | H | H | H | H | H | L$^{102}$ | N | CH | N | 4-biphenyl | 4-biphenyl |
| 1737. | H | H | D$^{126}$ | H | H | H | H | H | L$^{103}$ | N | N | N | Ph | Ph |
| 1738. | H | H | D$^{126}$ | H | H | H | H | H | L$^{103}$ | N | N | N | 4-biphenyl | 4-biphenyl |
| 1739. | H | H | D$^{126}$ | H | H | H | H | H | L$^{103}$ | N | CH | N | Ph | Ph |
| 1740. | H | H | D$^{126}$ | H | H | H | H | H | L$^{103}$ | N | CH | N | 4-biphenyl | 4-biphenyl |
| 1741. | H | H | D$^{126}$ | H | H | H | H | H | L$^{104}$ | N | N | N | Ph | Ph |
| 1742. | H | H | D$^{126}$ | H | H | H | H | H | L$^{104}$ | N | N | N | 4-biphenyl | 4-biphenyl |
| 1743. | H | H | D$^{126}$ | H | H | H | H | H | L$^{104}$ | N | CH | N | Ph | Ph |
| 1744. | H | H | D$^{126}$ | H | H | H | H | H | L$^{104}$ | N | CH | N | 4-biphenyl | 4-biphenyl |
| 1745. | H | H | D$^{126}$ | H | H | H | H | H | L$^{105}$ | N | N | N | Ph | Ph |
| 1746. | H | H | D$^{126}$ | H | H | H | H | H | L$^{105}$ | N | N | N | 4-biphenyl | 4-biphenyl |
| 1747. | H | H | D$^{126}$ | H | H | H | H | H | L$^{105}$ | N | CH | N | Ph | Ph |
| 1748. | H | H | D$^{126}$ | H | H | H | H | H | L$^{105}$ | N | CH | N | 4-biphenyl | 4-biphenyl |
| 1749. | H | H | D$^{126}$ | H | H | H | H | H | L$^{106}$ | N | N | N | Ph | Ph |
| 1750. | H | H | D$^{126}$ | H | H | H | H | H | L$^{106}$ | N | N | N | 4-biphenyl | 4-biphenyl |
| 1751. | H | H | D$^{126}$ | H | H | H | H | H | L$^{106}$ | N | CH | N | Ph | Ph |
| 1752. | H | H | D$^{126}$ | H | H | H | H | H | L$^{106}$ | N | CH | N | 4-biphenyl | 4-biphenyl |
| 1753. | H | H | D$^{126}$ | H | H | H | H | H | L$^{107}$ | N | N | N | Ph | Ph |
| 1754. | H | H | D$^{126}$ | H | H | H | H | H | L$^{107}$ | N | N | N | 4-biphenyl | 4-biphenyl |
| 1755. | H | H | D$^{126}$ | H | H | H | H | H | L$^{107}$ | N | CH | N | Ph | Ph |
| 1756. | H | H | D$^{126}$ | H | H | H | H | H | L$^{107}$ | N | CH | N | 4-biphenyl | 4-biphenyl |
| 1757. | H | H | D$^{126}$ | H | H | H | H | H | L$^{108}$ | N | N | N | Ph | Ph |
| 1758. | H | H | D$^{126}$ | H | H | H | H | H | L$^{108}$ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1759. | H | H | D¹²⁶ | H | H | H | H | H | L¹⁰⁸ | N | CH | N | Ph | Ph |
| 1760. | H | H | D¹²⁶ | H | H | H | H | H | L¹⁰⁸ | N | CH | N | 4-biphenyl | 4-biphenyl |
| 1761. | H | H | D¹²⁶ | H | H | H | H | H | L¹⁰⁹ | N | N | N | Ph | Ph |
| 1762. | H | H | D¹²⁶ | H | H | H | H | H | L¹⁰⁹ | N | N | N | 4-biphenyl | 4-biphenyl |
| 1763. | H | H | D¹²⁶ | H | H | H | H | H | L¹⁰⁹ | N | CH | N | Ph | Ph |
| 1764. | H | H | D¹²⁶ | H | H | H | H | H | L¹⁰⁹ | N | CH | N | 4-biphenyl | 4-biphenyl |
| 1765. | H | H | D¹²⁶ | H | H | H | H | H | L¹¹⁰ | N | N | N | Ph | Ph |
| 1766. | H | H | D¹²⁶ | H | H | H | H | H | L¹¹⁰ | N | N | N | 4-biphenyl | 4-biphenyl |
| 1767. | H | H | D¹²⁶ | H | H | H | H | H | L¹¹⁰ | N | CH | N | Ph | Ph |
| 1768. | H | H | D¹²⁶ | H | H | H | H | H | L¹¹⁰ | N | CH | N | 4-biphenyl | 4-biphenyl |
| 1769. | H | H | D¹²⁶ | H | H | H | H | H | L¹¹¹ | N | N | N | Ph | Ph |
| 1770. | H | H | D¹²⁶ | H | H | H | H | H | L¹¹¹ | N | N | N | 4-biphenyl | 4-biphenyl |
| 1771. | H | H | D¹²⁶ | H | H | H | H | H | L¹¹¹ | N | CH | N | Ph | Ph |
| 1772. | H | H | D¹²⁶ | H | H | H | H | H | L¹¹¹ | N | CH | N | 4-biphenyl | 4-biphenyl |
| 1773. | H | H | D¹²⁶ | H | H | H | H | H | L¹¹² | N | N | N | Ph | Ph |
| 1774. | H | H | D¹²⁶ | H | H | H | H | H | L¹¹² | N | N | N | 4-biphenyl | 4-biphenyl |
| 1775. | H | H | D¹²⁶ | H | H | H | H | H | L¹¹² | N | CH | N | Ph | Ph |
| 1776. | H | H | D¹²⁶ | H | H | H | H | H | L¹¹² | N | CH | N | 4-biphenyl | 4-biphenyl |
| 1777. | H | H | D¹²⁶ | H | H | H | H | H | L¹¹³ | N | N | N | Ph | Ph |
| 1778. | H | H | D¹²⁶ | H | H | H | H | H | L¹¹³ | N | N | N | 4-biphenyl | 4-biphenyl |
| 1779. | H | H | D¹²⁶ | H | H | H | H | H | L¹¹³ | N | CH | N | Ph | Ph |
| 1780. | H | H | D¹²⁶ | H | H | H | H | H | L¹¹³ | N | CH | N | 4-biphenyl | 4-biphenyl |
| 1781. | H | H | D¹²⁶ | H | H | H | H | H | L¹¹⁴ | N | N | N | Ph | Ph |
| 1782. | H | H | D¹²⁶ | H | H | H | H | H | L¹¹⁴ | N | N | N | 4-biphenyl | 4-biphenyl |
| 1783. | H | H | D¹²⁶ | H | H | H | H | H | L¹¹⁴ | N | CH | N | Ph | Ph |
| 1784. | H | H | D¹²⁶ | H | H | H | H | H | L¹¹⁴ | N | CH | N | 4-biphenyl | 4-biphenyl |
| 1785. | H | H | D¹²⁶ | H | H | H | H | H | L¹¹⁵ | N | N | N | Ph | Ph |
| 1786. | H | H | D¹²⁶ | H | H | H | H | H | L¹¹⁵ | N | N | N | 4-biphenyl | 4-biphenyl |
| 1787. | H | H | D¹²⁶ | H | H | H | H | H | L¹¹⁵ | N | CH | N | Ph | Ph |
| 1788. | H | H | D¹²⁶ | H | H | H | H | H | L¹¹⁵ | N | CH | N | 4-biphenyl | 4-biphenyl |
| 1789. | H | H | D¹²⁶ | H | H | H | H | H | L¹¹⁶ | N | N | N | Ph | Ph |
| 1790. | H | H | D¹²⁶ | H | H | H | H | H | L¹¹⁶ | N | N | N | 4-biphenyl | 4-biphenyl |
| 1791. | H | H | D¹²⁶ | H | H | H | H | H | L¹¹⁶ | N | CH | N | Ph | Ph |
| 1792. | H | H | D¹²⁶ | H | H | H | H | H | L¹¹⁶ | N | CH | N | 4-biphenyl | 4-biphenyl |
| 1793. | H | H | D¹²⁷ | H | H | H | H | H | L¹⁰¹ | N | N | N | Ph | Ph |
| 1794. | H | H | D¹²⁷ | H | H | H | H | H | L¹⁰¹ | N | N | N | 4-biphenyl | 4-biphenyl |
| 1795. | H | H | D¹²⁷ | H | H | H | H | H | L¹⁰¹ | N | CH | N | Ph | Ph |
| 1796. | H | H | D¹²⁷ | H | H | H | H | H | L¹⁰¹ | N | CH | N | 4-biphenyl | 4-biphenyl |
| 1797. | H | H | D¹²⁷ | H | H | H | H | H | L¹⁰² | N | N | N | Ph | Ph |
| 1798. | H | H | D¹²⁷ | H | H | H | H | H | L¹⁰² | N | N | N | 4-biphenyl | 4-biphenyl |
| 1799. | H | H | D¹²⁷ | H | H | H | H | H | L¹⁰² | N | CH | N | Ph | Ph |
| 1800. | H | H | D¹²⁷ | H | H | H | H | H | L¹⁰² | N | CH | N | 4-biphenyl | 4-biphenyl |
| 1801. | H | H | D¹²⁷ | H | H | H | H | H | L¹⁰³ | N | N | N | Ph | Ph |
| 1802. | H | H | D¹²⁷ | H | H | H | H | H | L¹⁰³ | N | N | N | 4-biphenyl | 4-biphenyl |
| 1803. | H | H | D¹²⁷ | H | H | H | H | H | L¹⁰³ | N | CH | N | Ph | Ph |
| 1804. | H | H | D¹²⁷ | H | H | H | H | H | L¹⁰³ | N | CH | N | 4-biphenyl | 4-biphenyl |
| 1805. | H | H | D¹²⁷ | H | H | H | H | H | L¹⁰⁴ | N | N | N | Ph | Ph |
| 1806. | H | H | D¹²⁷ | H | H | H | H | H | L¹⁰⁴ | N | N | N | 4-biphenyl | 4-biphenyl |
| 1807. | H | H | D¹²⁷ | H | H | H | H | H | L¹⁰⁴ | N | CH | N | Ph | Ph |
| 1808. | H | H | D¹²⁷ | H | H | H | H | H | L¹⁰⁴ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1809. | H | H | D¹²⁷ | H | H | H | H | H | L¹⁰⁵ | N | N | N | Ph | Ph |
| 1810. | H | H | D¹²⁷ | H | H | H | H | H | L¹⁰⁵ | N | N | N | 4-biphenyl | 4-biphenyl |
| 1811. | H | H | D¹²⁷ | H | H | H | H | H | L¹⁰⁵ | N | CH | N | Ph | Ph |
| 1812. | H | H | D¹²⁷ | H | H | H | H | H | L¹⁰⁵ | N | CH | N | 4-biphenyl | 4-biphenyl |
| 1813. | H | H | D¹²⁷ | H | H | H | H | H | L¹⁰⁶ | N | N | N | Ph | Ph |
| 1814. | H | H | D¹²⁷ | H | H | H | H | H | L¹⁰⁶ | N | N | N | 4-biphenyl | 4-biphenyl |
| 1815. | H | H | D¹²⁷ | H | H | H | H | H | L¹⁰⁶ | N | CH | N | Ph | Ph |
| 1816. | H | H | D¹²⁷ | H | H | H | H | H | L¹⁰⁶ | N | CH | N | 4-biphenyl | 4-biphenyl |
| 1817. | H | H | D¹²⁷ | H | H | H | H | H | L¹⁰⁷ | N | N | N | Ph | Ph |
| 1818. | H | H | D¹²⁷ | H | H | H | H | H | L¹⁰⁷ | N | N | N | 4-biphenyl | 4-biphenyl |
| 1819. | H | H | D¹²⁷ | H | H | H | H | H | L¹⁰⁷ | N | CH | N | Ph | Ph |
| 1820. | H | H | D¹²⁷ | H | H | H | H | H | L¹⁰⁷ | N | CH | N | 4-biphenyl | 4-biphenyl |
| 1821. | H | H | D¹²⁷ | H | H | H | H | H | L¹⁰⁸ | N | N | N | Ph | Ph |
| 1822. | H | H | D¹²⁷ | H | H | H | H | H | L¹⁰⁸ | N | N | N | 4-biphenyl | 4-biphenyl |
| 1823. | H | H | D¹²⁷ | H | H | H | H | H | L¹⁰⁸ | N | CH | N | Ph | Ph |
| 1824. | H | H | D¹²⁷ | H | H | H | H | H | L¹⁰⁸ | N | CH | N | 4-biphenyl | 4-biphenyl |
| 1825. | H | H | D¹²⁷ | H | H | H | H | H | L¹⁰⁹ | N | N | N | Ph | Ph |
| 1826. | H | H | D¹²⁷ | H | H | H | H | H | L¹⁰⁹ | N | N | N | 4-biphenyl | 4-biphenyl |
| 1827. | H | H | D¹²⁷ | H | H | H | H | H | L¹⁰⁹ | N | CH | N | Ph | Ph |
| 1828. | H | H | D¹²⁷ | H | H | H | H | H | L¹⁰⁹ | N | CH | N | 4-biphenyl | 4-biphenyl |
| 1829. | H | H | D¹²⁷ | H | H | H | H | H | L¹¹⁰ | N | N | N | Ph | Ph |
| 1830. | H | H | D¹²⁷ | H | H | H | H | H | L¹¹⁰ | N | N | N | 4-biphenyl | 4-biphenyl |
| 1831. | H | H | D¹²⁷ | H | H | H | H | H | L¹¹⁰ | N | CH | N | Ph | Ph |
| 1832. | H | H | D¹²⁷ | H | H | H | H | H | L¹¹⁰ | N | CH | N | 4-biphenyl | 4-biphenyl |
| 1833. | H | H | D¹²⁷ | H | H | H | H | H | L¹¹¹ | N | N | N | Ph | Ph |
| 1834. | H | H | D¹²⁷ | H | H | H | H | H | L¹¹¹ | N | N | N | 4-biphenyl | 4-biphenyl |
| 1835. | H | H | D¹²⁷ | H | H | H | H | H | L¹¹¹ | N | CH | N | Ph | Ph |
| 1836. | H | H | D¹²⁷ | H | H | H | H | H | L¹¹¹ | N | CH | N | 4-biphenyl | 4-biphenyl |
| 1837. | H | H | D¹²⁷ | H | H | H | H | H | L¹¹² | N | N | N | Ph | Ph |
| 1838. | H | H | D¹²⁷ | H | H | H | H | H | L¹¹² | N | N | N | 4-biphenyl | 4-biphenyl |
| 1839. | H | H | D¹²⁷ | H | H | H | H | H | L¹¹² | N | CH | N | Ph | Ph |
| 1840. | H | H | D¹²⁷ | H | H | H | H | H | L¹¹² | N | CH | N | 4-biphenyl | 4-biphenyl |
| 1841. | H | H | D¹²⁷ | H | H | H | H | H | L¹¹³ | N | N | N | Ph | Ph |
| 1842. | H | H | D¹²⁷ | H | H | H | H | H | L¹¹³ | N | N | N | 4-biphenyl | 4-biphenyl |
| 1843. | H | H | D¹²⁷ | H | H | H | H | H | L¹¹³ | N | CH | N | Ph | Ph |
| 1844. | H | H | D¹²⁷ | H | H | H | H | H | L¹¹³ | N | CH | N | 4-biphenyl | 4-biphenyl |
| 1845. | H | H | D¹²⁷ | H | H | H | H | H | L¹¹⁴ | N | N | N | Ph | Ph |
| 1846. | H | H | D¹²⁷ | H | H | H | H | H | L¹¹⁴ | N | N | N | 4-biphenyl | 4-biphenyl |
| 1847. | H | H | D¹²⁷ | H | H | H | H | H | L¹¹⁴ | N | CH | N | Ph | Ph |
| 1848. | H | H | D¹²⁷ | H | H | H | H | H | L¹¹⁴ | N | CH | N | 4-biphenyl | 4-biphenyl |
| 1849. | H | H | D¹²⁷ | H | H | H | H | H | L¹¹⁵ | N | N | N | Ph | Ph |
| 1850. | H | H | D¹²⁷ | H | H | H | H | H | L¹¹⁵ | N | N | N | 4-biphenyl | 4-biphenyl |
| 1851. | H | H | D¹²⁷ | H | H | H | H | H | L¹¹⁵ | N | CH | N | Ph | Ph |
| 1852. | H | H | D¹²⁷ | H | H | H | H | H | L¹¹⁵ | N | CH | N | 4-biphenyl | 4-biphenyl |
| 1853. | H | H | D¹²⁷ | H | H | H | H | H | L¹¹⁶ | N | N | N | Ph | Ph |
| 1854. | H | H | D¹²⁷ | H | H | H | H | H | L¹¹⁶ | N | N | N | 4-biphenyl | 4-biphenyl |
| 1855. | H | H | D¹²⁷ | H | H | H | H | H | L¹¹⁶ | N | CH | N | Ph | Ph |
| 1856. | H | H | D¹²⁷ | H | H | H | H | H | L¹¹⁶ | N | CH | N | 4-biphenyl | 4-biphenyl |
| 1857. | H | H | D¹²⁸ | H | H | H | H | H | L¹⁰¹ | N | N | N | Ph | Ph |
| 1858. | H | H | D¹²⁸ | H | H | H | H | H | L¹⁰¹ | N | N | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1859. | H | H | D¹²⁸ | H | H | H | H | H | L¹⁰¹ | N | CH | N | Ph | Ph |
| 1860. | H | H | D¹²⁸ | H | H | H | H | H | L¹⁰¹ | N | CH | N | 4-biphenyl | 4-biphenyl |
| 1861. | H | H | D¹²⁸ | H | H | H | H | H | L¹⁰² | N | N | N | Ph | Ph |
| 1862. | H | H | D¹²⁸ | H | H | H | H | H | L¹⁰² | N | N | N | 4-biphenyl | 4-biphenyl |
| 1863. | H | H | D¹²⁸ | H | H | H | H | H | L¹⁰² | N | CH | N | Ph | Ph |
| 1864. | H | H | D¹²⁸ | H | H | H | H | H | L¹⁰² | N | CH | N | 4-biphenyl | 4-biphenyl |
| 1865. | H | H | D¹²⁸ | H | H | H | H | H | L¹⁰³ | N | N | N | Ph | Ph |
| 1866. | H | H | D¹²⁸ | H | H | H | H | H | L¹⁰³ | N | N | N | 4-biphenyl | 4-biphenyl |
| 1867. | H | H | D¹²⁸ | H | H | H | H | H | L¹⁰³ | N | CH | N | Ph | Ph |
| 1868. | H | H | D¹²⁸ | H | H | H | H | H | L¹⁰³ | N | CH | N | 4-biphenyl | 4-biphenyl |
| 1869. | H | H | D¹²⁸ | H | H | H | H | H | L¹⁰⁴ | N | N | N | Ph | Ph |
| 1870. | H | H | D¹²⁸ | H | H | H | H | H | L¹⁰⁴ | N | N | N | 4-biphenyl | 4-biphenyl |
| 1871. | H | H | D¹²⁸ | H | H | H | H | H | L¹⁰⁴ | N | CH | N | Ph | Ph |
| 1872. | H | H | D¹²⁸ | H | H | H | H | H | L¹⁰⁴ | N | CH | N | 4-biphenyl | 4-biphenyl |
| 1873. | H | H | D¹²⁸ | H | H | H | H | H | L¹⁰⁵ | N | N | N | Ph | Ph |
| 1874. | H | H | D¹²⁸ | H | H | H | H | H | L¹⁰⁵ | N | N | N | 4-biphenyl | 4-biphenyl |
| 1875. | H | H | D¹²⁸ | H | H | H | H | H | L¹⁰⁵ | N | CH | N | Ph | Ph |
| 1876. | H | H | D¹²⁸ | H | H | H | H | H | L¹⁰⁵ | N | CH | N | 4-biphenyl | 4-biphenyl |
| 1877. | H | H | D¹²⁸ | H | H | H | H | H | L¹⁰⁶ | N | N | N | Ph | Ph |
| 1878. | H | H | D¹²⁸ | H | H | H | H | H | L¹⁰⁶ | N | N | N | 4-biphenyl | 4-biphenyl |
| 1879. | H | H | D¹²⁸ | H | H | H | H | H | L¹⁰⁶ | N | CH | N | Ph | Ph |
| 1880. | H | H | D¹²⁸ | H | H | H | H | H | L¹⁰⁶ | N | CH | N | 4-biphenyl | 4-biphenyl |
| 1881. | H | H | D¹²⁸ | H | H | H | H | H | L¹⁰⁷ | N | N | N | Ph | Ph |
| 1882. | H | H | D¹²⁸ | H | H | H | H | H | L¹⁰⁷ | N | N | N | 4-biphenyl | 4-biphenyl |
| 1883. | H | H | D¹²⁸ | H | H | H | H | H | L¹⁰⁷ | N | CH | N | Ph | Ph |
| 1884. | H | H | D¹²⁸ | H | H | H | H | H | L¹⁰⁷ | N | CH | N | 4-biphenyl | 4-biphenyl |
| 1885. | H | H | D¹²⁸ | H | H | H | H | H | L¹⁰⁸ | N | N | N | Ph | Ph |
| 1886. | H | H | D¹²⁸ | H | H | H | H | H | L¹⁰⁸ | N | N | N | 4-biphenyl | 4-biphenyl |
| 1887. | H | H | D¹²⁸ | H | H | H | H | H | L¹⁰⁸ | N | CH | N | Ph | Ph |
| 1888. | H | H | D¹²⁸ | H | H | H | H | H | L¹⁰⁸ | N | CH | N | 4-biphenyl | 4-biphenyl |
| 1889. | H | H | D¹²⁸ | H | H | H | H | H | L¹⁰⁹ | N | N | N | Ph | Ph |
| 1890. | H | H | D¹²⁸ | H | H | H | H | H | L¹⁰⁹ | N | N | N | 4-biphenyl | 4-biphenyl |
| 1891. | H | H | D¹²⁸ | H | H | H | H | H | L¹⁰⁹ | N | CH | N | Ph | Ph |
| 1892. | H | H | D¹²⁸ | H | H | H | H | H | L¹⁰⁹ | N | CH | N | 4-biphenyl | 4-biphenyl |
| 1893. | H | H | D¹²⁸ | H | H | H | H | H | L¹¹⁰ | N | N | N | Ph | Ph |
| 1894. | H | H | D¹²⁸ | H | H | H | H | H | L¹¹⁰ | N | N | N | 4-biphenyl | 4-biphenyl |
| 1895. | H | H | D¹²⁸ | H | H | H | H | H | L¹¹⁰ | N | CH | N | Ph | Ph |
| 1896. | H | H | D¹²⁸ | H | H | H | H | H | L¹¹⁰ | N | CH | N | 4-biphenyl | 4-biphenyl |
| 1897. | H | H | D¹²⁸ | H | H | H | H | H | L¹¹¹ | N | N | N | Ph | Ph |
| 1898. | H | H | D¹²⁸ | H | H | H | H | H | L¹¹¹ | N | N | N | 4-biphenyl | 4-biphenyl |
| 1899. | H | H | D¹²⁸ | H | H | H | H | H | L¹¹¹ | N | CH | N | Ph | Ph |
| 1900. | H | H | D¹²⁸ | H | H | H | H | H | L¹¹¹ | N | CH | N | 4-biphenyl | 4-biphenyl |
| 1901. | H | H | D¹²⁸ | H | H | H | H | H | L¹¹² | N | N | N | Ph | Ph |
| 1902. | H | H | D¹²⁸ | H | H | H | H | H | L¹¹² | N | N | N | 4-biphenyl | 4-biphenyl |
| 1903. | H | H | D¹²⁸ | H | H | H | H | H | L¹¹² | N | CH | N | Ph | Ph |
| 1904. | H | H | D¹²⁸ | H | H | H | H | H | L¹¹² | N | CH | N | 4-biphenyl | 4-biphenyl |
| 1905. | H | H | D¹²⁸ | H | H | H | H | H | L¹¹³ | N | N | N | Ph | Ph |
| 1906. | H | H | D¹²⁸ | H | H | H | H | H | L¹¹³ | N | N | N | 4-biphenyl | 4-biphenyl |
| 1907. | H | H | D¹²⁸ | H | H | H | H | H | L¹¹³ | N | CH | N | Ph | Ph |
| 1908. | H | H | D¹²⁸ | H | H | H | H | H | L¹¹³ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1909. | H | H | D¹²⁸ | H | H | H | H | H | L¹¹⁴ | N | N | N | Ph | Ph |
| 1910. | H | H | D¹²⁸ | H | H | H | H | H | L¹¹⁴ | N | N | N | 4-biphenyl | 4-biphenyl |
| 1911. | H | H | D¹²⁸ | H | H | H | H | H | L¹¹⁴ | N | CH | N | Ph | Ph |
| 1912. | H | H | D¹²⁸ | H | H | H | H | H | L¹¹⁴ | N | CH | N | 4-biphenyl | 4-biphenyl |
| 1913. | H | H | D¹²⁸ | H | H | H | H | H | L¹¹⁵ | N | N | N | Ph | Ph |
| 1914. | H | H | D¹²⁸ | H | H | H | H | H | L¹¹⁵ | N | N | N | 4-biphenyl | 4-biphenyl |
| 1915. | H | H | D¹²⁸ | H | H | H | H | H | L¹¹⁵ | N | CH | N | Ph | Ph |
| 1916. | H | H | D¹²⁸ | H | H | H | H | H | L¹¹⁵ | N | CH | N | 4-biphenyl | 4-biphenyl |
| 1917. | H | H | D¹²⁸ | H | H | H | H | H | L¹¹⁶ | N | N | N | Ph | Ph |
| 1918. | H | H | D¹²⁸ | H | H | H | H | H | L¹¹⁶ | N | N | N | 4-biphenyl | 4-biphenyl |
| 1919. | H | H | D¹²⁸ | H | H | H | H | H | L¹¹⁶ | N | CH | N | Ph | Ph |
| 1920. | H | H | D¹²⁸ | H | H | H | H | H | L¹¹⁶ | N | CH | N | 4-biphenyl | 4-biphenyl |
| 1921. | H | H | D¹²⁹ | H | H | H | H | H | L¹⁰¹ | N | N | N | Ph | Ph |
| 1922. | H | H | D¹²⁹ | H | H | H | H | H | L¹⁰¹ | N | N | N | 4-biphenyl | 4-biphenyl |
| 1923. | H | H | D¹²⁹ | H | H | H | H | H | L¹⁰¹ | N | CH | N | Ph | Ph |
| 1924. | H | H | D¹²⁹ | H | H | H | H | H | L¹⁰¹ | N | CH | N | 4-biphenyl | 4-biphenyl |
| 1925. | H | H | D¹²⁹ | H | H | H | H | H | L¹⁰² | N | N | N | Ph | Ph |
| 1926. | H | H | D¹²⁹ | H | H | H | H | H | L¹⁰² | N | N | N | 4-biphenyl | 4-biphenyl |
| 1927. | H | H | D¹²⁹ | H | H | H | H | H | L¹⁰² | N | CH | N | Ph | Ph |
| 1928. | H | H | D¹²⁹ | H | H | H | H | H | L¹⁰² | N | CH | N | 4-biphenyl | 4-biphenyl |
| 1929. | H | H | D¹²⁹ | H | H | H | H | H | L¹⁰³ | N | N | N | Ph | Ph |
| 1930. | H | H | D¹²⁹ | H | H | H | H | H | L¹⁰³ | N | N | N | 4-biphenyl | 4-biphenyl |
| 1931. | H | H | D¹²⁹ | H | H | H | H | H | L¹⁰³ | N | CH | N | Ph | Ph |
| 1932. | H | H | D¹²⁹ | H | H | H | H | H | L¹⁰³ | N | CH | N | 4-biphenyl | 4-biphenyl |
| 1933. | H | H | D¹²⁹ | H | H | H | H | H | L¹⁰⁴ | N | N | N | Ph | Ph |
| 1934. | H | H | D¹²⁹ | H | H | H | H | H | L¹⁰⁴ | N | N | N | 4-biphenyl | 4-biphenyl |
| 1935. | H | H | D¹²⁹ | H | H | H | H | H | L¹⁰⁴ | N | CH | N | Ph | Ph |
| 1936. | H | H | D¹²⁹ | H | H | H | H | H | L¹⁰⁴ | N | CH | N | 4-biphenyl | 4-biphenyl |
| 1937. | H | H | D¹²⁹ | H | H | H | H | H | L¹⁰⁵ | N | N | N | Ph | Ph |
| 1938. | H | H | D¹²⁹ | H | H | H | H | H | L¹⁰⁵ | N | N | N | 4-biphenyl | 4-biphenyl |
| 1939. | H | H | D¹²⁹ | H | H | H | H | H | L¹⁰⁵ | N | CH | N | Ph | Ph |
| 1940. | H | H | D¹²⁹ | H | H | H | H | H | L¹⁰⁵ | N | CH | N | 4-biphenyl | 4-biphenyl |
| 1941. | H | H | D¹²⁹ | H | H | H | H | H | L¹⁰⁶ | N | N | N | Ph | Ph |
| 1942. | H | H | D¹²⁹ | H | H | H | H | H | L¹⁰⁶ | N | N | N | 4-biphenyl | 4-biphenyl |
| 1943. | H | H | D¹²⁹ | H | H | H | H | H | L¹⁰⁶ | N | CH | N | Ph | Ph |
| 1944. | H | H | D¹²⁹ | H | H | H | H | H | L¹⁰⁶ | N | CH | N | 4-biphenyl | 4-biphenyl |
| 1945. | H | H | D¹²⁹ | H | H | H | H | H | L¹⁰⁷ | N | N | N | Ph | Ph |
| 1946. | H | H | D¹²⁹ | H | H | H | H | H | L¹⁰⁷ | N | N | N | 4-biphenyl | 4-biphenyl |
| 1947. | H | H | D¹²⁹ | H | H | H | H | H | L¹⁰⁷ | N | CH | N | Ph | Ph |
| 1948. | H | H | D¹²⁹ | H | H | H | H | H | L¹⁰⁷ | N | CH | N | 4-biphenyl | 4-biphenyl |
| 1949. | H | H | D¹²⁹ | H | H | H | H | H | L¹⁰⁸ | N | N | N | Ph | Ph |
| 1950. | H | H | D¹²⁹ | H | H | H | H | H | L¹⁰⁸ | N | N | N | 4-biphenyl | 4-biphenyl |
| 1951. | H | H | D¹²⁹ | H | H | H | H | H | L¹⁰⁸ | N | CH | N | Ph | Ph |
| 1952. | H | H | D¹²⁹ | H | H | H | H | H | L¹⁰⁸ | N | CH | N | 4-biphenyl | 4-biphenyl |
| 1953. | H | H | D¹²⁹ | H | H | H | H | H | L¹⁰⁹ | N | N | N | Ph | Ph |
| 1954. | H | H | D¹²⁹ | H | H | H | H | H | L¹⁰⁹ | N | N | N | 4-biphenyl | 4-biphenyl |
| 1955. | H | H | D¹²⁹ | H | H | H | H | H | L¹⁰⁹ | N | CH | N | Ph | Ph |
| 1956. | H | H | D¹²⁹ | H | H | H | H | H | L¹⁰⁹ | N | CH | N | 4-biphenyl | 4-biphenyl |
| 1957. | H | H | D¹²⁹ | H | H | H | H | H | L¹¹⁰ | N | N | N | Ph | Ph |
| 1958. | H | H | D¹²⁹ | H | H | H | H | H | L¹¹⁰ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 1959. | H | H | D¹²⁹ | H | H | H | H | H | L¹¹⁰ | N | CH | N | Ph | Ph |
| 1960. | H | H | D¹²⁹ | H | H | H | H | H | L¹¹⁰ | N | CH | N | 4-biphenyl | 4-biphenyl |
| 1961. | H | H | D¹²⁹ | H | H | H | H | H | L¹¹¹ | N | N | N | Ph | Ph |
| 1962. | H | H | D¹²⁹ | H | H | H | H | H | L¹¹¹ | N | N | N | 4-biphenyl | 4-biphenyl |
| 1963. | H | H | D¹²⁹ | H | H | H | H | H | L¹¹¹ | N | CH | N | Ph | Ph |
| 1964. | H | H | D¹²⁹ | H | H | H | H | H | L¹¹¹ | N | CH | N | 4-biphenyl | 4-biphenyl |
| 1965. | H | H | D¹²⁹ | H | H | H | H | H | L¹¹² | N | N | N | Ph | Ph |
| 1966. | H | H | D¹²⁹ | H | H | H | H | H | L¹¹² | N | N | N | 4-biphenyl | 4-biphenyl |
| 1967. | H | H | D¹²⁹ | H | H | H | H | H | L¹¹² | N | CH | N | Ph | Ph |
| 1968. | H | H | D¹²⁹ | H | H | H | H | H | L¹¹² | N | CH | N | 4-biphenyl | 4-biphenyl |
| 1969. | H | H | D¹²⁹ | H | H | H | H | H | L¹¹³ | N | N | N | Ph | Ph |
| 1970. | H | H | D¹²⁹ | H | H | H | H | H | L¹¹³ | N | N | N | 4-biphenyl | 4-biphenyl |
| 1971. | H | H | D¹²⁹ | H | H | H | H | H | L¹¹³ | N | CH | N | Ph | Ph |
| 1972. | H | H | D¹²⁹ | H | H | H | H | H | L¹¹³ | N | CH | N | 4-biphenyl | 4-biphenyl |
| 1973. | H | H | D¹²⁹ | H | H | H | H | H | L¹¹⁴ | N | N | N | Ph | Ph |
| 1974. | H | H | D¹²⁹ | H | H | H | H | H | L¹¹⁴ | N | N | N | 4-biphenyl | 4-biphenyl |
| 1975. | H | H | D¹²⁹ | H | H | H | H | H | L¹¹⁴ | N | CH | N | Ph | Ph |
| 1976. | H | H | D¹²⁹ | H | H | H | H | H | L¹¹⁴ | N | CH | N | 4-biphenyl | 4-biphenyl |
| 1977. | H | H | D¹²⁹ | H | H | H | H | H | L¹¹⁵ | N | N | N | Ph | Ph |
| 1978. | H | H | D¹²⁹ | H | H | H | H | H | L¹¹⁵ | N | N | N | 4-biphenyl | 4-biphenyl |
| 1979. | H | H | D¹²⁹ | H | H | H | H | H | L¹¹⁵ | N | CH | N | Ph | Ph |
| 1980. | H | H | D¹²⁹ | H | H | H | H | H | L¹¹⁵ | N | CH | N | 4-biphenyl | 4-biphenyl |
| 1981. | H | H | D¹²⁹ | H | H | H | H | H | L¹¹⁶ | N | N | N | Ph | Ph |
| 1982. | H | H | D¹²⁹ | H | H | H | H | H | L¹¹⁶ | N | N | N | 4-biphenyl | 4-biphenyl |
| 1983. | H | H | D¹²⁹ | H | H | H | H | H | L¹¹⁶ | N | CH | N | Ph | Ph |
| 1984. | H | H | D¹²⁹ | H | H | H | H | H | L¹¹⁶ | N | CH | N | 4-biphenyl | 4-biphenyl |
| 1985. | H | H | D¹³⁰ | H | H | H | H | H | L¹⁰¹ | N | N | N | Ph | Ph |
| 1986. | H | H | D¹³⁰ | H | H | H | H | H | L¹⁰¹ | N | N | N | 4-biphenyl | 4-biphenyl |
| 1987. | H | H | D¹³⁰ | H | H | H | H | H | L¹⁰¹ | N | CH | N | Ph | Ph |
| 1988. | H | H | D¹³⁰ | H | H | H | H | H | L¹⁰¹ | N | CH | N | 4-biphenyl | 4-biphenyl |
| 1989. | H | H | D¹³⁰ | H | H | H | H | H | L¹⁰² | N | N | N | Ph | Ph |
| 1990. | H | H | D¹³⁰ | H | H | H | H | H | L¹⁰² | N | N | N | 4-biphenyl | 4-biphenyl |
| 1991. | H | H | D¹³⁰ | H | H | H | H | H | L¹⁰² | N | CH | N | Ph | Ph |
| 1992. | H | H | D¹³⁰ | H | H | H | H | H | L¹⁰² | N | CH | N | 4-biphenyl | 4-biphenyl |
| 1993. | H | H | D¹³⁰ | H | H | H | H | H | L¹⁰³ | N | N | N | Ph | Ph |
| 1994. | H | H | D¹³⁰ | H | H | H | H | H | L¹⁰³ | N | N | N | 4-biphenyl | 4-biphenyl |
| 1995. | H | H | D¹³⁰ | H | H | H | H | H | L¹⁰³ | N | CH | N | Ph | Ph |
| 1996. | H | H | D¹³⁰ | H | H | H | H | H | L¹⁰³ | N | CH | N | 4-biphenyl | 4-biphenyl |
| 1997. | H | H | D¹³⁰ | H | H | H | H | H | L¹⁰⁴ | N | N | N | Ph | Ph |
| 1998. | H | H | D¹³⁰ | H | H | H | H | H | L¹⁰⁴ | N | N | N | 4-biphenyl | 4-biphenyl |
| 1999. | H | H | D¹³⁰ | H | H | H | H | H | L¹⁰⁴ | N | CH | N | Ph | Ph |
| 2000. | H | H | D¹³⁰ | H | H | H | H | H | L¹⁰⁴ | N | CH | N | 4-biphenyl | 4-biphenyl |
| 2001. | H | H | D¹³⁰ | H | H | H | H | H | L¹⁰⁵ | N | N | N | Ph | Ph |
| 2002. | H | H | D¹³⁰ | H | H | H | H | H | L¹⁰⁵ | N | N | N | 4-biphenyl | 4-biphenyl |
| 2003. | H | H | D¹³⁰ | H | H | H | H | H | L¹⁰⁵ | N | CH | N | Ph | Ph |
| 2004. | H | H | D¹³⁰ | H | H | H | H | H | L¹⁰⁵ | N | CH | N | 4-biphenyl | 4-biphenyl |
| 2005. | H | H | D¹³⁰ | H | H | H | H | H | L¹⁰⁶ | N | N | N | Ph | Ph |
| 2006. | H | H | D¹³⁰ | H | H | H | H | H | L¹⁰⁶ | N | N | N | 4-biphenyl | 4-biphenyl |
| 2007. | H | H | D¹³⁰ | H | H | H | H | H | L¹⁰⁶ | N | CH | N | Ph | Ph |
| 2008. | H | H | D¹³⁰ | H | H | H | H | H | L¹⁰⁶ | N | CH | N | 4-biphenyl | 4-biphenyl |

-continued

| Compound number | $R^1$ | $R^2$ | $R^3$ | $R^4$ | $R^5$ | $R^6$ | $R^7$ | $R^8$ | $L^1$ | $Z^1$ | $Z^3$ | $Z^5$ | $R^{91}$ | $R^{92}$ |
|---|---|---|---|---|---|---|---|---|---|---|---|---|---|---|
| 2009. | H | H | $D^{130}$ | H | H | H | H | H | $L^{107}$ | N | N | N | Ph | Ph |
| 2010. | H | H | $D^{130}$ | H | H | H | H | H | $L^{107}$ | N | N | N | 4-biphenyl | 4-biphenyl |
| 2011. | H | H | $D^{130}$ | H | H | H | H | H | $L^{107}$ | N | CH | N | Ph | Ph |
| 2012. | H | H | $D^{130}$ | H | H | H | H | H | $L^{107}$ | N | CH | N | 4-biphenyl | 4-biphenyl |
| 2013. | H | H | $D^{130}$ | H | H | H | H | H | $L^{108}$ | N | N | N | Ph | Ph |
| 2014. | H | H | $D^{130}$ | H | H | H | H | H | $L^{108}$ | N | N | N | 4-biphenyl | 4-biphenyl |
| 2015. | H | H | $D^{130}$ | H | H | H | H | H | $L^{108}$ | N | CH | N | Ph | Ph |
| 2016. | H | H | $D^{130}$ | H | H | H | H | H | $L^{108}$ | N | CH | N | 4-biphenyl | 4-biphenyl |
| 2017. | H | H | $D^{130}$ | H | H | H | H | H | $L^{109}$ | N | N | N | Ph | Ph |
| 2018. | H | H | $D^{130}$ | H | H | H | H | H | $L^{109}$ | N | N | N | 4-biphenyl | 4-biphenyl |
| 2019. | H | H | $D^{130}$ | H | H | H | H | H | $L^{109}$ | N | CH | N | Ph | Ph |
| 2020. | H | H | $D^{130}$ | H | H | H | H | H | $L^{109}$ | N | CH | N | 4-biphenyl | 4-biphenyl |
| 2021. | H | H | $D^{130}$ | H | H | H | H | H | $L^{110}$ | N | N | N | Ph | Ph |
| 2022. | H | H | $D^{130}$ | H | H | H | H | H | $L^{110}$ | N | N | N | 4-biphenyl | 4-biphenyl |
| 2023. | H | H | $D^{130}$ | H | H | H | H | H | $L^{110}$ | N | CH | N | Ph | Ph |
| 2024. | H | H | $D^{130}$ | H | H | H | H | H | $L^{110}$ | N | CH | N | 4-biphenyl | 4-biphenyl |
| 2025. | H | H | $D^{130}$ | H | H | H | H | H | $L^{111}$ | N | N | N | Ph | Ph |
| 2026. | H | H | $D^{130}$ | H | H | H | H | H | $L^{111}$ | N | N | N | 4-biphenyl | 4-biphenyl |
| 2027. | H | H | $D^{130}$ | H | H | H | H | H | $L^{111}$ | N | CH | N | Ph | Ph |
| 2028. | H | H | $D^{130}$ | H | H | H | H | H | $L^{111}$ | N | CH | N | 4-biphenyl | 4-biphenyl |
| 2029. | H | H | $D^{130}$ | H | H | H | H | H | $L^{112}$ | N | N | N | Ph | Ph |
| 2030. | H | H | $D^{130}$ | H | H | H | H | H | $L^{112}$ | N | N | N | 4-biphenyl | 4-biphenyl |
| 2031. | H | H | $D^{130}$ | H | H | H | H | H | $L^{112}$ | N | CH | N | Ph | Ph |
| 2032. | H | H | $D^{130}$ | H | H | H | H | H | $L^{112}$ | N | CH | N | 4-biphenyl | 4-biphenyl |
| 2033. | H | H | $D^{130}$ | H | H | H | H | H | $L^{113}$ | N | N | N | Ph | Ph |
| 2034. | H | H | $D^{130}$ | H | H | H | H | H | $L^{113}$ | N | N | N | 4-biphenyl | 4-biphenyl |
| 2035. | H | H | $D^{130}$ | H | H | H | H | H | $L^{113}$ | N | CH | N | Ph | Ph |
| 2036. | H | H | $D^{130}$ | H | H | H | H | H | $L^{113}$ | N | CH | N | 4-biphenyl | 4-biphenyl |
| 2037. | H | H | $D^{130}$ | H | H | H | H | H | $L^{114}$ | N | N | N | Ph | Ph |
| 2038. | H | H | $D^{130}$ | H | H | H | H | H | $L^{114}$ | N | N | N | 4-biphenyl | 4-biphenyl |
| 2039. | H | H | $D^{130}$ | H | H | H | H | H | $L^{114}$ | N | CH | N | Ph | Ph |
| 2040. | H | H | $D^{130}$ | H | H | H | H | H | $L^{114}$ | N | CH | N | 4-biphenyl | 4-biphenyl |
| 2041. | H | H | $D^{130}$ | H | H | H | H | H | $L^{115}$ | N | N | N | Ph | Ph |
| 2042. | H | H | $D^{130}$ | H | H | H | H | H | $L^{115}$ | N | N | N | 4-biphenyl | 4-biphenyl |
| 2043. | H | H | $D^{130}$ | H | H | H | H | H | $L^{115}$ | N | CH | N | Ph | Ph |
| 2044. | H | H | $D^{130}$ | H | H | H | H | H | $L^{115}$ | N | CH | N | 4-biphenyl | 4-biphenyl |
| 2045. | H | H | $D^{130}$ | H | H | H | H | H | $L^{116}$ | N | N | N | Ph | Ph |
| 2046. | H | H | $D^{130}$ | H | H | H | H | H | $L^{116}$ | N | N | N | 4-biphenyl | 4-biphenyl |
| 2047. | H | H | $D^{130}$ | H | H | H | H | H | $L^{116}$ | N | CH | N | Ph | Ph |
| 2048. | H | H | $D^{130}$ | H | H | H | H | H | $L^{116}$ | N | CH | N | 4-biphenyl | 4-biphenyl |
| 2049. | H | H | $D^{131}$ | H | H | H | H | H | $L^{101}$ | N | N | N | Ph | Ph |
| 2050. | H | H | $D^{131}$ | H | H | H | H | H | $L^{101}$ | N | N | N | 4-biphenyl | 4-biphenyl |
| 2051. | H | H | $D^{131}$ | H | H | H | H | H | $L^{101}$ | N | CH | N | Ph | Ph |
| 2052. | H | H | $D^{131}$ | H | H | H | H | H | $L^{101}$ | N | CH | N | 4-biphenyl | 4-biphenyl |
| 2053. | H | H | $D^{131}$ | H | H | H | H | H | $L^{102}$ | N | N | N | Ph | Ph |
| 2054. | H | H | $D^{131}$ | H | H | H | H | H | $L^{102}$ | N | N | N | 4-biphenyl | 4-biphenyl |
| 2055. | H | H | $D^{131}$ | H | H | H | H | H | $L^{102}$ | N | CH | N | Ph | Ph |
| 2056. | H | H | $D^{131}$ | H | H | H | H | H | $L^{102}$ | N | CH | N | 4-biphenyl | 4-biphenyl |
| 2057. | H | H | $D^{131}$ | H | H | H | H | H | $L^{103}$ | N | N | N | Ph | Ph |
| 2058. | H | H | $D^{131}$ | H | H | H | H | H | $L^{103}$ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2059. | H | H | D¹³¹ | H | H | H | H | H | L¹⁰³ | N | CH | N | Ph | Ph |
| 2060. | H | H | D¹³¹ | H | H | H | H | H | L¹⁰³ | N | CH | N | 4-biphenyl | 4-biphenyl |
| 2061. | H | H | D¹³¹ | H | H | H | H | H | L¹⁰⁴ | N | N | N | Ph | Ph |
| 2062. | H | H | D¹³¹ | H | H | H | H | H | L¹⁰⁴ | N | N | N | 4-biphenyl | 4-biphenyl |
| 2063. | H | H | D¹³¹ | H | H | H | H | H | L¹⁰⁴ | N | CH | N | Ph | Ph |
| 2064. | H | H | D¹³¹ | H | H | H | H | H | L¹⁰⁴ | N | CH | N | 4-biphenyl | 4-biphenyl |
| 2065. | H | H | D¹³¹ | H | H | H | H | H | L¹⁰⁵ | N | N | N | Ph | Ph |
| 2066. | H | H | D¹³¹ | H | H | H | H | H | L¹⁰⁵ | N | N | N | 4-biphenyl | 4-biphenyl |
| 2067. | H | H | D¹³¹ | H | H | H | H | H | L¹⁰⁵ | N | CH | N | Ph | Ph |
| 2068. | H | H | D¹³¹ | H | H | H | H | H | L¹⁰⁵ | N | CH | N | 4-biphenyl | 4-biphenyl |
| 2069. | H | H | D¹³¹ | H | H | H | H | H | L¹⁰⁶ | N | N | N | Ph | Ph |
| 2070. | H | H | D¹³¹ | H | H | H | H | H | L¹⁰⁶ | N | N | N | 4-biphenyl | 4-biphenyl |
| 2071. | H | H | D¹³¹ | H | H | H | H | H | L¹⁰⁶ | N | CH | N | Ph | Ph |
| 2072. | H | H | D¹³¹ | H | H | H | H | H | L¹⁰⁶ | N | CH | N | 4-biphenyl | 4-biphenyl |
| 2073. | H | H | D¹³¹ | H | H | H | H | H | L¹⁰⁷ | N | N | N | Ph | Ph |
| 2074. | H | H | D¹³¹ | H | H | H | H | H | L¹⁰⁷ | N | N | N | 4-biphenyl | 4-biphenyl |
| 2075. | H | H | D¹³¹ | H | H | H | H | H | L¹⁰⁷ | N | CH | N | Ph | Ph |
| 2076. | H | H | D¹³¹ | H | H | H | H | H | L¹⁰⁷ | N | CH | N | 4-biphenyl | 4-biphenyl |
| 2077. | H | H | D¹³¹ | H | H | H | H | H | L¹⁰⁸ | N | N | N | Ph | Ph |
| 2078. | H | H | D¹³¹ | H | H | H | H | H | L¹⁰⁸ | N | N | N | 4-biphenyl | 4-biphenyl |
| 2079. | H | H | D¹³¹ | H | H | H | H | H | L¹⁰⁸ | N | CH | N | Ph | Ph |
| 2080. | H | H | D¹³¹ | H | H | H | H | H | L¹⁰⁸ | N | CH | N | 4-biphenyl | 4-biphenyl |
| 2081. | H | H | D¹³¹ | H | H | H | H | H | L¹⁰⁹ | N | N | N | Ph | Ph |
| 2082. | H | H | D¹³¹ | H | H | H | H | H | L¹⁰⁹ | N | N | N | 4-biphenyl | 4-biphenyl |
| 2083. | H | H | D¹³¹ | H | H | H | H | H | L¹⁰⁹ | N | CH | N | Ph | Ph |
| 2084. | H | H | D¹³¹ | H | H | H | H | H | L¹⁰⁹ | N | CH | N | 4-biphenyl | 4-biphenyl |
| 2085. | H | H | D¹³¹ | H | H | H | H | H | L¹¹⁰ | N | N | N | Ph | Ph |
| 2086. | H | H | D¹³¹ | H | H | H | H | H | L¹¹⁰ | N | N | N | 4-biphenyl | 4-biphenyl |
| 2087. | H | H | D¹³¹ | H | H | H | H | H | L¹¹⁰ | N | CH | N | Ph | Ph |
| 2088. | H | H | D¹³¹ | H | H | H | H | H | L¹¹⁰ | N | CH | N | 4-biphenyl | 4-biphenyl |
| 2089. | H | H | D¹³¹ | H | H | H | H | H | L¹¹¹ | N | N | N | Ph | Ph |
| 2090. | H | H | D¹³¹ | H | H | H | H | H | L¹¹¹ | N | N | N | 4-biphenyl | 4-biphenyl |
| 2091. | H | H | D¹³¹ | H | H | H | H | H | L¹¹¹ | N | CH | N | Ph | Ph |
| 2092. | H | H | D¹³¹ | H | H | H | H | H | L¹¹¹ | N | CH | N | 4-biphenyl | 4-biphenyl |
| 2093. | H | H | D¹³¹ | H | H | H | H | H | L¹¹² | N | N | N | Ph | Ph |
| 2094. | H | H | D¹³¹ | H | H | H | H | H | L¹¹² | N | N | N | 4-biphenyl | 4-biphenyl |
| 2095. | H | H | D¹³¹ | H | H | H | H | H | L¹¹² | N | CH | N | Ph | Ph |
| 2096. | H | H | D¹³¹ | H | H | H | H | H | L¹¹² | N | CH | N | 4-biphenyl | 4-biphenyl |
| 2097. | H | H | D¹³¹ | H | H | H | H | H | L¹¹³ | N | N | N | Ph | Ph |
| 2098. | H | H | D¹³¹ | H | H | H | H | H | L¹¹³ | N | N | N | 4-biphenyl | 4-biphenyl |
| 2099. | H | H | D¹³¹ | H | H | H | H | H | L¹¹³ | N | CH | N | Ph | Ph |
| 2100. | H | H | D¹³¹ | H | H | H | H | H | L¹¹³ | N | CH | N | 4-biphenyl | 4-biphenyl |
| 2101. | H | H | D¹³¹ | H | H | H | H | H | L¹¹⁴ | N | N | N | Ph | Ph |
| 2102. | H | H | D¹³¹ | H | H | H | H | H | L¹¹⁴ | N | N | N | 4-biphenyl | 4-biphenyl |
| 2103. | H | H | D¹³¹ | H | H | H | H | H | L¹¹⁴ | N | CH | N | Ph | Ph |
| 2104. | H | H | D¹³¹ | H | H | H | H | H | L¹¹⁴ | N | CH | N | 4-biphenyl | 4-biphenyl |
| 2105. | H | H | D¹³¹ | H | H | H | H | H | L¹¹⁵ | N | N | N | Ph | Ph |
| 2106. | H | H | D¹³¹ | H | H | H | H | H | L¹¹⁵ | N | N | N | 4-biphenyl | 4-biphenyl |
| 2107. | H | H | D¹³¹ | H | H | H | H | H | L¹¹⁵ | N | CH | N | Ph | Ph |
| 2108. | H | H | D¹³¹ | H | H | H | H | H | L¹¹⁵ | N | CH | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2109. | H | H | D¹³¹ | H | H | H | H | H | L¹¹⁶ | N | N | N | Ph | Ph |
| 2110. | H | H | D¹³¹ | H | H | H | H | H | L¹¹⁶ | N | N | N | 4-biphenyl | 4-biphenyl |
| 2111. | H | H | D¹³¹ | H | H | H | H | H | L¹¹⁶ | N | CH | N | Ph | Ph |
| 2112. | H | H | D¹³¹ | H | H | H | H | H | L¹¹⁶ | N | CH | N | 4-biphenyl | 4-biphenyl |
| 2113. | H | H | D¹³² | H | H | H | H | H | L¹⁰¹ | N | N | N | Ph | Ph |
| 2114. | H | H | D¹³² | H | H | H | H | H | L¹⁰¹ | N | N | N | 4-biphenyl | 4-biphenyl |
| 2115. | H | H | D¹³² | H | H | H | H | H | L¹⁰¹ | N | CH | N | Ph | Ph |
| 2116. | H | H | D¹³² | H | H | H | H | H | L¹⁰¹ | N | CH | N | 4-biphenyl | 4-biphenyl |
| 2117. | H | H | D¹³² | H | H | H | H | H | L¹⁰² | N | N | N | Ph | Ph |
| 2118. | H | H | D¹³² | H | H | H | H | H | L¹⁰² | N | N | N | 4-biphenyl | 4-biphenyl |
| 2119. | H | H | D¹³² | H | H | H | H | H | L¹⁰² | N | CH | N | Ph | Ph |
| 2120. | H | H | D¹³² | H | H | H | H | H | L¹⁰² | N | CH | N | 4-biphenyl | 4-biphenyl |
| 2121. | H | H | D¹³² | H | H | H | H | H | L¹⁰³ | N | N | N | Ph | Ph |
| 2122. | H | H | D¹³² | H | H | H | H | H | L¹⁰³ | N | N | N | 4-biphenyl | 4-biphenyl |
| 2123. | H | H | D¹³² | H | H | H | H | H | L¹⁰³ | N | CH | N | Ph | Ph |
| 2124. | H | H | D¹³² | H | H | H | H | H | L¹⁰³ | N | CH | N | 4-biphenyl | 4-biphenyl |
| 2125. | H | H | D¹³² | H | H | H | H | H | L¹⁰⁴ | N | N | N | Ph | Ph |
| 2126. | H | H | D¹³² | H | H | H | H | H | L¹⁰⁴ | N | N | N | 4-biphenyl | 4-biphenyl |
| 2127. | H | H | D¹³² | H | H | H | H | H | L¹⁰⁴ | N | CH | N | Ph | Ph |
| 2128. | H | H | D¹³² | H | H | H | H | H | L¹⁰⁴ | N | CH | N | 4-biphenyl | 4-biphenyl |
| 2129. | H | H | D¹³² | H | H | H | H | H | L¹⁰⁵ | N | N | N | Ph | Ph |
| 2130. | H | H | D¹³² | H | H | H | H | H | L¹⁰⁵ | N | N | N | 4-biphenyl | 4-biphenyl |
| 2131. | H | H | D¹³² | H | H | H | H | H | L¹⁰⁵ | N | CH | N | Ph | Ph |
| 2132. | H | H | D¹³² | H | H | H | H | H | L¹⁰⁵ | N | CH | N | 4-biphenyl | 4-biphenyl |
| 2133. | H | H | D¹³² | H | H | H | H | H | L¹⁰⁶ | N | N | N | Ph | Ph |
| 2134. | H | H | D¹³² | H | H | H | H | H | L¹⁰⁶ | N | N | N | 4-biphenyl | 4-biphenyl |
| 2135. | H | H | D¹³² | H | H | H | H | H | L¹⁰⁶ | N | CH | N | Ph | Ph |
| 2136. | H | H | D¹³² | H | H | H | H | H | L¹⁰⁶ | N | CH | N | 4-biphenyl | 4-biphenyl |
| 2137. | H | H | D¹³² | H | H | H | H | H | L¹⁰⁷ | N | N | N | Ph | Ph |
| 2138. | H | H | D¹³² | H | H | H | H | H | L¹⁰⁷ | N | N | N | 4-biphenyl | 4-biphenyl |
| 2139. | H | H | D¹³² | H | H | H | H | H | L¹⁰⁷ | N | CH | N | Ph | Ph |
| 2140. | H | H | D¹³² | H | H | H | H | H | L¹⁰⁷ | N | CH | N | 4-biphenyl | 4-biphenyl |
| 2141. | H | H | D¹³² | H | H | H | H | H | L¹⁰⁸ | N | N | N | Ph | Ph |
| 2142. | H | H | D¹³² | H | H | H | H | H | L¹⁰⁸ | N | N | N | 4-biphenyl | 4-biphenyl |
| 2143. | H | H | D¹³² | H | H | H | H | H | L¹⁰⁸ | N | CH | N | Ph | Ph |
| 2144. | H | H | D¹³² | H | H | H | H | H | L¹⁰⁸ | N | CH | N | 4-biphenyl | 4-biphenyl |
| 2145. | H | H | D¹³² | H | H | H | H | H | L¹⁰⁹ | N | N | N | Ph | Ph |
| 2146. | H | H | D¹³² | H | H | H | H | H | L¹⁰⁹ | N | N | N | 4-biphenyl | 4-biphenyl |
| 2147. | H | H | D¹³² | H | H | H | H | H | L¹⁰⁹ | N | CH | N | Ph | Ph |
| 2148. | H | H | D¹³² | H | H | H | H | H | L¹⁰⁹ | N | CH | N | 4-biphenyl | 4-biphenyl |
| 2149. | H | H | D¹³² | H | H | H | H | H | L¹¹⁰ | N | N | N | Ph | Ph |
| 2150. | H | H | D¹³² | H | H | H | H | H | L¹¹⁰ | N | N | N | 4-biphenyl | 4-biphenyl |
| 2151. | H | H | D¹³² | H | H | H | H | H | L¹¹⁰ | N | CH | N | Ph | Ph |
| 2152. | H | H | D¹³² | H | H | H | H | H | L¹¹⁰ | N | CH | N | 4-biphenyl | 4-biphenyl |
| 2153. | H | H | D¹³² | H | H | H | H | H | L¹¹¹ | N | N | N | Ph | Ph |
| 2154. | H | H | D¹³² | H | H | H | H | H | L¹¹¹ | N | N | N | 4-biphenyl | 4-biphenyl |
| 2155. | H | H | D¹³² | H | H | H | H | H | L¹¹¹ | N | CH | N | Ph | Ph |
| 2156. | H | H | D¹³² | H | H | H | H | H | L¹¹¹ | N | CH | N | 4-biphenyl | 4-biphenyl |
| 2157. | H | H | D¹³² | H | H | H | H | H | L¹¹² | N | N | N | Ph | Ph |
| 2158. | H | H | D¹³² | H | H | H | H | H | L¹¹² | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2159. | H | H | D¹³² | H | H | H | H | H | L¹¹² | N | CH | N | Ph | Ph |
| 2160. | H | H | D¹³² | H | H | H | H | H | L¹¹² | N | CH | N | 4-biphenyl | 4-biphenyl |
| 2161. | H | H | D¹³² | H | H | H | H | H | L¹¹³ | N | N | N | Ph | Ph |
| 2162. | H | H | D¹³² | H | H | H | H | H | L¹¹³ | N | N | N | 4-biphenyl | 4-biphenyl |
| 2163. | H | H | D¹³² | H | H | H | H | H | L¹¹³ | N | CH | N | Ph | Ph |
| 2164. | H | H | D¹³² | H | H | H | H | H | L¹¹³ | N | CH | N | 4-biphenyl | 4-biphenyl |
| 2165. | H | H | D¹³² | H | H | H | H | H | L¹¹⁴ | N | N | N | Ph | Ph |
| 2166. | H | H | D¹³² | H | H | H | H | H | L¹¹⁴ | N | N | N | 4-biphenyl | 4-biphenyl |
| 2167. | H | H | D¹³² | H | H | H | H | H | L¹¹⁴ | N | CH | N | Ph | Ph |
| 2168. | H | H | D¹³² | H | H | H | H | H | L¹¹⁴ | N | CH | N | 4-biphenyl | 4-biphenyl |
| 2169. | H | H | D¹³² | H | H | H | H | H | L¹¹⁵ | N | N | N | Ph | Ph |
| 2170. | H | H | D¹³² | H | H | H | H | H | L¹¹⁵ | N | N | N | 4-biphenyl | 4-biphenyl |
| 2171. | H | H | D¹³² | H | H | H | H | H | L¹¹⁵ | N | CH | N | Ph | Ph |
| 2172. | H | H | D¹³² | H | H | H | H | H | L¹¹⁵ | N | CH | N | 4-biphenyl | 4-biphenyl |
| 2173. | H | H | D¹³² | H | H | H | H | H | L¹¹⁶ | N | N | N | Ph | Ph |
| 2174. | H | H | D¹³² | H | H | H | H | H | L¹¹⁶ | N | N | N | 4-biphenyl | 4-biphenyl |
| 2175. | H | H | D¹³² | H | H | H | H | H | L¹¹⁶ | N | CH | N | Ph | Ph |
| 2176. | H | H | D¹³² | H | H | H | H | H | L¹¹⁶ | N | CH | N | 4-biphenyl | 4-biphenyl |
| 2177. | H | H | D¹³² | H | H | D¹³² | H | H | L¹⁰¹ | N | N | N | Ph | Ph |
| 2178. | H | H | D¹³² | H | H | D¹³² | H | H | L¹⁰¹ | N | N | N | 4-biphenyl | 4-biphenyl |
| 2179. | H | H | D¹³² | H | H | D¹³² | H | H | L¹⁰¹ | N | CH | N | Ph | Ph |
| 2180. | H | H | D¹³² | H | H | D¹³² | H | H | L¹⁰¹ | N | CH | N | 4-biphenyl | 4-biphenyl |
| 2181. | H | H | D¹³² | H | H | D¹³² | H | H | L¹⁰² | N | N | N | Ph | Ph |
| 2182. | H | H | D¹³² | H | H | D¹³² | H | H | L¹⁰² | N | N | N | 4-biphenyl | 4-biphenyl |
| 2183. | H | H | D¹³² | H | H | D¹³² | H | H | L¹⁰² | N | CH | N | Ph | Ph |
| 2184. | H | H | D¹³² | H | H | D¹³² | H | H | L¹⁰² | N | CH | N | 4-biphenyl | 4-biphenyl |
| 2185. | H | H | D¹³² | H | H | D¹³² | H | H | L¹⁰³ | N | N | N | Ph | Ph |
| 2186. | H | H | D¹³² | H | H | D¹³² | H | H | L¹⁰³ | N | N | N | 4-biphenyl | 4-biphenyl |
| 2187. | H | H | D¹³² | H | H | D¹³² | H | H | L¹⁰³ | N | CH | N | Ph | Ph |
| 2188. | H | H | D¹³² | H | H | D¹³² | H | H | L¹⁰³ | N | CH | N | 4-biphenyl | 4-biphenyl |
| 2189. | H | H | D¹³² | H | H | D¹³² | H | H | L¹⁰⁴ | N | N | N | Ph | Ph |
| 2190. | H | H | D¹³² | H | H | D¹³² | H | H | L¹⁰⁴ | N | N | N | 4-biphenyl | 4-biphenyl |
| 2191. | H | H | D¹³² | H | H | D¹³² | H | H | L¹⁰⁴ | N | CH | N | Ph | Ph |
| 2192. | H | H | D¹³² | H | H | D¹³² | H | H | L¹⁰⁴ | N | CH | N | 4-biphenyl | 4-biphenyl |
| 2193. | H | H | D¹³² | H | H | D¹³² | H | H | L¹⁰⁵ | N | N | N | Ph | Ph |
| 2194. | H | H | D¹³² | H | H | D¹³² | H | H | L¹⁰⁵ | N | N | N | 4-biphenyl | 4-biphenyl |
| 2195. | H | H | D¹³² | H | H | D¹³² | H | H | L¹⁰⁵ | N | CH | N | Ph | Ph |
| 2196. | H | H | D¹³² | H | H | D¹³² | H | H | L¹⁰⁵ | N | CH | N | 4-biphenyl | 4-biphenyl |
| 2197. | H | H | D¹³² | H | H | D¹³² | H | H | L¹⁰⁶ | N | N | N | Ph | Ph |
| 2198. | H | H | D¹³² | H | H | D¹³² | H | H | L¹⁰⁶ | N | N | N | 4-biphenyl | 4-biphenyl |
| 2199. | H | H | D¹³² | H | H | D¹³² | H | H | L¹⁰⁶ | N | CH | N | Ph | Ph |
| 2200. | H | H | D¹³² | H | H | D¹³² | H | H | L¹⁰⁶ | N | CH | N | 4-biphenyl | 4-biphenyl |
| 2201. | H | H | D¹³² | H | H | D¹³² | H | H | L¹⁰⁷ | N | N | N | Ph | Ph |
| 2202. | H | H | D¹³² | H | H | D¹³² | H | H | L¹⁰⁷ | N | N | N | 4-biphenyl | 4-biphenyl |
| 2203. | H | H | D¹³² | H | H | D¹³² | H | H | L¹⁰⁷ | N | CH | N | Ph | Ph |
| 2204. | H | H | D¹³² | H | H | D¹³² | H | H | L¹⁰⁷ | N | CH | N | 4-biphenyl | 4-biphenyl |
| 2205. | H | H | D¹³² | H | H | D¹³² | H | H | L¹⁰⁸ | N | N | N | Ph | Ph |
| 2206. | H | H | D¹³² | H | H | D¹³² | H | H | L¹⁰⁸ | N | N | N | 4-biphenyl | 4-biphenyl |
| 2207. | H | H | D¹³² | H | H | D¹³² | H | H | L¹⁰⁸ | N | CH | N | Ph | Ph |
| 2208. | H | H | D¹³² | H | H | D¹³² | H | H | L¹⁰⁸ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2209. | H | H | D¹³² | H | H | D¹³² | H | H | L¹⁰⁹ | N | N | N | Ph | Ph |
| 2210. | H | H | D¹³² | H | H | D¹³² | H | H | L¹⁰⁹ | N | N | N | 4-biphenyl | 4-biphenyl |
| 2211. | H | H | D¹³² | H | H | D¹³² | H | H | L¹⁰⁹ | N | CH | N | Ph | Ph |
| 2212. | H | H | D¹³² | H | H | D¹³² | H | H | L¹⁰⁹ | N | CH | N | 4-biphenyl | 4-biphenyl |
| 2213. | H | H | D¹³² | H | H | D¹³² | H | H | L¹¹⁰ | N | N | N | Ph | Ph |
| 2214. | H | H | D¹³² | H | H | D¹³² | H | H | L¹¹⁰ | N | N | N | 4-biphenyl | 4-biphenyl |
| 2215. | H | H | D¹³² | H | H | D¹³² | H | H | L¹¹⁰ | N | CH | N | Ph | Ph |
| 2216. | H | H | D¹³² | H | H | D¹³² | H | H | L¹¹⁰ | N | CH | N | 4-biphenyl | 4-biphenyl |
| 2217. | H | H | D¹³² | H | H | D¹³² | H | H | L¹¹¹ | N | N | N | Ph | Ph |
| 2218. | H | H | D¹³² | H | H | D¹³² | H | H | L¹¹¹ | N | N | N | 4-biphenyl | 4-biphenyl |
| 2219. | H | H | D¹³² | H | H | D¹³² | H | H | L¹¹¹ | N | CH | N | Ph | Ph |
| 2220. | H | H | D¹³² | H | H | D¹³² | H | H | L¹¹¹ | N | CH | N | 4-biphenyl | 4-biphenyl |
| 2221. | H | H | D¹³² | H | H | D¹³² | H | H | L¹¹² | N | N | N | Ph | Ph |
| 2222. | H | H | D¹³² | H | H | D¹³² | H | H | L¹¹² | N | N | N | 4-biphenyl | 4-biphenyl |
| 2223. | H | H | D¹³² | H | H | D¹³² | H | H | L¹¹² | N | CH | N | Ph | Ph |
| 2224. | H | H | D¹³² | H | H | D¹³² | H | H | L¹¹² | N | CH | N | 4-biphenyl | 4-biphenyl |
| 2225. | H | H | D¹³² | H | H | D¹³² | H | H | L¹¹³ | N | N | N | Ph | Ph |
| 2226. | H | H | D¹³² | H | H | D¹³² | H | H | L¹¹³ | N | N | N | 4-biphenyl | 4-biphenyl |
| 2227. | H | H | D¹³² | H | H | D¹³² | H | H | L¹¹³ | N | CH | N | Ph | Ph |
| 2228. | H | H | D¹³² | H | H | D¹³² | H | H | L¹¹³ | N | CH | N | 4-biphenyl | 4-biphenyl |
| 2229. | H | H | D¹³² | H | H | D¹³² | H | H | L¹¹⁴ | N | N | N | Ph | Ph |
| 2230. | H | H | D¹³² | H | H | D¹³² | H | H | L¹¹⁴ | N | N | N | 4-biphenyl | 4-biphenyl |
| 2231. | H | H | D¹³² | H | H | D¹³² | H | H | L¹¹⁴ | N | CH | N | Ph | Ph |
| 2232. | H | H | D¹³² | H | H | D¹³² | H | H | L¹¹⁴ | N | CH | N | 4-biphenyl | 4-biphenyl |
| 2233. | H | H | D¹³² | H | H | D¹³² | H | H | L¹¹⁵ | N | N | N | Ph | Ph |
| 2234. | H | H | D¹³² | H | H | D¹³² | H | H | L¹¹⁵ | N | N | N | 4-biphenyl | 4-biphenyl |
| 2235. | H | H | D¹³² | H | H | D¹³² | H | H | L¹¹⁵ | N | CH | N | Ph | Ph |
| 2236. | H | H | D¹³² | H | H | D¹³² | H | H | L¹¹⁵ | N | CH | N | 4-biphenyl | 4-biphenyl |
| 2237. | H | H | D¹³² | H | H | D¹³² | H | H | L¹¹⁶ | N | N | N | Ph | Ph |
| 2238. | H | H | D¹³² | H | H | D¹³² | H | H | L¹¹⁶ | N | N | N | 4-biphenyl | 4-biphenyl |
| 2239. | H | H | D¹³² | H | H | D¹³² | H | H | L¹¹⁶ | N | CH | N | Ph | Ph |
| 2240. | H | H | D¹³² | H | H | D¹³² | H | H | L¹¹⁶ | N | CH | N | 4-biphenyl | 4-biphenyl |
| 2241. | H | H | D¹³³ | H | H | H | H | H | L¹⁰¹ | N | N | N | Ph | Ph |
| 2242. | H | H | D¹³³ | H | H | H | H | H | L¹⁰¹ | N | N | N | 4-biphenyl | 4-biphenyl |
| 2243. | H | H | D¹³³ | H | H | H | H | H | L¹⁰¹ | N | CH | N | Ph | Ph |
| 2244. | H | H | D¹³³ | H | H | H | H | H | L¹⁰¹ | N | CH | N | 4-biphenyl | 4-biphenyl |
| 2245. | H | H | D¹³³ | H | H | H | H | H | L¹⁰² | N | N | N | Ph | Ph |
| 2246. | H | H | D¹³³ | H | H | H | H | H | L¹⁰² | N | N | N | 4-biphenyl | 4-biphenyl |
| 2247. | H | H | D¹³³ | H | H | H | H | H | L¹⁰² | N | CH | N | Ph | Ph |
| 2248. | H | H | D¹³³ | H | H | H | H | H | L¹⁰² | N | CH | N | 4-biphenyl | 4-biphenyl |
| 2249. | H | H | D¹³³ | H | H | H | H | H | L¹⁰³ | N | N | N | Ph | Ph |
| 2250. | H | H | D¹³³ | H | H | H | H | H | L¹⁰³ | N | N | N | 4-biphenyl | 4-biphenyl |
| 2251. | H | H | D¹³³ | H | H | H | H | H | L¹⁰³ | N | CH | N | Ph | Ph |
| 2252. | H | H | D¹³³ | H | H | H | H | H | L¹⁰³ | N | CH | N | 4-biphenyl | 4-biphenyl |
| 2253. | H | H | D¹³³ | H | H | H | H | H | L¹⁰⁴ | N | N | N | Ph | Ph |
| 2254. | H | H | D¹³³ | H | H | H | H | H | L¹⁰⁴ | N | N | N | 4-biphenyl | 4-biphenyl |
| 2255. | H | H | D¹³³ | H | H | H | H | H | L¹⁰⁴ | N | CH | N | Ph | Ph |
| 2256. | H | H | D¹³³ | H | H | H | H | H | L¹⁰⁴ | N | CH | N | 4-biphenyl | 4-biphenyl |
| 2257. | H | H | D¹³³ | H | H | H | H | H | L¹⁰⁵ | N | N | N | Ph | Ph |
| 2258. | H | H | D¹³³ | H | H | H | H | H | L¹⁰⁵ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2259. | H | H | D¹³³ | H | H | H | H | H | L¹⁰⁵ | N | CH | N | Ph | Ph |
| 2260. | H | H | D¹³³ | H | H | H | H | H | L¹⁰⁵ | N | CH | N | 4-biphenyl | 4-biphenyl |
| 2261. | H | H | D¹³³ | H | H | H | H | H | L¹⁰⁶ | N | N | N | Ph | Ph |
| 2262. | H | H | D¹³³ | H | H | H | H | H | L¹⁰⁶ | N | N | N | 4-biphenyl | 4-biphenyl |
| 2263. | H | H | D¹³³ | H | H | H | H | H | L¹⁰⁶ | N | CH | N | Ph | Ph |
| 2264. | H | H | D¹³³ | H | H | H | H | H | L¹⁰⁶ | N | CH | N | 4-biphenyl | 4-biphenyl |
| 2265. | H | H | D¹³³ | H | H | H | H | H | L¹⁰⁷ | N | N | N | Ph | Ph |
| 2266. | H | H | D¹³³ | H | H | H | H | H | L¹⁰⁷ | N | N | N | 4-biphenyl | 4-biphenyl |
| 2267. | H | H | D¹³³ | H | H | H | H | H | L¹⁰⁷ | N | CH | N | Ph | Ph |
| 2268. | H | H | D¹³³ | H | H | H | H | H | L¹⁰⁷ | N | CH | N | 4-biphenyl | 4-biphenyl |
| 2269. | H | H | D¹³³ | H | H | H | H | H | L¹⁰⁸ | N | N | N | Ph | Ph |
| 2270. | H | H | D¹³³ | H | H | H | H | H | L¹⁰⁸ | N | N | N | 4-biphenyl | 4-biphenyl |
| 2271. | H | H | D¹³³ | H | H | H | H | H | L¹⁰⁸ | N | CH | N | Ph | Ph |
| 2272. | H | H | D¹³³ | H | H | H | H | H | L¹⁰⁸ | N | CH | N | 4-biphenyl | 4-biphenyl |
| 2273. | H | H | D¹³³ | H | H | H | H | H | L¹⁰⁹ | N | N | N | Ph | Ph |
| 2274. | H | H | D¹³³ | H | H | H | H | H | L¹⁰⁹ | N | N | N | 4-biphenyl | 4-biphenyl |
| 2275. | H | H | D¹³³ | H | H | H | H | H | L¹⁰⁹ | N | CH | N | Ph | Ph |
| 2276. | H | H | D¹³³ | H | H | H | H | H | L¹⁰⁹ | N | CH | N | 4-biphenyl | 4-biphenyl |
| 2277. | H | H | D¹³³ | H | H | H | H | H | L¹¹⁰ | N | N | N | Ph | Ph |
| 2278. | H | H | D¹³³ | H | H | H | H | H | L¹¹⁰ | N | N | N | 4-biphenyl | 4-biphenyl |
| 2279. | H | H | D¹³³ | H | H | H | H | H | L¹¹⁰ | N | CH | N | Ph | Ph |
| 2280. | H | H | D¹³³ | H | H | H | H | H | L¹¹⁰ | N | CH | N | 4-biphenyl | 4-biphenyl |
| 2281. | H | H | D¹³³ | H | H | H | H | H | L¹¹¹ | N | N | N | Ph | Ph |
| 2282. | H | H | D¹³³ | H | H | H | H | H | L¹¹¹ | N | N | N | 4-biphenyl | 4-biphenyl |
| 2283. | H | H | D¹³³ | H | H | H | H | H | L¹¹¹ | N | CH | N | Ph | Ph |
| 2284. | H | H | D¹³³ | H | H | H | H | H | L¹¹¹ | N | CH | N | 4-biphenyl | 4-biphenyl |
| 2285. | H | H | D¹³³ | H | H | H | H | H | L¹¹² | N | N | N | Ph | Ph |
| 2286. | H | H | D¹³³ | H | H | H | H | H | L¹¹² | N | N | N | 4-biphenyl | 4-biphenyl |
| 2287. | H | H | D¹³³ | H | H | H | H | H | L¹¹² | N | CH | N | Ph | Ph |
| 2288. | H | H | D¹³³ | H | H | H | H | H | L¹¹² | N | CH | N | 4-biphenyl | 4-biphenyl |
| 2289. | H | H | D¹³³ | H | H | H | H | H | L¹¹³ | N | N | N | Ph | Ph |
| 2290. | H | H | D¹³³ | H | H | H | H | H | L¹¹³ | N | N | N | 4-biphenyl | 4-biphenyl |
| 2291. | H | H | D¹³³ | H | H | H | H | H | L¹¹³ | N | CH | N | Ph | Ph |
| 2292. | H | H | D¹³³ | H | H | H | H | H | L¹¹³ | N | CH | N | 4-biphenyl | 4-biphenyl |
| 2293. | H | H | D¹³³ | H | H | H | H | H | L¹¹⁴ | N | N | N | Ph | Ph |
| 2294. | H | H | D¹³³ | H | H | H | H | H | L¹¹⁴ | N | N | N | 4-biphenyl | 4-biphenyl |
| 2295. | H | H | D¹³³ | H | H | H | H | H | L¹¹⁴ | N | CH | N | Ph | Ph |
| 2296. | H | H | D¹³³ | H | H | H | H | H | L¹¹⁴ | N | CH | N | 4-biphenyl | 4-biphenyl |
| 2297. | H | H | D¹³³ | H | H | H | H | H | L¹¹⁵ | N | N | N | Ph | Ph |
| 2298. | H | H | D¹³³ | H | H | H | H | H | L¹¹⁵ | N | N | N | 4-biphenyl | 4-biphenyl |
| 2299. | H | H | D¹³³ | H | H | H | H | H | L¹¹⁵ | N | CH | N | Ph | Ph |
| 2300. | H | H | D¹³³ | H | H | H | H | H | L¹¹⁵ | N | CH | N | 4-biphenyl | 4-biphenyl |
| 2301. | H | H | D¹³³ | H | H | H | H | H | L¹¹⁶ | N | N | N | Ph | Ph |
| 2302. | H | H | D¹³³ | H | H | H | H | H | L¹¹⁶ | N | N | N | 4-biphenyl | 4-biphenyl |
| 2303. | H | H | D¹³³ | H | H | H | H | H | L¹¹⁶ | N | CH | N | Ph | Ph |
| 2304. | H | H | D¹³³ | H | H | H | H | H | L¹¹⁶ | N | CH | N | 4-biphenyl | 4-biphenyl |
| 2305. | H | H | D¹³³ | H | H | D¹³³ | H | H | L¹⁰¹ | N | N | N | Ph | Ph |
| 2306. | H | H | D¹³³ | H | H | D¹³³ | H | H | L¹⁰¹ | N | N | N | 4-biphenyl | 4-biphenyl |
| 2307. | H | H | D¹³³ | H | H | D¹³³ | H | H | L¹⁰¹ | N | CH | N | Ph | Ph |
| 2308. | H | H | D¹³³ | H | H | D¹³³ | H | H | L¹⁰¹ | N | CH | N | 4-biphenyl | 4-biphenyl |

-continued

| Compound number | $R^1$ | $R^2$ | $R^3$ | $R^4$ | $R^5$ | $R^6$ | $R^7$ | $R^8$ | $L^1$ | $Z^1$ | $Z^3$ | $Z^5$ | $R^{91}$ | $R^{92}$ |
|---|---|---|---|---|---|---|---|---|---|---|---|---|---|---|
| 2309. | H | H | $D^{133}$ | H | H | $D^{133}$ | H | H | $L^{102}$ | N | N | N | Ph | Ph |
| 2310. | H | H | $D^{133}$ | H | H | $D^{133}$ | H | H | $L^{102}$ | N | N | N | 4-biphenyl | 4-biphenyl |
| 2311. | H | H | $D^{133}$ | H | H | $D^{133}$ | H | H | $L^{102}$ | N | CH | N | Ph | Ph |
| 2312. | H | H | $D^{133}$ | H | H | $D^{133}$ | H | H | $L^{102}$ | N | CH | N | 4-biphenyl | 4-biphenyl |
| 2313. | H | H | $D^{133}$ | H | H | $D^{133}$ | H | H | $L^{103}$ | N | N | N | Ph | Ph |
| 2314. | H | H | $D^{133}$ | H | H | $D^{133}$ | H | H | $L^{103}$ | N | N | N | 4-biphenyl | 4-biphenyl |
| 2315. | H | H | $D^{133}$ | H | H | $D^{133}$ | H | H | $L^{103}$ | N | CH | N | Ph | Ph |
| 2316. | H | H | $D^{133}$ | H | H | $D^{133}$ | H | H | $L^{103}$ | N | CH | N | 4-biphenyl | 4-biphenyl |
| 2317. | H | H | $D^{133}$ | H | H | $D^{133}$ | H | H | $L^{104}$ | N | N | N | Ph | Ph |
| 2318. | H | H | $D^{133}$ | H | H | $D^{133}$ | H | H | $L^{104}$ | N | N | N | 4-biphenyl | 4-biphenyl |
| 2319. | H | H | $D^{133}$ | H | H | $D^{133}$ | H | H | $L^{104}$ | N | CH | N | Ph | Ph |
| 2320. | H | H | $D^{133}$ | H | H | $D^{133}$ | H | H | $L^{104}$ | N | CH | N | 4-biphenyl | 4-biphenyl |
| 2321. | H | H | $D^{133}$ | H | H | $D^{133}$ | H | H | $L^{105}$ | N | N | N | Ph | Ph |
| 2322. | H | H | $D^{133}$ | H | H | $D^{133}$ | H | H | $L^{105}$ | N | N | N | 4-biphenyl | 4-biphenyl |
| 2323. | H | H | $D^{133}$ | H | H | $D^{133}$ | H | H | $L^{105}$ | N | CH | N | Ph | Ph |
| 2324. | H | H | $D^{133}$ | H | H | $D^{133}$ | H | H | $L^{105}$ | N | CH | N | 4-biphenyl | 4-biphenyl |
| 2325. | H | H | $D^{133}$ | H | H | $D^{133}$ | H | H | $L^{106}$ | N | N | N | Ph | Ph |
| 2326. | H | H | $D^{133}$ | H | H | $D^{133}$ | H | H | $L^{106}$ | N | N | N | 4-biphenyl | 4-biphenyl |
| 2327. | H | H | $D^{133}$ | H | H | $D^{133}$ | H | H | $L^{106}$ | N | CH | N | Ph | Ph |
| 2328. | H | H | $D^{133}$ | H | H | $D^{133}$ | H | H | $L^{106}$ | N | CH | N | 4-biphenyl | 4-biphenyl |
| 2329. | H | H | $D^{133}$ | H | H | $D^{133}$ | H | H | $L^{107}$ | N | N | N | Ph | Ph |
| 2330. | H | H | $D^{133}$ | H | H | $D^{133}$ | H | H | $L^{107}$ | N | N | N | 4-biphenyl | 4-biphenyl |
| 2331. | H | H | $D^{133}$ | H | H | $D^{133}$ | H | H | $L^{107}$ | N | CH | N | Ph | Ph |
| 2332. | H | H | $D^{133}$ | H | H | $D^{133}$ | H | H | $L^{107}$ | N | CH | N | 4-biphenyl | 4-biphenyl |
| 2333. | H | H | $D^{133}$ | H | H | $D^{133}$ | H | H | $L^{108}$ | N | N | N | Ph | Ph |
| 2334. | H | H | $D^{133}$ | H | H | $D^{133}$ | H | H | $L^{108}$ | N | N | N | 4-biphenyl | 4-biphenyl |
| 2335. | H | H | $D^{133}$ | H | H | $D^{133}$ | H | H | $L^{108}$ | N | CH | N | Ph | Ph |
| 2336. | H | H | $D^{133}$ | H | H | $D^{133}$ | H | H | $L^{108}$ | N | CH | N | 4-biphenyl | 4-biphenyl |
| 2337. | H | H | $D^{133}$ | H | H | $D^{133}$ | H | H | $L^{109}$ | N | N | N | Ph | Ph |
| 2338. | H | H | $D^{133}$ | H | H | $D^{133}$ | H | H | $L^{109}$ | N | N | N | 4-biphenyl | 4-biphenyl |
| 2339. | H | H | $D^{133}$ | H | H | $D^{133}$ | H | H | $L^{109}$ | N | CH | N | Ph | Ph |
| 2340. | H | H | $D^{133}$ | H | H | $D^{133}$ | H | H | $L^{109}$ | N | CH | N | 4-biphenyl | 4-biphenyl |
| 2341. | H | H | $D^{133}$ | H | H | $D^{133}$ | H | H | $L^{110}$ | N | N | N | Ph | Ph |
| 2342. | H | H | $D^{133}$ | H | H | $D^{133}$ | H | H | $L^{110}$ | N | N | N | 4-biphenyl | 4-biphenyl |
| 2343. | H | H | $D^{133}$ | H | H | $D^{133}$ | H | H | $L^{110}$ | N | CH | N | Ph | Ph |
| 2344. | H | H | $D^{133}$ | H | H | $D^{133}$ | H | H | $L^{110}$ | N | CH | N | 4-biphenyl | 4-biphenyl |
| 2345. | H | H | $D^{133}$ | H | H | $D^{133}$ | H | H | $L^{111}$ | N | N | N | Ph | Ph |
| 2346. | H | H | $D^{133}$ | H | H | $D^{133}$ | H | H | $L^{111}$ | N | N | N | 4-biphenyl | 4-biphenyl |
| 2347. | H | H | $D^{133}$ | H | H | $D^{133}$ | H | H | $L^{111}$ | N | CH | N | Ph | Ph |
| 2348. | H | H | $D^{133}$ | H | H | $D^{133}$ | H | H | $L^{111}$ | N | CH | N | 4-biphenyl | 4-biphenyl |
| 2349. | H | H | $D^{133}$ | H | H | $D^{133}$ | H | H | $L^{112}$ | N | N | N | Ph | Ph |
| 2350. | H | H | $D^{133}$ | H | H | $D^{133}$ | H | H | $L^{112}$ | N | N | N | 4-biphenyl | 4-biphenyl |
| 2351. | H | H | $D^{133}$ | H | H | $D^{133}$ | H | H | $L^{112}$ | N | CH | N | Ph | Ph |
| 2352. | H | H | $D^{133}$ | H | H | $D^{133}$ | H | H | $L^{112}$ | N | CH | N | 4-biphenyl | 4-biphenyl |
| 2353. | H | H | $D^{133}$ | H | H | $D^{133}$ | H | H | $L^{113}$ | N | N | N | Ph | Ph |
| 2354. | H | H | $D^{133}$ | H | H | $D^{133}$ | H | H | $L^{113}$ | N | N | N | 4-biphenyl | 4-biphenyl |
| 2355. | H | H | $D^{133}$ | H | H | $D^{133}$ | H | H | $L^{113}$ | N | CH | N | Ph | Ph |
| 2356. | H | H | $D^{133}$ | H | H | $D^{133}$ | H | H | $L^{113}$ | N | CH | N | 4-biphenyl | 4-biphenyl |
| 2357. | H | H | $D^{133}$ | H | H | $D^{133}$ | H | H | $L^{114}$ | N | N | N | Ph | Ph |
| 2358. | H | H | $D^{133}$ | H | H | $D^{133}$ | H | H | $L^{114}$ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2359. | H | H | D¹³³ | H | H | D¹³³ | H | H | L¹¹⁴ | N | CH | N | Ph | Ph |
| 2360. | H | H | D¹³³ | H | H | D¹³³ | H | H | L¹¹⁴ | N | CH | N | 4-biphenyl | 4-biphenyl |
| 2361. | H | H | D¹³³ | H | H | D¹³³ | H | H | L¹¹⁵ | N | N | N | Ph | Ph |
| 2362. | H | H | D¹³³ | H | H | D¹³³ | H | H | L¹¹⁵ | N | N | N | 4-biphenyl | 4-biphenyl |
| 2363. | H | H | D¹³³ | H | H | D¹³³ | H | H | L¹¹⁵ | N | CH | N | Ph | Ph |
| 2364. | H | H | D¹³³ | H | H | D¹³³ | H | H | L¹¹⁵ | N | CH | N | 4-biphenyl | 4-biphenyl |
| 2365. | H | H | D¹³³ | H | H | D¹³³ | H | H | L¹¹⁶ | N | N | N | Ph | Ph |
| 2366. | H | H | D¹³³ | H | H | D¹³³ | H | H | L¹¹⁶ | N | N | N | 4-biphenyl | 4-biphenyl |
| 2367. | H | H | D¹³³ | H | H | D¹³³ | H | H | L¹¹⁶ | N | CH | N | Ph | Ph |
| 2368. | H | H | D¹³³ | H | H | D¹³³ | H | H | L¹¹⁶ | N | CH | N | 4-biphenyl | 4-biphenyl |
| 2369. | H | H | D¹³⁴ | H | H | H | H | H | L¹⁰¹ | N | N | N | Ph | Ph |
| 2370. | H | H | D¹³⁴ | H | H | H | H | H | L¹⁰¹ | N | N | N | 4-biphenyl | 4-biphenyl |
| 2371. | H | H | D¹³⁴ | H | H | H | H | H | L¹⁰¹ | N | CH | N | Ph | Ph |
| 2372. | H | H | D¹³⁴ | H | H | H | H | H | L¹⁰¹ | N | CH | N | 4-biphenyl | 4-biphenyl |
| 2373. | H | H | D¹³⁴ | H | H | H | H | H | L¹⁰² | N | N | N | Ph | Ph |
| 2374. | H | H | D¹³⁴ | H | H | H | H | H | L¹⁰² | N | N | N | 4-biphenyl | 4-biphenyl |
| 2375. | H | H | D¹³⁴ | H | H | H | H | H | L¹⁰² | N | CH | N | Ph | Ph |
| 2376. | H | H | D¹³⁴ | H | H | H | H | H | L¹⁰² | N | CH | N | 4-biphenyl | 4-biphenyl |
| 2377. | H | H | D¹³⁴ | H | H | H | H | H | L¹⁰³ | N | N | N | Ph | Ph |
| 2378. | H | H | D¹³⁴ | H | H | H | H | H | L¹⁰³ | N | N | N | 4-biphenyl | 4-biphenyl |
| 2379. | H | H | D¹³⁴ | H | H | H | H | H | L¹⁰³ | N | CH | N | Ph | Ph |
| 2380. | H | H | D¹³⁴ | H | H | H | H | H | L¹⁰³ | N | CH | N | 4-biphenyl | 4-biphenyl |
| 2381. | H | H | D¹³⁴ | H | H | H | H | H | L¹⁰⁴ | N | N | N | Ph | Ph |
| 2382. | H | H | D¹³⁴ | H | H | H | H | H | L¹⁰⁴ | N | N | N | 4-biphenyl | 4-biphenyl |
| 2383. | H | H | D¹³⁴ | H | H | H | H | H | L¹⁰⁴ | N | CH | N | Ph | Ph |
| 2384. | H | H | D¹³⁴ | H | H | H | H | H | L¹⁰⁴ | N | CH | N | 4-biphenyl | 4-biphenyl |
| 2385. | H | H | D¹³⁴ | H | H | H | H | H | L¹⁰⁵ | N | N | N | Ph | Ph |
| 2386. | H | H | D¹³⁴ | H | H | H | H | H | L¹⁰⁵ | N | N | N | 4-biphenyl | 4-biphenyl |
| 2387. | H | H | D¹³⁴ | H | H | H | H | H | L¹⁰⁵ | N | CH | N | Ph | Ph |
| 2388. | H | H | D¹³⁴ | H | H | H | H | H | L¹⁰⁵ | N | CH | N | 4-biphenyl | 4-biphenyl |
| 2389. | H | H | D¹³⁴ | H | H | H | H | H | L¹⁰⁶ | N | N | N | Ph | Ph |
| 2390. | H | H | D¹³⁴ | H | H | H | H | H | L¹⁰⁶ | N | N | N | 4-biphenyl | 4-biphenyl |
| 2391. | H | H | D¹³⁴ | H | H | H | H | H | L¹⁰⁶ | N | CH | N | Ph | Ph |
| 2392. | H | H | D¹³⁴ | H | H | H | H | H | L¹⁰⁶ | N | CH | N | 4-biphenyl | 4-biphenyl |
| 2393. | H | H | D¹³⁴ | H | H | H | H | H | L¹⁰⁷ | N | N | N | Ph | Ph |
| 2394. | H | H | D¹³⁴ | H | H | H | H | H | L¹⁰⁷ | N | N | N | 4-biphenyl | 4-biphenyl |
| 2395. | H | H | D¹³⁴ | H | H | H | H | H | L¹⁰⁷ | N | CH | N | Ph | Ph |
| 2396. | H | H | D¹³⁴ | H | H | H | H | H | L¹⁰⁷ | N | CH | N | 4-biphenyl | 4-biphenyl |
| 2397. | H | H | D¹³⁴ | H | H | H | H | H | L¹⁰⁸ | N | N | N | Ph | Ph |
| 2398. | H | H | D¹³⁴ | H | H | H | H | H | L¹⁰⁸ | N | N | N | 4-biphenyl | 4-biphenyl |
| 2399. | H | H | D¹³⁴ | H | H | H | H | H | L¹⁰⁸ | N | CH | N | Ph | Ph |
| 2400. | H | H | D¹³⁴ | H | H | H | H | H | L¹⁰⁸ | N | CH | N | 4-biphenyl | 4-biphenyl |
| 2401. | H | H | D¹³⁴ | H | H | H | H | H | L¹⁰⁹ | N | N | N | Ph | Ph |
| 2402. | H | H | D¹³⁴ | H | H | H | H | H | L¹⁰⁹ | N | N | N | 4-biphenyl | 4-biphenyl |
| 2403. | H | H | D¹³⁴ | H | H | H | H | H | L¹⁰⁹ | N | CH | N | Ph | Ph |
| 2404. | H | H | D¹³⁴ | H | H | H | H | H | L¹⁰⁹ | N | CH | N | 4-biphenyl | 4-biphenyl |
| 2405. | H | H | D¹³⁴ | H | H | H | H | H | L¹¹⁰ | N | N | N | Ph | Ph |
| 2406. | H | H | D¹³⁴ | H | H | H | H | H | L¹¹⁰ | N | N | N | 4-biphenyl | 4-biphenyl |
| 2407. | H | H | D¹³⁴ | H | H | H | H | H | L¹¹⁰ | N | CH | N | Ph | Ph |
| 2408. | H | H | D¹³⁴ | H | H | H | H | H | L¹¹⁰ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2409. | H | H | D¹³⁴ | H | H | H | H | H | L¹¹¹ | N | N | N | Ph | Ph |
| 2410. | H | H | D¹³⁴ | H | H | H | H | H | L¹¹¹ | N | N | N | 4-biphenyl | 4-biphenyl |
| 2411. | H | H | D¹³⁴ | H | H | H | H | H | L¹¹¹ | N | CH | N | Ph | Ph |
| 2412. | H | H | D¹³⁴ | H | H | H | H | H | L¹¹¹ | N | CH | N | 4-biphenyl | 4-biphenyl |
| 2413. | H | H | D¹³⁴ | H | H | H | H | H | L¹¹² | N | N | N | Ph | Ph |
| 2414. | H | H | D¹³⁴ | H | H | H | H | H | L¹¹² | N | N | N | 4-biphenyl | 4-biphenyl |
| 2415. | H | H | D¹³⁴ | H | H | H | H | H | L¹¹² | N | CH | N | Ph | Ph |
| 2416. | H | H | D¹³⁴ | H | H | H | H | H | L¹¹² | N | CH | N | 4-biphenyl | 4-biphenyl |
| 2417. | H | H | D¹³⁴ | H | H | H | H | H | L¹¹³ | N | N | N | Ph | Ph |
| 2418. | H | H | D¹³⁴ | H | H | H | H | H | L¹¹³ | N | N | N | 4-biphenyl | 4-biphenyl |
| 2419. | H | H | D¹³⁴ | H | H | H | H | H | L¹¹³ | N | CH | N | Ph | Ph |
| 2420. | H | H | D¹³⁴ | H | H | H | H | H | L¹¹³ | N | CH | N | 4-biphenyl | 4-biphenyl |
| 2421. | H | H | D¹³⁴ | H | H | H | H | H | L¹¹⁴ | N | N | N | Ph | Ph |
| 2422. | H | H | D¹³⁴ | H | H | H | H | H | L¹¹⁴ | N | N | N | 4-biphenyl | 4-biphenyl |
| 2423. | H | H | D¹³⁴ | H | H | H | H | H | L¹¹⁴ | N | CH | N | Ph | Ph |
| 2424. | H | H | D¹³⁴ | H | H | H | H | H | L¹¹⁴ | N | CH | N | 4-biphenyl | 4-biphenyl |
| 2425. | H | H | D¹³⁴ | H | H | H | H | H | L¹¹⁵ | N | N | N | Ph | Ph |
| 2426. | H | H | D¹³⁴ | H | H | H | H | H | L¹¹⁵ | N | N | N | 4-biphenyl | 4-biphenyl |
| 2427. | H | H | D¹³⁴ | H | H | H | H | H | L¹¹⁵ | N | CH | N | Ph | Ph |
| 2428. | H | H | D¹³⁴ | H | H | H | H | H | L¹¹⁵ | N | CH | N | 4-biphenyl | 4-biphenyl |
| 2429. | H | H | D¹³⁴ | H | H | H | H | H | L¹¹⁶ | N | N | N | Ph | Ph |
| 2430. | H | H | D¹³⁴ | H | H | H | H | H | L¹¹⁶ | N | N | N | 4-biphenyl | 4-biphenyl |
| 2431. | H | H | D¹³⁴ | H | H | H | H | H | L¹¹⁶ | N | CH | N | Ph | Ph |
| 2432. | H | H | D¹³⁴ | H | H | H | H | H | L¹¹⁶ | N | CH | N | 4-biphenyl | 4-biphenyl |
| 2433. | H | H | D¹³⁴ | H | H | D¹³⁴ | H | H | L¹⁰¹ | N | N | N | Ph | Ph |
| 2434. | H | H | D¹³⁴ | H | H | D¹³⁴ | H | H | L¹⁰¹ | N | N | N | 4-biphenyl | 4-biphenyl |
| 2435. | H | H | D¹³⁴ | H | H | D¹³⁴ | H | H | L¹⁰¹ | N | CH | N | Ph | Ph |
| 2436. | H | H | D¹³⁴ | H | H | D¹³⁴ | H | H | L¹⁰¹ | N | CH | N | 4-biphenyl | 4-biphenyl |
| 2437. | H | H | D¹³⁴ | H | H | D¹³⁴ | H | H | L¹⁰² | N | N | N | Ph | Ph |
| 2438. | H | H | D¹³⁴ | H | H | D¹³⁴ | H | H | L¹⁰² | N | N | N | 4-biphenyl | 4-biphenyl |
| 2439. | H | H | D¹³⁴ | H | H | D¹³⁴ | H | H | L¹⁰² | N | CH | N | Ph | Ph |
| 2440. | H | H | D¹³⁴ | H | H | D¹³⁴ | H | H | L¹⁰² | N | CH | N | 4-biphenyl | 4-biphenyl |
| 2441. | H | H | D¹³⁴ | H | H | D¹³⁴ | H | H | L¹⁰³ | N | N | N | Ph | Ph |
| 2442. | H | H | D¹³⁴ | H | H | D¹³⁴ | H | H | L¹⁰³ | N | N | N | 4-biphenyl | 4-biphenyl |
| 2443. | H | H | D¹³⁴ | H | H | D¹³⁴ | H | H | L¹⁰³ | N | CH | N | Ph | Ph |
| 2444. | H | H | D¹³⁴ | H | H | D¹³⁴ | H | H | L¹⁰³ | N | CH | N | 4-biphenyl | 4-biphenyl |
| 2445. | H | H | D¹³⁴ | H | H | D¹³⁴ | H | H | L¹⁰⁴ | N | N | N | Ph | Ph |
| 2446. | H | H | D¹³⁴ | H | H | D¹³⁴ | H | H | L¹⁰⁴ | N | N | N | 4-biphenyl | 4-biphenyl |
| 2447. | H | H | D¹³⁴ | H | H | D¹³⁴ | H | H | L¹⁰⁴ | N | CH | N | Ph | Ph |
| 2448. | H | H | D¹³⁴ | H | H | D¹³⁴ | H | H | L¹⁰⁴ | N | CH | N | 4-biphenyl | 4-biphenyl |
| 2449. | H | H | D¹³⁴ | H | H | D¹³⁴ | H | H | L¹⁰⁵ | N | N | N | Ph | Ph |
| 2450. | H | H | D¹³⁴ | H | H | D¹³⁴ | H | H | L¹⁰⁵ | N | N | N | 4-biphenyl | 4-biphenyl |
| 2451. | H | H | D¹³⁴ | H | H | D¹³⁴ | H | H | L¹⁰⁵ | N | CH | N | Ph | Ph |
| 2452. | H | H | D¹³⁴ | H | H | D¹³⁴ | H | H | L¹⁰⁵ | N | CH | N | 4-biphenyl | 4-biphenyl |
| 2453. | H | H | D¹³⁴ | H | H | D¹³⁴ | H | H | L¹⁰⁶ | N | N | N | Ph | Ph |
| 2454. | H | H | D¹³⁴ | H | H | D¹³⁴ | H | H | L¹⁰⁶ | N | N | N | 4-biphenyl | 4-biphenyl |
| 2455. | H | H | D¹³⁴ | H | H | D¹³⁴ | H | H | L¹⁰⁶ | N | CH | N | Ph | Ph |
| 2456. | H | H | D¹³⁴ | H | H | D¹³⁴ | H | H | L¹⁰⁶ | N | CH | N | 4-biphenyl | 4-biphenyl |
| 2457. | H | H | D¹³⁴ | H | H | D¹³⁴ | H | H | L¹⁰⁷ | N | N | N | Ph | Ph |
| 2458. | H | H | D¹³⁴ | H | H | D¹³⁴ | H | H | L¹⁰⁷ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2459. | H | H | D¹³⁴ | H | H | D¹³⁴ | H | H | L¹⁰⁷ | N | CH | N | Ph | Ph |
| 2460. | H | H | D¹³⁴ | H | H | D¹³⁴ | H | H | L¹⁰⁷ | N | CH | N | 4-biphenyl | 4-biphenyl |
| 2461. | H | H | D¹³⁴ | H | H | D¹³⁴ | H | H | L¹⁰⁸ | N | N | N | Ph | Ph |
| 2462. | H | H | D¹³⁴ | H | H | D¹³⁴ | H | H | L¹⁰⁸ | N | N | N | 4-biphenyl | 4-biphenyl |
| 2463. | H | H | D¹³⁴ | H | H | D¹³⁴ | H | H | L¹⁰⁸ | N | CH | N | Ph | Ph |
| 2464. | H | H | D¹³⁴ | H | H | D¹³⁴ | H | H | L¹⁰⁸ | N | CH | N | 4-biphenyl | 4-biphenyl |
| 2465. | H | H | D¹³⁴ | H | H | D¹³⁴ | H | H | L¹⁰⁹ | N | N | N | Ph | Ph |
| 2466. | H | H | D¹³⁴ | H | H | D¹³⁴ | H | H | L¹⁰⁹ | N | N | N | 4-biphenyl | 4-biphenyl |
| 2467. | H | H | D¹³⁴ | H | H | D¹³⁴ | H | H | L¹⁰⁹ | N | CH | N | Ph | Ph |
| 2468. | H | H | D¹³⁴ | H | H | D¹³⁴ | H | H | L¹⁰⁹ | N | CH | N | 4-biphenyl | 4-biphenyl |
| 2469. | H | H | D¹³⁴ | H | H | D¹³⁴ | H | H | L¹¹⁰ | N | N | N | Ph | Ph |
| 2470. | H | H | D¹³⁴ | H | H | D¹³⁴ | H | H | L¹¹⁰ | N | N | N | 4-biphenyl | 4-biphenyl |
| 2471. | H | H | D¹³⁴ | H | H | D¹³⁴ | H | H | L¹¹⁰ | N | CH | N | Ph | Ph |
| 2472. | H | H | D¹³⁴ | H | H | D¹³⁴ | H | H | L¹¹⁰ | N | CH | N | 4-biphenyl | 4-biphenyl |
| 2473. | H | H | D¹³⁴ | H | H | D¹³⁴ | H | H | L¹¹¹ | N | N | N | Ph | Ph |
| 2474. | H | H | D¹³⁴ | H | H | D¹³⁴ | H | H | L¹¹¹ | N | N | N | 4-biphenyl | 4-biphenyl |
| 2475. | H | H | D¹³⁴ | H | H | D¹³⁴ | H | H | L¹¹¹ | N | CH | N | Ph | Ph |
| 2476. | H | H | D¹³⁴ | H | H | D¹³⁴ | H | H | L¹¹¹ | N | CH | N | 4-biphenyl | 4-biphenyl |
| 2477. | H | H | D¹³⁴ | H | H | D¹³⁴ | H | H | L¹¹² | N | N | N | Ph | Ph |
| 2478. | H | H | D¹³⁴ | H | H | D¹³⁴ | H | H | L¹¹² | N | N | N | 4-biphenyl | 4-biphenyl |
| 2479. | H | H | D¹³⁴ | H | H | D¹³⁴ | H | H | L¹¹² | N | CH | N | Ph | Ph |
| 2480. | H | H | D¹³⁴ | H | H | D¹³⁴ | H | H | L¹¹² | N | CH | N | 4-biphenyl | 4-biphenyl |
| 2481. | H | H | D¹³⁴ | H | H | D¹³⁴ | H | H | L¹¹³ | N | N | N | Ph | Ph |
| 2482. | H | H | D¹³⁴ | H | H | D¹³⁴ | H | H | L¹¹³ | N | N | N | 4-biphenyl | 4-biphenyl |
| 2483. | H | H | D¹³⁴ | H | H | D¹³⁴ | H | H | L¹¹³ | N | CH | N | Ph | Ph |
| 2484. | H | H | D¹³⁴ | H | H | D¹³⁴ | H | H | L¹¹³ | N | CH | N | 4-biphenyl | 4-biphenyl |
| 2485. | H | H | D¹³⁴ | H | H | D¹³⁴ | H | H | L¹¹⁴ | N | N | N | Ph | Ph |
| 2486. | H | H | D¹³⁴ | H | H | D¹³⁴ | H | H | L¹¹⁴ | N | N | N | 4-biphenyl | 4-biphenyl |
| 2487. | H | H | D¹³⁴ | H | H | D¹³⁴ | H | H | L¹¹⁴ | N | CH | N | Ph | Ph |
| 2488. | H | H | D¹³⁴ | H | H | D¹³⁴ | H | H | L¹¹⁴ | N | CH | N | 4-biphenyl | 4-biphenyl |
| 2489. | H | H | D¹³⁴ | H | H | D¹³⁴ | H | H | L¹¹⁵ | N | N | N | Ph | Ph |
| 2490. | H | H | D¹³⁴ | H | H | D¹³⁴ | H | H | L¹¹⁵ | N | N | N | 4-biphenyl | 4-biphenyl |
| 2491. | H | H | D¹³⁴ | H | H | D¹³⁴ | H | H | L¹¹⁵ | N | CH | N | Ph | Ph |
| 2492. | H | H | D¹³⁴ | H | H | D¹³⁴ | H | H | L¹¹⁵ | N | CH | N | 4-biphenyl | 4-biphenyl |
| 2493. | H | H | D¹³⁴ | H | H | D¹³⁴ | H | H | L¹¹⁶ | N | N | N | Ph | Ph |
| 2494. | H | H | D¹³⁴ | H | H | D¹³⁴ | H | H | L¹¹⁶ | N | N | N | 4-biphenyl | 4-biphenyl |
| 2495. | H | H | D¹³⁴ | H | H | D¹³⁴ | H | H | L¹¹⁶ | N | CH | N | Ph | Ph |
| 2496. | H | H | D¹³⁴ | H | H | D¹³⁴ | H | H | L¹¹⁶ | N | CH | N | 4-biphenyl | 4-biphenyl |
| 2497. | H | H | D¹³⁵ | H | H | H | H | H | L¹⁰¹ | N | N | N | Ph | Ph |
| 2498. | H | H | D¹³⁵ | H | H | H | H | H | L¹⁰¹ | N | N | N | 4-biphenyl | 4-biphenyl |
| 2499. | H | H | D¹³⁵ | H | H | H | H | H | L¹⁰¹ | N | CH | N | Ph | Ph |
| 2500. | H | H | D¹³⁵ | H | H | H | H | H | L¹⁰¹ | N | CH | N | 4-biphenyl | 4-biphenyl |
| 2501. | H | H | D¹³⁵ | H | H | H | H | H | L¹⁰² | N | N | N | Ph | Ph |
| 2502. | H | H | D¹³⁵ | H | H | H | H | H | L¹⁰² | N | N | N | 4-biphenyl | 4-biphenyl |
| 2503. | H | H | D¹³⁵ | H | H | H | H | H | L¹⁰² | N | CH | N | Ph | Ph |
| 2504. | H | H | D¹³⁵ | H | H | H | H | H | L¹⁰² | N | CH | N | 4-biphenyl | 4-biphenyl |
| 2505. | H | H | D¹³⁵ | H | H | H | H | H | L¹⁰³ | N | N | N | Ph | Ph |
| 2506. | H | H | D¹³⁵ | H | H | H | H | H | L¹⁰³ | N | N | N | 4-biphenyl | 4-biphenyl |
| 2507. | H | H | D¹³⁵ | H | H | H | H | H | L¹⁰³ | N | CH | N | Ph | Ph |
| 2508. | H | H | D¹³⁵ | H | H | H | H | H | L¹⁰³ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2509. | H | H | D¹³⁵ | H | H | H | H | H | L¹⁰⁴ | N | N | N | Ph | Ph |
| 2510. | H | H | D¹³⁵ | H | H | H | H | H | L¹⁰⁴ | N | N | N | 4-biphenyl | 4-biphenyl |
| 2511. | H | H | D¹³⁵ | H | H | H | H | H | L¹⁰⁴ | N | CH | N | Ph | Ph |
| 2512. | H | H | D¹³⁵ | H | H | H | H | H | L¹⁰⁴ | N | CH | N | 4-biphenyl | 4-biphenyl |
| 2513. | H | H | D¹³⁵ | H | H | H | H | H | L¹⁰⁵ | N | N | N | Ph | Ph |
| 2514. | H | H | D¹³⁵ | H | H | H | H | H | L¹⁰⁵ | N | N | N | 4-biphenyl | 4-biphenyl |
| 2515. | H | H | D¹³⁵ | H | H | H | H | H | L¹⁰⁵ | N | CH | N | Ph | Ph |
| 2516. | H | H | D¹³⁵ | H | H | H | H | H | L¹⁰⁵ | N | CH | N | 4-biphenyl | 4-biphenyl |
| 2517. | H | H | D¹³⁵ | H | H | H | H | H | L¹⁰⁶ | N | N | N | Ph | Ph |
| 2518. | H | H | D¹³⁵ | H | H | H | H | H | L¹⁰⁶ | N | N | N | 4-biphenyl | 4-biphenyl |
| 2519. | H | H | D¹³⁵ | H | H | H | H | H | L¹⁰⁶ | N | CH | N | Ph | Ph |
| 2520. | H | H | D¹³⁵ | H | H | H | H | H | L¹⁰⁶ | N | CH | N | 4-biphenyl | 4-biphenyl |
| 2521. | H | H | D¹³⁵ | H | H | H | H | H | L¹⁰⁷ | N | N | N | Ph | Ph |
| 2522. | H | H | D¹³⁵ | H | H | H | H | H | L¹⁰⁷ | N | N | N | 4-biphenyl | 4-biphenyl |
| 2523. | H | H | D¹³⁵ | H | H | H | H | H | L¹⁰⁷ | N | CH | N | Ph | Ph |
| 2524. | H | H | D¹³⁵ | H | H | H | H | H | L¹⁰⁷ | N | CH | N | 4-biphenyl | 4-biphenyl |
| 2525. | H | H | D¹³⁵ | H | H | H | H | H | L¹⁰⁸ | N | N | N | Ph | Ph |
| 2526. | H | H | D¹³⁵ | H | H | H | H | H | L¹⁰⁸ | N | N | N | 4-biphenyl | 4-biphenyl |
| 2527. | H | H | D¹³⁵ | H | H | H | H | H | L¹⁰⁸ | N | CH | N | Ph | Ph |
| 2528. | H | H | D¹³⁵ | H | H | H | H | H | L¹⁰⁸ | N | CH | N | 4-biphenyl | 4-biphenyl |
| 2529. | H | H | D¹³⁵ | H | H | H | H | H | L¹⁰⁹ | N | N | N | Ph | Ph |
| 2530. | H | H | D¹³⁵ | H | H | H | H | H | L¹⁰⁹ | N | N | N | 4-biphenyl | 4-biphenyl |
| 2531. | H | H | D¹³⁵ | H | H | H | H | H | L¹⁰⁹ | N | CH | N | Ph | Ph |
| 2532. | H | H | D¹³⁵ | H | H | H | H | H | L¹⁰⁹ | N | CH | N | 4-biphenyl | 4-biphenyl |
| 2533. | H | H | D¹³⁵ | H | H | H | H | H | L¹¹⁰ | N | N | N | Ph | Ph |
| 2534. | H | H | D¹³⁵ | H | H | H | H | H | L¹¹⁰ | N | N | N | 4-biphenyl | 4-biphenyl |
| 2535. | H | H | D¹³⁵ | H | H | H | H | H | L¹¹⁰ | N | CH | N | Ph | Ph |
| 2536. | H | H | D¹³⁵ | H | H | H | H | H | L¹¹⁰ | N | CH | N | 4-biphenyl | 4-biphenyl |
| 2537. | H | H | D¹³⁵ | H | H | H | H | H | L¹¹¹ | N | N | N | Ph | Ph |
| 2538. | H | H | D¹³⁵ | H | H | H | H | H | L¹¹¹ | N | N | N | 4-biphenyl | 4-biphenyl |
| 2539. | H | H | D¹³⁵ | H | H | H | H | H | L¹¹¹ | N | CH | N | Ph | Ph |
| 2540. | H | H | D¹³⁵ | H | H | H | H | H | L¹¹¹ | N | CH | N | 4-biphenyl | 4-biphenyl |
| 2541. | H | H | D¹³⁵ | H | H | H | H | H | L¹¹² | N | N | N | Ph | Ph |
| 2542. | H | H | D¹³⁵ | H | H | H | H | H | L¹¹² | N | N | N | 4-biphenyl | 4-biphenyl |
| 2543. | H | H | D¹³⁵ | H | H | H | H | H | L¹¹² | N | CH | N | Ph | Ph |
| 2544. | H | H | D¹³⁵ | H | H | H | H | H | L¹¹² | N | CH | N | 4-biphenyl | 4-biphenyl |
| 2545. | H | H | D¹³⁵ | H | H | H | H | H | L¹¹³ | N | N | N | Ph | Ph |
| 2546. | H | H | D¹³⁵ | H | H | H | H | H | L¹¹³ | N | N | N | 4-biphenyl | 4-biphenyl |
| 2547. | H | H | D¹³⁵ | H | H | H | H | H | L¹¹³ | N | CH | N | Ph | Ph |
| 2548. | H | H | D¹³⁵ | H | H | H | H | H | L¹¹³ | N | CH | N | 4-biphenyl | 4-biphenyl |
| 2549. | H | H | D¹³⁵ | H | H | H | H | H | L¹¹⁴ | N | N | N | Ph | Ph |
| 2550. | H | H | D¹³⁵ | H | H | H | H | H | L¹¹⁴ | N | N | N | 4-biphenyl | 4-biphenyl |
| 2551. | H | H | D¹³⁵ | H | H | H | H | H | L¹¹⁴ | N | CH | N | Ph | Ph |
| 2552. | H | H | D¹³⁵ | H | H | H | H | H | L¹¹⁴ | N | CH | N | 4-biphenyl | 4-biphenyl |
| 2553. | H | H | D¹³⁵ | H | H | H | H | H | L¹¹⁵ | N | N | N | Ph | Ph |
| 2554. | H | H | D¹³⁵ | H | H | H | H | H | L¹¹⁵ | N | N | N | 4-biphenyl | 4-biphenyl |
| 2555. | H | H | D¹³⁵ | H | H | H | H | H | L¹¹⁵ | N | CH | N | Ph | Ph |
| 2556. | H | H | D¹³⁵ | H | H | H | H | H | L¹¹⁵ | N | CH | N | 4-biphenyl | 4-biphenyl |
| 2557. | H | H | D¹³⁵ | H | H | H | H | H | L¹¹⁶ | N | N | N | Ph | Ph |
| 2558. | H | H | D¹³⁵ | H | H | H | H | H | L¹¹⁶ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2559. | H | H | D¹³⁵ | H | H | H | H | H | L¹¹⁶ | N | CH | N | Ph | Ph |
| 2560. | H | H | D¹³⁵ | H | H | H | H | H | L¹¹⁶ | N | CH | N | 4-biphenyl | 4-biphenyl |
| 2561. | H | H | D¹³⁵ | H | H | D¹³⁵ | H | H | L¹⁰¹ | N | N | N | Ph | Ph |
| 2562. | H | H | D¹³⁵ | H | H | D¹³⁵ | H | H | L¹⁰¹ | N | N | N | 4-biphenyl | 4-biphenyl |
| 2563. | H | H | D¹³⁵ | H | H | D¹³⁵ | H | H | L¹⁰¹ | N | CH | N | Ph | Ph |
| 2564. | H | H | D¹³⁵ | H | H | D¹³⁵ | H | H | L¹⁰¹ | N | CH | N | 4-biphenyl | 4-biphenyl |
| 2565. | H | H | D¹³⁵ | H | H | D¹³⁵ | H | H | L¹⁰² | N | N | N | Ph | Ph |
| 2566. | H | H | D¹³⁵ | H | H | D¹³⁵ | H | H | L¹⁰² | N | N | N | 4-biphenyl | 4-biphenyl |
| 2567. | H | H | D¹³⁵ | H | H | D¹³⁵ | H | H | L¹⁰² | N | CH | N | Ph | Ph |
| 2568. | H | H | D¹³⁵ | H | H | D¹³⁵ | H | H | L¹⁰² | N | CH | N | 4-biphenyl | 4-biphenyl |
| 2569. | H | H | D¹³⁵ | H | H | D¹³⁵ | H | H | L¹⁰³ | N | N | N | Ph | Ph |
| 2570. | H | H | D¹³⁵ | H | H | D¹³⁵ | H | H | L¹⁰³ | N | N | N | 4-biphenyl | 4-biphenyl |
| 2571. | H | H | D¹³⁵ | H | H | D¹³⁵ | H | H | L¹⁰³ | N | CH | N | Ph | Ph |
| 2572. | H | H | D¹³⁵ | H | H | D¹³⁵ | H | H | L¹⁰³ | N | CH | N | 4-biphenyl | 4-biphenyl |
| 2573. | H | H | D¹³⁵ | H | H | D¹³⁵ | H | H | L¹⁰⁴ | N | N | N | Ph | Ph |
| 2574. | H | H | D¹³⁵ | H | H | D¹³⁵ | H | H | L¹⁰⁴ | N | N | N | 4-biphenyl | 4-biphenyl |
| 2575. | H | H | D¹³⁵ | H | H | D¹³⁵ | H | H | L¹⁰⁴ | N | CH | N | Ph | Ph |
| 2576. | H | H | D¹³⁵ | H | H | D¹³⁵ | H | H | L¹⁰⁴ | N | CH | N | 4-biphenyl | 4-biphenyl |
| 2577. | H | H | D¹³⁵ | H | H | D¹³⁵ | H | H | L¹⁰⁵ | N | N | N | Ph | Ph |
| 2578. | H | H | D¹³⁵ | H | H | D¹³⁵ | H | H | L¹⁰⁵ | N | N | N | 4-biphenyl | 4-biphenyl |
| 2579. | H | H | D¹³⁵ | H | H | D¹³⁵ | H | H | L¹⁰⁵ | N | CH | N | Ph | Ph |
| 2580. | H | H | D¹³⁵ | H | H | D¹³⁵ | H | H | L¹⁰⁵ | N | CH | N | 4-biphenyl | 4-biphenyl |
| 2581. | H | H | D¹³⁵ | H | H | D¹³⁵ | H | H | L¹⁰⁶ | N | N | N | Ph | Ph |
| 2582. | H | H | D¹³⁵ | H | H | D¹³⁵ | H | H | L¹⁰⁶ | N | N | N | 4-biphenyl | 4-biphenyl |
| 2583. | H | H | D¹³⁵ | H | H | D¹³⁵ | H | H | L¹⁰⁶ | N | CH | N | Ph | Ph |
| 2584. | H | H | D¹³⁵ | H | H | D¹³⁵ | H | H | L¹⁰⁶ | N | CH | N | 4-biphenyl | 4-biphenyl |
| 2585. | H | H | D¹³⁵ | H | H | D¹³⁵ | H | H | L¹⁰⁷ | N | N | N | Ph | Ph |
| 2586. | H | H | D¹³⁵ | H | H | D¹³⁵ | H | H | L¹⁰⁷ | N | N | N | 4-biphenyl | 4-biphenyl |
| 2587. | H | H | D¹³⁵ | H | H | D¹³⁵ | H | H | L¹⁰⁷ | N | CH | N | Ph | Ph |
| 2588. | H | H | D¹³⁵ | H | H | D¹³⁵ | H | H | L¹⁰⁷ | N | CH | N | 4-biphenyl | 4-biphenyl |
| 2589. | H | H | D¹³⁵ | H | H | D¹³⁵ | H | H | L¹⁰⁸ | N | N | N | Ph | Ph |
| 2590. | H | H | D¹³⁵ | H | H | D¹³⁵ | H | H | L¹⁰⁸ | N | N | N | 4-biphenyl | 4-biphenyl |
| 2591. | H | H | D¹³⁵ | H | H | D¹³⁵ | H | H | L¹⁰⁸ | N | CH | N | Ph | Ph |
| 2592. | H | H | D¹³⁵ | H | H | D¹³⁵ | H | H | L¹⁰⁸ | N | CH | N | 4-biphenyl | 4-biphenyl |
| 2593. | H | H | D¹³⁵ | H | H | D¹³⁵ | H | H | L¹⁰⁹ | N | N | N | Ph | Ph |
| 2594. | H | H | D¹³⁵ | H | H | D¹³⁵ | H | H | L¹⁰⁹ | N | N | N | 4-biphenyl | 4-biphenyl |
| 2595. | H | H | D¹³⁵ | H | H | D¹³⁵ | H | H | L¹⁰⁹ | N | CH | N | Ph | Ph |
| 2596. | H | H | D¹³⁵ | H | H | D¹³⁵ | H | H | L¹⁰⁹ | N | CH | N | 4-biphenyl | 4-biphenyl |
| 2597. | H | H | D¹³⁵ | H | H | D¹³⁵ | H | H | L¹¹⁰ | N | N | N | Ph | Ph |
| 2598. | H | H | D¹³⁵ | H | H | D¹³⁵ | H | H | L¹¹⁰ | N | N | N | 4-biphenyl | 4-biphenyl |
| 2599. | H | H | D¹³⁵ | H | H | D¹³⁵ | H | H | L¹¹⁰ | N | CH | N | Ph | Ph |
| 2600. | H | H | D¹³⁵ | H | H | D¹³⁵ | H | H | L¹¹⁰ | N | CH | N | 4-biphenyl | 4-biphenyl |
| 2601. | H | H | D¹³⁵ | H | H | D¹³⁵ | H | H | L¹¹¹ | N | N | N | Ph | Ph |
| 2602. | H | H | D¹³⁵ | H | H | D¹³⁵ | H | H | L¹¹¹ | N | N | N | 4-biphenyl | 4-biphenyl |
| 2603. | H | H | D¹³⁵ | H | H | D¹³⁵ | H | H | L¹¹¹ | N | CH | N | Ph | Ph |
| 2604. | H | H | D¹³⁵ | H | H | D¹³⁵ | H | H | L¹¹¹ | N | CH | N | 4-biphenyl | 4-biphenyl |
| 2605. | H | H | D¹³⁵ | H | H | D¹³⁵ | H | H | L¹¹² | N | N | N | Ph | Ph |
| 2606. | H | H | D¹³⁵ | H | H | D¹³⁵ | H | H | L¹¹² | N | N | N | 4-biphenyl | 4-biphenyl |
| 2607. | H | H | D¹³⁵ | H | H | D¹³⁵ | H | H | L¹¹² | N | CH | N | Ph | Ph |
| 2608. | H | H | D¹³⁵ | H | H | D¹³⁵ | H | H | L¹¹² | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2609. | H | H | $D^{135}$ | H | H | $D^{135}$ | H | H | $L^{113}$ | N | N | N | Ph | Ph |
| 2610. | H | H | $D^{135}$ | H | H | $D^{135}$ | H | H | $L^{113}$ | N | N | N | 4-biphenyl | 4-biphenyl |
| 2611. | H | H | $D^{135}$ | H | H | $D^{135}$ | H | H | $L^{113}$ | N | CH | N | Ph | Ph |
| 2612. | H | H | $D^{135}$ | H | H | $D^{135}$ | H | H | $L^{113}$ | N | CH | N | 4-biphenyl | 4-biphenyl |
| 2613. | H | H | $D^{135}$ | H | H | $D^{135}$ | H | H | $L^{114}$ | N | N | N | Ph | Ph |
| 2614. | H | H | $D^{135}$ | H | H | $D^{135}$ | H | H | $L^{114}$ | N | N | N | 4-biphenyl | 4-biphenyl |
| 2615. | H | H | $D^{135}$ | H | H | $D^{135}$ | H | H | $L^{114}$ | N | CH | N | Ph | Ph |
| 2616. | H | H | $D^{135}$ | H | H | $D^{135}$ | H | H | $L^{114}$ | N | CH | N | 4-biphenyl | 4-biphenyl |
| 2617. | H | H | $D^{135}$ | H | H | $D^{135}$ | H | H | $L^{115}$ | N | N | N | Ph | Ph |
| 2618. | H | H | $D^{135}$ | H | H | $D^{135}$ | H | H | $L^{115}$ | N | N | N | 4-biphenyl | 4-biphenyl |
| 2619. | H | H | $D^{135}$ | H | H | $D^{135}$ | H | H | $L^{115}$ | N | CH | N | Ph | Ph |
| 2620. | H | H | $D^{135}$ | H | H | $D^{135}$ | H | H | $L^{115}$ | N | CH | N | 4-biphenyl | 4-biphenyl |
| 2621. | H | H | $D^{135}$ | H | H | $D^{135}$ | H | H | $L^{116}$ | N | N | N | Ph | Ph |
| 2622. | H | H | $D^{135}$ | H | H | $D^{135}$ | H | H | $L^{116}$ | N | N | N | 4-biphenyl | 4-biphenyl |
| 2623. | H | H | $D^{135}$ | H | H | $D^{135}$ | H | H | $L^{116}$ | N | CH | N | Ph | Ph |
| 2624. | H | H | $D^{135}$ | H | H | $D^{135}$ | H | H | $L^{116}$ | N | CH | N | 4-biphenyl | 4-biphenyl |
| 2625. | H | H | $D^{136}$ | H | H | H | H | H | $L^{101}$ | N | N | N | Ph | Ph |
| 2626. | H | H | $D^{136}$ | H | H | H | H | H | $L^{101}$ | N | N | N | 4-biphenyl | 4-biphenyl |
| 2627. | H | H | $D^{136}$ | H | H | H | H | H | $L^{101}$ | N | CH | N | Ph | Ph |
| 2628. | H | H | $D^{136}$ | H | H | H | H | H | $L^{101}$ | N | CH | N | 4-biphenyl | 4-biphenyl |
| 2629. | H | H | $D^{136}$ | H | H | H | H | H | $L^{102}$ | N | N | N | Ph | Ph |
| 2630. | H | H | $D^{136}$ | H | H | H | H | H | $L^{102}$ | N | N | N | 4-biphenyl | 4-biphenyl |
| 2631. | H | H | $D^{136}$ | H | H | H | H | H | $L^{102}$ | N | CH | N | Ph | Ph |
| 2632. | H | H | $D^{136}$ | H | H | H | H | H | $L^{102}$ | N | CH | N | 4-biphenyl | 4-biphenyl |
| 2633. | H | H | $D^{136}$ | H | H | H | H | H | $L^{103}$ | N | N | N | Ph | Ph |
| 2634. | H | H | $D^{136}$ | H | H | H | H | H | $L^{103}$ | N | N | N | 4-biphenyl | 4-biphenyl |
| 2635. | H | H | $D^{136}$ | H | H | H | H | H | $L^{103}$ | N | CH | N | Ph | Ph |
| 2636. | H | H | $D^{136}$ | H | H | H | H | H | $L^{103}$ | N | CH | N | 4-biphenyl | 4-biphenyl |
| 2637. | H | H | $D^{136}$ | H | H | H | H | H | $L^{104}$ | N | N | N | Ph | Ph |
| 2638. | H | H | $D^{136}$ | H | H | H | H | H | $L^{104}$ | N | N | N | 4-biphenyl | 4-biphenyl |
| 2639. | H | H | $D^{136}$ | H | H | H | H | H | $L^{104}$ | N | CH | N | Ph | Ph |
| 2640. | H | H | $D^{136}$ | H | H | H | H | H | $L^{104}$ | N | CH | N | 4-biphenyl | 4-biphenyl |
| 2641. | H | H | $D^{136}$ | H | H | H | H | H | $L^{105}$ | N | N | N | Ph | Ph |
| 2642. | H | H | $D^{136}$ | H | H | H | H | H | $L^{105}$ | N | N | N | 4-biphenyl | 4-biphenyl |
| 2643. | H | H | $D^{136}$ | H | H | H | H | H | $L^{105}$ | N | CH | N | Ph | Ph |
| 2644. | H | H | $D^{136}$ | H | H | H | H | H | $L^{105}$ | N | CH | N | 4-biphenyl | 4-biphenyl |
| 2645. | H | H | $D^{136}$ | H | H | H | H | H | $L^{106}$ | N | N | N | Ph | Ph |
| 2646. | H | H | $D^{136}$ | H | H | H | H | H | $L^{106}$ | N | N | N | 4-biphenyl | 4-biphenyl |
| 2647. | H | H | $D^{136}$ | H | H | H | H | H | $L^{106}$ | N | CH | N | Ph | Ph |
| 2648. | H | H | $D^{136}$ | H | H | H | H | H | $L^{106}$ | N | CH | N | 4-biphenyl | 4-biphenyl |
| 2649. | H | H | $D^{136}$ | H | H | H | H | H | $L^{107}$ | N | N | N | Ph | Ph |
| 2650. | H | H | $D^{136}$ | H | H | H | H | H | $L^{107}$ | N | N | N | 4-biphenyl | 4-biphenyl |
| 2651. | H | H | $D^{136}$ | H | H | H | H | H | $L^{107}$ | N | CH | N | Ph | Ph |
| 2652. | H | H | $D^{136}$ | H | H | H | H | H | $L^{107}$ | N | CH | N | 4-biphenyl | 4-biphenyl |
| 2653. | H | H | $D^{136}$ | H | H | H | H | H | $L^{108}$ | N | N | N | Ph | Ph |
| 2654. | H | H | $D^{136}$ | H | H | H | H | H | $L^{108}$ | N | N | N | 4-biphenyl | 4-biphenyl |
| 2655. | H | H | $D^{136}$ | H | H | H | H | H | $L^{108}$ | N | CH | N | Ph | Ph |
| 2656. | H | H | $D^{136}$ | H | H | H | H | H | $L^{108}$ | N | CH | N | 4-biphenyl | 4-biphenyl |
| 2657. | H | H | $D^{136}$ | H | H | H | H | H | $L^{109}$ | N | N | N | Ph | Ph |
| 2658. | H | H | $D^{136}$ | H | H | H | H | H | $L^{109}$ | N | N | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2659. | H | H | D¹³⁶ | H | H | H | H | H | L¹⁰⁹ | N | CH | N | Ph | Ph |
| 2660. | H | H | D¹³⁶ | H | H | H | H | H | L¹⁰⁹ | N | CH | N | 4-biphenyl | 4-biphenyl |
| 2661. | H | H | D¹³⁶ | H | H | H | H | H | L¹¹⁰ | N | N | N | Ph | Ph |
| 2662. | H | H | D¹³⁶ | H | H | H | H | H | L¹¹⁰ | N | N | N | 4-biphenyl | 4-biphenyl |
| 2663. | H | H | D¹³⁶ | H | H | H | H | H | L¹¹⁰ | N | CH | N | Ph | Ph |
| 2664. | H | H | D¹³⁶ | H | H | H | H | H | L¹¹⁰ | N | CH | N | 4-biphenyl | 4-biphenyl |
| 2665. | H | H | D¹³⁶ | H | H | H | H | H | L¹¹¹ | N | N | N | Ph | Ph |
| 2666. | H | H | D¹³⁶ | H | H | H | H | H | L¹¹¹ | N | N | N | 4-biphenyl | 4-biphenyl |
| 2667. | H | H | D¹³⁶ | H | H | H | H | H | L¹¹¹ | N | CH | N | Ph | Ph |
| 2668. | H | H | D¹³⁶ | H | H | H | H | H | L¹¹¹ | N | CH | N | 4-biphenyl | 4-biphenyl |
| 2669. | H | H | D¹³⁶ | H | H | H | H | H | L¹¹² | N | N | N | Ph | Ph |
| 2670. | H | H | D¹³⁶ | H | H | H | H | H | L¹¹² | N | N | N | 4-biphenyl | 4-biphenyl |
| 2671. | H | H | D¹³⁶ | H | H | H | H | H | L¹¹² | N | CH | N | Ph | Ph |
| 2672. | H | H | D¹³⁶ | H | H | H | H | H | L¹¹² | N | CH | N | 4-biphenyl | 4-biphenyl |
| 2673. | H | H | D¹³⁶ | H | H | H | H | H | L¹¹³ | N | N | N | Ph | Ph |
| 2674. | H | H | D¹³⁶ | H | H | H | H | H | L¹¹³ | N | N | N | 4-biphenyl | 4-biphenyl |
| 2675. | H | H | D¹³⁶ | H | H | H | H | H | L¹¹³ | N | CH | N | Ph | Ph |
| 2676. | H | H | D¹³⁶ | H | H | H | H | H | L¹¹³ | N | CH | N | 4-biphenyl | 4-biphenyl |
| 2677. | H | H | D¹³⁶ | H | H | H | H | H | L¹¹⁴ | N | N | N | Ph | Ph |
| 2678. | H | H | D¹³⁶ | H | H | H | H | H | L¹¹⁴ | N | N | N | 4-biphenyl | 4-biphenyl |
| 2679. | H | H | D¹³⁶ | H | H | H | H | H | L¹¹⁴ | N | CH | N | Ph | Ph |
| 2680. | H | H | D¹³⁶ | H | H | H | H | H | L¹¹⁴ | N | CH | N | 4-biphenyl | 4-biphenyl |
| 2681. | H | H | D¹³⁶ | H | H | H | H | H | L¹¹⁵ | N | N | N | Ph | Ph |
| 2682. | H | H | D¹³⁶ | H | H | H | H | H | L¹¹⁵ | N | N | N | 4-biphenyl | 4-biphenyl |
| 2683. | H | H | D¹³⁶ | H | H | H | H | H | L¹¹⁵ | N | CH | N | Ph | Ph |
| 2684. | H | H | D¹³⁶ | H | H | H | H | H | L¹¹⁵ | N | CH | N | 4-biphenyl | 4-biphenyl |
| 2685. | H | H | D¹³⁶ | H | H | H | H | H | L¹¹⁶ | N | N | N | Ph | Ph |
| 2686. | H | H | D¹³⁶ | H | H | H | H | H | L¹¹⁶ | N | N | N | 4-biphenyl | 4-biphenyl |
| 2687. | H | H | D¹³⁶ | H | H | H | H | H | L¹¹⁶ | N | CH | N | Ph | Ph |
| 2688. | H | H | D¹³⁶ | H | H | H | H | H | L¹¹⁶ | N | CH | N | 4-biphenyl | 4-biphenyl |
| 2689. | H | H | D¹³⁶ | H | H | D¹³⁶ | H | H | L¹⁰¹ | N | N | N | Ph | Ph |
| 2690. | H | H | D¹³⁶ | H | H | D¹³⁶ | H | H | L¹⁰¹ | N | N | N | 4-biphenyl | 4-biphenyl |
| 2691. | H | H | D¹³⁶ | H | H | D¹³⁶ | H | H | L¹⁰¹ | N | CH | N | Ph | Ph |
| 2692. | H | H | D¹³⁶ | H | H | D¹³⁶ | H | H | L¹⁰¹ | N | CH | N | 4-biphenyl | 4-biphenyl |
| 2693. | H | H | D¹³⁶ | H | H | D¹³⁶ | H | H | L¹⁰² | N | N | N | Ph | Ph |
| 2694. | H | H | D¹³⁶ | H | H | D¹³⁶ | H | H | L¹⁰² | N | N | N | 4-biphenyl | 4-biphenyl |
| 2695. | H | H | D¹³⁶ | H | H | D¹³⁶ | H | H | L¹⁰² | N | CH | N | Ph | Ph |
| 2696. | H | H | D¹³⁶ | H | H | D¹³⁶ | H | H | L¹⁰² | N | CH | N | 4-biphenyl | 4-biphenyl |
| 2697. | H | H | D¹³⁶ | H | H | D¹³⁶ | H | H | L¹⁰³ | N | N | N | Ph | Ph |
| 2698. | H | H | D¹³⁶ | H | H | D¹³⁶ | H | H | L¹⁰³ | N | N | N | 4-biphenyl | 4-biphenyl |
| 2699. | H | H | D¹³⁶ | H | H | D¹³⁶ | H | H | L¹⁰³ | N | CH | N | Ph | Ph |
| 2700. | H | H | D¹³⁶ | H | H | D¹³⁶ | H | H | L¹⁰³ | N | CH | N | 4-biphenyl | 4-biphenyl |
| 2701. | H | H | D¹³⁶ | H | H | D¹³⁶ | H | H | L¹⁰⁴ | N | N | N | Ph | Ph |
| 2702. | H | H | D¹³⁶ | H | H | D¹³⁶ | H | H | L¹⁰⁴ | N | N | N | 4-biphenyl | 4-biphenyl |
| 2703. | H | H | D¹³⁶ | H | H | D¹³⁶ | H | H | L¹⁰⁴ | N | CH | N | Ph | Ph |
| 2704. | H | H | D¹³⁶ | H | H | D¹³⁶ | H | H | L¹⁰⁴ | N | CH | N | 4-biphenyl | 4-biphenyl |
| 2705. | H | H | D¹³⁶ | H | H | D¹³⁶ | H | H | L¹⁰⁵ | N | N | N | Ph | Ph |
| 2706. | H | H | D¹³⁶ | H | H | D¹³⁶ | H | H | L¹⁰⁵ | N | N | N | 4-biphenyl | 4-biphenyl |
| 2707. | H | H | D¹³⁶ | H | H | D¹³⁶ | H | H | L¹⁰⁵ | N | CH | N | Ph | Ph |
| 2708. | H | H | D¹³⁶ | H | H | D¹³⁶ | H | H | L¹⁰⁵ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2709. | H | H | D¹³⁶ | H | H | D¹³⁶ | H | H | L¹⁰⁶ | N | N | N | Ph | Ph |
| 2710. | H | H | D¹³⁶ | H | H | D¹³⁶ | H | H | L¹⁰⁶ | N | N | N | 4-biphenyl | 4-biphenyl |
| 2711. | H | H | D¹³⁶ | H | H | D¹³⁶ | H | H | L¹⁰⁶ | N | CH | N | Ph | Ph |
| 2712. | H | H | D¹³⁶ | H | H | D¹³⁶ | H | H | L¹⁰⁶ | N | CH | N | 4-biphenyl | 4-biphenyl |
| 2713. | H | H | D¹³⁶ | H | H | D¹³⁶ | H | H | L¹⁰⁷ | N | N | N | Ph | Ph |
| 2714. | H | H | D¹³⁶ | H | H | D¹³⁶ | H | H | L¹⁰⁷ | N | N | N | 4-biphenyl | 4-biphenyl |
| 2715. | H | H | D¹³⁶ | H | H | D¹³⁶ | H | H | L¹⁰⁷ | N | CH | N | Ph | Ph |
| 2716. | H | H | D¹³⁶ | H | H | D¹³⁶ | H | H | L¹⁰⁷ | N | CH | N | 4-biphenyl | 4-biphenyl |
| 2717. | H | H | D¹³⁶ | H | H | D¹³⁶ | H | H | L¹⁰⁸ | N | N | N | Ph | Ph |
| 2718. | H | H | D¹³⁶ | H | H | D¹³⁶ | H | H | L¹⁰⁸ | N | N | N | 4-biphenyl | 4-biphenyl |
| 2719. | H | H | D¹³⁶ | H | H | D¹³⁶ | H | H | L¹⁰⁸ | N | CH | N | Ph | Ph |
| 2720. | H | H | D¹³⁶ | H | H | D¹³⁶ | H | H | L¹⁰⁸ | N | CH | N | 4-biphenyl | 4-biphenyl |
| 2721. | H | H | D¹³⁶ | H | H | D¹³⁶ | H | H | L¹⁰⁹ | N | N | N | Ph | Ph |
| 2722. | H | H | D¹³⁶ | H | H | D¹³⁶ | H | H | L¹⁰⁹ | N | N | N | 4-biphenyl | 4-biphenyl |
| 2723. | H | H | D¹³⁶ | H | H | D¹³⁶ | H | H | L¹⁰⁹ | N | CH | N | Ph | Ph |
| 2724. | H | H | D¹³⁶ | H | H | D¹³⁶ | H | H | L¹⁰⁹ | N | CH | N | 4-biphenyl | 4-biphenyl |
| 2725. | H | H | D¹³⁶ | H | H | D¹³⁶ | H | H | L¹¹⁰ | N | N | N | Ph | Ph |
| 2726. | H | H | D¹³⁶ | H | H | D¹³⁶ | H | H | L¹¹⁰ | N | N | N | 4-biphenyl | 4-biphenyl |
| 2727. | H | H | D¹³⁶ | H | H | D¹³⁶ | H | H | L¹¹⁰ | N | CH | N | Ph | Ph |
| 2728. | H | H | D¹³⁶ | H | H | D¹³⁶ | H | H | L¹¹⁰ | N | CH | N | 4-biphenyl | 4-biphenyl |
| 2729. | H | H | D¹³⁶ | H | H | D¹³⁶ | H | H | L¹¹¹ | N | N | N | Ph | Ph |
| 2730. | H | H | D¹³⁶ | H | H | D¹³⁶ | H | H | L¹¹¹ | N | N | N | 4-biphenyl | 4-biphenyl |
| 2731. | H | H | D¹³⁶ | H | H | D¹³⁶ | H | H | L¹¹¹ | N | CH | N | Ph | Ph |
| 2732. | H | H | D¹³⁶ | H | H | D¹³⁶ | H | H | L¹¹¹ | N | CH | N | 4-biphenyl | 4-biphenyl |
| 2733. | H | H | D¹³⁶ | H | H | D¹³⁶ | H | H | L¹¹² | N | N | N | Ph | Ph |
| 2734. | H | H | D¹³⁶ | H | H | D¹³⁶ | H | H | L¹¹² | N | N | N | 4-biphenyl | 4-biphenyl |
| 2735. | H | H | D¹³⁶ | H | H | D¹³⁶ | H | H | L¹¹² | N | CH | N | Ph | Ph |
| 2736. | H | H | D¹³⁶ | H | H | D¹³⁶ | H | H | L¹¹² | N | CH | N | 4-biphenyl | 4-biphenyl |
| 2737. | H | H | D¹³⁶ | H | H | D¹³⁶ | H | H | L¹¹³ | N | N | N | Ph | Ph |
| 2738. | H | H | D¹³⁶ | H | H | D¹³⁶ | H | H | L¹¹³ | N | N | N | 4-biphenyl | 4-biphenyl |
| 2739. | H | H | D¹³⁶ | H | H | D¹³⁶ | H | H | L¹¹³ | N | CH | N | Ph | Ph |
| 2740. | H | H | D¹³⁶ | H | H | D¹³⁶ | H | H | L¹¹³ | N | CH | N | 4-biphenyl | 4-biphenyl |
| 2741. | H | H | D¹³⁶ | H | H | D¹³⁶ | H | H | L¹¹⁴ | N | N | N | Ph | Ph |
| 2742. | H | H | D¹³⁶ | H | H | D¹³⁶ | H | H | L¹¹⁴ | N | N | N | 4-biphenyl | 4-biphenyl |
| 2743. | H | H | D¹³⁶ | H | H | D¹³⁶ | H | H | L¹¹⁴ | N | CH | N | Ph | Ph |
| 2744. | H | H | D¹³⁶ | H | H | D¹³⁶ | H | H | L¹¹⁴ | N | CH | N | 4-biphenyl | 4-biphenyl |
| 2745. | H | H | D¹³⁶ | H | H | D¹³⁶ | H | H | L¹¹⁵ | N | N | N | Ph | Ph |
| 2746. | H | H | D¹³⁶ | H | H | D¹³⁶ | H | H | L¹¹⁵ | N | N | N | 4-biphenyl | 4-biphenyl |
| 2747. | H | H | D¹³⁶ | H | H | D¹³⁶ | H | H | L¹¹⁵ | N | CH | N | Ph | Ph |
| 2748. | H | H | D¹³⁶ | H | H | D¹³⁶ | H | H | L¹¹⁵ | N | CH | N | 4-biphenyl | 4-biphenyl |
| 2749. | H | H | D¹³⁶ | H | H | D¹³⁶ | H | H | L¹¹⁶ | N | N | N | Ph | Ph |
| 2750. | H | H | D¹³⁶ | H | H | D¹³⁶ | H | H | L¹¹⁶ | N | N | N | 4-biphenyl | 4-biphenyl |
| 2751. | H | H | D¹³⁶ | H | H | D¹³⁶ | H | H | L¹¹⁶ | N | CH | N | Ph | Ph |
| 2752. | H | H | D¹³⁶ | H | H | D¹³⁶ | H | H | L¹¹⁶ | N | CH | N | 4-biphenyl | 4-biphenyl |
| 2753. | H | H | D¹³⁷ | H | H | H | H | H | L¹⁰¹ | N | N | N | Ph | Ph |
| 2754. | H | H | D¹³⁷ | H | H | H | H | H | L¹⁰¹ | N | N | N | 4-biphenyl | 4-biphenyl |
| 2755. | H | H | D¹³⁷ | H | H | H | H | H | L¹⁰¹ | N | CH | N | Ph | Ph |
| 2756. | H | H | D¹³⁷ | H | H | H | H | H | L¹⁰¹ | N | CH | N | 4-biphenyl | 4-biphenyl |
| 2757. | H | H | D¹³⁷ | H | H | H | H | H | L¹⁰² | N | N | N | Ph | Ph |
| 2758. | H | H | D¹³⁷ | H | H | H | H | H | L¹⁰² | N | N | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2759. | H | H | D¹³⁷ | H | H | H | H | H | L¹⁰² | N | CH | N | Ph | Ph |
| 2760. | H | H | D¹³⁷ | H | H | H | H | H | L¹⁰² | N | CH | N | 4-biphenyl | 4-biphenyl |
| 2761. | H | H | D¹³⁷ | H | H | H | H | H | L¹⁰³ | N | N | N | Ph | Ph |
| 2762. | H | H | D¹³⁷ | H | H | H | H | H | L¹⁰³ | N | N | N | 4-biphenyl | 4-biphenyl |
| 2763. | H | H | D¹³⁷ | H | H | H | H | H | L¹⁰³ | N | CH | N | Ph | Ph |
| 2764. | H | H | D¹³⁷ | H | H | H | H | H | L¹⁰³ | N | CH | N | 4-biphenyl | 4-biphenyl |
| 2765. | H | H | D¹³⁷ | H | H | H | H | H | L¹⁰⁴ | N | N | N | Ph | Ph |
| 2766. | H | H | D¹³⁷ | H | H | H | H | H | L¹⁰⁴ | N | N | N | 4-biphenyl | 4-biphenyl |
| 2767. | H | H | D¹³⁷ | H | H | H | H | H | L¹⁰⁴ | N | CH | N | Ph | Ph |
| 2768. | H | H | D¹³⁷ | H | H | H | H | H | L¹⁰⁴ | N | CH | N | 4-biphenyl | 4-biphenyl |
| 2769. | H | H | D¹³⁷ | H | H | H | H | H | L¹⁰⁵ | N | N | N | Ph | Ph |
| 2770. | H | H | D¹³⁷ | H | H | H | H | H | L¹⁰⁵ | N | N | N | 4-biphenyl | 4-biphenyl |
| 2771. | H | H | D¹³⁷ | H | H | H | H | H | L¹⁰⁵ | N | CH | N | Ph | Ph |
| 2772. | H | H | D¹³⁷ | H | H | H | H | H | L¹⁰⁵ | N | CH | N | 4-biphenyl | 4-biphenyl |
| 2773. | H | H | D¹³⁷ | H | H | H | H | H | L¹⁰⁶ | N | N | N | Ph | Ph |
| 2774. | H | H | D¹³⁷ | H | H | H | H | H | L¹⁰⁶ | N | N | N | 4-biphenyl | 4-biphenyl |
| 2775. | H | H | D¹³⁷ | H | H | H | H | H | L¹⁰⁶ | N | CH | N | Ph | Ph |
| 2776. | H | H | D¹³⁷ | H | H | H | H | H | L¹⁰⁶ | N | CH | N | 4-biphenyl | 4-biphenyl |
| 2777. | H | H | D¹³⁷ | H | H | H | H | H | L¹⁰⁷ | N | N | N | Ph | Ph |
| 2778. | H | H | D¹³⁷ | H | H | H | H | H | L¹⁰⁷ | N | N | N | 4-biphenyl | 4-biphenyl |
| 2779. | H | H | D¹³⁷ | H | H | H | H | H | L¹⁰⁷ | N | CH | N | Ph | Ph |
| 2780. | H | H | D¹³⁷ | H | H | H | H | H | L¹⁰⁷ | N | CH | N | 4-biphenyl | 4-biphenyl |
| 2781. | H | H | D¹³⁷ | H | H | H | H | H | L¹⁰⁸ | N | N | N | Ph | Ph |
| 2782. | H | H | D¹³⁷ | H | H | H | H | H | L¹⁰⁸ | N | N | N | 4-biphenyl | 4-biphenyl |
| 2783. | H | H | D¹³⁷ | H | H | H | H | H | L¹⁰⁸ | N | CH | N | Ph | Ph |
| 2784. | H | H | D¹³⁷ | H | H | H | H | H | L¹⁰⁸ | N | CH | N | 4-biphenyl | 4-biphenyl |
| 2785. | H | H | D¹³⁷ | H | H | H | H | H | L¹⁰⁹ | N | N | N | Ph | Ph |
| 2786. | H | H | D¹³⁷ | H | H | H | H | H | L¹⁰⁹ | N | N | N | 4-biphenyl | 4-biphenyl |
| 2787. | H | H | D¹³⁷ | H | H | H | H | H | L¹⁰⁹ | N | CH | N | Ph | Ph |
| 2788. | H | H | D¹³⁷ | H | H | H | H | H | L¹⁰⁹ | N | CH | N | 4-biphenyl | 4-biphenyl |
| 2789. | H | H | D¹³⁷ | H | H | H | H | H | L¹¹⁰ | N | N | N | Ph | Ph |
| 2790. | H | H | D¹³⁷ | H | H | H | H | H | L¹¹⁰ | N | N | N | 4-biphenyl | 4-biphenyl |
| 2791. | H | H | D¹³⁷ | H | H | H | H | H | L¹¹⁰ | N | CH | N | Ph | Ph |
| 2792. | H | H | D¹³⁷ | H | H | H | H | H | L¹¹⁰ | N | CH | N | 4-biphenyl | 4-biphenyl |
| 2793. | H | H | D¹³⁷ | H | H | H | H | H | L¹¹¹ | N | N | N | Ph | Ph |
| 2794. | H | H | D¹³⁷ | H | H | H | H | H | L¹¹¹ | N | N | N | 4-biphenyl | 4-biphenyl |
| 2795. | H | H | D¹³⁷ | H | H | H | H | H | L¹¹¹ | N | CH | N | Ph | Ph |
| 2796. | H | H | D¹³⁷ | H | H | H | H | H | L¹¹¹ | N | CH | N | 4-biphenyl | 4-biphenyl |
| 2797. | H | H | D¹³⁷ | H | H | H | H | H | L¹¹² | N | N | N | Ph | Ph |
| 2798. | H | H | D¹³⁷ | H | H | H | H | H | L¹¹² | N | N | N | 4-biphenyl | 4-biphenyl |
| 2799. | H | H | D¹³⁷ | H | H | H | H | H | L¹¹² | N | CH | N | Ph | Ph |
| 2800. | H | H | D¹³⁷ | H | H | H | H | H | L¹¹² | N | CH | N | 4-biphenyl | 4-biphenyl |
| 2801. | H | H | D¹³⁷ | H | H | H | H | H | L¹¹³ | N | N | N | Ph | Ph |
| 2802. | H | H | D¹³⁷ | H | H | H | H | H | L¹¹³ | N | N | N | 4-biphenyl | 4-biphenyl |
| 2803. | H | H | D¹³⁷ | H | H | H | H | H | L¹¹³ | N | CH | N | Ph | Ph |
| 2804. | H | H | D¹³⁷ | H | H | H | H | H | L¹¹³ | N | CH | N | 4-biphenyl | 4-biphenyl |
| 2805. | H | H | D¹³⁷ | H | H | H | H | H | L¹¹⁴ | N | N | N | Ph | Ph |
| 2806. | H | H | D¹³⁷ | H | H | H | H | H | L¹¹⁴ | N | N | N | 4-biphenyl | 4-biphenyl |
| 2807. | H | H | D¹³⁷ | H | H | H | H | H | L¹¹⁴ | N | CH | N | Ph | Ph |
| 2808. | H | H | D¹³⁷ | H | H | H | H | H | L¹¹⁴ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2809. | H | H | D¹³⁷ | H | H | H | H | H | L¹¹⁵ | N | N | N | Ph | Ph |
| 2810. | H | H | D¹³⁷ | H | H | H | H | H | L¹¹⁵ | N | N | N | 4-biphenyl | 4-biphenyl |
| 2811. | H | H | D¹³⁷ | H | H | H | H | H | L¹¹⁵ | N | CH | N | Ph | Ph |
| 2812. | H | H | D¹³⁷ | H | H | H | H | H | L¹¹⁵ | N | CH | N | 4-biphenyl | 4-biphenyl |
| 2813. | H | H | D¹³⁷ | H | H | H | H | H | L¹¹⁶ | N | N | N | Ph | Ph |
| 2814. | H | H | D¹³⁷ | H | H | H | H | H | L¹¹⁶ | N | N | N | 4-biphenyl | 4-biphenyl |
| 2815. | H | H | D¹³⁷ | H | H | H | H | H | L¹¹⁶ | N | CH | N | Ph | Ph |
| 2816. | H | H | D¹³⁷ | H | H | H | H | H | L¹¹⁶ | N | CH | N | 4-biphenyl | 4-biphenyl |
| 2817. | H | H | D¹³⁷ | H | H | D¹³⁷ | H | H | L¹⁰¹ | N | N | N | Ph | Ph |
| 2818. | H | H | D¹³⁷ | H | H | D¹³⁷ | H | H | L¹⁰¹ | N | N | N | 4-biphenyl | 4-biphenyl |
| 2819. | H | H | D¹³⁷ | H | H | D¹³⁷ | H | H | L¹⁰¹ | N | CH | N | Ph | Ph |
| 2820. | H | H | D¹³⁷ | H | H | D¹³⁷ | H | H | L¹⁰¹ | N | CH | N | 4-biphenyl | 4-biphenyl |
| 2821. | H | H | D¹³⁷ | H | H | D¹³⁷ | H | H | L¹⁰² | N | N | N | Ph | Ph |
| 2822. | H | H | D¹³⁷ | H | H | D¹³⁷ | H | H | L¹⁰² | N | N | N | 4-biphenyl | 4-biphenyl |
| 2823. | H | H | D¹³⁷ | H | H | D¹³⁷ | H | H | L¹⁰² | N | CH | N | Ph | Ph |
| 2824. | H | H | D¹³⁷ | H | H | D¹³⁷ | H | H | L¹⁰² | N | CH | N | 4-biphenyl | 4-biphenyl |
| 2825. | H | H | D¹³⁷ | H | H | D¹³⁷ | H | H | L¹⁰³ | N | N | N | Ph | Ph |
| 2826. | H | H | D¹³⁷ | H | H | D¹³⁷ | H | H | L¹⁰³ | N | N | N | 4-biphenyl | 4-biphenyl |
| 2827. | H | H | D¹³⁷ | H | H | D¹³⁷ | H | H | L¹⁰³ | N | CH | N | Ph | Ph |
| 2828. | H | H | D¹³⁷ | H | H | D¹³⁷ | H | H | L¹⁰³ | N | CH | N | 4-biphenyl | 4-biphenyl |
| 2829. | H | H | D¹³⁷ | H | H | D¹³⁷ | H | H | L¹⁰⁴ | N | N | N | Ph | Ph |
| 2830. | H | H | D¹³⁷ | H | H | D¹³⁷ | H | H | L¹⁰⁴ | N | N | N | 4-biphenyl | 4-biphenyl |
| 2831. | H | H | D¹³⁷ | H | H | D¹³⁷ | H | H | L¹⁰⁴ | N | CH | N | Ph | Ph |
| 2832. | H | H | D¹³⁷ | H | H | D¹³⁷ | H | H | L¹⁰⁴ | N | CH | N | 4-biphenyl | 4-biphenyl |
| 2833. | H | H | D¹³⁷ | H | H | D¹³⁷ | H | H | L¹⁰⁵ | N | N | N | Ph | Ph |
| 2834. | H | H | D¹³⁷ | H | H | D¹³⁷ | H | H | L¹⁰⁵ | N | N | N | 4-biphenyl | 4-biphenyl |
| 2835. | H | H | D¹³⁷ | H | H | D¹³⁷ | H | H | L¹⁰⁵ | N | CH | N | Ph | Ph |
| 2836. | H | H | D¹³⁷ | H | H | D¹³⁷ | H | H | L¹⁰⁵ | N | CH | N | 4-biphenyl | 4-biphenyl |
| 2837. | H | H | D¹³⁷ | H | H | D¹³⁷ | H | H | L¹⁰⁶ | N | N | N | Ph | Ph |
| 2838. | H | H | D¹³⁷ | H | H | D¹³⁷ | H | H | L¹⁰⁶ | N | N | N | 4-biphenyl | 4-biphenyl |
| 2839. | H | H | D¹³⁷ | H | H | D¹³⁷ | H | H | L¹⁰⁶ | N | CH | N | Ph | Ph |
| 2840. | H | H | D¹³⁷ | H | H | D¹³⁷ | H | H | L¹⁰⁶ | N | CH | N | 4-biphenyl | 4-biphenyl |
| 2841. | H | H | D¹³⁷ | H | H | D¹³⁷ | H | H | L¹⁰⁷ | N | N | N | Ph | Ph |
| 2842. | H | H | D¹³⁷ | H | H | D¹³⁷ | H | H | L¹⁰⁷ | N | N | N | 4-biphenyl | 4-biphenyl |
| 2843. | H | H | D¹³⁷ | H | H | D¹³⁷ | H | H | L¹⁰⁷ | N | CH | N | Ph | Ph |
| 2844. | H | H | D¹³⁷ | H | H | D¹³⁷ | H | H | L¹⁰⁷ | N | CH | N | 4-biphenyl | 4-biphenyl |
| 2845. | H | H | D¹³⁷ | H | H | D¹³⁷ | H | H | L¹⁰⁸ | N | N | N | Ph | Ph |
| 2846. | H | H | D¹³⁷ | H | H | D¹³⁷ | H | H | L¹⁰⁸ | N | N | N | 4-biphenyl | 4-biphenyl |
| 2847. | H | H | D¹³⁷ | H | H | D¹³⁷ | H | H | L¹⁰⁸ | N | CH | N | Ph | Ph |
| 2848. | H | H | D¹³⁷ | H | H | D¹³⁷ | H | H | L¹⁰⁸ | N | CH | N | 4-biphenyl | 4-biphenyl |
| 2849. | H | H | D¹³⁷ | H | H | D¹³⁷ | H | H | L¹⁰⁹ | N | N | N | Ph | Ph |
| 2850. | H | H | D¹³⁷ | H | H | D¹³⁷ | H | H | L¹⁰⁹ | N | N | N | 4-biphenyl | 4-biphenyl |
| 2851. | H | H | D¹³⁷ | H | H | D¹³⁷ | H | H | L¹⁰⁹ | N | CH | N | Ph | Ph |
| 2852. | H | H | D¹³⁷ | H | H | D¹³⁷ | H | H | L¹⁰⁹ | N | CH | N | 4-biphenyl | 4-biphenyl |
| 2853. | H | H | D¹³⁷ | H | H | D¹³⁷ | H | H | L¹¹⁰ | N | N | N | Ph | Ph |
| 2854. | H | H | D¹³⁷ | H | H | D¹³⁷ | H | H | L¹¹⁰ | N | N | N | 4-biphenyl | 4-biphenyl |
| 2855. | H | H | D¹³⁷ | H | H | D¹³⁷ | H | H | L¹¹⁰ | N | CH | N | Ph | Ph |
| 2856. | H | H | D¹³⁷ | H | H | D¹³⁷ | H | H | L¹¹⁰ | N | CH | N | 4-biphenyl | 4-biphenyl |
| 2857. | H | H | D¹³⁷ | H | H | D¹³⁷ | H | H | L¹¹¹ | N | N | N | Ph | Ph |
| 2858. | H | H | D¹³⁷ | H | H | D¹³⁷ | H | H | L¹¹¹ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2859. | H | H | D¹³⁷ | H | H | D¹³⁷ | H | H | L¹¹¹ | N | CH | N | Ph | Ph |
| 2860. | H | H | D¹³⁷ | H | H | D¹³⁷ | H | H | L¹¹¹ | N | CH | N | 4-biphenyl | 4-biphenyl |
| 2861. | H | H | D¹³⁷ | H | H | D¹³⁷ | H | H | L¹¹² | N | N | N | Ph | Ph |
| 2862. | H | H | D¹³⁷ | H | H | D¹³⁷ | H | H | L¹¹² | N | N | N | 4-biphenyl | 4-biphenyl |
| 2863. | H | H | D¹³⁷ | H | H | D¹³⁷ | H | H | L¹¹² | N | CH | N | Ph | Ph |
| 2864. | H | H | D¹³⁷ | H | H | D¹³⁷ | H | H | L¹¹² | N | CH | N | 4-biphenyl | 4-biphenyl |
| 2865. | H | H | D¹³⁷ | H | H | D¹³⁷ | H | H | L¹¹³ | N | N | N | Ph | Ph |
| 2866. | H | H | D¹³⁷ | H | H | D¹³⁷ | H | H | L¹¹³ | N | N | N | 4-biphenyl | 4-biphenyl |
| 2867. | H | H | D¹³⁷ | H | H | D¹³⁷ | H | H | L¹¹³ | N | CH | N | Ph | Ph |
| 2868. | H | H | D¹³⁷ | H | H | D¹³⁷ | H | H | L¹¹³ | N | CH | N | 4-biphenyl | 4-biphenyl |
| 2869. | H | H | D¹³⁷ | H | H | D¹³⁷ | H | H | L¹¹⁴ | N | N | N | Ph | Ph |
| 2870. | H | H | D¹³⁷ | H | H | D¹³⁷ | H | H | L¹¹⁴ | N | N | N | 4-biphenyl | 4-biphenyl |
| 2871. | H | H | D¹³⁷ | H | H | D¹³⁷ | H | H | L¹¹⁴ | N | CH | N | Ph | Ph |
| 2872. | H | H | D¹³⁷ | H | H | D¹³⁷ | H | H | L¹¹⁴ | N | CH | N | 4-biphenyl | 4-biphenyl |
| 2873. | H | H | D¹³⁷ | H | H | D¹³⁷ | H | H | L¹¹⁵ | N | N | N | Ph | Ph |
| 2874. | H | H | D¹³⁷ | H | H | D¹³⁷ | H | H | L¹¹⁵ | N | N | N | 4-biphenyl | 4-biphenyl |
| 2875. | H | H | D¹³⁷ | H | H | D¹³⁷ | H | H | L¹¹⁵ | N | CH | N | Ph | Ph |
| 2876. | H | H | D¹³⁷ | H | H | D¹³⁷ | H | H | L¹¹⁵ | N | CH | N | 4-biphenyl | 4-biphenyl |
| 2877. | H | H | D¹³⁷ | H | H | D¹³⁷ | H | H | L¹¹⁶ | N | N | N | Ph | Ph |
| 2878. | H | H | D¹³⁷ | H | H | D¹³⁷ | H | H | L¹¹⁶ | N | N | N | 4-biphenyl | 4-biphenyl |
| 2879. | H | H | D¹³⁷ | H | H | D¹³⁷ | H | H | L¹¹⁶ | N | CH | N | Ph | Ph |
| 2880. | H | H | D¹³⁷ | H | H | D¹³⁷ | H | H | L¹¹⁶ | N | CH | N | 4-biphenyl | 4-biphenyl |
| 2881. | H | H | D¹³⁸ | H | H | H | H | H | L¹⁰¹ | N | N | N | Ph | Ph |
| 2882. | H | H | D¹³⁸ | H | H | H | H | H | L¹⁰¹ | N | N | N | 4-biphenyl | 4-biphenyl |
| 2883. | H | H | D¹³⁸ | H | H | H | H | H | L¹⁰¹ | N | CH | N | Ph | Ph |
| 2884. | H | H | D¹³⁸ | H | H | H | H | H | L¹⁰¹ | N | CH | N | 4-biphenyl | 4-biphenyl |
| 2885. | H | H | D¹³⁸ | H | H | H | H | H | L¹⁰² | N | N | N | Ph | Ph |
| 2886. | H | H | D¹³⁸ | H | H | H | H | H | L¹⁰² | N | N | N | 4-biphenyl | 4-biphenyl |
| 2887. | H | H | D¹³⁸ | H | H | H | H | H | L¹⁰² | N | CH | N | Ph | Ph |
| 2888. | H | H | D¹³⁸ | H | H | H | H | H | L¹⁰² | N | CH | N | 4-biphenyl | 4-biphenyl |
| 2889. | H | H | D¹³⁸ | H | H | H | H | H | L¹⁰³ | N | N | N | Ph | Ph |
| 2890. | H | H | D¹³⁸ | H | H | H | H | H | L¹⁰³ | N | N | N | 4-biphenyl | 4-biphenyl |
| 2891. | H | H | D¹³⁸ | H | H | H | H | H | L¹⁰³ | N | CH | N | Ph | Ph |
| 2892. | H | H | D¹³⁸ | H | H | H | H | H | L¹⁰³ | N | CH | N | 4-biphenyl | 4-biphenyl |
| 2893. | H | H | D¹³⁸ | H | H | H | H | H | L¹⁰⁴ | N | N | N | Ph | Ph |
| 2894. | H | H | D¹³⁸ | H | H | H | H | H | L¹⁰⁴ | N | N | N | 4-biphenyl | 4-biphenyl |
| 2895. | H | H | D¹³⁸ | H | H | H | H | H | L¹⁰⁴ | N | CH | N | Ph | Ph |
| 2896. | H | H | D¹³⁸ | H | H | H | H | H | L¹⁰⁴ | N | CH | N | 4-biphenyl | 4-biphenyl |
| 2897. | H | H | D¹³⁸ | H | H | H | H | H | L¹⁰⁵ | N | N | N | Ph | Ph |
| 2898. | H | H | D¹³⁸ | H | H | H | H | H | L¹⁰⁵ | N | N | N | 4-biphenyl | 4-biphenyl |
| 2899. | H | H | D¹³⁸ | H | H | H | H | H | L¹⁰⁵ | N | CH | N | Ph | Ph |
| 2900. | H | H | D¹³⁸ | H | H | H | H | H | L¹⁰⁵ | N | CH | N | 4-biphenyl | 4-biphenyl |
| 2901. | H | H | D¹³⁸ | H | H | H | H | H | L¹⁰⁶ | N | N | N | Ph | Ph |
| 2902. | H | H | D¹³⁸ | H | H | H | H | H | L¹⁰⁶ | N | N | N | 4-biphenyl | 4-biphenyl |
| 2903. | H | H | D¹³⁸ | H | H | H | H | H | L¹⁰⁶ | N | CH | N | Ph | Ph |
| 2904. | H | H | D¹³⁸ | H | H | H | H | H | L¹⁰⁶ | N | CH | N | 4-biphenyl | 4-biphenyl |
| 2905. | H | H | D¹³⁸ | H | H | H | H | H | L¹⁰⁷ | N | N | N | Ph | Ph |
| 2906. | H | H | D¹³⁸ | H | H | H | H | H | L¹⁰⁷ | N | N | N | 4-biphenyl | 4-biphenyl |
| 2907. | H | H | D¹³⁸ | H | H | H | H | H | L¹⁰⁷ | N | CH | N | Ph | Ph |
| 2908. | H | H | D¹³⁸ | H | H | H | H | H | L¹⁰⁷ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2909. | H | H | D¹³⁸ | H | H | H | H | H | L¹⁰⁸ | N | N | N | Ph | Ph |
| 2910. | H | H | D¹³⁸ | H | H | H | H | H | L¹⁰⁸ | N | N | N | 4-biphenyl | 4-biphenyl |
| 2911. | H | H | D¹³⁸ | H | H | H | H | H | L¹⁰⁸ | N | CH | N | Ph | Ph |
| 2912. | H | H | D¹³⁸ | H | H | H | H | H | L¹⁰⁸ | N | CH | N | 4-biphenyl | 4-biphenyl |
| 2913. | H | H | D¹³⁸ | H | H | H | H | H | L¹⁰⁹ | N | N | N | Ph | Ph |
| 2914. | H | H | D¹³⁸ | H | H | H | H | H | L¹⁰⁹ | N | N | N | 4-biphenyl | 4-biphenyl |
| 2915. | H | H | D¹³⁸ | H | H | H | H | H | L¹⁰⁹ | N | CH | N | Ph | Ph |
| 2916. | H | H | D¹³⁸ | H | H | H | H | H | L¹⁰⁹ | N | CH | N | 4-biphenyl | 4-biphenyl |
| 2917. | H | H | D¹³⁸ | H | H | H | H | H | L¹¹⁰ | N | N | N | Ph | Ph |
| 2918. | H | H | D¹³⁸ | H | H | H | H | H | L¹¹⁰ | N | N | N | 4-biphenyl | 4-biphenyl |
| 2919. | H | H | D¹³⁸ | H | H | H | H | H | L¹¹⁰ | N | CH | N | Ph | Ph |
| 2920. | H | H | D¹³⁸ | H | H | H | H | H | L¹¹⁰ | N | CH | N | 4-biphenyl | 4-biphenyl |
| 2921. | H | H | D¹³⁸ | H | H | H | H | H | L¹¹¹ | N | N | N | Ph | Ph |
| 2922. | H | H | D¹³⁸ | H | H | H | H | H | L¹¹¹ | N | N | N | 4-biphenyl | 4-biphenyl |
| 2923. | H | H | D¹³⁸ | H | H | H | H | H | L¹¹¹ | N | CH | N | Ph | Ph |
| 2924. | H | H | D¹³⁸ | H | H | H | H | H | L¹¹¹ | N | CH | N | 4-biphenyl | 4-biphenyl |
| 2925. | H | H | D¹³⁸ | H | H | H | H | H | L¹¹² | N | N | N | Ph | Ph |
| 2926. | H | H | D¹³⁸ | H | H | H | H | H | L¹¹² | N | N | N | 4-biphenyl | 4-biphenyl |
| 2927. | H | H | D¹³⁸ | H | H | H | H | H | L¹¹² | N | CH | N | Ph | Ph |
| 2928. | H | H | D¹³⁸ | H | H | H | H | H | L¹¹² | N | CH | N | 4-biphenyl | 4-biphenyl |
| 2929. | H | H | D¹³⁸ | H | H | H | H | H | L¹¹³ | N | N | N | Ph | Ph |
| 2930. | H | H | D¹³⁸ | H | H | H | H | H | L¹¹³ | N | N | N | 4-biphenyl | 4-biphenyl |
| 2931. | H | H | D¹³⁸ | H | H | H | H | H | L¹¹³ | N | CH | N | Ph | Ph |
| 2932. | H | H | D¹³⁸ | H | H | H | H | H | L¹¹³ | N | CH | N | 4-biphenyl | 4-biphenyl |
| 2933. | H | H | D¹³⁸ | H | H | H | H | H | L¹¹⁴ | N | N | N | Ph | Ph |
| 2934. | H | H | D¹³⁸ | H | H | H | H | H | L¹¹⁴ | N | N | N | 4-biphenyl | 4-biphenyl |
| 2935. | H | H | D¹³⁸ | H | H | H | H | H | L¹¹⁴ | N | CH | N | Ph | Ph |
| 2936. | H | H | D¹³⁸ | H | H | H | H | H | L¹¹⁴ | N | CH | N | 4-biphenyl | 4-biphenyl |
| 2937. | H | H | D¹³⁸ | H | H | H | H | H | L¹¹⁵ | N | N | N | Ph | Ph |
| 2938. | H | H | D¹³⁸ | H | H | H | H | H | L¹¹⁵ | N | N | N | 4-biphenyl | 4-biphenyl |
| 2939. | H | H | D¹³⁸ | H | H | H | H | H | L¹¹⁵ | N | CH | N | Ph | Ph |
| 2940. | H | H | D¹³⁸ | H | H | H | H | H | L¹¹⁵ | N | CH | N | 4-biphenyl | 4-biphenyl |
| 2941. | H | H | D¹³⁸ | H | H | H | H | H | L¹¹⁶ | N | N | N | Ph | Ph |
| 2942. | H | H | D¹³⁸ | H | H | H | H | H | L¹¹⁶ | N | N | N | 4-biphenyl | 4-biphenyl |
| 2943. | H | H | D¹³⁸ | H | H | H | H | H | L¹¹⁶ | N | CH | N | Ph | Ph |
| 2944. | H | H | D¹³⁸ | H | H | H | H | H | L¹¹⁶ | N | CH | N | 4-biphenyl | 4-biphenyl |
| 2945. | H | H | D¹³⁹ | H | H | H | H | H | L¹⁰¹ | N | N | N | Ph | Ph |
| 2946. | H | H | D¹³⁹ | H | H | H | H | H | L¹⁰¹ | N | N | N | 4-biphenyl | 4-biphenyl |
| 2947. | H | H | D¹³⁹ | H | H | H | H | H | L¹⁰¹ | N | CH | N | Ph | Ph |
| 2948. | H | H | D¹³⁹ | H | H | H | H | H | L¹⁰¹ | N | CH | N | 4-biphenyl | 4-biphenyl |
| 2949. | H | H | D¹³⁹ | H | H | H | H | H | L¹⁰² | N | N | N | Ph | Ph |
| 2950. | H | H | D¹³⁹ | H | H | H | H | H | L¹⁰² | N | N | N | 4-biphenyl | 4-biphenyl |
| 2951. | H | H | D¹³⁹ | H | H | H | H | H | L¹⁰² | N | CH | N | Ph | Ph |
| 2952. | H | H | D¹³⁹ | H | H | H | H | H | L¹⁰² | N | CH | N | 4-biphenyl | 4-biphenyl |
| 2953. | H | H | D¹³⁹ | H | H | H | H | H | L¹⁰³ | N | N | N | Ph | Ph |
| 2954. | H | H | D¹³⁹ | H | H | H | H | H | L¹⁰³ | N | N | N | 4-biphenyl | 4-biphenyl |
| 2955. | H | H | D¹³⁹ | H | H | H | H | H | L¹⁰³ | N | CH | N | Ph | Ph |
| 2956. | H | H | D¹³⁹ | H | H | H | H | H | L¹⁰³ | N | CH | N | 4-biphenyl | 4-biphenyl |
| 2957. | H | H | D¹³⁹ | H | H | H | H | H | L¹⁰⁴ | N | N | N | Ph | Ph |
| 2958. | H | H | D¹³⁹ | H | H | H | H | H | L¹⁰⁴ | N | N | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 2959. | H | H | D¹³⁹ | H | H | H | H | H | L¹⁰⁴ | N | CH | N | Ph | Ph |
| 2960. | H | H | D¹³⁹ | H | H | H | H | H | L¹⁰⁴ | N | CH | N | 4-biphenyl | 4-biphenyl |
| 2961. | H | H | D¹³⁹ | H | H | H | H | H | L¹⁰⁵ | N | N | N | Ph | Ph |
| 2962. | H | H | D¹³⁹ | H | H | H | H | H | L¹⁰⁵ | N | N | N | 4-biphenyl | 4-biphenyl |
| 2963. | H | H | D¹³⁹ | H | H | H | H | H | L¹⁰⁵ | N | CH | N | Ph | Ph |
| 2964. | H | H | D¹³⁹ | H | H | H | H | H | L¹⁰⁵ | N | CH | N | 4-biphenyl | 4-biphenyl |
| 2965. | H | H | D¹³⁹ | H | H | H | H | H | L¹⁰⁶ | N | N | N | Ph | Ph |
| 2966. | H | H | D¹³⁹ | H | H | H | H | H | L¹⁰⁶ | N | N | N | 4-biphenyl | 4-biphenyl |
| 2967. | H | H | D¹³⁹ | H | H | H | H | H | L¹⁰⁶ | N | CH | N | Ph | Ph |
| 2968. | H | H | D¹³⁹ | H | H | H | H | H | L¹⁰⁶ | N | CH | N | 4-biphenyl | 4-biphenyl |
| 2969. | H | H | D¹³⁹ | H | H | H | H | H | L¹⁰⁷ | N | N | N | Ph | Ph |
| 2970. | H | H | D¹³⁹ | H | H | H | H | H | L¹⁰⁷ | N | N | N | 4-biphenyl | 4-biphenyl |
| 2971. | H | H | D¹³⁹ | H | H | H | H | H | L¹⁰⁷ | N | CH | N | Ph | Ph |
| 2972. | H | H | D¹³⁹ | H | H | H | H | H | L¹⁰⁷ | N | CH | N | 4-biphenyl | 4-biphenyl |
| 2973. | H | H | D¹³⁹ | H | H | H | H | H | L¹⁰⁸ | N | N | N | Ph | Ph |
| 2974. | H | H | D¹³⁹ | H | H | H | H | H | L¹⁰⁸ | N | N | N | 4-biphenyl | 4-biphenyl |
| 2975. | H | H | D¹³⁹ | H | H | H | H | H | L¹⁰⁸ | N | CH | N | Ph | Ph |
| 2976. | H | H | D¹³⁹ | H | H | H | H | H | L¹⁰⁸ | N | CH | N | 4-biphenyl | 4-biphenyl |
| 2977. | H | H | D¹³⁹ | H | H | H | H | H | L¹⁰⁹ | N | N | N | Ph | Ph |
| 2978. | H | H | D¹³⁹ | H | H | H | H | H | L¹⁰⁹ | N | N | N | 4-biphenyl | 4-biphenyl |
| 2979. | H | H | D¹³⁹ | H | H | H | H | H | L¹⁰⁹ | N | CH | N | Ph | Ph |
| 2980. | H | H | D¹³⁹ | H | H | H | H | H | L¹⁰⁹ | N | CH | N | 4-biphenyl | 4-biphenyl |
| 2981. | H | H | D¹³⁹ | H | H | H | H | H | L¹¹⁰ | N | N | N | Ph | Ph |
| 2982. | H | H | D¹³⁹ | H | H | H | H | H | L¹¹⁰ | N | N | N | 4-biphenyl | 4-biphenyl |
| 2983. | H | H | D¹³⁹ | H | H | H | H | H | L¹¹⁰ | N | CH | N | Ph | Ph |
| 2984. | H | H | D¹³⁹ | H | H | H | H | H | L¹¹⁰ | N | CH | N | 4-biphenyl | 4-biphenyl |
| 2985. | H | H | D¹³⁹ | H | H | H | H | H | L¹¹¹ | N | N | N | Ph | Ph |
| 2986. | H | H | D¹³⁹ | H | H | H | H | H | L¹¹¹ | N | N | N | 4-biphenyl | 4-biphenyl |
| 2987. | H | H | D¹³⁹ | H | H | H | H | H | L¹¹¹ | N | CH | N | Ph | Ph |
| 2988. | H | H | D¹³⁹ | H | H | H | H | H | L¹¹¹ | N | CH | N | 4-biphenyl | 4-biphenyl |
| 2989. | H | H | D¹³⁹ | H | H | H | H | H | L¹¹² | N | N | N | Ph | Ph |
| 2990. | H | H | D¹³⁹ | H | H | H | H | H | L¹¹² | N | N | N | 4-biphenyl | 4-biphenyl |
| 2991. | H | H | D¹³⁹ | H | H | H | H | H | L¹¹² | N | CH | N | Ph | Ph |
| 2992. | H | H | D¹³⁹ | H | H | H | H | H | L¹¹² | N | CH | N | 4-biphenyl | 4-biphenyl |
| 2993. | H | H | D¹³⁹ | H | H | H | H | H | L¹¹³ | N | N | N | Ph | Ph |
| 2994. | H | H | D¹³⁹ | H | H | H | H | H | L¹¹³ | N | N | N | 4-biphenyl | 4-biphenyl |
| 2995. | H | H | D¹³⁹ | H | H | H | H | H | L¹¹³ | N | CH | N | Ph | Ph |
| 2996. | H | H | D¹³⁹ | H | H | H | H | H | L¹¹³ | N | CH | N | 4-biphenyl | 4-biphenyl |
| 2997. | H | H | D¹³⁹ | H | H | H | H | H | L¹¹⁴ | N | N | N | Ph | Ph |
| 2998. | H | H | D¹³⁹ | H | H | H | H | H | L¹¹⁴ | N | N | N | 4-biphenyl | 4-biphenyl |
| 2999. | H | H | D¹³⁹ | H | H | H | H | H | L¹¹⁴ | N | CH | N | Ph | Ph |
| 3000. | H | H | D¹³⁹ | H | H | H | H | H | L¹¹⁴ | N | CH | N | 4-biphenyl | 4-biphenyl |
| 3001. | H | H | D¹³⁹ | H | H | H | H | H | L¹¹⁵ | N | N | N | Ph | Ph |
| 3002. | H | H | D¹³⁹ | H | H | H | H | H | L¹¹⁵ | N | N | N | 4-biphenyl | 4-biphenyl |
| 3003. | H | H | D¹³⁹ | H | H | H | H | H | L¹¹⁵ | N | CH | N | Ph | Ph |
| 3004. | H | H | D¹³⁹ | H | H | H | H | H | L¹¹⁵ | N | CH | N | 4-biphenyl | 4-biphenyl |
| 3005. | H | H | D¹³⁹ | H | H | H | H | H | L¹¹⁶ | N | N | N | Ph | Ph |
| 3006. | H | H | D¹³⁹ | H | H | H | H | H | L¹¹⁶ | N | N | N | 4-biphenyl | 4-biphenyl |
| 3007. | H | H | D¹³⁹ | H | H | H | H | H | L¹¹⁶ | N | CH | N | Ph | Ph |
| 3008. | H | H | D¹³⁹ | H | H | H | H | H | L¹¹⁶ | N | CH | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 3009. | H | H | D¹⁴⁰ | H | H | H | H | H | L¹⁰¹ | N | N | N | Ph | Ph |
| 3010. | H | H | D¹⁴⁰ | H | H | H | H | H | L¹⁰¹ | N | N | N | 4-biphenyl | 4-biphenyl |
| 3011. | H | H | D¹⁴⁰ | H | H | H | H | H | L¹⁰¹ | N | CH | N | Ph | Ph |
| 3012. | H | H | D¹⁴⁰ | H | H | H | H | H | L¹⁰¹ | N | CH | N | 4-biphenyl | 4-biphenyl |
| 3013. | H | H | D¹⁴⁰ | H | H | H | H | H | L¹⁰² | N | N | N | Ph | Ph |
| 3014. | H | H | D¹⁴⁰ | H | H | H | H | H | L¹⁰² | N | N | N | 4-biphenyl | 4-biphenyl |
| 3015. | H | H | D¹⁴⁰ | H | H | H | H | H | L¹⁰² | N | CH | N | Ph | Ph |
| 3016. | H | H | D¹⁴⁰ | H | H | H | H | H | L¹⁰² | N | CH | N | 4-biphenyl | 4-biphenyl |
| 3017. | H | H | D¹⁴⁰ | H | H | H | H | H | L¹⁰³ | N | N | N | Ph | Ph |
| 3018. | H | H | D¹⁴⁰ | H | H | H | H | H | L¹⁰³ | N | N | N | 4-biphenyl | 4-biphenyl |
| 3019. | H | H | D¹⁴⁰ | H | H | H | H | H | L¹⁰³ | N | CH | N | Ph | Ph |
| 3020. | H | H | D¹⁴⁰ | H | H | H | H | H | L¹⁰³ | N | CH | N | 4-biphenyl | 4-biphenyl |
| 3021. | H | H | D¹⁴⁰ | H | H | H | H | H | L¹⁰⁴ | N | N | N | Ph | Ph |
| 3022. | H | H | D¹⁴⁰ | H | H | H | H | H | L¹⁰⁴ | N | N | N | 4-biphenyl | 4-biphenyl |
| 3023. | H | H | D¹⁴⁰ | H | H | H | H | H | L¹⁰⁴ | N | CH | N | Ph | Ph |
| 3024. | H | H | D¹⁴⁰ | H | H | H | H | H | L¹⁰⁴ | N | CH | N | 4-biphenyl | 4-biphenyl |
| 3025. | H | H | D¹⁴⁰ | H | H | H | H | H | L¹⁰⁵ | N | N | N | Ph | Ph |
| 3026. | H | H | D¹⁴⁰ | H | H | H | H | H | L¹⁰⁵ | N | N | N | 4-biphenyl | 4-biphenyl |
| 3027. | H | H | D¹⁴⁰ | H | H | H | H | H | L¹⁰⁵ | N | CH | N | Ph | Ph |
| 3028. | H | H | D¹⁴⁰ | H | H | H | H | H | L¹⁰⁵ | N | CH | N | 4-biphenyl | 4-biphenyl |
| 3029. | H | H | D¹⁴⁰ | H | H | H | H | H | L¹⁰⁶ | N | N | N | Ph | Ph |
| 3030. | H | H | D¹⁴⁰ | H | H | H | H | H | L¹⁰⁶ | N | N | N | 4-biphenyl | 4-biphenyl |
| 3031. | H | H | D¹⁴⁰ | H | H | H | H | H | L¹⁰⁶ | N | CH | N | Ph | Ph |
| 3032. | H | H | D¹⁴⁰ | H | H | H | H | H | L¹⁰⁶ | N | CH | N | 4-biphenyl | 4-biphenyl |
| 3033. | H | H | D¹⁴⁰ | H | H | H | H | H | L¹⁰⁷ | N | N | N | Ph | Ph |
| 3034. | H | H | D¹⁴⁰ | H | H | H | H | H | L¹⁰⁷ | N | N | N | 4-biphenyl | 4-biphenyl |
| 3035. | H | H | D¹⁴⁰ | H | H | H | H | H | L¹⁰⁷ | N | CH | N | Ph | Ph |
| 3036. | H | H | D¹⁴⁰ | H | H | H | H | H | L¹⁰⁷ | N | CH | N | 4-biphenyl | 4-biphenyl |
| 3037. | H | H | D¹⁴⁰ | H | H | H | H | H | L¹⁰⁸ | N | N | N | Ph | Ph |
| 3038. | H | H | D¹⁴⁰ | H | H | H | H | H | L¹⁰⁸ | N | N | N | 4-biphenyl | 4-biphenyl |
| 3039. | H | H | D¹⁴⁰ | H | H | H | H | H | L¹⁰⁸ | N | CH | N | Ph | Ph |
| 3040. | H | H | D¹⁴⁰ | H | H | H | H | H | L¹⁰⁸ | N | CH | N | 4-biphenyl | 4-biphenyl |
| 3041. | H | H | D¹⁴⁰ | H | H | H | H | H | L¹⁰⁹ | N | N | N | Ph | Ph |
| 3042. | H | H | D¹⁴⁰ | H | H | H | H | H | L¹⁰⁹ | N | N | N | 4-biphenyl | 4-biphenyl |
| 3043. | H | H | D¹⁴⁰ | H | H | H | H | H | L¹⁰⁹ | N | CH | N | Ph | Ph |
| 3044. | H | H | D¹⁴⁰ | H | H | H | H | H | L¹⁰⁹ | N | CH | N | 4-biphenyl | 4-biphenyl |
| 3045. | H | H | D¹⁴⁰ | H | H | H | H | H | L¹¹⁰ | N | N | N | Ph | Ph |
| 3046. | H | H | D¹⁴⁰ | H | H | H | H | H | L¹¹⁰ | N | N | N | 4-biphenyl | 4-biphenyl |
| 3047. | H | H | D¹⁴⁰ | H | H | H | H | H | L¹¹⁰ | N | CH | N | Ph | Ph |
| 3048. | H | H | D¹⁴⁰ | H | H | H | H | H | L¹¹⁰ | N | CH | N | 4-biphenyl | 4-biphenyl |
| 3049. | H | H | D¹⁴⁰ | H | H | H | H | H | L¹¹¹ | N | N | N | Ph | Ph |
| 3050. | H | H | D¹⁴⁰ | H | H | H | H | H | L¹¹¹ | N | N | N | 4-biphenyl | 4-biphenyl |
| 3051. | H | H | D¹⁴⁰ | H | H | H | H | H | L¹¹¹ | N | CH | N | Ph | Ph |
| 3052. | H | H | D¹⁴⁰ | H | H | H | H | H | L¹¹¹ | N | CH | N | 4-biphenyl | 4-biphenyl |
| 3053. | H | H | D¹⁴⁰ | H | H | H | H | H | L¹¹² | N | N | N | Ph | Ph |
| 3054. | H | H | D¹⁴⁰ | H | H | H | H | H | L¹¹² | N | N | N | 4-biphenyl | 4-biphenyl |
| 3055. | H | H | D¹⁴⁰ | H | H | H | H | H | L¹¹² | N | CH | N | Ph | Ph |
| 3056. | H | H | D¹⁴⁰ | H | H | H | H | H | L¹¹² | N | CH | N | 4-biphenyl | 4-biphenyl |
| 3057. | H | H | D¹⁴⁰ | H | H | H | H | H | L¹¹³ | N | N | N | Ph | Ph |
| 3058. | H | H | D¹⁴⁰ | H | H | H | H | H | L¹¹³ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 3059. | H | H | D¹⁴⁰ | H | H | H | H | H | L¹¹³ | N | CH | N | Ph | Ph |
| 3060. | H | H | D¹⁴⁰ | H | H | H | H | H | L¹¹³ | N | CH | N | 4-biphenyl | 4-biphenyl |
| 3061. | H | H | D¹⁴⁰ | H | H | H | H | H | L¹¹⁴ | N | N | N | Ph | Ph |
| 3062. | H | H | D¹⁴⁰ | H | H | H | H | H | L¹¹⁴ | N | N | N | 4-biphenyl | 4-biphenyl |
| 3063. | H | H | D¹⁴⁰ | H | H | H | H | H | L¹¹⁴ | N | CH | N | Ph | Ph |
| 3064. | H | H | D¹⁴⁰ | H | H | H | H | H | L¹¹⁴ | N | CH | N | 4-biphenyl | 4-biphenyl |
| 3065. | H | H | D¹⁴⁰ | H | H | H | H | H | L¹¹⁵ | N | N | N | Ph | Ph |
| 3066. | H | H | D¹⁴⁰ | H | H | H | H | H | L¹¹⁵ | N | N | N | 4-biphenyl | 4-biphenyl |
| 3067. | H | H | D¹⁴⁰ | H | H | H | H | H | L¹¹⁵ | N | CH | N | Ph | Ph |
| 3068. | H | H | D¹⁴⁰ | H | H | H | H | H | L¹¹⁵ | N | CH | N | 4-biphenyl | 4-biphenyl |
| 3069. | H | H | D¹⁴⁰ | H | H | H | H | H | L¹¹⁶ | N | N | N | Ph | Ph |
| 3070. | H | H | D¹⁴⁰ | H | H | H | H | H | L¹¹⁶ | N | N | N | 4-biphenyl | 4-biphenyl |
| 3071. | H | H | D¹⁴⁰ | H | H | H | H | H | L¹¹⁶ | N | CH | N | Ph | Ph |
| 3072. | H | H | D¹⁴⁰ | H | H | H | H | H | L¹¹⁶ | N | CH | N | 4-biphenyl | 4-biphenyl |
| 3073. | H | H | D¹⁰¹ | H | H | D¹⁰² | H | H | L¹⁰¹ | N | N | N | Ph | Ph |
| 3074. | H | H | D¹⁰¹ | H | H | D¹⁰² | H | H | L¹⁰¹ | N | N | N | 4-biphenyl | 4-biphenyl |
| 3075. | H | H | D¹⁰¹ | H | H | D¹⁰² | H | H | L¹⁰¹ | N | CH | N | Ph | Ph |
| 3076. | H | H | D¹⁰¹ | H | H | D¹⁰² | H | H | L¹⁰¹ | N | CH | N | 4-biphenyl | 4-biphenyl |
| 3077. | H | H | D¹⁰¹ | H | H | D¹⁰² | H | H | L¹⁰² | N | N | N | Ph | Ph |
| 3078. | H | H | D¹⁰¹ | H | H | D¹⁰² | H | H | L¹⁰² | N | N | N | 4-biphenyl | 4-biphenyl |
| 3079. | H | H | D¹⁰¹ | H | H | D¹⁰² | H | H | L¹⁰² | N | CH | N | Ph | Ph |
| 3080. | H | H | D¹⁰¹ | H | H | D¹⁰² | H | H | L¹⁰² | N | CH | N | 4-biphenyl | 4-biphenyl |
| 3081. | H | H | D¹⁰¹ | H | H | D¹⁰² | H | H | L¹⁰³ | N | N | N | Ph | Ph |
| 3082. | H | H | D¹⁰¹ | H | H | D¹⁰² | H | H | L¹⁰³ | N | N | N | 4-biphenyl | 4-biphenyl |
| 3083. | H | H | D¹⁰¹ | H | H | D¹⁰² | H | H | L¹⁰³ | N | CH | N | Ph | Ph |
| 3084. | H | H | D¹⁰¹ | H | H | D¹⁰² | H | H | L¹⁰³ | N | CH | N | 4-biphenyl | 4-biphenyl |
| 3085. | H | H | D¹⁰¹ | H | H | D¹⁰² | H | H | L¹⁰⁴ | N | N | N | Ph | Ph |
| 3086. | H | H | D¹⁰¹ | H | H | D¹⁰² | H | H | L¹⁰⁴ | N | N | N | 4-biphenyl | 4-biphenyl |
| 3087. | H | H | D¹⁰¹ | H | H | D¹⁰² | H | H | L¹⁰⁴ | N | CH | N | Ph | Ph |
| 3088. | H | H | D¹⁰¹ | H | H | D¹⁰² | H | H | L¹⁰⁴ | N | CH | N | 4-biphenyl | 4-biphenyl |
| 3089. | H | H | D¹⁰¹ | H | H | D¹⁰² | H | H | L¹⁰⁵ | N | N | N | Ph | Ph |
| 3090. | H | H | D¹⁰¹ | H | H | D¹⁰² | H | H | L¹⁰⁵ | N | N | N | 4-biphenyl | 4-biphenyl |
| 3091. | H | H | D¹⁰¹ | H | H | D¹⁰² | H | H | L¹⁰⁵ | N | CH | N | Ph | Ph |
| 3092. | H | H | D¹⁰¹ | H | H | D¹⁰² | H | H | L¹⁰⁵ | N | CH | N | 4-biphenyl | 4-biphenyl |
| 3093. | H | H | D¹⁰¹ | H | H | D¹⁰² | H | H | L¹⁰⁶ | N | N | N | Ph | Ph |
| 3094. | H | H | D¹⁰¹ | H | H | D¹⁰² | H | H | L¹⁰⁶ | N | N | N | 4-biphenyl | 4-biphenyl |
| 3095. | H | H | D¹⁰¹ | H | H | D¹⁰² | H | H | L¹⁰⁶ | N | CH | N | Ph | Ph |
| 3096. | H | H | D¹⁰¹ | H | H | D¹⁰² | H | H | L¹⁰⁶ | N | CH | N | 4-biphenyl | 4-biphenyl |
| 3097. | H | H | D¹⁰¹ | H | H | D¹⁰² | H | H | L¹⁰⁷ | N | N | N | Ph | Ph |
| 3098. | H | H | D¹⁰¹ | H | H | D¹⁰² | H | H | L¹⁰⁷ | N | N | N | 4-biphenyl | 4-biphenyl |
| 3099. | H | H | D¹⁰¹ | H | H | D¹⁰² | H | H | L¹⁰⁷ | N | CH | N | Ph | Ph |
| 3100. | H | H | D¹⁰¹ | H | H | D¹⁰² | H | H | L¹⁰⁷ | N | CH | N | 4-biphenyl | 4-biphenyl |
| 3101. | H | H | D¹⁰¹ | H | H | D¹⁰² | H | H | L¹⁰⁸ | N | N | N | Ph | Ph |
| 3102. | H | H | D¹⁰¹ | H | H | D¹⁰² | H | H | L¹⁰⁸ | N | N | N | 4-biphenyl | 4-biphenyl |
| 3103. | H | H | D¹⁰¹ | H | H | D¹⁰² | H | H | L¹⁰⁸ | N | CH | N | Ph | Ph |
| 3104. | H | H | D¹⁰¹ | H | H | D¹⁰² | H | H | L¹⁰⁸ | N | CH | N | 4-biphenyl | 4-biphenyl |
| 3105. | H | H | D¹⁰¹ | H | H | D¹⁰² | H | H | L¹⁰⁹ | N | N | N | Ph | Ph |
| 3106. | H | H | D¹⁰¹ | H | H | D¹⁰² | H | H | L¹⁰⁹ | N | N | N | 4-biphenyl | 4-biphenyl |
| 3107. | H | H | D¹⁰¹ | H | H | D¹⁰² | H | H | L¹⁰⁹ | N | CH | N | Ph | Ph |
| 3108. | H | H | D¹⁰¹ | H | H | D¹⁰² | H | H | L¹⁰⁹ | N | CH | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 3109. | H | H | D¹⁰¹ | H | H | D¹⁰² | H | H | L¹¹⁰ | N | N | N | Ph | Ph |
| 3110. | H | H | D¹⁰¹ | H | H | D¹⁰² | H | H | L¹¹⁰ | N | N | N | 4-biphenyl | 4-biphenyl |
| 3111. | H | H | D¹⁰¹ | H | H | D¹⁰² | H | H | L¹¹⁰ | N | CH | N | Ph | Ph |
| 3112. | H | H | D¹⁰¹ | H | H | D¹⁰² | H | H | L¹¹⁰ | N | CH | N | 4-biphenyl | 4-biphenyl |
| 3113. | H | H | D¹⁰¹ | H | H | D¹⁰² | H | H | L¹¹¹ | N | N | N | Ph | Ph |
| 3114. | H | H | D¹⁰¹ | H | H | D¹⁰² | H | H | L¹¹¹ | N | N | N | 4-biphenyl | 4-biphenyl |
| 3115. | H | H | D¹⁰¹ | H | H | D¹⁰² | H | H | L¹¹¹ | N | CH | N | Ph | Ph |
| 3116. | H | H | D¹⁰¹ | H | H | D¹⁰² | H | H | L¹¹¹ | N | CH | N | 4-biphenyl | 4-biphenyl |
| 3117. | H | H | D¹⁰¹ | H | H | D¹⁰² | H | H | L¹¹² | N | N | N | Ph | Ph |
| 3118. | H | H | D¹⁰¹ | H | H | D¹⁰² | H | H | L¹¹² | N | N | N | 4-biphenyl | 4-biphenyl |
| 3119. | H | H | D¹⁰¹ | H | H | D¹⁰² | H | H | L¹¹² | N | CH | N | Ph | Ph |
| 3120. | H | H | D¹⁰¹ | H | H | D¹⁰² | H | H | L¹¹² | N | CH | N | 4-biphenyl | 4-biphenyl |
| 3121. | H | H | D¹⁰¹ | H | H | D¹⁰² | H | H | L¹¹³ | N | N | N | Ph | Ph |
| 3122. | H | H | D¹⁰¹ | H | H | D¹⁰² | H | H | L¹¹³ | N | N | N | 4-biphenyl | 4-biphenyl |
| 3123. | H | H | D¹⁰¹ | H | H | D¹⁰² | H | H | L¹¹³ | N | CH | N | Ph | Ph |
| 3124. | H | H | D¹⁰¹ | H | H | D¹⁰² | H | H | L¹¹³ | N | CH | N | 4-biphenyl | 4-biphenyl |
| 3125. | H | H | D¹⁰¹ | H | H | D¹⁰² | H | H | L¹¹⁴ | N | N | N | Ph | Ph |
| 3126. | H | H | D¹⁰¹ | H | H | D¹⁰² | H | H | L¹¹⁴ | N | N | N | 4-biphenyl | 4-biphenyl |
| 3127. | H | H | D¹⁰¹ | H | H | D¹⁰² | H | H | L¹¹⁴ | N | CH | N | Ph | Ph |
| 3128. | H | H | D¹⁰¹ | H | H | D¹⁰² | H | H | L¹¹⁴ | N | CH | N | 4-biphenyl | 4-biphenyl |
| 3129. | H | H | D¹⁰¹ | H | H | D¹⁰² | H | H | L¹¹⁵ | N | N | N | Ph | Ph |
| 3130. | H | H | D¹⁰¹ | H | H | D¹⁰² | H | H | L¹¹⁵ | N | N | N | 4-biphenyl | 4-biphenyl |
| 3131. | H | H | D¹⁰¹ | H | H | D¹⁰² | H | H | L¹¹⁵ | N | CH | N | Ph | Ph |
| 3132. | H | H | D¹⁰¹ | H | H | D¹⁰² | H | H | L¹¹⁵ | N | CH | N | 4-biphenyl | 4-biphenyl |
| 3133. | H | H | D¹⁰¹ | H | H | D¹⁰² | H | H | L¹¹⁶ | N | N | N | Ph | Ph |
| 3134. | H | H | D¹⁰¹ | H | H | D¹⁰² | H | H | L¹¹⁶ | N | N | N | 4-biphenyl | 4-biphenyl |
| 3135. | H | H | D¹⁰¹ | H | H | D¹⁰² | H | H | L¹¹⁶ | N | CH | N | Ph | Ph |
| 3136. | H | H | D¹⁰¹ | H | H | D¹⁰² | H | H | L¹¹⁶ | N | CH | N | 4-biphenyl | 4-biphenyl |
| 3137. | H | H | D¹³² | H | H | D¹³⁷ | H | H | L¹⁰¹ | N | N | N | Ph | Ph |
| 3138. | H | H | D¹³² | H | H | D¹³⁷ | H | H | L¹⁰¹ | N | N | N | 4-biphenyl | 4-biphenyl |
| 3139. | H | H | D¹³² | H | H | D¹³⁷ | H | H | L¹⁰¹ | N | CH | N | Ph | Ph |
| 3140. | H | H | D¹³² | H | H | D¹³⁷ | H | H | L¹⁰¹ | N | CH | N | 4-biphenyl | 4-biphenyl |
| 3141. | H | H | D¹³² | H | H | D¹³⁷ | H | H | L¹⁰² | N | N | N | Ph | Ph |
| 3142. | H | H | D¹³² | H | H | D¹³⁷ | H | H | L¹⁰² | N | N | N | 4-biphenyl | 4-biphenyl |
| 3143. | H | H | D¹³² | H | H | D¹³⁷ | H | H | L¹⁰² | N | CH | N | Ph | Ph |
| 3144. | H | H | D¹³² | H | H | D¹³⁷ | H | H | L¹⁰² | N | CH | N | 4-biphenyl | 4-biphenyl |
| 3145. | H | H | D¹³² | H | H | D¹³⁷ | H | H | L¹⁰³ | N | N | N | Ph | Ph |
| 3146. | H | H | D¹³² | H | H | D¹³⁷ | H | H | L¹⁰³ | N | N | N | 4-biphenyl | 4-biphenyl |
| 3147. | H | H | D¹³² | H | H | D¹³⁷ | H | H | L¹⁰³ | N | CH | N | Ph | Ph |
| 3148. | H | H | D¹³² | H | H | D¹³⁷ | H | H | L¹⁰³ | N | CH | N | 4-biphenyl | 4-biphenyl |
| 3149. | H | H | D¹³² | H | H | D¹³⁷ | H | H | L¹⁰⁴ | N | N | N | Ph | Ph |
| 3150. | H | H | D¹³² | H | H | D¹³⁷ | H | H | L¹⁰⁴ | N | N | N | 4-biphenyl | 4-biphenyl |
| 3151. | H | H | D¹³² | H | H | D¹³⁷ | H | H | L¹⁰⁴ | N | CH | N | Ph | Ph |
| 3152. | H | H | D¹³² | H | H | D¹³⁷ | H | H | L¹⁰⁴ | N | CH | N | 4-biphenyl | 4-biphenyl |
| 3153. | H | H | D¹³² | H | H | D¹³⁷ | H | H | L¹⁰⁵ | N | N | N | Ph | Ph |
| 3154. | H | H | D¹³² | H | H | D¹³⁷ | H | H | L¹⁰⁵ | N | N | N | 4-biphenyl | 4-biphenyl |
| 3155. | H | H | D¹³² | H | H | D¹³⁷ | H | H | L¹⁰⁵ | N | CH | N | Ph | Ph |
| 3156. | H | H | D¹³² | H | H | D¹³⁷ | H | H | L¹⁰⁵ | N | CH | N | 4-biphenyl | 4-biphenyl |
| 3157. | H | H | D¹³² | H | H | D¹³⁷ | H | H | L¹⁰⁶ | N | N | N | Ph | Ph |
| 3158. | H | H | D¹³² | H | H | D¹³⁷ | H | H | L¹⁰⁶ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 3159. | H | H | D¹³² | H | H | D¹³⁷ | H | H | L¹⁰⁶ | N | CH | N | Ph | Ph |
| 3160. | H | H | D¹³² | H | H | D¹³⁷ | H | H | L¹⁰⁶ | N | CH | N | 4-biphenyl | 4-biphenyl |
| 3161. | H | H | D¹³² | H | H | D¹³⁷ | H | H | L¹⁰⁷ | N | N | N | Ph | Ph |
| 3162. | H | H | D¹³² | H | H | D¹³⁷ | H | H | L¹⁰⁷ | N | N | N | 4-biphenyl | 4-biphenyl |
| 3163. | H | H | D¹³² | H | H | D¹³⁷ | H | H | L¹⁰⁷ | N | CH | N | Ph | Ph |
| 3164. | H | H | D¹³² | H | H | D¹³⁷ | H | H | L¹⁰⁷ | N | CH | N | 4-biphenyl | 4-biphenyl |
| 3165. | H | H | D¹³² | H | H | D¹³⁷ | H | H | L¹⁰⁸ | N | N | N | Ph | Ph |
| 3166. | H | H | D¹³² | H | H | D¹³⁷ | H | H | L¹⁰⁸ | N | N | N | 4-biphenyl | 4-biphenyl |
| 3167. | H | H | D¹³² | H | H | D¹³⁷ | H | H | L¹⁰⁸ | N | CH | N | Ph | Ph |
| 3168. | H | H | D¹³² | H | H | D¹³⁷ | H | H | L¹⁰⁸ | N | CH | N | 4-biphenyl | 4-biphenyl |
| 3169. | H | H | D¹³² | H | H | D¹³⁷ | H | H | L¹⁰⁹ | N | N | N | Ph | Ph |
| 3170. | H | H | D¹³² | H | H | D¹³⁷ | H | H | L¹⁰⁹ | N | N | N | 4-biphenyl | 4-biphenyl |
| 3171. | H | H | D¹³² | H | H | D¹³⁷ | H | H | L¹⁰⁹ | N | CH | N | Ph | Ph |
| 3172. | H | H | D¹³² | H | H | D¹³⁷ | H | H | L¹⁰⁹ | N | CH | N | 4-biphenyl | 4-biphenyl |
| 3173. | H | H | D¹³² | H | H | D¹³⁷ | H | H | L¹¹⁰ | N | N | N | Ph | Ph |
| 3174. | H | H | D¹³² | H | H | D¹³⁷ | H | H | L¹¹⁰ | N | N | N | 4-biphenyl | 4-biphenyl |
| 3175. | H | H | D¹³² | H | H | D¹³⁷ | H | H | L¹¹⁰ | N | CH | N | Ph | Ph |
| 3176. | H | H | D¹³² | H | H | D¹³⁷ | H | H | L¹¹⁰ | N | CH | N | 4-biphenyl | 4-biphenyl |
| 3177. | H | H | D¹³² | H | H | D¹³⁷ | H | H | L¹¹¹ | N | N | N | Ph | Ph |
| 3178. | H | H | D¹³² | H | H | D¹³⁷ | H | H | L¹¹¹ | N | N | N | 4-biphenyl | 4-biphenyl |
| 3179. | H | H | D¹³² | H | H | D¹³⁷ | H | H | L¹¹¹ | N | CH | N | Ph | Ph |
| 3180. | H | H | D¹³² | H | H | D¹³⁷ | H | H | L¹¹¹ | N | CH | N | 4-biphenyl | 4-biphenyl |
| 3181. | H | H | D¹³² | H | H | D¹³⁷ | H | H | L¹¹² | N | N | N | Ph | Ph |
| 3182. | H | H | D¹³² | H | H | D¹³⁷ | H | H | L¹¹² | N | N | N | 4-biphenyl | 4-biphenyl |
| 3183. | H | H | D¹³² | H | H | D¹³⁷ | H | H | L¹¹² | N | CH | N | Ph | Ph |
| 3184. | H | H | D¹³² | H | H | D¹³⁷ | H | H | L¹¹² | N | CH | N | 4-biphenyl | 4-biphenyl |
| 3185. | H | H | D¹³² | H | H | D¹³⁷ | H | H | L¹¹³ | N | N | N | Ph | Ph |
| 3186. | H | H | D¹³² | H | H | D¹³⁷ | H | H | L¹¹³ | N | N | N | 4-biphenyl | 4-biphenyl |
| 3187. | H | H | D¹³² | H | H | D¹³⁷ | H | H | L¹¹³ | N | CH | N | Ph | Ph |
| 3188. | H | H | D¹³² | H | H | D¹³⁷ | H | H | L¹¹³ | N | CH | N | 4-biphenyl | 4-biphenyl |
| 3189. | H | H | D¹³² | H | H | D¹³⁷ | H | H | L¹¹⁴ | N | N | N | Ph | Ph |
| 3190. | H | H | D¹³² | H | H | D¹³⁷ | H | H | L¹¹⁴ | N | N | N | 4-biphenyl | 4-biphenyl |
| 3191. | H | H | D¹³² | H | H | D¹³⁷ | H | H | L¹¹⁴ | N | CH | N | Ph | Ph |
| 3192. | H | H | D¹³² | H | H | D¹³⁷ | H | H | L¹¹⁴ | N | CH | N | 4-biphenyl | 4-biphenyl |
| 3193. | H | H | D¹³² | H | H | D¹³⁷ | H | H | L¹¹⁵ | N | N | N | Ph | Ph |
| 3194. | H | H | D¹³² | H | H | D¹³⁷ | H | H | L¹¹⁵ | N | N | N | 4-biphenyl | 4-biphenyl |
| 3195. | H | H | D¹³² | H | H | D¹³⁷ | H | H | L¹¹⁵ | N | CH | N | Ph | Ph |
| 3196. | H | H | D¹³² | H | H | D¹³⁷ | H | H | L¹¹⁵ | N | CH | N | 4-biphenyl | 4-biphenyl |
| 3197. | H | H | D¹³² | H | H | D¹³⁷ | H | H | L¹¹⁶ | N | N | N | Ph | Ph |
| 3198. | H | H | D¹³² | H | H | D¹³⁷ | H | H | L¹¹⁶ | N | N | N | 4-biphenyl | 4-biphenyl |
| 3199. | H | H | D¹³² | H | H | D¹³⁷ | H | H | L¹¹⁶ | N | CH | N | Ph | Ph |
| 3200. | H | H | D¹³² | H | H | D¹³⁷ | H | H | L¹¹⁶ | N | CH | N | 4-biphenyl | 4-biphenyl |
| 3201. | H | H | D¹³³ | H | H | D¹³⁷ | H | H | L¹⁰¹ | N | N | N | Ph | Ph |
| 3202. | H | H | D¹³³ | H | H | D¹³⁷ | H | H | L¹⁰¹ | N | N | N | 4-biphenyl | 4-biphenyl |
| 3203. | H | H | D¹³³ | H | H | D¹³⁷ | H | H | L¹⁰¹ | N | CH | N | Ph | Ph |
| 3204. | H | H | D¹³³ | H | H | D¹³⁷ | H | H | L¹⁰¹ | N | CH | N | 4-biphenyl | 4-biphenyl |
| 3205. | H | H | D¹³³ | H | H | D¹³⁷ | H | H | L¹⁰² | N | N | N | Ph | Ph |
| 3206. | H | H | D¹³³ | H | H | D¹³⁷ | H | H | L¹⁰² | N | N | N | 4-biphenyl | 4-biphenyl |
| 3207. | H | H | D¹³³ | H | H | D¹³⁷ | H | H | L¹⁰² | N | CH | N | Ph | Ph |
| 3208. | H | H | D¹³³ | H | H | D¹³⁷ | H | H | L¹⁰² | N | CH | N | 4-biphenyl | 4-biphenyl |

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 3209. | H | H | D¹³³ | H | H | D¹³⁷ | H | H | L¹⁰³ | N | N | N | Ph | Ph |
| 3210. | H | H | D¹³³ | H | H | D¹³⁷ | H | H | L¹⁰³ | N | N | N | 4-biphenyl | 4-biphenyl |
| 3211. | H | H | D¹³³ | H | H | D¹³⁷ | H | H | L¹⁰³ | N | CH | N | Ph | Ph |
| 3212. | H | H | D¹³³ | H | H | D¹³⁷ | H | H | L¹⁰³ | N | CH | N | 4-biphenyl | 4-biphenyl |
| 3213. | H | H | D¹³³ | H | H | D¹³⁷ | H | H | L¹⁰⁴ | N | N | N | Ph | Ph |
| 3214. | H | H | D¹³³ | H | H | D¹³⁷ | H | H | L¹⁰⁴ | N | N | N | 4-biphenyl | 4-biphenyl |
| 3215. | H | H | D¹³³ | H | H | D¹³⁷ | H | H | L¹⁰⁴ | N | CH | N | Ph | Ph |
| 3216. | H | H | D¹³³ | H | H | D¹³⁷ | H | H | L¹⁰⁴ | N | CH | N | 4-biphenyl | 4-biphenyl |
| 3217. | H | H | D¹³³ | H | H | D¹³⁷ | H | H | L¹⁰⁵ | N | N | N | Ph | Ph |
| 3218. | H | H | D¹³³ | H | H | D¹³⁷ | H | H | L¹⁰⁵ | N | N | N | 4-biphenyl | 4-biphenyl |
| 3219. | H | H | D¹³³ | H | H | D¹³⁷ | H | H | L¹⁰⁵ | N | CH | N | Ph | Ph |
| 3220. | H | H | D¹³³ | H | H | D¹³⁷ | H | H | L¹⁰⁵ | N | CH | N | 4-biphenyl | 4-biphenyl |
| 3221. | H | H | D¹³³ | H | H | D¹³⁷ | H | H | L¹⁰⁶ | N | N | N | Ph | Ph |
| 3222. | H | H | D¹³³ | H | H | D¹³⁷ | H | H | L¹⁰⁶ | N | N | N | 4-biphenyl | 4-biphenyl |
| 3223. | H | H | D¹³³ | H | H | D¹³⁷ | H | H | L¹⁰⁶ | N | CH | N | Ph | Ph |
| 3224. | H | H | D¹³³ | H | H | D¹³⁷ | H | H | L¹⁰⁶ | N | CH | N | 4-biphenyl | 4-biphenyl |
| 3225. | H | H | D¹³³ | H | H | D¹³⁷ | H | H | L¹⁰⁷ | N | N | N | Ph | Ph |
| 3226. | H | H | D¹³³ | H | H | D¹³⁷ | H | H | L¹⁰⁷ | N | N | N | 4-biphenyl | 4-biphenyl |
| 3227. | H | H | D¹³³ | H | H | D¹³⁷ | H | H | L¹⁰⁷ | N | CH | N | Ph | Ph |
| 3228. | H | H | D¹³³ | H | H | D¹³⁷ | H | H | L¹⁰⁷ | N | CH | N | 4-biphenyl | 4-biphenyl |
| 3229. | H | H | D¹³³ | H | H | D¹³⁷ | H | H | L¹⁰⁸ | N | N | N | Ph | Ph |
| 3230. | H | H | D¹³³ | H | H | D¹³⁷ | H | H | L¹⁰⁸ | N | N | N | 4-biphenyl | 4-biphenyl |
| 3231. | H | H | D¹³³ | H | H | D¹³⁷ | H | H | L¹⁰⁸ | N | CH | N | Ph | Ph |
| 3232. | H | H | D¹³³ | H | H | D¹³⁷ | H | H | L¹⁰⁸ | N | CH | N | 4-biphenyl | 4-biphenyl |
| 3233. | H | H | D¹³³ | H | H | D¹³⁷ | H | H | L¹⁰⁹ | N | N | N | Ph | Ph |
| 3234. | H | H | D¹³³ | H | H | D¹³⁷ | H | H | L¹⁰⁹ | N | N | N | 4-biphenyl | 4-biphenyl |
| 3235. | H | H | D¹³³ | H | H | D¹³⁷ | H | H | L¹⁰⁹ | N | CH | N | Ph | Ph |
| 3236. | H | H | D¹³³ | H | H | D¹³⁷ | H | H | L¹⁰⁹ | N | CH | N | 4-biphenyl | 4-biphenyl |
| 3237. | H | H | D¹³³ | H | H | D¹³⁷ | H | H | L¹¹⁰ | N | N | N | Ph | Ph |
| 3238. | H | H | D¹³³ | H | H | D¹³⁷ | H | H | L¹¹⁰ | N | N | N | 4-biphenyl | 4-biphenyl |
| 3239. | H | H | D¹³³ | H | H | D¹³⁷ | H | H | L¹¹⁰ | N | CH | N | Ph | Ph |
| 3240. | H | H | D¹³³ | H | H | D¹³⁷ | H | H | L¹¹⁰ | N | CH | N | 4-biphenyl | 4-biphenyl |
| 3241. | H | H | D¹³³ | H | H | D¹³⁷ | H | H | L¹¹¹ | N | N | N | Ph | Ph |
| 3242. | H | H | D¹³³ | H | H | D¹³⁷ | H | H | L¹¹¹ | N | N | N | 4-biphenyl | 4-biphenyl |
| 3243. | H | H | D¹³³ | H | H | D¹³⁷ | H | H | L¹¹¹ | N | CH | N | Ph | Ph |
| 3244. | H | H | D¹³³ | H | H | D¹³⁷ | H | H | L¹¹¹ | N | CH | N | 4-biphenyl | 4-biphenyl |
| 3245. | H | H | D¹³³ | H | H | D¹³⁷ | H | H | L¹¹² | N | N | N | Ph | Ph |
| 3246. | H | H | D¹³³ | H | H | D¹³⁷ | H | H | L¹¹² | N | N | N | 4-biphenyl | 4-biphenyl |
| 3247. | H | H | D¹³³ | H | H | D¹³⁷ | H | H | L¹¹² | N | CH | N | Ph | Ph |
| 3248. | H | H | D¹³³ | H | H | D¹³⁷ | H | H | L¹¹² | N | CH | N | 4-biphenyl | 4-biphenyl |
| 3249. | H | H | D¹³³ | H | H | D¹³⁷ | H | H | L¹¹³ | N | N | N | Ph | Ph |
| 3250. | H | H | D¹³³ | H | H | D¹³⁷ | H | H | L¹¹³ | N | N | N | 4-biphenyl | 4-biphenyl |
| 3251. | H | H | D¹³³ | H | H | D¹³⁷ | H | H | L¹¹³ | N | CH | N | Ph | Ph |
| 3252. | H | H | D¹³³ | H | H | D¹³⁷ | H | H | L¹¹³ | N | CH | N | 4-biphenyl | 4-biphenyl |
| 3253. | H | H | D¹³³ | H | H | D¹³⁷ | H | H | L¹¹⁴ | N | N | N | Ph | Ph |
| 3254. | H | H | D¹³³ | H | H | D¹³⁷ | H | H | L¹¹⁴ | N | N | N | 4-biphenyl | 4-biphenyl |

-continued

| Compound number | R¹ | R² | R³ | R⁴ | R⁵ | R⁶ | R⁷ | R⁸ | L¹ | Z¹ | Z³ | Z⁵ | R⁹¹ | R⁹² |
|---|---|---|---|---|---|---|---|---|---|---|---|---|---|---|
| 3255. | H | H | D¹³³ | H | H | D¹³⁷ | H | H | L¹¹⁴ | N | CH | N | Ph | Ph |
| 3256. | H | H | D¹³³ | H | H | D¹³⁷ | H | H | L¹¹⁴ | N | CH | N | 4-biphenyl | 4-biphenyl |
| 3257. | H | H | D¹³³ | H | H | D¹³⁷ | H | H | L¹¹⁵ | N | N | N | Ph | Ph |
| 3258. | H | H | D¹³³ | H | H | D¹³⁷ | H | H | L¹¹⁵ | N | N | N | 4-biphenyl | 4-biphenyl |
| 3259. | H | H | D¹³³ | H | H | D¹³⁷ | H | H | L¹¹⁵ | N | CH | N | Ph | Ph |
| 3260. | H | H | D¹³³ | H | H | D¹³⁷ | H | H | L¹¹⁵ | N | CH | N | 4-biphenyl | 4-biphenyl |
| 3261. | H | H | D¹³³ | H | H | D¹³⁷ | H | H | L¹¹⁶ | N | N | N | Ph | Ph |
| 3262. | H | H | D¹³³ | H | H | D¹³⁷ | H | H | L¹¹⁶ | N | N | N | 4-biphenyl | 4-biphenyl |
| 3263. | H | H | D¹³³ | H | H | D¹³⁷ | H | H | L¹¹⁶ | N | CH | N | Ph | Ph |
| 3264. | H | H | D¹³³ | H | H | D¹³⁷ | H | H | L¹¹⁶ | N | CH | N | 4-biphenyl | 4-biphenyl |
| 3265. | H | H | D¹³⁴ | H | H | D¹³⁷ | H | H | L¹⁰¹ | N | N | N | Ph | Ph |
| 3266. | H | H | D¹³⁴ | H | H | D¹³⁷ | H | H | L¹⁰¹ | N | N | N | 4-biphenyl | 4-biphenyl |
| 3267. | H | H | D¹³⁴ | H | H | D¹³⁷ | H | H | L¹⁰¹ | N | CH | N | Ph | Ph |
| 3268. | H | H | D¹³⁴ | H | H | D¹³⁷ | H | H | L¹⁰¹ | N | CH | N | 4-biphenyl | 4-biphenyl |
| 3269. | H | H | D¹³⁴ | H | H | D¹³⁷ | H | H | L¹⁰² | N | N | N | Ph | Ph |
| 3270. | H | H | D¹³⁴ | H | H | D¹³⁷ | H | H | L¹⁰² | N | N | N | 4-biphenyl | 4-biphenyl |
| 3271. | H | H | D¹³⁴ | H | H | D¹³⁷ | H | H | L¹⁰² | N | CH | N | Ph | Ph |
| 3272. | H | H | D¹³⁴ | H | H | D¹³⁷ | H | H | L¹⁰² | N | CH | N | 4-biphenyl | 4-biphenyl |
| 3273. | H | H | D¹³⁴ | H | H | D¹³⁷ | H | H | L¹⁰³ | N | N | N | Ph | Ph |
| 3274. | H | H | D¹³⁴ | H | H | D¹³⁷ | H | H | L¹⁰³ | N | N | N | 4-biphenyl | 4-biphenyl |
| 3275. | H | H | D¹³⁴ | H | H | D¹³⁷ | H | H | L¹⁰³ | N | CH | N | Ph | Ph |
| 3276. | H | H | D¹³⁴ | H | H | D¹³⁷ | H | H | L¹⁰³ | N | CH | N | 4-biphenyl | 4-biphenyl |
| 3277. | H | H | D¹³⁴ | H | H | D¹³⁷ | H | H | L¹⁰⁴ | N | N | N | Ph | Ph |
| 3278. | H | H | D¹³⁴ | H | H | D¹³⁷ | H | H | L¹⁰⁴ | N | N | N | 4-biphenyl | 4-biphenyl |
| 3279. | H | H | D¹³⁴ | H | H | D¹³⁷ | H | H | L¹⁰⁴ | N | CH | N | Ph | Ph |
| 3280. | H | H | D¹³⁴ | H | H | D¹³⁷ | H | H | L¹⁰⁴ | N | CH | N | 4-biphenyl | 4-biphenyl |
| 3281. | H | H | D¹³⁴ | H | H | D¹³⁷ | H | H | L¹⁰⁵ | N | N | N | Ph | Ph |
| 3282. | H | H | D¹³⁴ | H | H | D¹³⁷ | H | H | L¹⁰⁵ | N | N | N | 4-biphenyl | 4-biphenyl |
| 3283. | H | H | D¹³⁴ | H | H | D¹³⁷ | H | H | L¹⁰⁵ | N | CH | N | Ph | Ph |
| 3284. | H | H | D¹³⁴ | H | H | D¹³⁷ | H | H | L¹⁰⁵ | N | CH | N | 4-biphenyl | 4-biphenyl |
| 3285. | H | H | D¹³⁴ | H | H | D¹³⁷ | H | H | L¹⁰⁶ | N | N | N | Ph | Ph |
| 3286. | H | H | D¹³⁴ | H | H | D¹³⁷ | H | H | L¹⁰⁶ | N | N | N | 4-biphenyl | 4-biphenyl |
| 3287. | H | H | D¹³⁴ | H | H | D¹³⁷ | H | H | L¹⁰⁶ | N | CH | N | Ph | Ph |
| 3288. | H | H | D¹³⁴ | H | H | D¹³⁷ | H | H | L¹⁰⁶ | N | CH | N | 4-biphenyl | 4-biphenyl |
| 3289. | H | H | D¹³⁴ | H | H | D¹³⁷ | H | H | L¹⁰⁷ | N | N | N | Ph | Ph |
| 3290. | H | H | D¹³⁴ | H | H | D¹³⁷ | H | H | L¹⁰⁷ | N | N | N | 4-biphenyl | 4-biphenyl |
| 3291. | H | H | D¹³⁴ | H | H | D¹³⁷ | H | H | L¹⁰⁷ | N | CH | N | Ph | Ph |
| 3292. | H | H | D¹³⁴ | H | H | D¹³⁷ | H | H | L¹⁰⁷ | N | CH | N | 4-biphenyl | 4-biphenyl |
| 3293. | H | H | D¹³⁴ | H | H | D¹³⁷ | H | H | L¹⁰⁸ | N | N | N | Ph | Ph |
| 3294. | H | H | D¹³⁴ | H | H | D¹³⁷ | H | H | L¹⁰⁸ | N | N | N | 4-biphenyl | 4-biphenyl |
| 3295. | H | H | D¹³⁴ | H | H | D¹³⁷ | H | H | L¹⁰⁸ | N | CH | N | Ph | Ph |
| 3296. | H | H | D¹³⁴ | H | H | D¹³⁷ | H | H | L¹⁰⁸ | N | CH | N | 4-biphenyl | 4-biphenyl |
| 3297. | H | H | D¹³⁴ | H | H | D¹³⁷ | H | H | L¹⁰⁹ | N | N | N | Ph | Ph |
| 3298. | H | H | D¹³⁴ | H | H | D¹³⁷ | H | H | L¹⁰⁹ | N | N | N | 4-biphenyl | 4-biphenyl |
| 3299. | H | H | D¹³⁴ | H | H | D¹³⁷ | H | H | L¹⁰⁹ | N | CH | N | Ph | Ph |
| 3300. | H | H | D¹³⁴ | H | H | D¹³⁷ | H | H | L¹⁰⁹ | N | CH | N | 4-biphenyl | 4-biphenyl |
| 3301. | H | H | D¹³⁴ | H | H | D¹³⁷ | H | H | L¹¹⁰ | N | N | N | Ph | Ph |
| 3302. | H | H | D¹³⁴ | H | H | D¹³⁷ | H | H | L¹¹⁰ | N | N | N | 4-biphenyl | 4-biphenyl |

-continued

| Compound number | $R^1$ | $R^2$ | $R^3$ | $R^4$ | $R^5$ | $R^6$ | $R^7$ | $R^8$ | $L^1$ | $Z^1$ | $Z^3$ | $Z^5$ | $R^{91}$ | $R^{92}$ |
|---|---|---|---|---|---|---|---|---|---|---|---|---|---|---|
| 3303. | H | H | $D^{134}$ | H | H | $D^{137}$ | H | H | $L^{110}$ | N | CH | N | Ph | Ph |
| 3304. | H | H | $D^{134}$ | H | H | $D^{137}$ | H | H | $L^{110}$ | N | CH | N | 4-biphenyl | 4-biphenyl |
| 3305. | H | H | $D^{134}$ | H | H | $D^{137}$ | H | H | $L^{111}$ | N | N | N | Ph | Ph |
| 3306. | H | H | $D^{134}$ | H | H | $D^{137}$ | H | H | $L^{111}$ | N | N | N | 4-biphenyl | 4-biphenyl |
| 3307. | H | H | $D^{134}$ | H | H | $D^{137}$ | H | H | $L^{111}$ | N | CH | N | Ph | Ph |
| 3308. | H | H | $D^{134}$ | H | H | $D^{137}$ | H | H | $L^{111}$ | N | CH | N | 4-biphenyl | 4-biphenyl |
| 3309. | H | H | $D^{134}$ | H | H | $D^{137}$ | H | H | $L^{112}$ | N | N | N | Ph | Ph |
| 3310. | H | H | $D^{134}$ | H | H | $D^{137}$ | H | H | $L^{112}$ | N | N | N | 4-biphenyl | 4-biphenyl |
| 3311. | H | H | $D^{134}$ | H | H | $D^{137}$ | H | H | $L^{112}$ | N | CH | N | Ph | Ph |
| 3312. | H | H | $D^{134}$ | H | H | $D^{137}$ | H | H | $L^{112}$ | N | CH | N | 4-biphenyl | 4-biphenyl |
| 3313. | H | H | $D^{134}$ | H | H | $D^{137}$ | H | H | $L^{113}$ | N | N | N | Ph | Ph |
| 3314. | H | H | $D^{134}$ | H | H | $D^{137}$ | H | H | $L^{113}$ | N | N | N | 4-biphenyl | 4-biphenyl |
| 3315. | H | H | $D^{134}$ | H | H | $D^{137}$ | H | H | $L^{113}$ | N | CH | N | Ph | Ph |
| 3316. | H | H | $D^{134}$ | H | H | $D^{137}$ | H | H | $L^{113}$ | N | CH | N | 4-biphenyl | 4-biphenyl |
| 3317. | H | H | $D^{134}$ | H | H | $D^{137}$ | H | H | $L^{114}$ | N | N | N | Ph | Ph |
| 3318. | H | H | $D^{134}$ | H | H | $D^{137}$ | H | H | $L^{114}$ | N | N | N | 4-biphenyl | 4-biphenyl |
| 3319. | H | H | $D^{134}$ | H | H | $D^{137}$ | H | H | $L^{114}$ | N | CH | N | Ph | Ph |
| 3320. | H | H | $D^{134}$ | H | H | $D^{137}$ | H | H | $L^{114}$ | N | CH | N | 4-biphenyl | 4-biphenyl |
| 3321. | H | H | $D^{134}$ | H | H | $D^{137}$ | H | H | $L^{115}$ | N | N | N | Ph | Ph |
| 3322. | H | H | $D^{134}$ | H | H | $D^{137}$ | H | H | $L^{115}$ | N | N | N | 4-biphenyl | 4-biphenyl |
| 3323. | H | H | $D^{134}$ | H | H | $D^{137}$ | H | H | $L^{115}$ | N | CH | N | Ph | Ph |
| 3324. | H | H | $D^{134}$ | H | H | $D^{137}$ | H | H | $L^{115}$ | N | CH | N | 4-biphenyl | 4-biphenyl |
| 3325. | H | H | $D^{134}$ | H | H | $D^{137}$ | H | H | $L^{116}$ | N | N | N | Ph | Ph |
| 3326. | H | H | $D^{134}$ | H | H | $D^{137}$ | H | H | $L^{116}$ | N | N | N | 4-biphenyl | 4-biphenyl |
| 3327. | H | H | $D^{134}$ | H | H | $D^{137}$ | H | H | $L^{116}$ | N | CH | N | Ph | Ph |
| 3328. | H | H | $D^{134}$ | H | H | $D^{137}$ | H | H | $L^{116}$ | N | CH | N | 4-biphenyl | 4-biphenyl |

In one embodiment, the first device emits a luminescent radiation at room temperature when a voltage is applied across the organic light emitting device, wherein the luminescent radiation comprises a delayed fluorescence process.

In one embodiment, the emissive layer further comprises a first phosphorescent emitting material.

In one embodiment, the emissive layer further comprises a second phosphorescent emitting material.

In one embodiment, the emissive layer further comprises a host material.

In one embodiment, the first device emits a white light at room temperature when a voltage is applied across the organic light emitting device.

In one embodiment, the first emitting compound emits a blue light with a peak wavelength of about 400 nm to about 500 nm.

In one embodiment, the emitting compound emits a yellow light with a peak wavelength of about 530 nm to about 580 nm.

In one embodiment, the first device comprises a second organic light emitting device, wherein the second organic light emitting device is stacked on the first organic light emitting device.

In one embodiment, the first device is a consumer product.

In one embodiment, the first device is an organic light-emitting device.

In one embodiment, the first device is a lighting panel.

Table 1 shows the PLQY of compounds with or without a phenylene spacer doped in poly(methyl methacrylate) (PMMA) films. The compounds of Formula I were doped at 5% in all the films. Compound A has a photoluminescent quantum yield (PLQY) of 42% compared to 100% for Compound 2757. Compound B has a PLQY of 46% compared to 88% for Compound 2117. Without being bound by theory, it is believed that the unexpectedly PLQY of the compounds of Formula I was achieved by the use of the spacer $L_1$.

TABLE 1

PLQY of inventive compounds and comparative compounds in 5% doped PMMA films

| Compound | PLQY in 5% doped PMMA |
|---|---|
| Comparative Compound A | 42% |
| Comparative Compound B | 46% |
| Compound 2757 | 100% |
| Compound 2117 | 88% |

The structures of the compounds used in the device examples are as follows:

Compound A
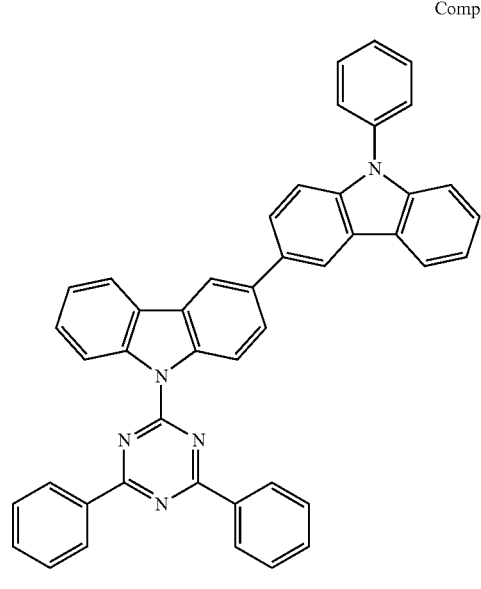
Compound B
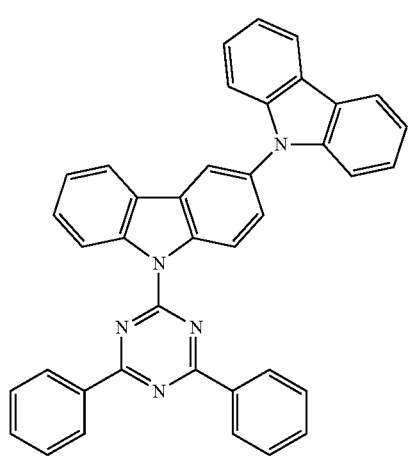
Compound 2757
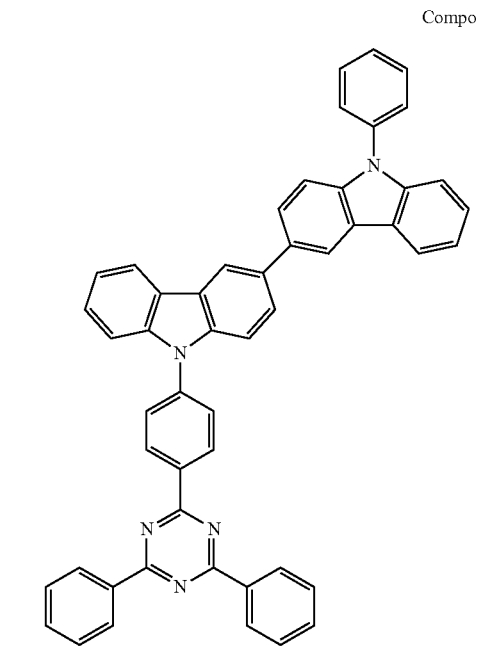
Compound 2117
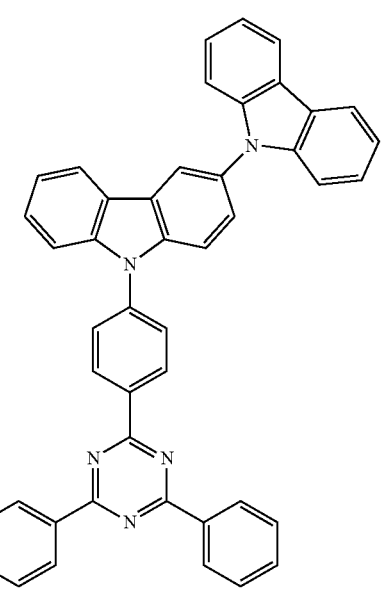
TAPC
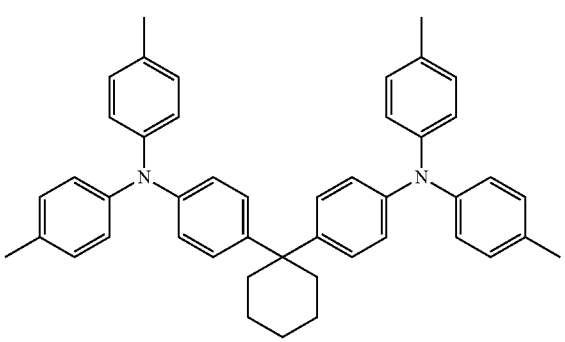
TmPyPB
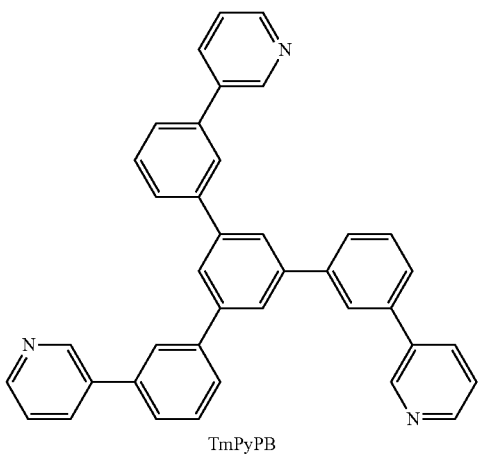

Host 1

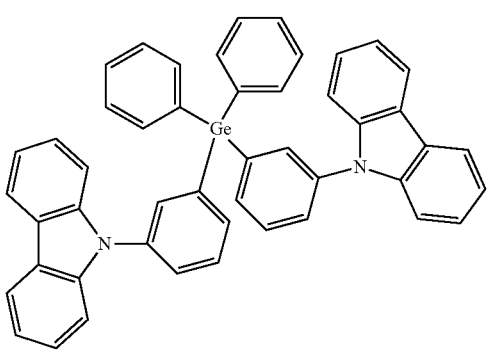

Device Examples

All example devices were fabricated by high vacuum ($<10^{-7}$ Torr) thermal evaporation. The anode electrode is 800 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The device described herein have the following architectures:

Device 1=ITO/TAPC (200 Å)/Host1:Compound 2757 (5%, 400 Å)/TmPyPB (400 Å)/LiF/Al.

TABLE 2

Performance of electroluminescent devices using Compound 2757 as emitting material

| | | | | | | Maximum EQE | | @1000 nits | | |
|---|---|---|---|---|---|---|---|---|---|---|
| Device # | x | y | $\lambda_{max}$ (nm) | L nits | V (V) | $LE_{max}$ (cd/A) | $EQE_{max}$ (%) | Voltage (V) | LE (cd/A) | EQE (%) |
| Device 1 | 0.155 | 0.163 | 460 | 2 | 4.2 | 25.8 | 20 | 8.8 | 10.5 | 8.1 |

Device 1 was fabricated with TAPC as HIL/HTL, a 5% Compound 2757 doped in Host 1 as EML, and TmPyPB as ETL. The results are shown in Table 2. Deep blue emission with a $\lambda_{max}$ of 460 nm and CIE of (0.155, 0.163) was observed from the device. The maximum external quantum efficiency (EQE) was 20% that was observed at the brightness of 2 nits. The maximum luminous efficiency (LE) was 25.8 cd/A at the same brightness. At 100 nits, the EQE and LE were 13.4% and 17.2 cd/A, respectively. At 1000 nits, the EQE and LE were 8.1% and 10.5 cd/A, respectively.

The photoluminescence quantum yield (PLQY) of the 5% Compound 2757 doped in Host 1 was measured to be around 90% (PL quantum efficiency measurements were carried out on a Hamamatsu C9920 system equipped with a xenon lamp, integrating sphere and a model C10027 photonic multi-channel analyzer). For a standard fluorescent OLED with only prompt singlet emission, the theoretical percentage of singlet excitons is 25%. The outcoupling efficiency of a bottom-emitting lambertian OLED is considered to be around 20-25%. Therefore, for a fluorescent emitter having a PLQY of 90% without delayed fluorescence, the highest EQE should not exceed 6% based on the statistical value of 25% for electrically generated singlet excitons. The devices with compounds of Formula I, such as Compound 2757, as the emitter showed EQE far exceeding the theoretical limit even with a non-optimal device structure.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

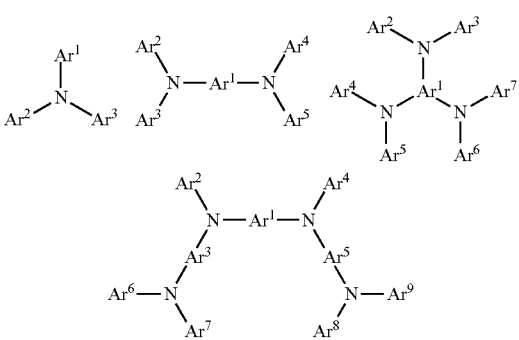

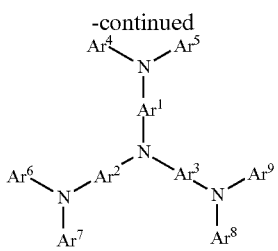

Each of Ar¹ to Ar⁹ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, Ar¹ to Ar⁹ is independently selected from the group consisting of:

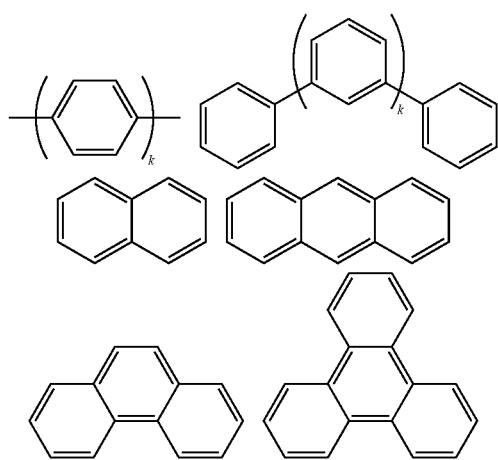

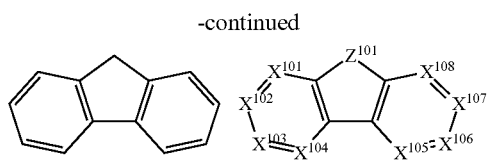

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

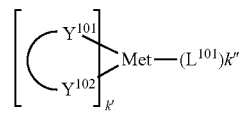

Met is a metal; $(Y^{101}\text{-}Y^{102})$ is a bidentate ligand, $Y^{101}$ and $Y^{102}$ are independently selected from C, N, O, P, and S; $L^{101}$ is another ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative.

In another aspect, $(Y^{101}\text{-}Y^{102})$ is a carbene ligand.

In another aspect, Met is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

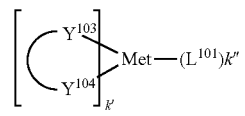

Met is a metal; $(Y^{103}\text{-}Y^{104})$ is a bidentate ligand, $Y^{103}$ and $Y^{104}$ are independently selected from C, N, O, P, and S; $L^{101}$ is another ligand; k' is an integer value from 1 to the maximum number of ligands that may be attached to the metal; and k'+k" is the maximum number of ligands that may be attached to the metal.

In one aspect, the metal complexes are:

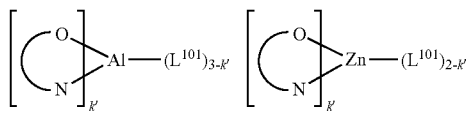

(O—N) is a bidentate ligand, having metal coordinated to atoms O and N.

In another aspect, Met is selected from Ir and Pt.

In a further aspect, $(Y^{103}\text{-}Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

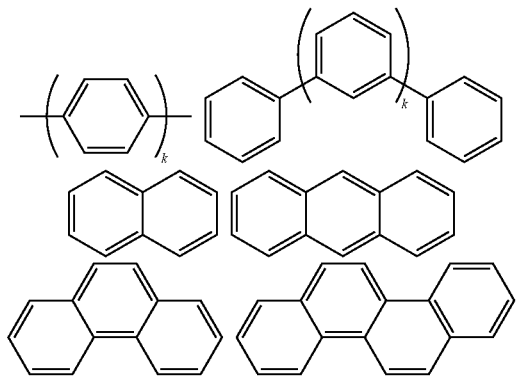

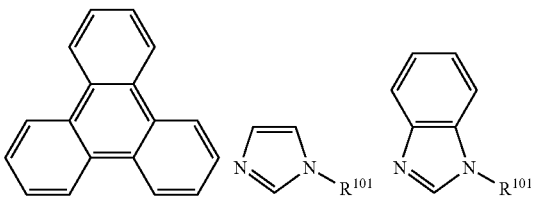

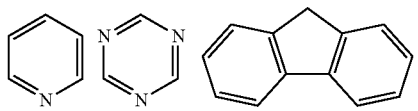

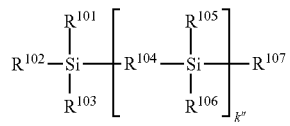

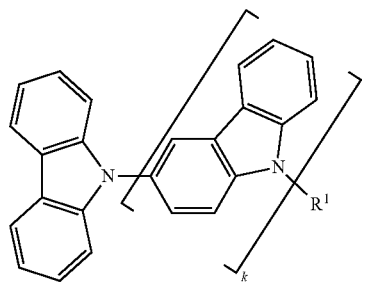

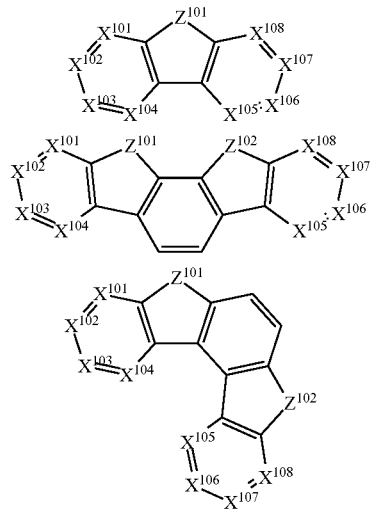

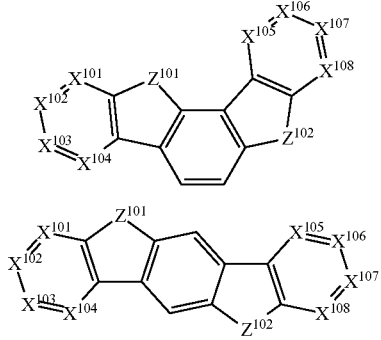

-continued

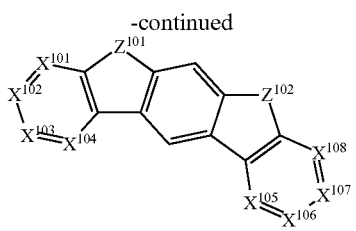

R¹⁰¹ to R¹⁰⁷ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

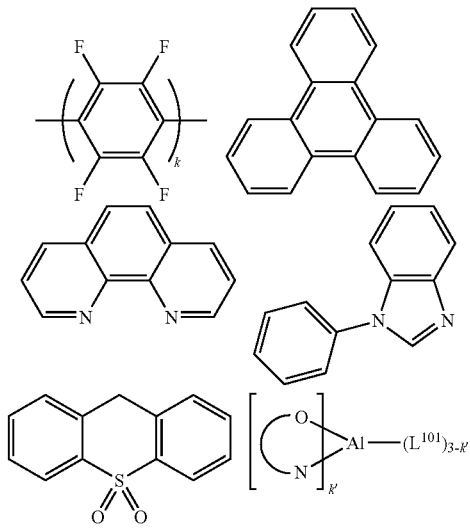

k is an integer from 1 to 20; $L^{101}$ is another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

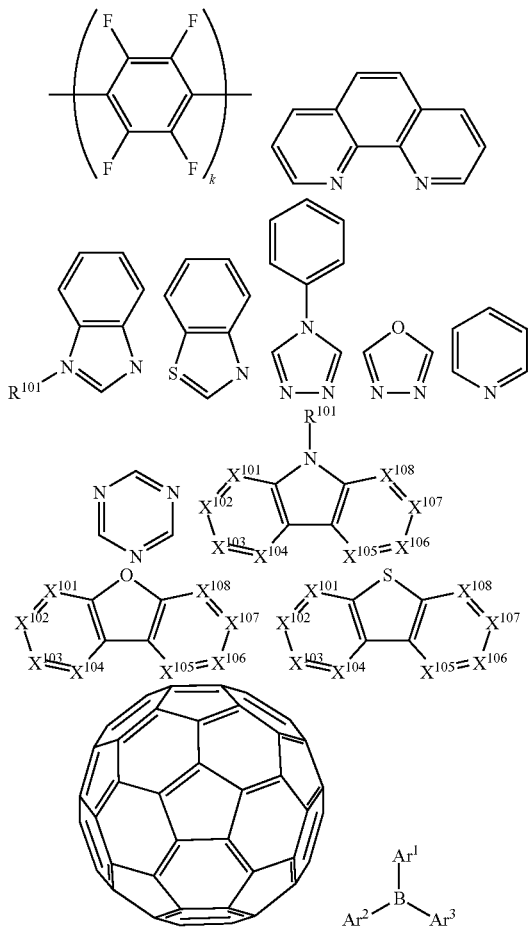

$R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 1 to 20.

$X^{101}$ to $X^{108}$ is selected from C (including CH) or N.

In another aspect, the metal complexes used in ETL contains, but not limit to the following general formula:

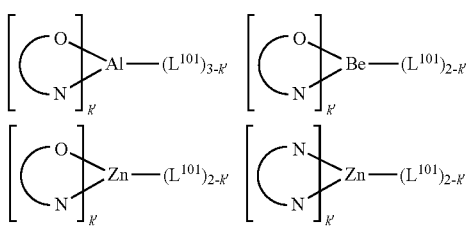

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of compounds for each class, and references that disclose the materials.

TABLE 3

| MATERIAL | EXAMPLES OF MATERIAL | PUBLICATIONS |
| --- | --- | --- |
| Hole injection materials | | |
| Phthalocyanine and porphryin compounds | 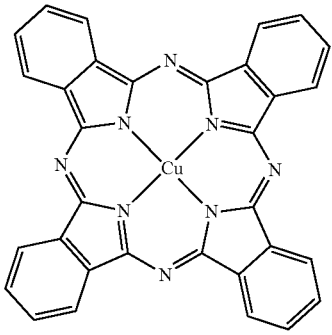 | Appl. Phys. Lett. 69, 2160 (1996) |
| Starburst triarylamines | 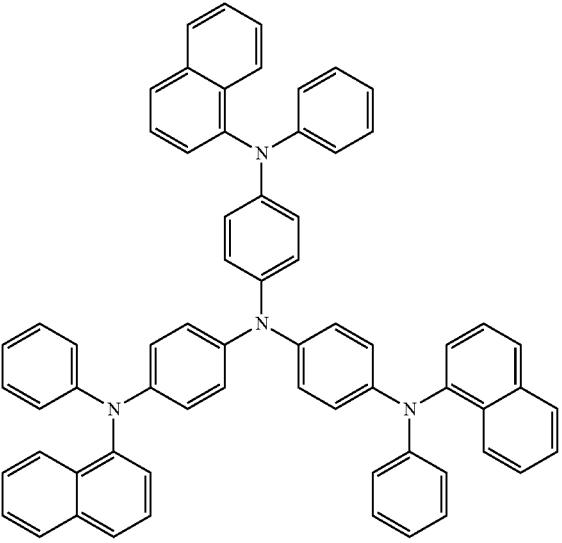 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-\!\!\!-\!\!(CH_xF_y)_n\!\!-\!\!\!-$ | Appl. Phys. Lett. 78, 673 (2001) |
| Conducting polymers (e.g., PEDOT:PSS, polyaniline, polypthiophene) | 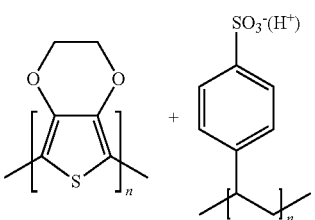 | Synth. Met. 87, 171 (1997) WO2007002683 |

TABLE 3-continued

| MATERIAL | EXAMPLES OF MATERIAL | PUBLICATIONS |
| --- | --- | --- |
| Phosphonic acid and sliane SAMs | | US20030162053 |
| Triarylamine or polythiophene polymers with conductivity dopants | and | EP1725079A1 |
| Organic compounds with conductive inorganic compounds, such as molybdenum and tungsten oxides | + MoO$_x$ | US20050123751<br>SID Symposium Digest, 37, 923 (2006)<br>WO2009018009 |

TABLE 3-continued

| MATERIAL | EXAMPLES OF MATERIAL | PUBLICATIONS |
| --- | --- | --- |
| n-type semiconducting organic complexes | | US20020158242 |
| Metal organometallic complexes | | US20060240279 |
| Cross-linkable compounds | | US20080220265 |
| Polythiophene based polymers and copolymers | | WO 2011075644<br>EP2350216 |

TABLE 3-continued
| MATERIAL | EXAMPLES OF MATERIAL | PUBLICATIONS |
|---|---|---|
| Hole transporting materials | | |
| Triarylamines (e.g., TPD, α-NPD) | 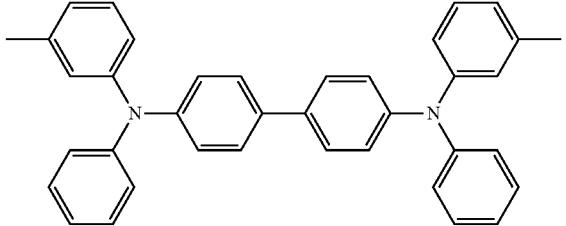 | Appl. Phys. Lett. 51, 913 (1987) |
| | 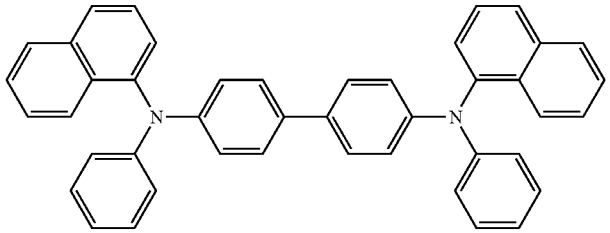 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 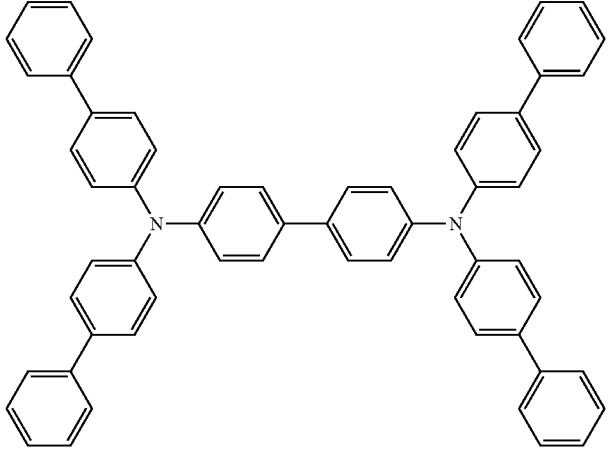 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 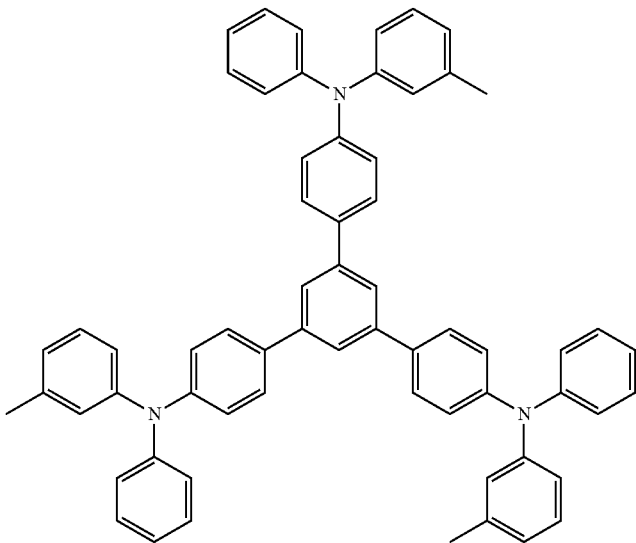 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 3-continued
| MATERIAL | EXAMPLES OF MATERIAL | PUBLICATIONS |
|---|---|---|
| | 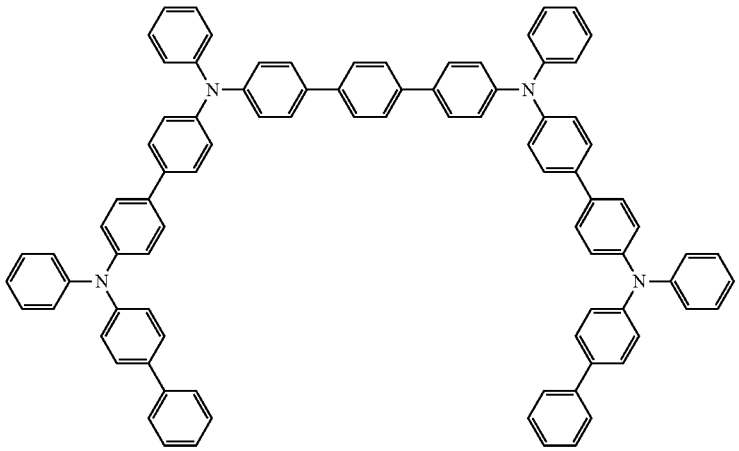 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| | 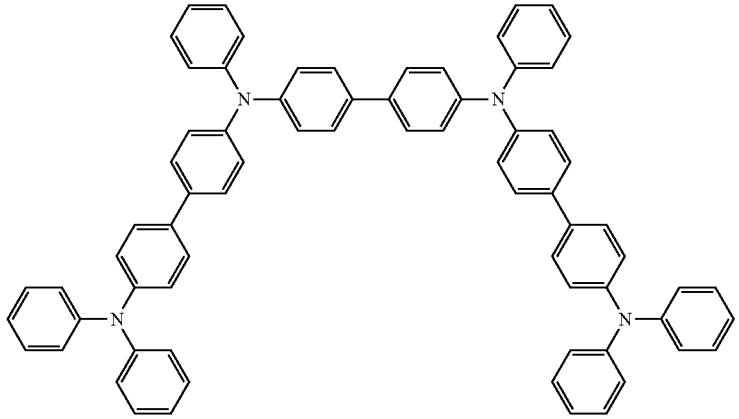 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 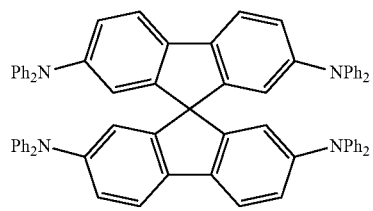 | Synth. Met. 91, 209 (1997) |
| Arylamine carbazole compounds | 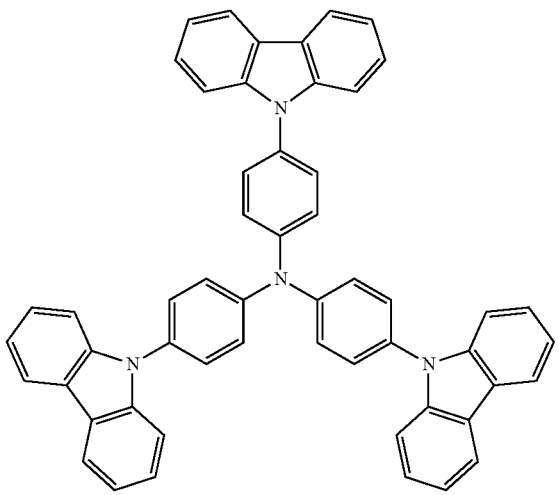 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |

TABLE 3-continued

| MATERIAL | EXAMPLES OF MATERIAL | PUBLICATIONS |
|---|---|---|
| Triarylamine with (di)benzothiophene/ (di)benzofuran | | US20070278938, US20080106190 US20110163302 |
| Indolocarbazoles | | Synth. Met. 111, 421 (2000) |
| Isoindole compounds | | Chem. Mater. 15, 3148 (2003) |
| Metal carbene complexes | | US20080018221 |

TABLE 3-continued

| MATERIAL | EXAMPLES OF MATERIAL | PUBLICATIONS |
| --- | --- | --- |
| | Phosphorescent OLED host materials Red hosts | |
| Arylcarbazoles | | Appl. Phys. Lett. 78, 1622 (2001) |
| Metal 8-hydroxyquinolates (e.g., Alq₃, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 3-continued

| MATERIAL | EXAMPLES OF MATERIAL | PUBLICATIONS |
| --- | --- | --- |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
| --- | --- | --- |
| Arylcarbazoles | | Appl. Phys. Lett. 78, 1622 (2001) |
| | | US20030175553 |
| | | WO2001039234 |

TABLE 3-continued
| MATERIAL | EXAMPLES OF MATERIAL | PUBLICATIONS |
|---|---|---|
| Aryltriphenylene compounds | 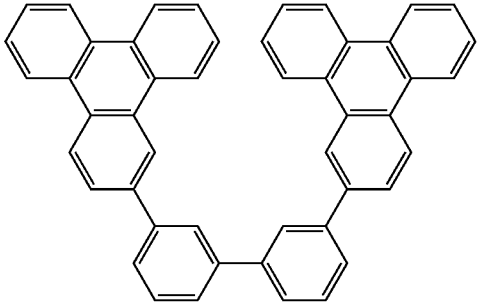 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 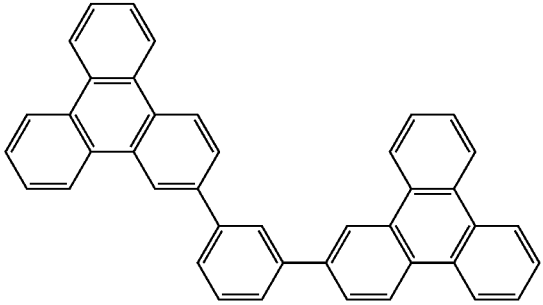 [SMILES: c1cc(-c2ccc3c4ccccc4c4ccccc4c3c2)cc(-c2ccc3c4ccccc4c4ccccc4c3c2)c1] | US20060280965 |
| | 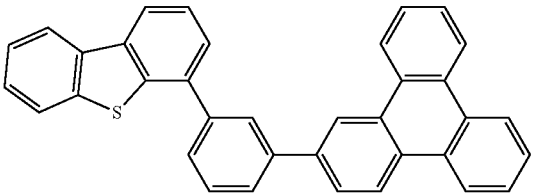 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 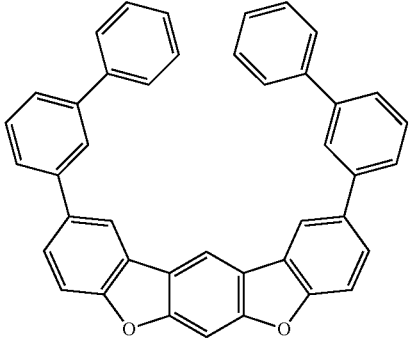 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 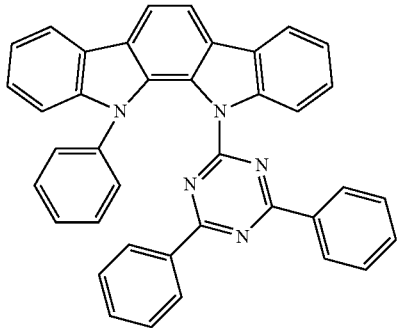 [SMILES: c1ccc(-c2nc(-c3ccccc3)nc(-n3c4ccccc4c4ccc5c6ccccc6n(-c6ccccc6)c5c43)n2)cc1] | WO2008056746 |

TABLE 3-continued
| MATERIAL | EXAMPLES OF MATERIAL | PUBLICATIONS |
|---|---|---|
| | 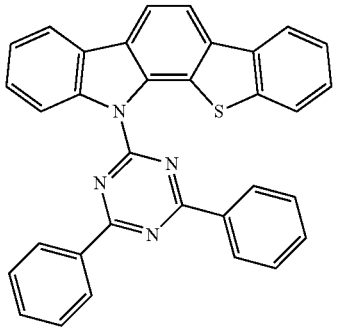 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 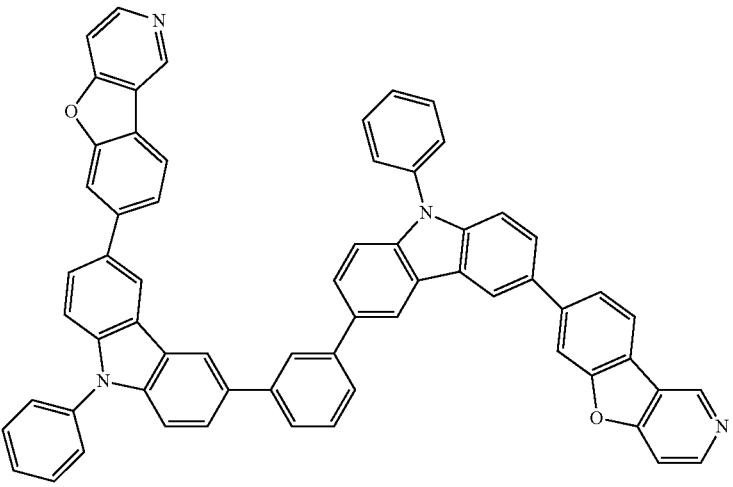 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 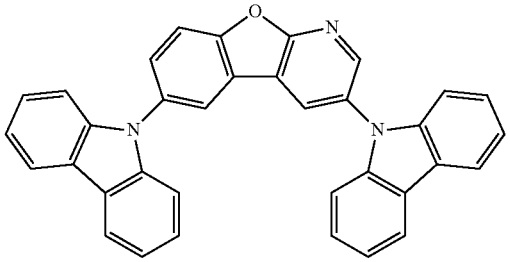 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 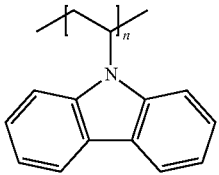 | Appl. Phys. Lett. 77, 2280 (2000) |
| Spirofluorene compounds | 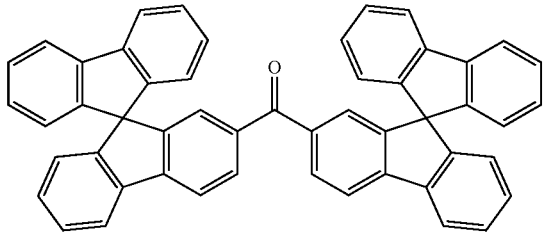 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 3-continued

| MATERIAL | EXAMPLES OF MATERIAL | PUBLICATIONS |
| --- | --- | --- |
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE 3-continued
| MATERIAL | EXAMPLES OF MATERIAL | PUBLICATIONS |
|---|---|---|
| Indolocabazoles | 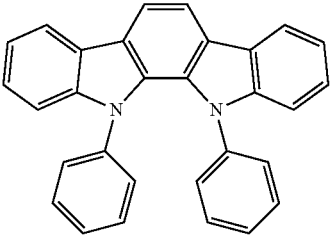 [SMILES: c1ccc(-n2c3ccccc3c3ccc4c5ccccc5n(-c5ccccc5)c4c32)cc1] | WO2007063796 |
| | 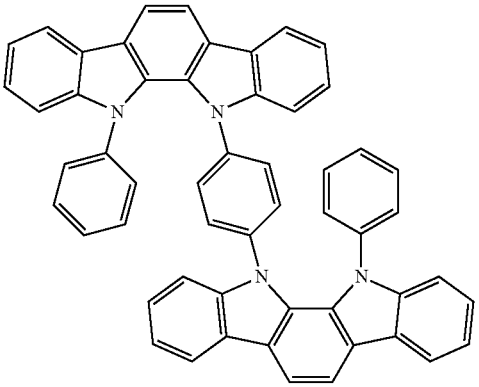 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 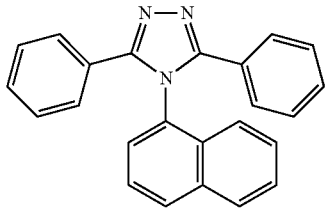 [SMILES: c1ccc(-c2nnc(-c3ccccc3)n2-c2cccc3ccccc23)cc1] | J. Appl. Phys. 90, 5048 (2001) |
| | 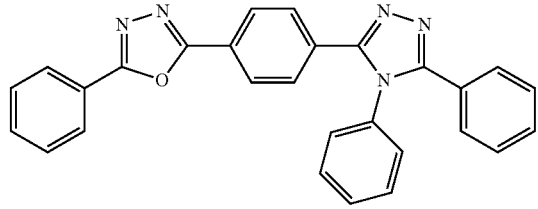 [SMILES: c1ccc(-c2nnc(-c3ccc(-c4nnc(-c5ccccc5)n4-c4ccccc4)cc3)o2)cc1] | WO2004107822 |
| Tetraphenylene complexes | 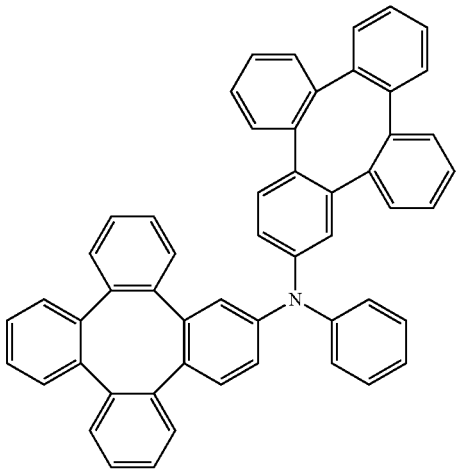 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |

TABLE 3-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |

Blue hosts

| | | |
| --- | --- | --- |
| Arylcarbazoles | | Appl. Phys. Lett, 82, 2422 (2003) |
| | | US20070190359 |
| Dibenzothiophene/Dibenzofuran-carbazole compounds | | WO2006114966, US20090167162 |
| | | US20090167162 |

| MATERIAL | EXAMPLES OF MATERIAL | PUBLICATIONS |
|---|---|---|
| | 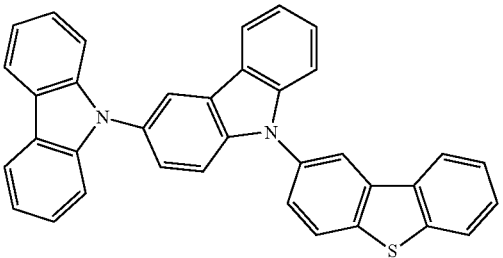 [SMILES: c1ccc2c(c1)sc1ccc(-n3c4ccccc4c4cc(-n5c6ccccc6c6ccccc65)ccc43)cc12] | WO2009086028 |
| | 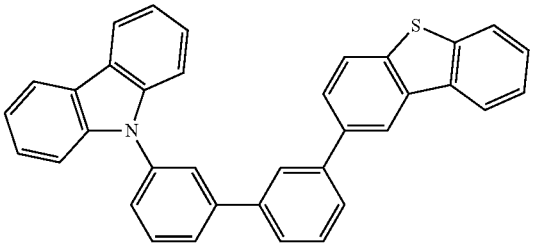 [SMILES: c1cc(-c2cccc(-n3c4ccccc4c4ccccc43)c2)cc(-c2ccc3sc4ccccc4c3c2)c1] | US20090030202, US20090017330 |
| | 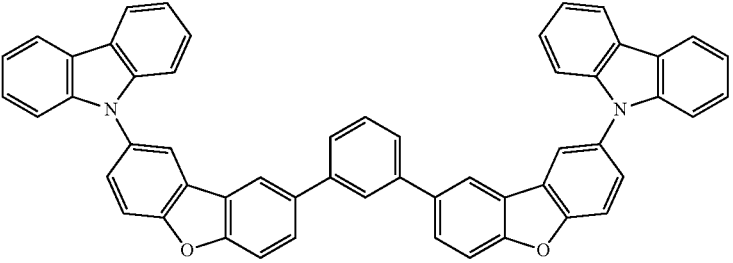 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 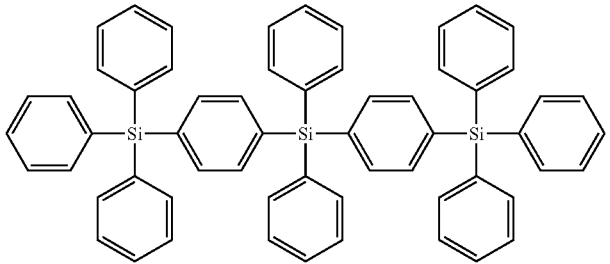 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 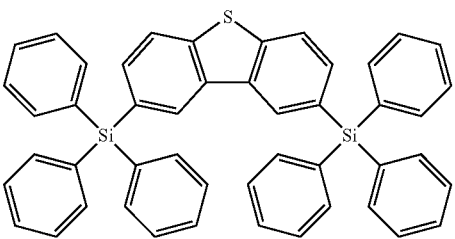 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 3-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

TABLE 3-continued

| MATERIAL | EXAMPLES OF MATERIAL | PUBLICATIONS |
| --- | --- | --- |
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |
| | | US20060202194 |

TABLE 3-continued

| MATERIAL | EXAMPLES OF MATERIAL | PUBLICATIONS |
|---|---|---|
| | | US20060202194 |
| | | US20070087321 |
| | | US20080261076<br>US20100090591 |
| | | US20070087321 |
| | | Adv. Mater. 19, 739 (2007) |

TABLE 3-continued

| MATERIAL | EXAMPLES OF MATERIAL | PUBLICATIONS |
|---|---|---|
| | | WO2009100991 |
| | | WO2008101842 |
| | | U.S. Pat. No. 7,232,618 |
| Platinum(II) organometallic complexes | | WO2003040257 |
| | | US20070103060 |

TABLE 3-continued

| MATERIAL | EXAMPLES OF MATERIAL | PUBLICATIONS |
| --- | --- | --- |
| Osminum(III) complexes | | Chem. Mater. 17, 3532 (2005) |
| Ruthenium(II) complexes | | Adv. Mater. 17, 1059 (2005) |
| Rhenium (I), (II), and (III) complexes | | US20050244673 |

Green dopants

| | | |
| --- | --- | --- |
| Iridium(III) organometallic complexes | and its derivatives | Inorg. Chem. 40, 1704 (2001) |
| | | US20020034656 |

TABLE 3-continued

| MATERIAL | EXAMPLES OF MATERIAL | PUBLICATIONS |
|---|---|---|
| | | U.S. Pat. No. 7,332,232 |
| | | US20090108737 |
| | | WO2010028151 |

TABLE 3-continued
| MATERIAL | EXAMPLES OF MATERIAL | PUBLICATIONS |
|---|---|---|
| | 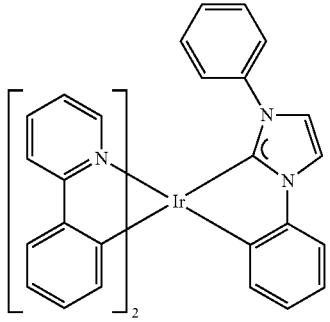 | EP1841834B |
| | 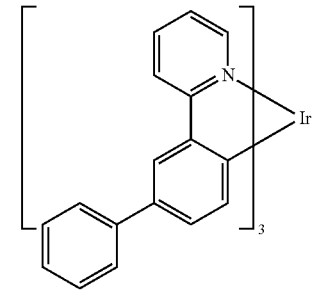 | US20060127696 |
| | 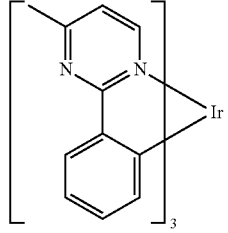 | US20090039776 |
| | 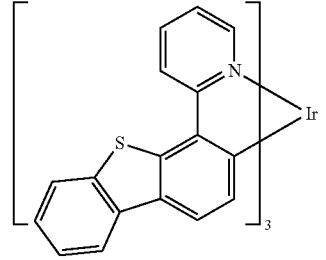 | U.S. Pat. No. 6,921,915 |
| | 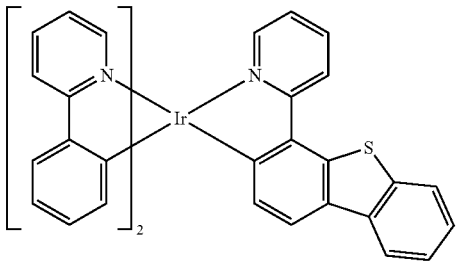 | US20100244004 |

TABLE 3-continued
| MATERIAL | EXAMPLES OF MATERIAL | PUBLICATIONS |
|---|---|---|
| | 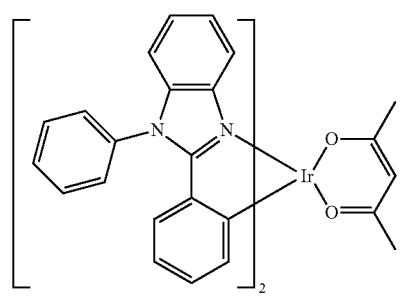 | U.S. Pat. No. 6,687,266 |
| | 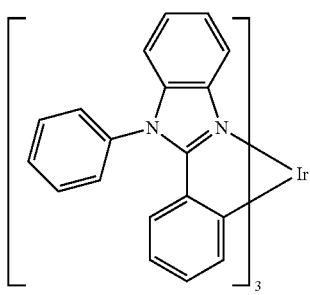 | Chem. Mater. 16, 2480 (2004) |
| | 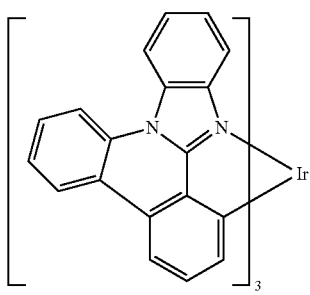 | US20070190359 |
| | 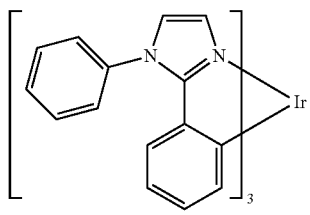 | US 20060008670 JP2007123392 |
| | 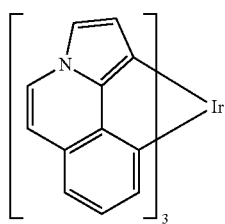 | WO2010086089, WO2011044988 |
| | 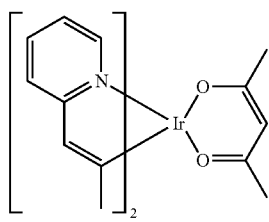 | Adv. Mater. 16, 2003 (2004) |

TABLE 3-continued
| MATERIAL | EXAMPLES OF MATERIAL | PUBLICATIONS |
|---|---|---|
| | 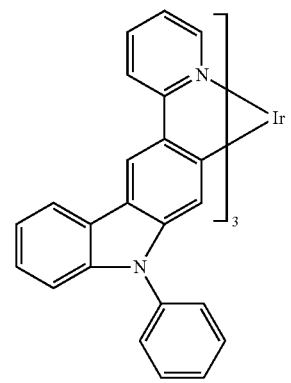 | Angew. Chem. Int. Ed. 2006, 45, 7800 |
| | 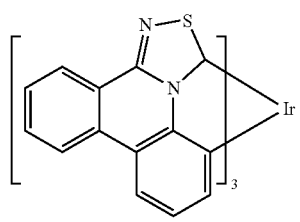 | WO2009050290 |
| | 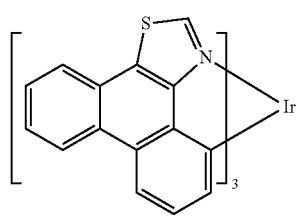 | US20090165846 |
| | 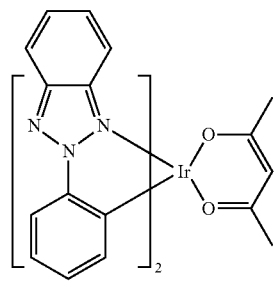 | US20080015355 |
| | 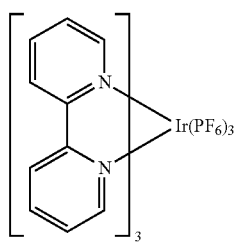 | US20010015432 |
| | 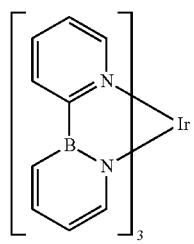 | US20100295032 |

TABLE 3-continued

| MATERIAL | EXAMPLES OF MATERIAL | PUBLICATIONS |
| --- | --- | --- |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

| MATERIAL | EXAMPLES OF MATERIAL | PUBLICATIONS |
|---|---|---|
| | [Pt complex with pyridyl-pyrazole ligands and isopropylidene bridge, N-Ph substituents] | US20060263635 |
| | [Pt complex with diphenylamine-bridged bipyridine ligand] | US20060182992<br>US20070103060 |
| Cu complexes | [Cu complex with bis(diphenylphosphino)diphenyl ether ligand and phenyl-triazole-pyridine ligand] | WO2009000673 |
| | [Dinuclear Cu complex with (iBu)$_2$P and N-aryl bridging ligands] | US20070111026 |

| MATERIAL | EXAMPLES OF MATERIAL | PUBLICATIONS |
|---|---|---|
| Gold complexes | 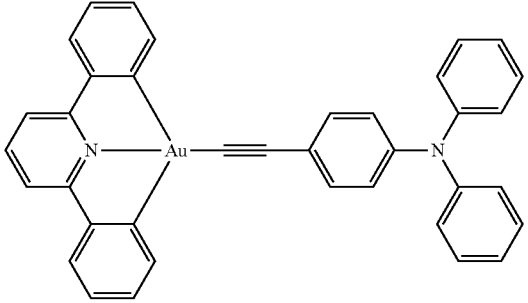 | Chem. Commun. 2906 (2005) |
| Rhenium(III) complexes | 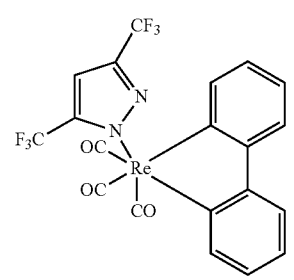 | Inorg. Chem. 42, 1248 (2003) |
| Osmium(II) complexes | 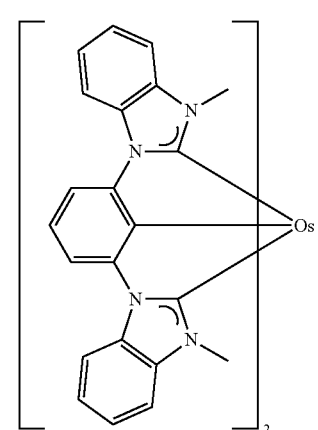 | U.S. Pat. No. 7,279,704 |
| Deuterated organometallic complexes | 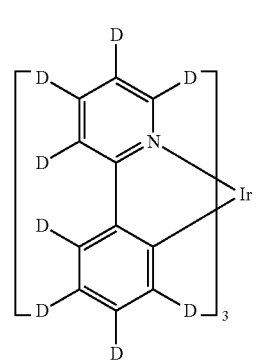 | US20030138657 |

| MATERIAL | EXAMPLES OF MATERIAL | PUBLICATIONS |
|---|---|---|
| Organometallic complexes with two or more metal centers | 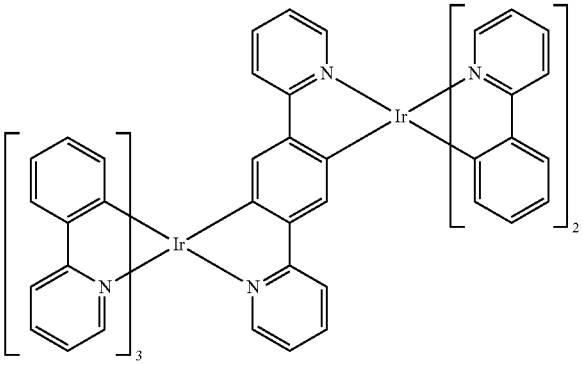 | US20030152802 |
| | 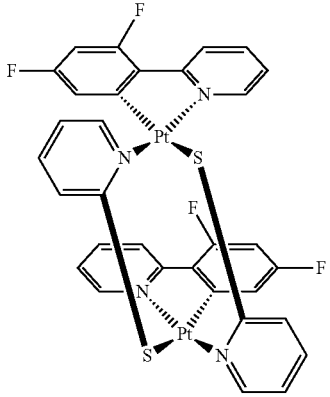 | U.S. Pat. No. 7,090,928 |
| Blue dopants | | |
| Iridium(III) organometallic complexes | 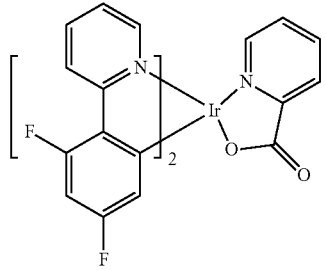 | WO2002002714 |
| | 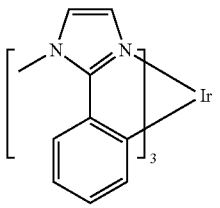 | WO2006009024 |
| | 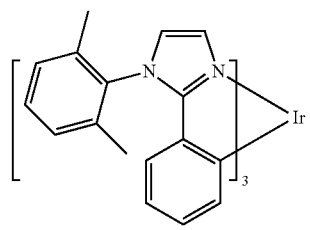 | US20060251923<br>US20110057559<br>US20110204333 |

TABLE 3-continued

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | WO2011051404 |
| | | U.S. Pat. No. 7,445,855 |
| | | US20070190359, US20080297033 US20100148663 |

TABLE 3-continued
| MATERIAL | EXAMPLES OF MATERIAL | PUBLICATIONS |
|---|---|---|
| | 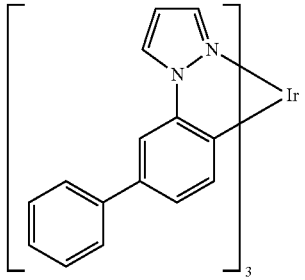 | U.S. Pat. No. 7,338,722 |
| | 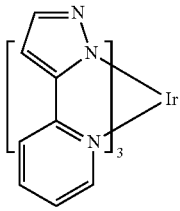 | US20020134984 |
| | 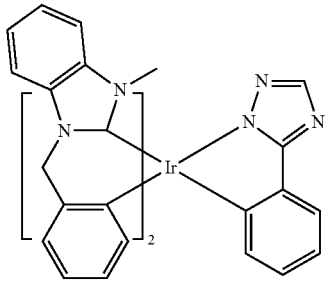 | Angew. Chem. Int. Ed. 47, 1 (2008) |
| | 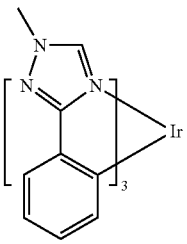 | Chem. Mater. 18, 5119 (2006) |
| | 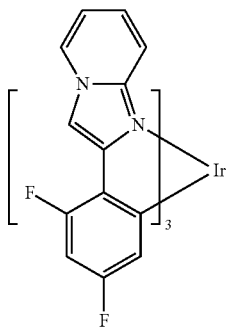 | Inorg. Chem. 46, 4308 (2007) |

| MATERIAL | EXAMPLES OF MATERIAL | PUBLICATIONS |
| --- | --- | --- |
| | | WO2005123873 |
| | | WO2005123873 |
| | | WO2007004380 |
| | | WO2006082742 |
| Osmium(II) complexes | | U.S. Pat. No. 7,279,704 |

TABLE 3-continued

| MATERIAL | EXAMPLES OF MATERIAL | PUBLICATIONS |
|---|---|---|
| | 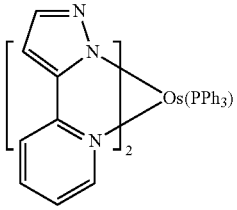 | Organometallics 23, 3745 (2004) |
| Gold complexes | 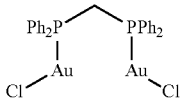 | Appl. Phys. Lett. 74, 1361 (1999) |
| Platinum(II) complexes | 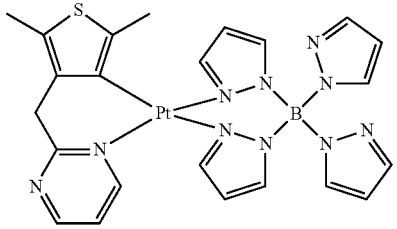 | WO2006098120, WO2006103874 |
| Pt tetradentate complexes with at least one metal-carbene bond | 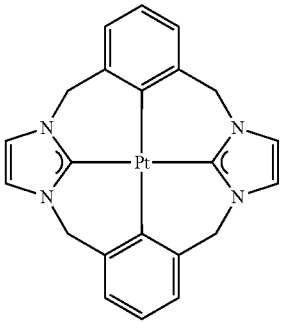 | U.S. Pat. No. 7,655,323 |
| Exciton/hole blocking layer materials | | |
| Bathocuprine compounds (e.g., BCP, BPhen) | 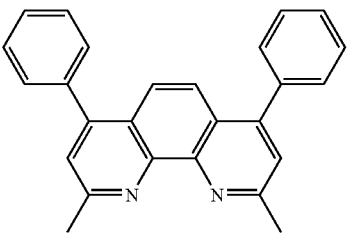 [SMILES: Cc1cc(-c2ccccc2)c2ccc3c(-c4ccccc4)cc(C)nc3c2n1] | Appl. Phys. Lett. 75, 4 (1999) |
| | 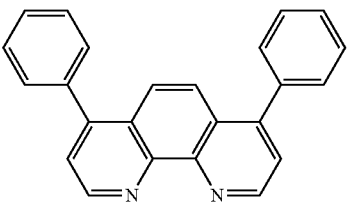 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 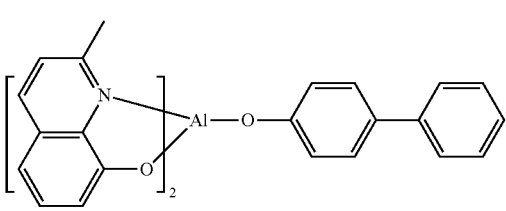 | Appl. Phys. Lett. 81, 162 (2002) |

TABLE 3-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 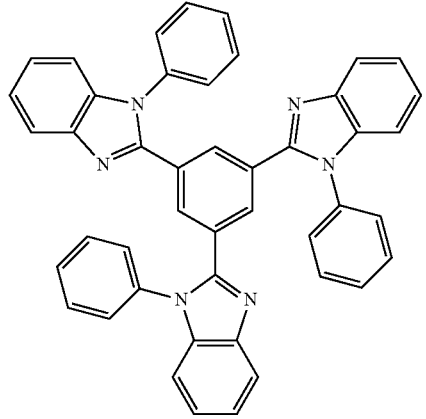 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 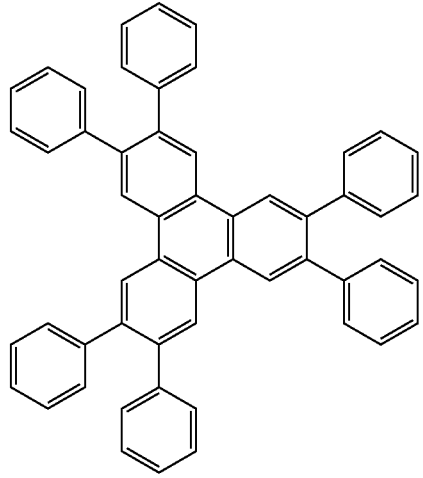 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 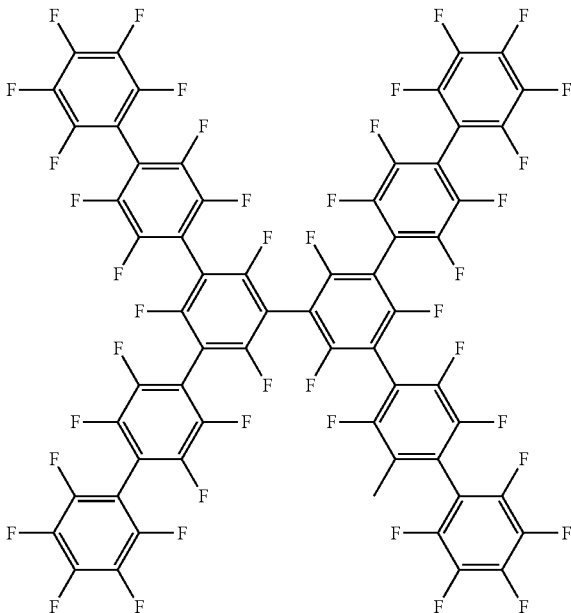 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE 3-continued
| MATERIAL | EXAMPLES OF MATERIAL | PUBLICATIONS |
|---|---|---|
| Phenothiazine-S-oxide | 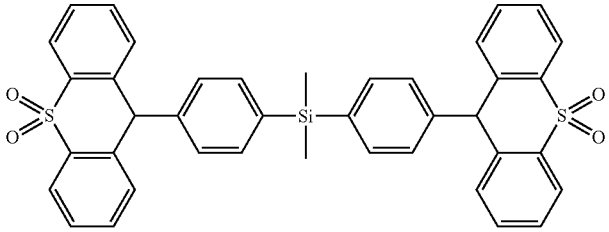 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 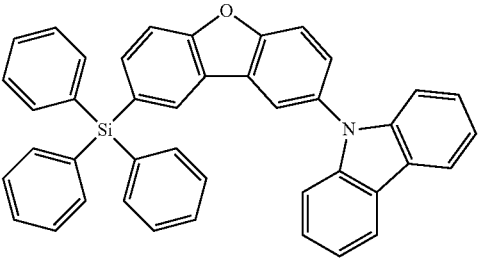 [SMILES: c1ccc([Si](c2ccccc2)(c2ccccc2)c2ccc3oc4ccc(-n5c6ccccc6c6ccccc65)cc4c3c2)cc1] | WO2010079051 |
| Aza-carbazoles | 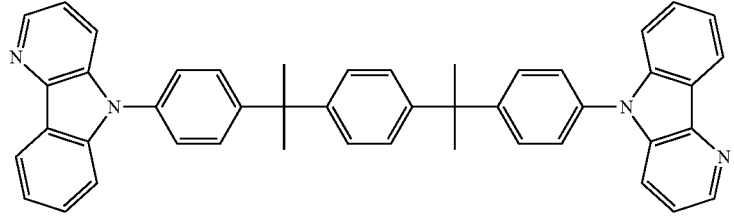 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 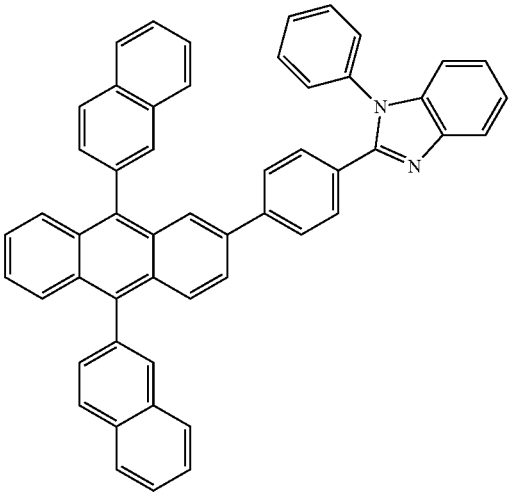 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 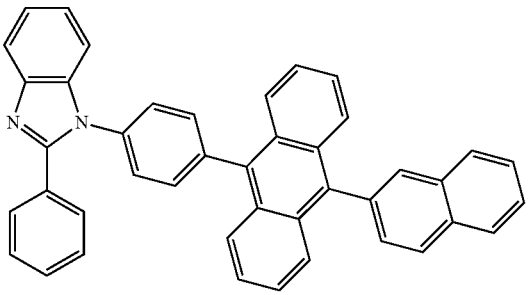 [SMILES: c1ccc(-c2nc3ccccc3n2-c2ccc(-c3c4ccccc4c(-c4ccc5ccccc5c4)c4ccccc34)cc2)cc1] | US20090179554 |

TABLE 3-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987)<br>U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007)<br><br>Appl. Phys. Lett. 79, 449 (2001) |

TABLE 3-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 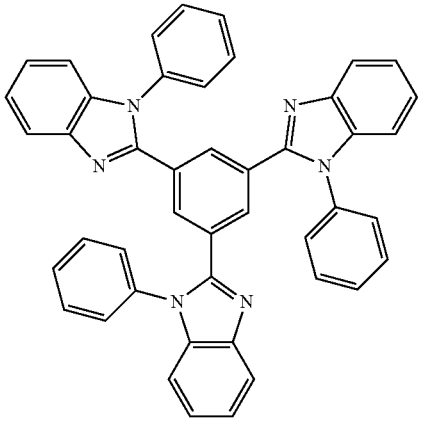 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 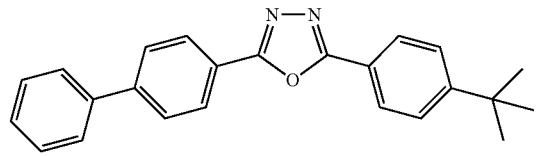 [SMILES: CC(C)(C)c1ccc(-c2nnc(-c3ccc(-c4ccccc4)cc3)o2)cc1] | Appl. Phys. Lett. 55, 1489 (1989) |
| | 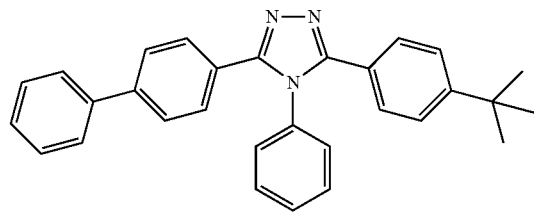 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 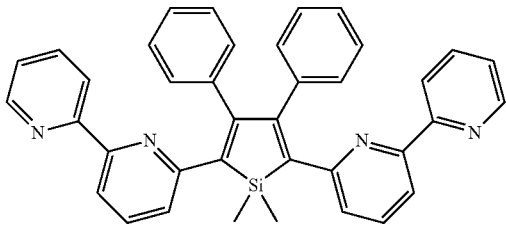 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 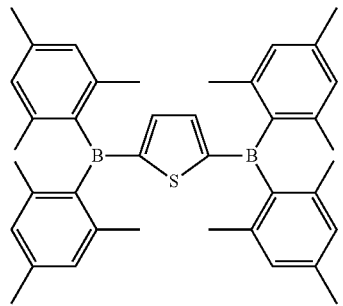 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |
| Fluorinated aromatic compounds | 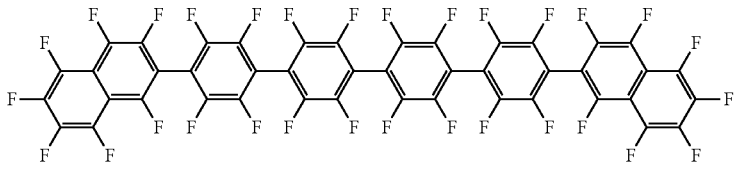 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE 3-continued

| MATERIAL | EXAMPLES OF MATERIAL | PUBLICATIONS |
| --- | --- | --- |
| Fullerene (e.g., C60) | | US20090101870 |
| Triazine complexes | | US20040036077 |
| Zn (N^N) complexes | | U.S. Pat. No. 6,528,187 |

EXPERIMENTAL

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having the formula:

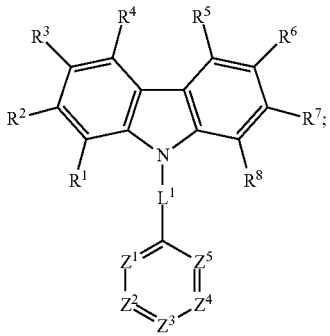

Formula I wherein $Z^1$, $Z^2$, $Z^3$, $Z^4$ and $Z^5$ are each independently selected from group consisting of $CR^9$ and N;
wherein any adjacent $R^9$ are optionally joined to form a fused ring;
wherein at least one of $Z^1$, $Z^2$, $Z^3$, $Z^4$ and $Z^5$ is N;
wherein $L^1$ is selected from the group consisting of:

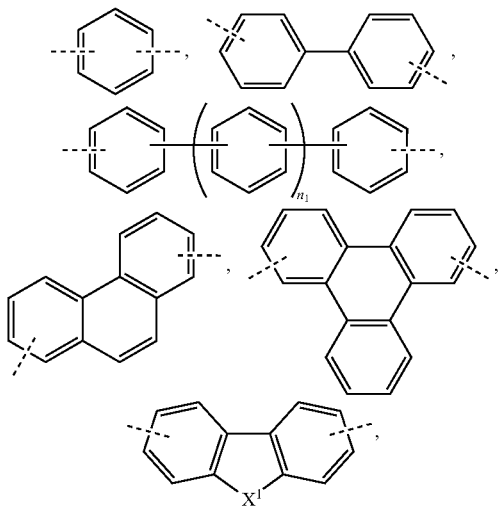

and combinations thereof;
wherein $X^1$ is O, S, or CRR';
wherein R, R' are optionally joined to form a ring;
wherein $n_1$ is an integer from 1 to 20;
wherein $L^1$ can be further substituted by a substituent selected from the group consisting of alkyl, aryl, and heteroaryl;
wherein at least one of $R^1$, $R^2$, $R^3$, $R^4$, $R^5$, $R^6$, $R^7$, and $R^8$ comprises at least one electron donor group selected from the group consisting of:

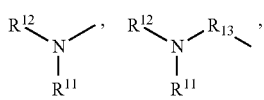

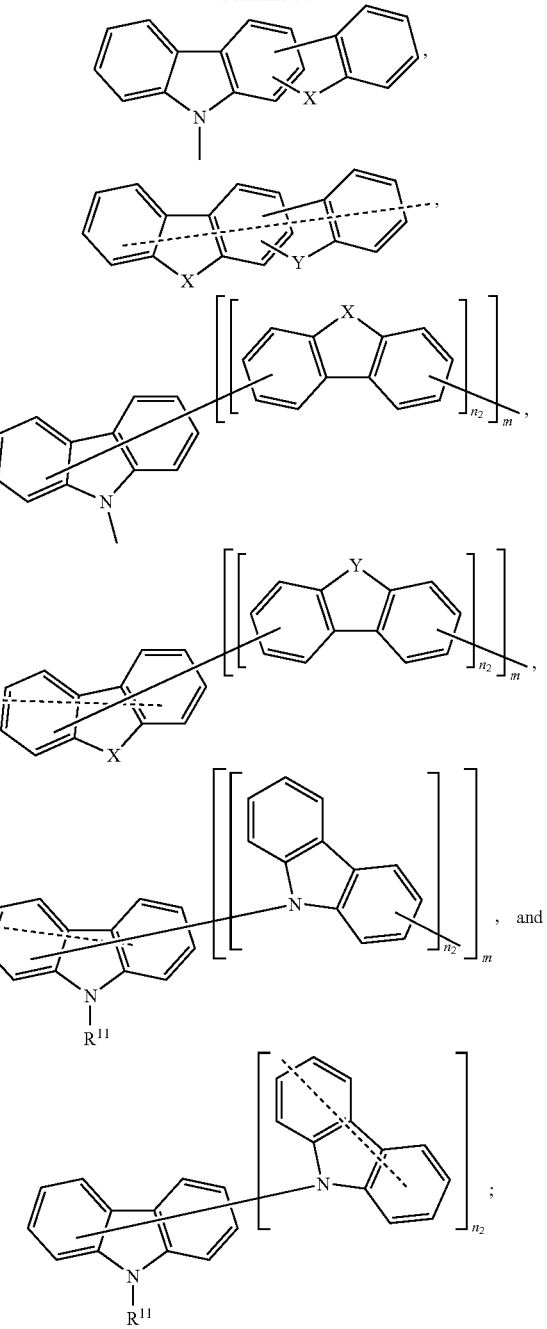

wherein X and Y is selected from the group consisting of O, S, $NR^{14}$; and
wherein $R^{11}$, $R^{12}$, $R^{13}$ and $R^{14}$ are selected from the group consisting of aryl and heteroaryl,
wherein any two adjacent $R^1$, $R^2$, $R^3$, $R^4$, $R^5$, $R^6$, $R^7$, and $R^8$ are not joined to form a ring;
wherein m is an integer from 1 to 20;
wherein $n_2$ is an integer from 1 to 20;
wherein $R^1$, $R^2$, $R^3$, $R^4$, $R^5$, $R^6$, $R^7$, and $R^8$ do not contain an electron acceptor group;
wherein $R^9$ does not contain an electron donor group;
wherein $R^1$, $R^2$, $R^3$, $R^4$, $R^5$, $R^6$, $R^7$, and $R^8$ are independently selected from the group consisting of hydrogen, deuterium, alkyl, cycloalkyl, arylalkyl, alkoxy, aryloxy, amino, silyl, alkenyl, cycloalkenyl, heteroalkenyl, alkynyl, aryl, heteroaryl, and combinations thereof; and wherein $R^9$, R, and R' are independently selected from the group consisting of hydrogen, deuterium, alkyl, cycloalkyl, heteroalkyl, arylalkyl, silyl, alkenyl, cycloalkenyl, heteroalkenyl, alkynyl, aryl, heteroaryl, and combinations thereof; wherein at least one Z1, Z2, Z3, Z4 and Z5 is $CR^9$ wherein $R^9$ is selected from aryl and heteroaryl, and can be further substituted.

2. The compound of claim 1, wherein at least one of $R^1$, $R^2$, $R^3$, $R^4$, $R^5$, $R^6$, $R^7$, and $R^8$ comprises the electron donor group selected from the group consisting of:

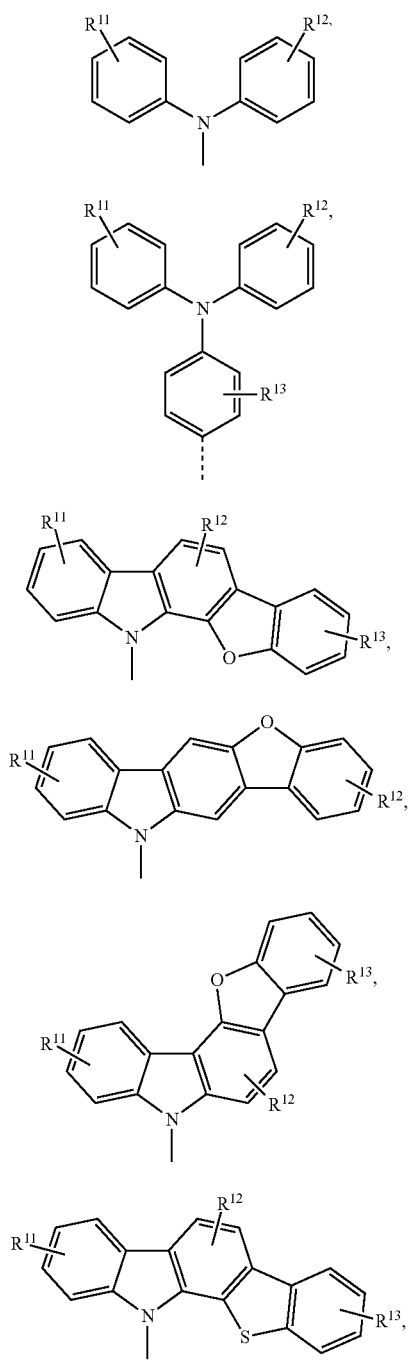

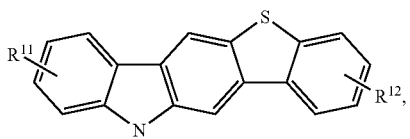

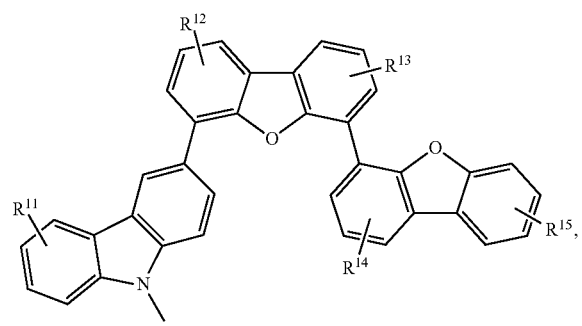
D13
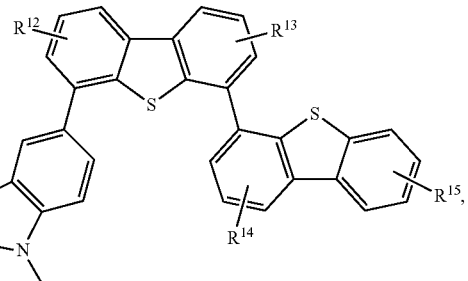
D19
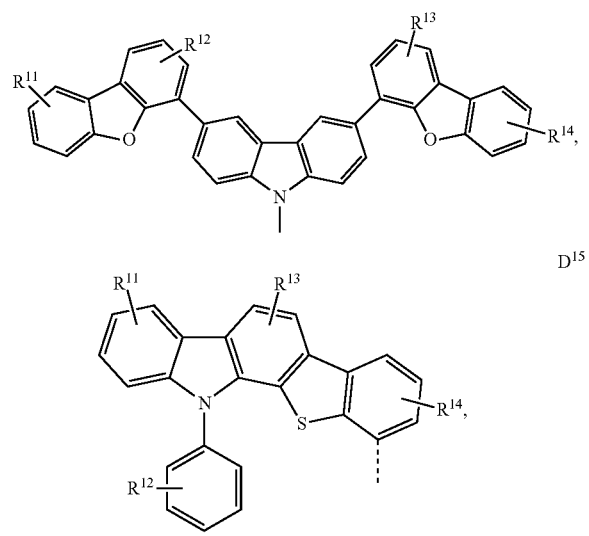
D14, D15, D16, D17, D18
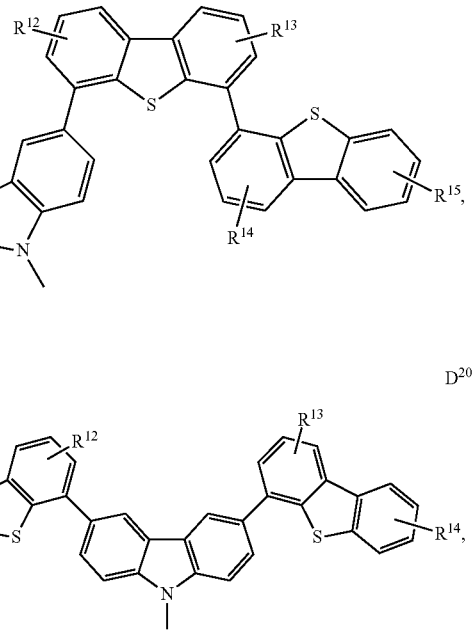
D20, D21
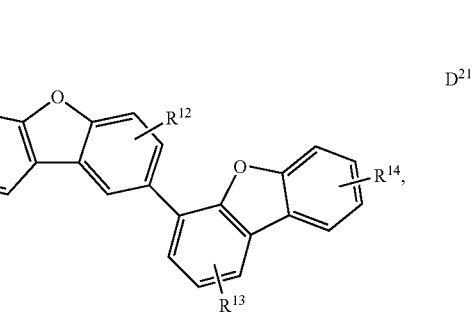
D22
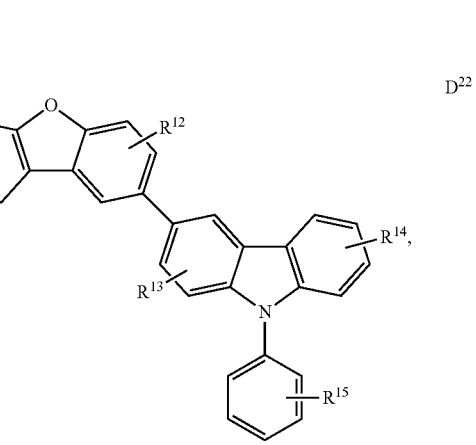
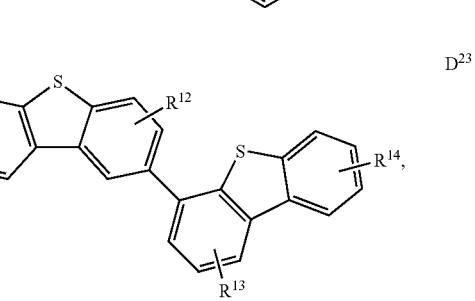
D23

-continued
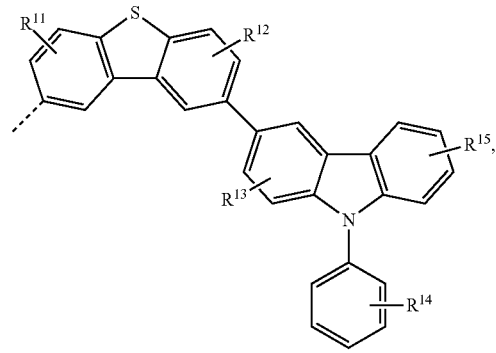
D24
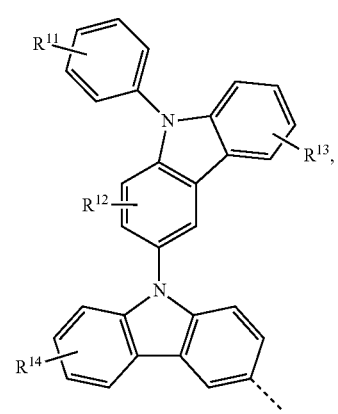
D28
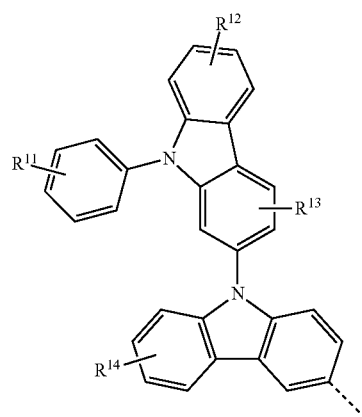
D29
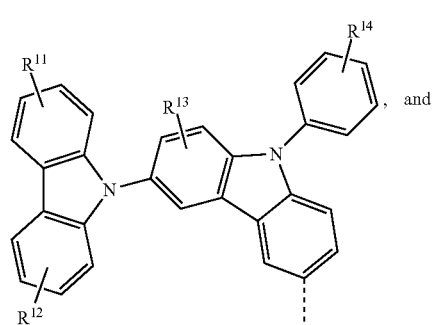
D30
-continued
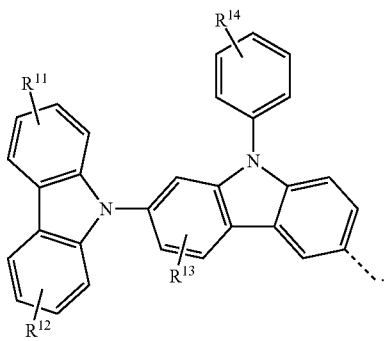
D31
3. The compound of claim 1, wherein the compound has the formula:
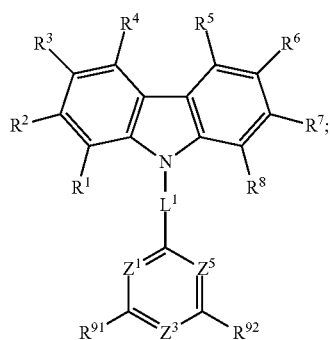
and
wherein $R^{91}$ and $R^{92}$ are independently selected from aryl or heteroaryl, and can be further substituted.
4. The compound of claim 1, wherein the electron donor group is selected from the group consisting of:
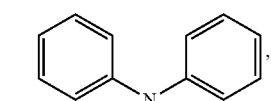
D101
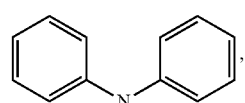
D102
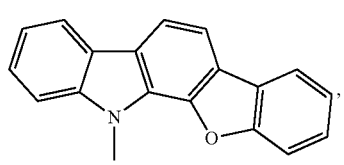
D103

D104
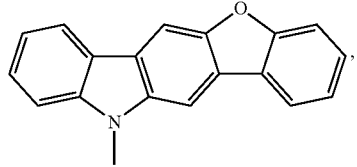
D105
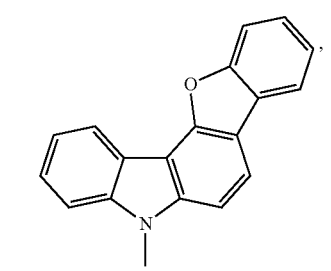
D106
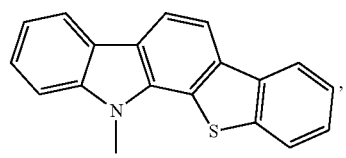
D107
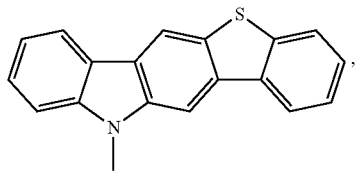
D108
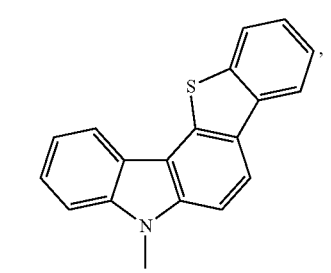
D109
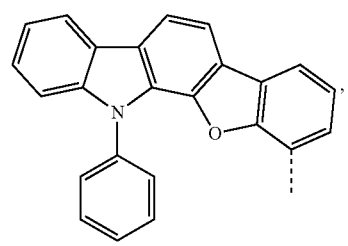
D110
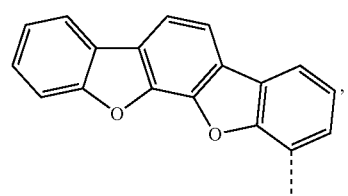
D111
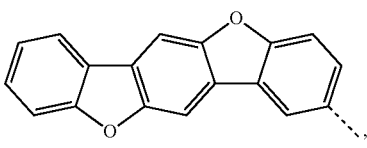
D112
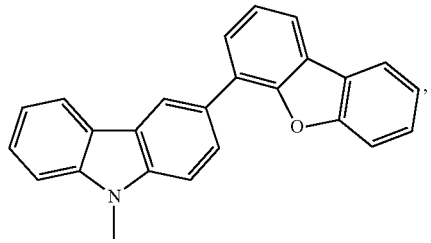
D113
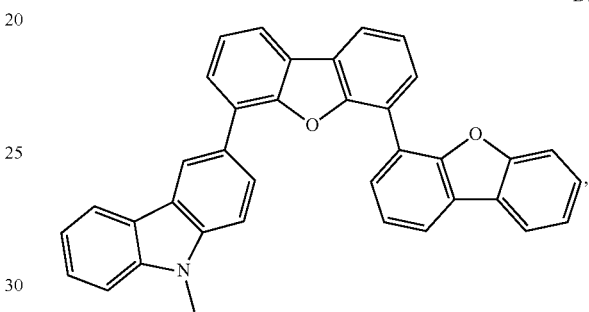
D114
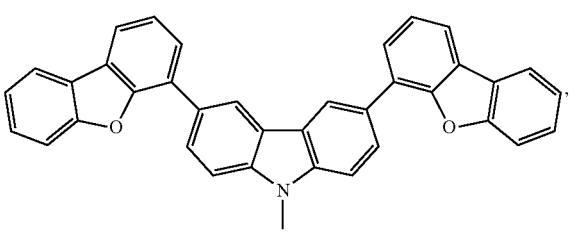
D115
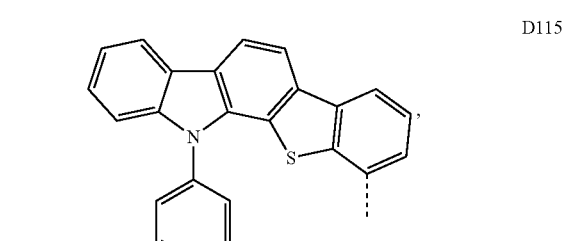
D116
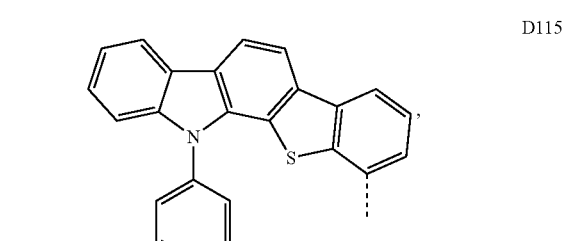
D117
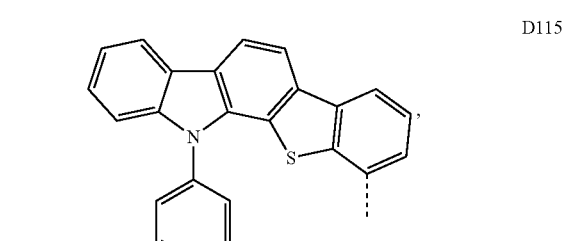

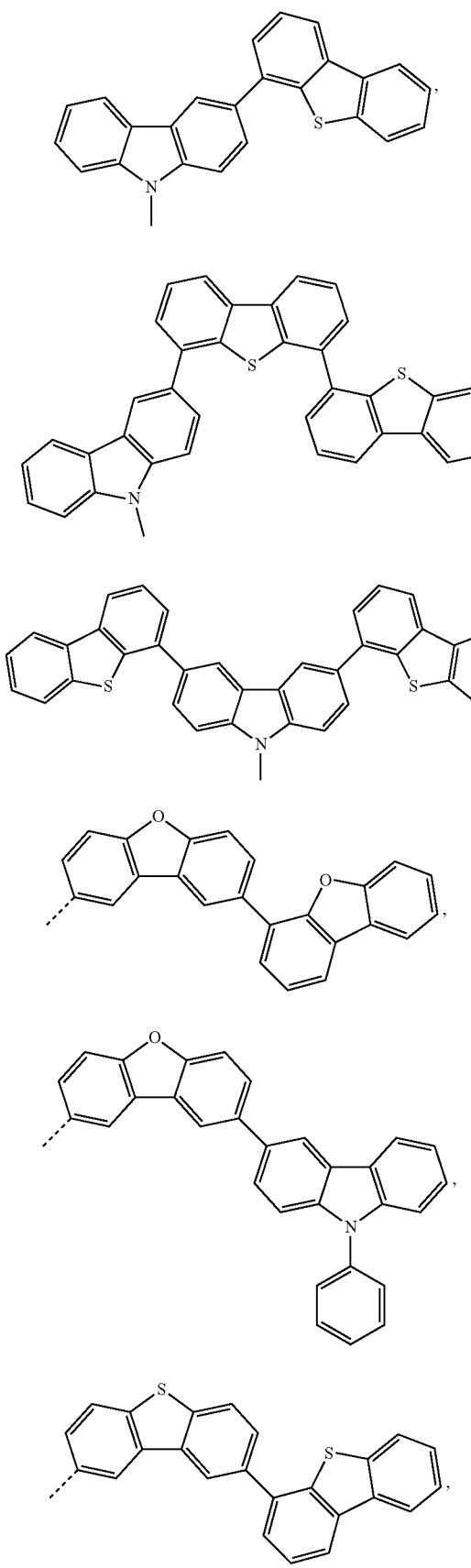
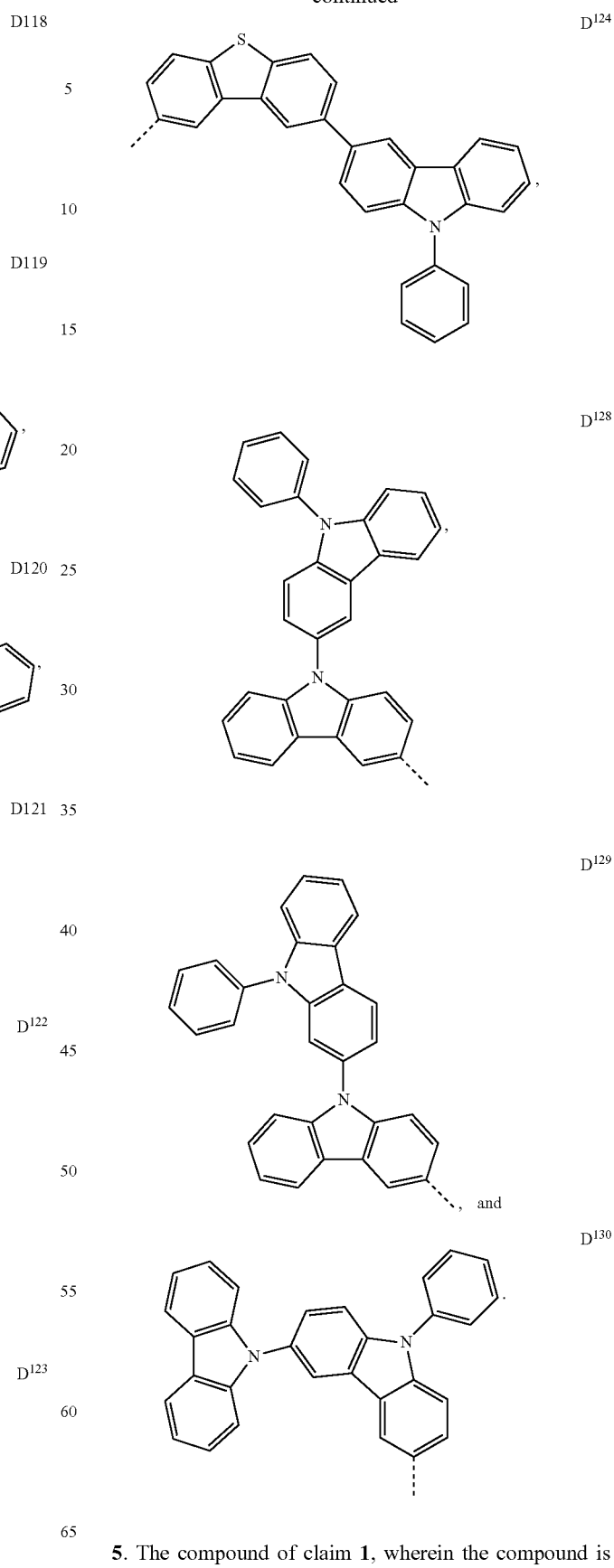
5. The compound of claim 1, wherein the compound is selected from the group consisting of:

Compound 1
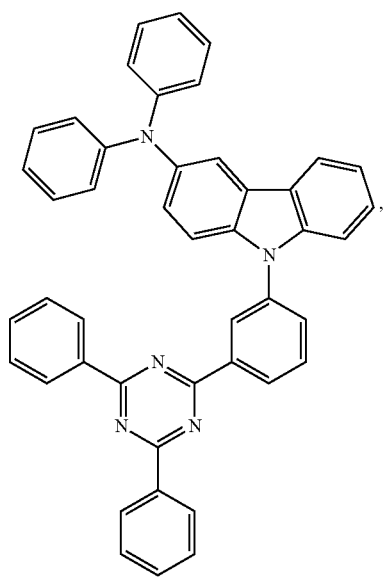
Compound 13
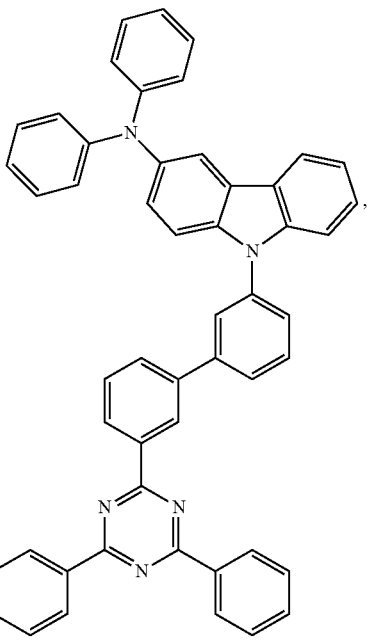
Compound 5
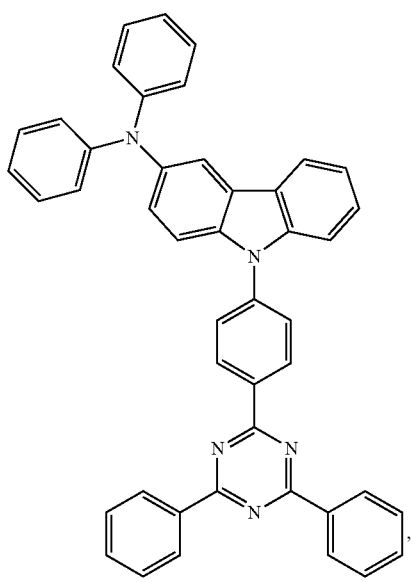
Compound 9
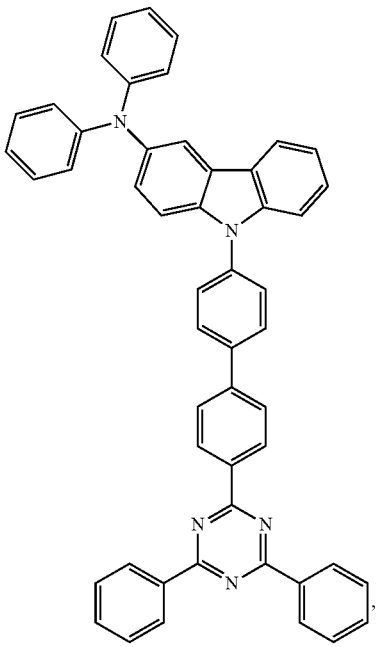

-continued
Compound 33
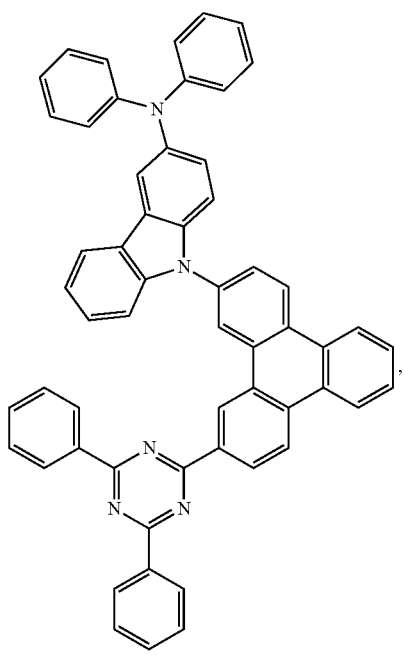
Compound 37
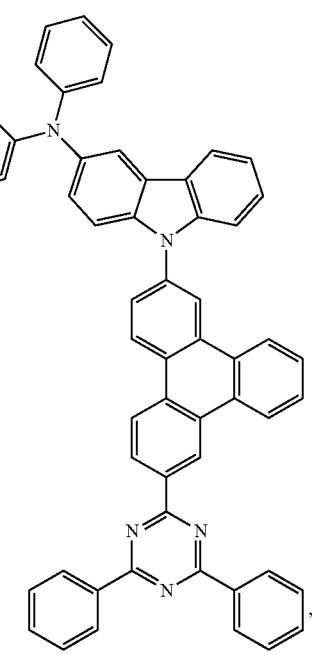
Compound 41
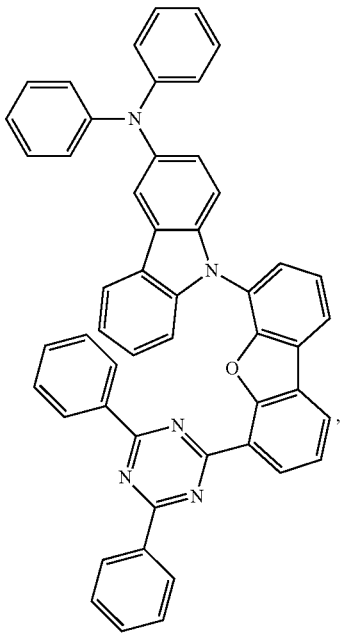
Compound 45
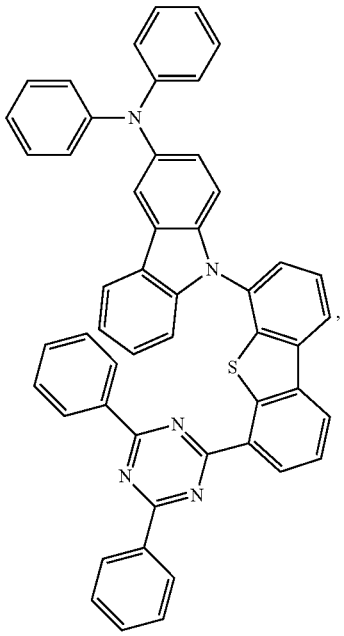

Compound 57
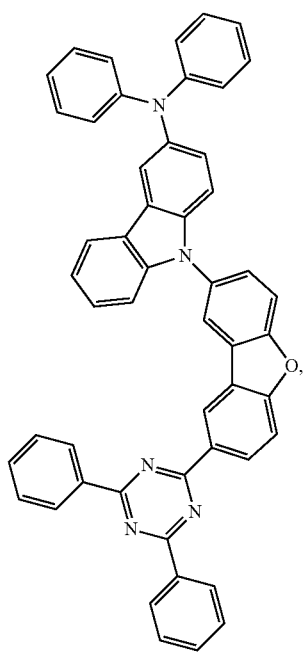
Compound 61
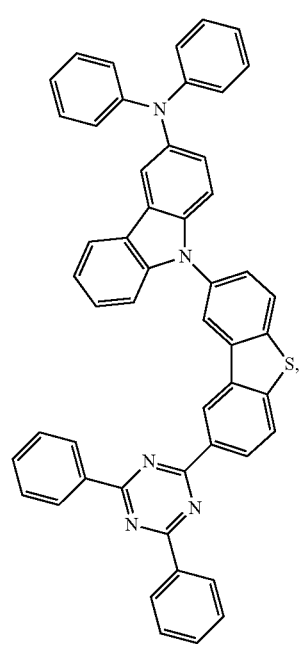
Compound 69
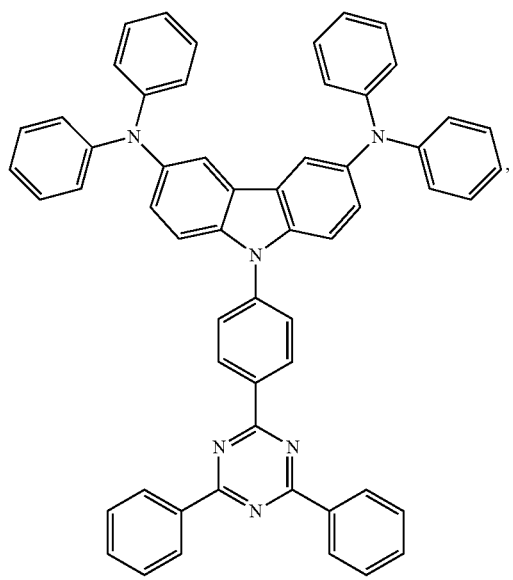
Compound 65
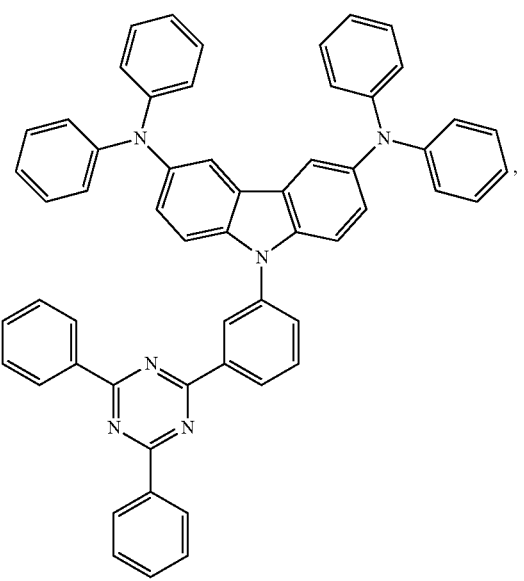

Compound 77
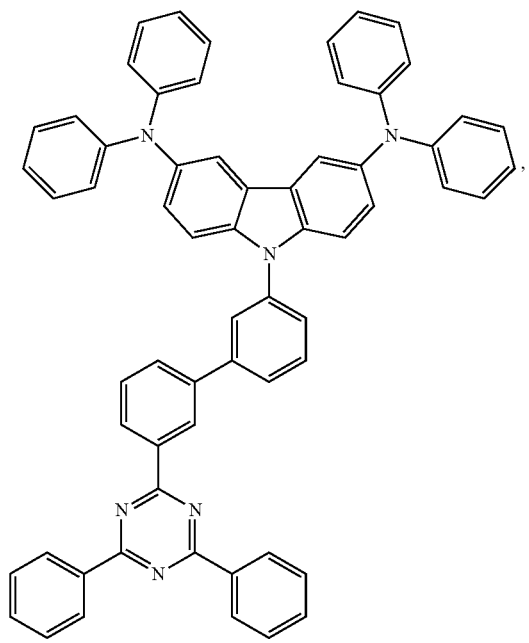
Compound 97
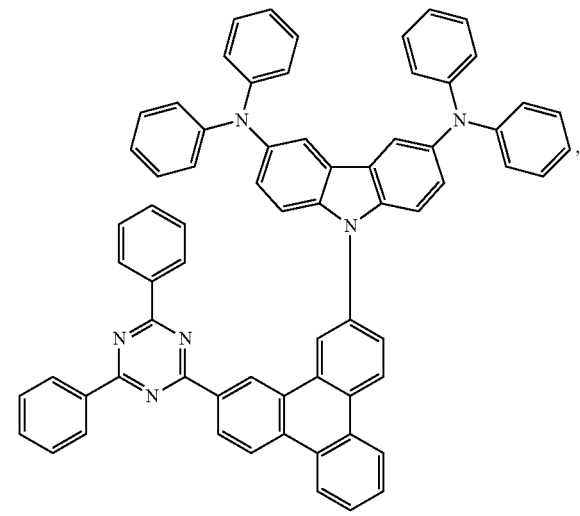
Compound 73
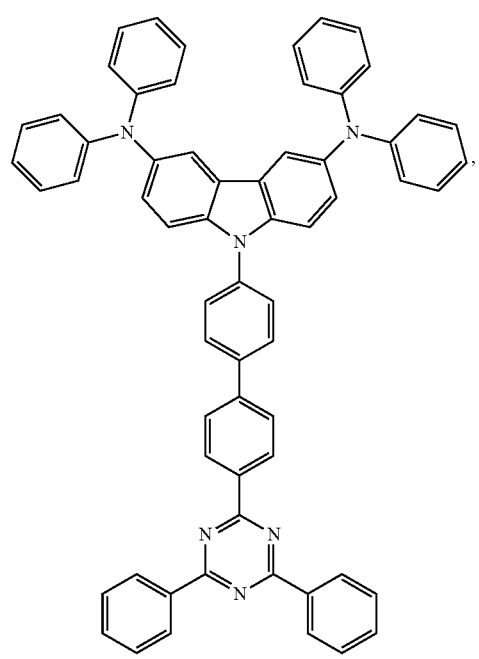
Compound 101
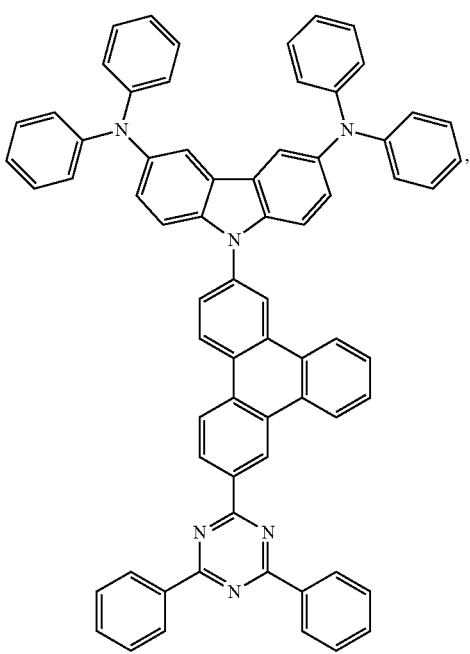

Compound 105
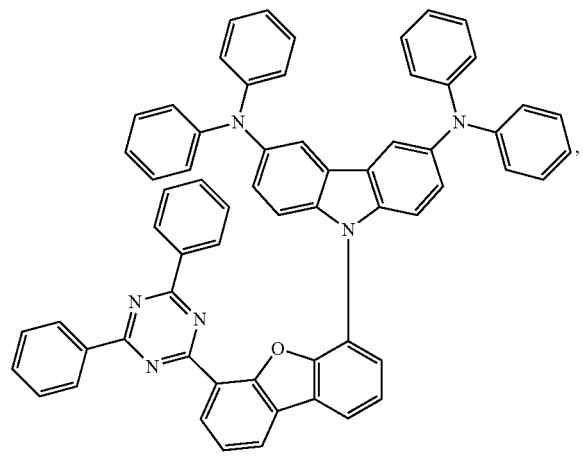
Compound 109
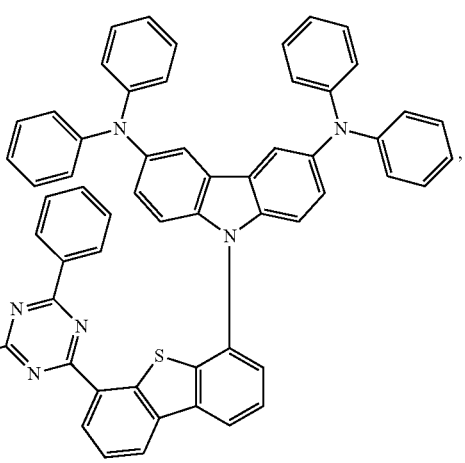
Compound 121
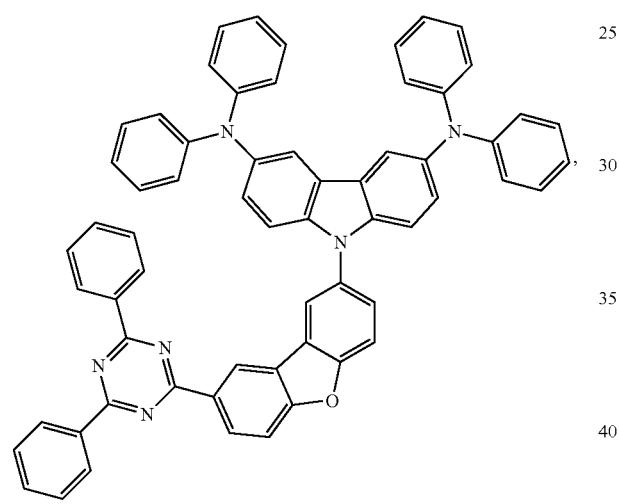
Compound 125
Compound 133
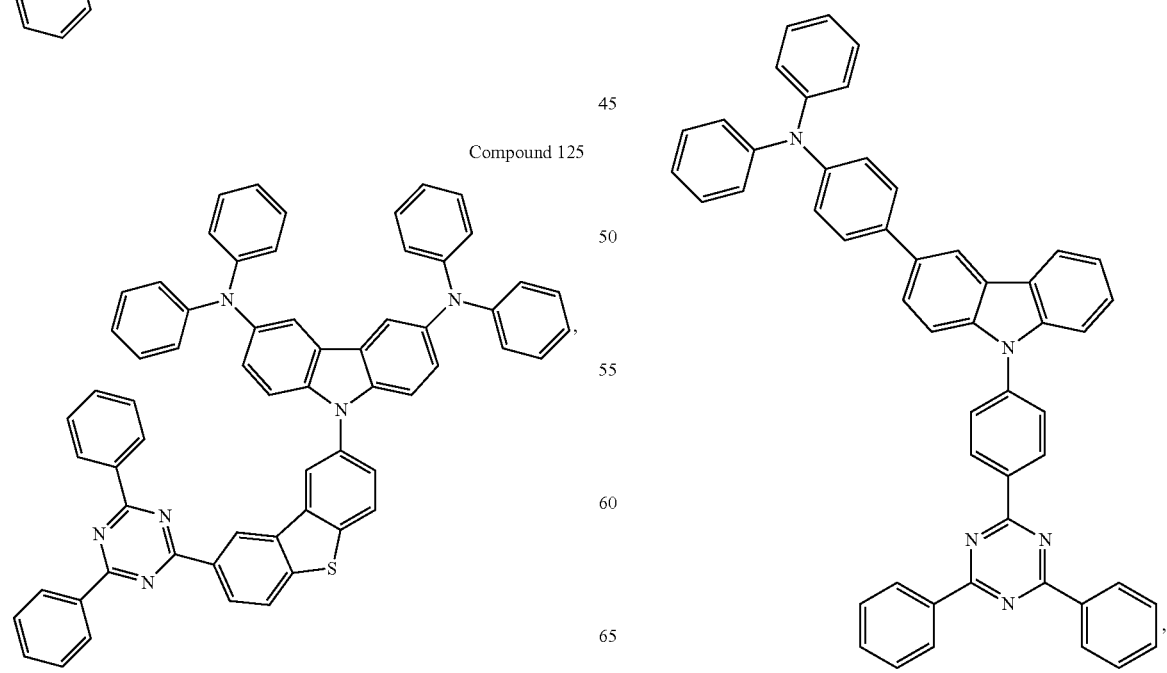

Compound 129
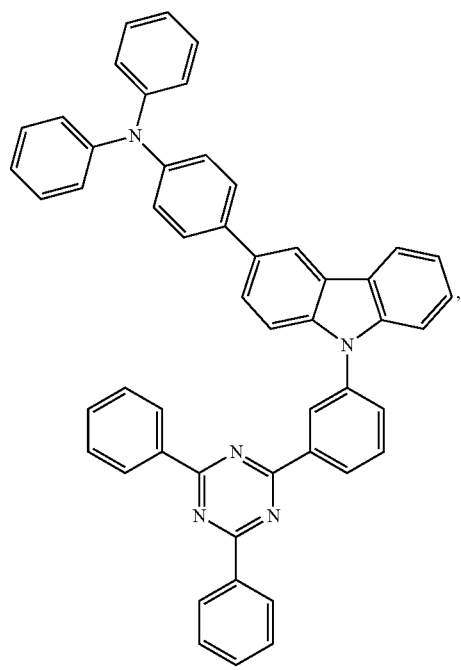
Compound 137
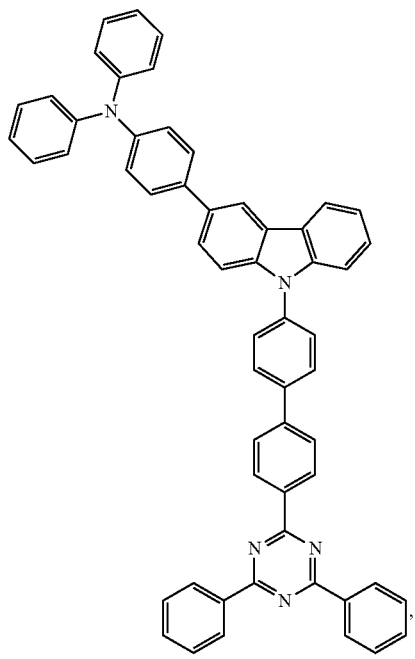
Compound 141
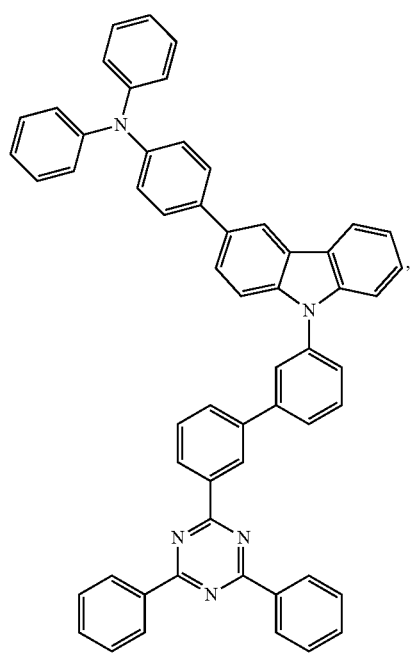
Compound 161
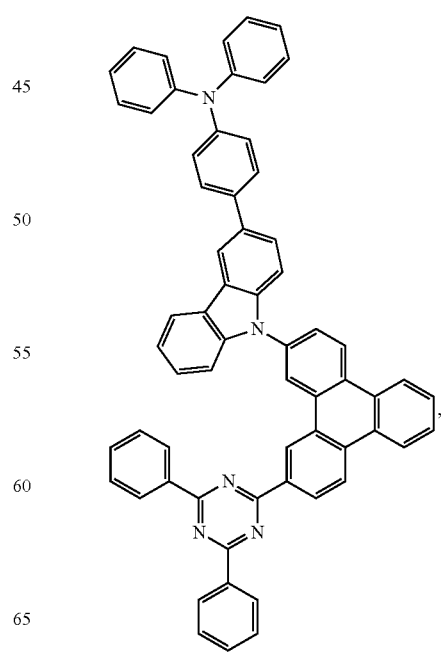

Compound 165
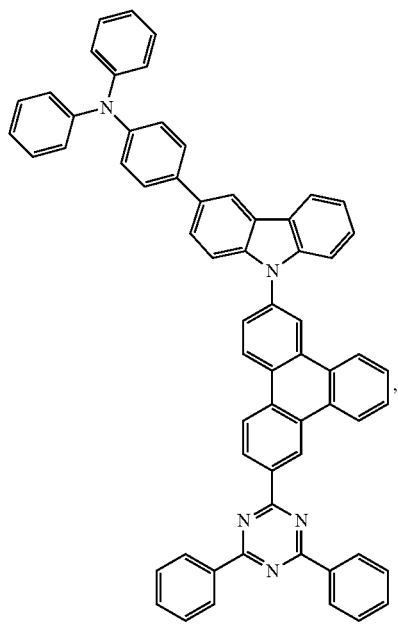
Compound 173
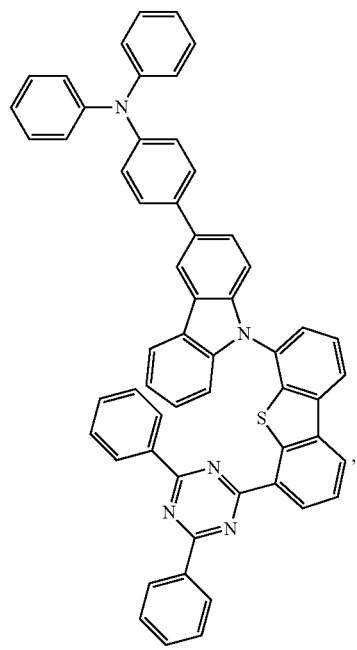
Compound 169
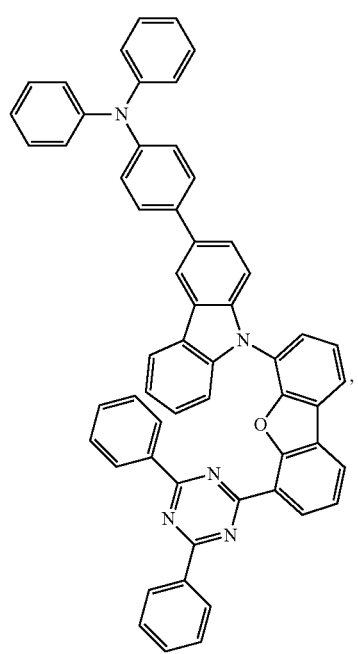
Compound 185
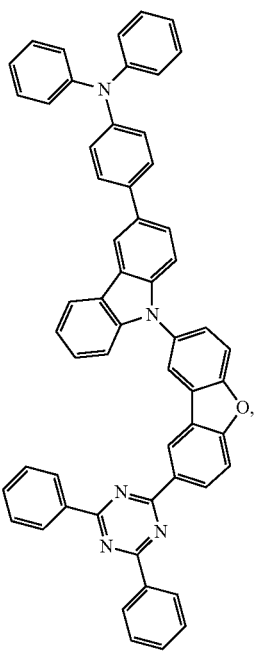

Compound 189
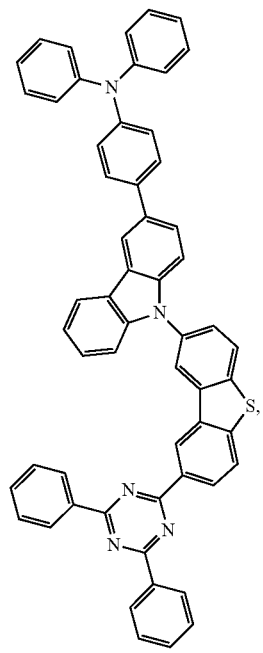
Compound 193
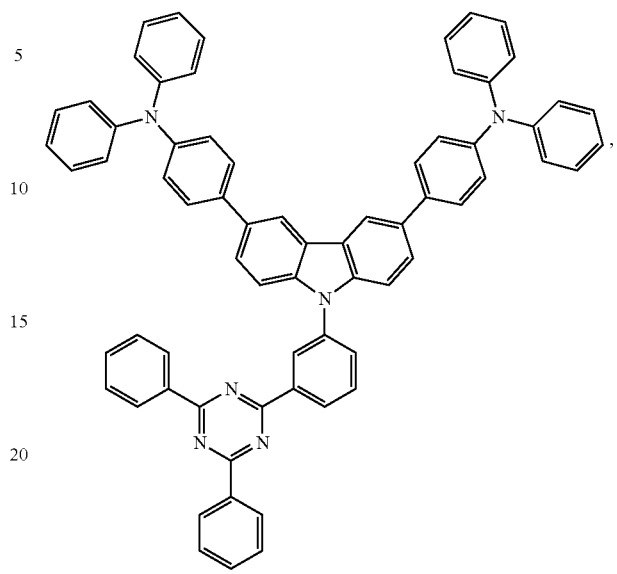
Compound 197
Compound 205
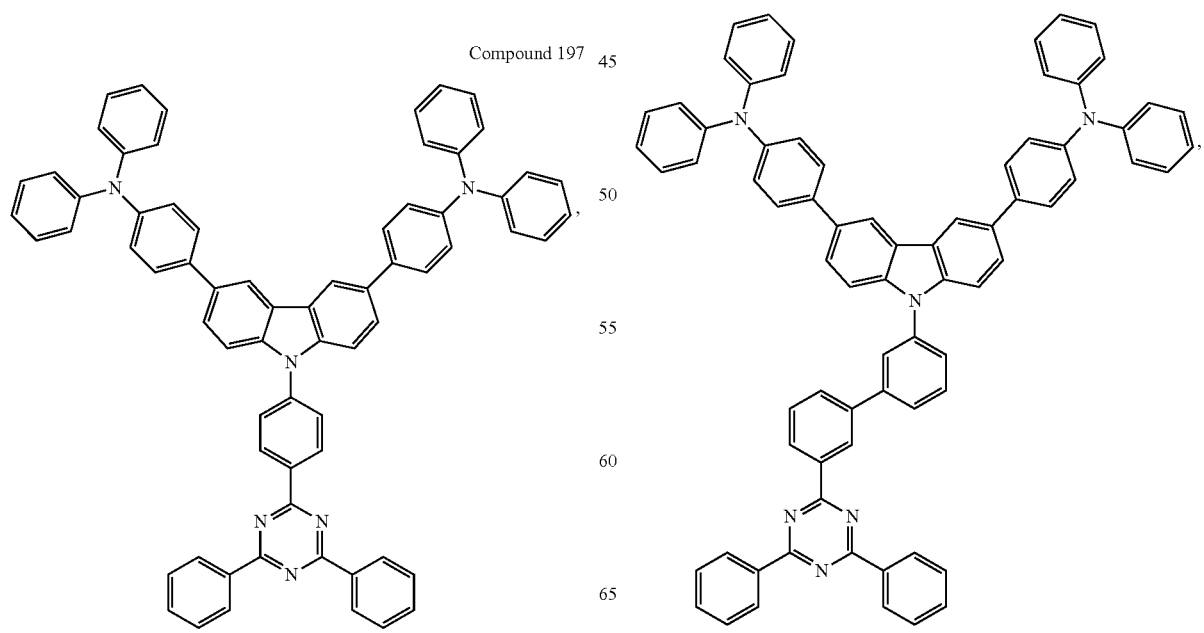

Compound 201
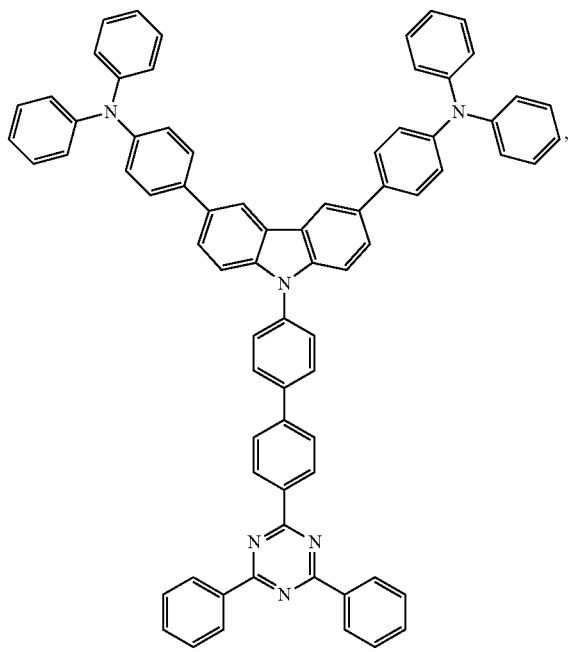
Compound 229
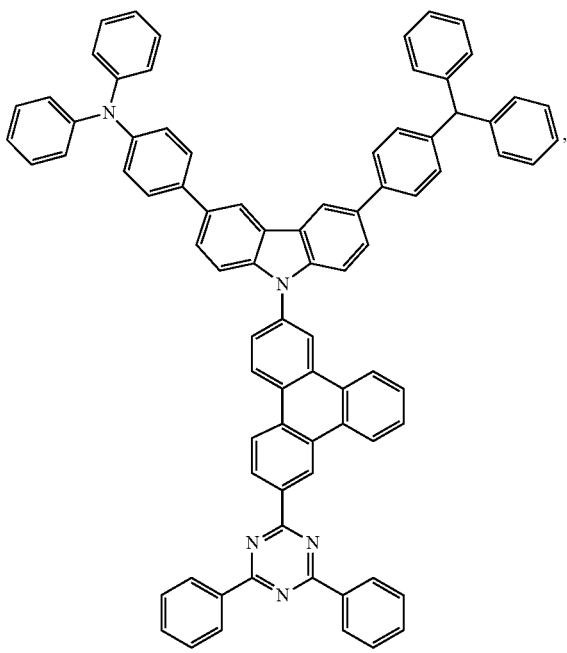
Compound 225
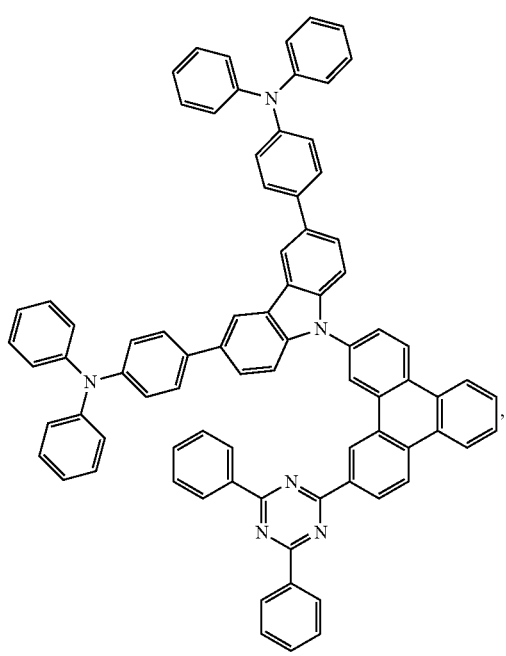
Compound 233
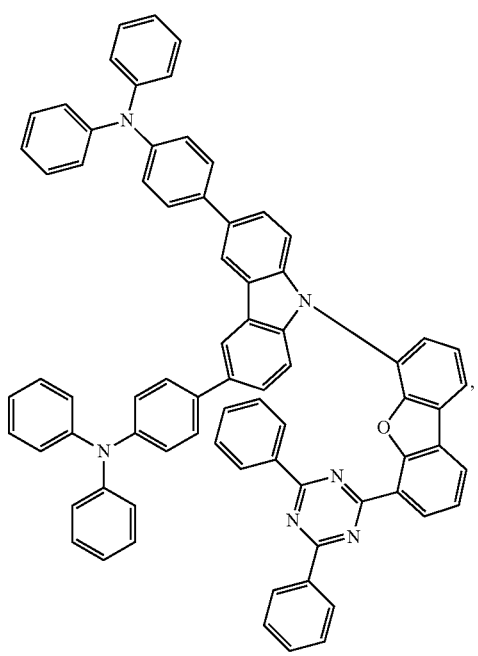

Compound 237
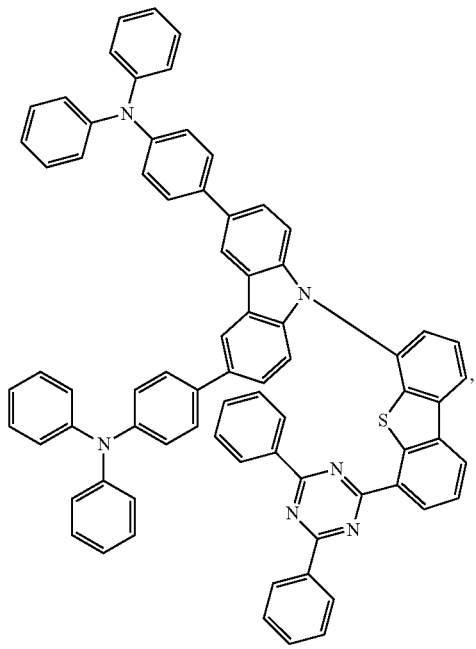
Compound 253
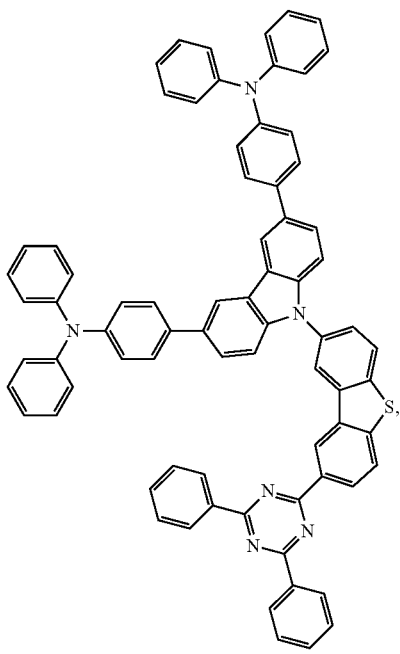
Compound 249
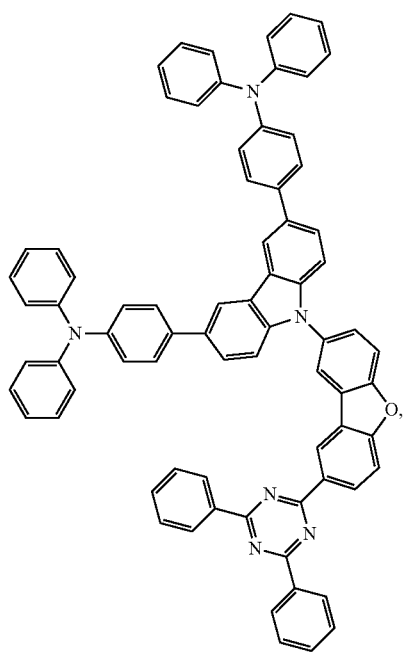
Compound 261
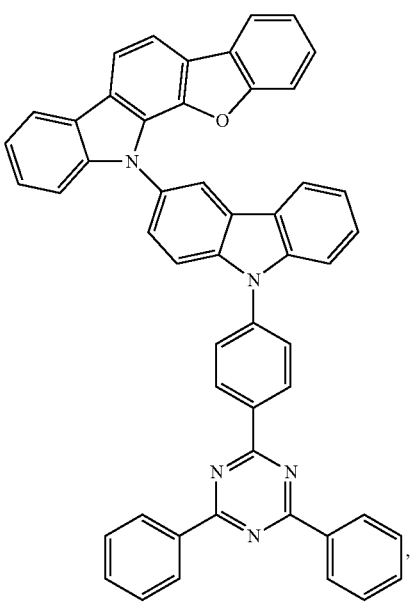

Compound 257
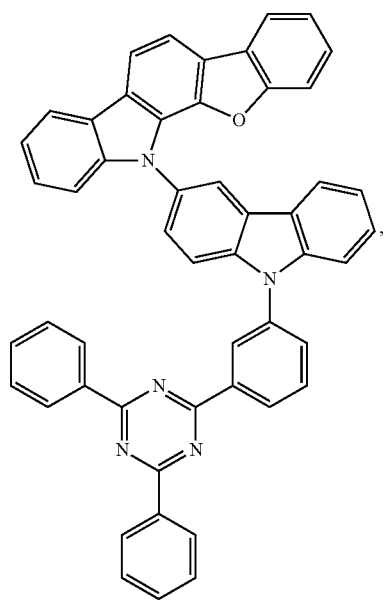
Compound 265
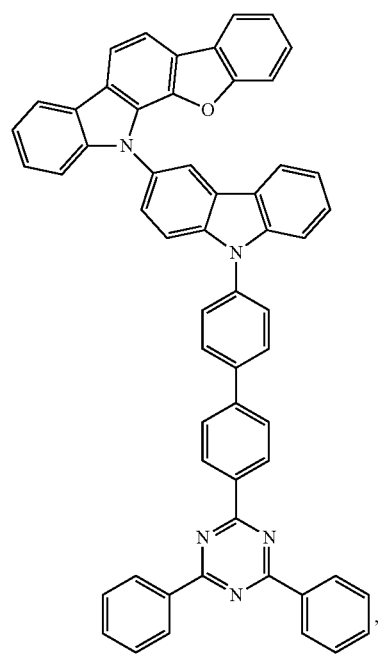
Compound 269
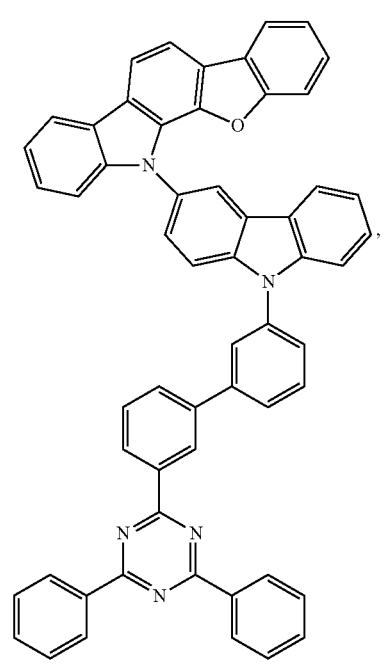
Compound 289
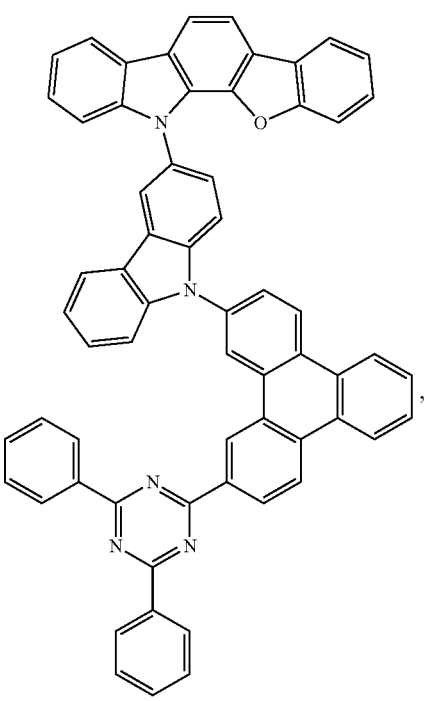

Compound 293
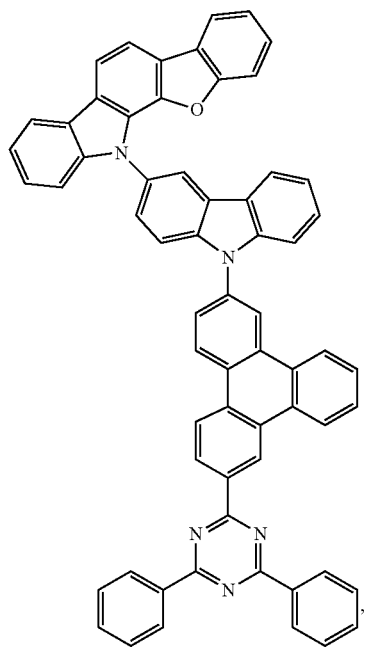
Compound 301
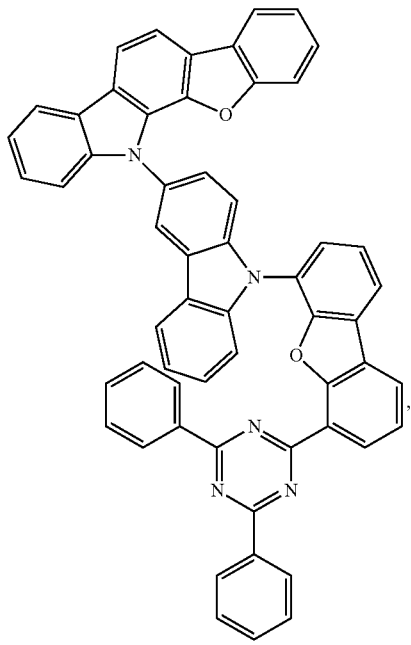
Compound 297
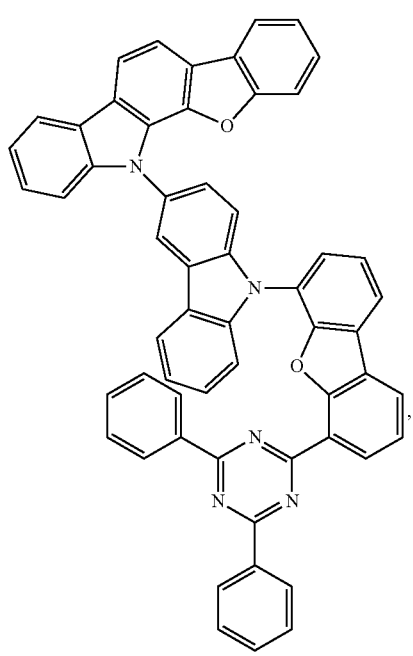
Compound 313
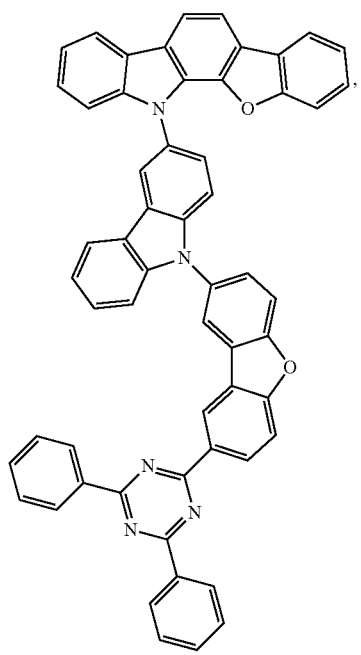

-continued
Compound 317
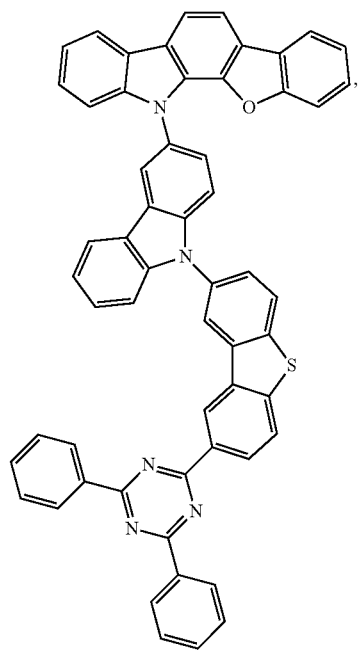
Compound 321
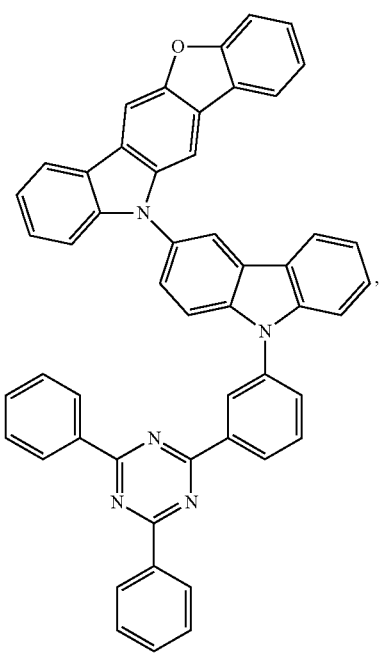
Compound 325
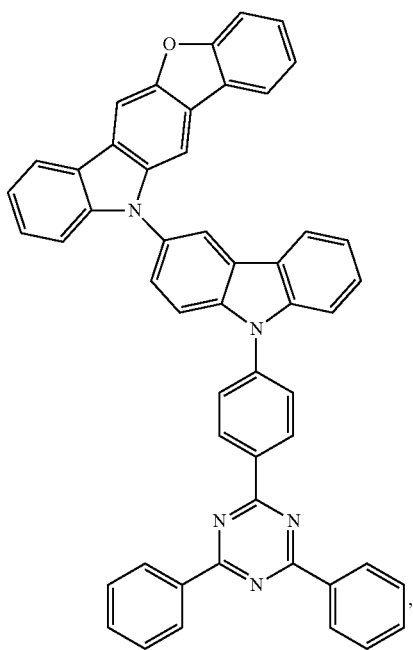
Compound 333
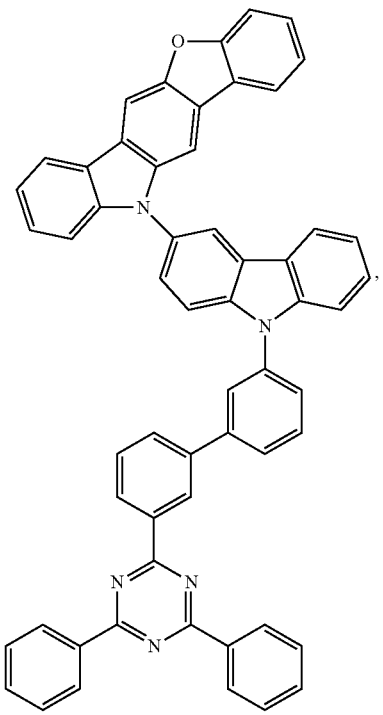

Compound 329
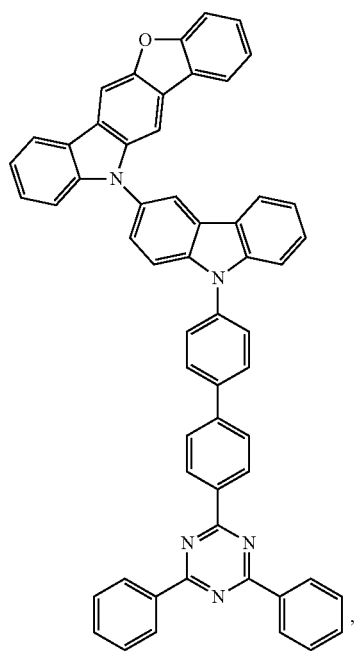
Compound 357
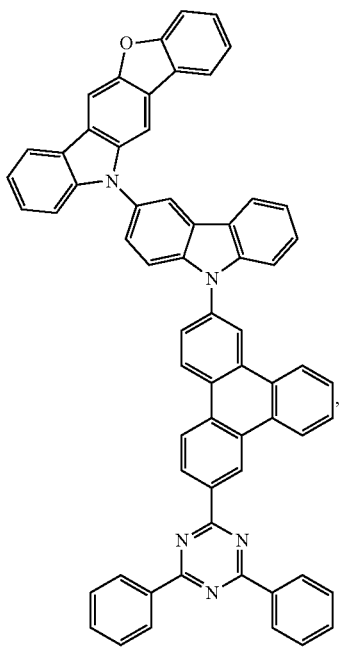
Compound 353
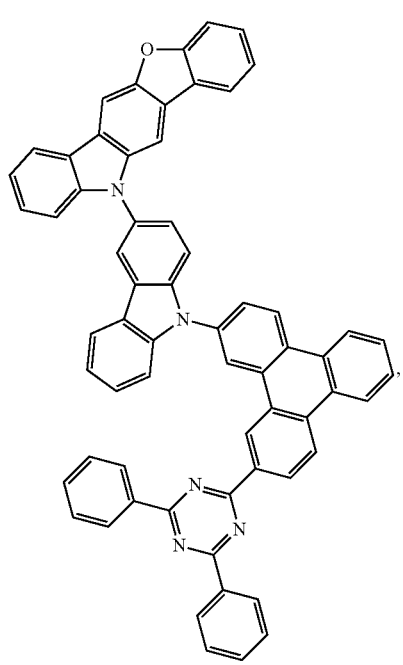
Compound 361
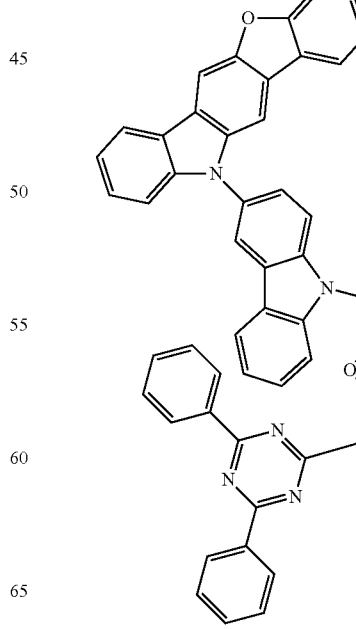

Compound 365
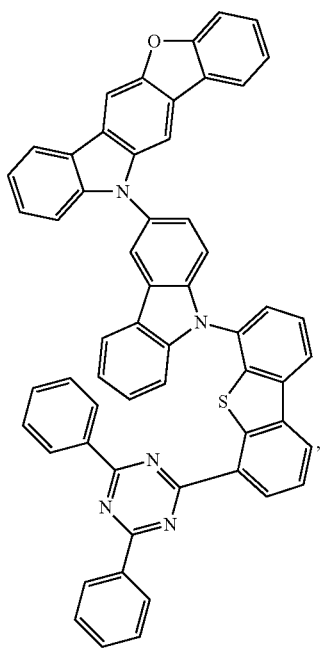
Compound 381
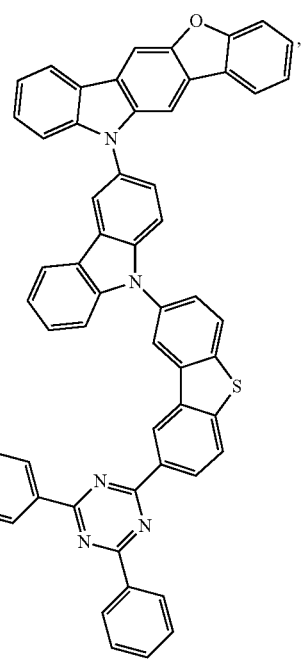
Compound 377
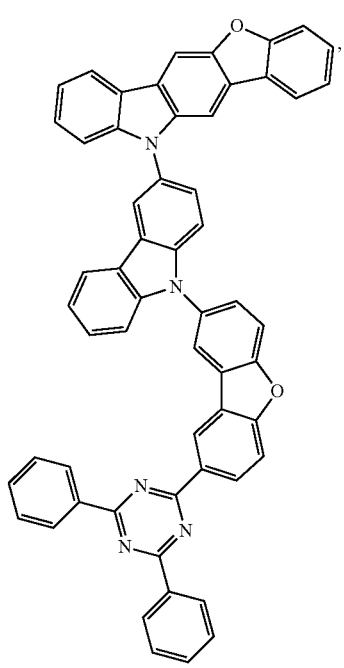
Compound 389
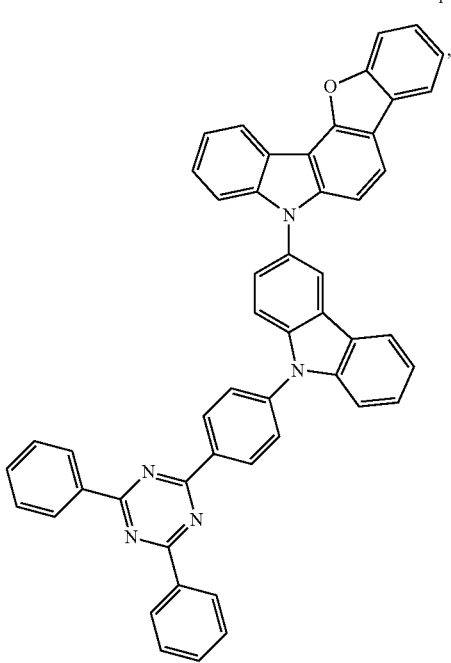

617
-continued
Computer 385
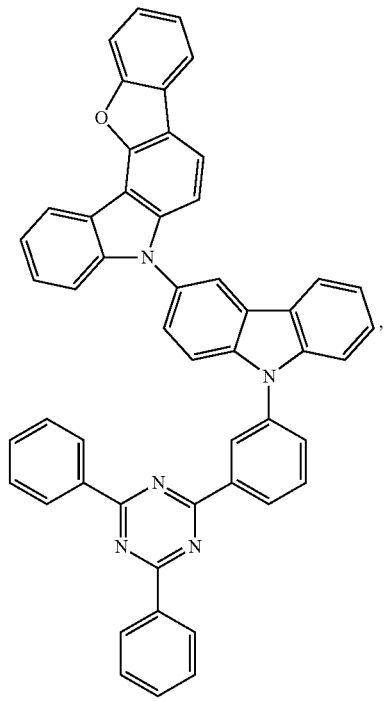
618
-continued
Compound 393
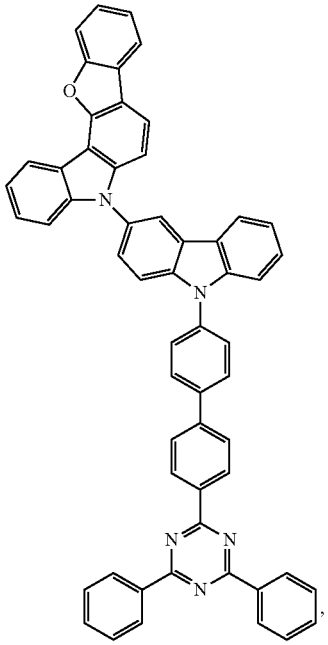
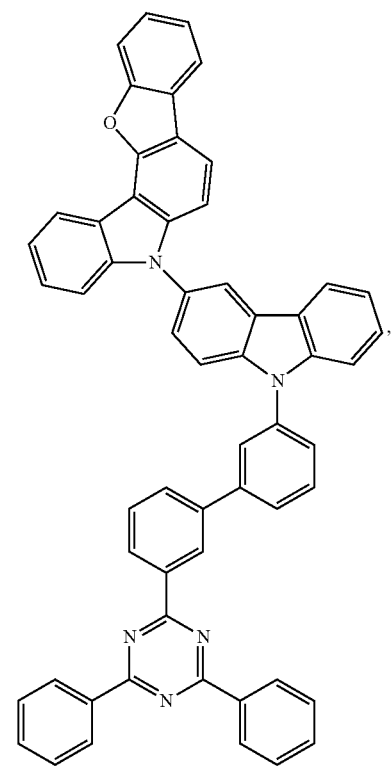
Compound 417
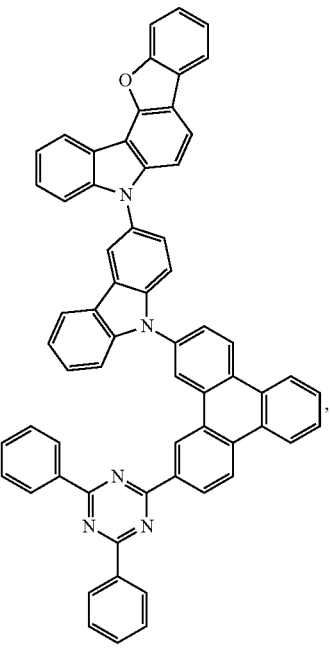

-continued
Compound 421
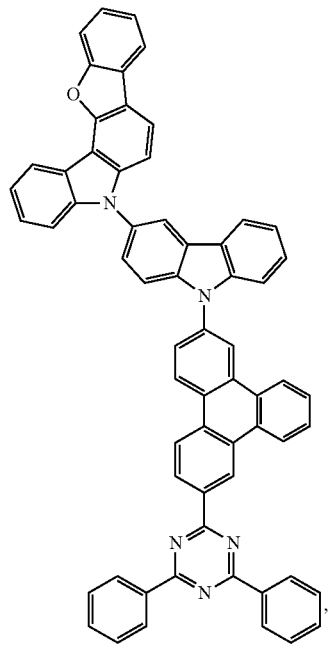
Compound 429
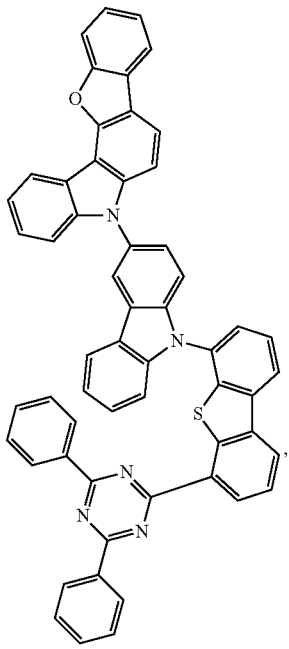
Compound 425
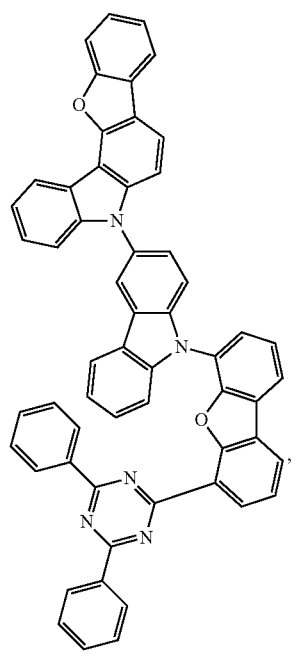
Compound 441
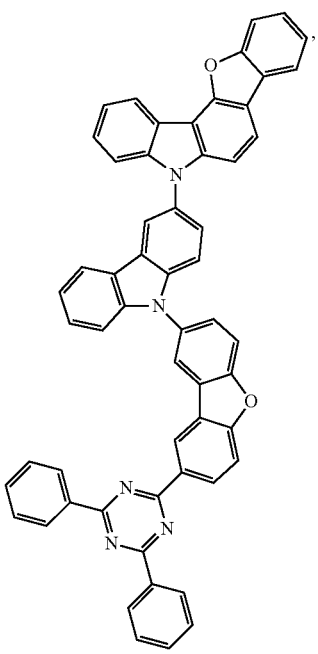

Compound 445
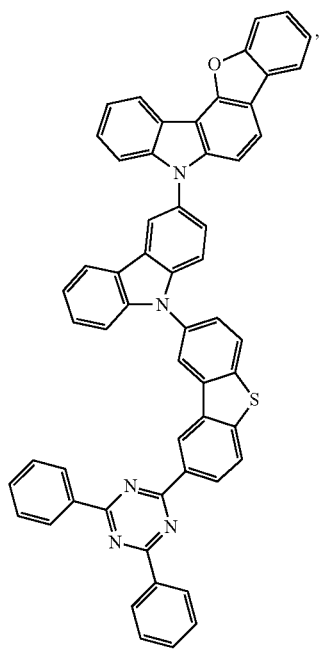
Compound 449
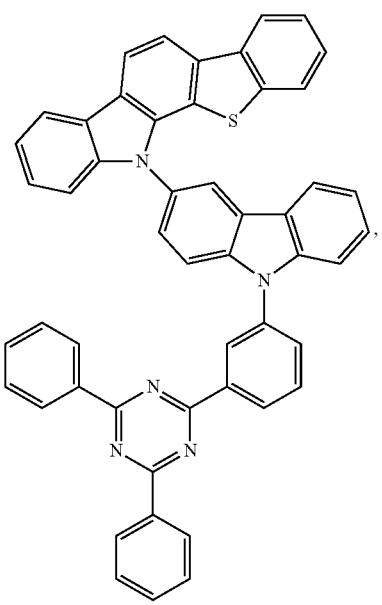
Compound 453
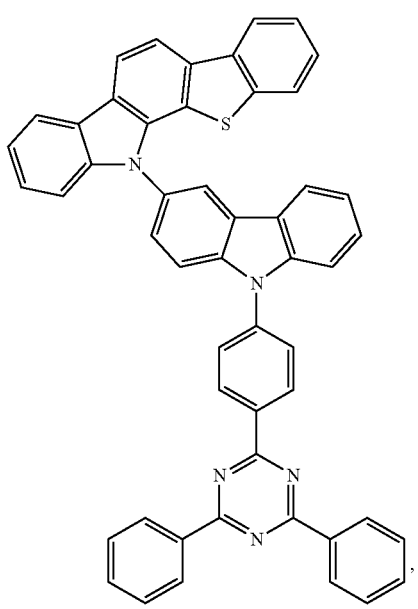
Compound 461
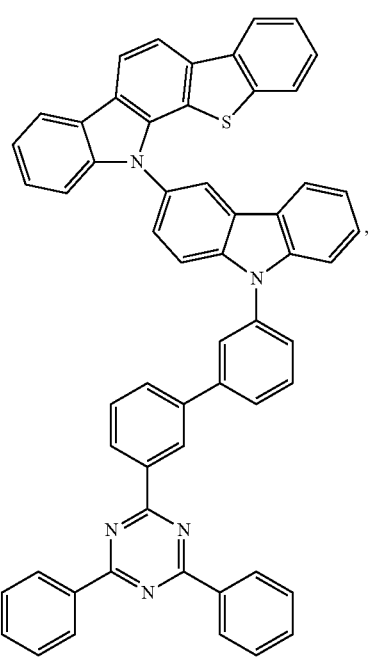

Compound 457
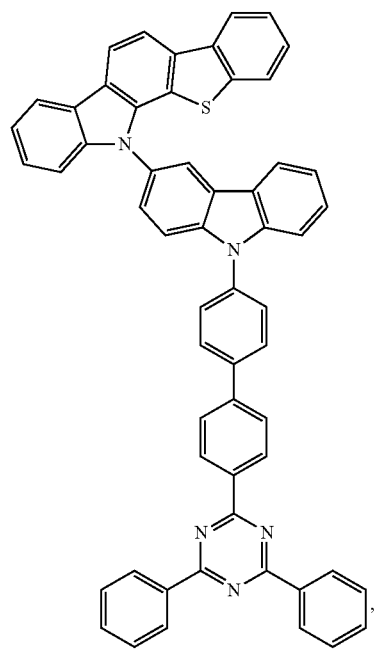
Compound 485
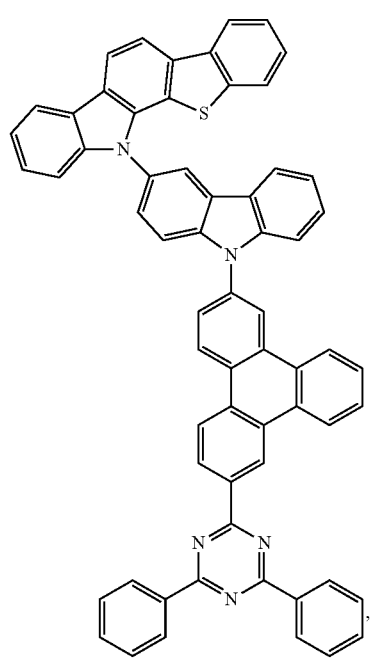
Compound 481
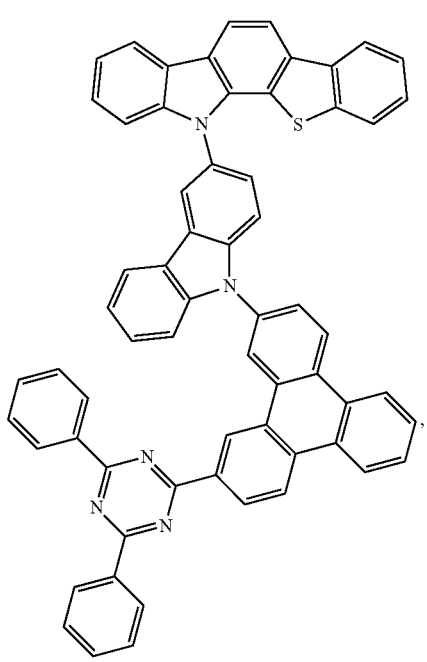
Compound 489
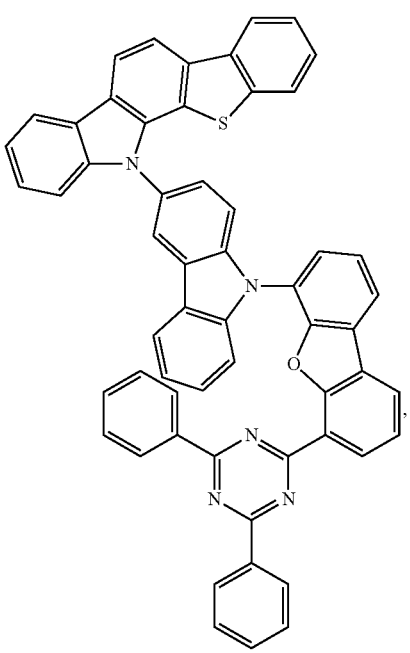

Compound 493
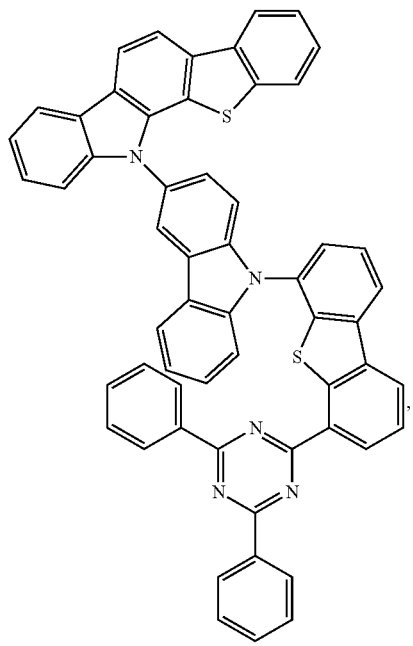
Compound 509
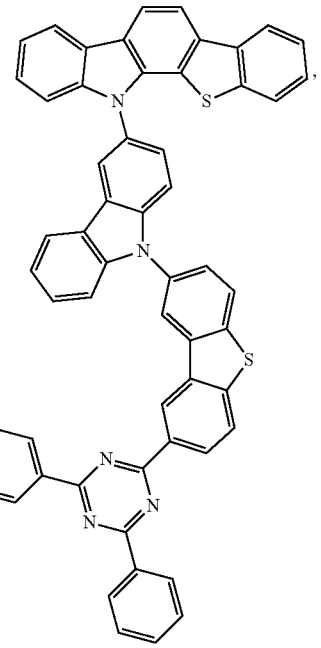
Compound 505
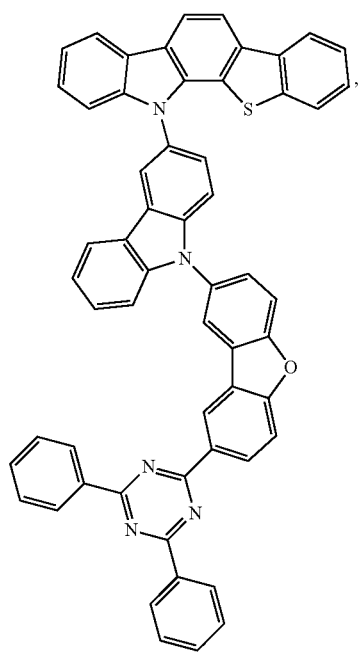
Compound 517
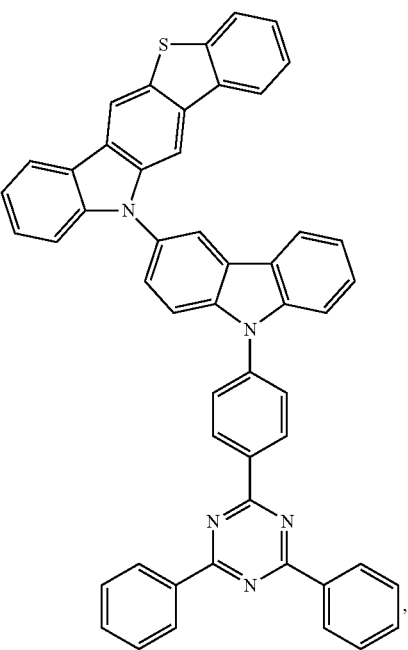

Compound 513
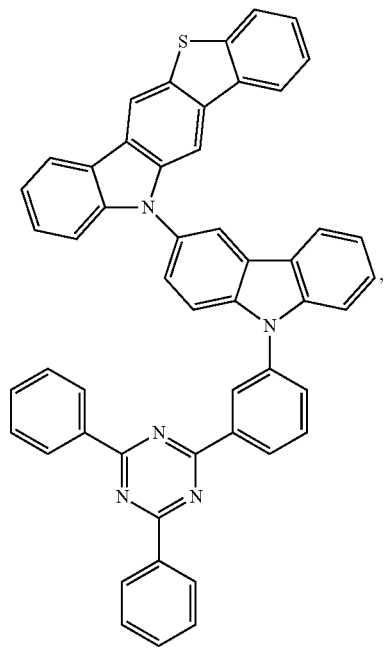
Compound 521
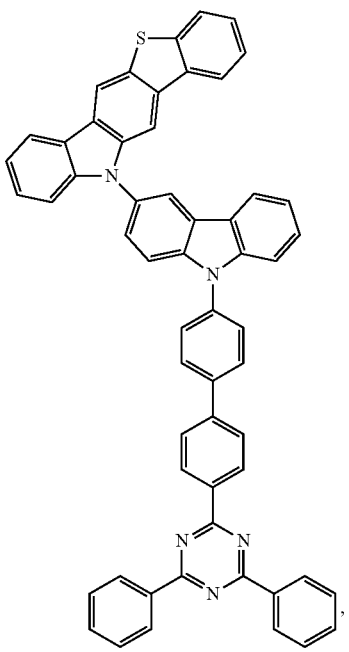
Compound 525
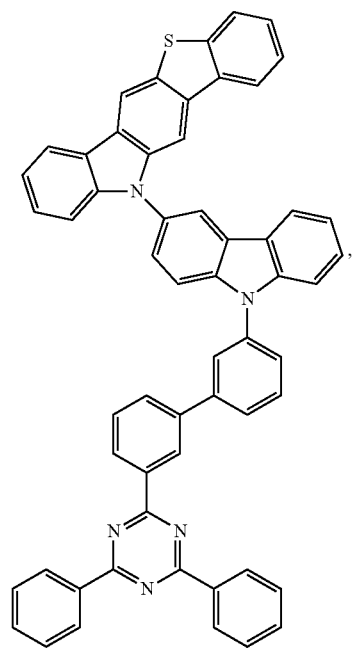
Compound 545
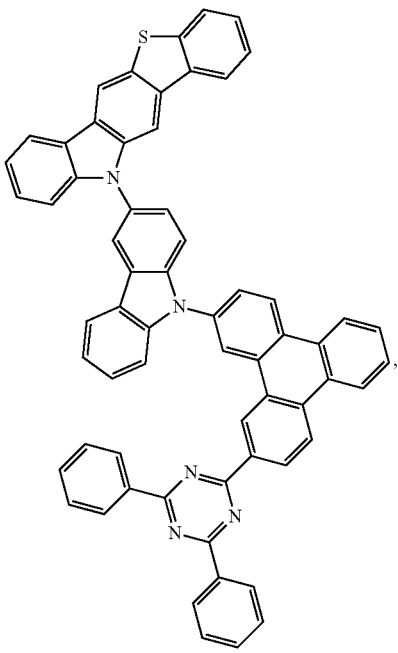

Compound 549
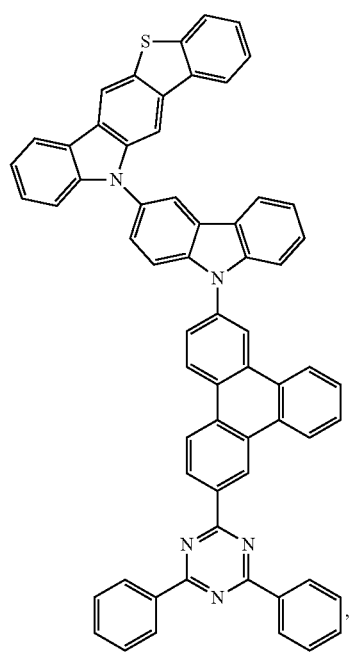
Compound 553
Compound 557
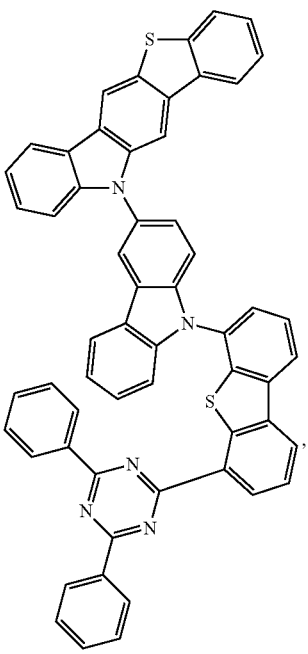
Copound 569
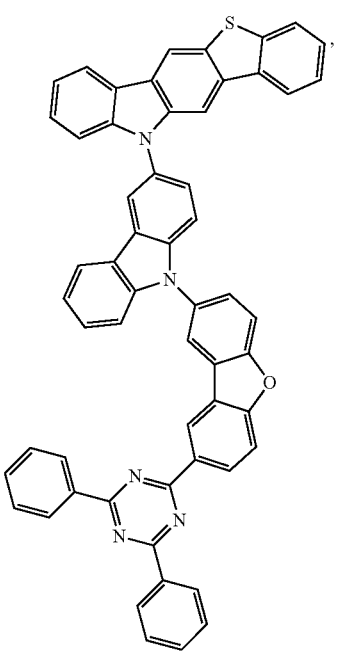

Compound 573
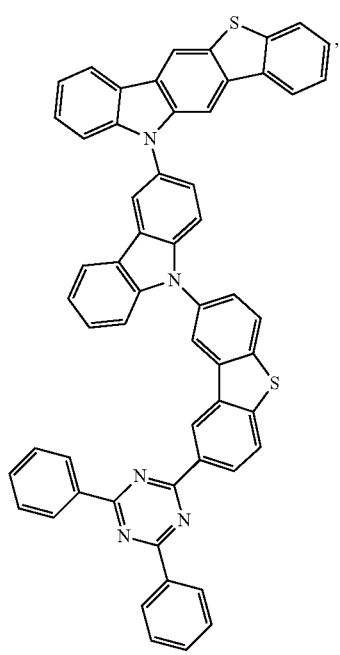
Compound 577
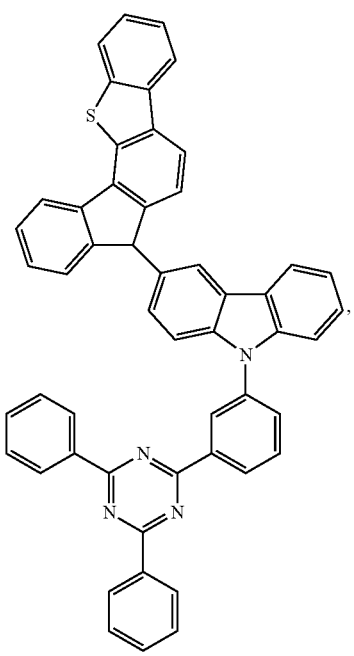
Compound 581
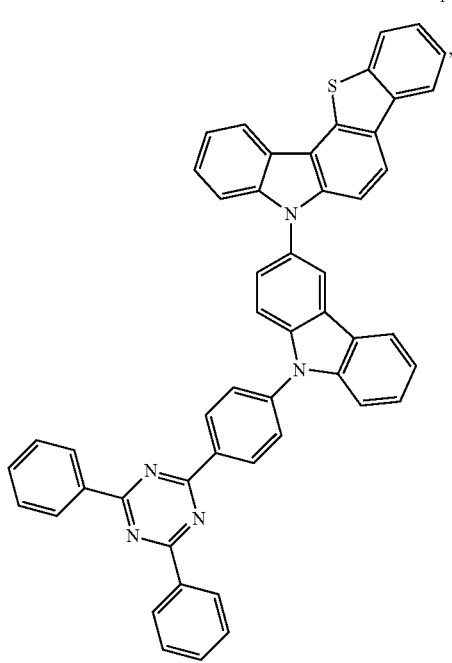
Compound 589
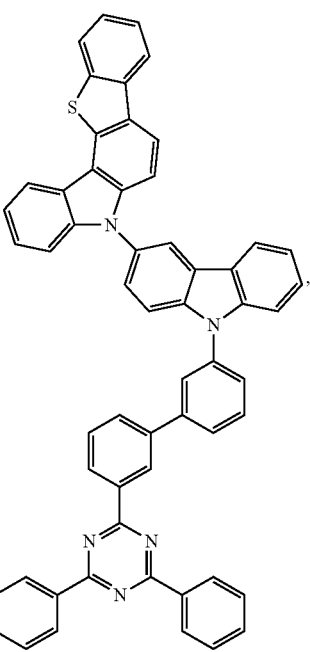

Compound 585
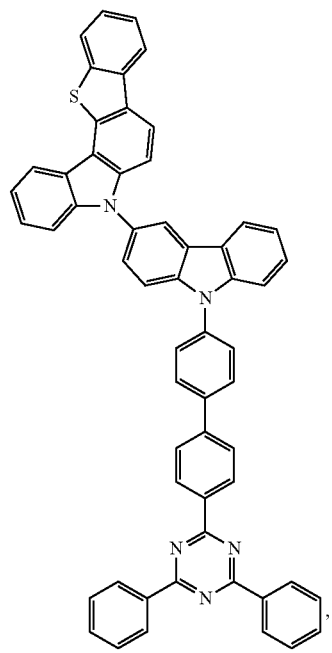
Compound 613
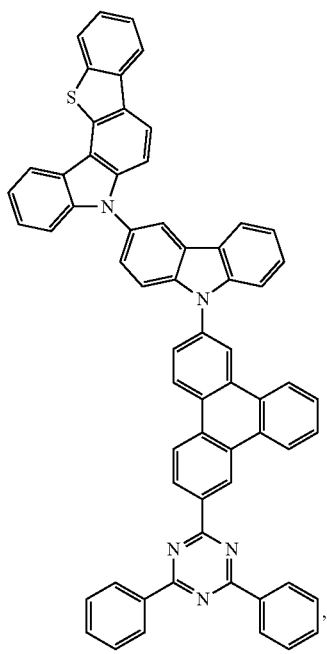
Compound 609
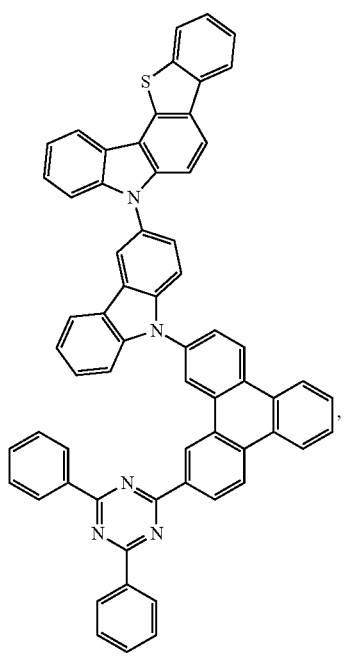
Compound 617
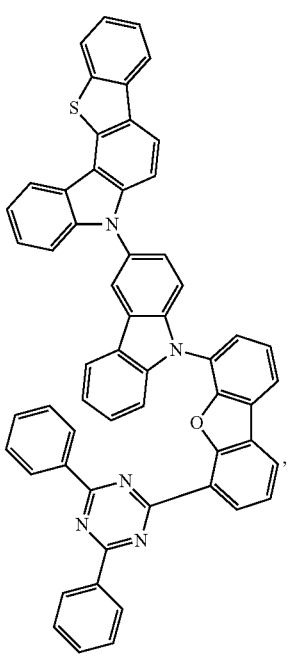

-continued
Compound 621
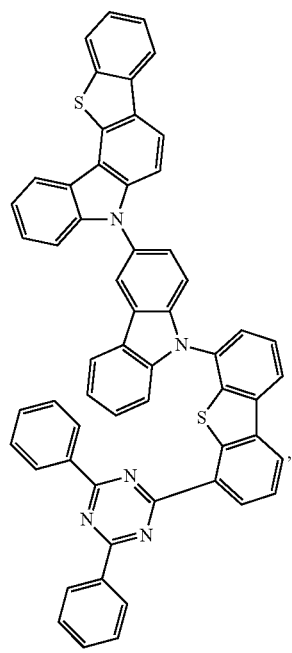
Compound 637
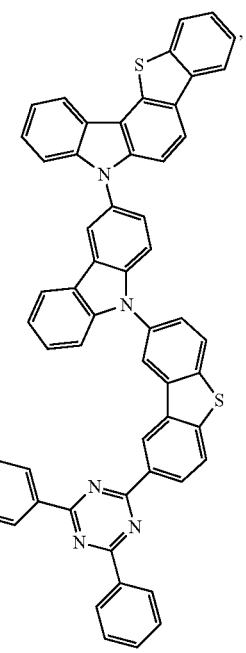
Compound 633
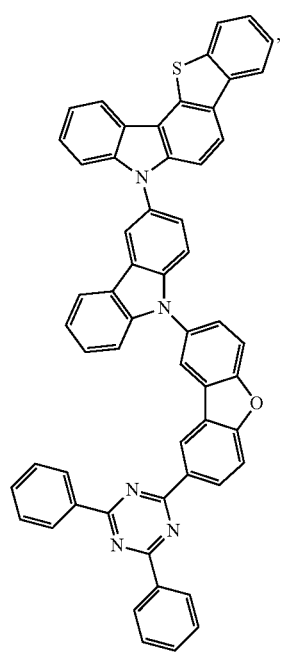
Compound 645
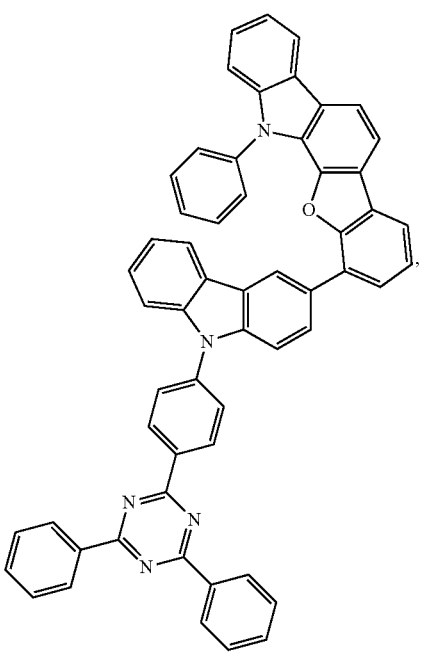

-continued
Computer 641
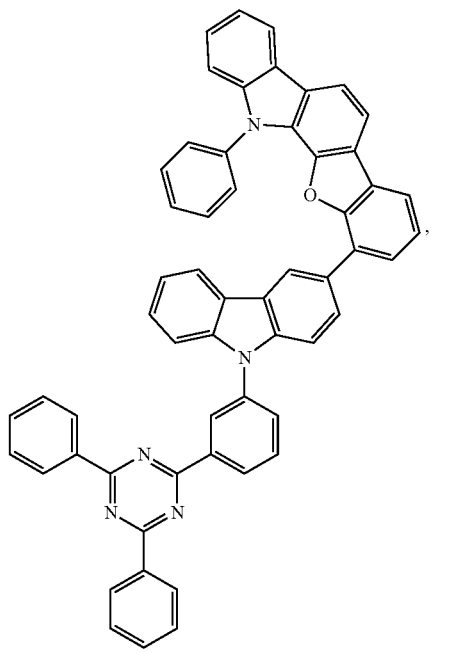
-continued
Compound 649
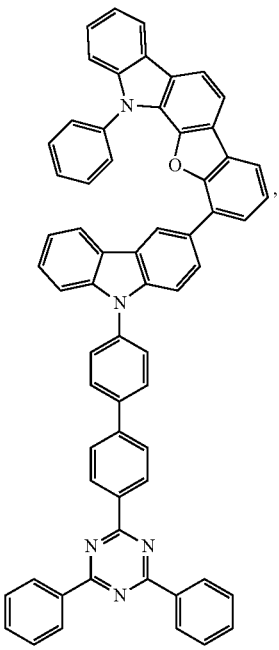
Computer 653
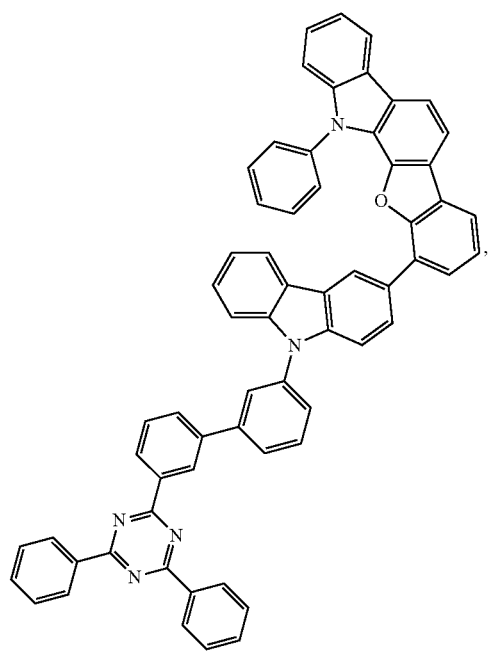
Compound 673
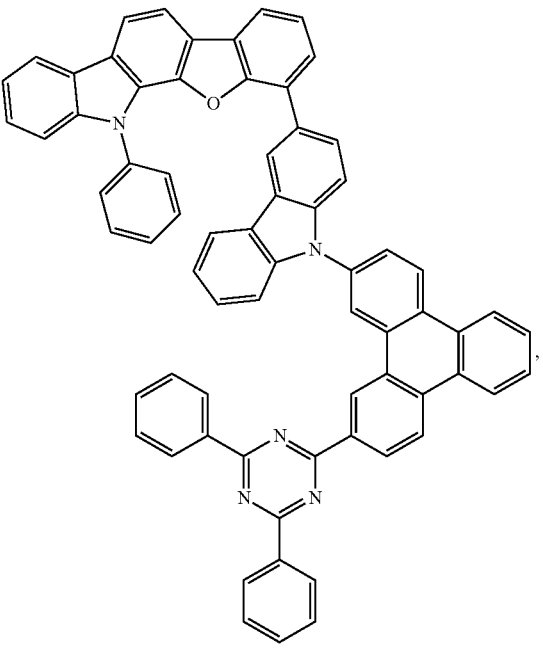

Compound 677
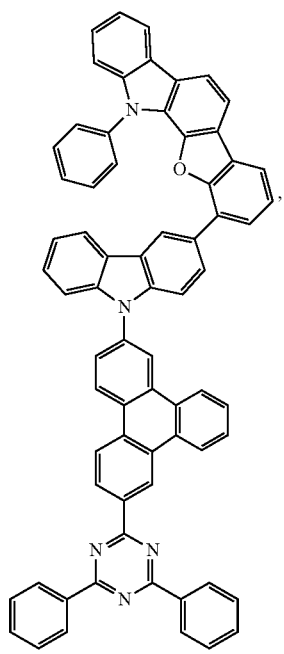
Compound 685
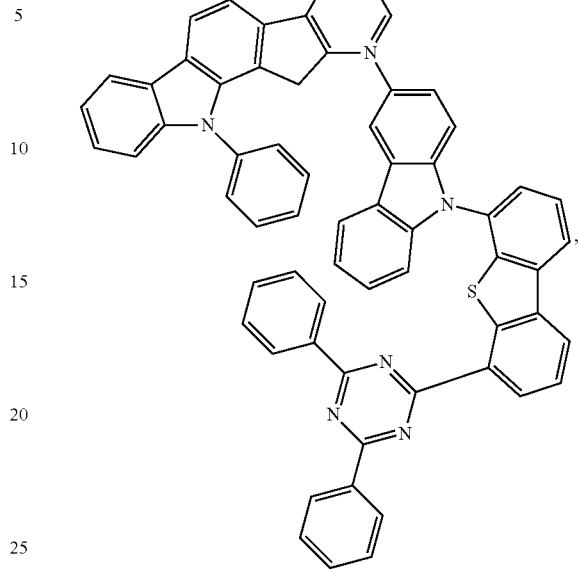
Compound 681
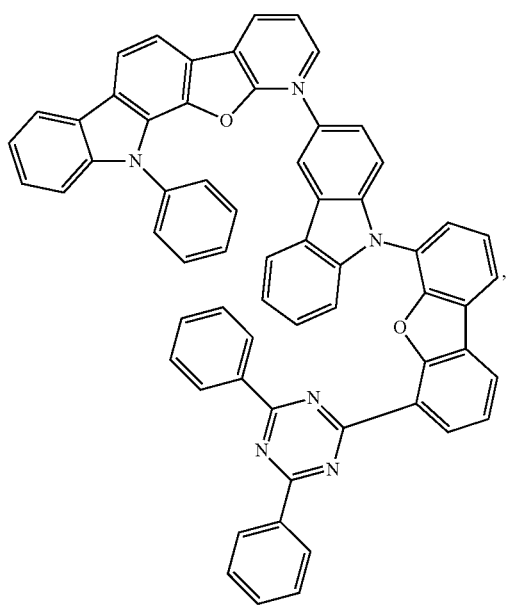
Compound 697
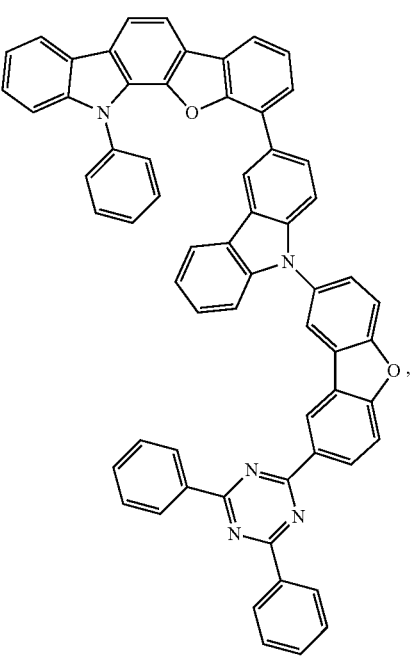

-continued
Compound 701
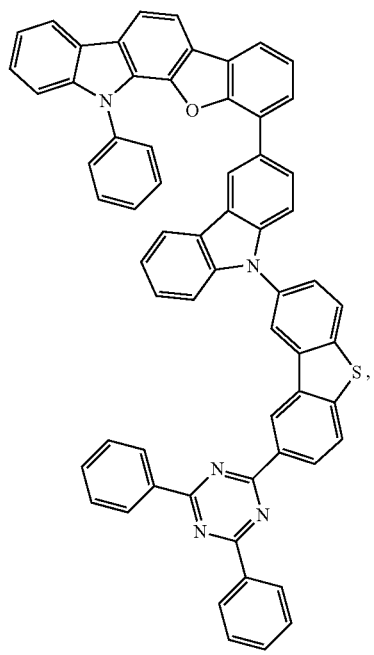
Compound 705
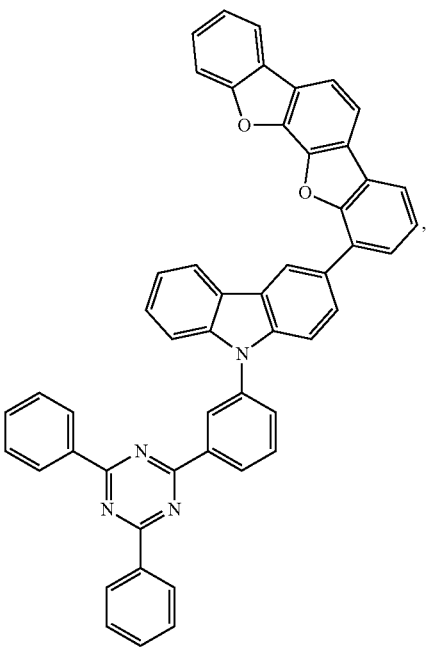
Compound 709
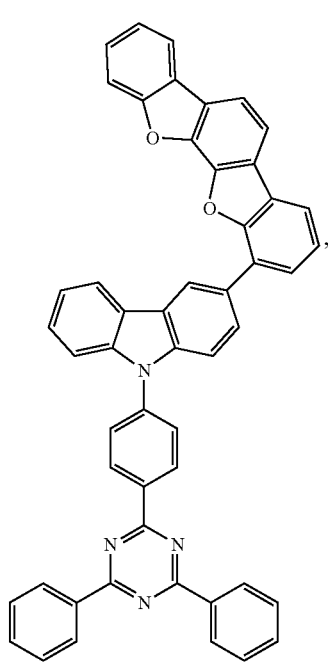
Compound 717
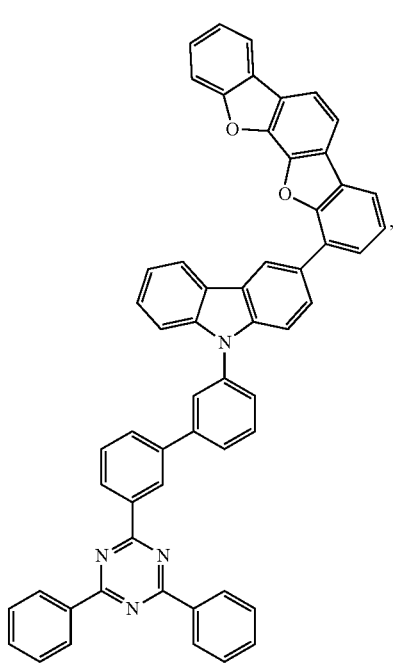

Compound 713
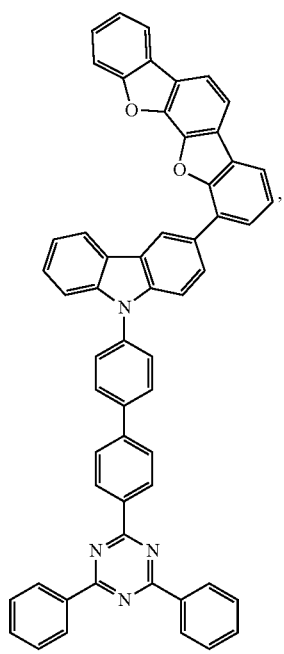
Compound 741
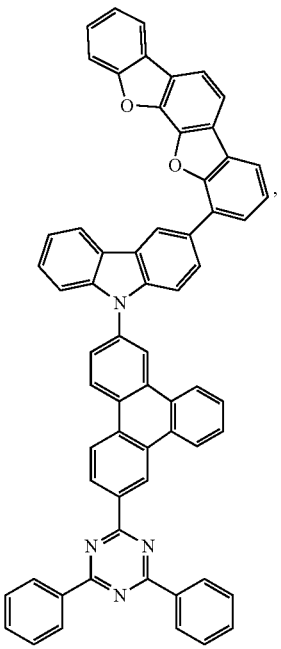
Compound 737
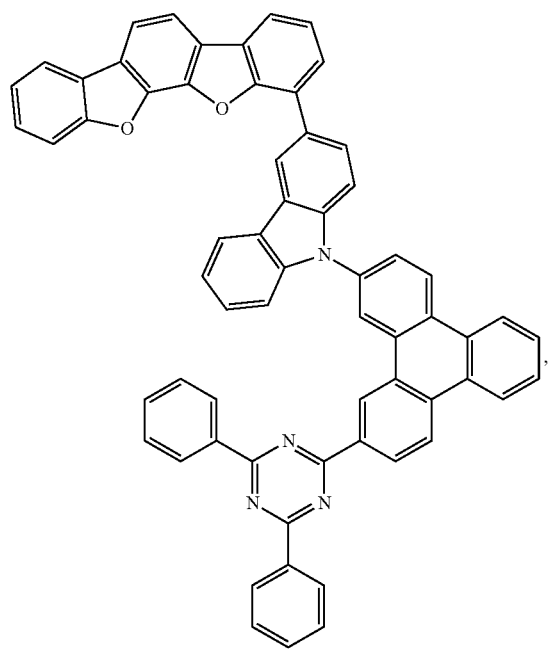
Compound 745
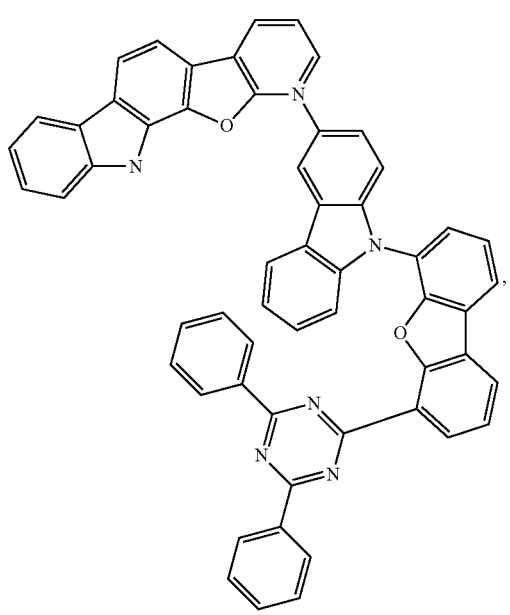

Compound 749
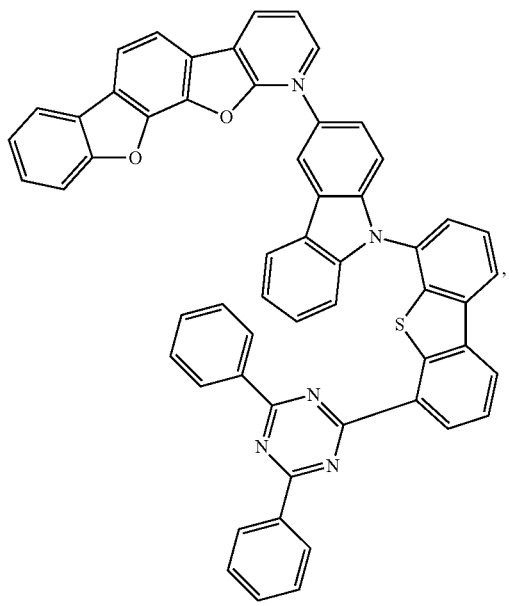
Compound 765
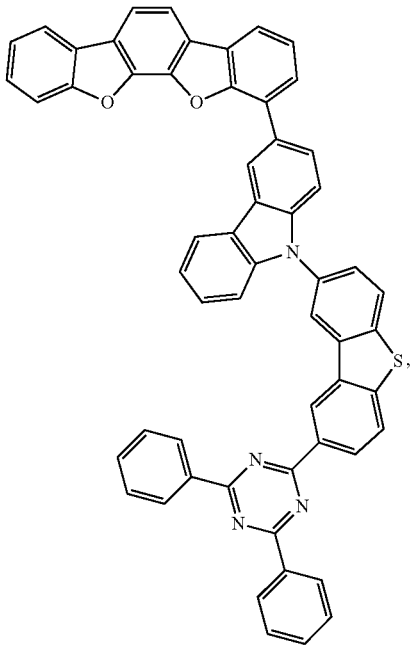
Compound 761
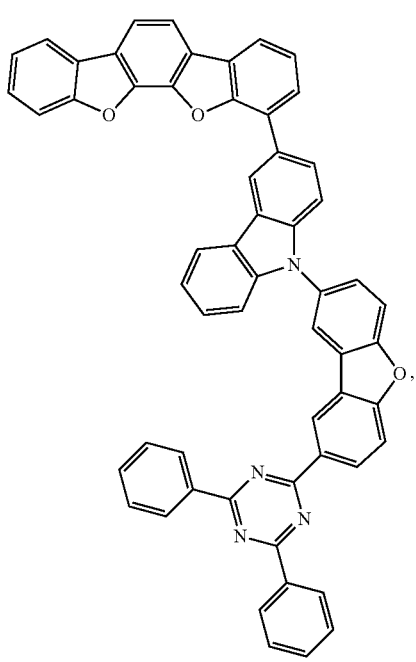
Compound 773
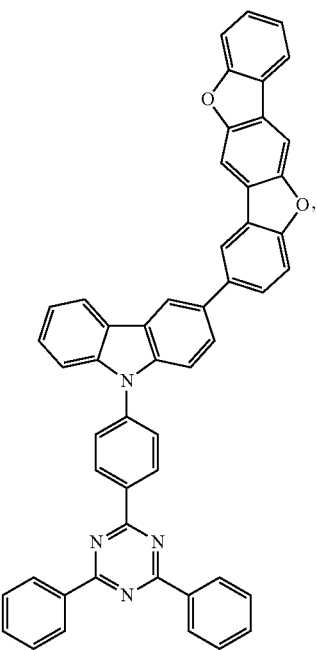

Compound 769
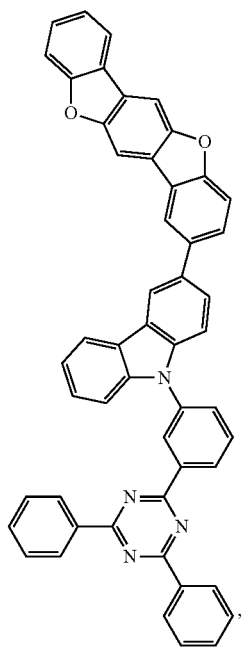
Compound 777
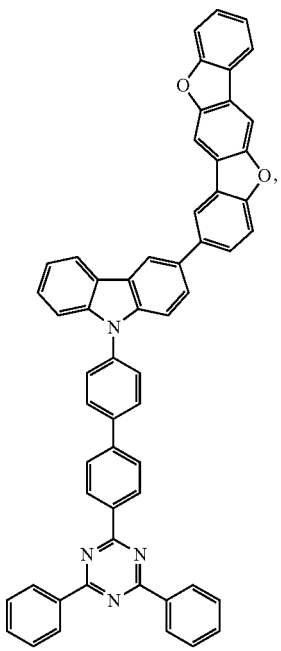
Compound 781
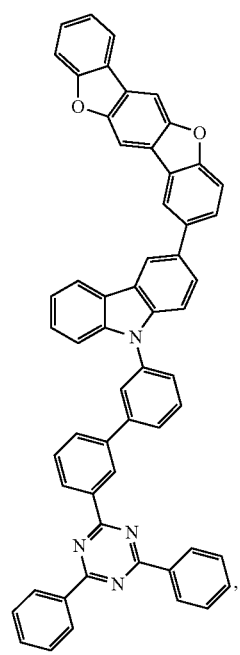
Compound 801
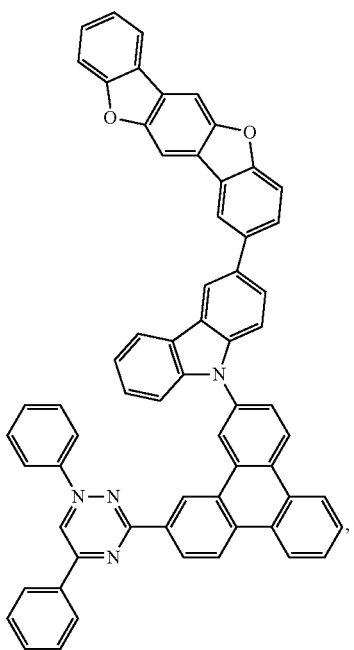

Compound 805
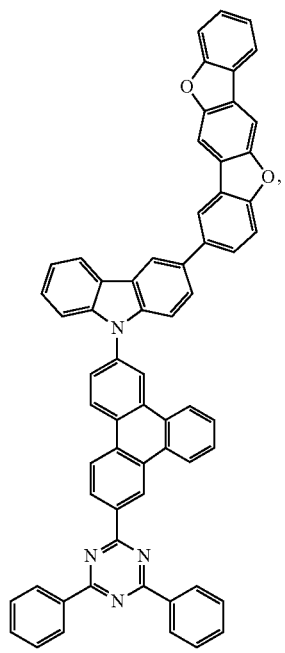
Compound 809
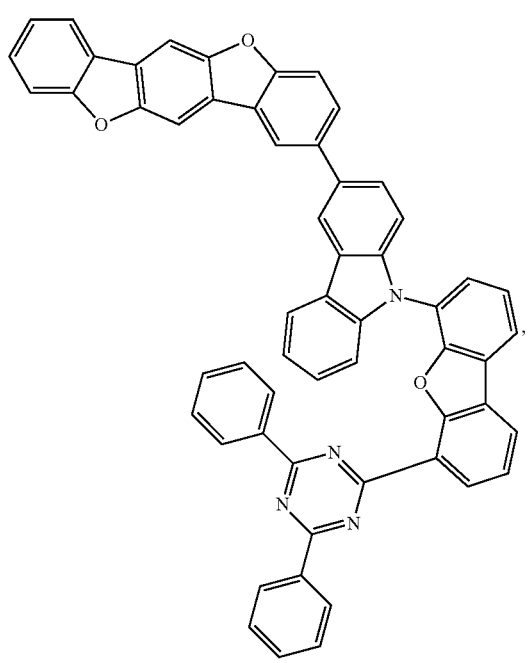
Compound 813
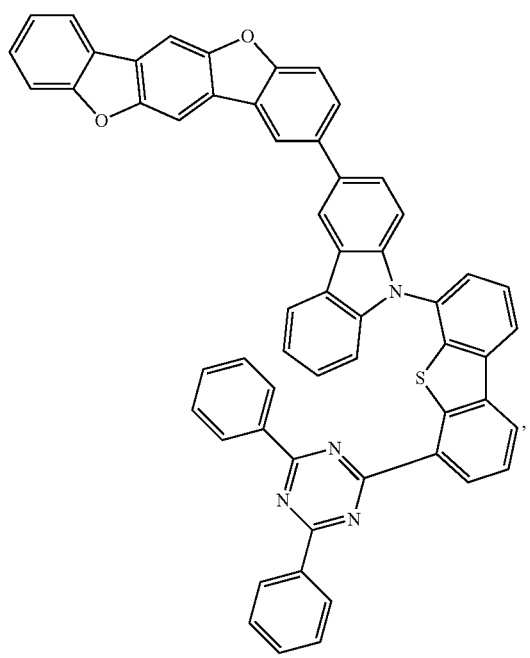
Compound 825
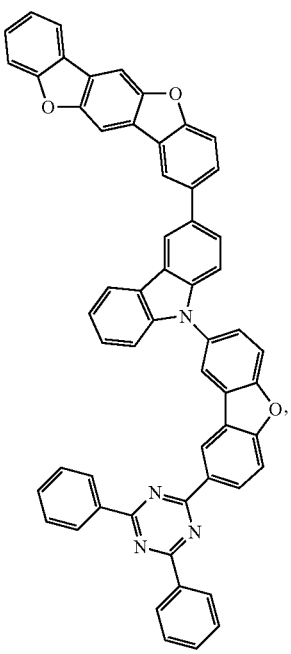

651
-continued
Compound 829
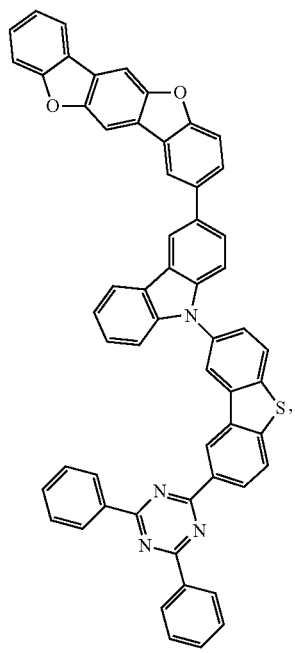
652
-continued
Compound 833
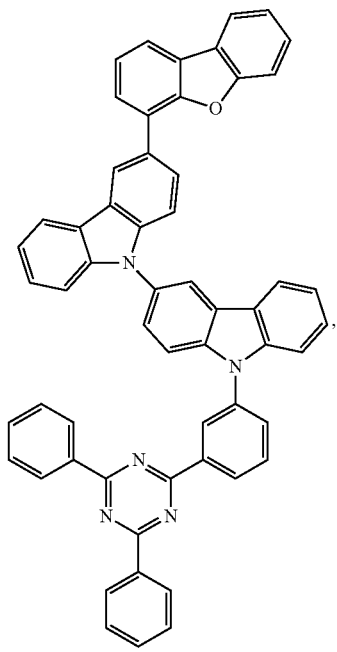
Compound 837
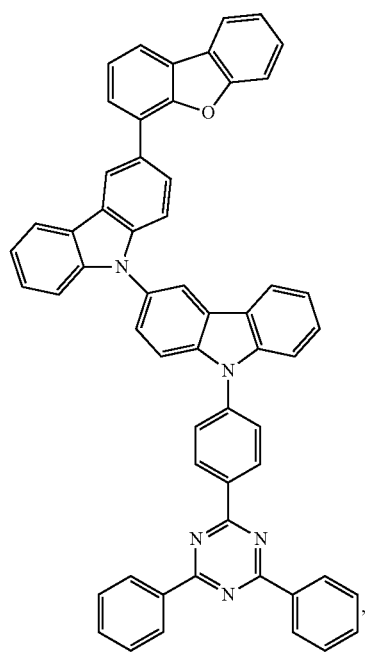
Compound 845
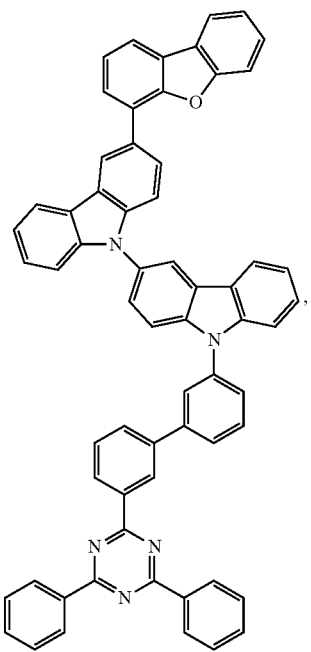

Compound 841
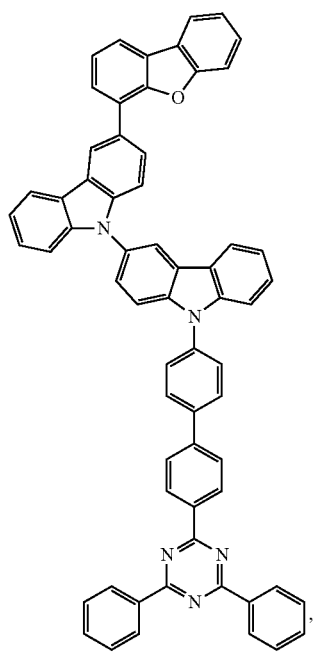
Compound 869
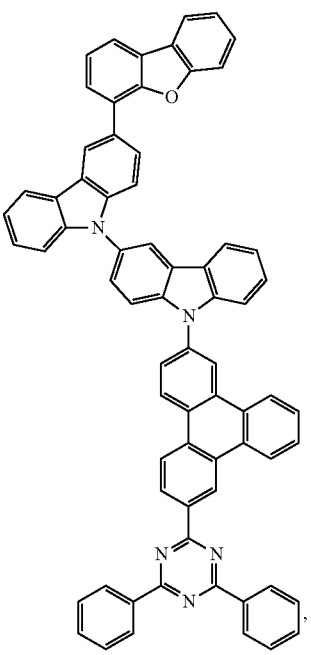
Compound 865
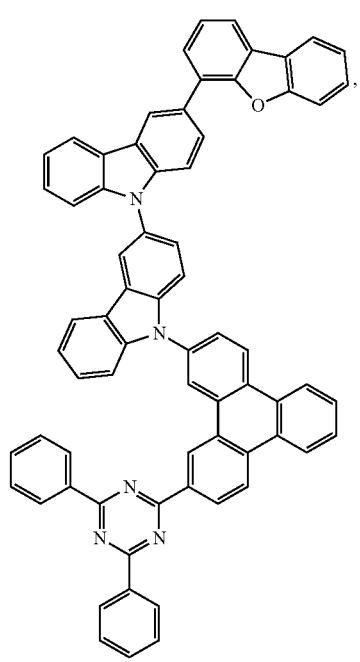
Compound 873
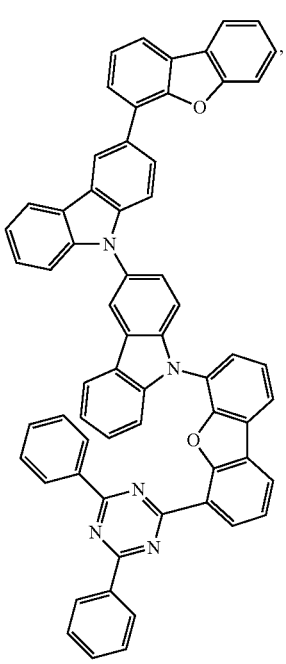

Compound 877
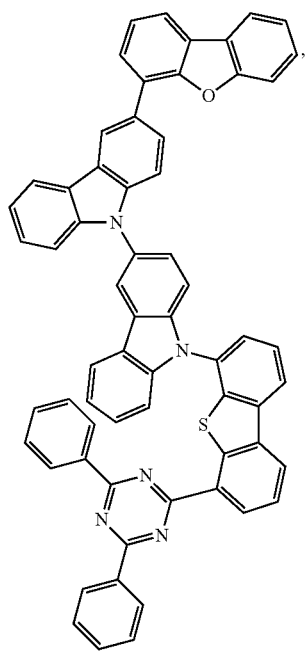
Compound 889
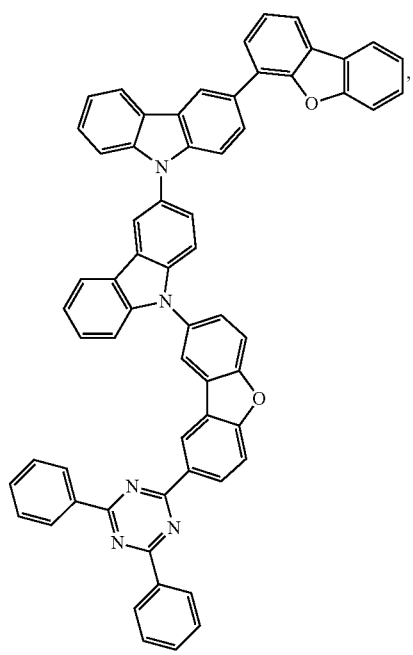
Compound 893
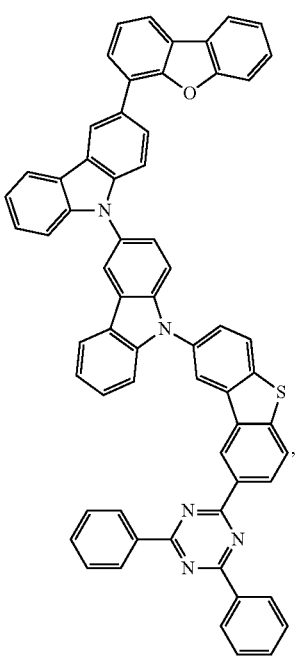
Compound 1029
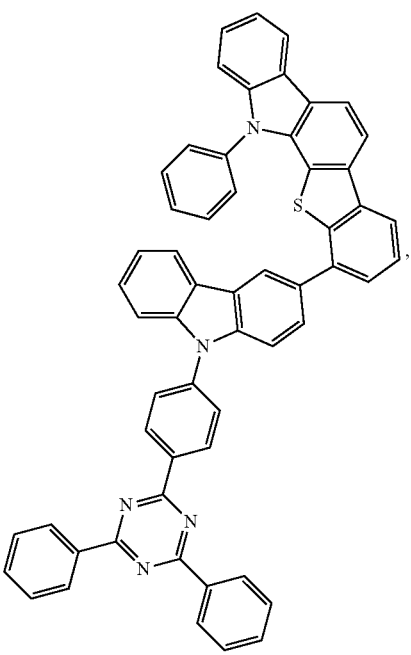

Compound 1025
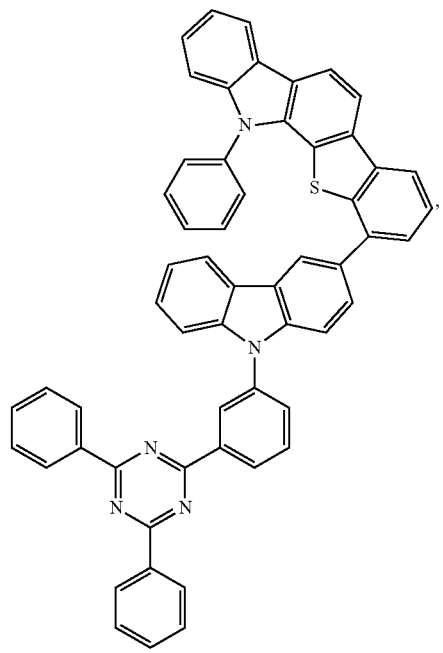
Compound 1033
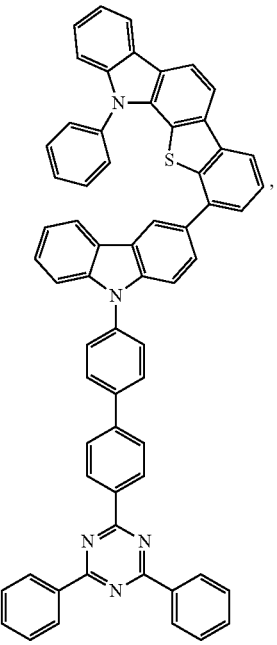
Compound 1037
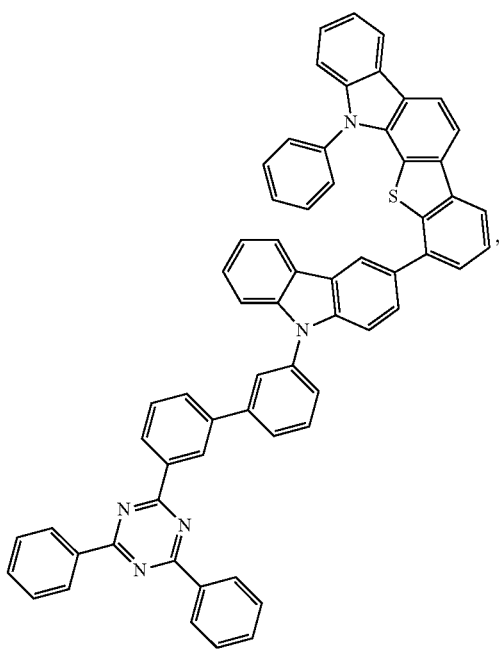
Compound 1057
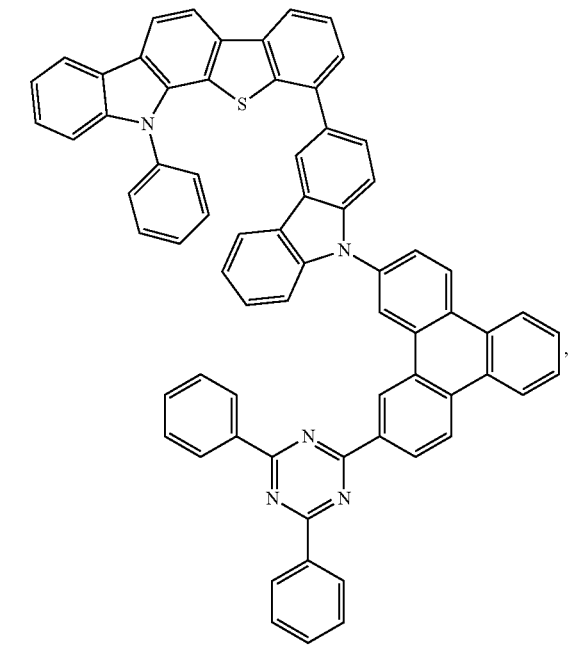

Compound 1061
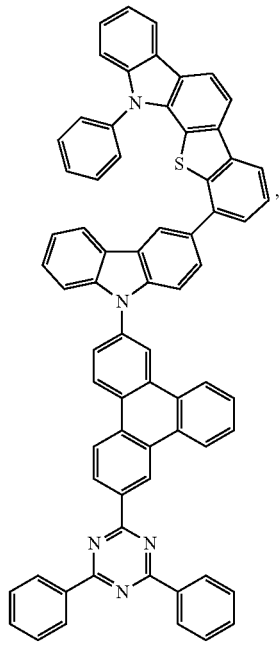
Compound 1069
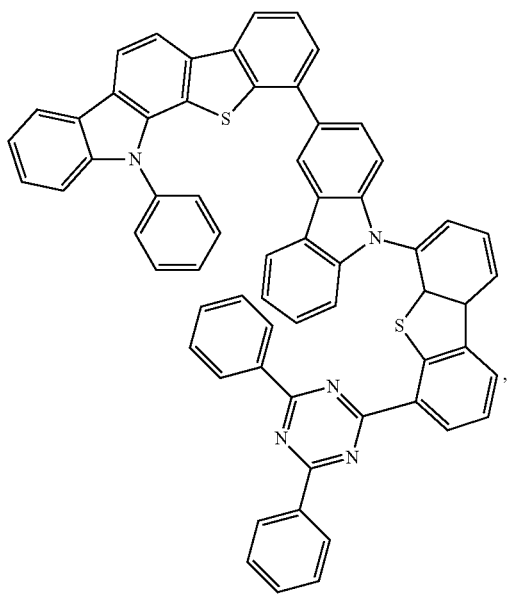
Compound 1065
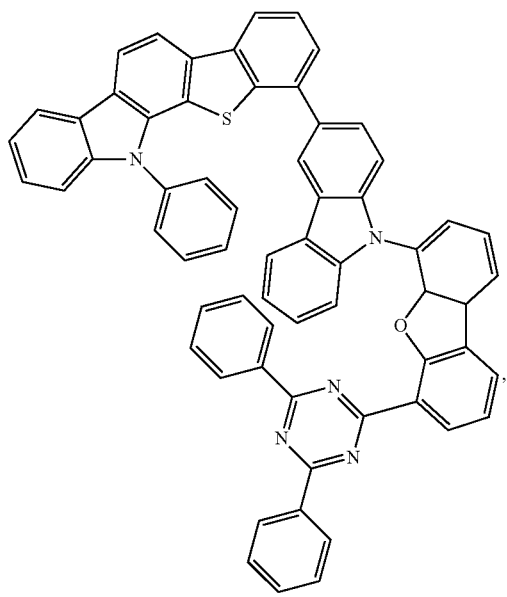
Compound 1081
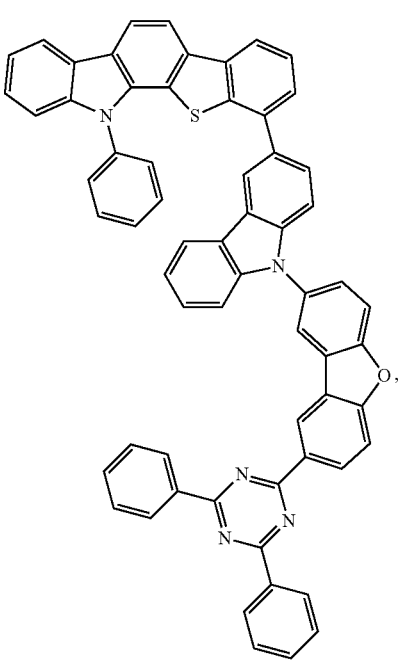

Compound 1085
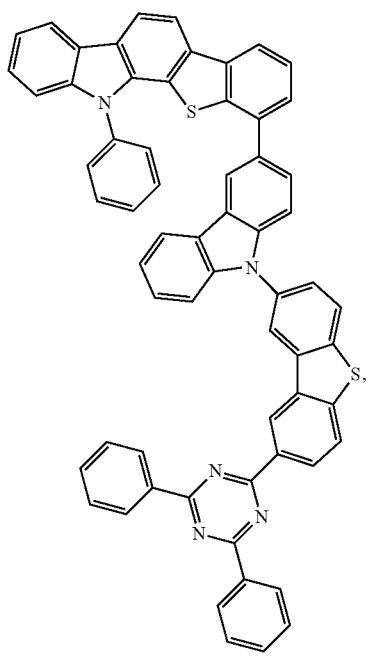
Compound 1089
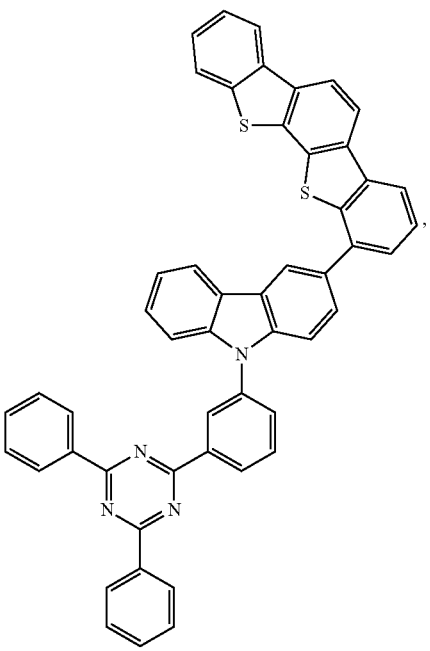
Compound 1093
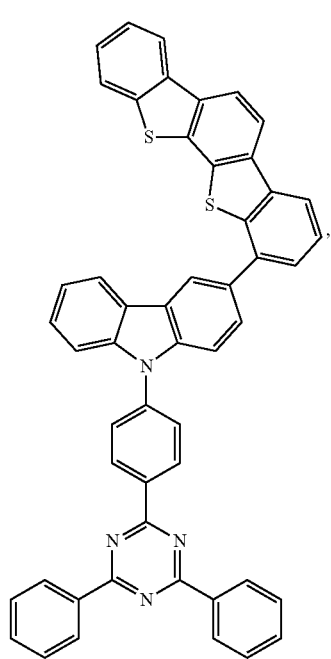
Compound 1111
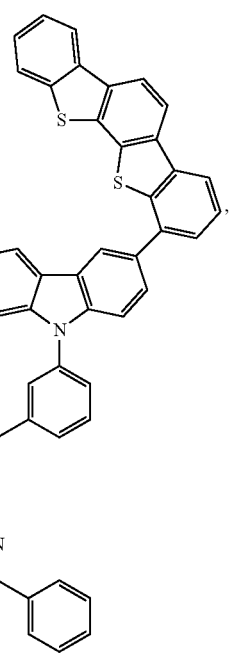

Compound 1097
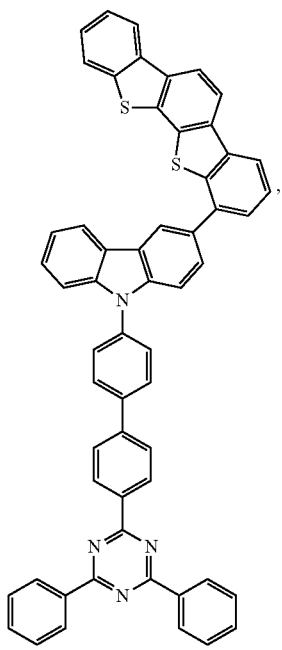
Compound 1125
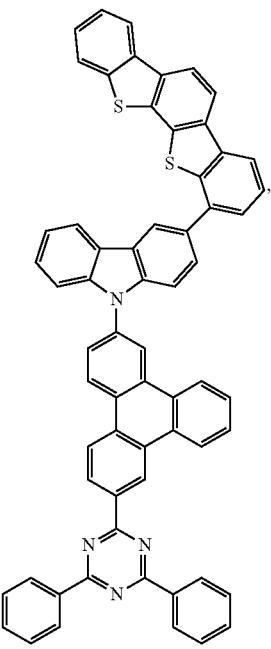
Compound 1121
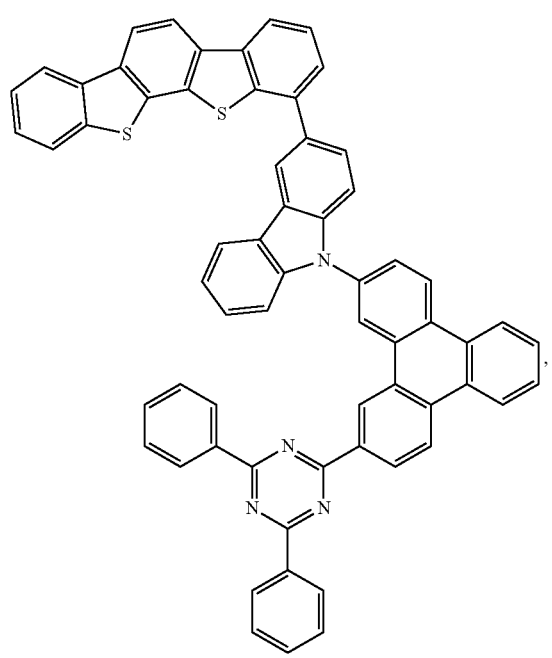
Compound 1129
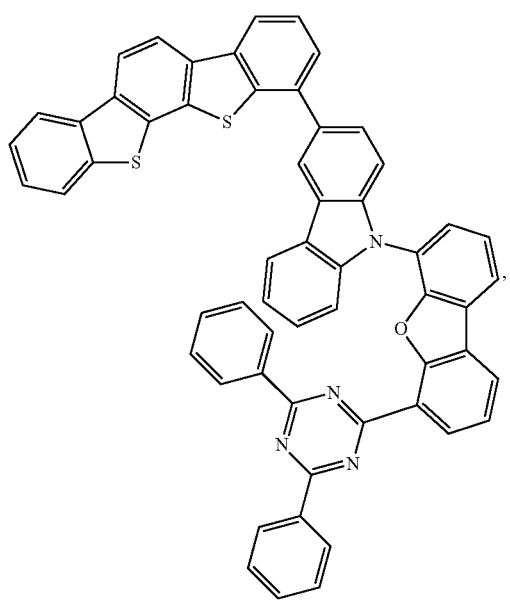

Cmpound 1133
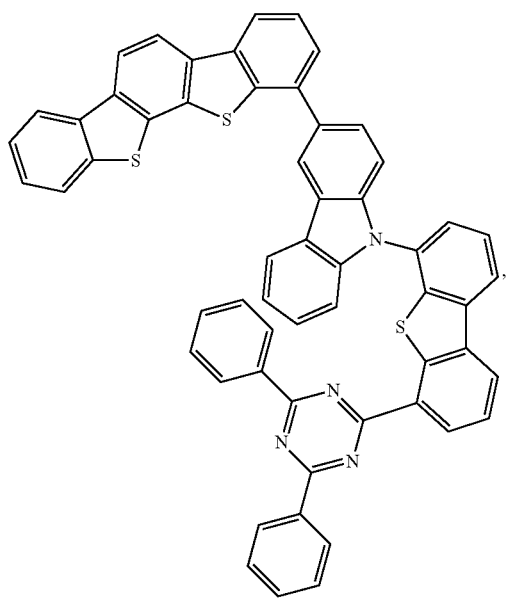
Compound 1149
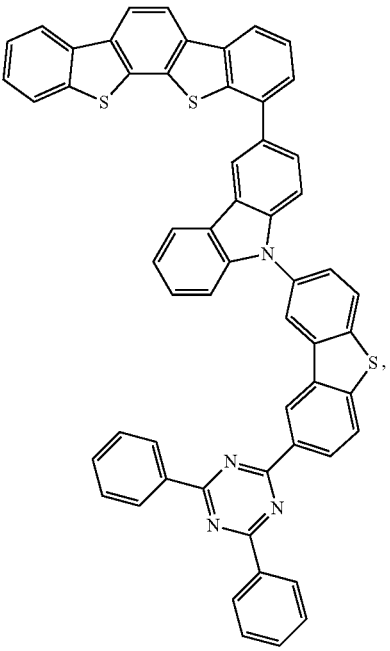
Complound 1145
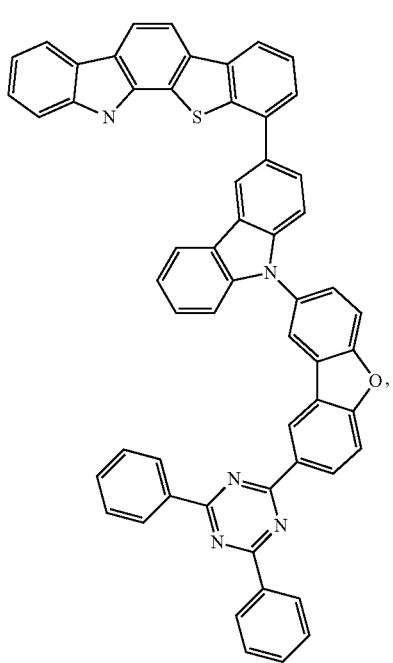
Compound 1157
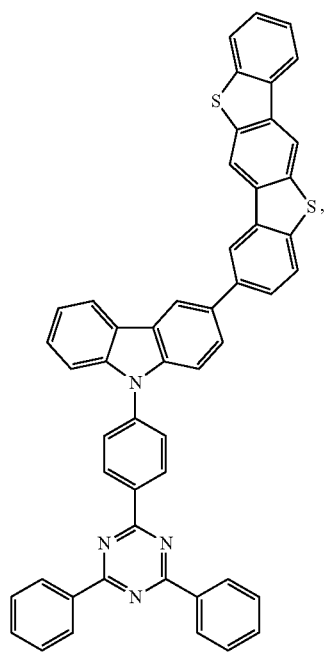

Compound 1153
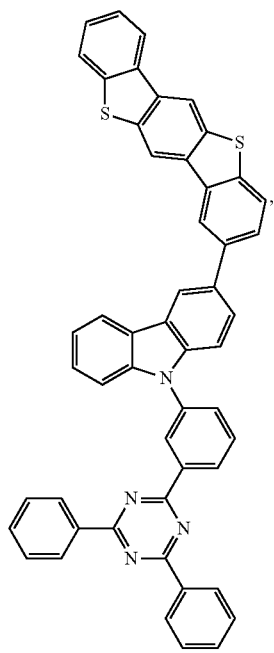
Compound 1161
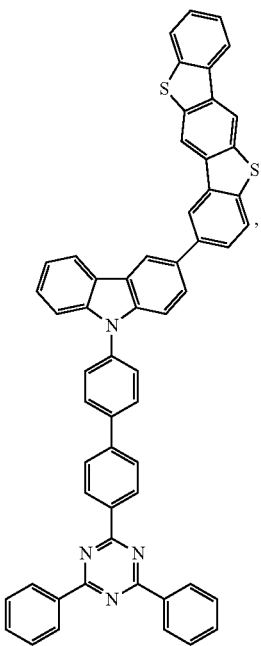
Compound 1165
Compound 1185
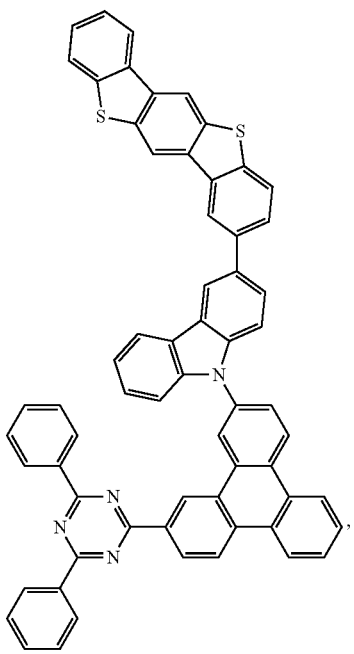

Compound 1189
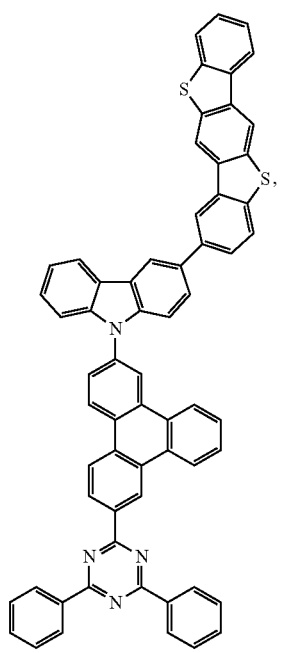
Compound 1197
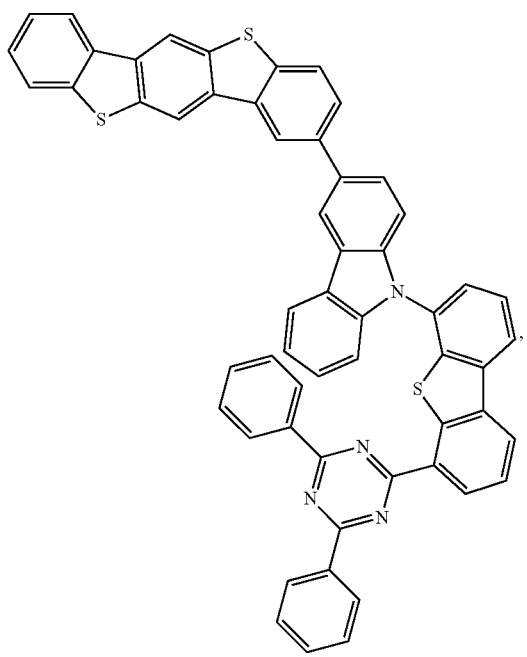
Compound 1193
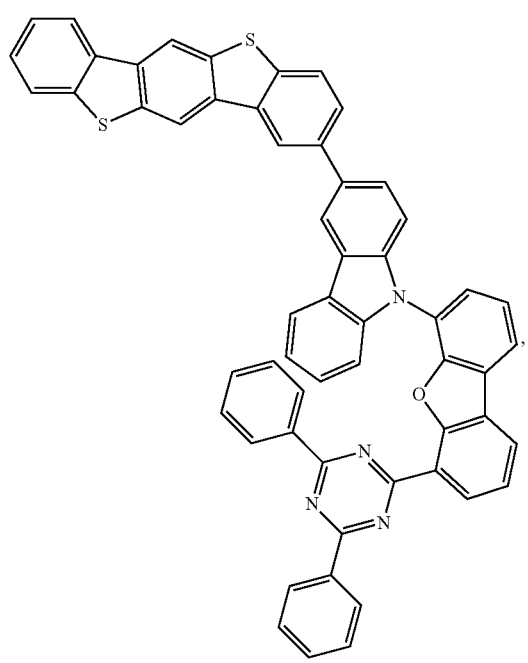
Compound 1209
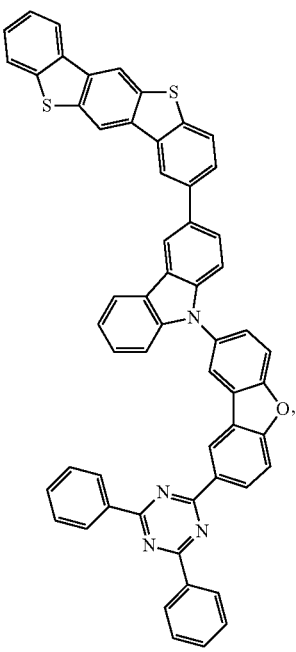

-continued
Compound 1213
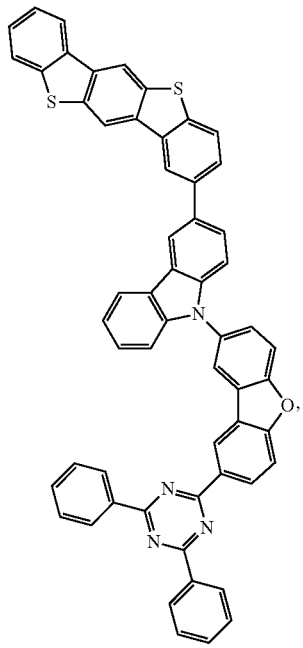
Compound 1217
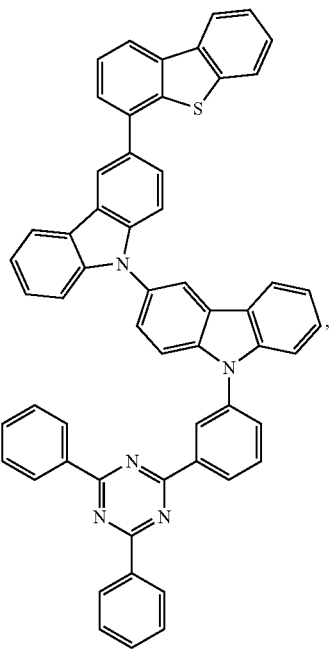
Compound 1221
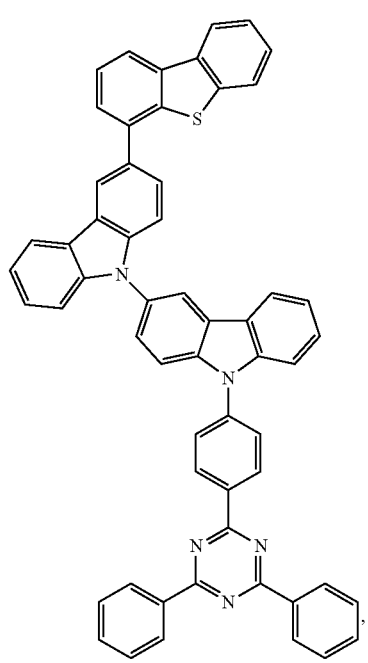
Compound 1229
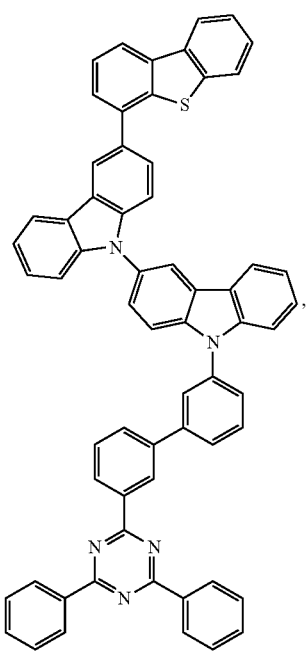

Compound 1225
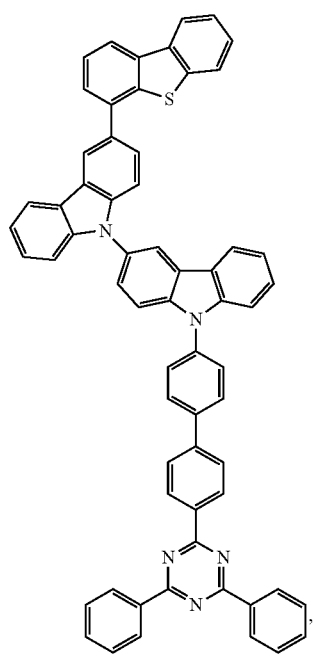
Compound 1253
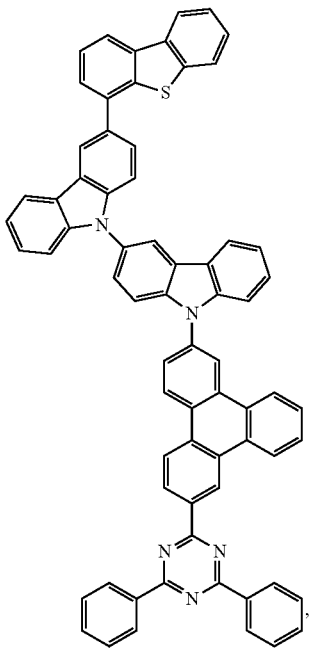
Compound 1249
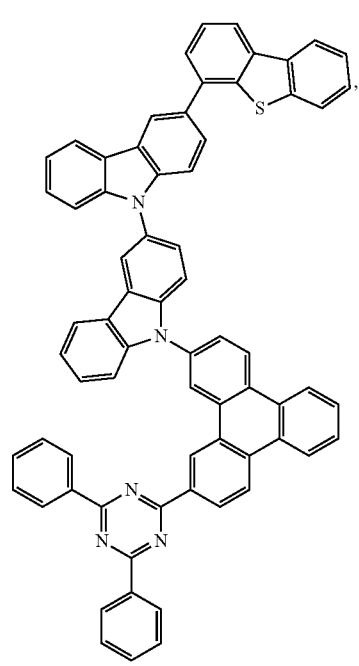
Compound 1257
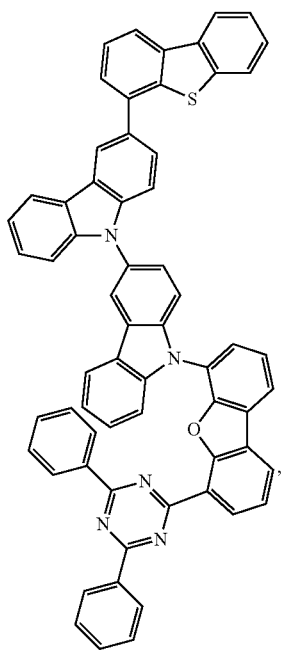

Compound 1261
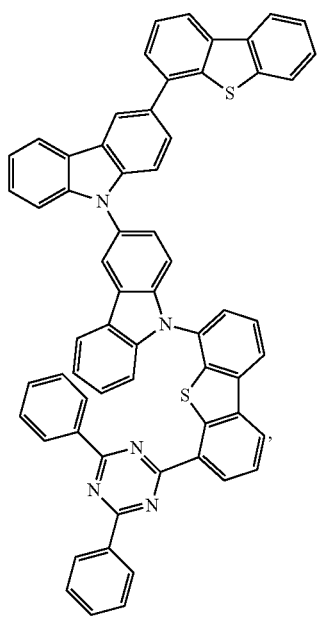
Compound 1177
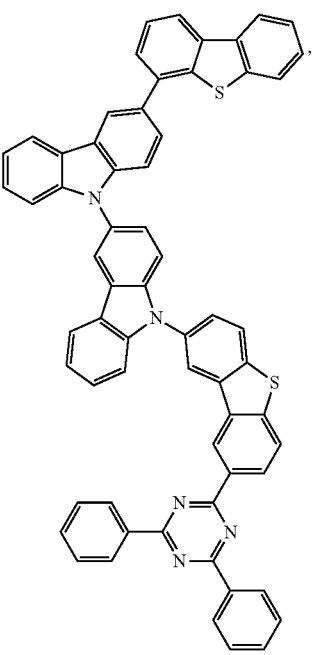
Compound 1173
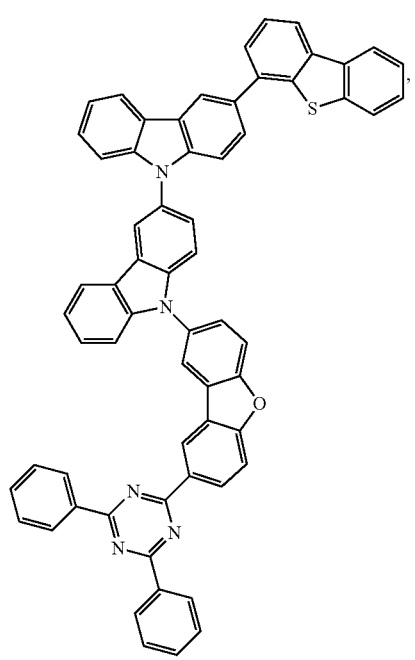
Compound 1477
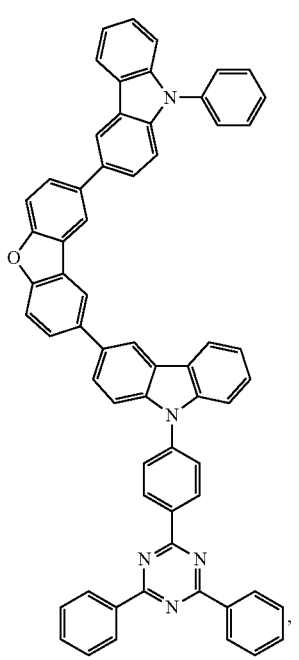

Compound 1473
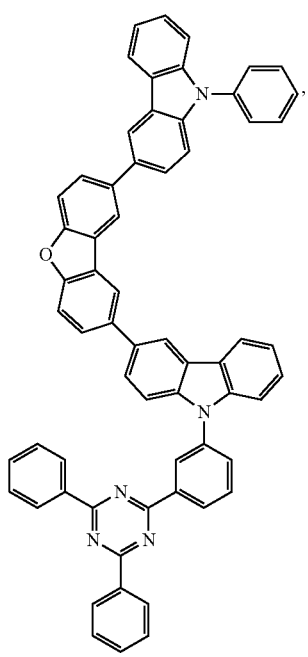
Compound 1481
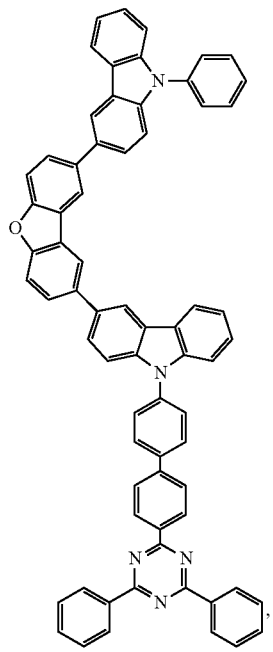
Compound 1485
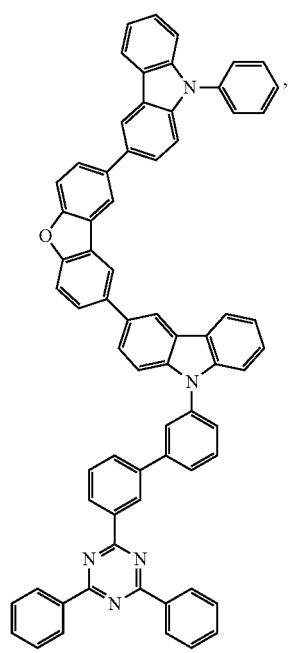
Compound 1505
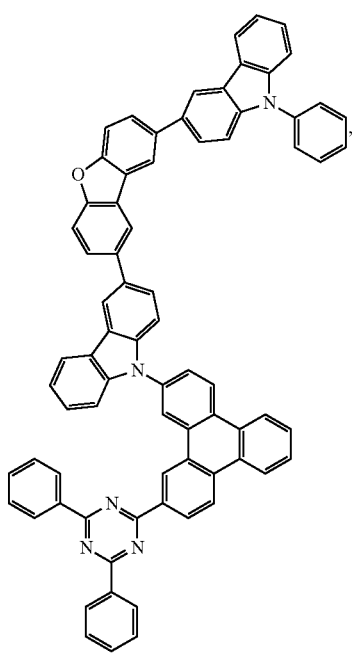

Compound 1509
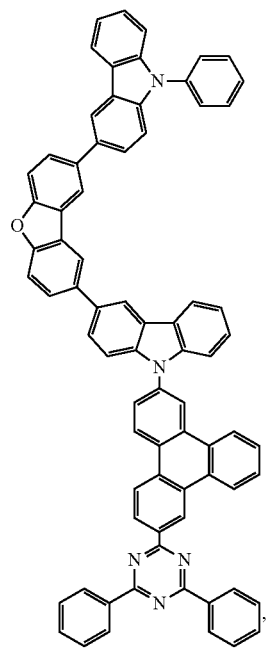
Compound 1513
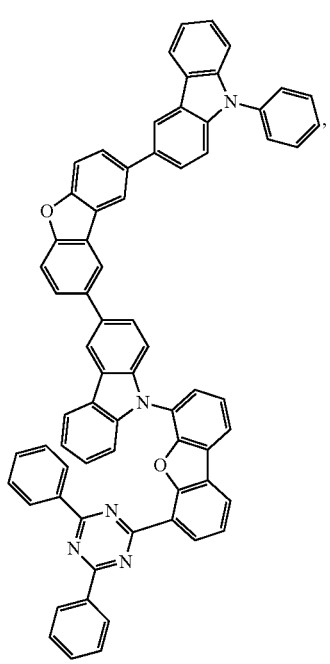
Compound 1517
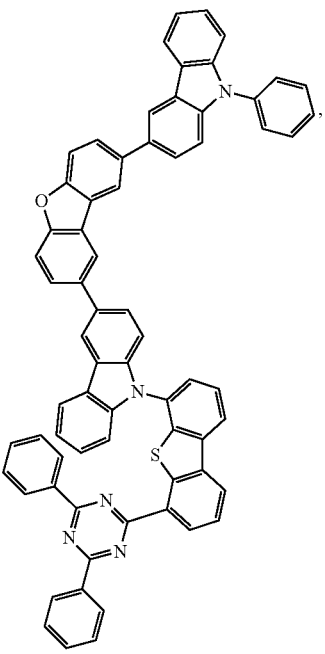
Compound 1529
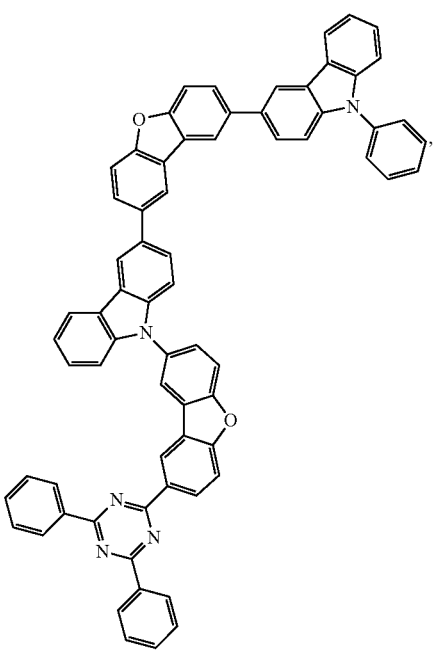

Compound 1533
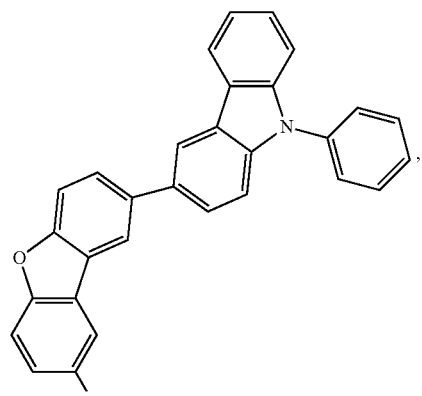
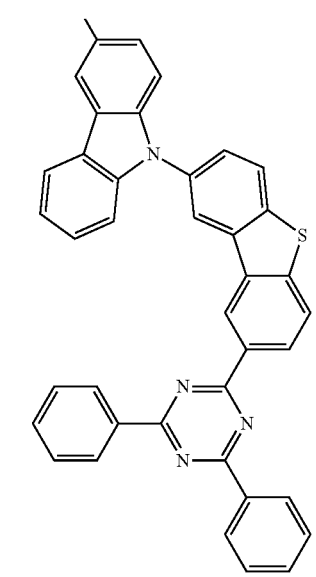
Compound 1601
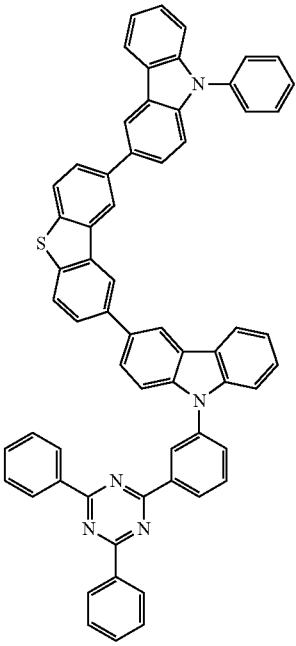
Compound 1605
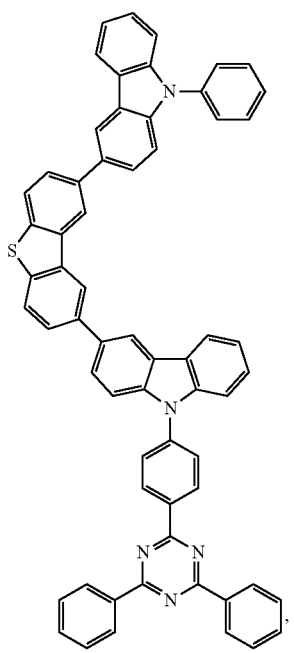
Compound 1613
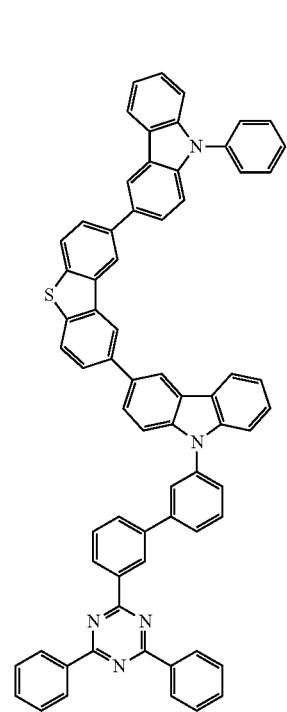

Compound 1609
Compound 1637
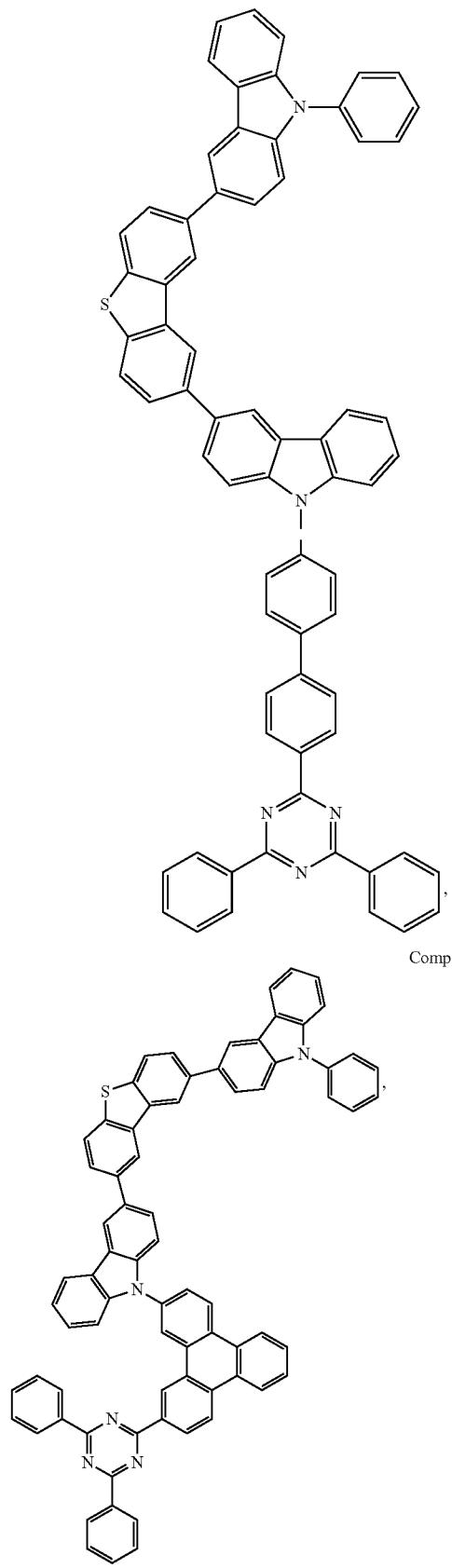
Compound 1633
Compound 1641
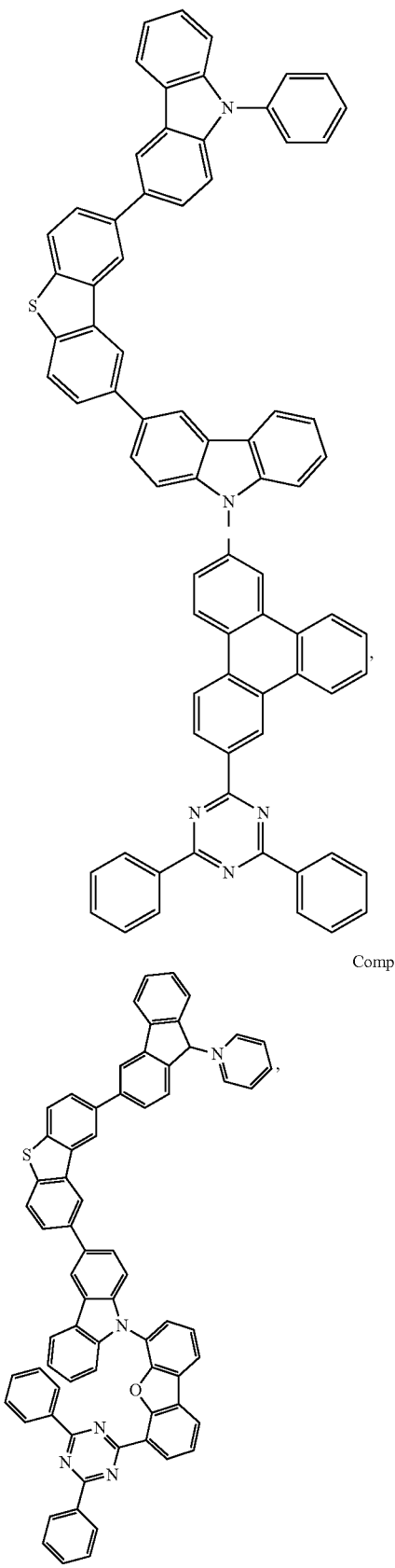

Compound 1645
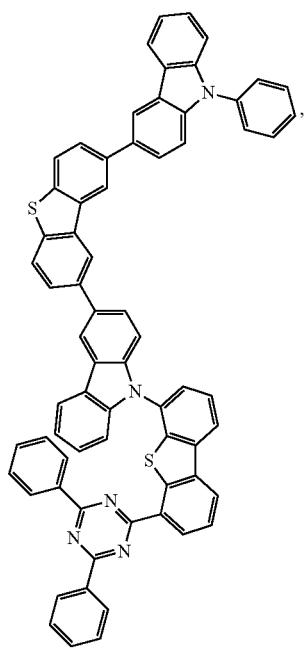
Compound 1661
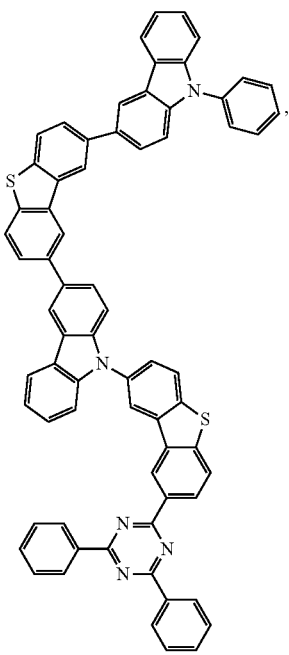
Compound 1657
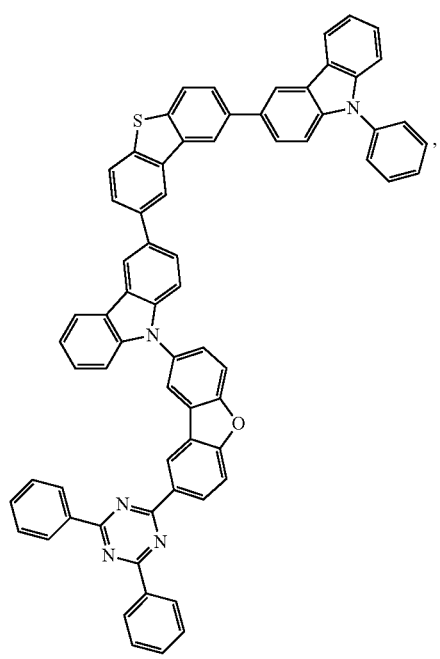
Compound 1861
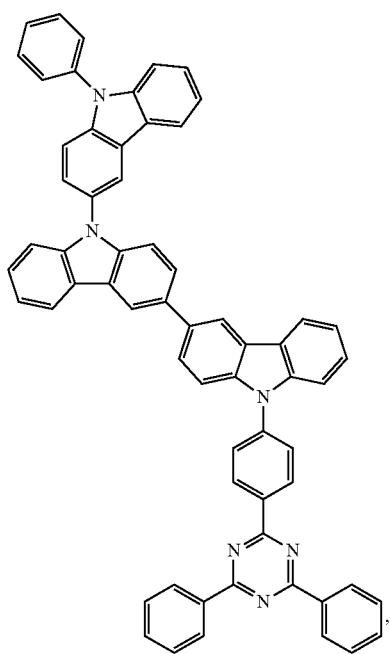

Compound 1857
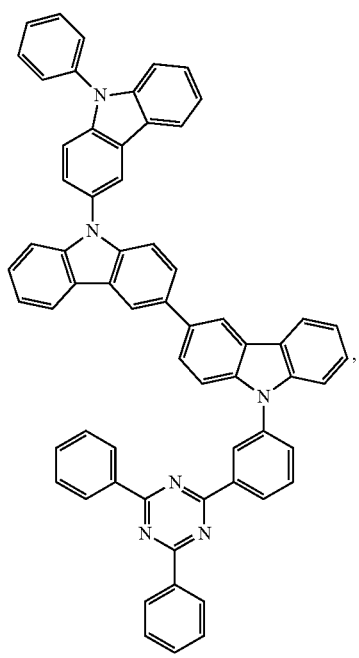
Compound 1865
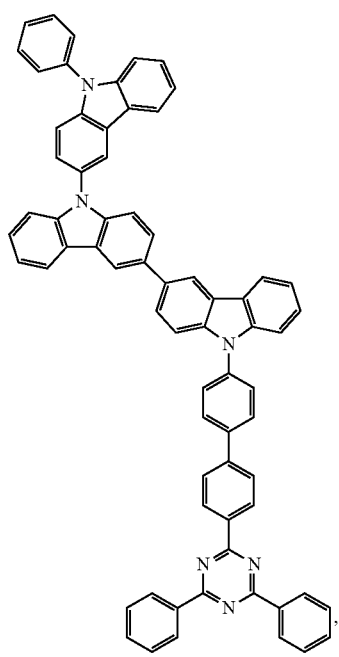
Compound 1869
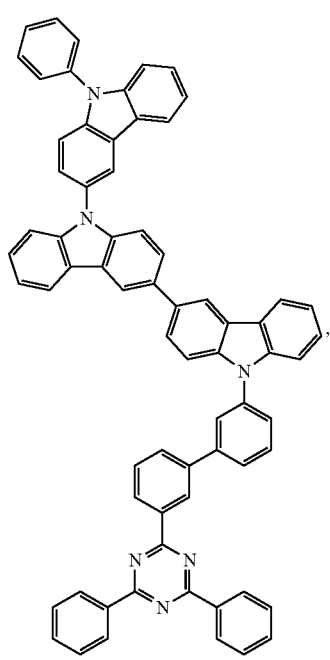
Compound 1889
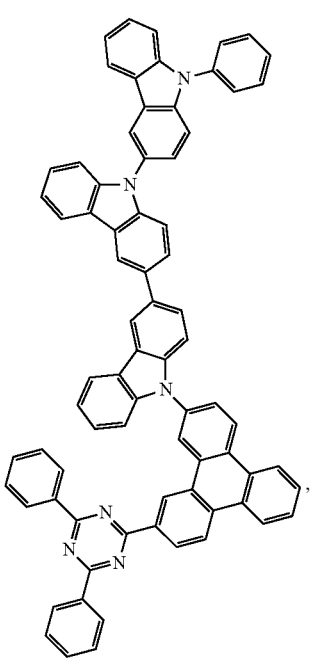

Compound 1893
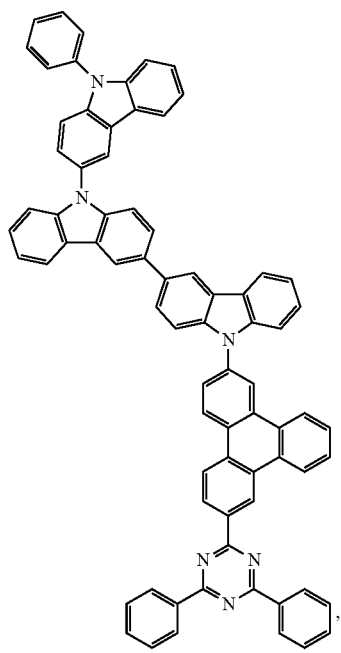
Compound 1897
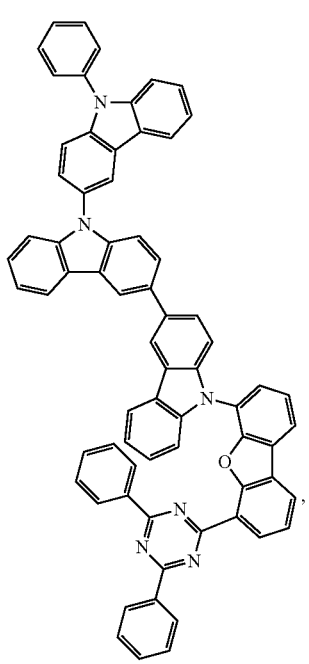
Compound 1901
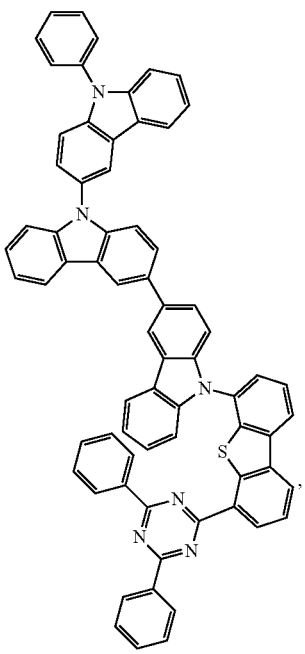
Compound 1913
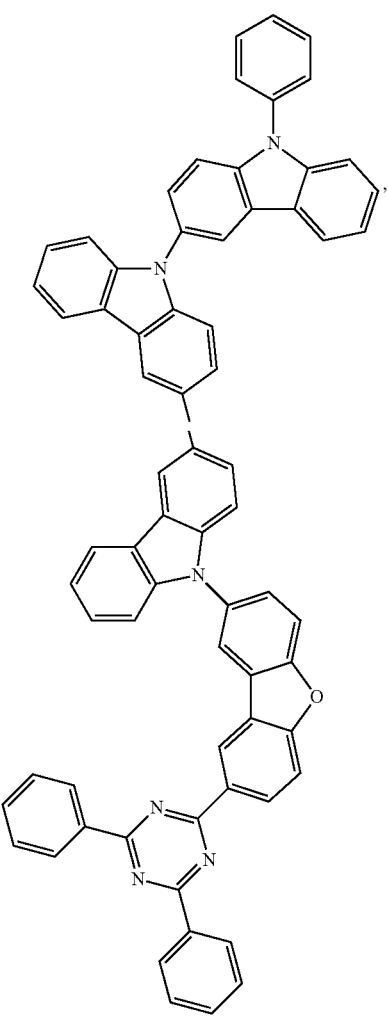

Compound 1917
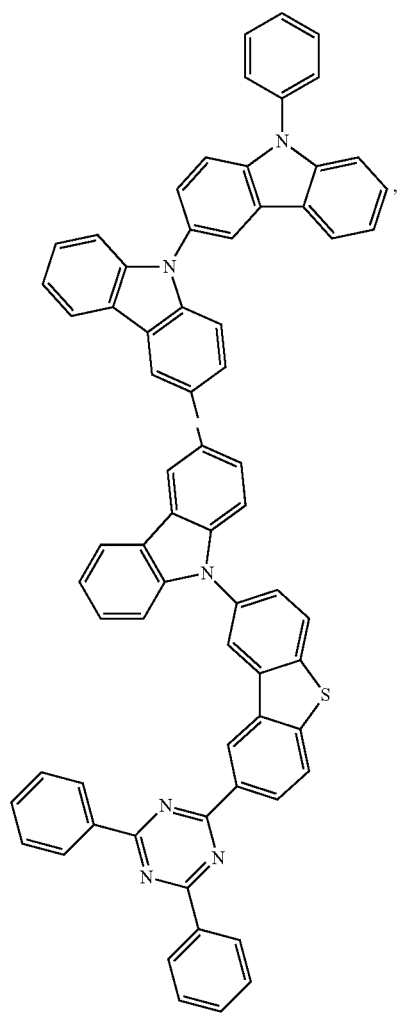
Compound 1985
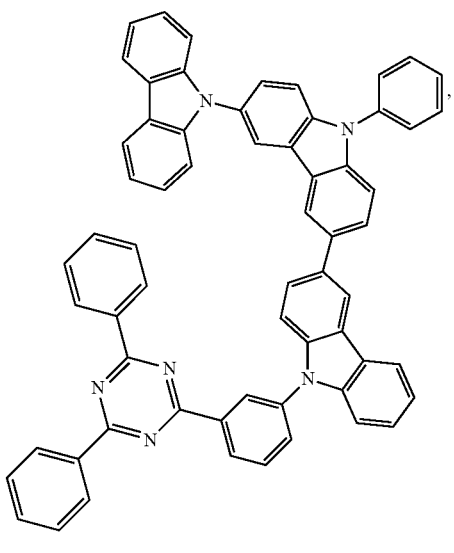
Compound 1989
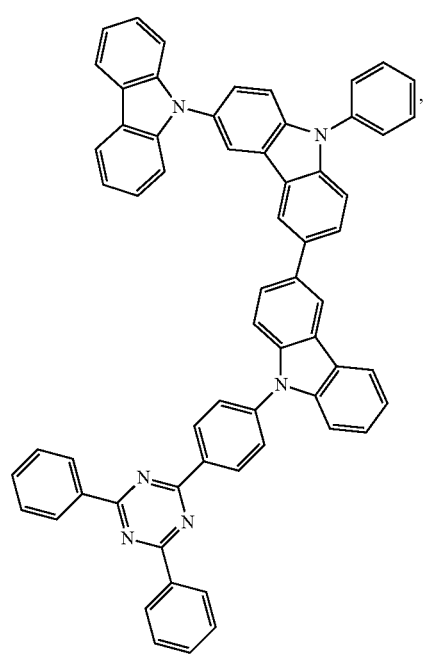
Compound 1997
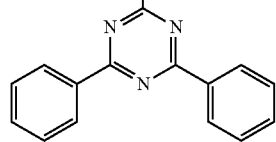

Compound 1993
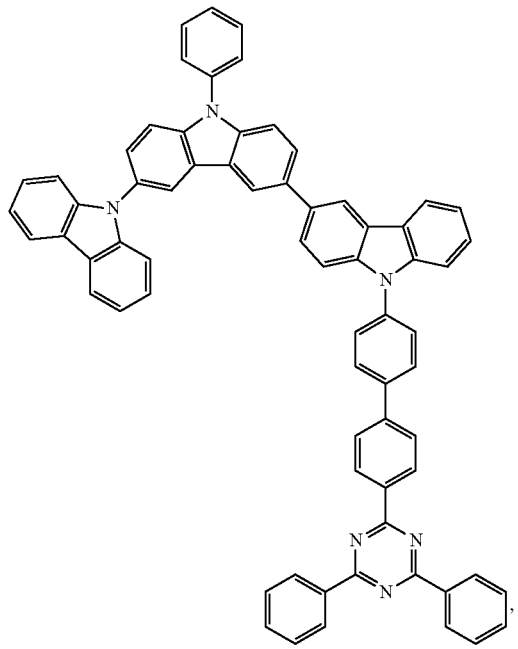
Compound 2021
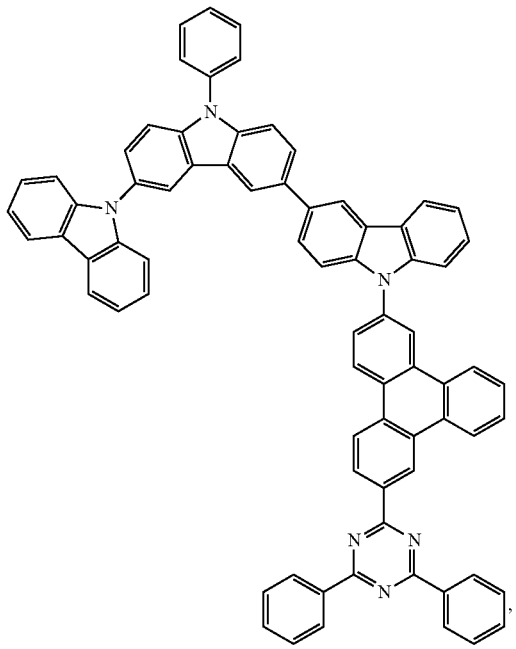
Compound 2017
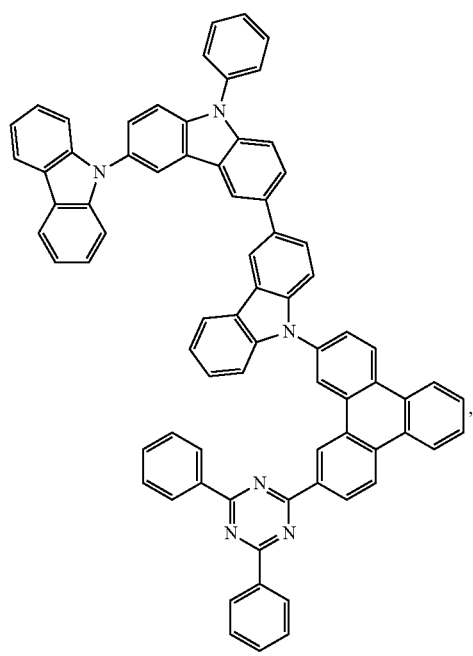
Compound 2025
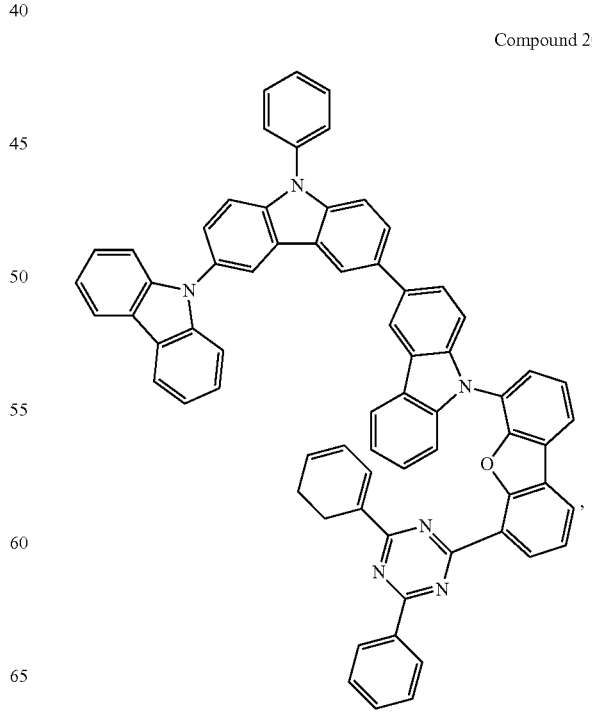

Compound 2029

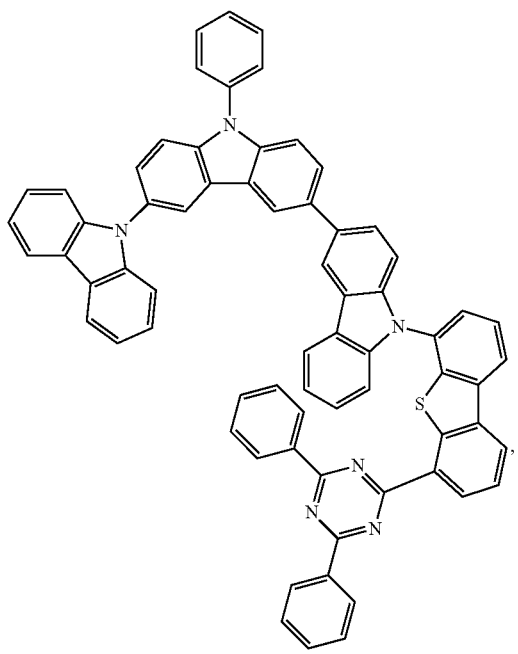

Compound 2045

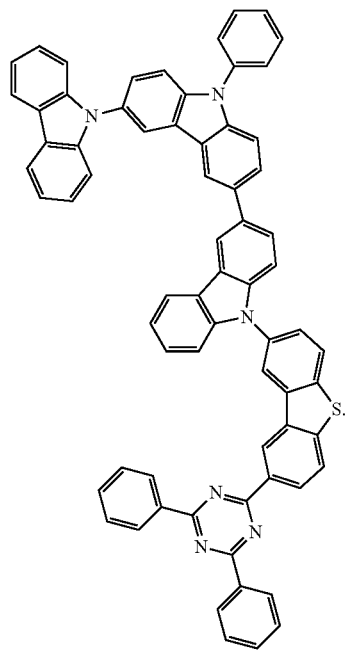

6. The compound of claim 1, wherein at least one of $R^1$, $R^2$, $R^3$, $R^4$, $R^5$, $R^6$, $R^7$, and $R^8$ comprises at least one electron donor group having the structure

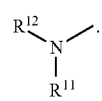

7. The compound of claim 1, wherein at least one of $R^1$, $R^2$, $R^3$, $R^4$, $R^5$, $R^6$, $R^7$, and $R^8$ comprises at least one electron donor group having the structure

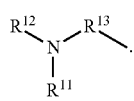

Compound 2041

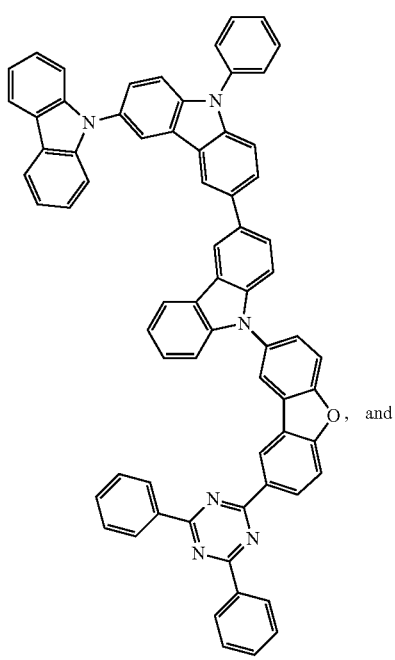

8. The compound of claim 1, wherein at least one of $R^1$, $R^2$, $R^3$, $R^4$, $R^5$, $R^6$, $R^7$, and $R^8$ comprises at least one electron donor group having the structure

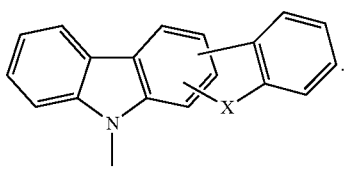

9. The compound of claim 1, wherein at least one of $R^1$, $R^2$, $R^3$, $R^4$, $R^5$, $R^6$, $R^7$, and $R^8$ comprises at least one electron donor group having the structure

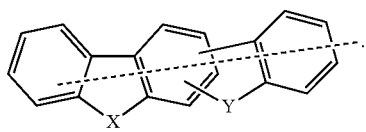

10. The compound of claim 1, wherein at least one of $R^1$, $R^2$, $R^3$, $R^4$, $R^5$, $R^6$, $R^7$, and $R^8$ comprises at least one electron donor group having the structure

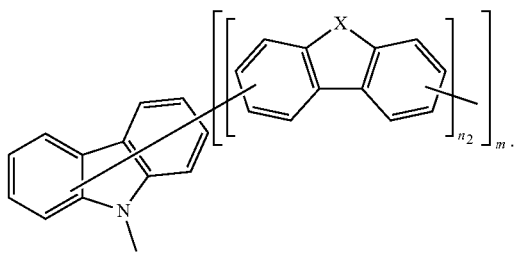

11. The compound of claim 1, wherein at least one of $R^1$, $R^2$, $R^3$, $R^4$, $R^5$, $R^6$, $R^7$, and $R^8$ comprises at least one electron donor group having the structure

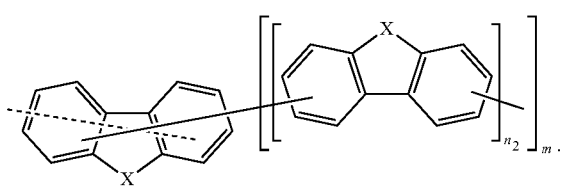

12. The compound of claim 1, wherein at least one of $R^1$, $R^2$, $R^3$, $R^4$, $R^5$, $R^6$, $R^7$, and $R^8$ comprises at least one electron donor group having the structure

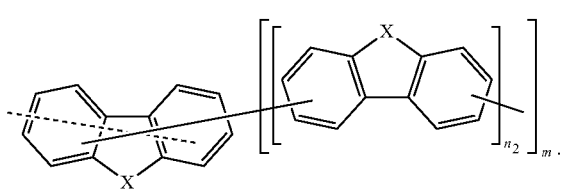

13. The compound of claim 1, wherein at least one of $R^1$, $R^2$, $R^3$, $R^4$, $R^5$, $R^6$, $R^7$, and $R^8$ comprises at least one electron donor group having the structure

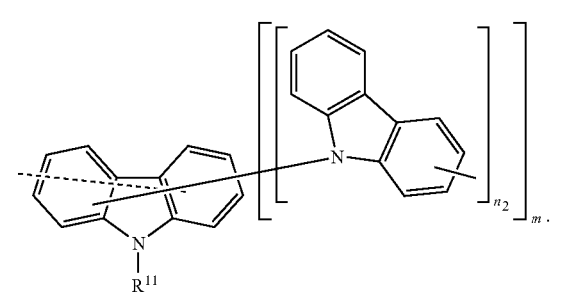

14. The compound of claim 1, wherein at least one of $R^1$, $R^2$, $R^3$, $R^4$, $R^5$, $R^6$, $R^7$, and $R^8$ comprises at least one electron donor group having the structure

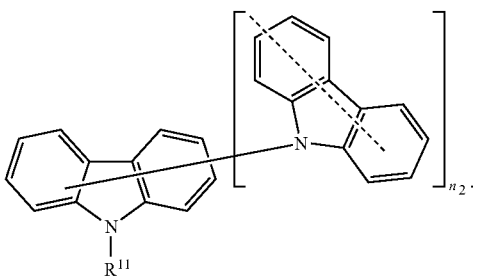

15. The compound of claim 1, wherein $L^1$ is

16. The compound of claim 1, wherein $L^1$ is

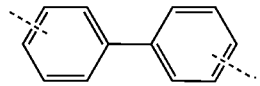

17. The compound of claim 1, wherein $L^1$ is

18. The compound of claim 1, wherein $L^1$ is

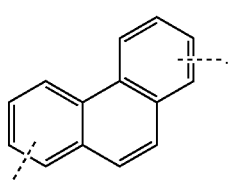

19. The compound of claim 1, wherein $L^1$ is

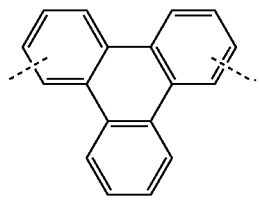

20. The compound of claim 1, wherein $L^1$ is
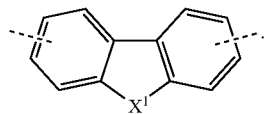
* * * * *

UNITED STATES PATENT AND TRADEMARK OFFICE
CERTIFICATE OF CORRECTION

PATENT NO. : 9,670,185 B2
APPLICATION NO. : 14/921446
DATED : June 6, 2017
INVENTOR(S) : Chuanjun Xia et al.

It is certified that error appears in the above-identified patent and that said Letters Patent is hereby corrected as shown below:

In the Specification

Column 4, Lines 8-12, please delete " 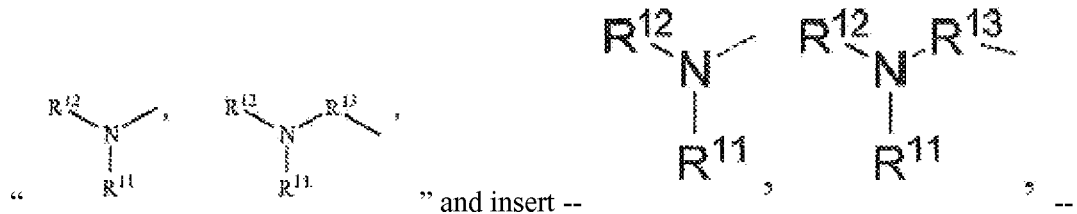 " and insert --

Column 4, Lines 13-18, please delete " 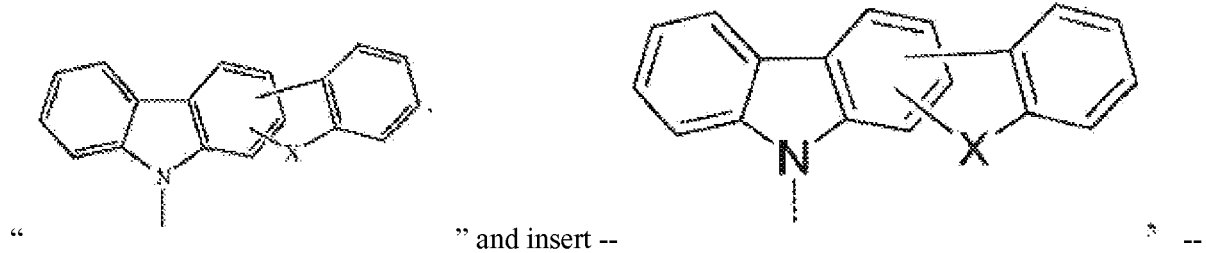 " and insert --  --

Column 4, Lines 22-33, please delete " 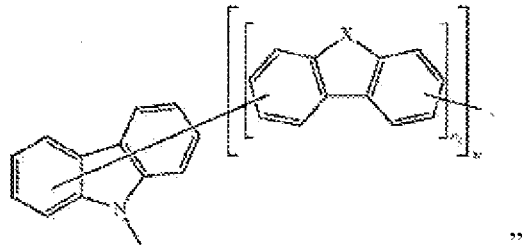 "

Signed and Sealed this
Twenty-ninth Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,670,185 B2

Page 2 of 88

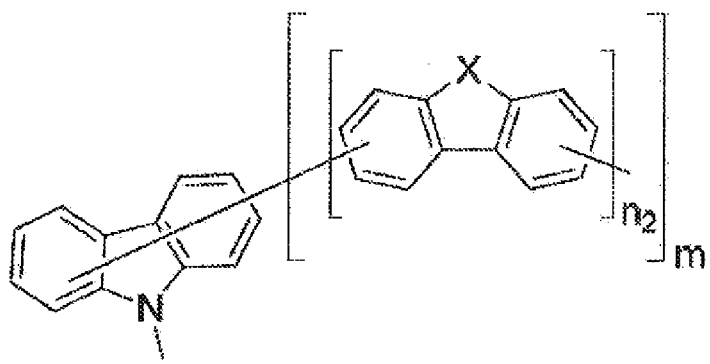

and insert --

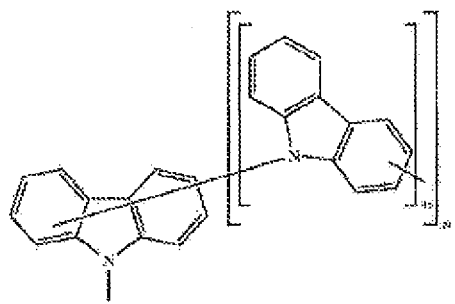

--

Column 4, Lines 43-54, please delete "

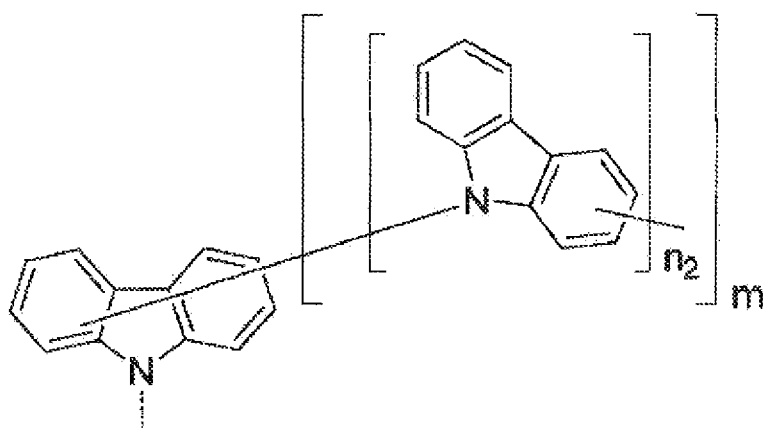

"

and insert --

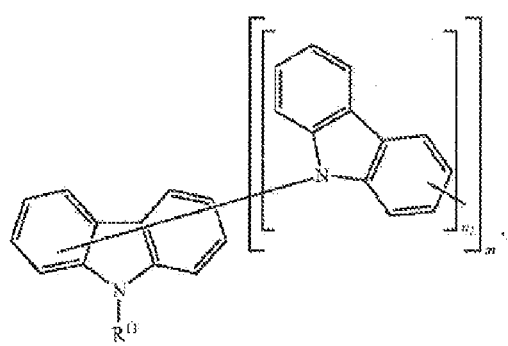

--

Column 4, Lines 55-66, please delete "                            "

CERTIFICATE OF CORRECTION (continued)
U.S. Pat. No. 9,670,185 B2

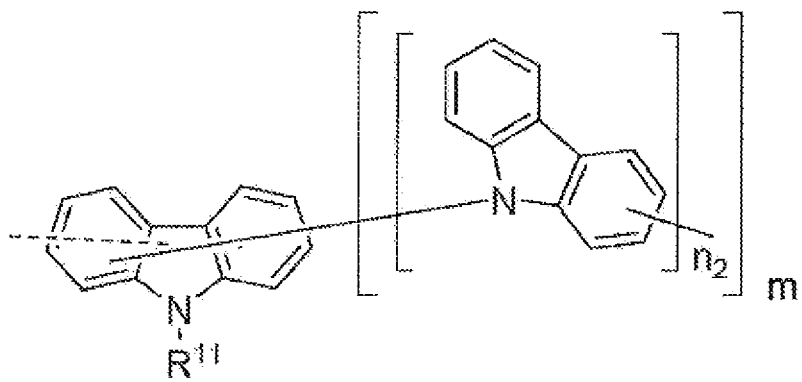

and insert -- --

Column 5, Lines 40-46, please delete

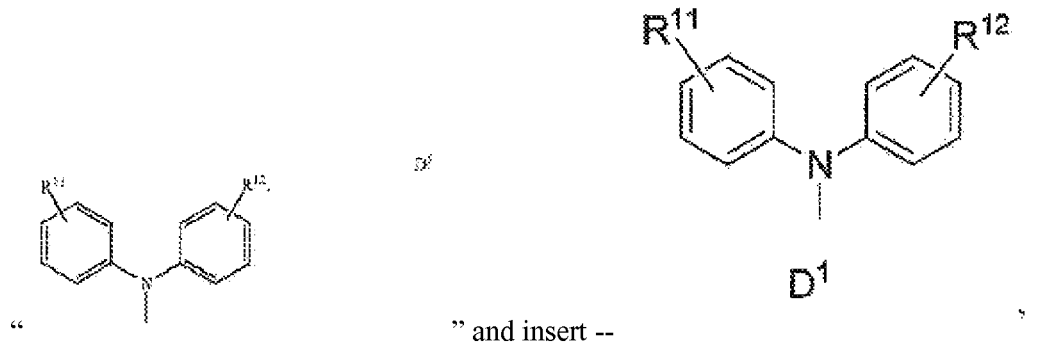

" and insert -- --

Column 5, Lines 58-66, please delete " "

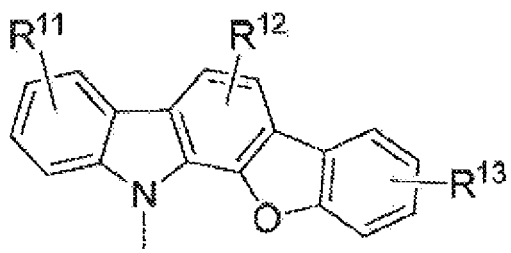

and insert -- --

CERTIFICATE OF CORRECTION (continued)
U.S. Pat. No. 9,670,185 B2

Column 6, Lines 1-8, please delete " " and insert --

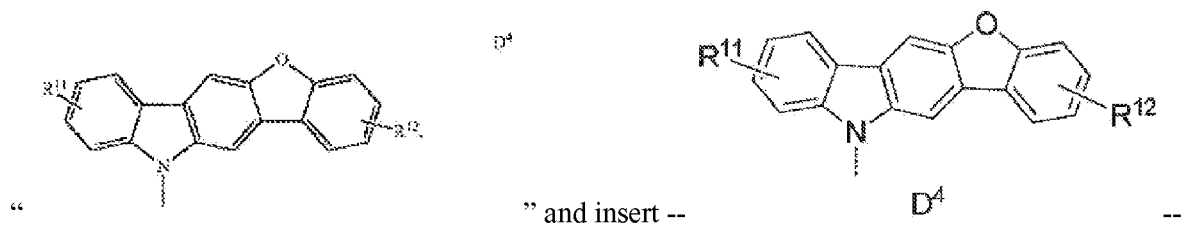

--

Column 6, Lines 9-21, please delete " " and insert --

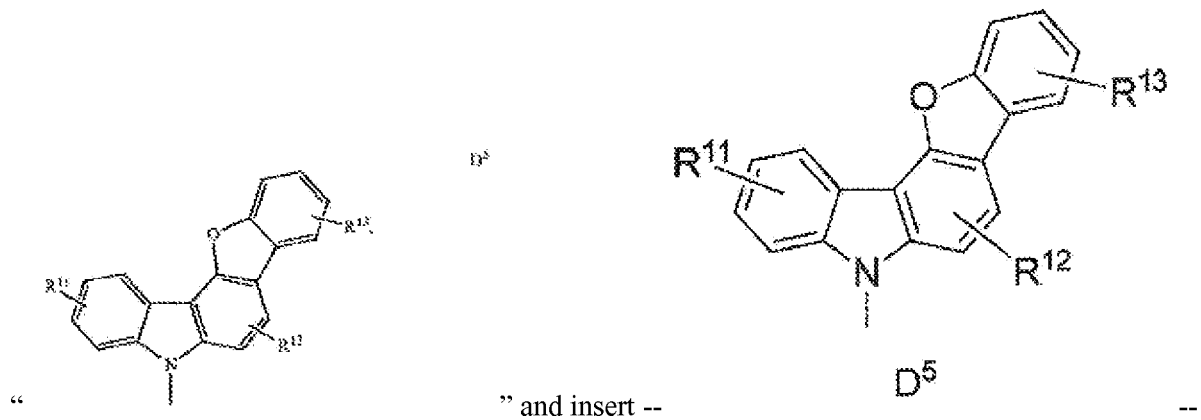

--

Column 6, Lines 22-27, please delete " " and insert --

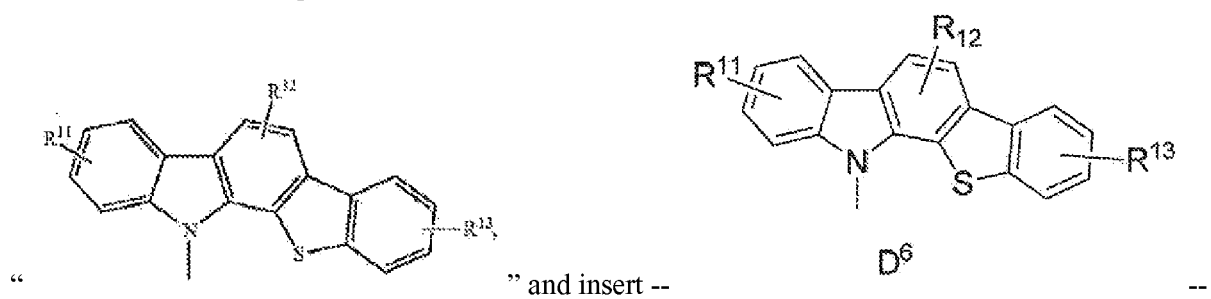

--

Column 6, Lines 28-35, please delete " "

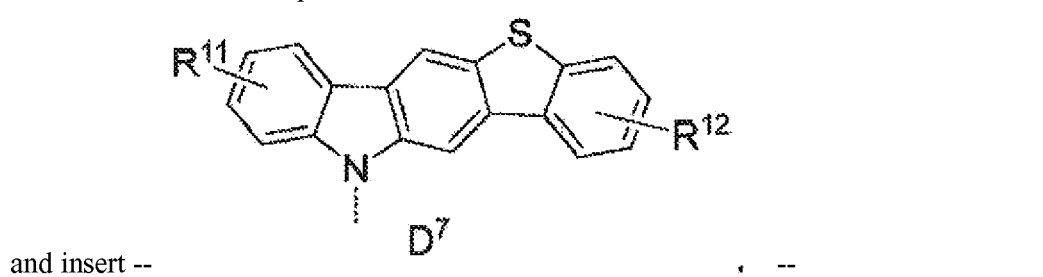

and insert -- . --

CERTIFICATE OF CORRECTION (continued)
U.S. Pat. No. 9,670,185 B2

Column 6, Lines 36-45, please delete " " and insert -- -- 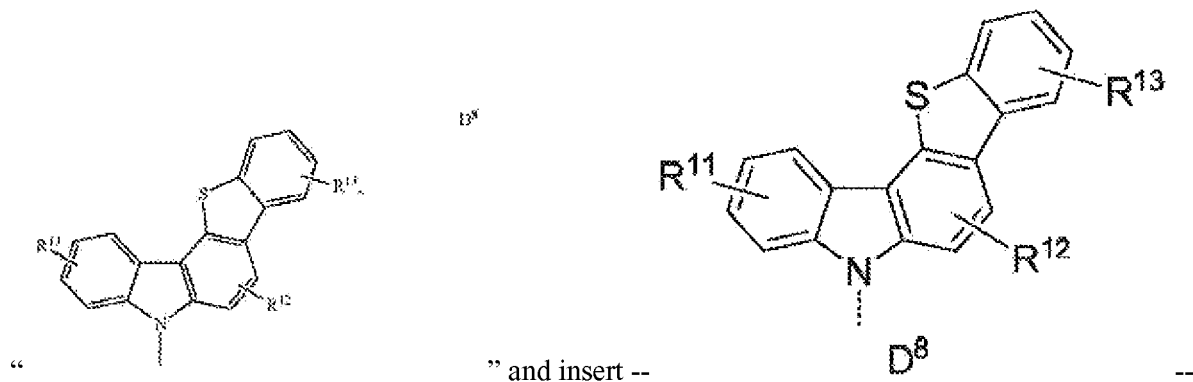

Column 7, Lines 10-20, please delete " " and insert -- -- 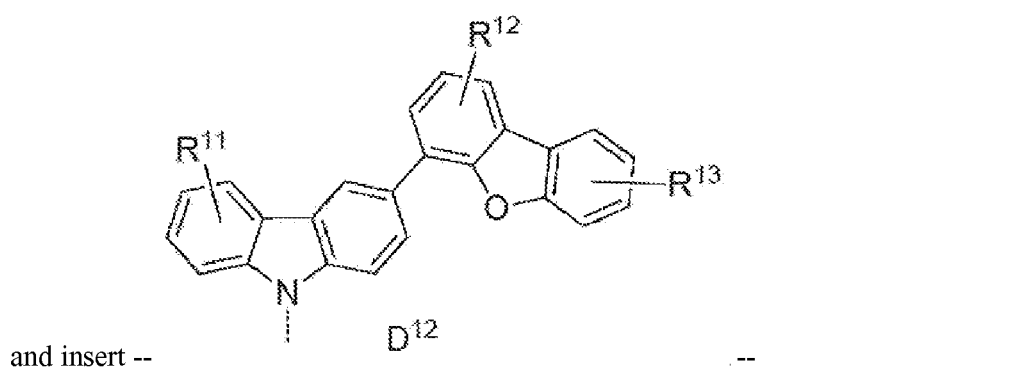

Column 7, Lines 21-34, please delete " "

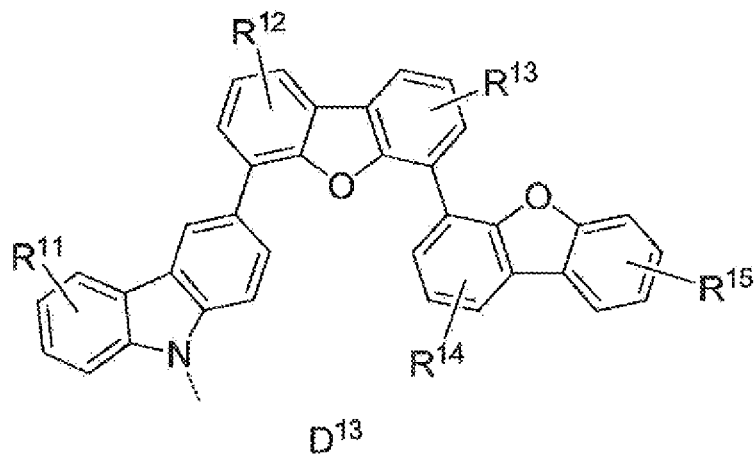
and insert --
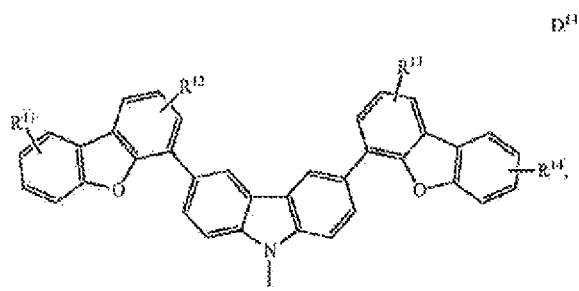
Column 7, Lines 35-45, please delete "
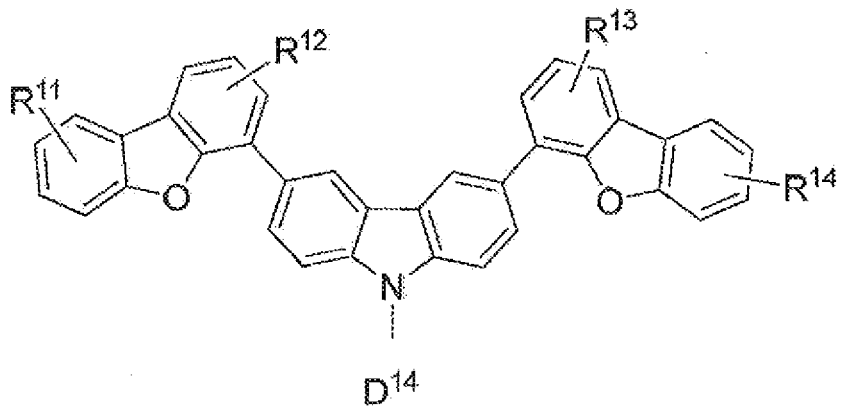
and insert --
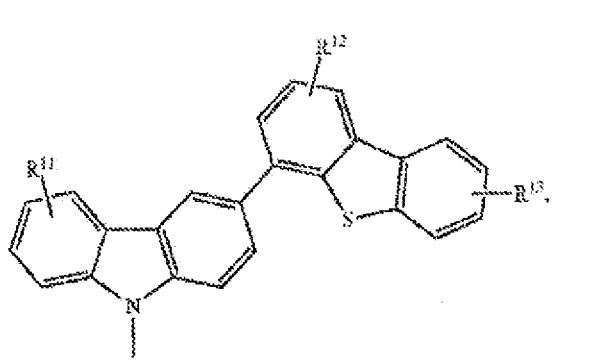
Column 8, Lines 8-19, please delete "

and insert --
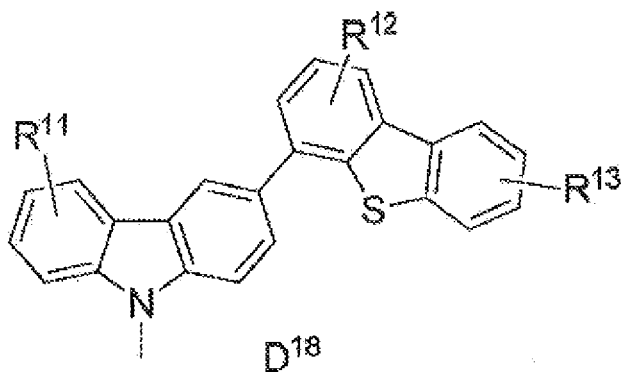
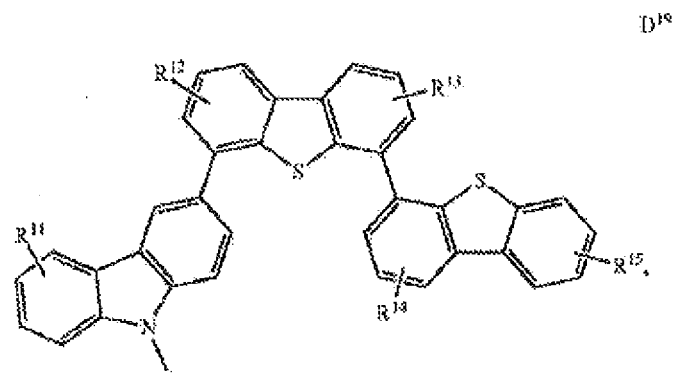
Column 8, Lines 20-31, please delete "
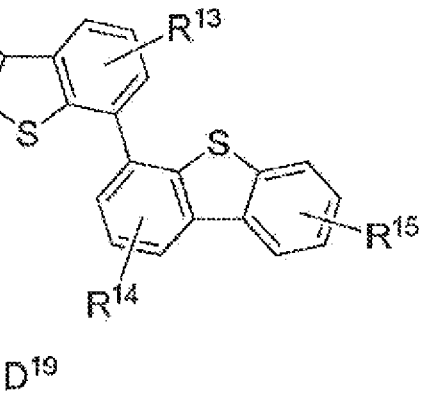
and insert --
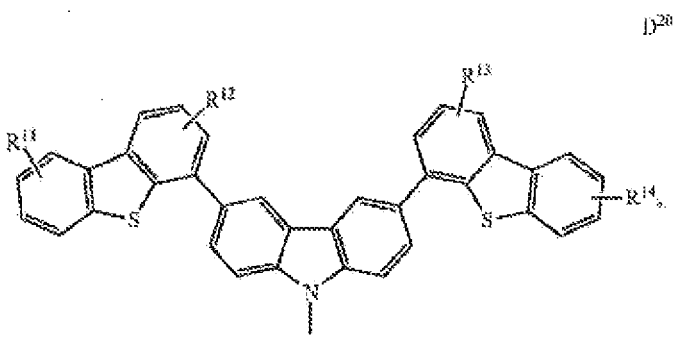
Column 8, Lines 32-41, please delete "

and insert -- 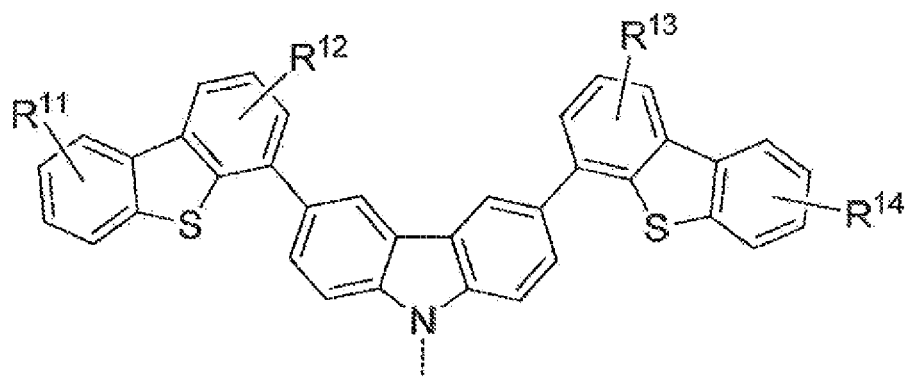 --
Column 9, Lines 27-40, please delete " 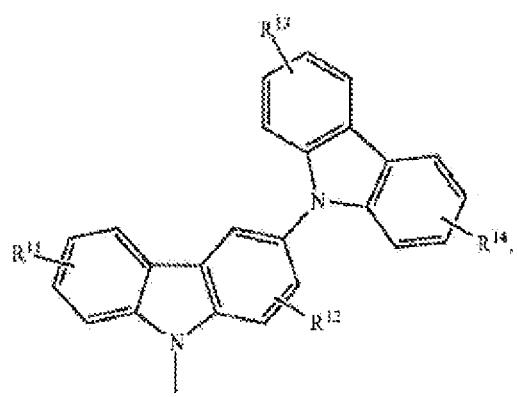 "
and insert -- 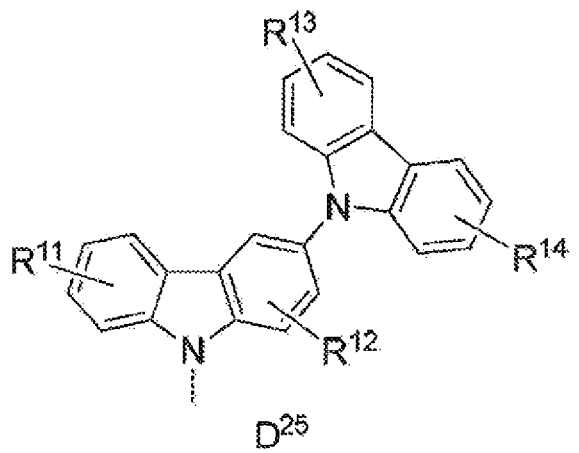 --

CERTIFICATE OF CORRECTION (continued)
U.S. Pat. No. 9,670,185 B2

Column 9, Lines 41-52, please delete " 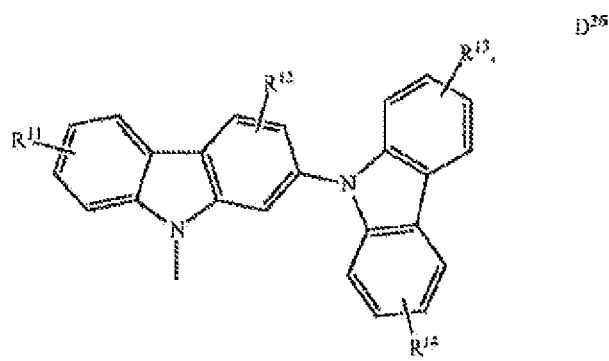 "

and insert -- 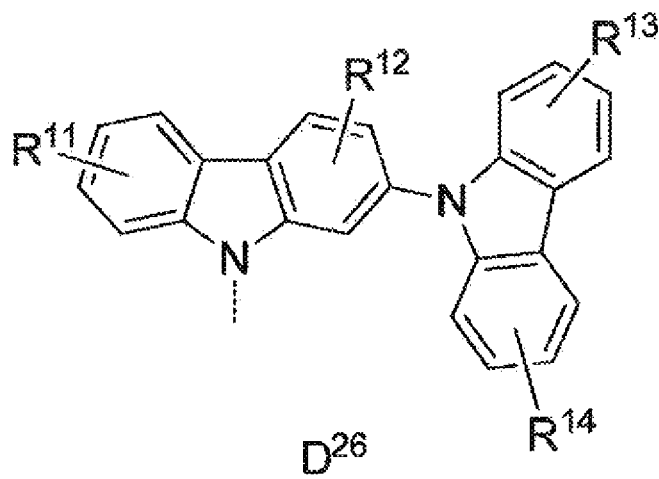 , --

Column 9, Lines 53-65, please delete " 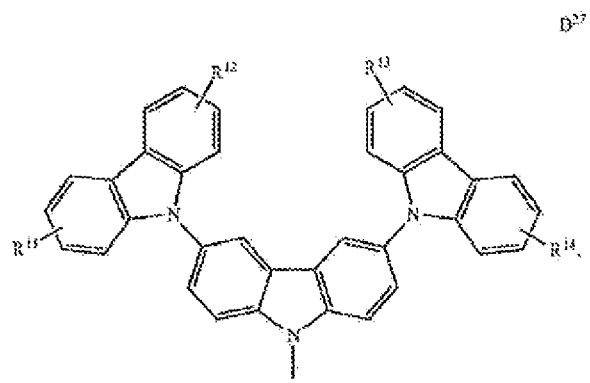 "

CERTIFICATE OF CORRECTION (continued)
U.S. Pat. No. 9,670,185 B2

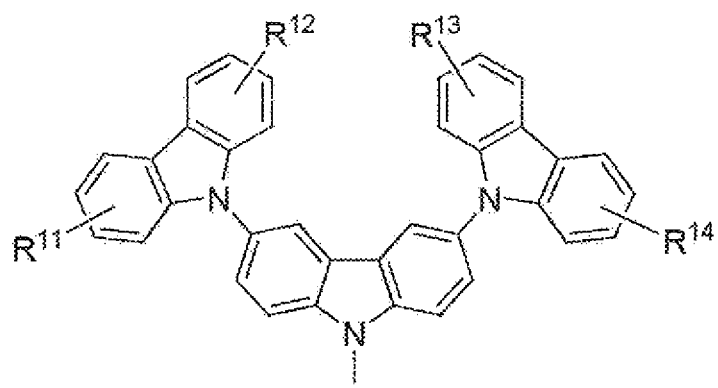

and insert -- --

Column 11, Lines 25-30, please delete

" 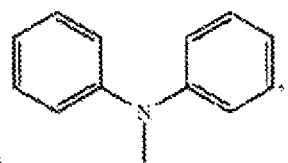 " and insert -- 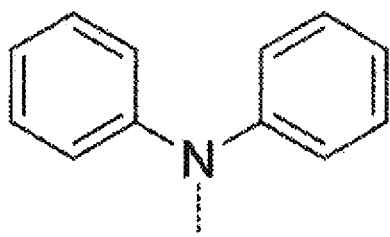 --

Column 11, Lines 43-47, please delete " 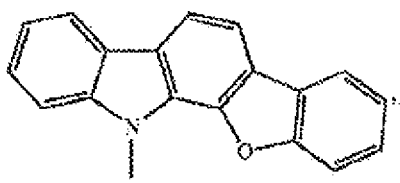 "

and insert -- 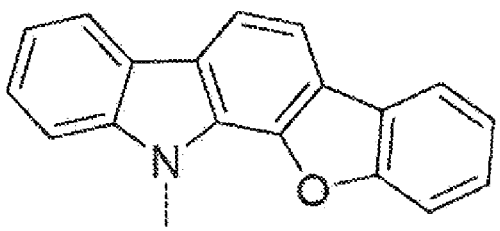 --

Column 11, Lines 48-55, please delete
" 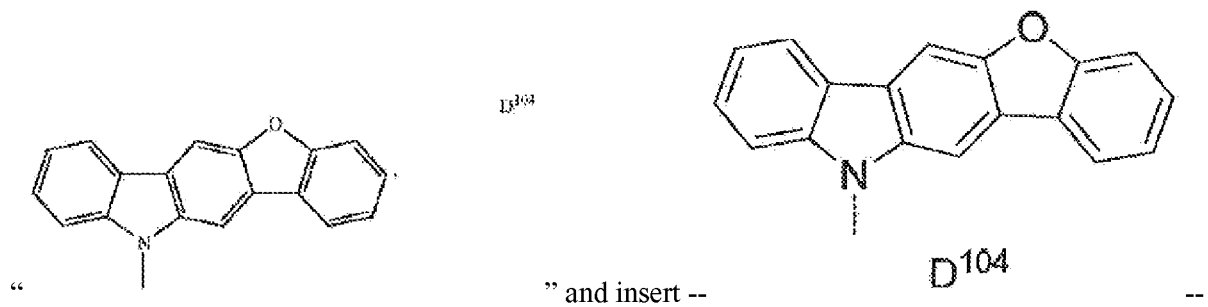 " and insert --  --
Column 11, Lines 56-66, please delete " 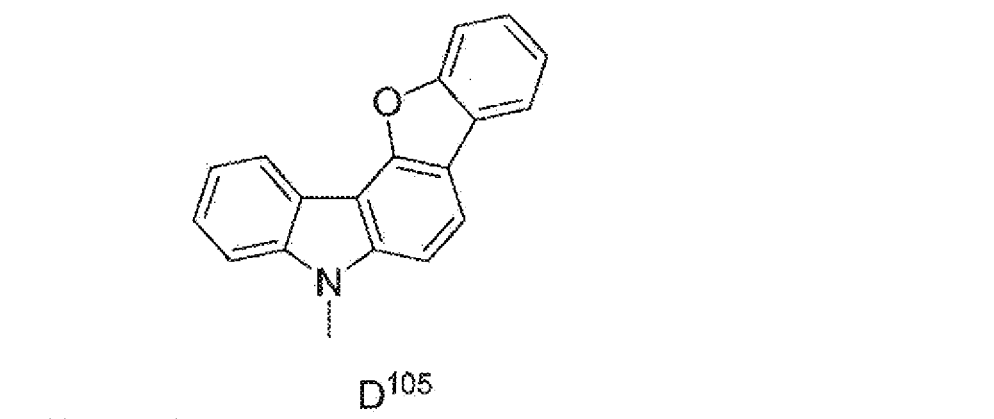 "
and insert --  --
Column 12, Lines 1-10, please delete " 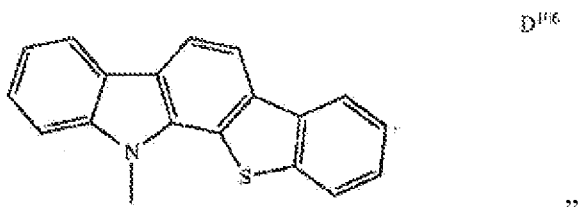 "

CERTIFICATE OF CORRECTION (continued)
U.S. Pat. No. 9,670,185 B2

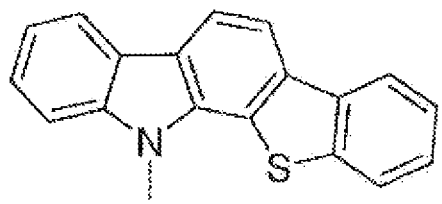

and insert --

Column 12, Lines 11-19, please delete "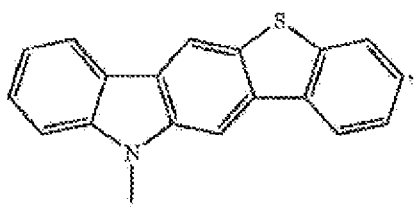"

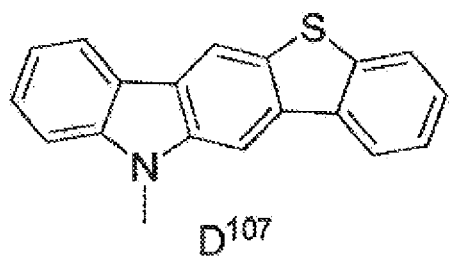

and insert --

Column 12, Lines 20-30, please delete "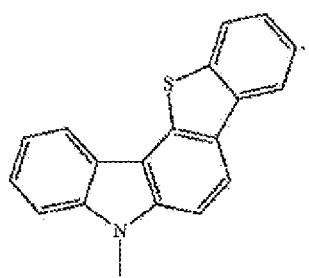"

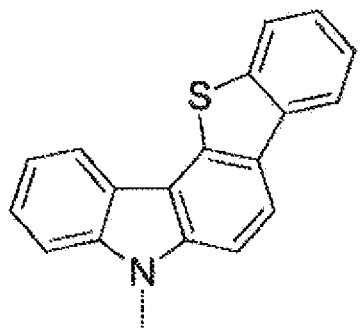

and insert --

CERTIFICATE OF CORRECTION (continued)
U.S. Pat. No. 9,670,185 B2

Column 12, Lines 57-66, please delete " 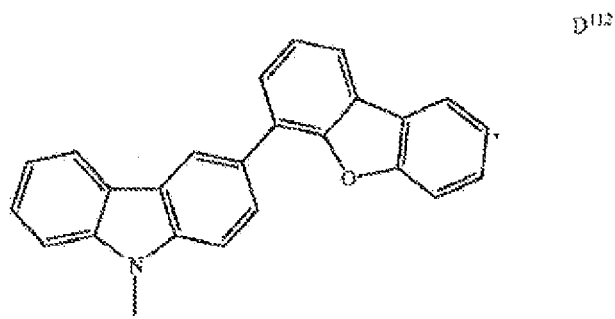 "

and insert -- 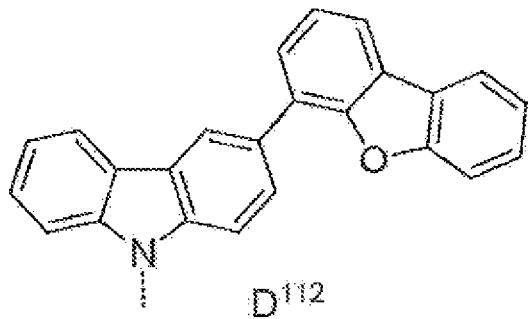 --

Column 13, Lines 1-14, please delete " 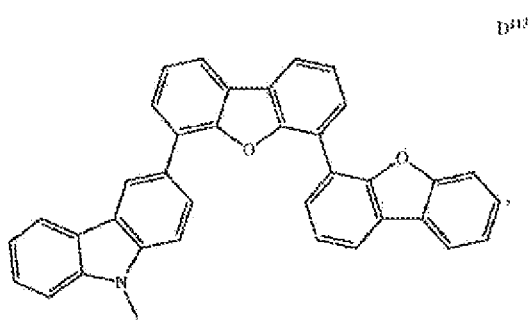 "

and insert -- 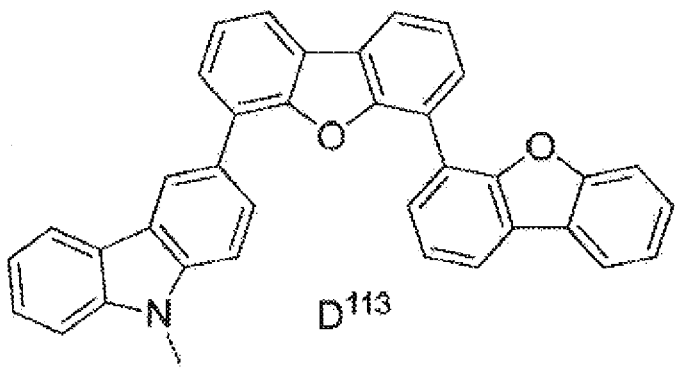 --

CERTIFICATE OF CORRECTION (continued)
U.S. Pat. No. 9,670,185 B2

Column 13, Lines 15-26, please delete " 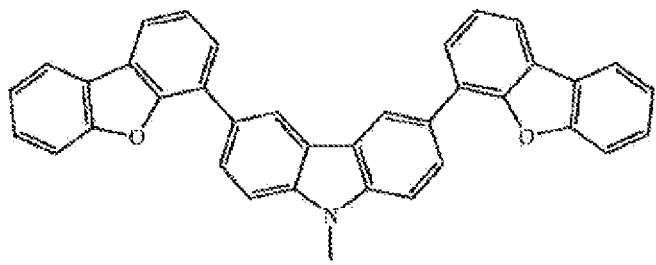 "

and insert -- 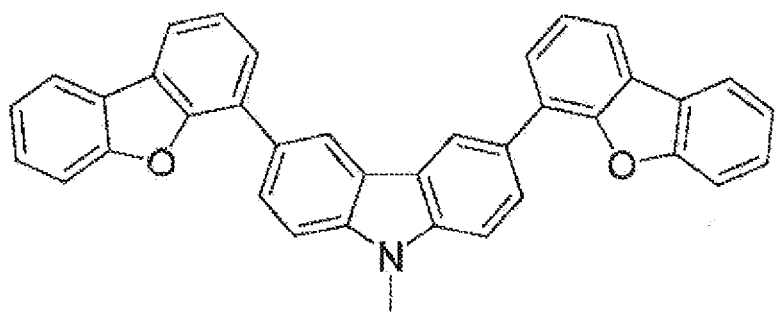 --

Column 13, Lines 57-66, please delete " 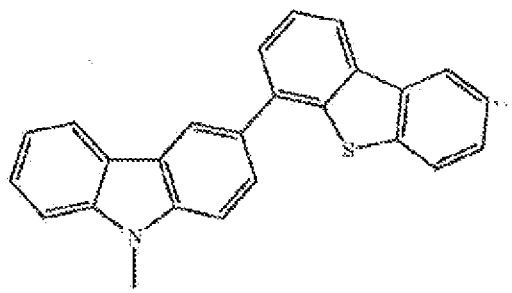 "

and insert -- 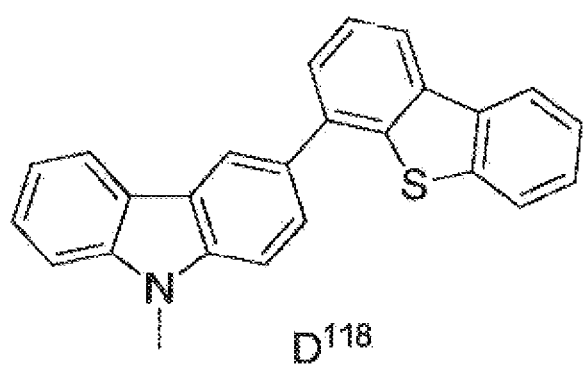 --

Column 14, Lines 1-14, please delete " 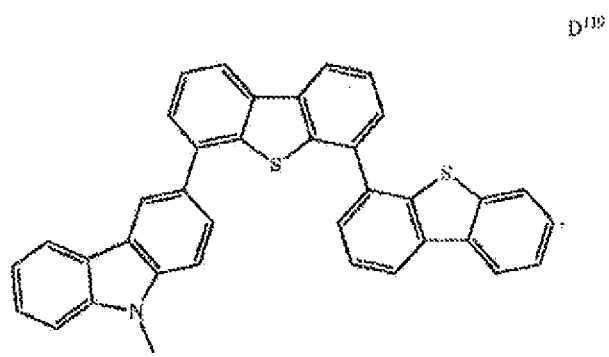 "
and insert -- 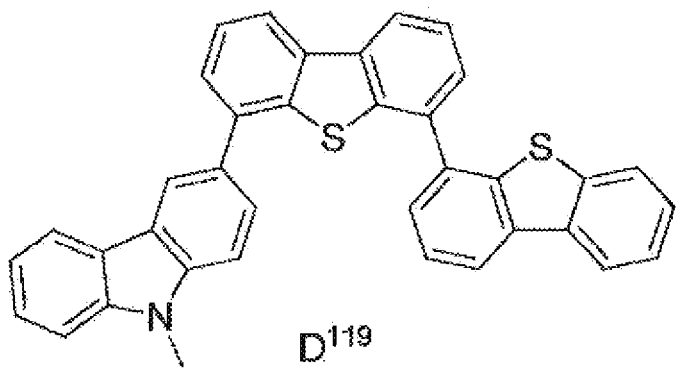 --
Column 14, Lines 15-26, please delete " 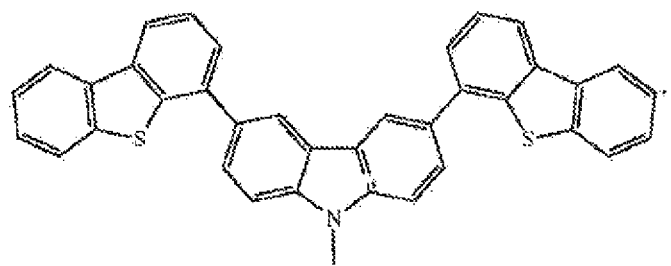 "
and insert -- 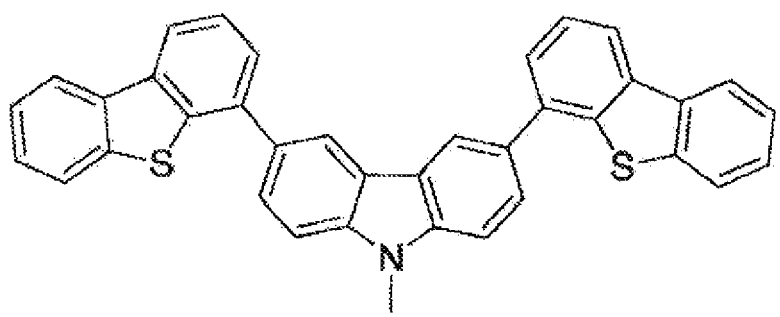 --

Column 15, Lines 16-27, please delete " 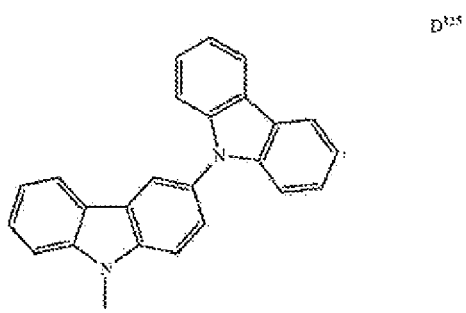 "
and insert -- 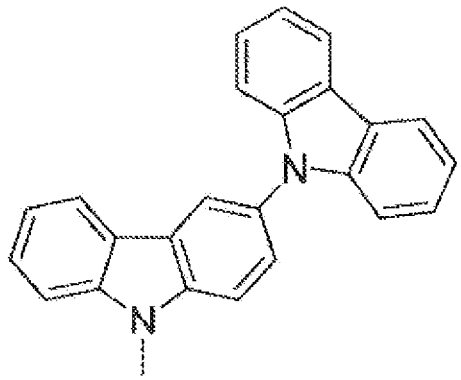 --
Column 15, Lines 28-37, please delete " 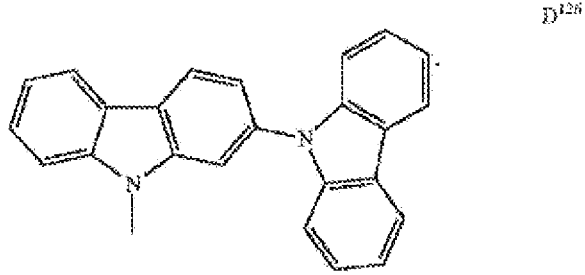 "
and insert -- 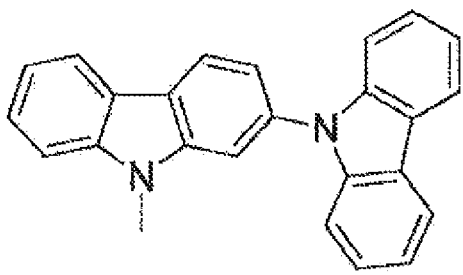 --

CERTIFICATE OF CORRECTION (continued)
U.S. Pat. No. 9,670,185 B2

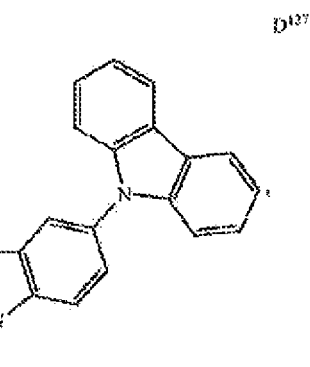

Column 15, Lines 38-50, please delete "

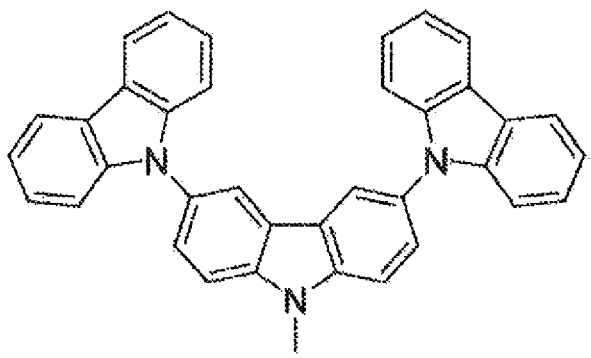

and insert --

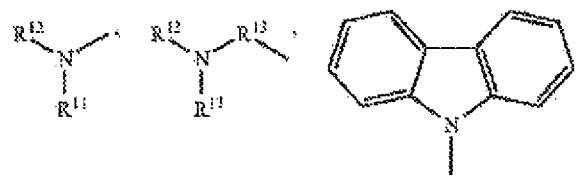

Column 18, Lines 6-14, please delete " " and insert

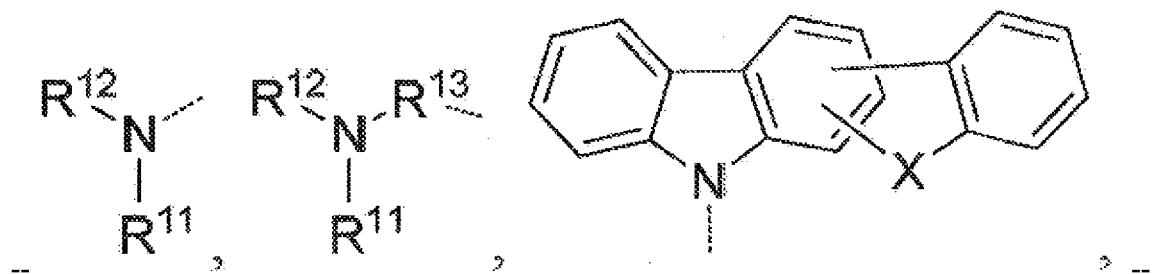

Column 18, Lines 34-40, please delete
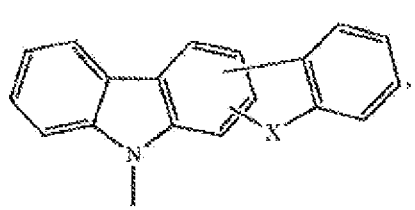
" and insert -- 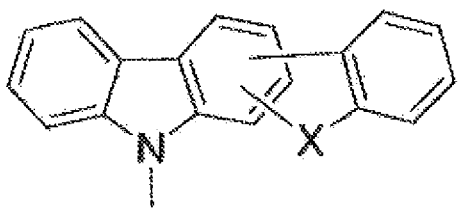 --
Column 18, Lines 41-48, please delete " 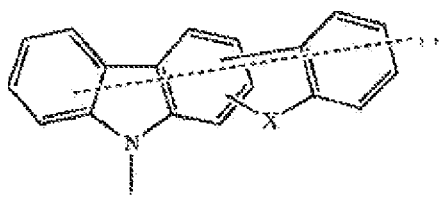 "
and insert -- 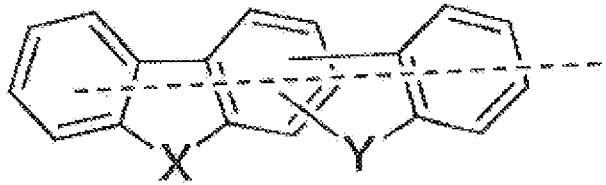 --
Column 18, Lines 49-58, please delete " 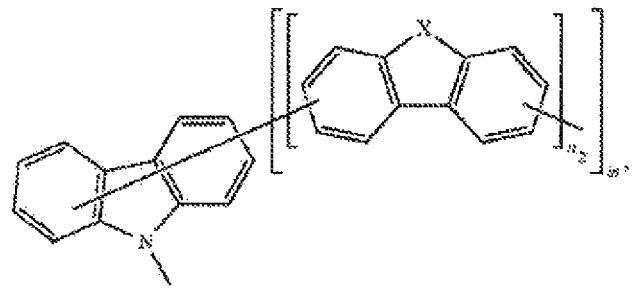 "
and insert --  --

Column 18, Lines 58-65, please delete " 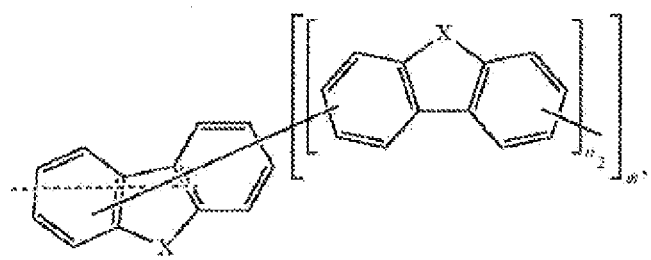 "
and insert -- 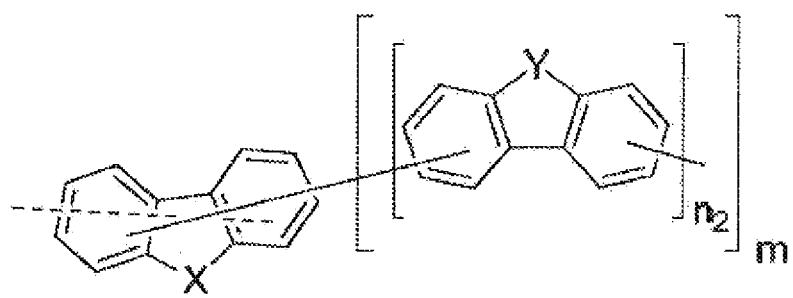 --
Column 19, Lines 1-14, please delete " 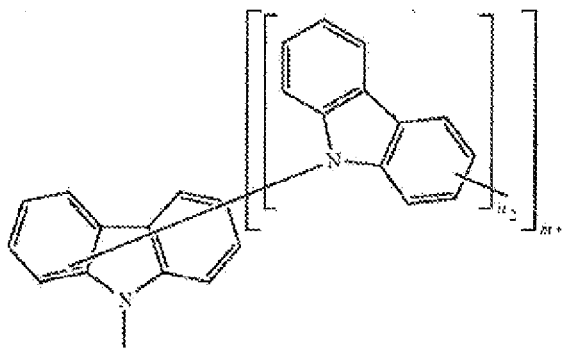 "
and insert -- 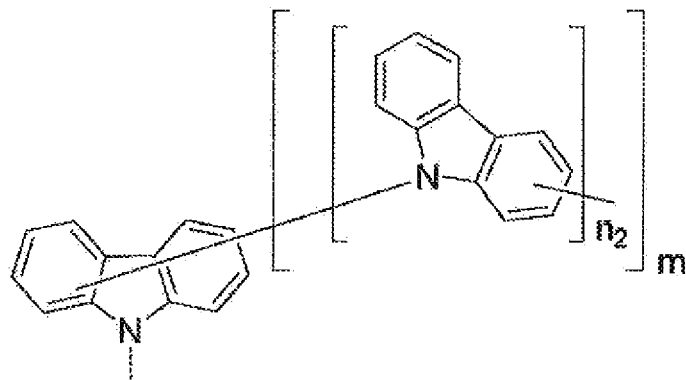 --

Column 19, Lines 48-54, please delete "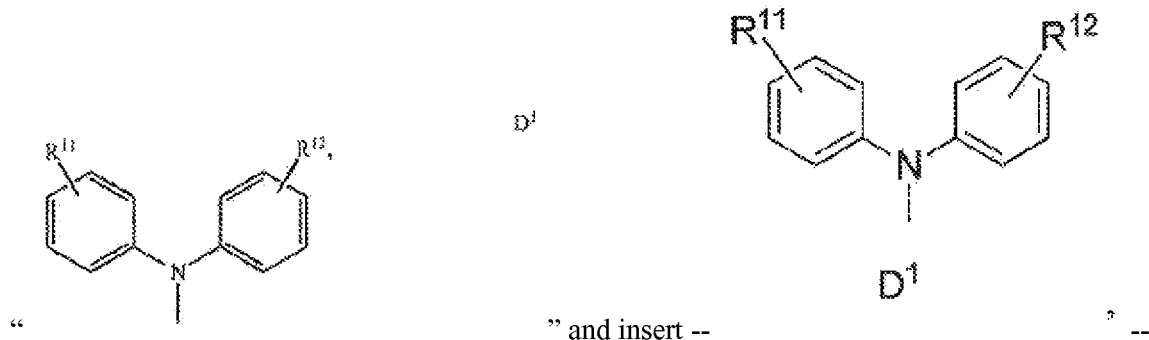" and insert --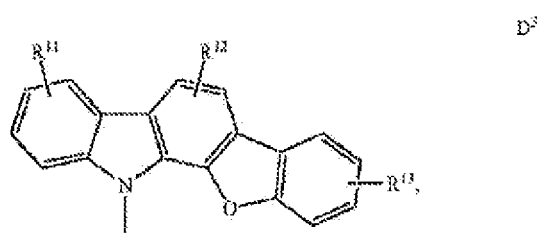--
Column 20, Lines 1-10, please delete "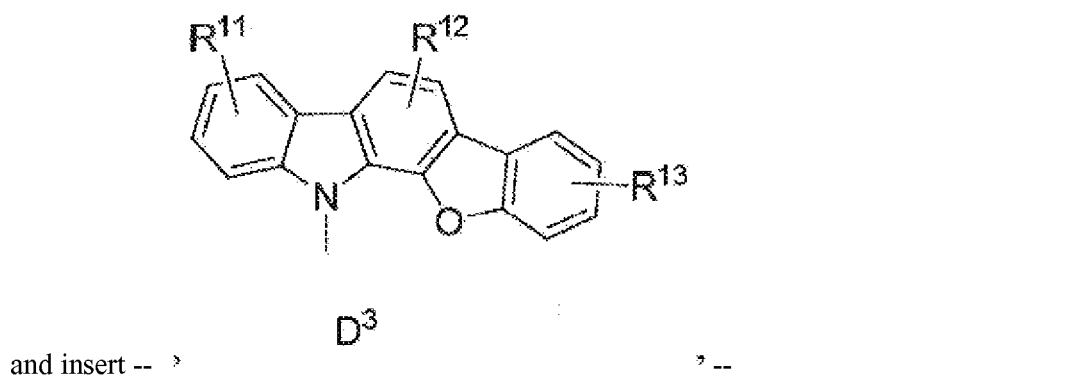" and insert --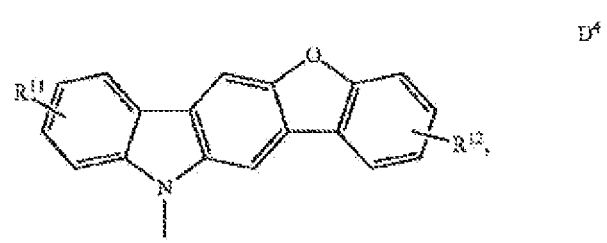--
Column 20, Lines 11-17, please delete "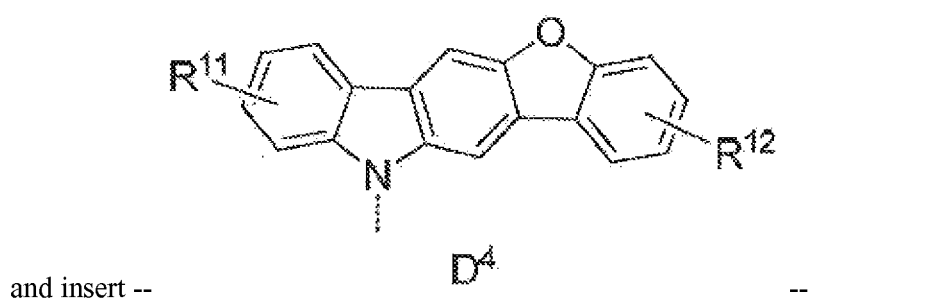" and insert -- --

CERTIFICATE OF CORRECTION (continued)
U.S. Pat. No. 9,670,185 B2

Column 20, Lines 18-27, please delete " 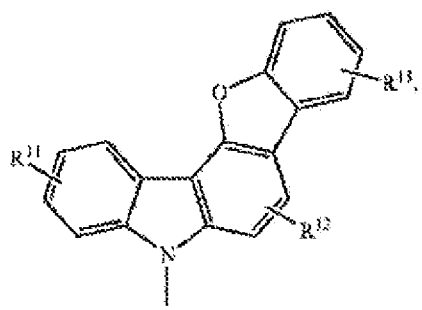 "

and insert -- 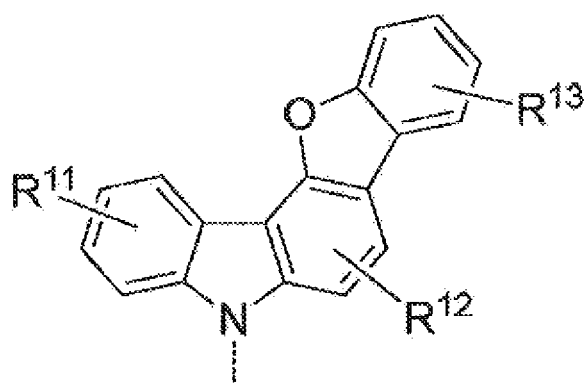 --.

Column 20, Lines 30-36, please delete

" 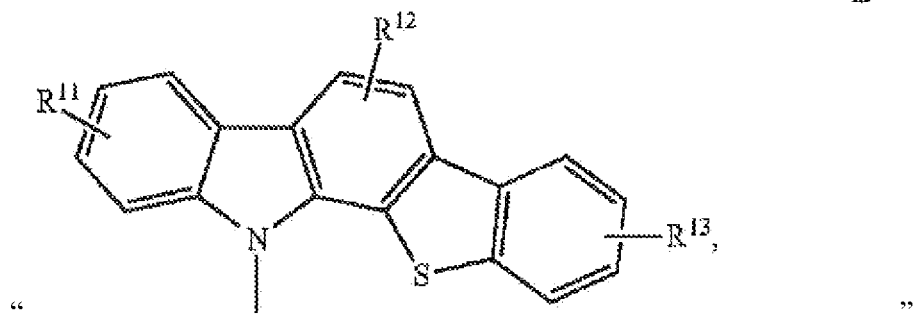 "

CERTIFICATE OF CORRECTION (continued)
U.S. Pat. No. 9,670,185 B2

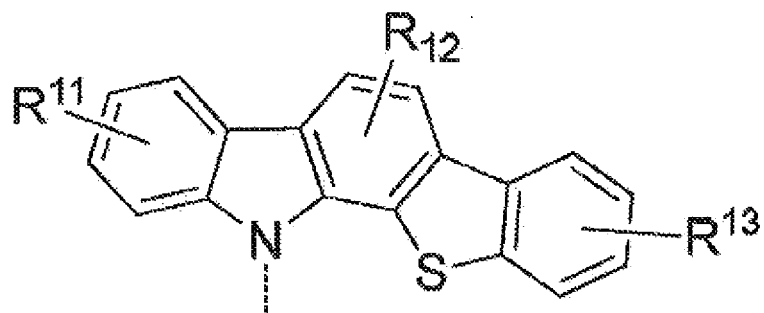

and insert --                                                      --

Column 20, Lines 37-43, please delete

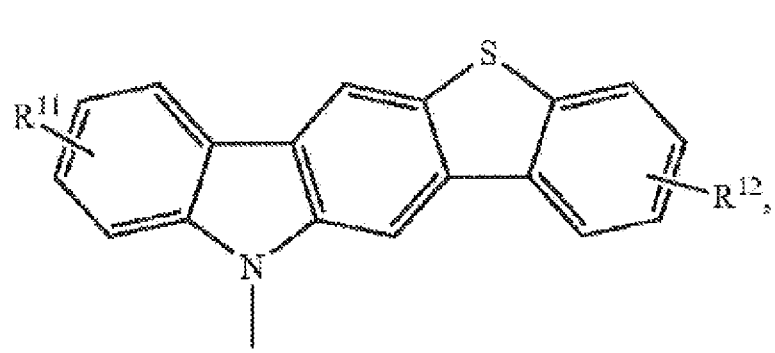

"                                                                  "

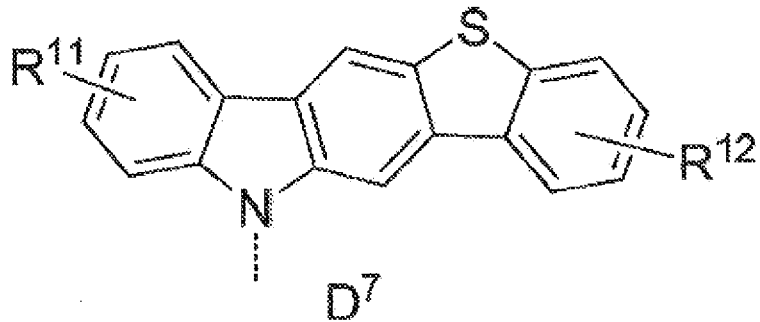

and insert --                                                      --

Column 20, Lines 44-54, please delete "

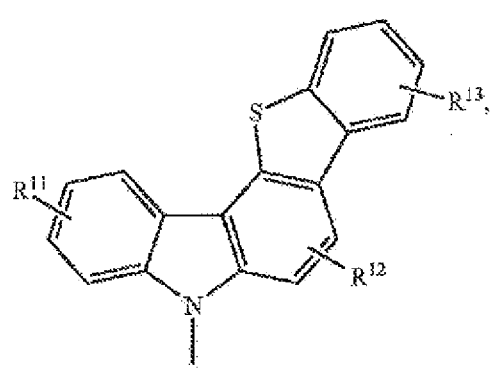

"

CERTIFICATE OF CORRECTION (continued)
U.S. Pat. No. 9,670,185 B2

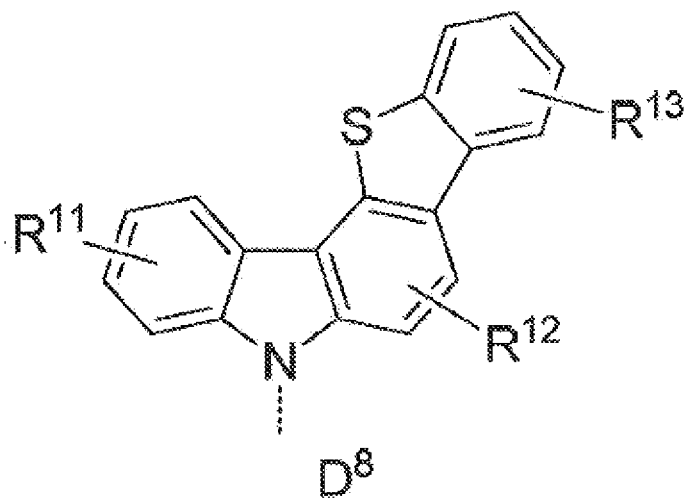

and insert --

Column 21, Lines 20-30, please delete "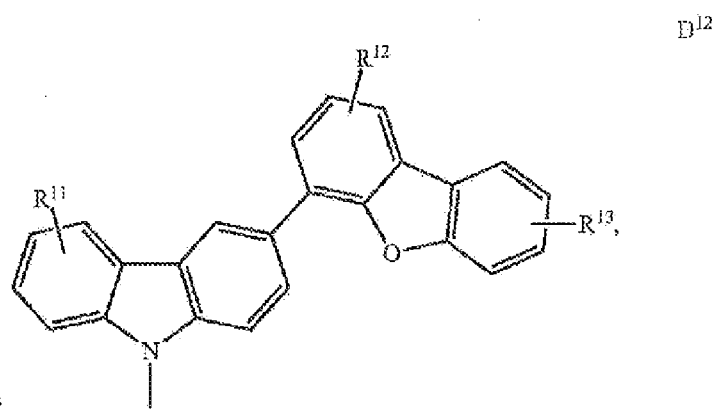"

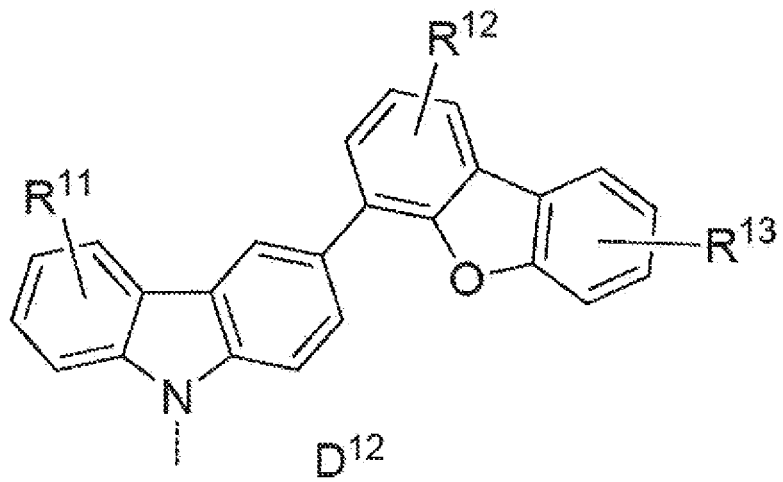

and insert --  --

CERTIFICATE OF CORRECTION (continued)
U.S. Pat. No. 9,670,185 B2

Column 21, Lines 31-44, please delete " 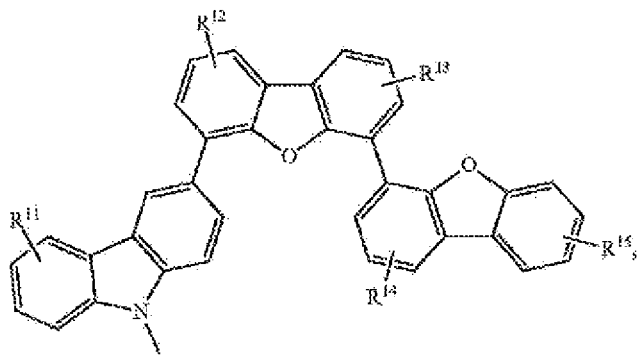 "

and insert -- 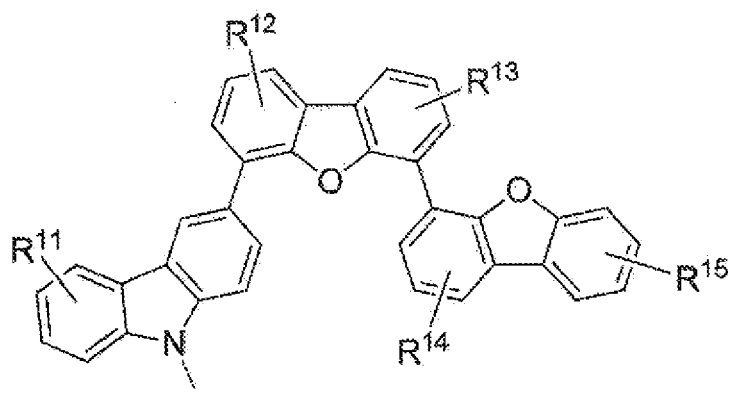 --

Column 21, Lines 45-55, please delete

" 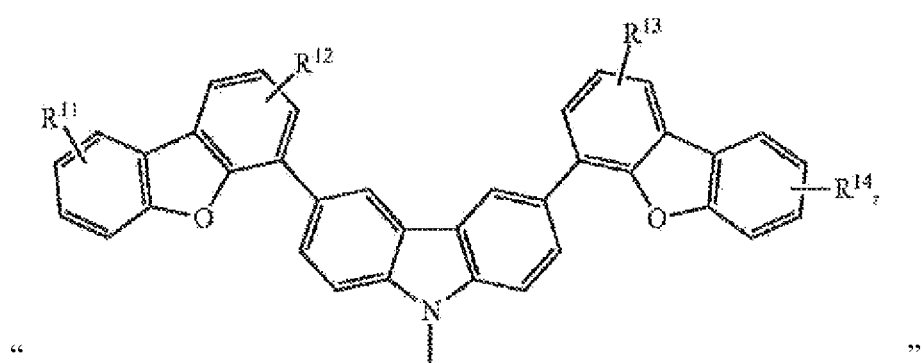 "

CERTIFICATE OF CORRECTION (continued)
U.S. Pat. No. 9,670,185 B2 and insert --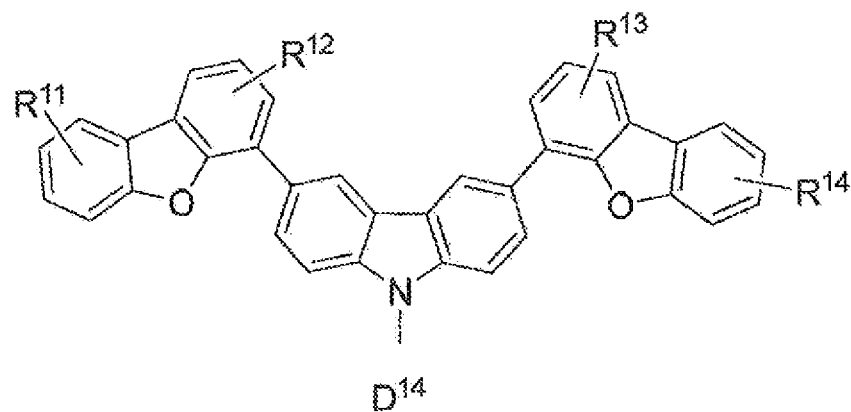--

Column 22, Lines 20-32, please delete "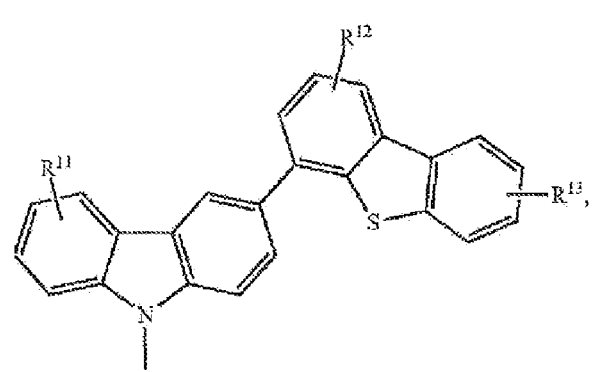"

and insert --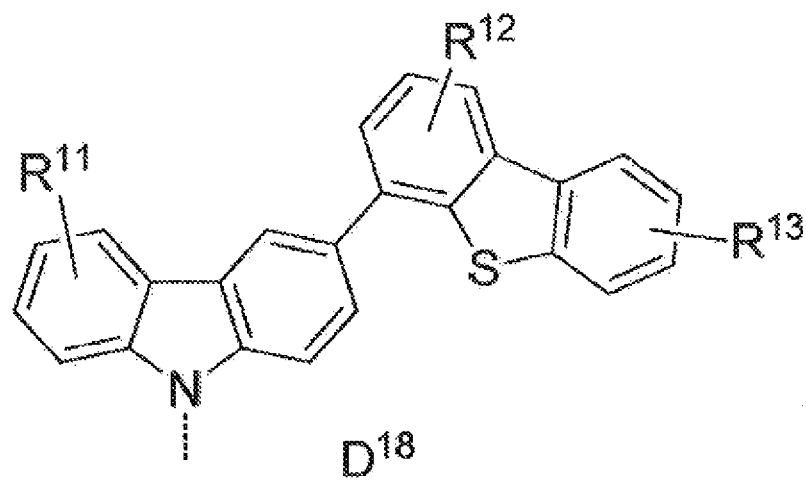--

Column 22, Lines 33-44, please delete
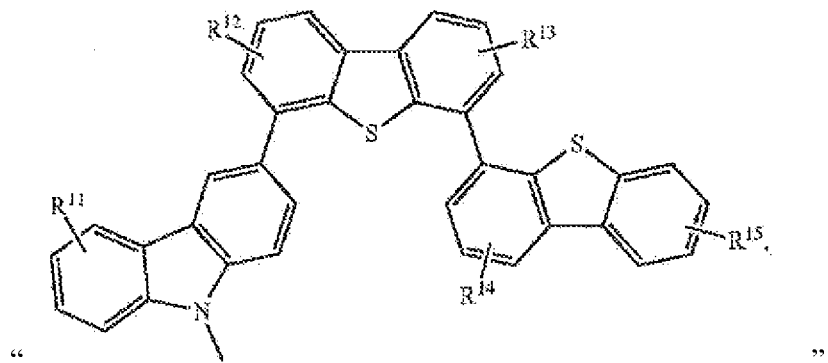
"                                    "
and insert --
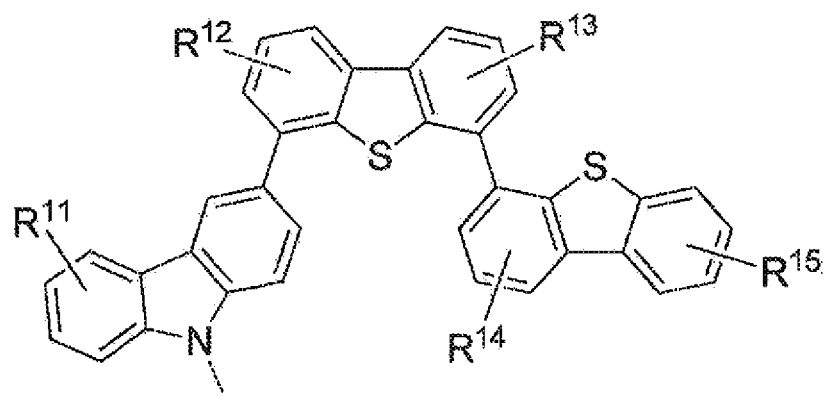
--
Column 22, Lines 45-57, please delete
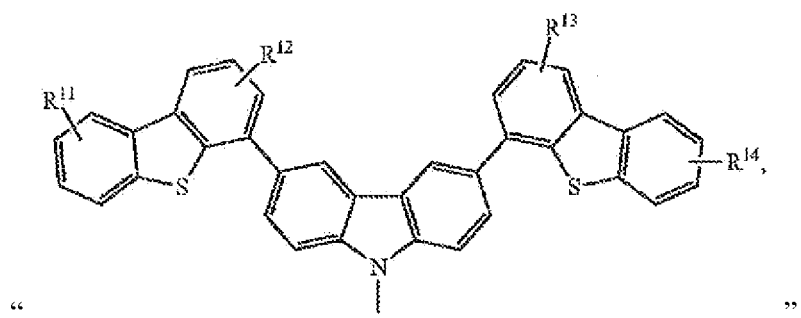
"                                    "

CERTIFICATE OF CORRECTION (continued)
U.S. Pat. No. 9,670,185 B2

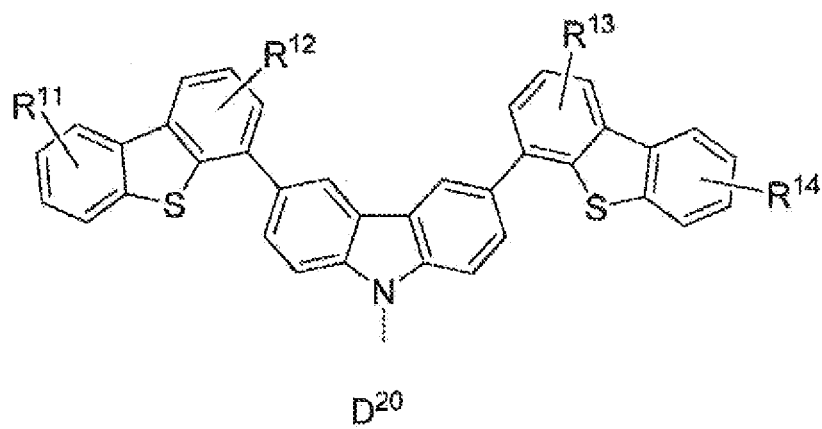

and insert -- `

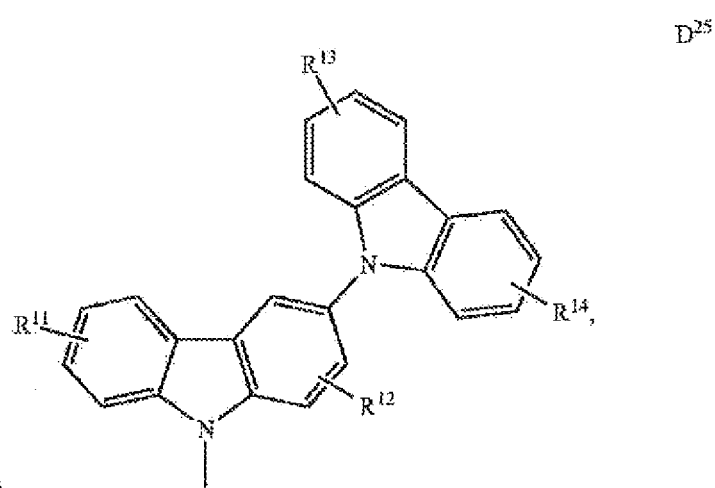

Column 23, Lines 42-54, please delete " "

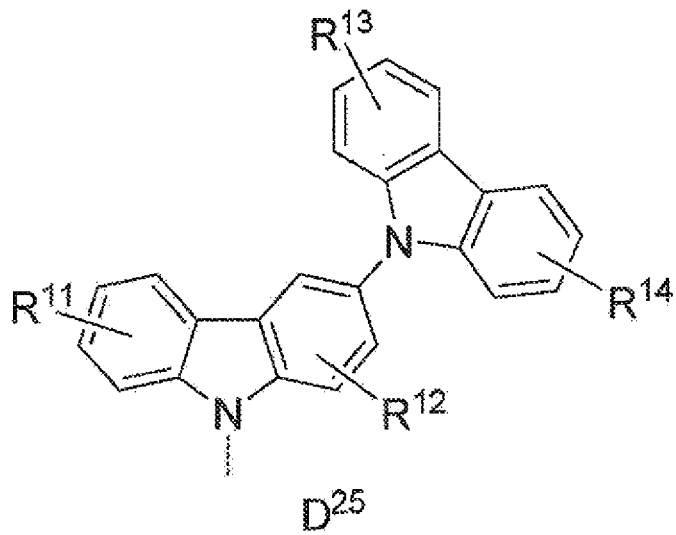

and insert --  --

CERTIFICATE OF CORRECTION (continued)
U.S. Pat. No. 9,670,185 B2

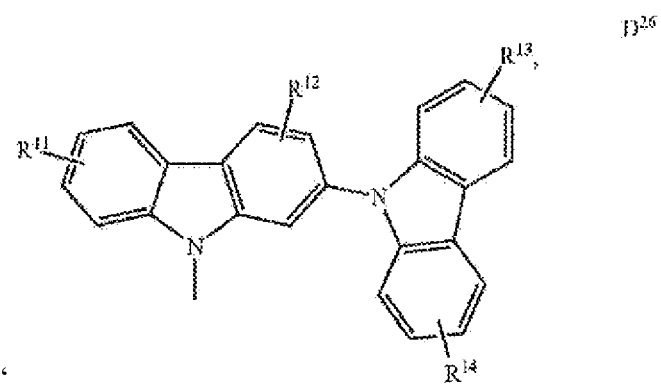

Column 23, Lines 55-66, please delete "

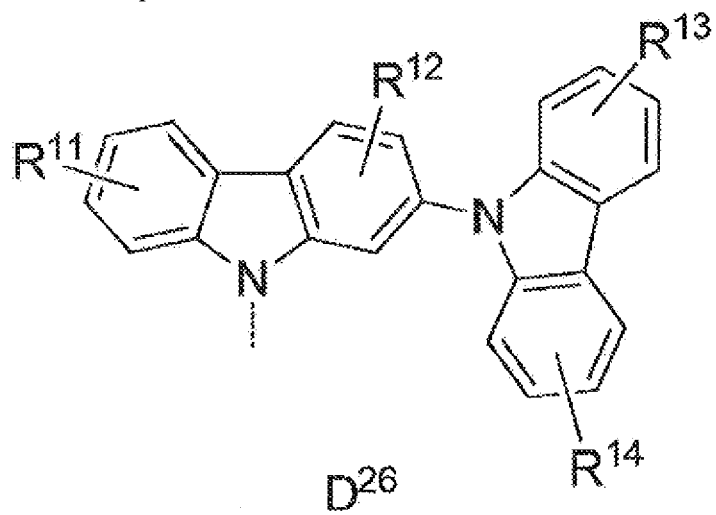

and insert -- "                    " --

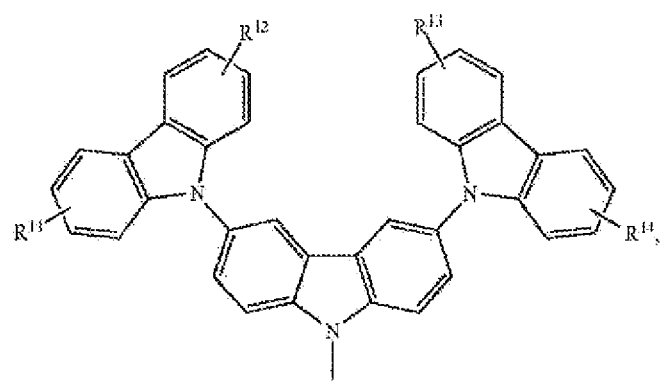

Column 24, Lines 1-15, please delete "                    "

and insert -- 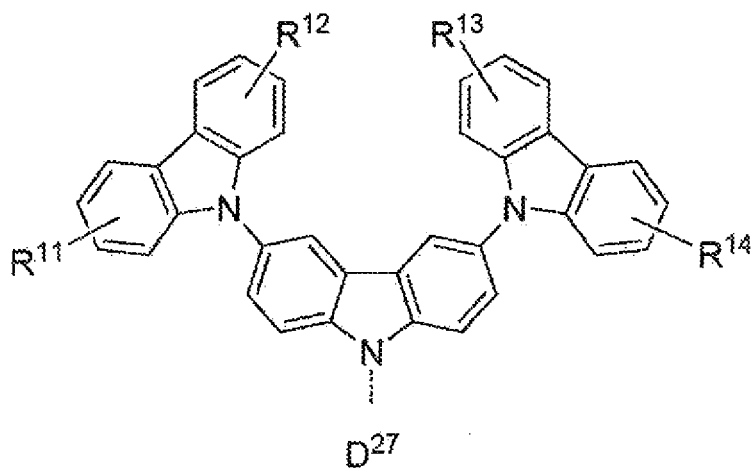 --
Column 25, Lines 15-25, please delete " 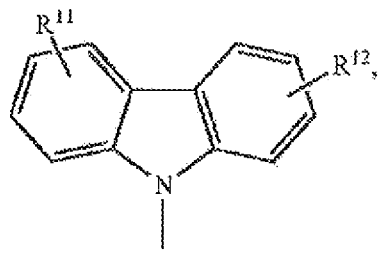
and insert -- 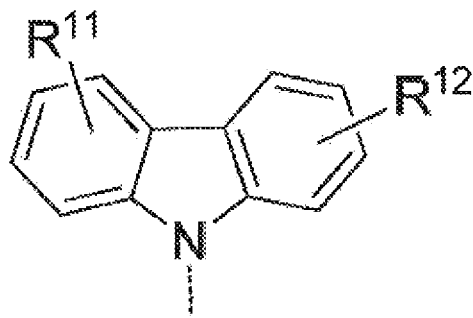 --
Column 27, Lines 1-9, please delete " 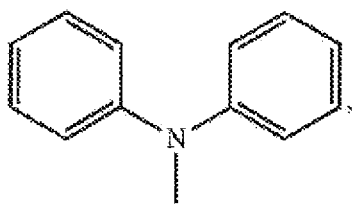 "

and insert -- 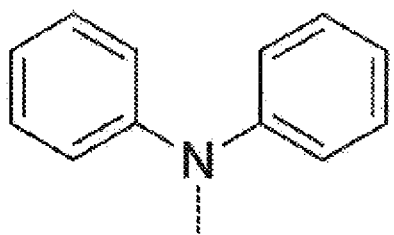 --
Column 27, Lines 21-29, please delete " 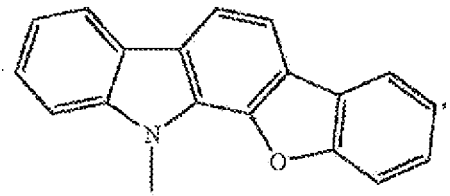 "
and insert -- 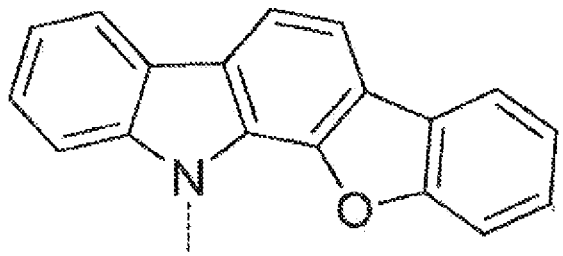 --
Column 27, Lines 30-38, please delete " 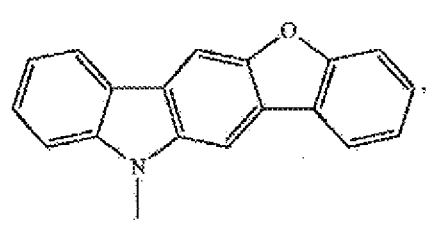 "

and insert -- 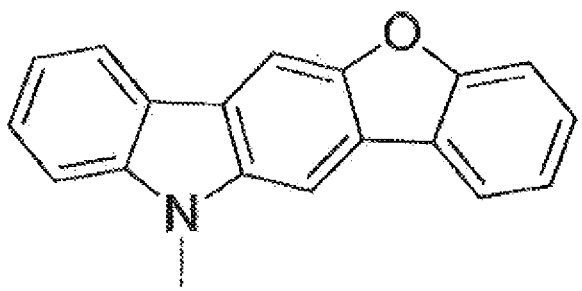 --
Column 27, Lines 39-49, please delete " 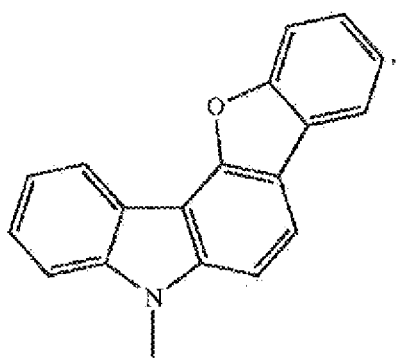 "
and insert -- 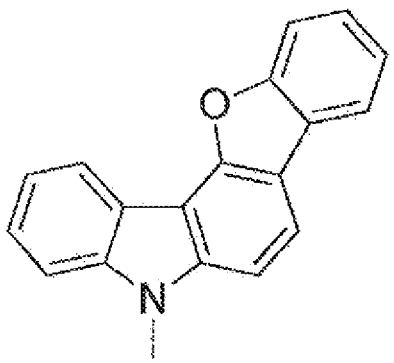 --
Column 27, Lines 50-58, please delete " 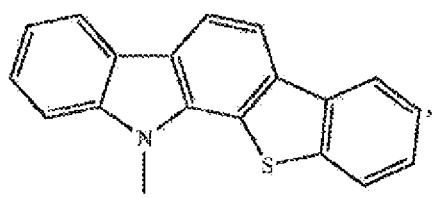 "

CERTIFICATE OF CORRECTION (continued)
U.S. Pat. No. 9,670,185 B2

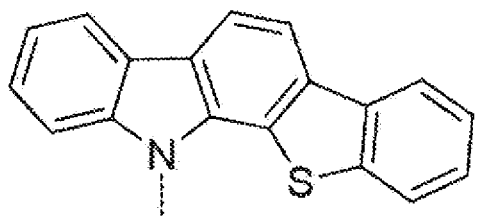

and insert-- $D^{106}$ --

Column 27, Lines 59-66, please delete "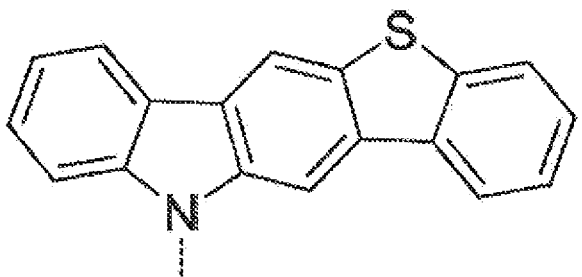"

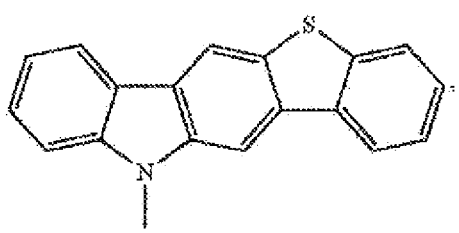

and insert -- $D^{107}$ , --

Column 28, Lines 1-14, please delete "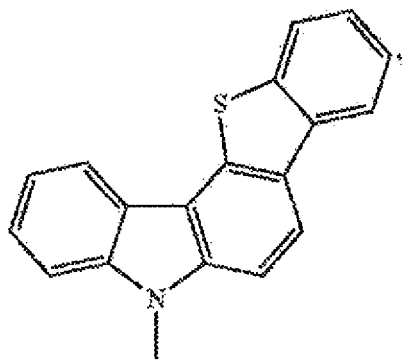"

CERTIFICATE OF CORRECTION (continued)
U.S. Pat. No. 9,670,185 B2 and insert -- 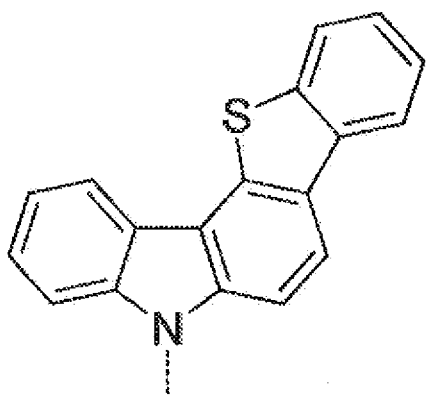 --

Column 27, Lines 59-66, please delete " 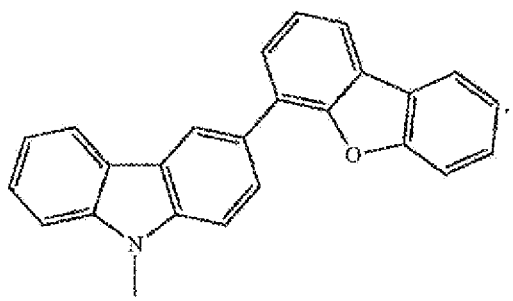 "

and insert -- 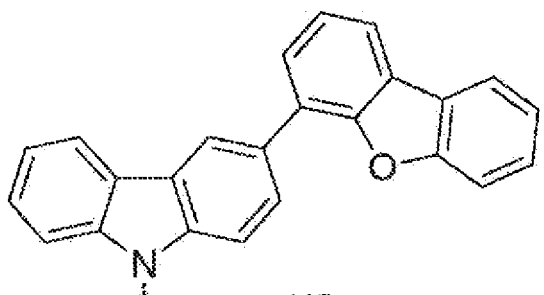 --

Column 28, Lines 1-14, please delete " 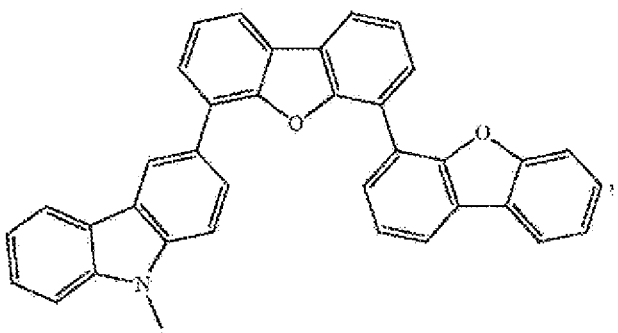 "

and insert -- 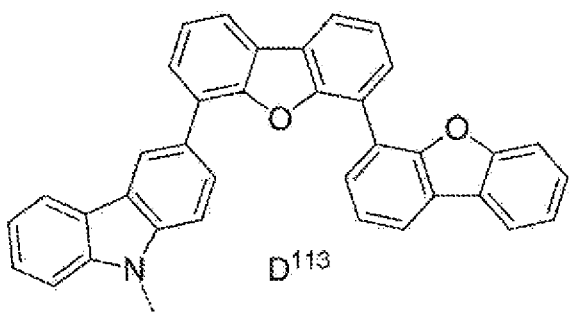 --
Column 29, Lines 1-13, please, delete " 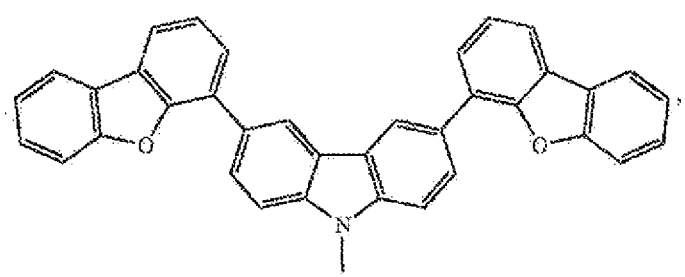 "
and insert -- 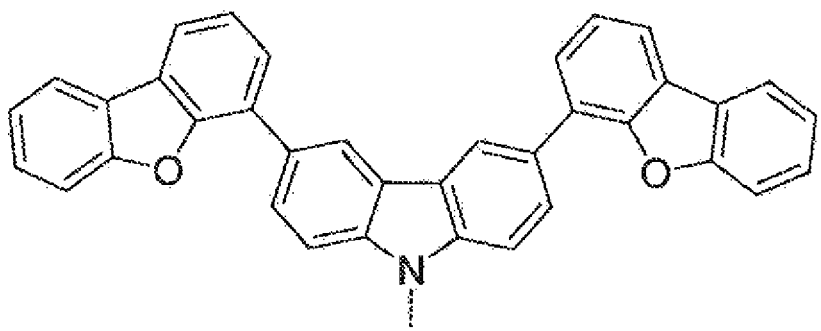 --
Column 29, Lines 43-53, please delete " 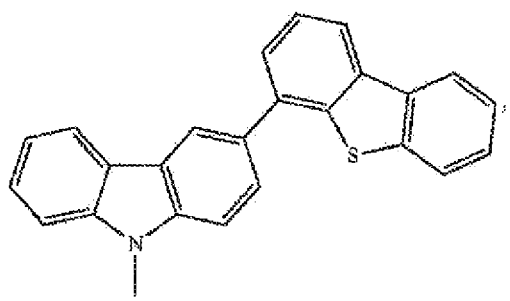 "

and insert -- 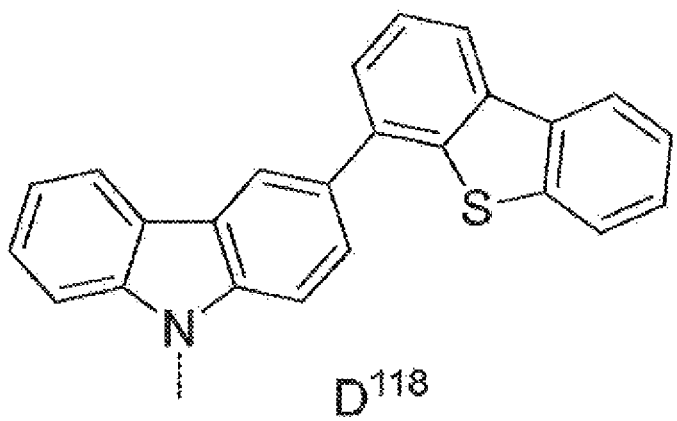 --
Column 29, Lines 54-66, please delete " 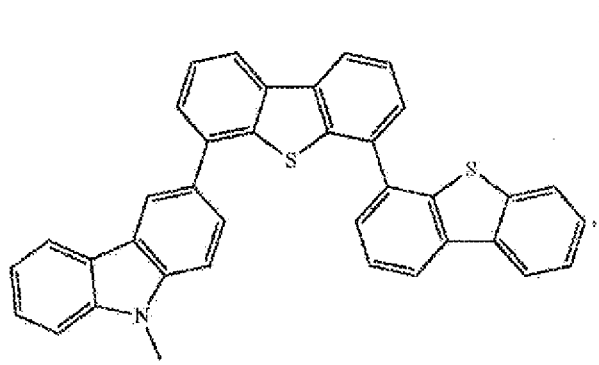 "
and insert -- ' 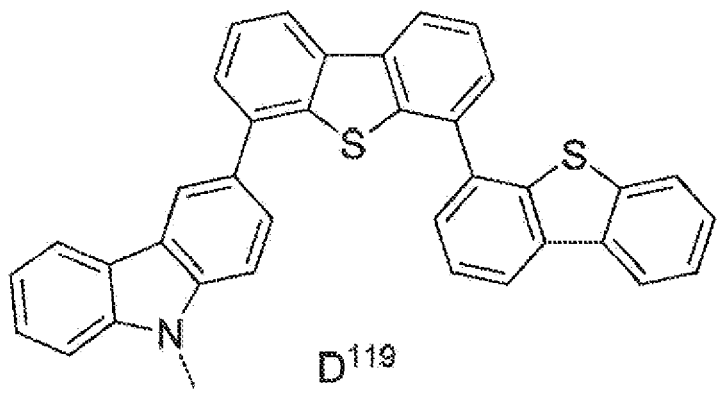 ' --

Column 30, Lines 1-13, please delete "
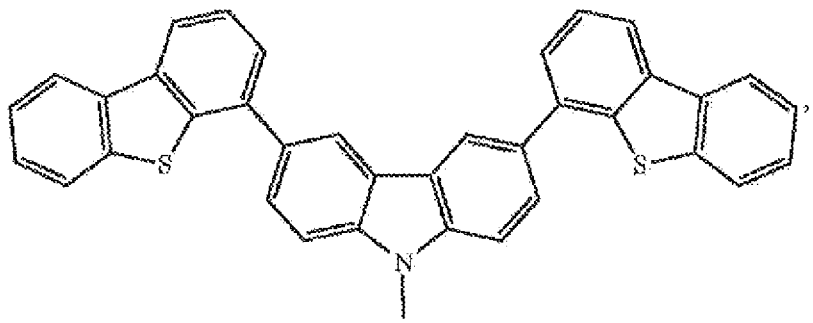
"
and insert --
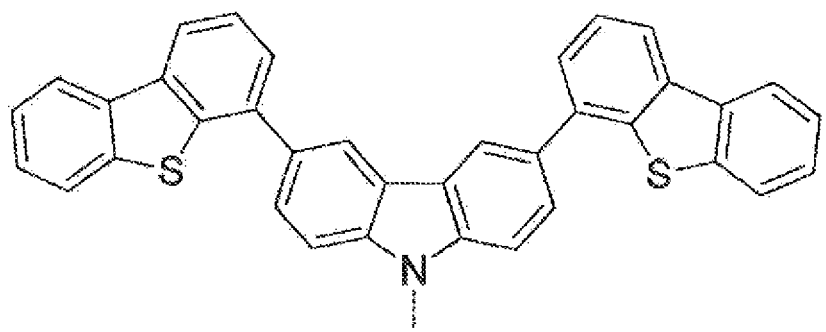
--
Column 31, Lines 1-15, please delete "
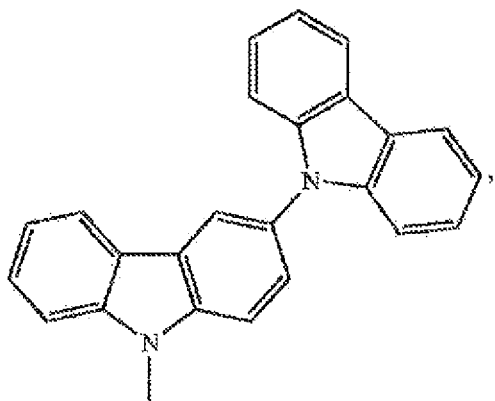
"

and insert -- 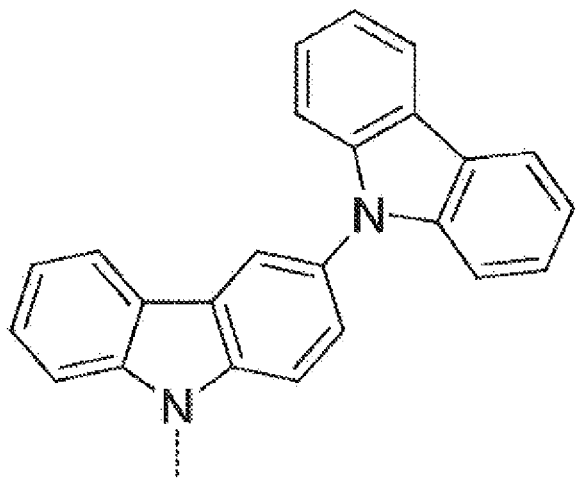 --
Column 31, Lines 16-30, please delete
" 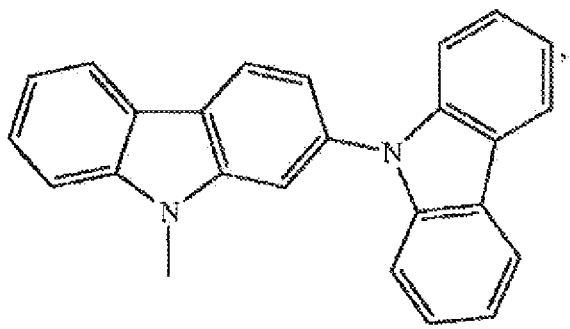 "
and insert -- 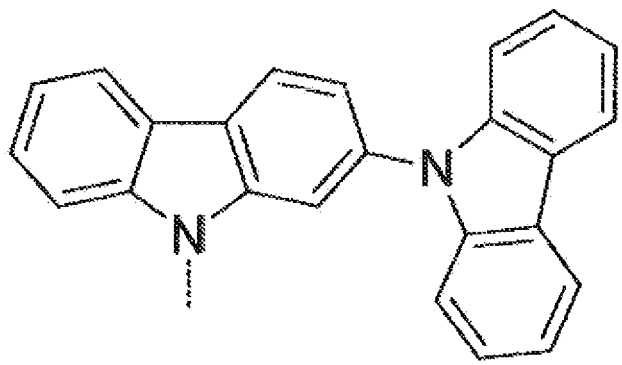 --

Column 31, Lines 31-46, please delete " 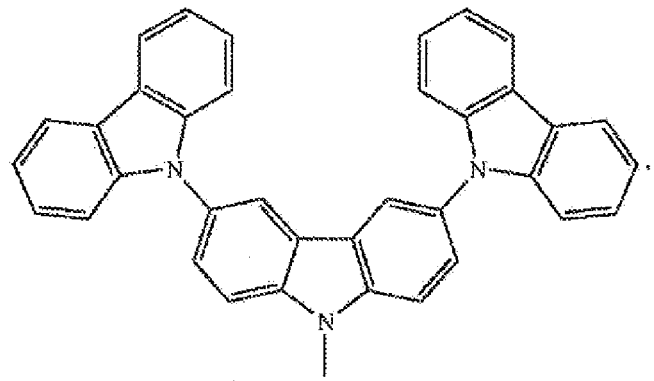 "
and insert -- 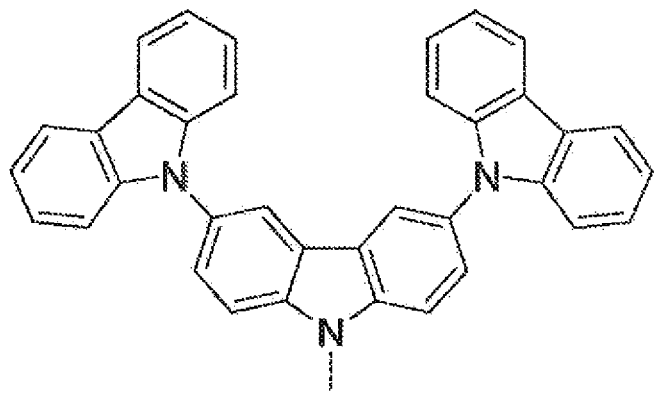 , --
Column 32, Lines 42-47, please delete " 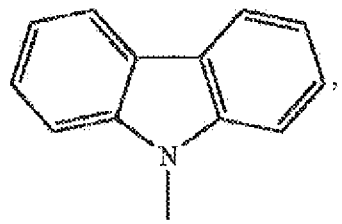 "
and insert -- 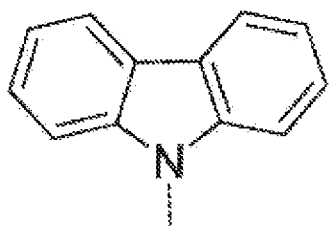 --

CERTIFICATE OF CORRECTION (continued)
U.S. Pat. No. 9,670,185 B2

Column 39, Lines 40-44, please delete " 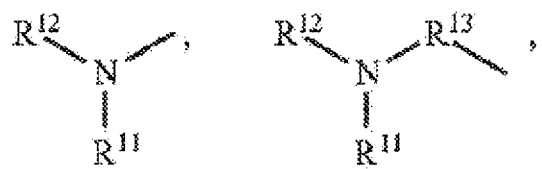 "

and insert -- 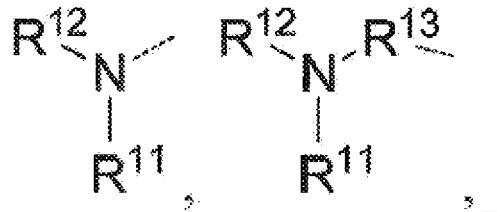 --

Column 39, Lines 45-52, please delete " 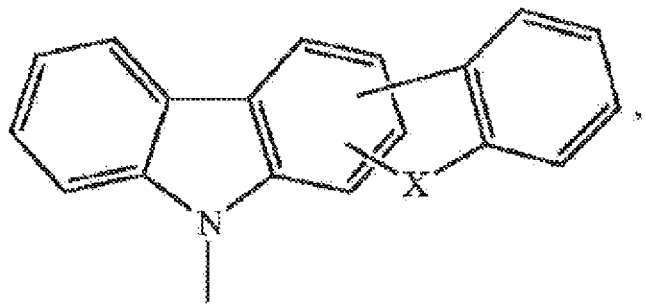 "

and insert -- 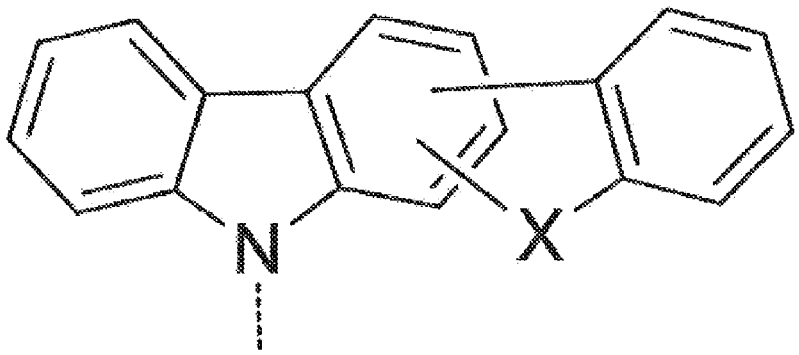 --

Column 39, Lines 57-66, please delete

" 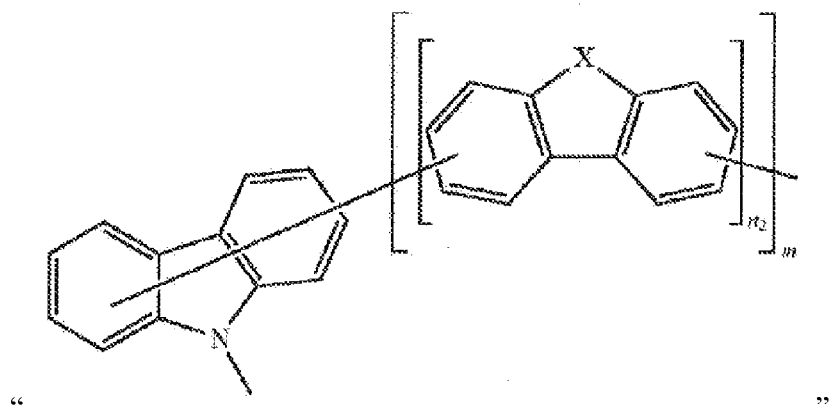 "

and insert -- 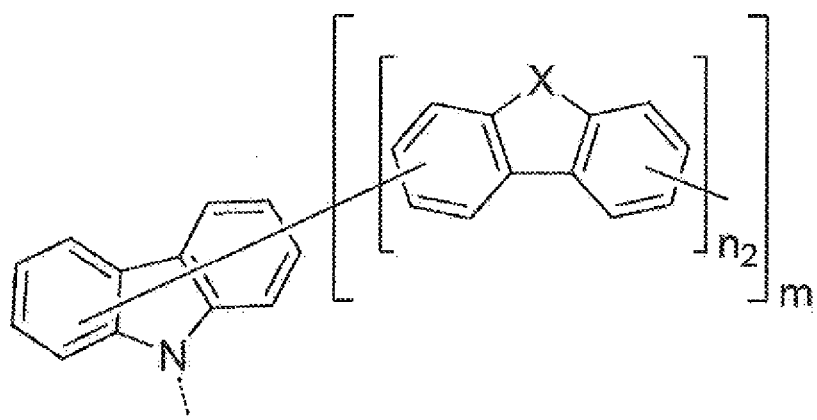 --
Column 40, Lines 11-23, please delete " 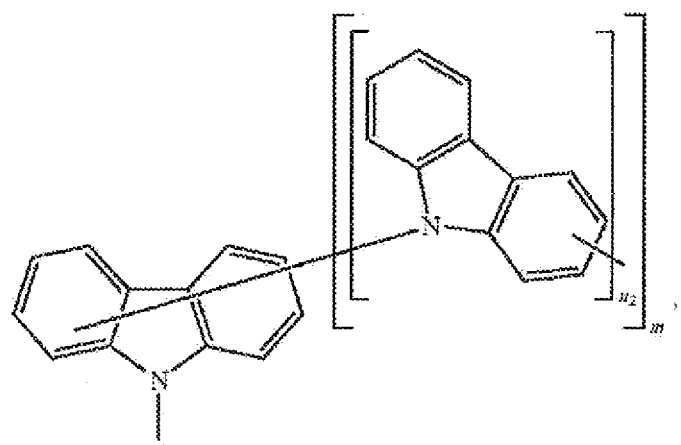 "
and insert -- 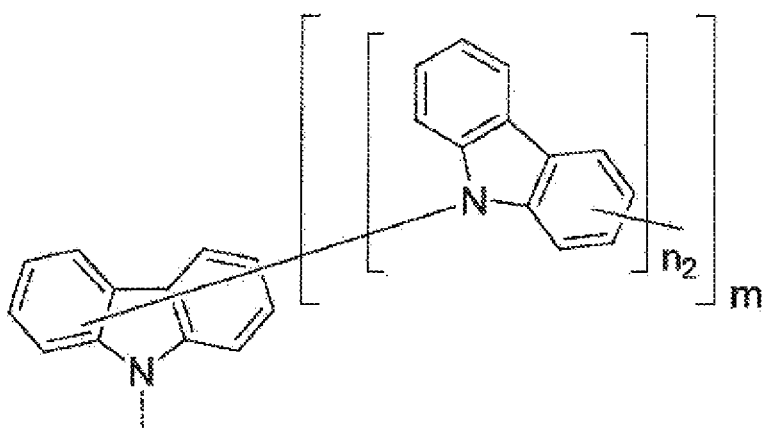 , --

CERTIFICATE OF CORRECTION (continued)
U.S. Pat. No. 9,670,185 B2

Column 40, Lines 24-33, please delete " 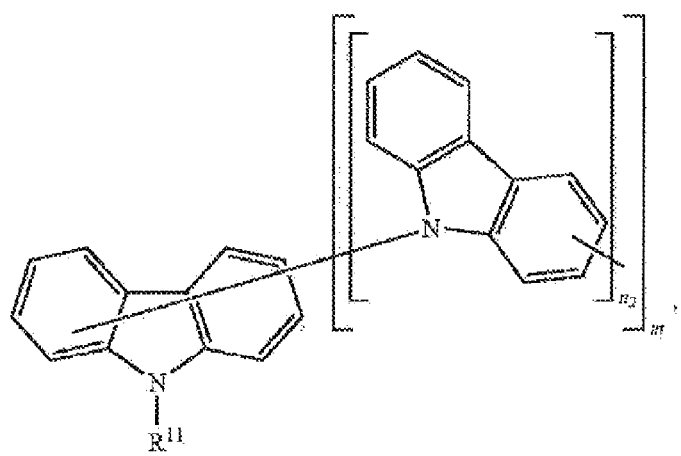 "

and insert -- 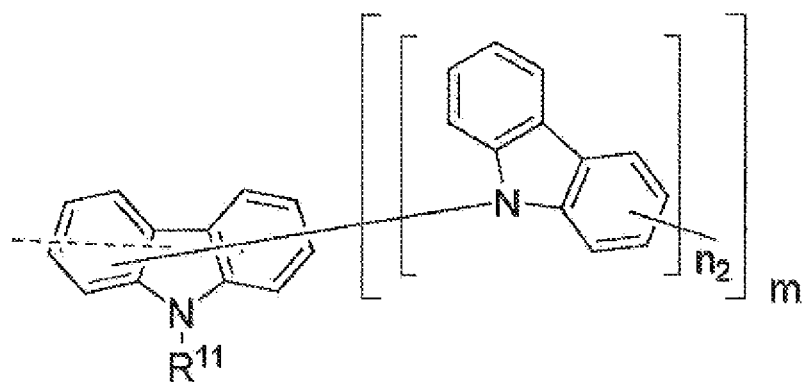 --

Column 41, Lines 1-9, please delete

" 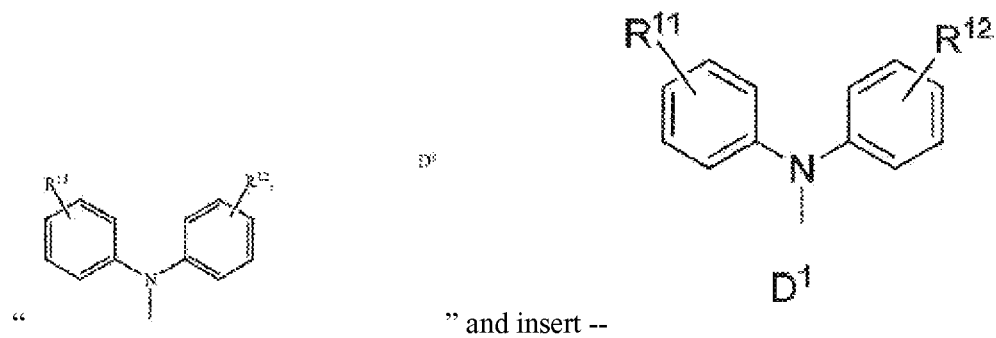 " and insert --

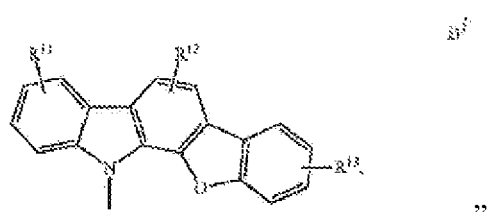 --

Column 41, Lines 24-32, please delete " "

Column 41, Lines 33-39, please delete "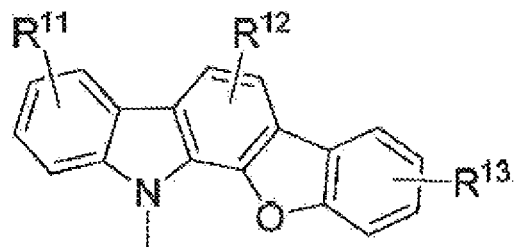" and insert --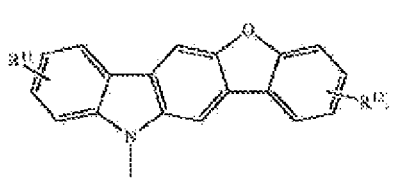--
Column 41, Lines 40-50, please delete "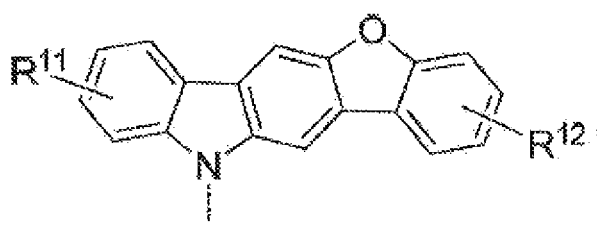" and insert --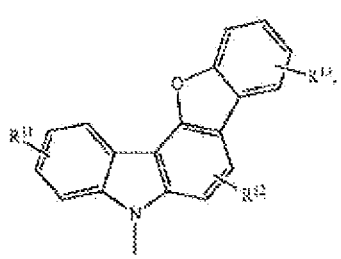--

CERTIFICATE OF CORRECTION (continued)

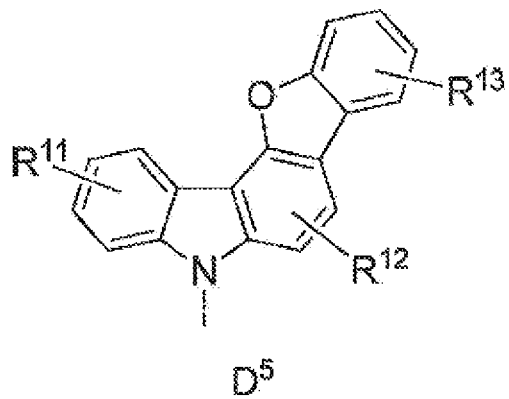

and insert --

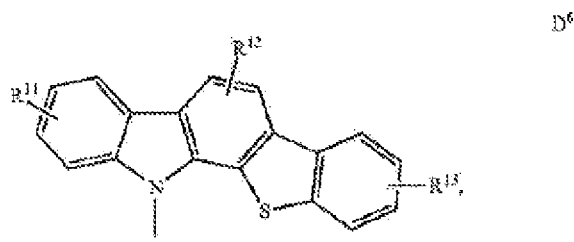

--

Column 41, Lines 51-58, please delete "

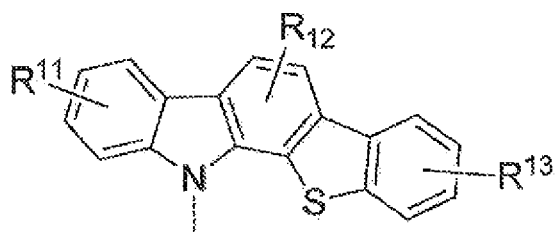

"

and insert --

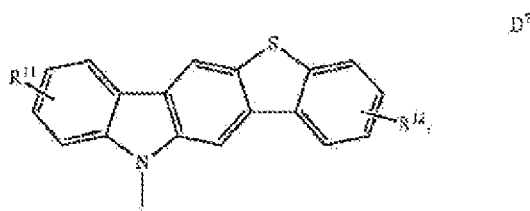

--

Column 41, Lines 59-67, please delete "

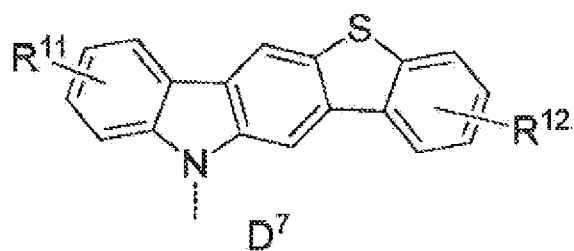

"

and insert -- , --

Column 42, Lines 1-14, please delete " " and insert -- 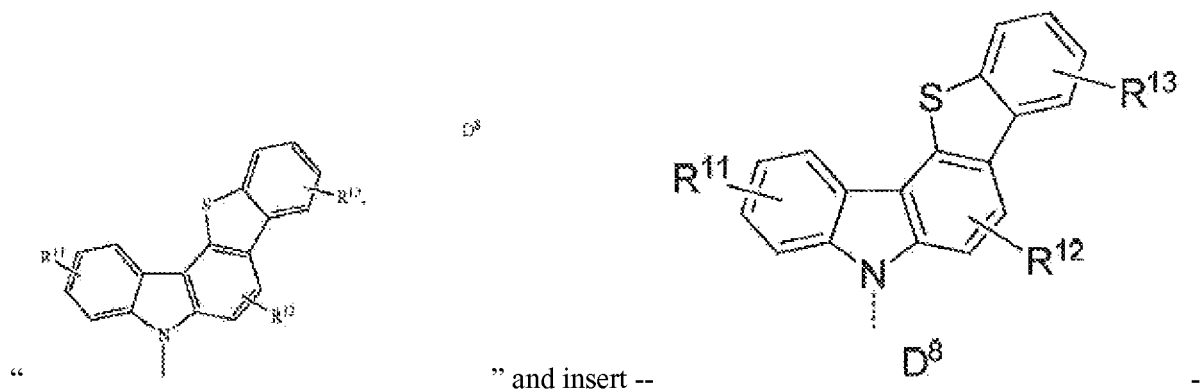 --
Column 42, Lines 43-54, please delete " 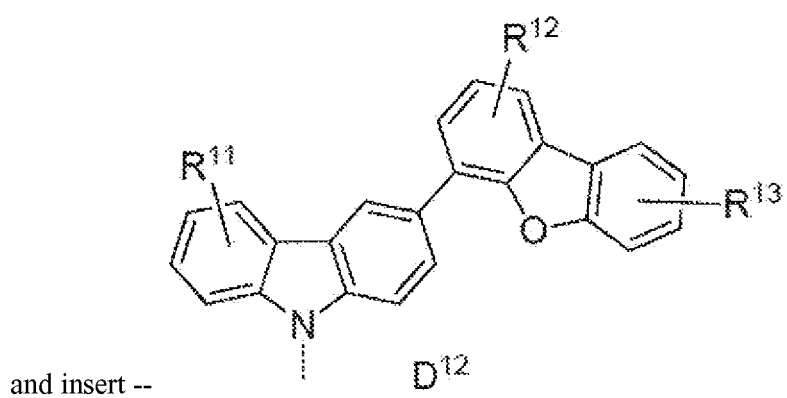 " and insert -- 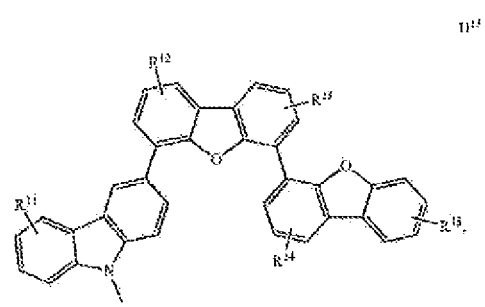 --
Column 42, Lines 55-67, please delete " "

CERTIFICATE OF CORRECTION (continued)
U.S. Pat. No. 9,670,185 B2

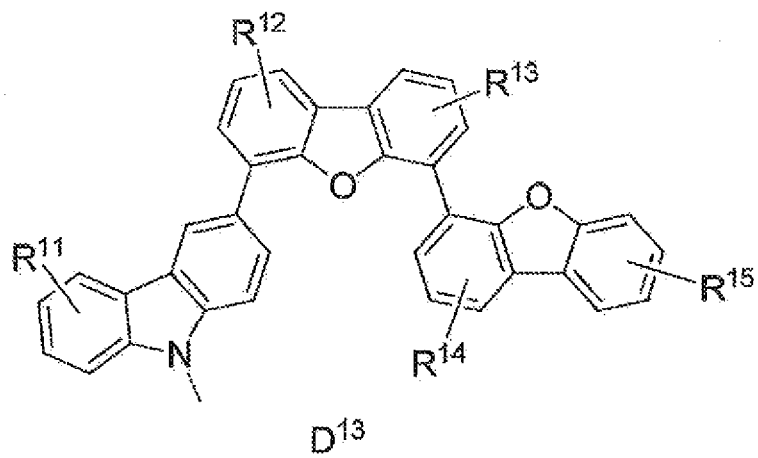

and insert --

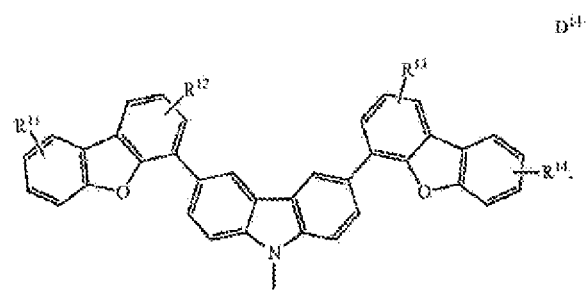

, --

Column 43, Lines 1-13, please delete "

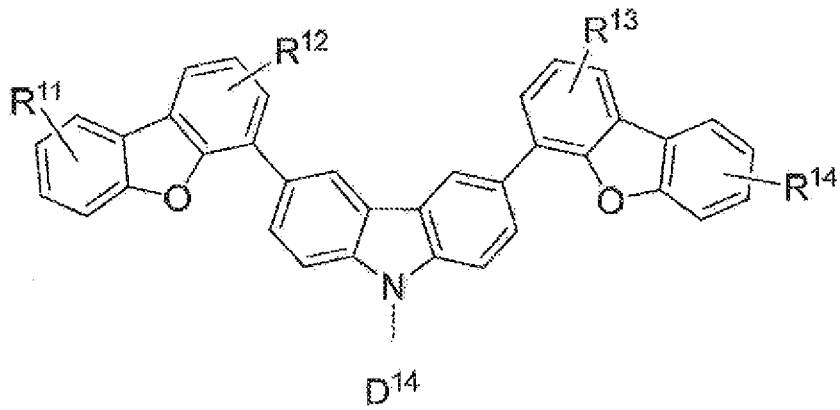

"

and insert --

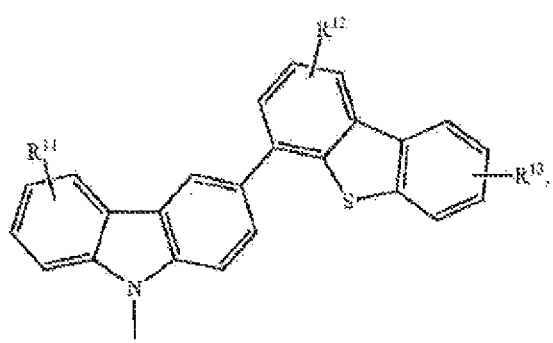

--

Column 43, Lines 43-53, please delete "

CERTIFICATE OF CORRECTION (continued)
U.S. Pat. No. 9,670,185 B2

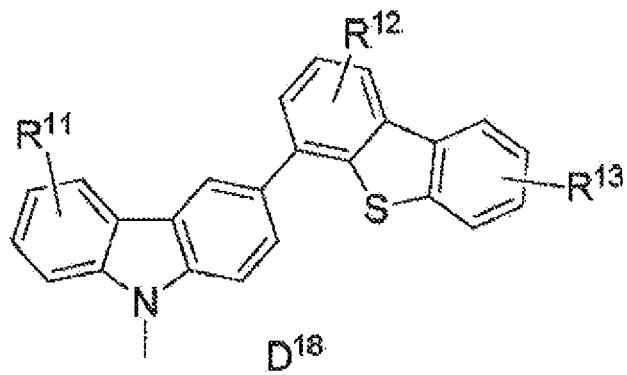

and insert --

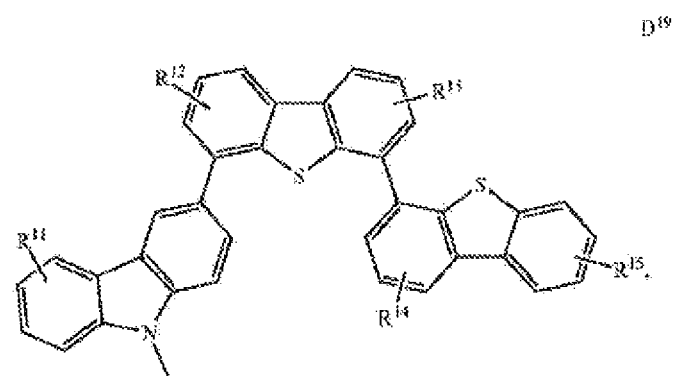

--

Column 43, Lines 54-66, please delete "

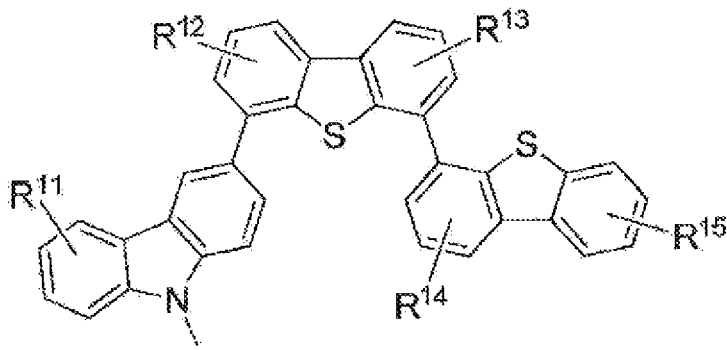

"

and insert --

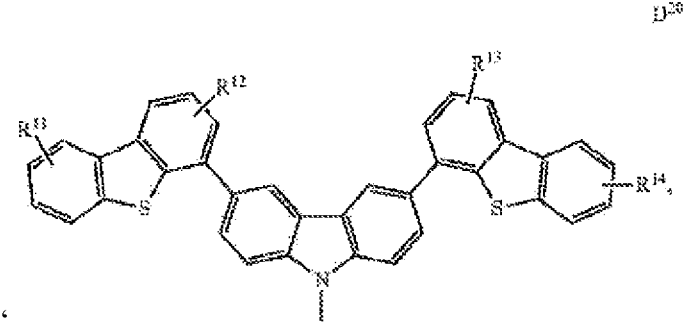

--

Column 44, Lines 1-13, please delete "

and insert --
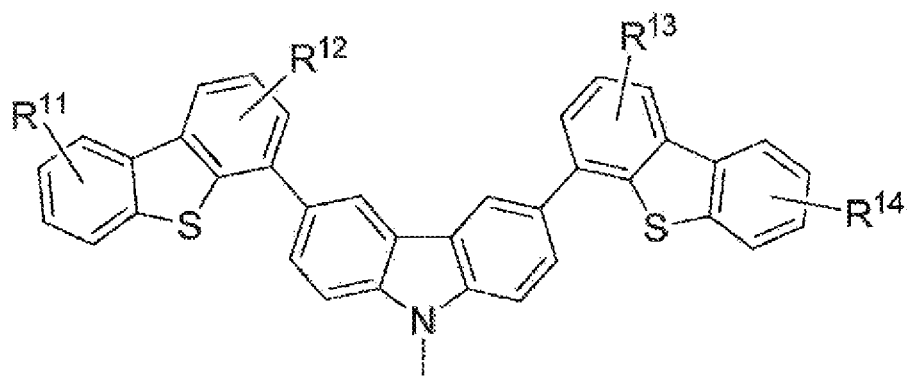
--
Column 45, Lines 1-14, please delete "
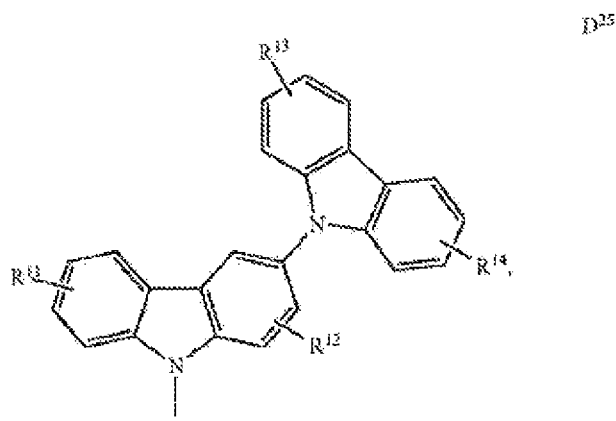
"
and insert --
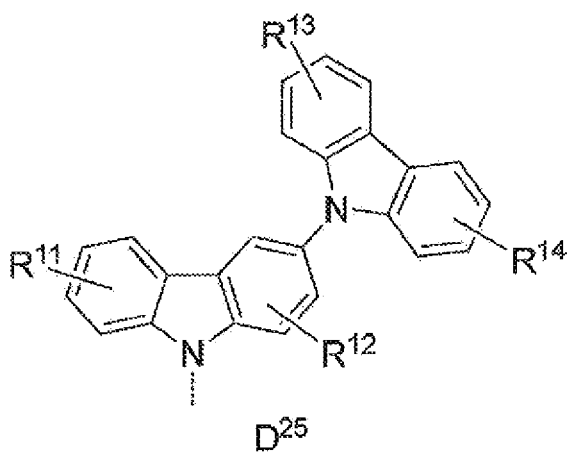
--

Column 45, Lines 15-30, please delete " 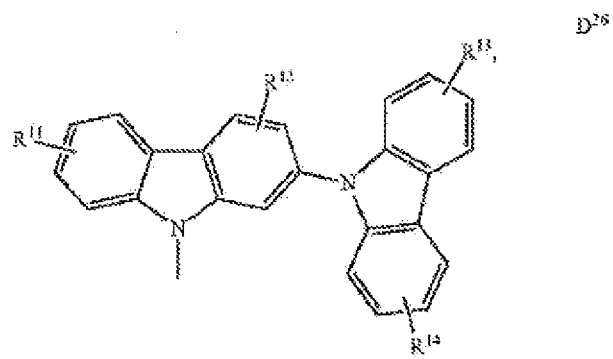 "
and insert -- 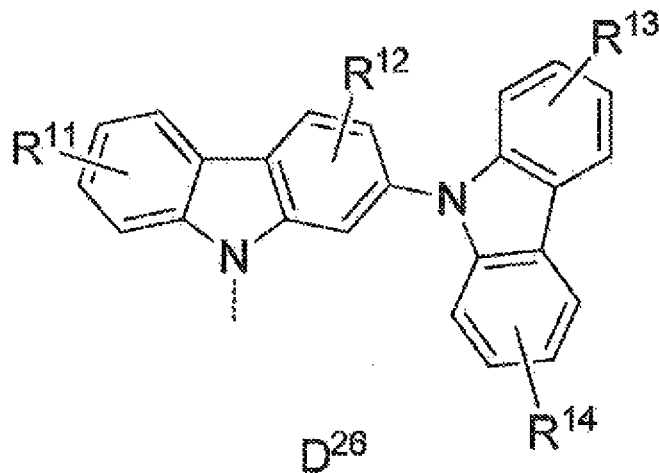 --
Column 45, Lines 31-47, please delete " 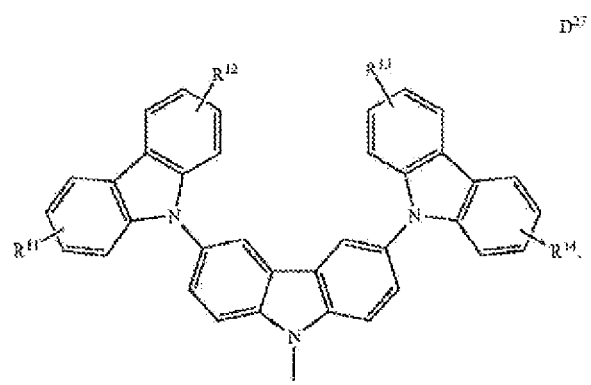 "

and insert -- 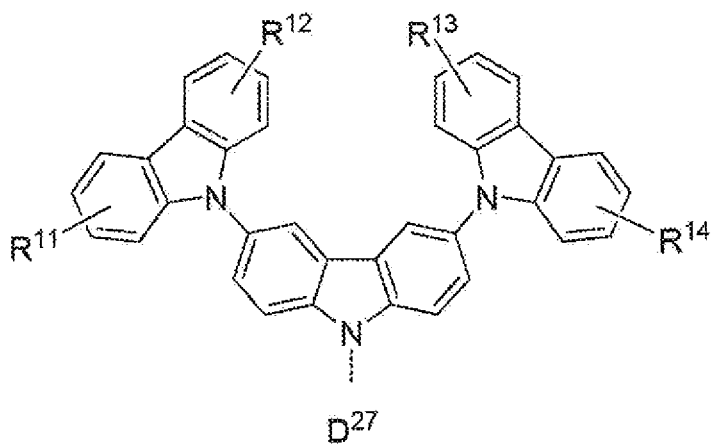 --
Column 47, Lines 5-13, please delete 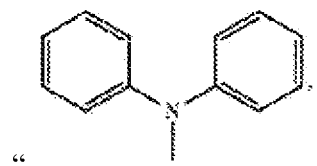 " and insert -- 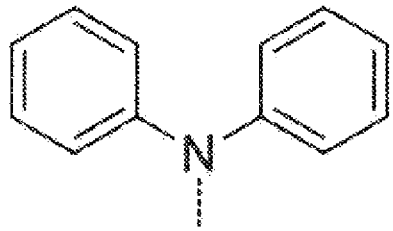 --
Column 47, Lines 27-32 please delete " 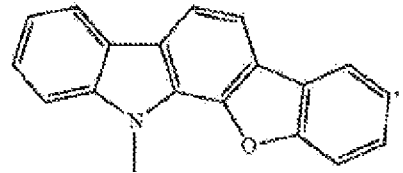 "
and insert -- 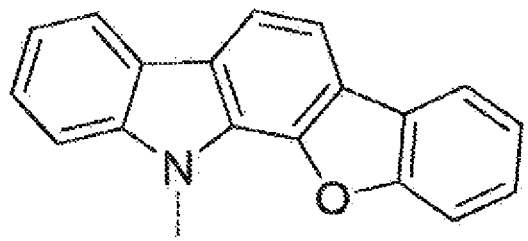 --

Column 47, Lines 33-40, please delete " 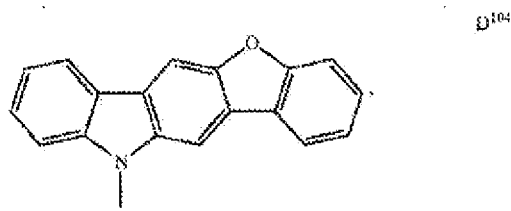 " and insert -- 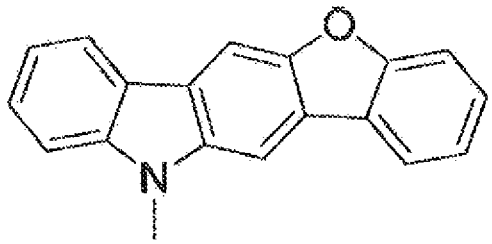 --
Column 47, Lines 41-52, please delete
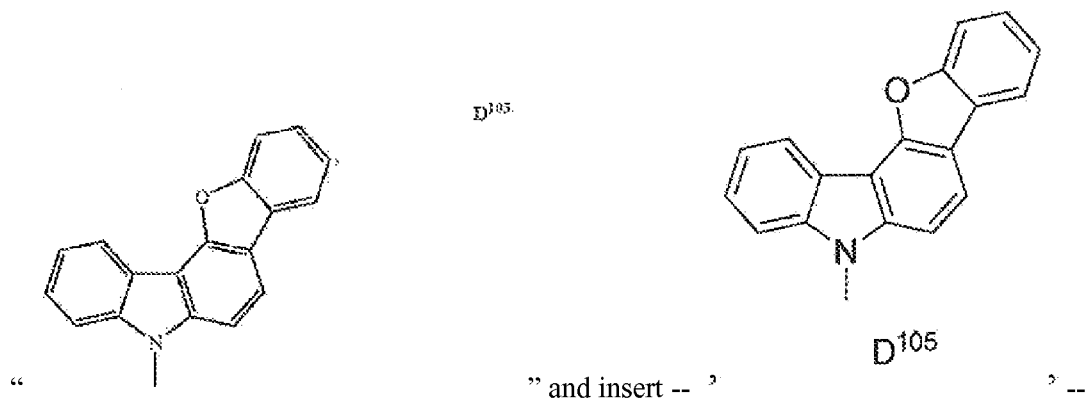
" and insert -- " --
Column 47, Lines 53-57, please delete " 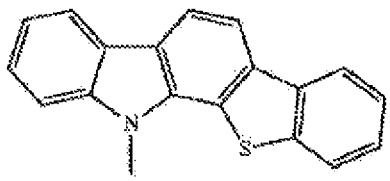
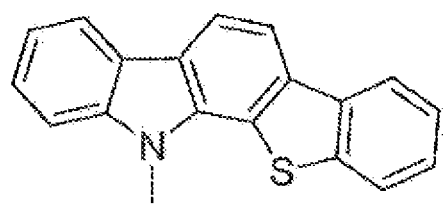
and insert -- " --

CERTIFICATE OF CORRECTION (continued)
U.S. Pat. No. 9,670,185 B2

Column 47, Lines 58-65, please delete " 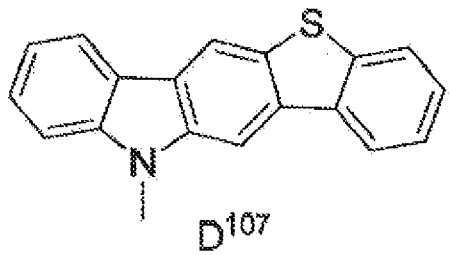 and insert -- 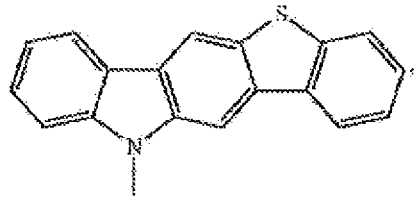 --

Column 48, Lines 1-13, please delete 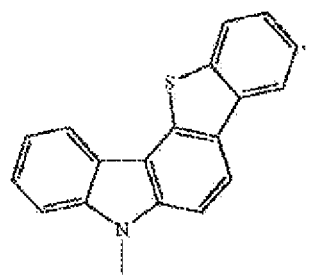 " and insert -- 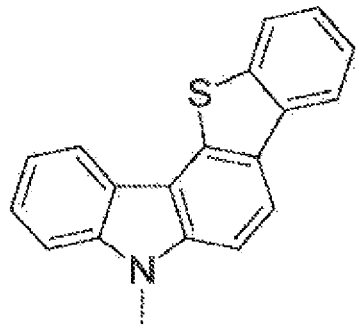 --

Column 48, Lines 43-52, please delete " 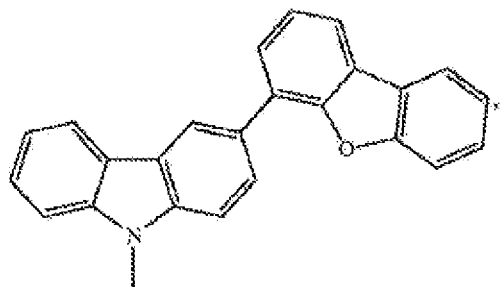 "

and insert -- 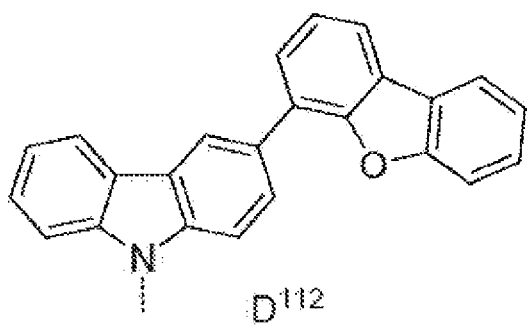 --
Column 48, Lines 53-67, please delete " 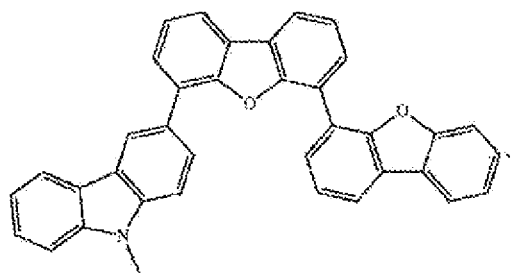 "
and insert -- 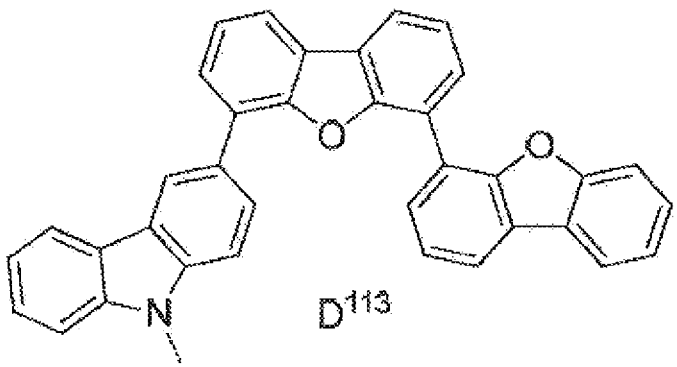 --
Column 49, Lines 1-13, please delete " 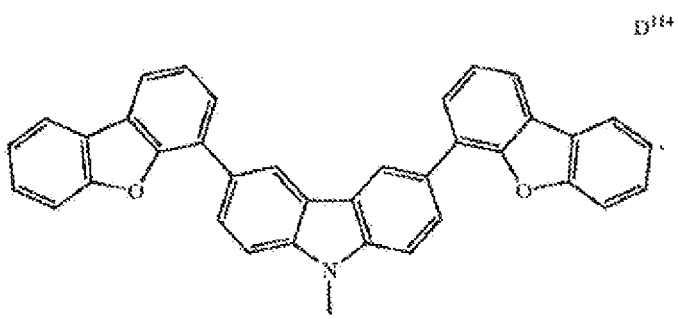 "

CERTIFICATE OF CORRECTION (continued)
U.S. Pat. No. 9,670,185 B2 and insert --  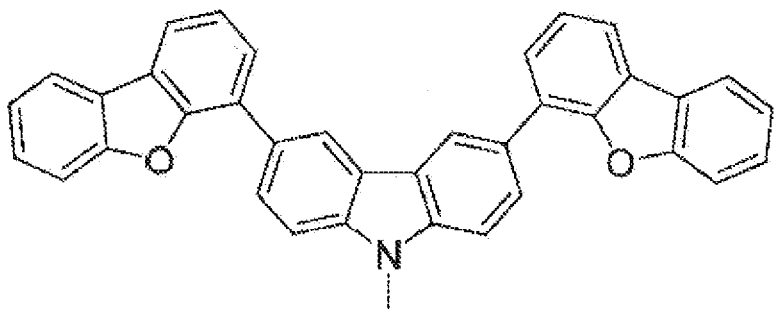  --

Column 49, Lines 43-52, please delete " 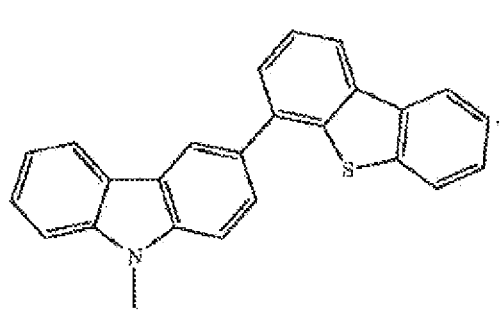 "

and insert -- 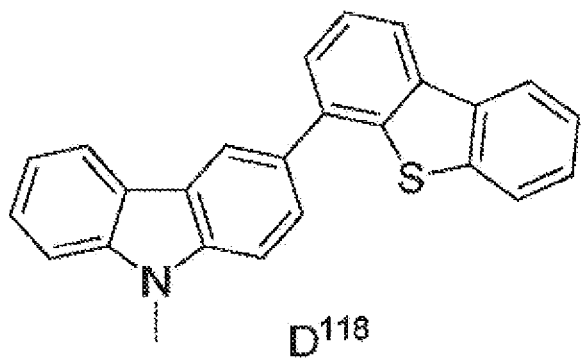 --

Column 49, Lines 53-65, please delete " 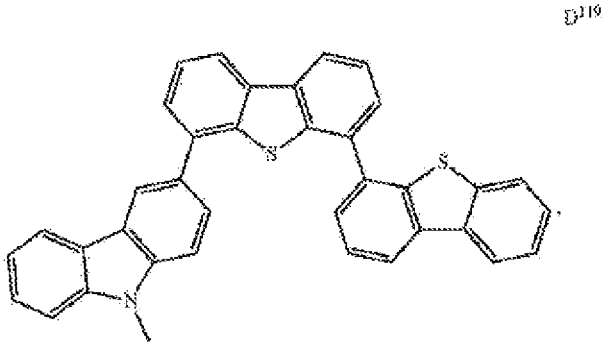 "

CERTIFICATE OF CORRECTION (continued)

U.S. Pat. No. 9,670,185 B2

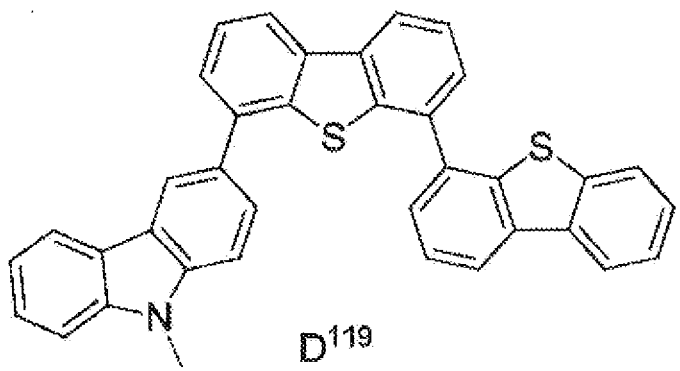

and insert --                                  , --

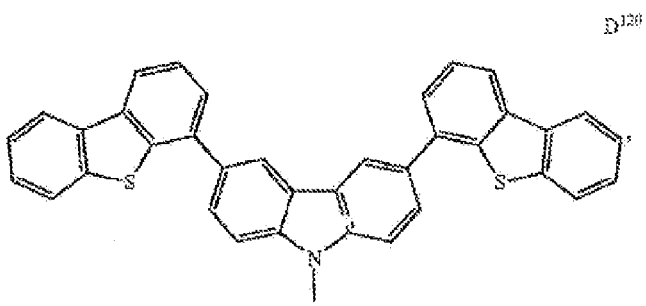

Column 50, Lines 1-12, please delete "

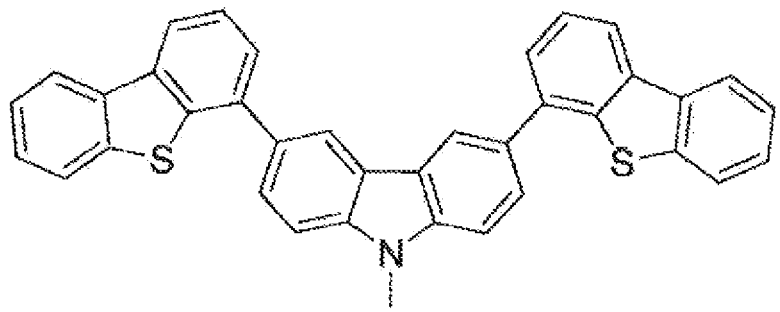

and insert --                                  --

Column 51, Lines 1-14, please delete

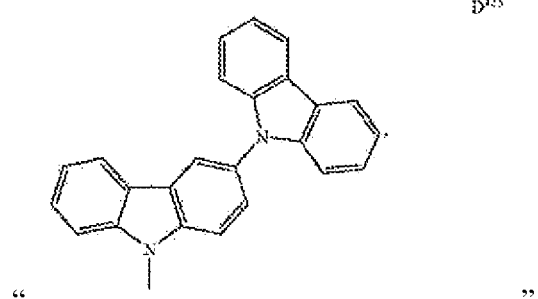

"                                  "

and insert -- 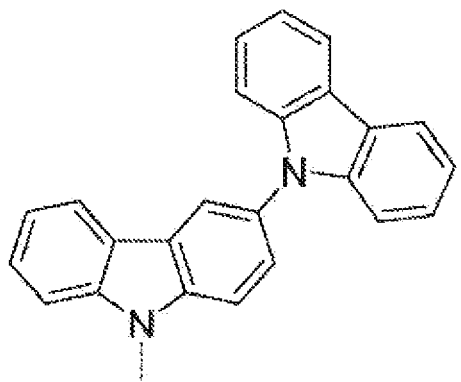 --
Column 51, Lines 15-27, please delete " 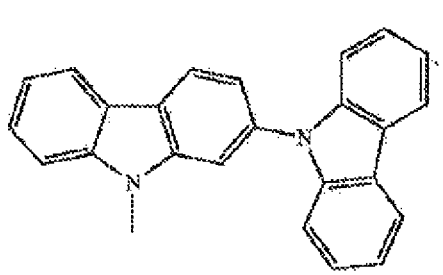 "
and insert -- 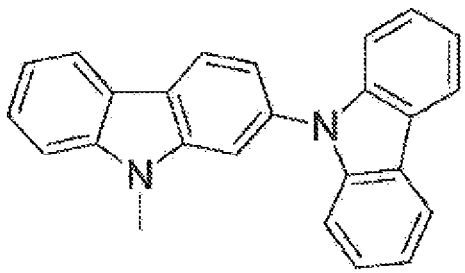 --
Column 51, Lines 28-45, please delete " 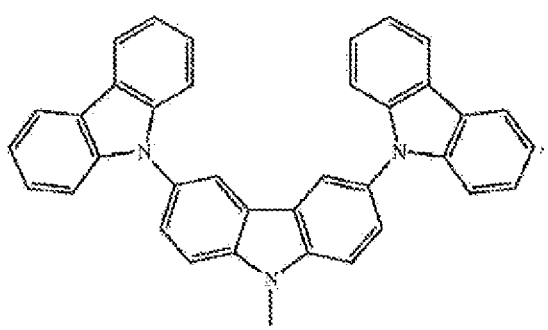 "

CERTIFICATE OF CORRECTION (continued)
U.S. Pat. No. 9,670,185 B2 and insert -- 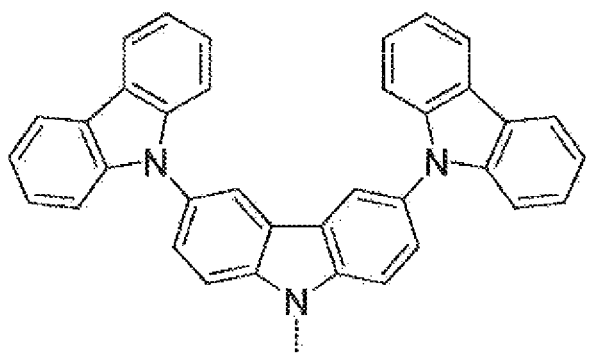 --

Column 172, Lines 8-13, please delete " 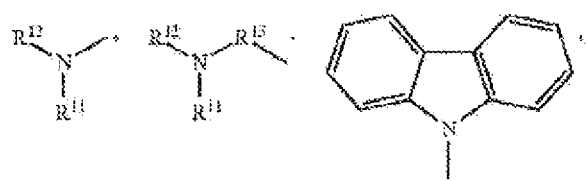

and insert -- 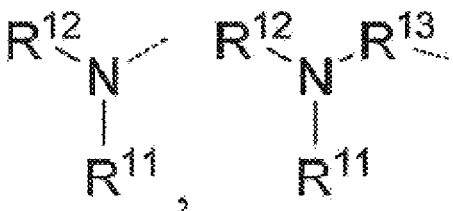 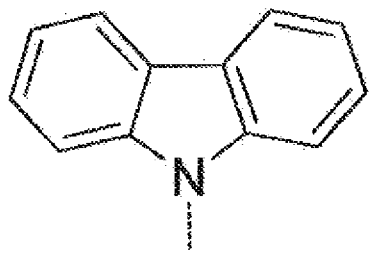 --

Column 172, Lines 27-32, please delete

" 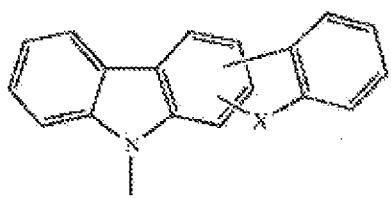 " and insert -- 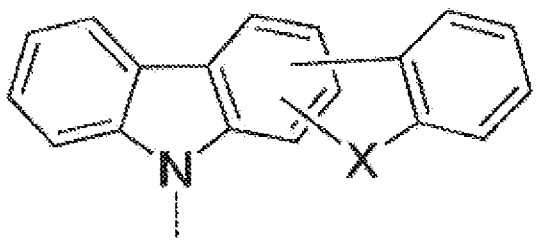 --

Column 172, Lines 38-47, please delete " 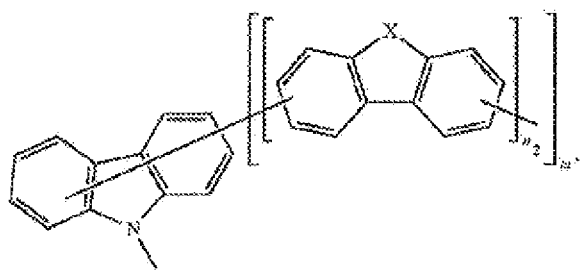 "

and insert -- 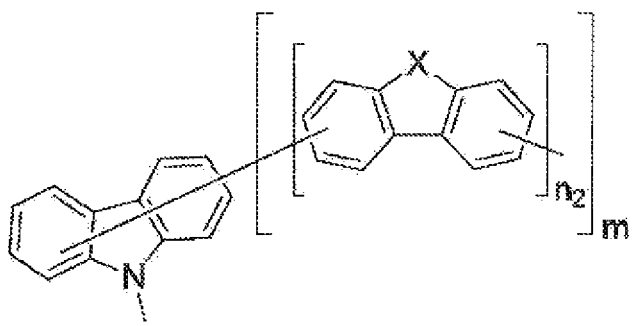 --
Column 172, Lines 55-66, please delete " 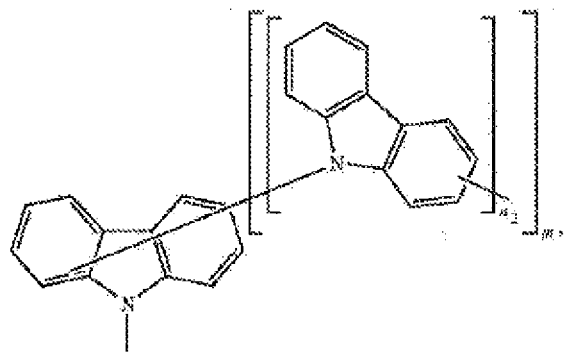 "
and insert -- 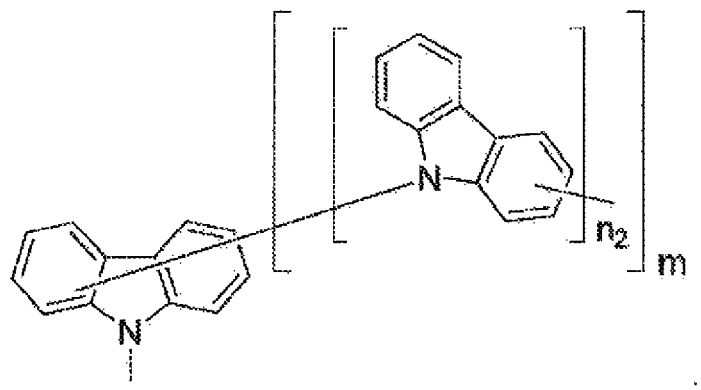 --
Column 173, Lines 38-46, please delete
" 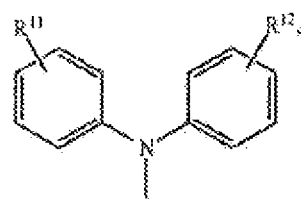 " and insert -- 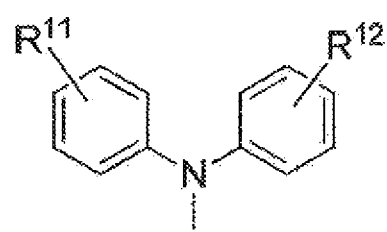 --

Column 173, Lines 58-66, please delete " 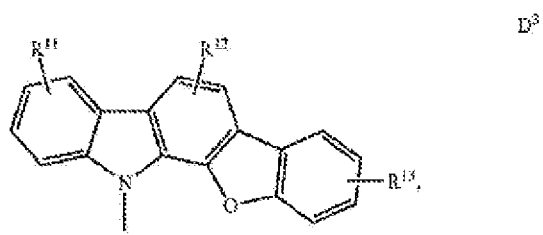 "
and insert -- 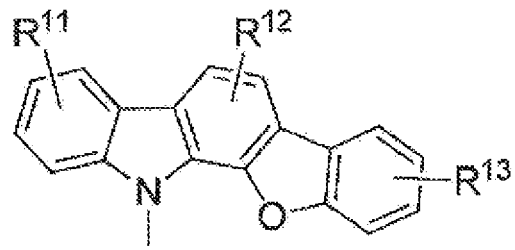 --
Column 174, Lines 1-9, please delete " 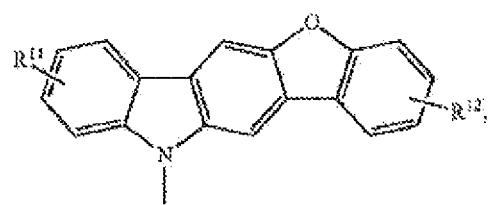 "
and insert -- 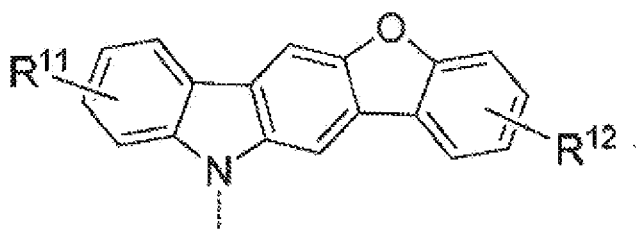 --
Column 174, Lines 10-19, please delete " 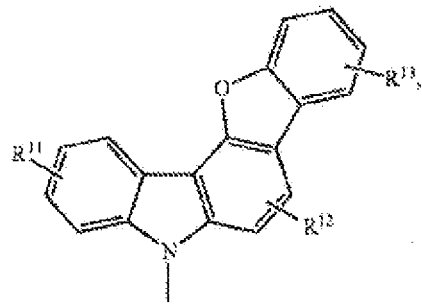 "

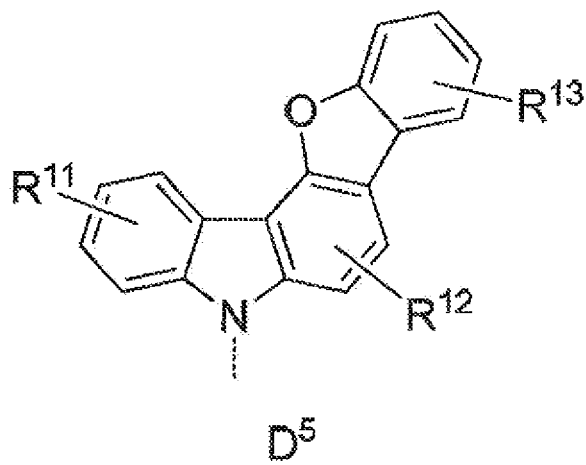
and insert -- " --
Column 174, Lines 20-27, please delete
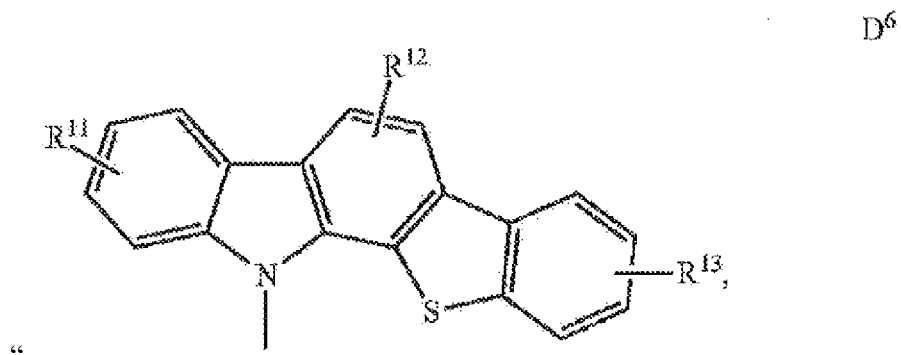
" "
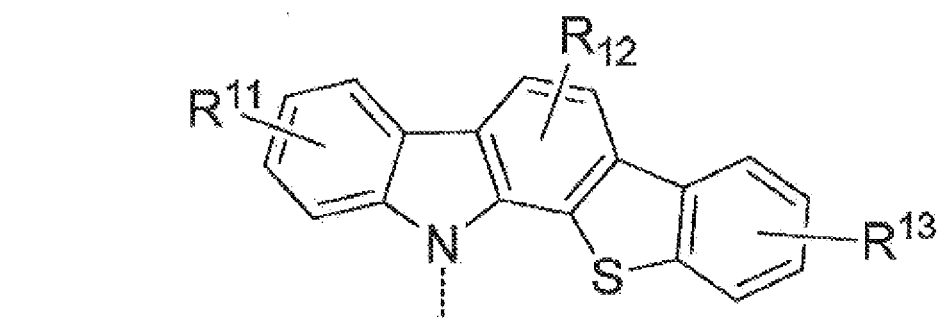
and insert -- --

CERTIFICATE OF CORRECTION (continued)
U.S. Pat. No. 9,670,185 B2

Column 174, Lines 28-35, please delete

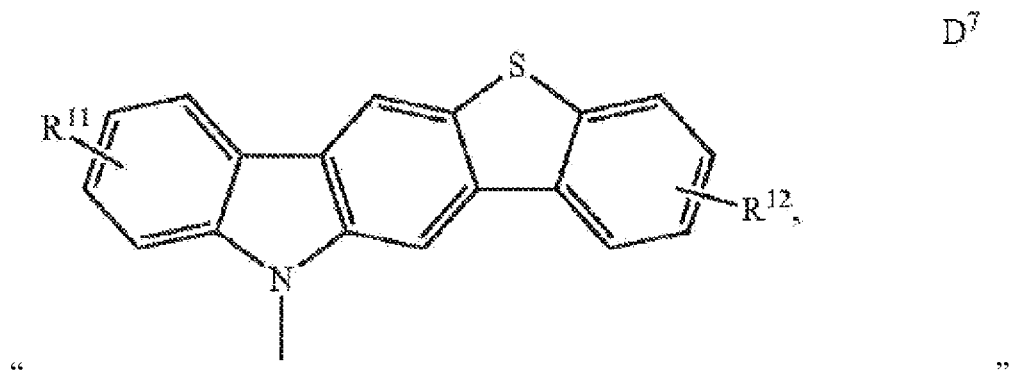

and insert --

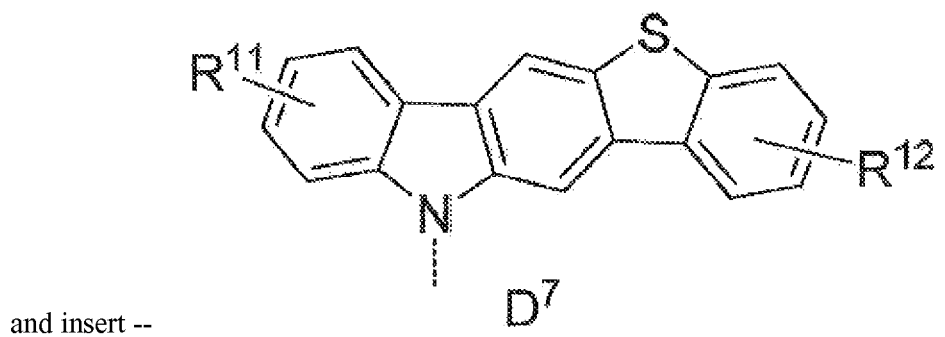
--

Column 174, Lines 36-46, please delete

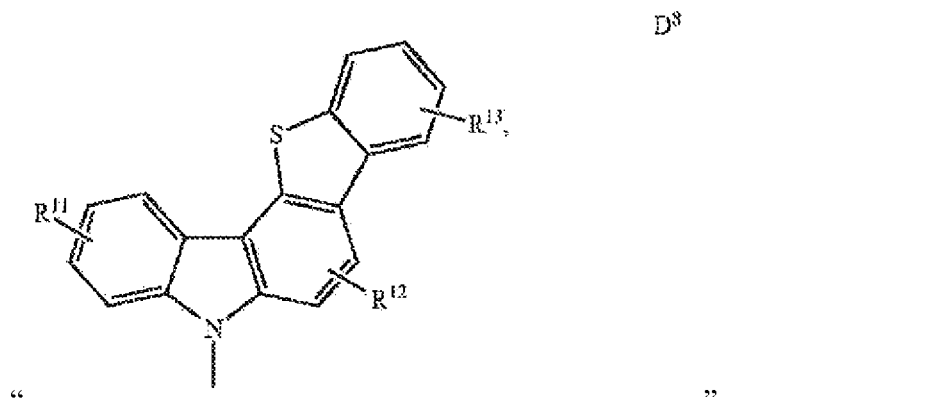

CERTIFICATE OF CORRECTION (continued)
U.S. Pat. No. 9,670,185 B2

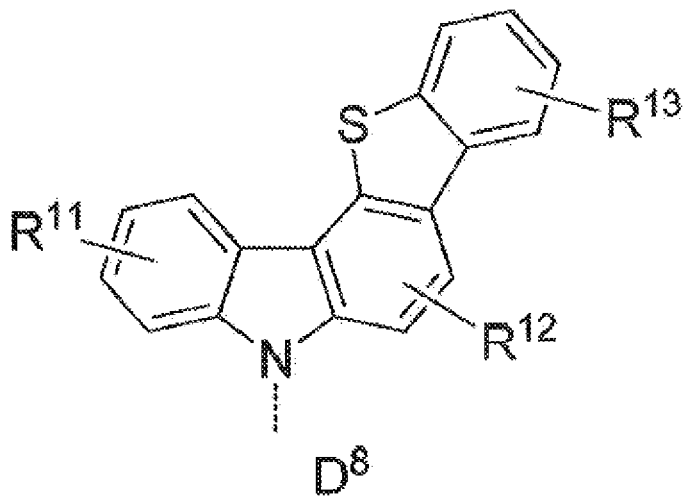

and insert --                                                                 --

Column 175, Lines 10-21, please delete

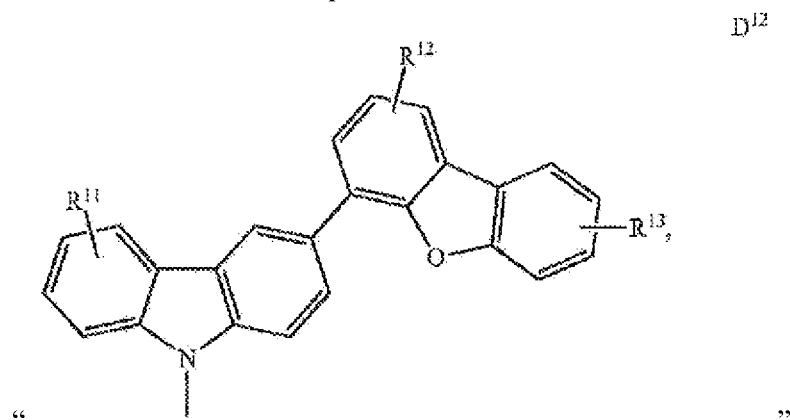

"                                                                 ,"

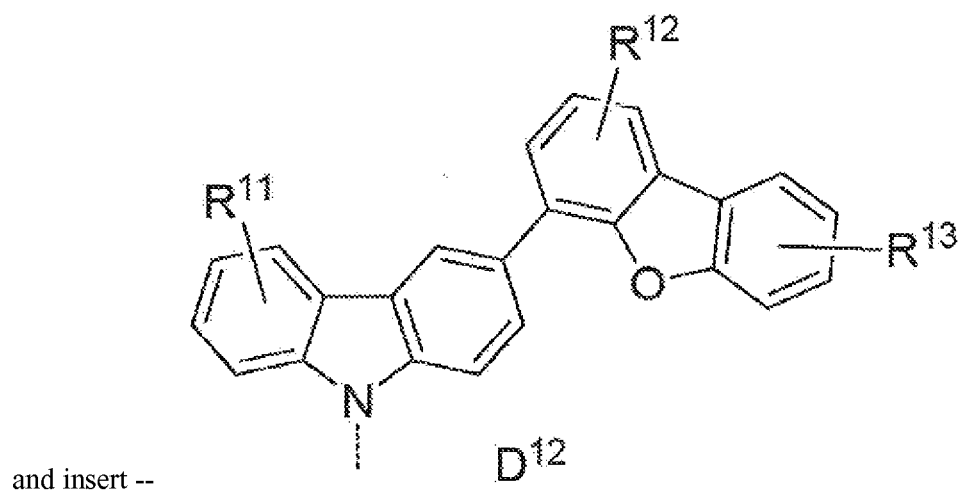

and insert --                                                                 --

Column 175, Lines 22-35, please delete " 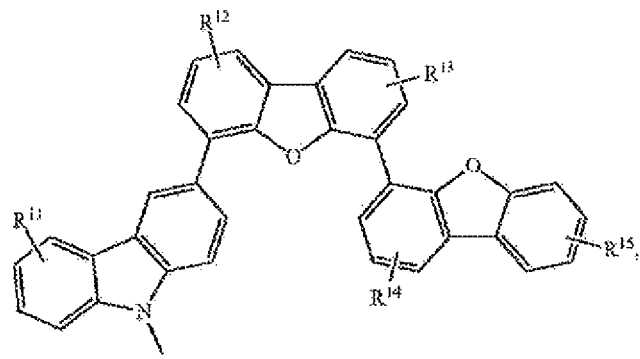 "
and insert -- 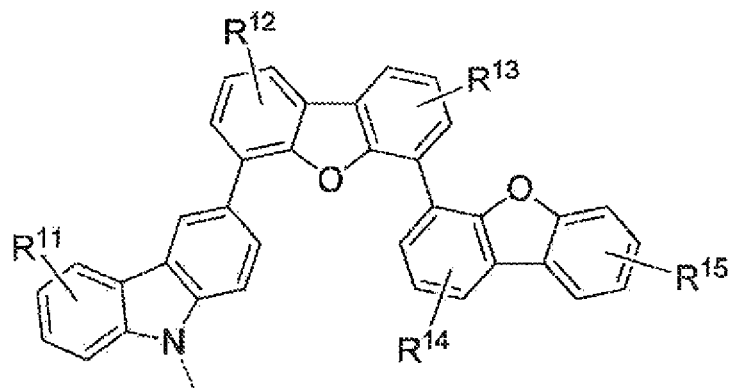 --
Column 175, Lines 36-45, please delete
" 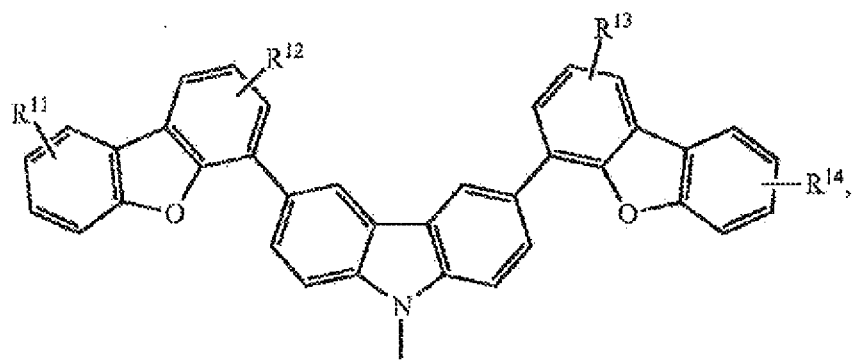 "

CERTIFICATE OF CORRECTION (continued)
U.S. Pat. No. 9,670,185 B2

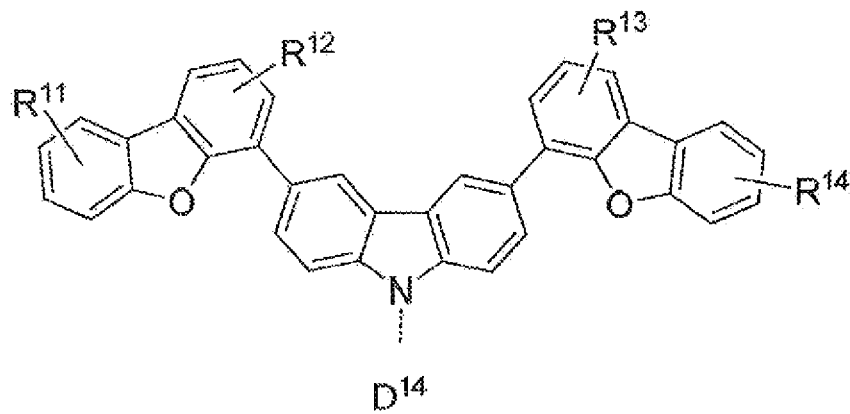

and insert --                                                                   --

Column 176, Lines 9-19, please delete "

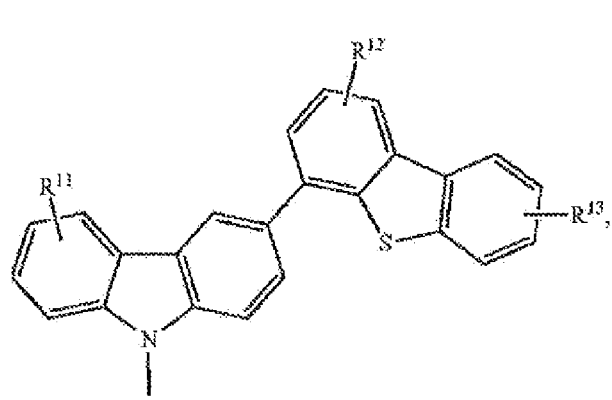

"

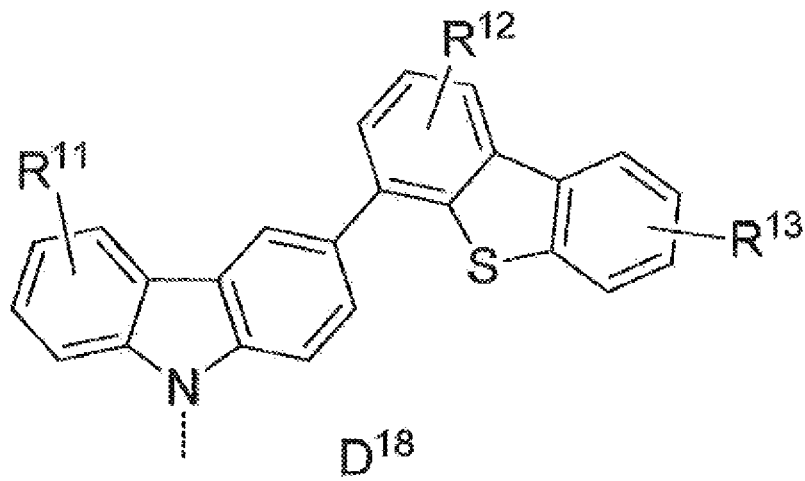

and insert --                                                                   --

Column 176, Lines 20-32, please delete
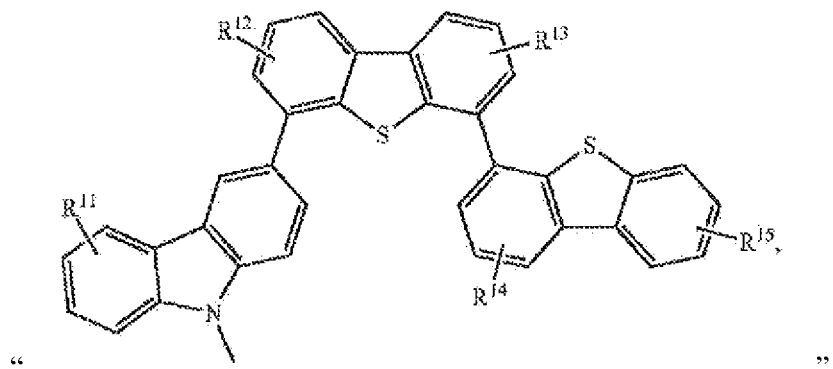
and insert --
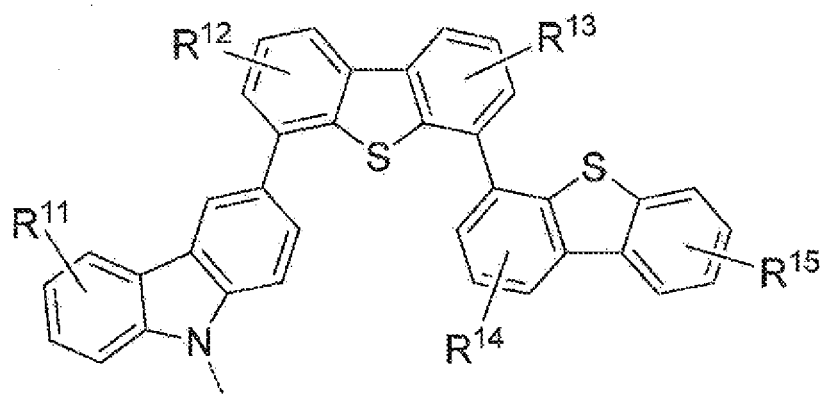
--
Column 176, Lines 33-42, please delete
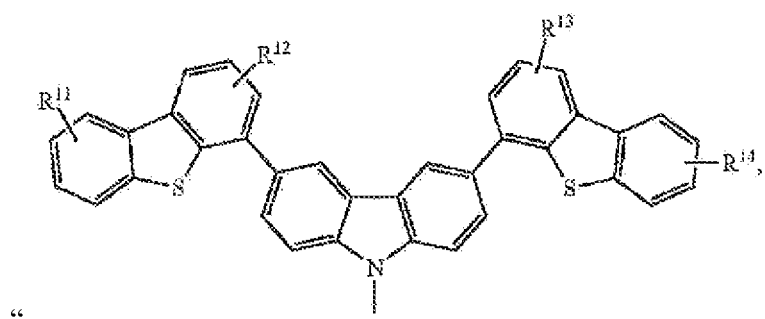

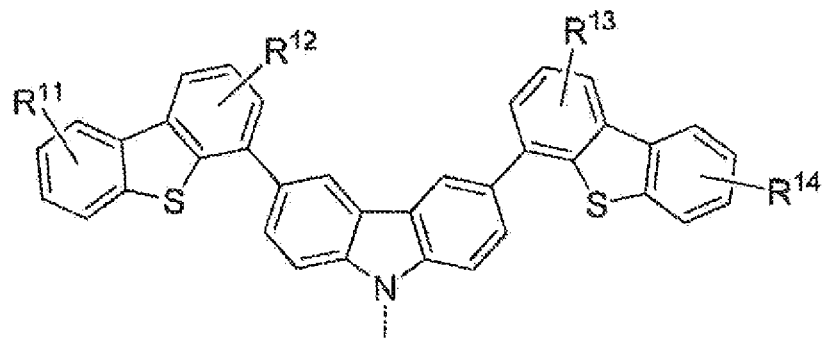
and insert -- --
Column 177, Lines 28-41, please delete "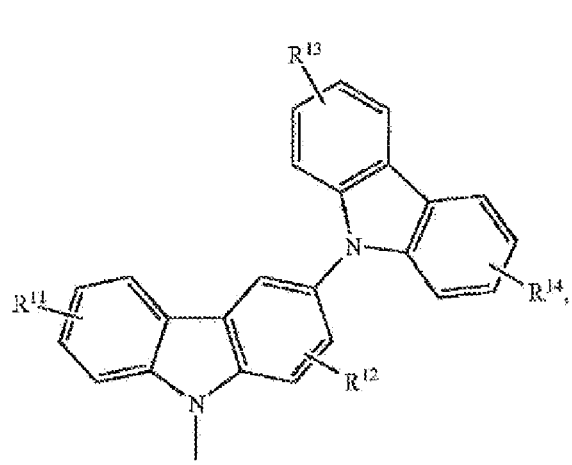"
and insert --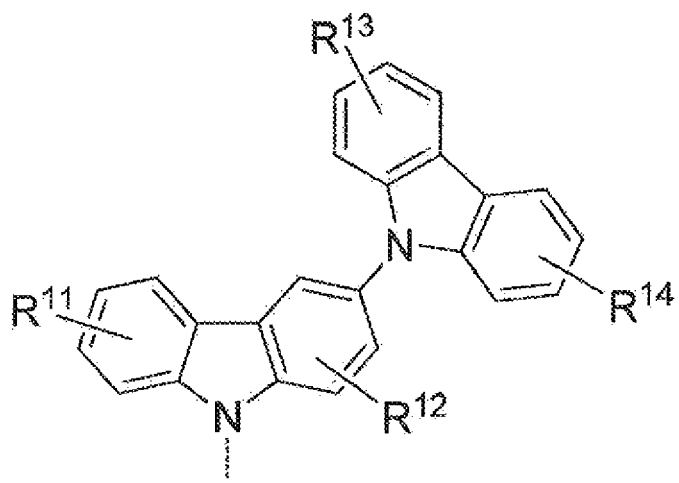--

Column 177, Lines 42-52, please delete " 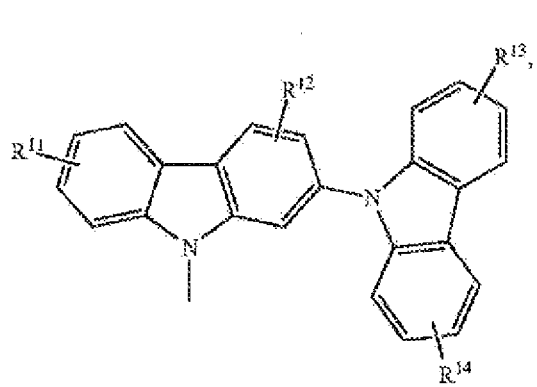
and insert -- 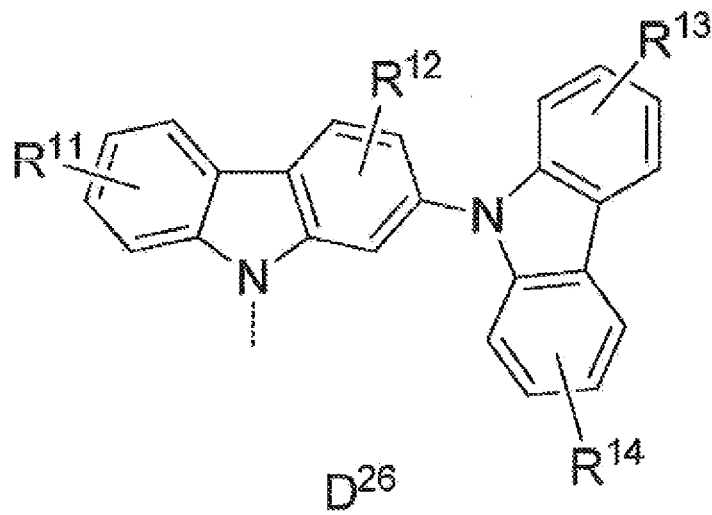 --
Column 177, Lines 53-66, please delete " 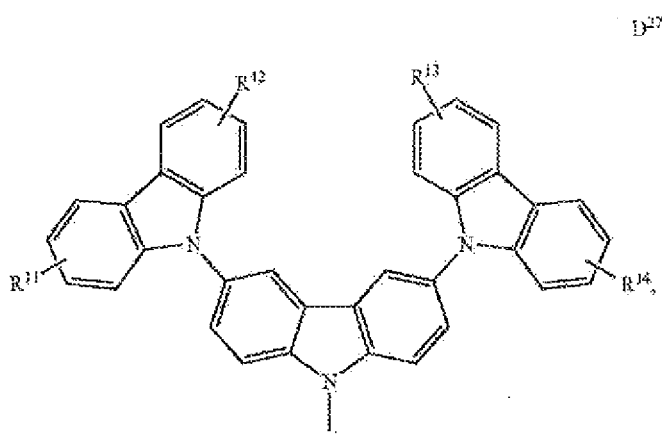 "

and insert -- 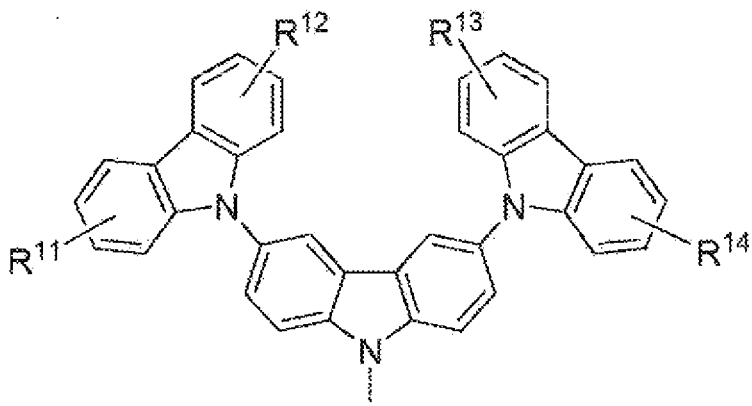 --
Column 179, Lines 1-8, please delete " 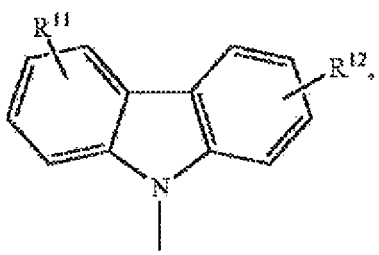 "
and insert -- 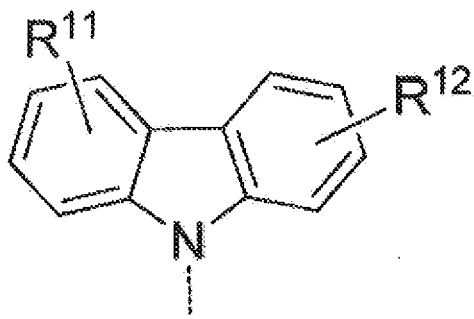 --
Column 180, Lines 60-66, please delete
" 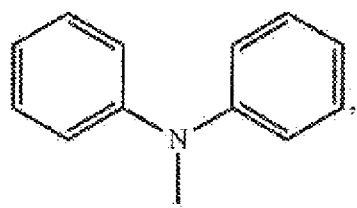 "

and insert -- 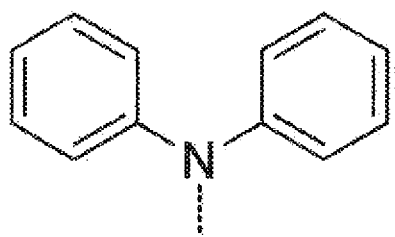 ; --
Column 181, Lines 15-22, please delete " 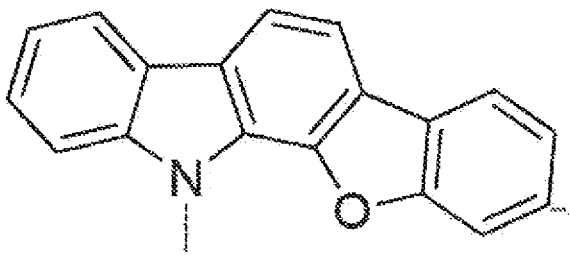 "
and insert -- 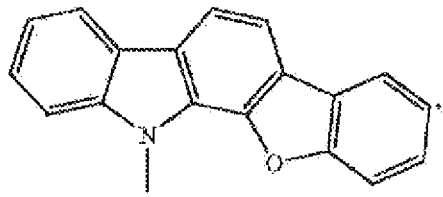 ; --
Column 181, Lines 23-29, please delete " 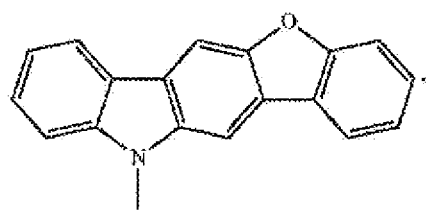 "

CERTIFICATE OF CORRECTION (continued)
U.S. Pat. No. 9,670,185 B2 and insert -- 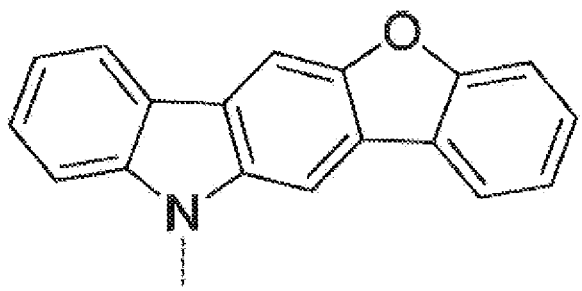 --

Column 181, Lines 30-41, please delete " 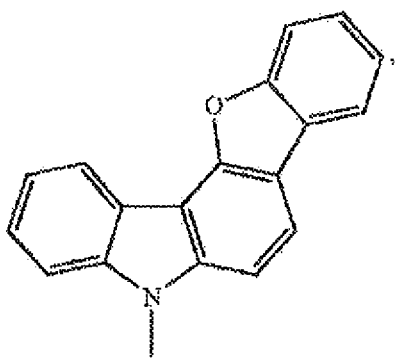 "

and insert -- 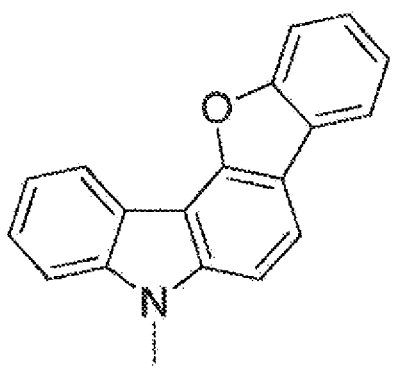 --

Column 181, Lines 42-46, please delete " 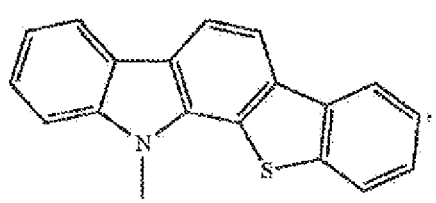 "

CERTIFICATE OF CORRECTION (continued)
U.S. Pat. No. 9,670,185 B2

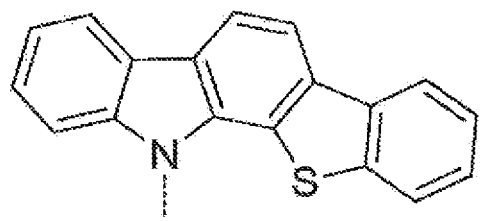

and insert -- --

Column 181, Lines 47-54, please delete "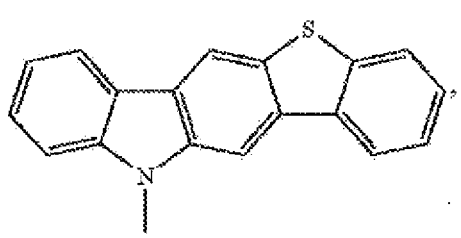"

and insert -- 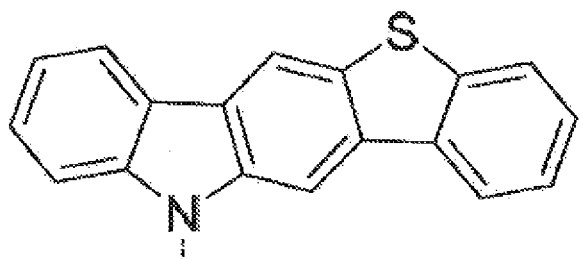 --

Column 181, Lines 55-66, please delete "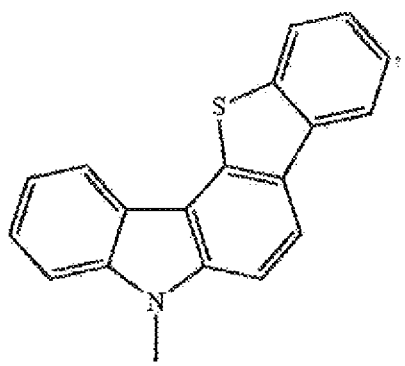"

CERTIFICATE OF CORRECTION (continued)
U.S. Pat. No. 9,670,185 B2

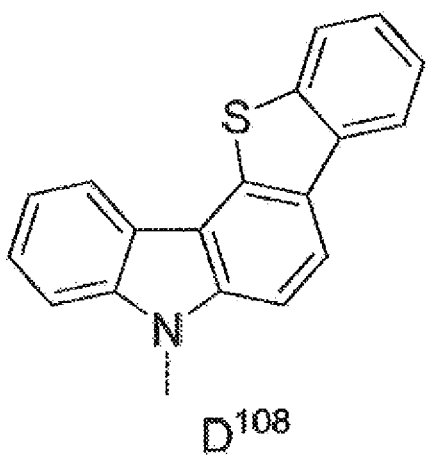

and insert --                                 --

Column 182, Lines 34-43, please delete "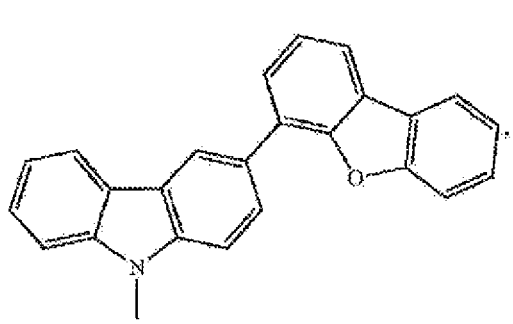"

and insert --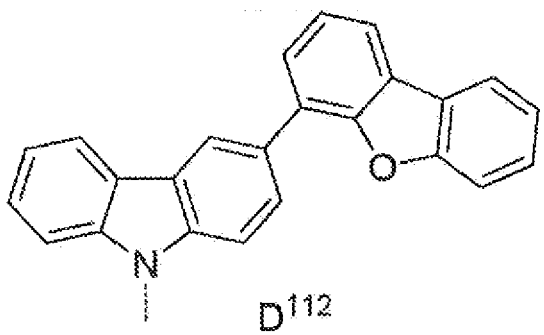--

Column 182, Lines 44-57, please delete "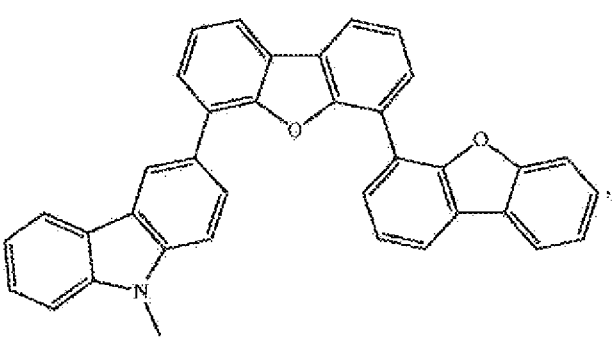"

CERTIFICATE OF CORRECTION (continued)
U.S. Pat. No. 9,670,185 B2

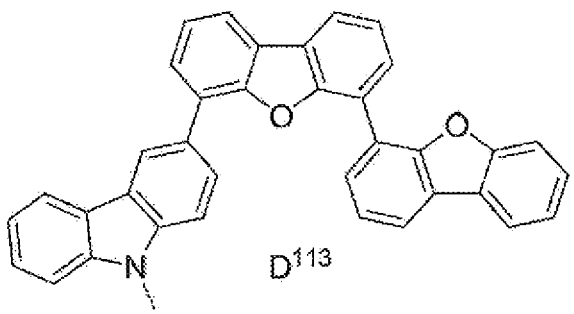

and insert --

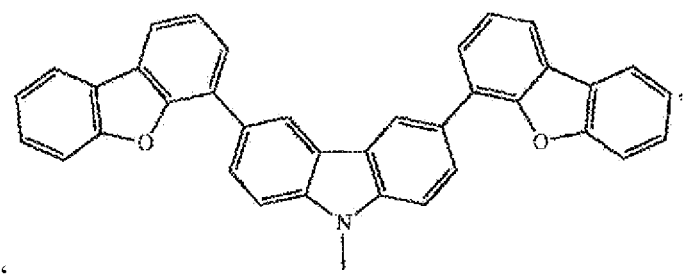

Column 182, Lines 58-66, please delete "

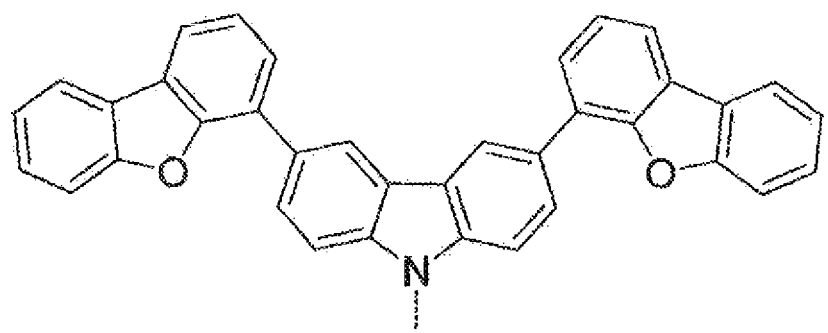

and insert --

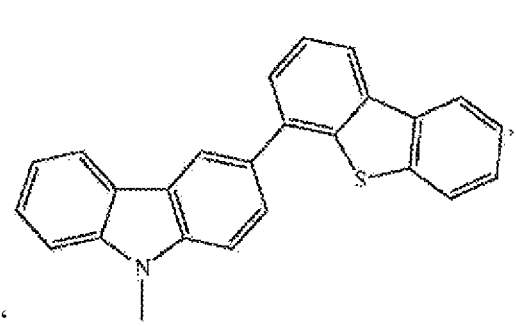

Column 183, Lines 26-35, please delete "

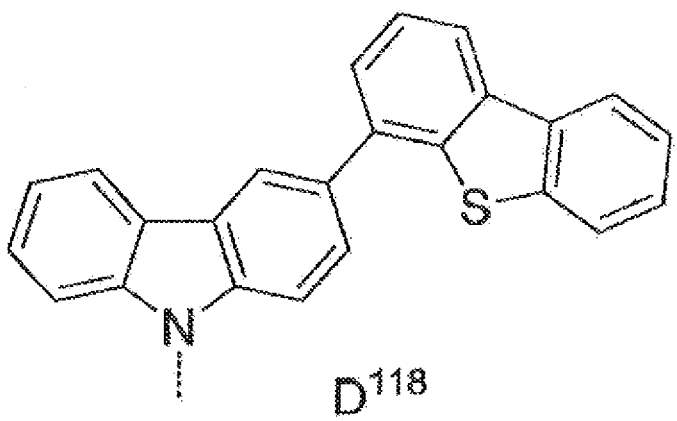
and insert --
Column 183, Lines 36-47, please delete "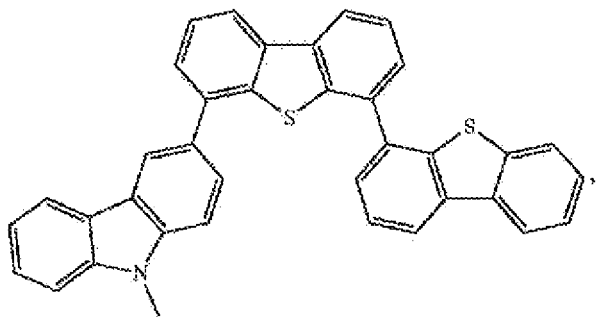"
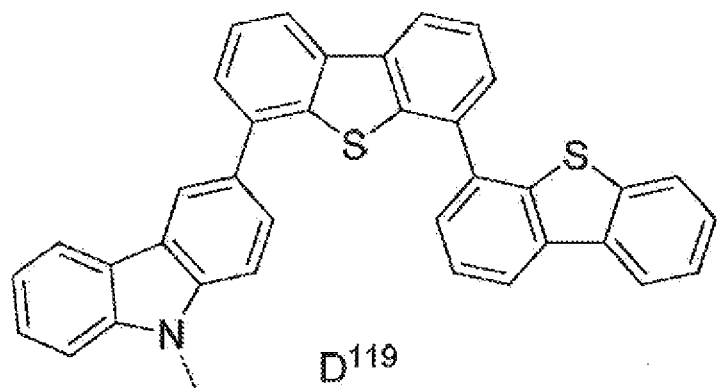
and insert -- ' ' --

Column 183, Lines 48-57, please delete
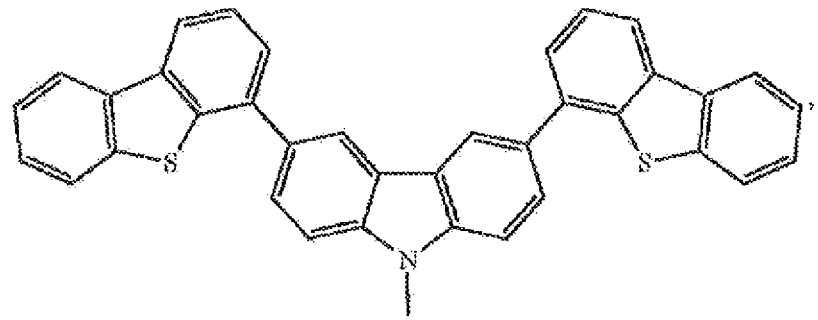
and insert --
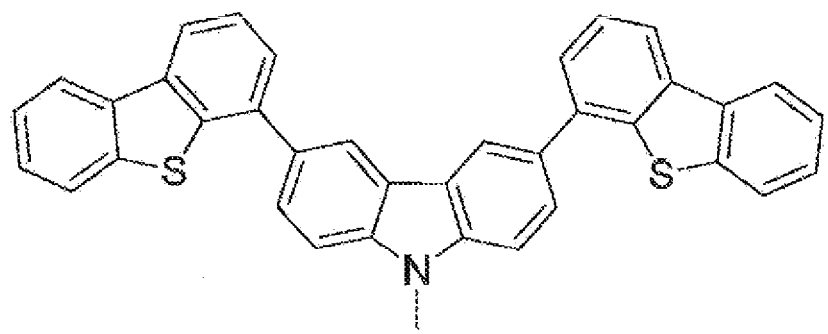
--
Column 184, Lines 58-66, please delete
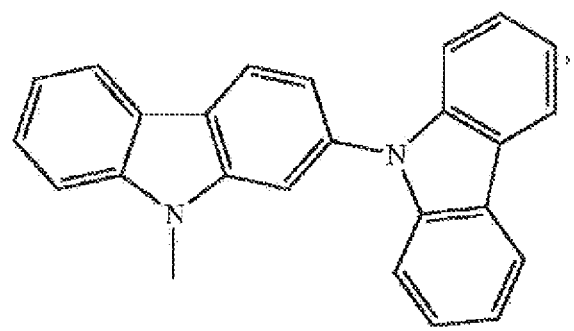

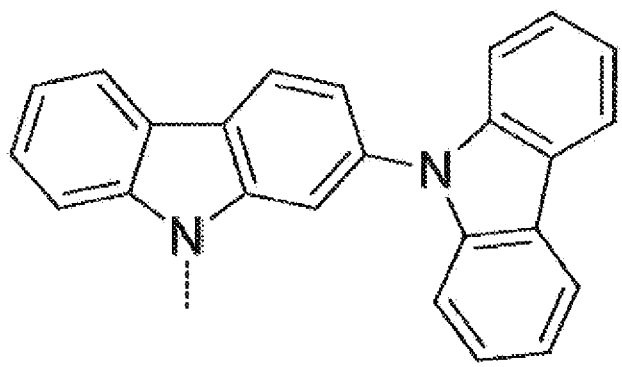
and insert --                                          ,   --
Column 184, Lines 45-57, please delete "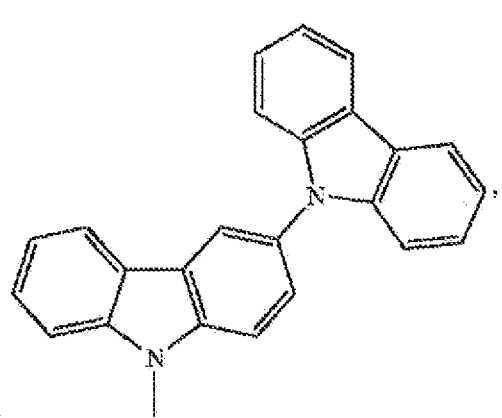"
and insert -- 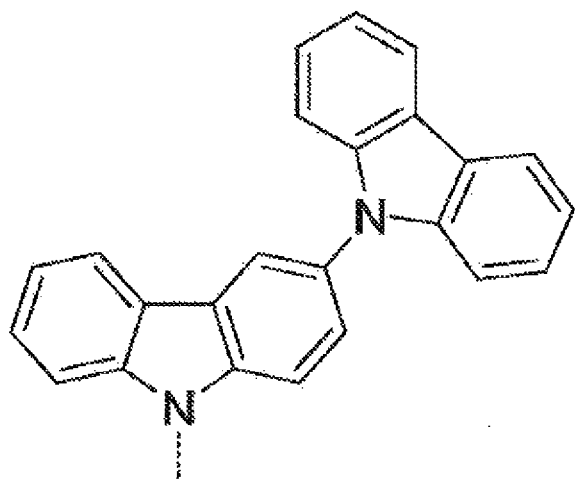   --

Column 185, Lines 1-14, please delete "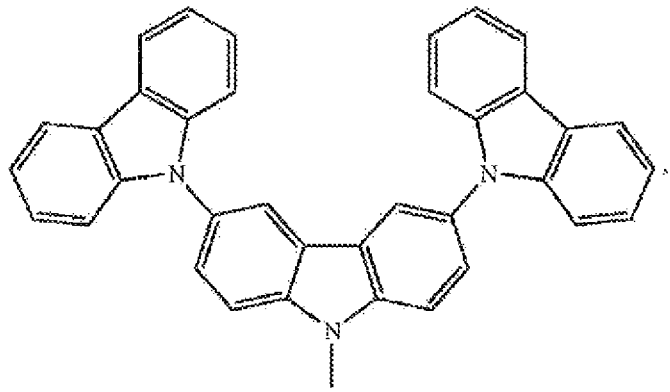"
and insert -- 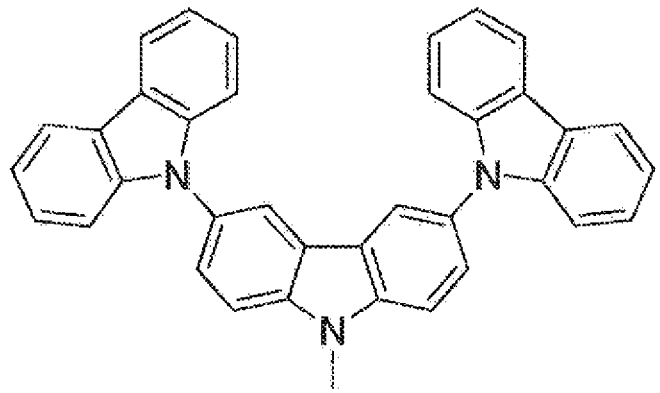 --
Column 186, Lines 14-18, please delete "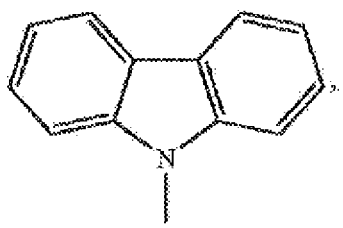"
and insert -- 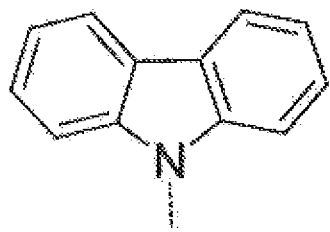 --

In the Claims
Column 577, Lines 15-21, please delete "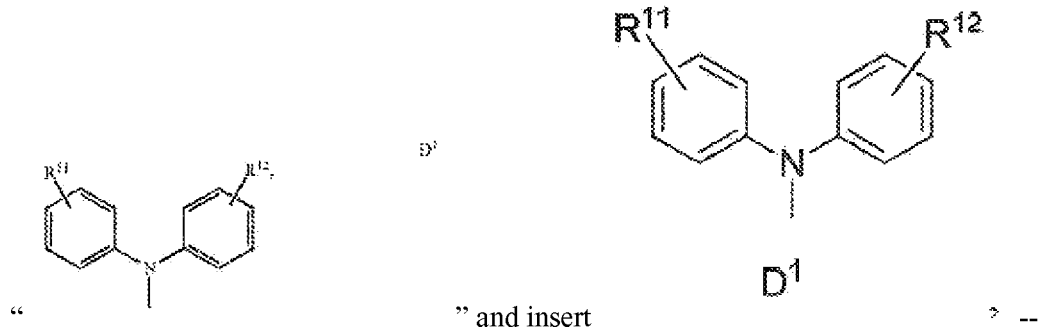" and insert --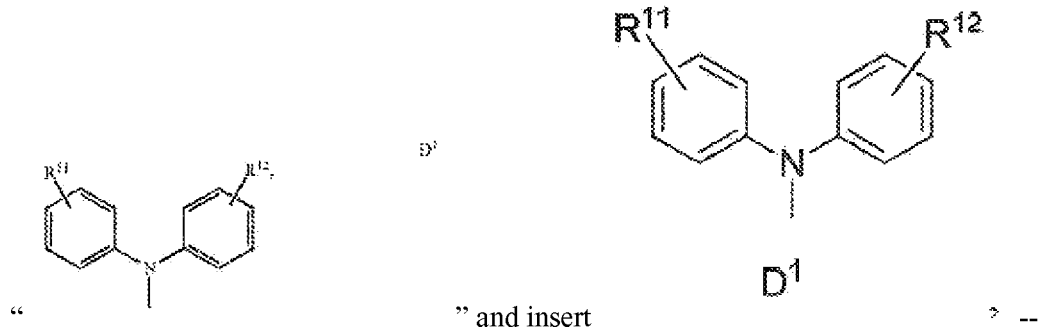--
Column 577, Lines 33-41, please delete "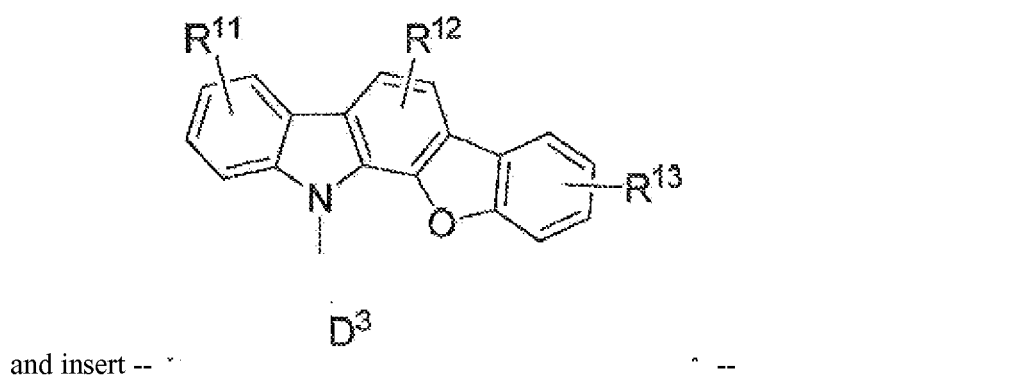" and insert --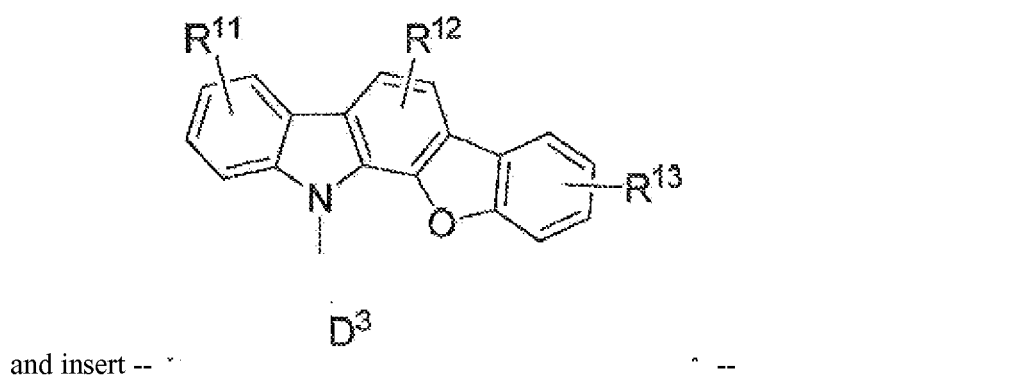--
Column 577, Lines 42-47, please delete "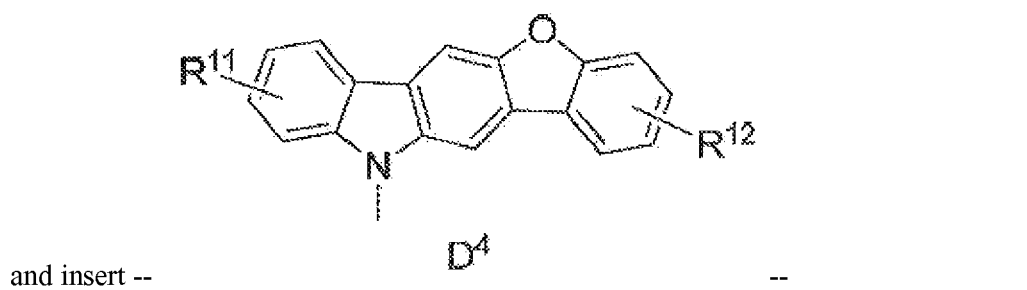" and insert --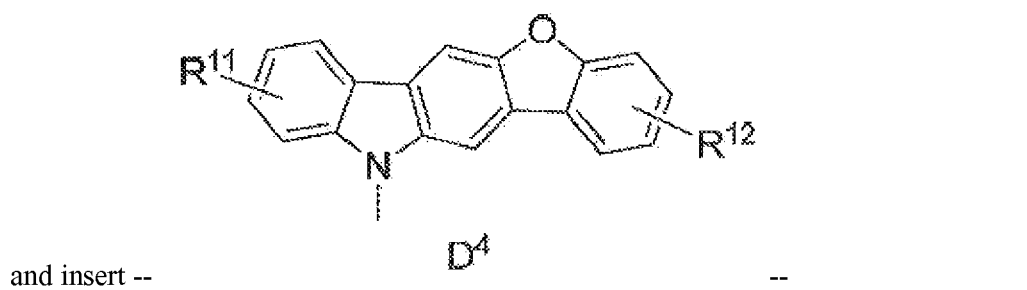--

Column 577, Lines 48-57, please delete " 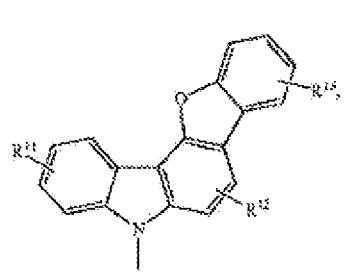 "
and insert -- 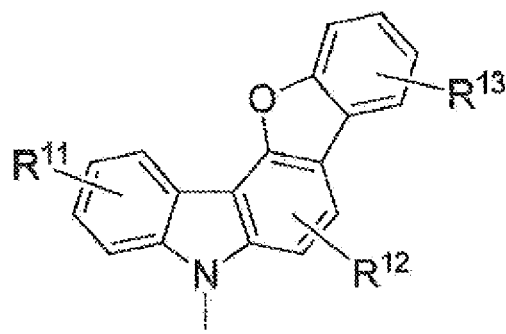 --
Column 577, Lines 59-67, please delete " 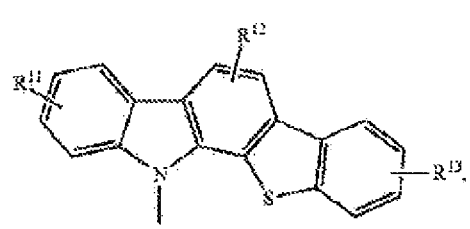 "
and insert -- 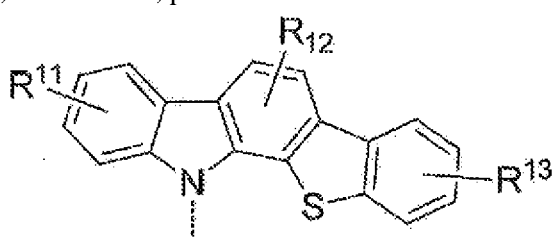 --
Column 578, Lines 1-10, please delete " 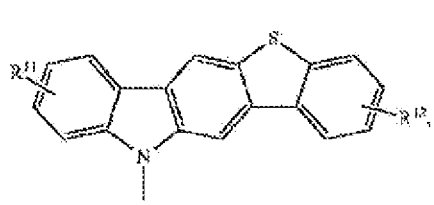 "

CERTIFICATE OF CORRECTION (continued)
U.S. Pat. No. 9,670,185 B2

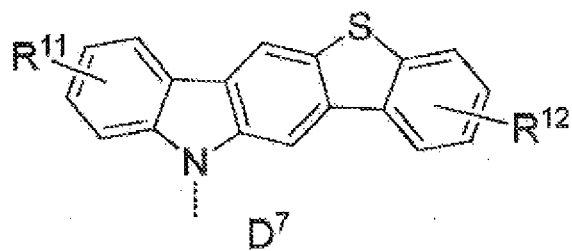

and insert -- " --

Column 578, Lines 1-10, please delete

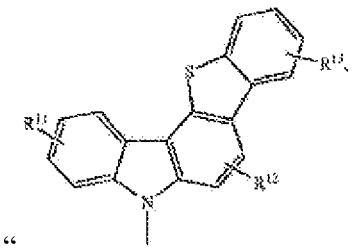

" and insert -- 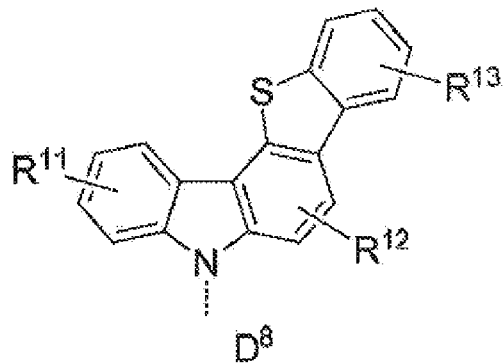 --

Column 578, Lines 56-66, please delete " 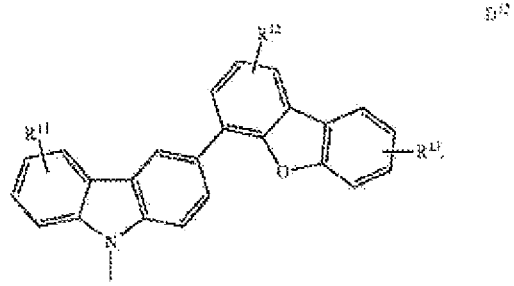 "

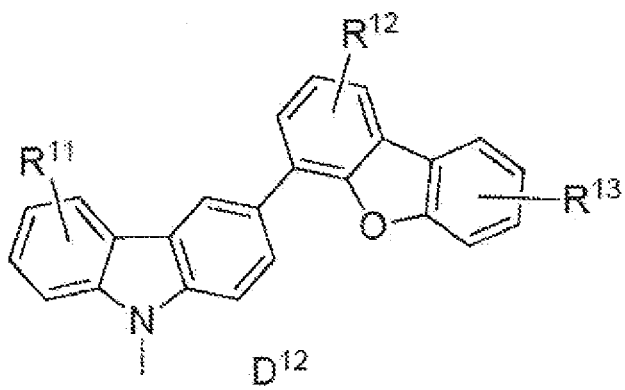

and insert -- --

Column 579, Lines 1-15, please delete " 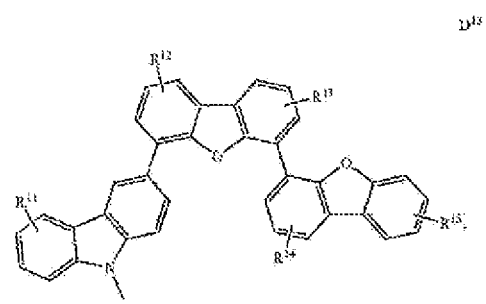 "
and insert -- 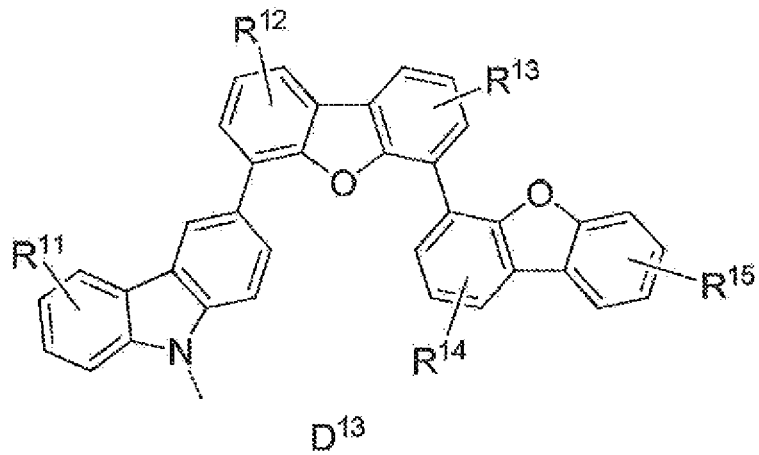 , --
Column 579, Lines 16-27, please delete " 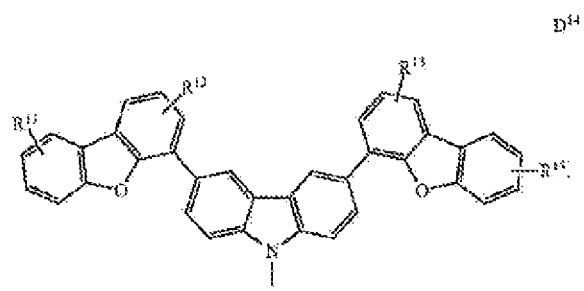 "
and insert -- 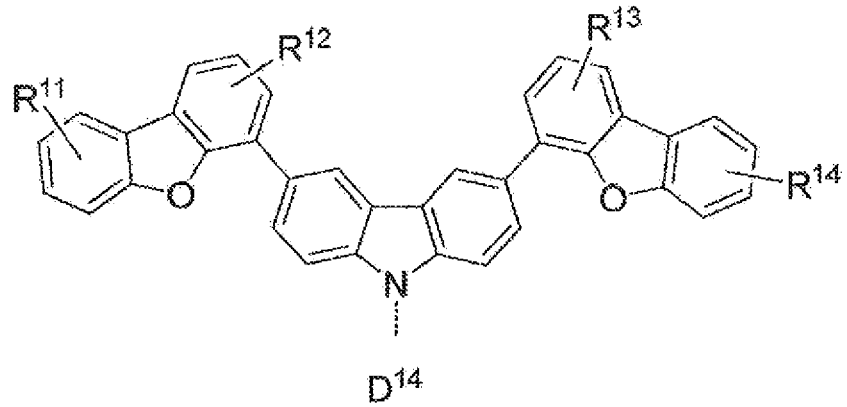 --

Column 579, Lines 56-66, please delete " 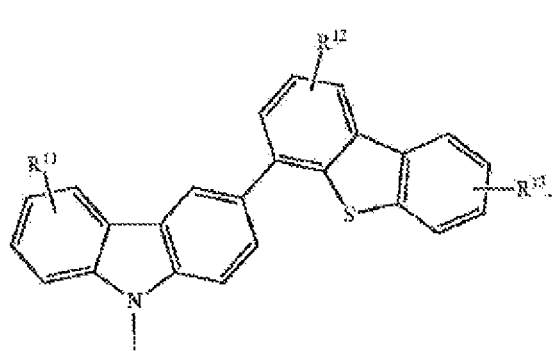 "
and insert -- 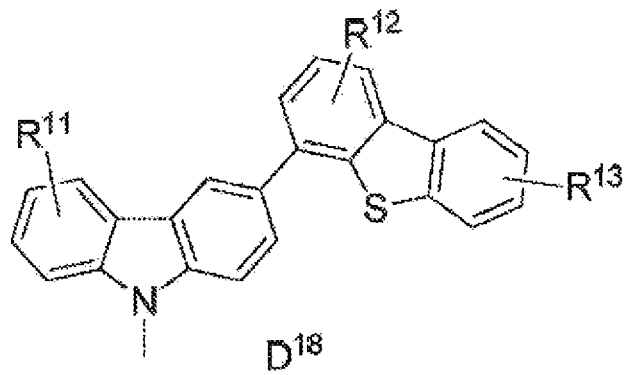 --
Column 580, Lines 1-15, please delete " 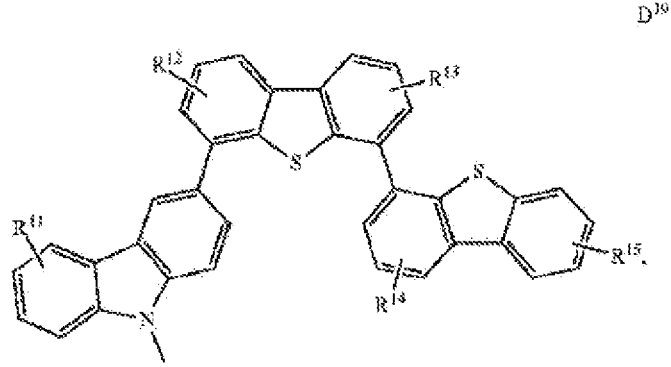 "
and insert -- 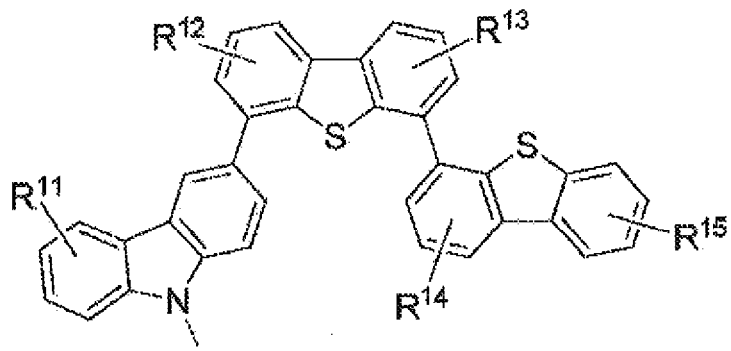 --

CERTIFICATE OF CORRECTION (continued)
U.S. Pat. No. 9,670,185 B2

Column 580, Lines 16-28, please delete "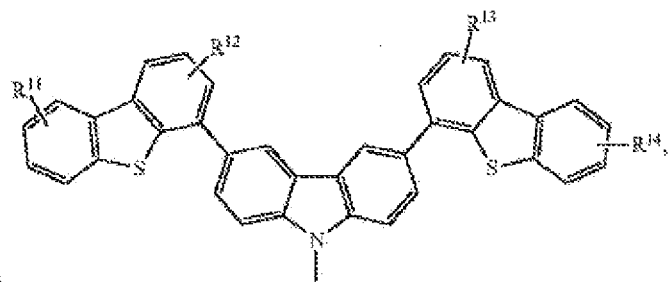"

and insert -- 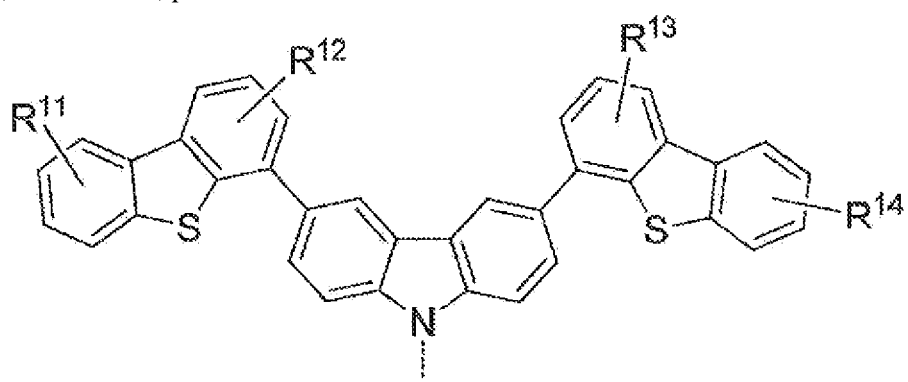 --

Column 582, Lines 43-48, please delete "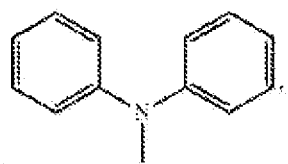" and insert -- 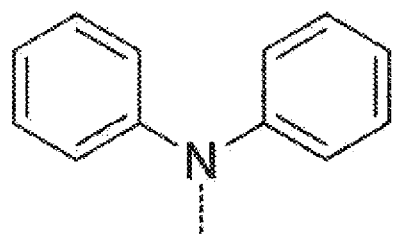 --

Column 582, Lines 60-66, please delete "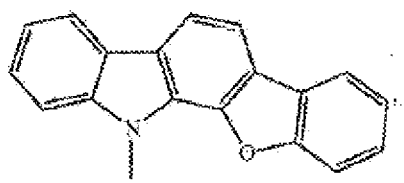"

CERTIFICATE OF CORRECTION (continued)
U.S. Pat. No. 9,670,185 B2

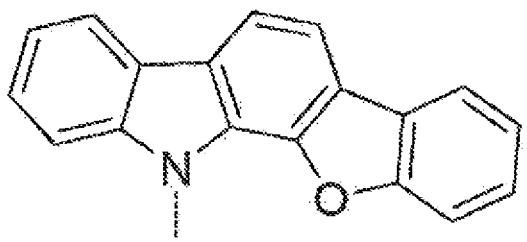

and insert --

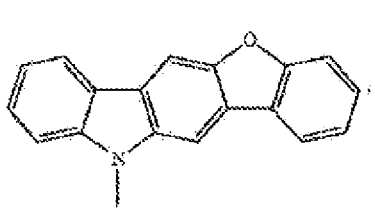

Column 583, Lines 1-10, please delete "

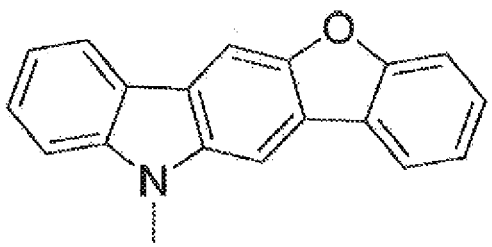

and insert -- --

Column 583, Lines 11-22, please delete

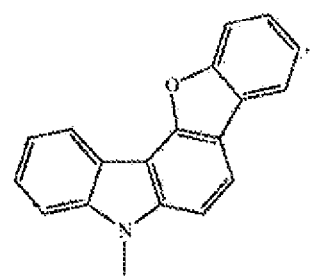

" and insert --

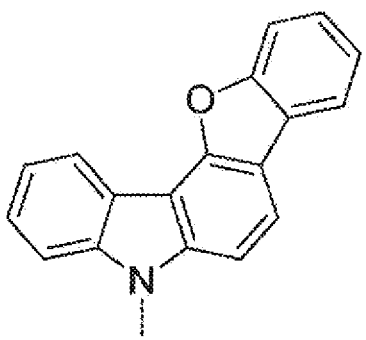

--

Column 583, Lines 23-29, please delete " 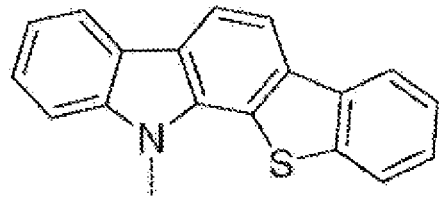 "
and insert -- 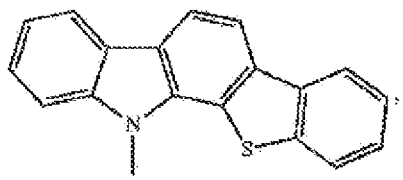 --
Column 583, Lines 30-37, please delete " 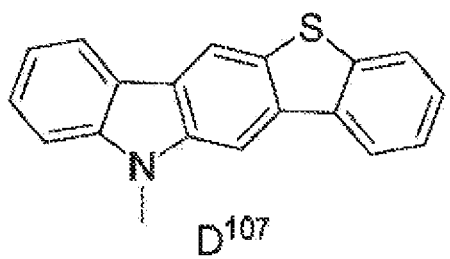 "
and insert -- 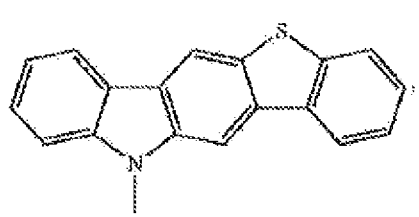 --
Column 583, Lines 38-48, please delete " 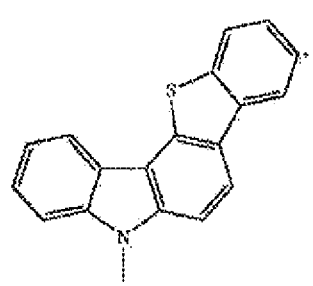 "

and insert -- 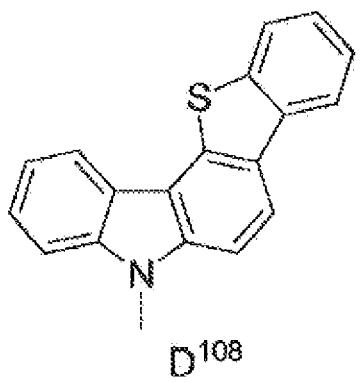 --
Column 584, Lines 9-18, please delete " 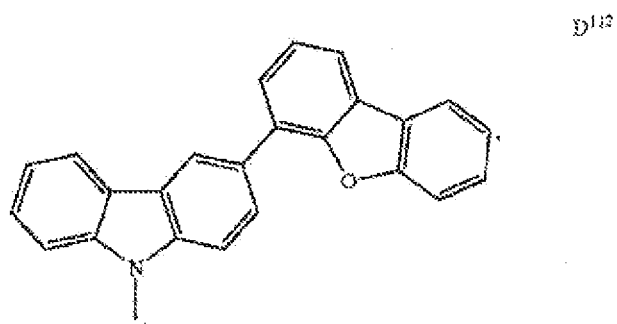 "
and insert -- 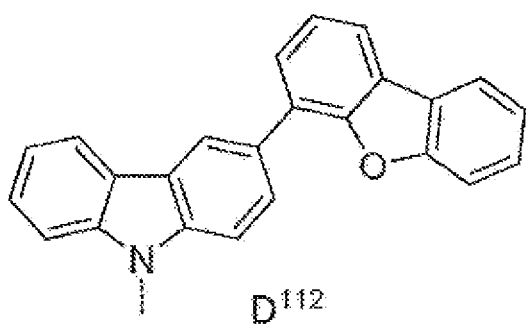 --
Column 584, Lines 19-31, please delete " 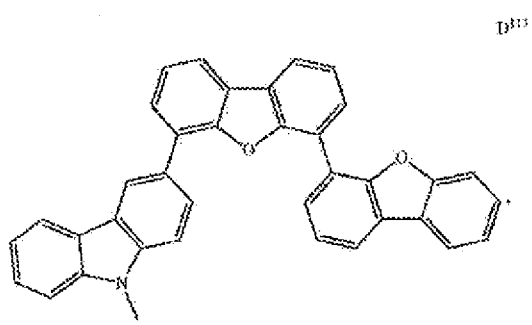 "

CERTIFICATE OF CORRECTION (continued)
U.S. Pat. No. 9,670,185 B2

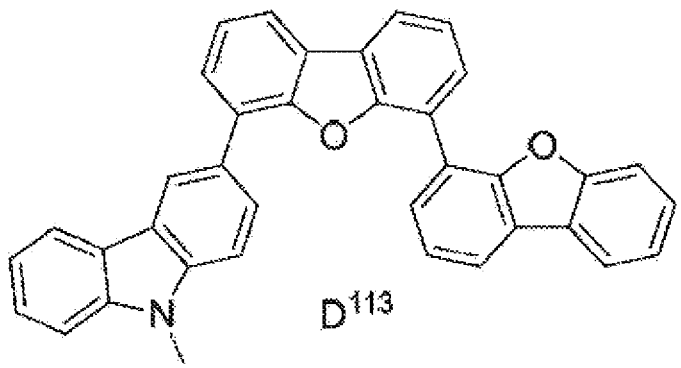

and insert --

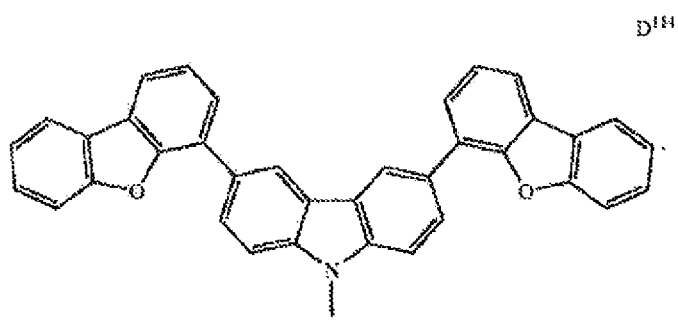

Column 584, Lines 32-41, please delete " "

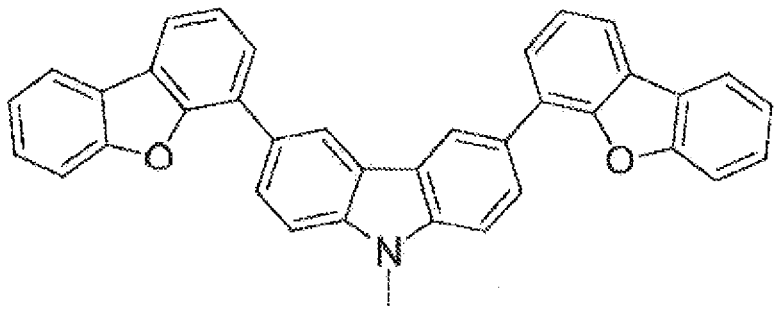

and insert -- --

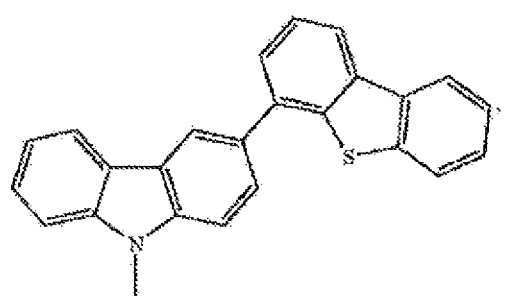

Column 585, Lines 1-11, please delete " "

CERTIFICATE OF CORRECTION (continued)
U.S. Pat. No. 9,670,185 B2

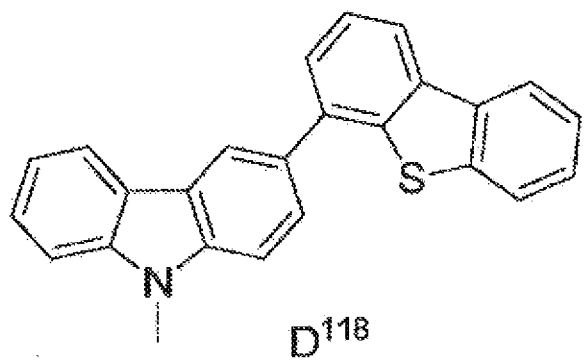

and insert --

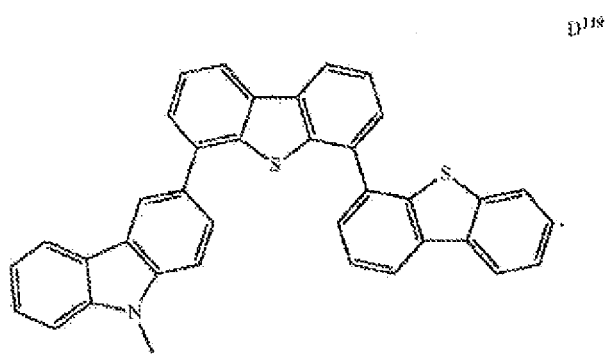

Column 585, Lines 12-24, please delete "

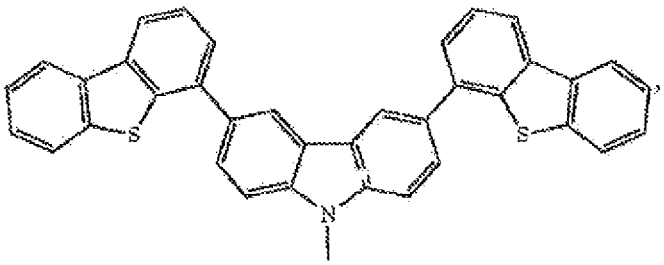

and insert -- --

Column 585, Lines 25-34, please delete "

CERTIFICATE OF CORRECTION (continued)

U.S. Pat. No. 9,670,185 B2

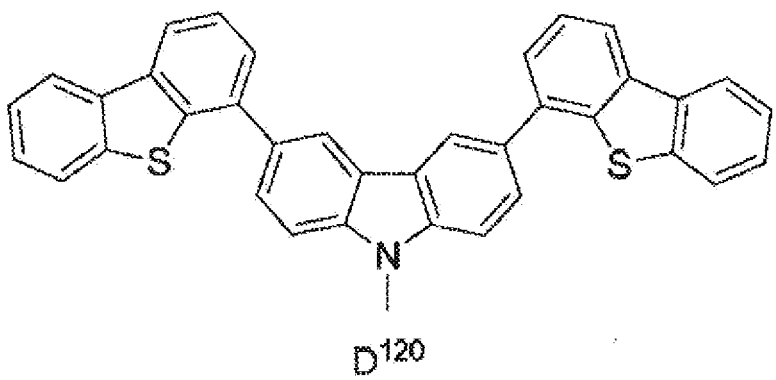

and insert --                                      --

Column 648, Lines 43-66, please delete

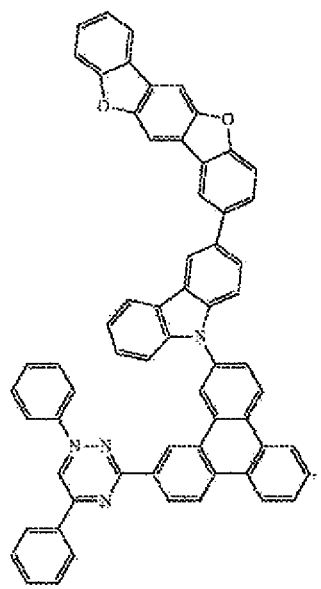

" and insert --

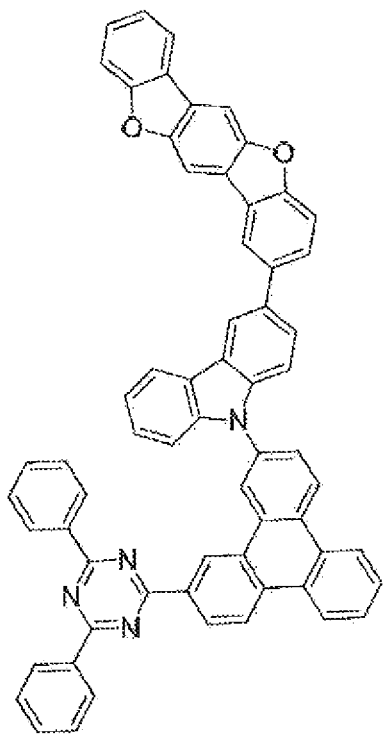

--